United States Patent
Baell et al.

(10) Patent No.: US 8,232,273 B2
(45) Date of Patent: Jul. 31, 2012

(54) HETEROCYCLIC COMPOUNDS AND METHODS OF USE

(75) Inventors: Jonathan Bayldon Baell, Bundoora (AU); Chinh Thien Bui, Balwyn North (AU); Peter Colman, East Melbourne (AU); Peter Czabotar, Melbourne (AU); Danette A. Dudley, Pacifica, CA (US); Wayne J. Fairbrother, Burlingame, CA (US); John A. Flygare, Burlingame, CA (US); Guillaume Laurent Lessene, Coburg (AU); Chudi Ndubaku, San Francisco, CA (US); George Nikolakopoulos, Thomastown (AU); Brad Edmund Sleebs, Reservoir (AU); Brian John Smith, Sunbury (AU); Keith Geoffrey Watson, Surry Hills (AU); Steven W. Elmore, Northbrook, IL (US); Lisa A. Hasvold, Grayslake, IL (US); Andrew M. Petros, Mundelein, IL (US); Andrew J. Souers, Evanston, IL (US); Zhi-Fu Tao, Gurnee, IL (US); Le Wang, Vernon Hills, IL (US); Xilu Wang, Grayslake, IL (US); Kurt Deshayes, San Francisco, CA (US)

(73) Assignees: Genentech, Inc., South San Francisco, CA (US); Abbott Laboratories, Abbott Park, IL (US); The Walter and Eliza Hall Institute of Medical Research, Victoria (AU)

(*) Notice: Subject to any disclaimer, the term of this patent is extended or adjusted under 35 U.S.C. 154(b) by 336 days.

(21) Appl. No.: 12/641,141

(22) Filed: Dec. 17, 2009

(65) Prior Publication Data

US 2010/0210622 A1    Aug. 19, 2010

Related U.S. Application Data

(60) Provisional application No. 61/139,492, filed on Dec. 19, 2008.

(51) Int. Cl.
*A61K 31/5377* (2006.01)
*C07D 413/14* (2006.01)

(52) U.S. Cl. .................... 514/233.8; 544/111

(58) Field of Classification Search .................. 514/266, 514/233.8; 544/264, 111
See application file for complete search history.

(56) References Cited

U.S. PATENT DOCUMENTS

| | | | |
|---|---|---|---|
| 7,767,684 B2 | 8/2010 | Bruncko et al. |
| 7,981,888 B2 | 7/2011 | Song et al. |
| 8,114,893 B2 | 2/2012 | Baell et al. |
| 2004/0077643 A1 | 4/2004 | Ogawa et al. |
| 2005/0124614 A1 | 6/2005 | Gangloff et al. |
| 2007/0054892 A1 | 3/2007 | Isaacs et al. |
| 2007/0173506 A1 | 7/2007 | Zeng et al. |
| 2009/0054402 A1 | 2/2009 | Wang et al. |
| 2010/0190782 A1 | 7/2010 | Baell et al. |

FOREIGN PATENT DOCUMENTS

WO    WO 2009/039553    4/2009

OTHER PUBLICATIONS

ISA, International Search Report and Written Opinion dated Mar. 5, 2010 for International application PCT/US2009/068496.

*Primary Examiner* — Taofiq A Solola
(74) *Attorney, Agent, or Firm* — Jones Day

(57) ABSTRACT

In one aspect, the present invention provides for a compound of Formula I

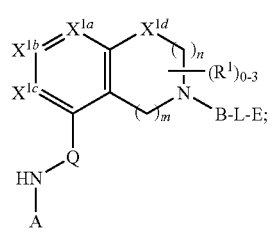

in which the variable $X^{1a}, X^{1b}, X^{1c}, X^{1d}, Q, A, R^1, B, L, E$, and the subscripts m and n have the meanings as described herein. In another aspect, the present invention provides for pharmaceutical compositions comprising compounds of Formula I as well as methods for using compounds of Formula I for the treatment of diseases and conditions (e.g., cancer, thrombocythemia, etc) characterized by the expression or over-expression of Bcl-2 anti-apoptotic proteins, e.g., of anti-apoptotic Bcl-$x_L$ proteins.

31 Claims, 6 Drawing Sheets

Figure 2-A
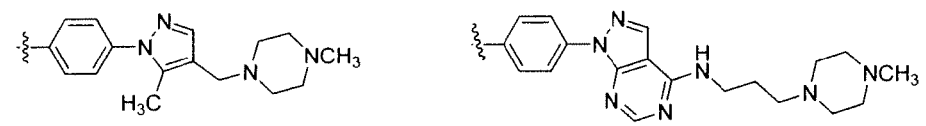
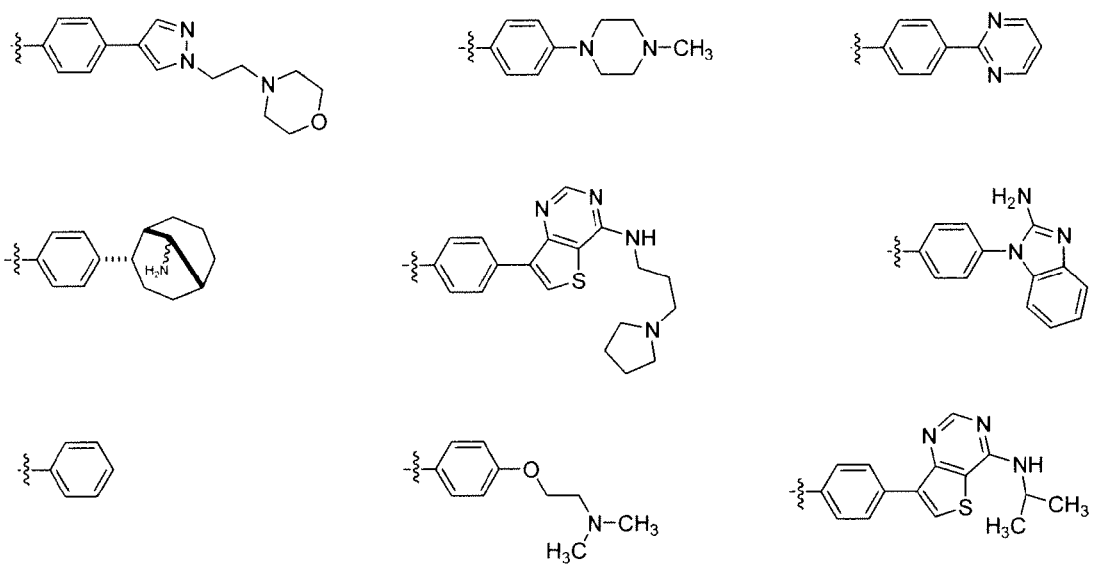
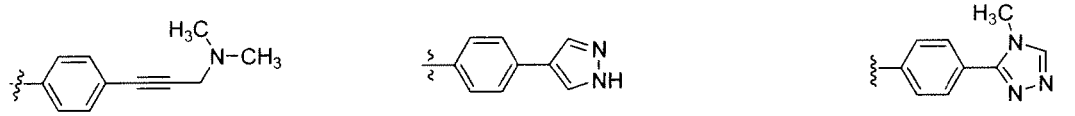
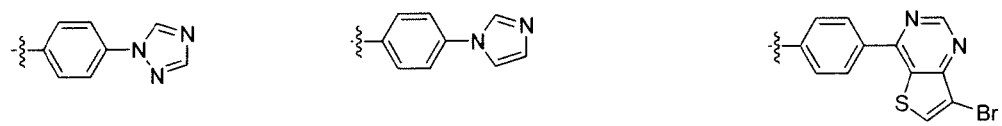
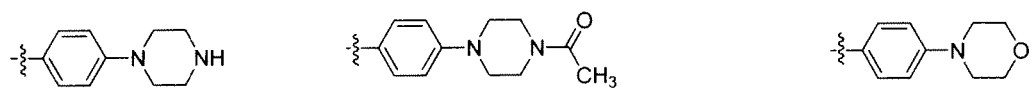

Figure 2-B
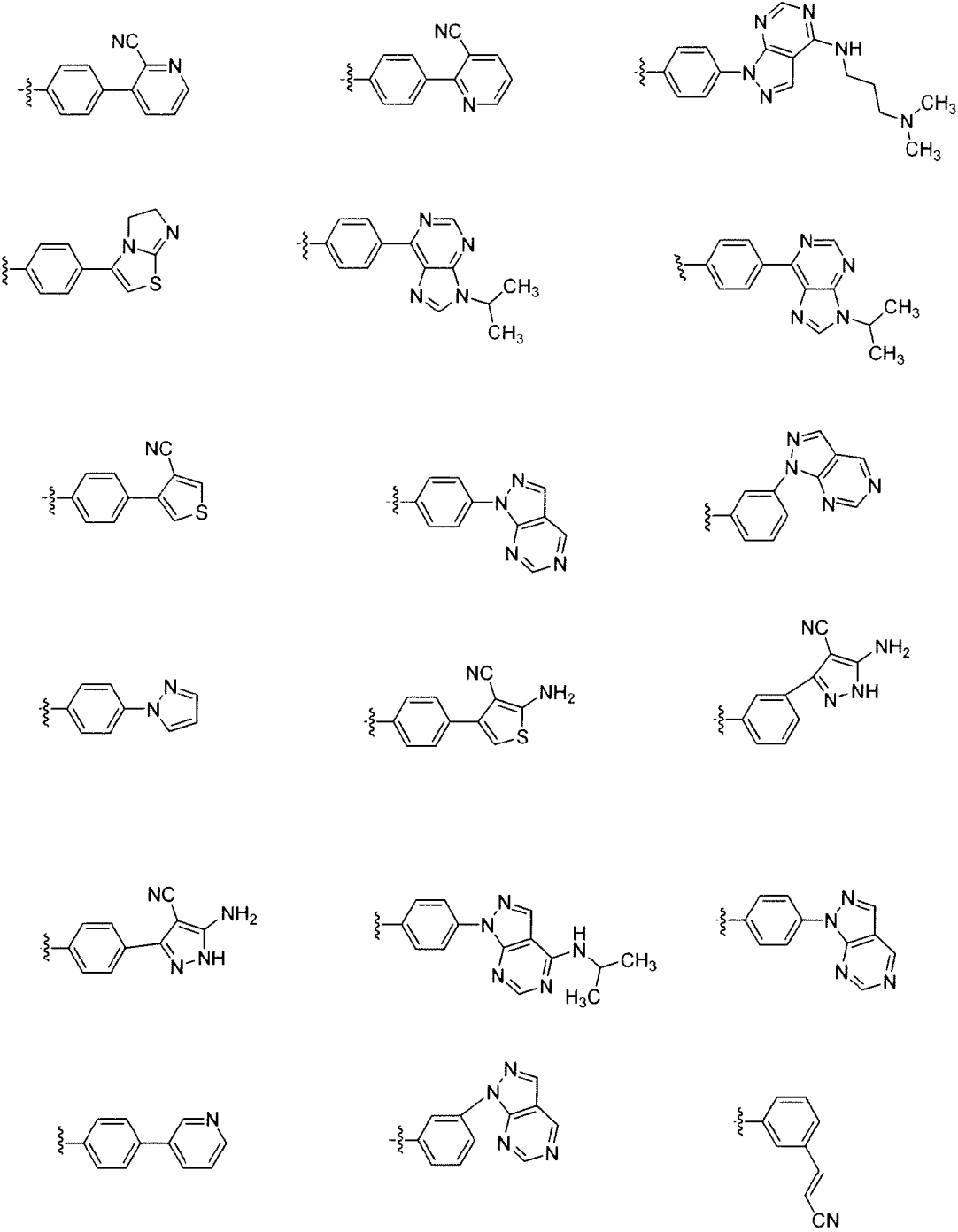

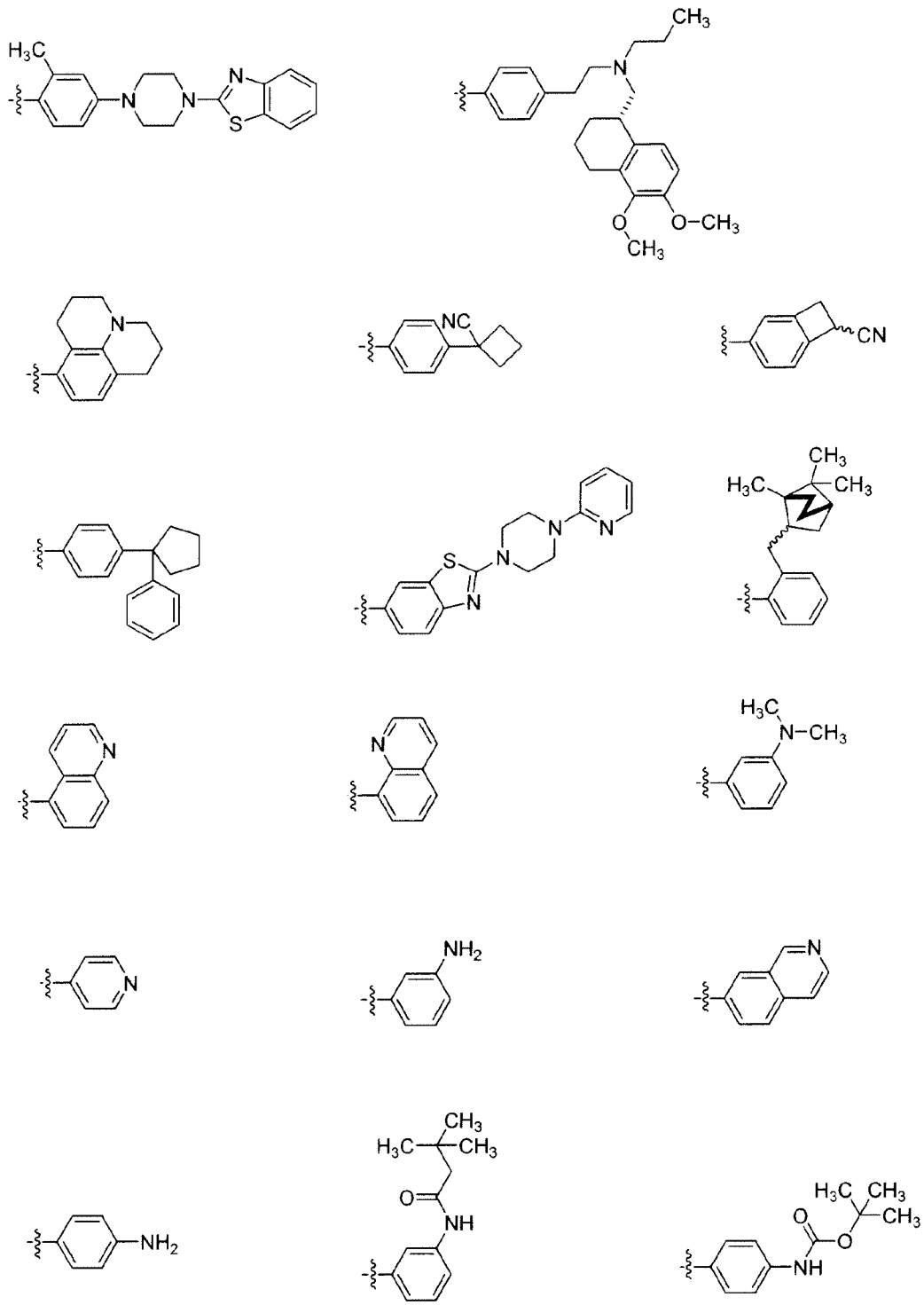
Figure 2-C

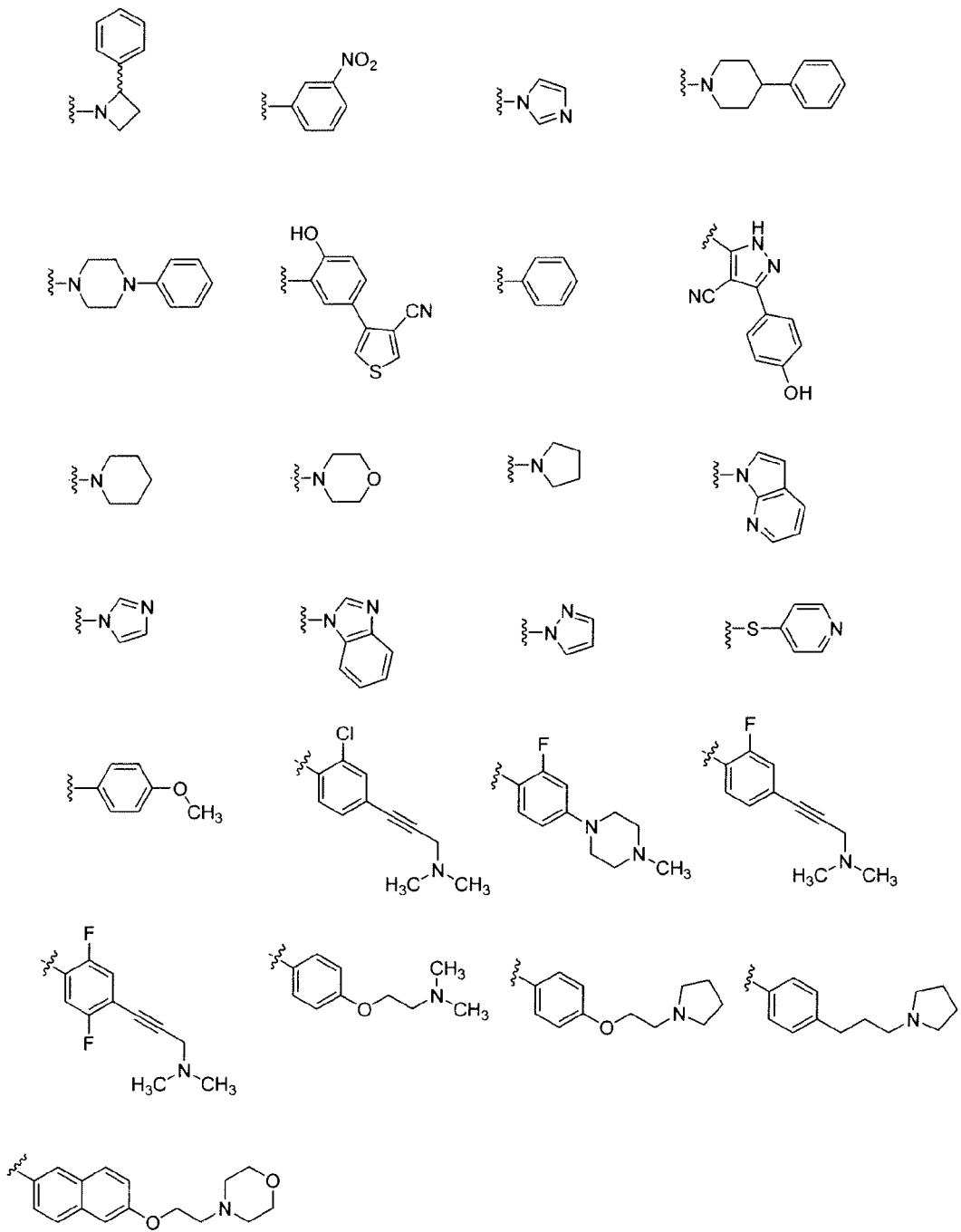
Figure 2-D

Figure 2-E
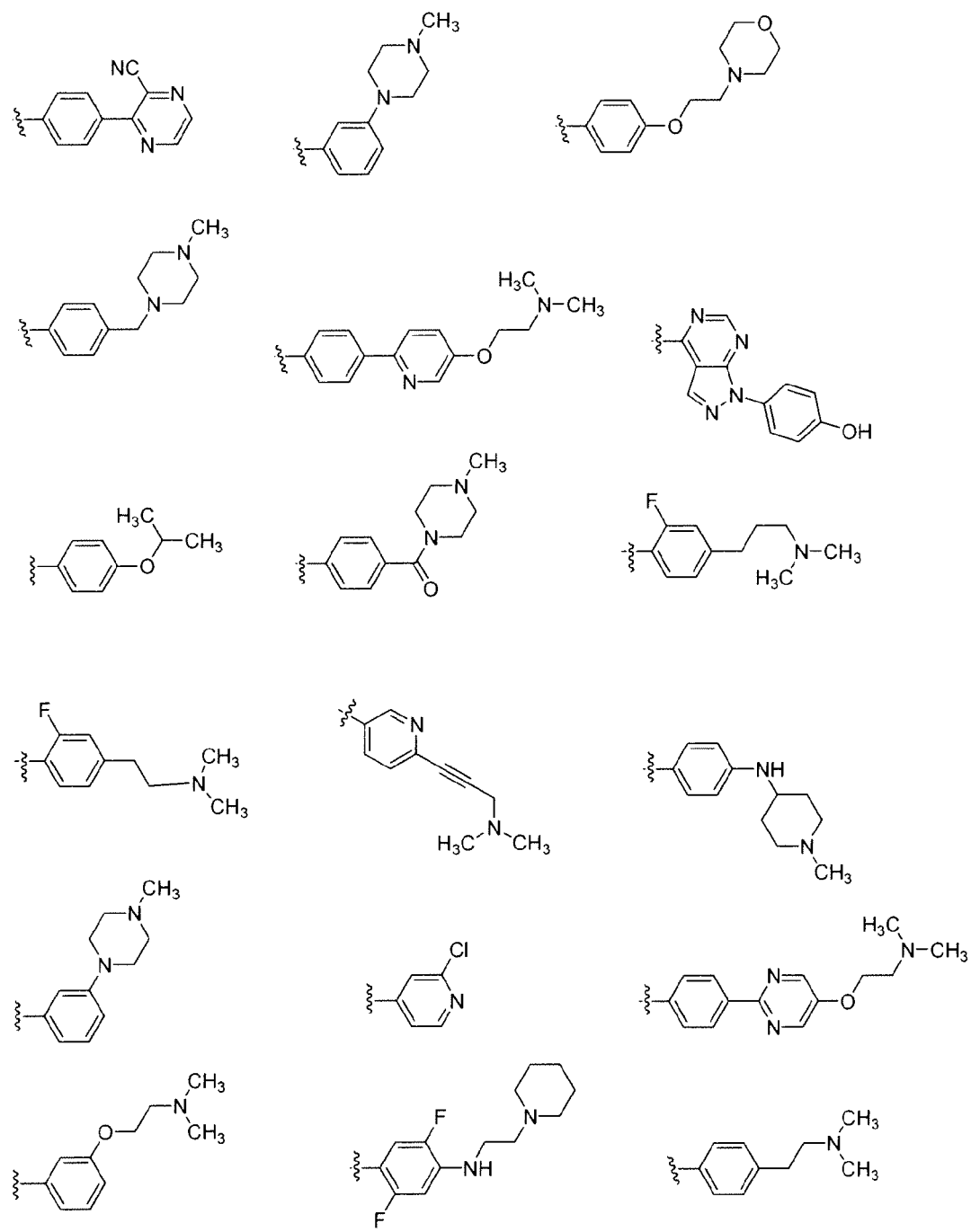

HETEROCYCLIC COMPOUNDS AND METHODS OF USE

CROSS-REFERENCE TO RELATED APPLICATIONS

This application claims the benefit of U.S. Provisional Application No. 61/139,492, filed Dec. 19, 2008, the content of which is hereby incorporated by reference in its entirety.

BACKGROUND OF INVENTION

Apoptosis is now recognized as an essential biological process for tissue homeostasis of all living species. In mammals in particular, it has been shown to regulate early embryonic development. Later in life, cell death is a default mechanism by which potentially dangerous cells (e.g., cells carrying cancerous defects) are removed. Several apoptotic pathways have been uncovered, and one of the most important involves the Bcl-2 family of proteins, which are key regulators of the mitochondrial (also called "intrinsic") pathway of apoptosis. See, Danial, N. N. and Korsmeyer, S. J. Cell (2004) 116, 205-219. The structural homology domains BH1, BH2, BH3 and BH4 are characteristic of this family of proteins. The Bcl-2 family of proteins can be further classified into three subfamilies depending on how many of the homology domains each protein contains and on its biological activity (i.e., whether it has pro- or anti-apoptotic function).

The first subgroup contains proteins having all 4 homology domains, i.e., BH1, BH2, BH3 and BH4. Their general effect is anti-apoptotic, that is to preserve a cell from starting a cell death process. Proteins such as, for example, Bcl-2, Bcl-w, Bcl-$x_L$, Mcl-1 and Bfl-1/A1 are members of this first subgroup. Proteins belonging to the second subgroup contain the three homology domains BH1, BH2 and BH3, and have a pro-apoptotic effect. The two main representative proteins of this second subgroup are Bax and Bak. Finally, the third subgroup is composed of proteins containing only the BH3 domain and members of this subgroup are usually referred to as "BH3-only proteins." Their biological effect on the cell is pro-apoptotic. Bim, Bid, Bad, Bik, Noxa, Hrk, Bmf, and Puma are examples of this third subfamily of proteins. The exact mechanism by which the Bcl-2 family proteins regulate cell death is still not entirely known and understanding this mechanism is an active area of research in the science community. In one hypothesis of regulation of cell death by Bcl-2 family proteins, the BH3-only proteins are further categorized as either "activator" (e.g., Bim and Bid) or "sensitizer" (e.g., Bad, Bik, Noxa, Hrk, Bmf, and Puma) proteins depending on their regulatory function.

The key to tissue homeostasis is achieving the delicate balance in the interactions among the three subgroups of protein in cells. Recent studies have tried to elucidate the mechanisms by which pro-apoptotic and anti-apoptotic subgroups of Bcl-2 family proteins interact to allow a cell to undergo programmed cell death. After receiving intra- or extra-cellular signals in cells, post-translational or transcriptional activation of BH3-only proteins occurs. The BH3-only proteins are the primary inducers of an apoptotic cascade that includes, as one step, the activation of the pro-apoptotic proteins Bax and Bak on the mitochondrial membrane in cells. Upon activation of Bax and/or Bak that are either already anchored to the mitochondrial membrane or migrate to this membrane, Bax and/or Bak oligomerize to result in mitochondrial outer membrane permeabilization (MOMP), the release of cytochrome C, and downstream activation of effector caspases, to ultimately result in cell apoptosis. Some researchers hypothesize that certain BH3-only proteins (e.g., Puma, Bim, Bid) are "activators" in that these proteins directly engage pro-apoptotic proteins Bax and Bak to initiate MOMP, while other BH3-only proteins (e.g., Bad, Bik and Noxa) are "sensitizers" and induce Bax and Bak oligomerization indirectly by binding anti-apoptotic proteins (e.g., Bcl-2, Bcl-$x_L$, Bcl-w, Mcl-1) and displacing and "freeing-up" the "activator" BH3-only proteins, which subsequently bind to and activate pro-apoptotic proteins (e.g., Bax, Bak) to induce cell death. Other researchers suggest that anti-apoptotic proteins engage and seqeuester Bax and Bak directly and all BH3-only proteins regulates this interaction by binding to anti-apoptotic proteins (e.g., Bcl-2, Bcl-$x_L$, Bcl-w, Mcl-1) which results in the release Bax and Bak. See, Adams, J. M. and Cory S. *Oncogene* (2007) 26, 1324-1337; Willis, S. N. et al. *Science* (2007) 315, 856-859. Although, the exact interactions through which the anti- and pro-apoptotic Bcl-2 family proteins regulate apoptosis remain under debate, there is a large body of scientific evidence to show that compounds which inhibit the binding of BH3-only proteins to anti-apoptotic Bcl-2 family proteins promote apoptosis in cells.

Dysregulated apoptotic pathways have been implicated in the pathology of many significant diseases such as neurodegenerative conditions (up-regulated apoptosis), such as for example, Alzheimer's disease; and proliferative diseases (down-regulated apoptosis) such as for example, cancer, autoimmune diseases and pro-thrombotic conditions.

In one aspect, the implication that down-regulated apoptosis (and more particularly the Bcl-2 family of proteins) is involved in the onset of cancerous malignancy has revealed a novel way of targeting this still elusive disease. Research has shown, for example, the anti-apoptotic proteins, Bcl-2 and Bcl-$x_L$, are over-expressed in many cancer cell types. See, Zhang J. Y., *Nature Reviews/Drug Discovery*, (2002) 1, 101; Kirkin, V. et al. *Biochimica et Biophysica Acta* (2004) 1644, 229-249; and Amundson, S. A. et al. *Cancer Research* (2000) 60, 6101-6110. The effect of this deregulation is the survival of altered cells which would otherwise have undergone apoptosis in normal conditions. The repetition of these defects associated with unregulated proliferation is thought to be the starting point of cancerous evolution. Additionally, research has shown that BH3-only proteins can act as tumor suppressors when expressed in diseased animals.

These findings as well as numerous others have made possible the emergence of new strategies in drug discovery for targeting cancer: If a small molecule that could mimic the effect of BH3-only proteins were able to enter the cell and overcome the anti-apoptotic protein over-expression, then it could be possible to reset the apoptotic process. This strategy can have the advantage that it can alleviate the problem of drug resistance which is usually a consequence of apoptotic deregulation (abnormal survival).

Researchers also have demonstrated that platelets also contain the necessary apoptotic machinery (e.g., Bax, Bak, Bcl-$x_L$, Bcl-2, cytochrome c, caspase-9, caspase-3 and APAF-1) to execute programmed cell death through the intrinsic apoptotic pathway. Although circulating platelet production is a normal physiological process, a number of diseases are caused or exacerbated by excess of, or undesired activation of, platelets. The above suggests that therapeutic agents capable of inhibiting anti-apoptotic proteins in platelets and reducing the number of platelets in mammals maybe useful in treating pro-thrombotic conditions and diseases that are characterized by an excess of, or undesired activation of, platelets.

Abbott Laboratories Inc. has developed a class of small molecule BH3-only protein mimetics, i.e., ABT-737 and ABT-263, that bind strongly to a subset of anti-apoptotic Bcl-2 proteins including Bcl-2, Bcl-w and Bcl-$x_L$, but only weakly to Mcl-1 and A1, and exhibits mechanism-based cytotoxicity. These compounds were tested in animal studies and demonstrated cytotoxic activity in certain xenograft models as single agents, as well as enhanced the effects of a number of chemotherapeutic agents on other xenograft models when used in combination. See, Tse, C. et al. *Cancer Res* (2008) 68, 3421-3428; and van Delft, M. F. et al. *Cancer Cell* (2006) 10, 389-399. These in vivo studies suggest the potential utility of inhibitors of anti-apoptotic Bcl-2 family proteins for the treatment of diseases that involve a dysregulated apoptotic pathway.

The natural expression levels of anti-apoptotic Bcl-2 family proteins members vary in different cell types. For example, in young platelets, Bcl-$x_L$ protein is highly expressed and plays an important role in regulating cell death (life span) of platelets. Also, in certain cancer cell types, the cancer cell's survival is attributed to the dysregulation of the apoptotic pathway caused by the over-expression of one or more anti-apoptotic Bcl-2 protein family members. In view of the important role for Bcl-2 family of proteins in regulating apoptosis in both cancerous and normal (i.e., non-cancerous) cells, and the recognized inter-cell type variability of Bcl-2 family protein expression, it is advantageous, to have a small molecule inhibitor that selectively targets and preferably binds to one type or a subset of anti-apoptotic Bcl-2 protein(s), for example, to an anti-apoptotic Bcl-2 family member that overexpressed in a certain cancer type. Such a selective compound also may confer certain advantages in the clinical setting, by providing, for example, the flexibility to select a dosing regimen, a reduced on-target toxic effect in normal cells, among others (e.g., lymphopenia has been observed in Bcl-2 deficient mice). See, Nakayama, K. et al. *PNAS* (1994) 91, 3700-3704.

In view of the above, there is a need in the art for small molecules therapeutics that can selectively inhibit the activity of one type or a subset of anti-apoptotic Bcl-2 proteins, for example, of a Bcl-$x_L$ anti-apoptotic protein. The present invention fulfills at least this need.

SUMMARY OF INVENTION

In one aspect, the present invention provides for a compound of Formula I

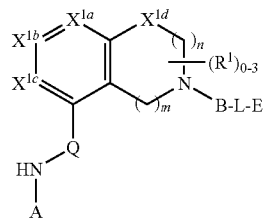

or a pharmaceutically acceptable salt thereof. In Formula I, Q is selected from the group consisting of —C(O)—, —CH$_2$—, —CH(R$^a$)— and —C(R$^a$)$_2$—, wherein R$^a$ is C$_{1-4}$ alkyl or C$_{1-4}$ haloalkyl. R$^1$, if present, is independently a member selected from the group consisting of halogen, =O, C$_{1-6}$ alkyl, C$_{1-6}$ heteroalkyl, C$_{2-6}$ alkenyl, C$_{2-6}$ alkynyl and C$_{1-6}$ haloalkyl. X$^{1a}$, X$^{1b}$ and X$^{1c}$ are each independently selected from the group consisting of C(H), C(R$^2$) and N, in which at least one of X$^{1a}$, X$^{1b}$ and X$^{1c}$ is C(H) or C(R$^2$). R$^2$ is independently selected from the group consisting of —OR$^b$, —NR$^b$R$^c$, —SR$^b$, —C(O)OR$^c$, —C(O)NR$^b$R$^c$, —NR$^b$C(O) R$^d$, —S(O)$_2$R$^d$, —S(O)R$^d$, —S(O)$_2$NR$^b$R$^c$, —R$^d$, halogen, —CN and —NO$_2$, in which R$^b$ and R$^c$ are each independently selected from the group consisting of hydrogen, C$_{1-4}$ alkyl, C$_{2-4}$ alkenyl, C$_{2-4}$ alkynyl, C$_{1-4}$ haloalkyl, or optionally R$^b$ and R$^c$, together with the atoms to which each is attached, are combined to form a 3- to 7-membered heterocyclic ring comprising 1 to 2 heteroatoms selected from N, O and S as ring vertices; and R$^d$ is selected from the group consisting of C$_{1-4}$ alkyl, C$_{2-4}$ alkenyl, C$_{2-4}$ alkynyl and C$_{1-4}$ haloalkyl. In Formula I, X$^{1d}$ is absent or is selected from the group consisting of —O—, —NH—, —N(C$_{1-4}$ alkyl)- and —N(C(O)C$_{1-4}$ alkyl)-, the subscript m is an integer from 1 to 2, and the subscript n is an integer from 1 to 3; in which if X$^{1d}$ is present, then the subscript n is 2 or 3. In Formula I, A is a member selected from the group consisting of:

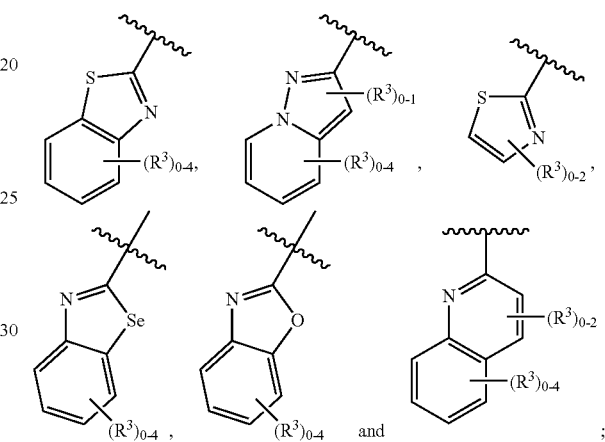

in which R$^3$, if present, independently is selected from the group consisting of —NR$^e$R$^f$, —OR$^e$, —CN, —NO$_2$, halogen, —C(O)OR$^e$, —C(O)NR$^e$R$^f$, —NR$^e$C(O)R$^f$, —NR$^e$S(O)$_2$R$^g$, —NR$^e$S(O)R$^g$, —S(O)$_2$R$^g$, —S(O)R$^g$ and —R$^g$. R$^e$ and R$^f$ at each occurrence are each independently selected from the group consisting of hydrogen, C$_{1-4}$ alkyl, C$_{2-4}$ alkenyl, C$_{2-4}$ alkynyl, C$_{1-4}$ haloalkyl and —(CH$_2$)$_{1-4}$ phenyl, or R$^e$ and R$^f$, or R$^e$ and R$^g$, together with the atom to which each is attached, are optionally combined to form a 3- to 7-membered heterocyclic ring comprising 1 to 2 heteroatoms selected from N, O and S as ring vertices; and R$^g$ is selected from the group consisting of C$_{1-4}$ alkyl, C$_{2-4}$ alkenyl, C$_{2-4}$ alkynyl and C$_{1-4}$ haloalkyl. In Formula I, B is a member selected from the group consisting of:

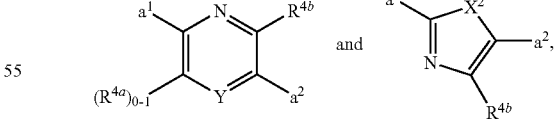

in which Y is N, C(H) or C(R$^{4a}$); X$^2$ is —N(H)—, —N(C$_{1-3}$ alkyl)-, O or S. R$^{4a}$, if present, is independently selected from C$_{1-4}$ alkyl, C$_{1-4}$ haloalkyl, C$_{2-4}$ alkenyl, C$_{2-4}$ alkynyl, halogen and —CN; R$^{4b}$ is independently selected from the group consisting of —C(O)OR$^j$, —C(O)NR$^h$R$^i$, —C(O)R$^i$, —NR$^h$C(O)R$^i$, —NR$^h$C(O)NR$^h$R$^i$, —OC(O)NR$^h$R$^i$, —NR$^h$C(O)OR$^j$, —C(=NOR$^h$)NR$^h$R$^i$, —NR$^h$C(=NCN) NR$^h$R$^i$, —NR$^h$S(O)$_2$NR$^h$R$^i$, —S(O)$_2$R$^j$, —S(O)$_2$NR$^h$R$^i$, —N(R$^h$)S(O)$_2$R$^i$, —NR$^h$C(=NR$^i$)NR$^h$R$^i$, —C(=S)NR$^h$R$^i$, —C(=NR$^h$)NR$^h$R$^i$, halogen, —NO$_2$, and —CN, in which R$^h$ and R$^i$ at each occurrence are each independently selected from the group consisting of hydrogen, C$_{1-6}$ alkyl, C$_{2-6}$ alkenyl, C$_{2-6}$ alkynyl, C$_{3-6}$ cycloalkyl, C$_{1-6}$ haloalkyl, phenyl and —(CH$_2$)$_{1-4}$-phenyl. R$^j$ is selected from the group consisting of C$_{1-6}$ alkyl, C$_{2-6}$ alkenyl, C$_{2-6}$ alkynyl, C$_{1-6}$ haloalkyl, C$_{3-7}$ cycloalkyl, phenyl and —(CH$_2$)$_{1-4}$ phenyl. R$^h$ and R$^i$, or R$^h$ and R$^j$, together with the atom to which each is attached are optionally combined to form a 3- to 7-membered heterocyclic ring comprising 1 to 2 heteroatoms selected from N, O and S as ring vertices; or in the alternative, R$^{4b}$ is selected from the group consisting of:

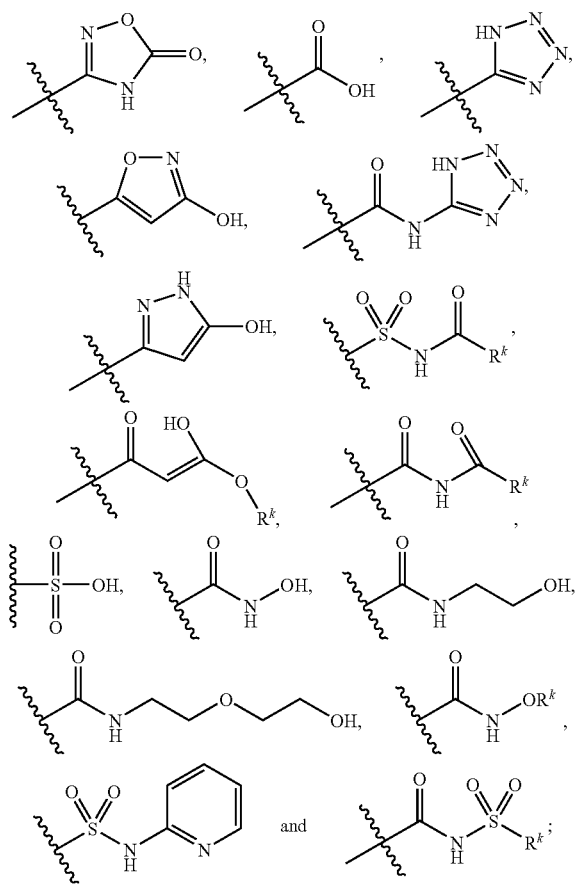

in which R$^k$ is selected from C$_{1-6}$ alkyl, C$_{2-6}$ alkenyl, C$_{2-6}$ alkynyl, C$_{3-7}$ cycloalkyl and C$_{1-6}$ haloalkyl. For the B group in Formula I, the group a$^1$ represents the point of attachment of the B group to the nitrogen atom in Formula I and a$^2$ represents the point of attachment of the B group to the L group in Formula I. In Formula I, L is absent or is a linker selected from the group consisting of C$_{6-10}$ arylene-C$_{1-6}$ heteroalkylene, C$_{5-9}$ heteroarylene-C$_{1-6}$ heteroalkylene, C$_{1-6}$ heteroalkylene, C$_{1-6}$ alkylene, C$_{1-6}$ haloalkylene, C$_{2-6}$ alkenylene, C$_{2-6}$ alkynylene, —NH—, —S— and —O—, wherein the alkylene, alkenylene, alkynylene or heteroalkylene portions of the L group is substituted with 0 to 4 R$^{5a}$ substituents selected from the group consisting of halogen, —R$^m$ and =O, and the aromatic portions of the L group is substituted with 0 to 4 R$^{5b}$ substituents selected from the group consisting of halogen, —OR$^n$, —NR$^n$R$^o$, —R$^n$, —NO$_2$, and CN; wherein R$^m$ is selected from the group consisting of C$_{1-6}$ alkyl, C$_{2-6}$ alkenyl, C$_{2-6}$ alkynyl, C$_{1-6}$ heteroalkyl, C$_{3-6}$ heterocycloalkyl-C$_{1-6}$ alkyl, C$_{3-7}$ heterocycloalkyl-C$_{1-6}$ heterocycloalkyl and C$_{1-6}$ haloalkyl. Optionally any two R$^{5a}$ substituents attached to the same or different atoms of L can be combined to form a 5- to 7-membered carbocyclic ring or a 5- to 7-membered heterocyclic ring comprising 1 to 2 heteroatoms selected from N, O and S as ring vertices; and in which R$^n$ and R$^o$, at each occurrence, is independently selected from the group consisting of hydrogen, C$_{1-6}$ alkyl, C$_{2-6}$ alkenyl, C$_{2-6}$ alkynyl and C$_{1-6}$ haloalkyl, and wherein optionally R$^n$ and R$^o$, together with the atoms to which each is attached, are combined to form a 3- to 7-membered heterocyclic ring comprising 1 to 2 heteroatoms selected from N, O and S as ring vertices. In Formula I, E is hydrogen or halogen; or in the alternative E is selected from the group consisting of phenyl, C$_{5-6}$ heteroaryl, C$_{3-7}$ heterocycloalkyl and C$_{3-7}$ cycloalkyl, and optionally fused to E is 1 or 2 rings independently selected from the group consisting of a 3- to 7-membered carbocyclic ring, a 3- to 7-membered heterocyclic ring, a benzene ring and a 5- to 6-membered heteroaromatic ring, wherein E and each ring optionally fused to E is independently substituted with 0 to 5 R$^6$ substituents selected from the group consisting of halogen, —NR$^p$R$^q$, —SR$^p$, —OR$^p$, —C(O)OR$^p$, —C(O)NR$^p$R$^q$, —C(O)R$^p$, —NR$^p$C(O)R$^q$, —OC(O)R$^r$, —NR$^p$C(O)NR$^p$R$^q$, —OC(O)NR$^p$R$^q$, —NR$^p$C(O)OR$^r$, —C(=NOR$^p$)NR$^p$R$^q$, —NR$^p$C(=N—CN)NR$^p$R$^q$, —NR$^p$S(O)$_2$NR$^p$R$^q$, —S(O)$_2$R$^r$, —S(O)$_2$NR$^p$R$^q$, —R$^r$, —R$^s$, —NO$_2$, —N$_3$, =O, —CN, —Z$^1$—NR$^p$R$^q$, —Z$^1$—SR$^p$, —Z$^1$—OR$^p$, —Z$^1$—C(O)OR$^p$, —Z$^1$—C(O)NR$^p$R$^q$, —Z$^1$—C(O)R$^p$, —Z$^1$—NR$^p$C(O)R$^q$, —Z$^1$—OC(O)R$^r$, —Z$^1$—NR$^p$C(O)NR$^p$R$^q$, —Z$^1$—OC(O) NR$^p$R$^q$, —Z$^1$—NR$^p$C(O)OR$^r$, —Z$^1$—C(=NOR$^p$)NR$^p$R$^q$, —Z$^1$—NR$^p$C(=N—CN)NR$^p$R$^q$, —Z$^1$—NR$^p$S(O)$_2$NR$^p$R$^q$, —Z$^1$—S(O)$_2$R$^r$, —Z$^1$—S(O)$_2$NR$^p$R$^q$, —Z$^1$—NO$_2$, —Z$^1$—N$_3$, —Z$^1$—R$^s$ and —Z$^1$—CN; in which Z$^1$ is selected from the group consisting of C$_{1-6}$ alkylene, C$_{2-6}$ alkenylene, C$_{2-6}$ alkynylene, C$_{1-6}$ heteroalkylene, C$_{3-7}$ heterocycloalkyl and C$_{3-7}$ cycloalkyl; R$^p$ and R$^q$ are each independently selected from the group consisting of hydrogen, C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl, phenyl and —(CH$_2$)$_{1-4}$-phenyl; and R$^r$ is selected from the group consisting of C$_{1-6}$ alkyl, C$_{1-6}$ haloalkyl, C$_{2-6}$ alkenyl, C$_{2-6}$ alkynyl, C$_{3-10}$ cycloalkyl, C$_{3-10}$ heterocycloalkyl, phenyl and —(CH$_2$)$_{1-4}$-phenyl. Optionally within each R$^6$ substituent R$^p$ and R$^q$ or R$^p$ and R$^r$, together with the atom to which each is attached, are optionally combined to form a 3- to 7-membered heterocyclic ring optionally comprising 1 to 2 heteroatoms selected from N, O and S as ring vertices; R$^s$ is selected from the group consisting of phenyl, C$_{5-6}$ heteroaryl, C$_{3-7}$ heterocycloalkyl, C$_{3-7}$ cycloalkyl, and optionally fused to R$^s$ is 1 or 2 rings each independently selected from the group consisting of a 5- to 7-membered carbocyclic ring, a 5- to 7-membered heterocyclic ring, a benzene ring and a 5- to 6-membered heteroaromatic ring, and wherein R$^s$ and each ring optionally fused to R$^s$ is each independently substituted with 0 to 5 R$^7$ substituents selected from the group consisting of halogen, —NR$^t$R$^u$, —SR$^t$, —OR$^t$, —C(O)OR$^t$, —C(O)NR$^t$R$^u$, —C(O)R$^t$, —NR$^t$C(O)R$^v$, —OC(O)R$^v$, —NR$^t$C(O)NR$^t$R$^u$, —OC(O) NR$^t$R$^r$, —NR$^t$C(O)OR$^v$, —C(=NOR$^t$)NR$^t$R$^u$, —NR$^t$C (=N—CN)NR$^t$R$^u$, —NR$^t$S(O)$_2$NR$^t$R$^u$, —S(O)$_2$R$^v$, —S(O)$_2$ R$^t$R$^u$, —R$^v$, —NO$_2$, —N$_3$, =O, —CN, —Z$^2$—NR$^t$R$^u$, —Z$^2$—SR$^t$, —Z$^2$—OR$^t$Z$^2$—C(O)OR$^t$, —Z$^2$—C(O)NR$^t$R$^u$, —Z$^2$—, C(O)R$^v$, —Z$^2$—NR$^t$C(O)R$^v$, —Z$^2$—OC(O)R$^v$, —Z$^2$—NR$^t$C(O)NR$^t$R$^u$, —Z$^2$—OC(O)NR$^t$R$^u$, —Z$^2$—NR$^t$C (O)OR$^v$, —Z$^2$—C(=NOR$^t$)NR$^t$R$^u$, —Z$^2$—NR$^t$C(=N—CN)NR$^t$R$^u$, —Z$^2$—NR$^t$S(O)$_2$NR$^t$R$^u$, —Z$^2$—S(O)$_2$R$^v$, —Z$^2$—S(O)$_2$NR$^t$R$^u$, —Z$^2$—NO$_2$, —Z$^2$—N$_3$ and —Z$^2$—CN. Z$^2$ is selected from the group consisting of C$_{1-6}$ alkylene, $C_{2-6}$ alkenylene, $C_{2-6}$ alkynylene, $C_{1-6}$ heteroalkylene, $R^t$ and $R^u$ are each independently selected from the group consisting of hydrogen, $C_{1-6}$ alkyl, $C_{1-6}$ haloalkyl, $C_{2-6}$ alkenyl, $X_{2-6}$ alkynyl, —$(CH_2)_{1-4}$-phenyl, $C_{3-7}$ cycloalkyl and $C_{3-7}$ heterocycloalkyl; $R^v$ is selected from $C_{1-4}$ alkyl, $C_{1-4}$ haloalkyl, $C_{2-6}$ alkenyl, $C_{2-6}$ alkynyl, —$(CH_2)_{1-4}$-phenyl, $C_{3-7}$ cycloalkyl and $C_{3-7}$ heterocycloalkyl; and within each $R^7$ substituent, $R^t$ and $R^u$ or $R^t$ and $R^v$, together with the atom to which each is attached, optionally are combined to form a 3- to 7-membered heterocyclic ring having 1 to 2 heteroatoms selected from N, O and S as ring vertices.

In another aspect, the present invention provides for pharmaceutical compositions comprising compounds of Formula I as well as methods for using compounds of Formula I for the treatment of diseases and conditions (e.g., cancer, thrombocythemia, etc) characterized by the expression or over-expression of Bcl-2 anti-apoptotic proteins, e.g., of anti-apoptotic Bcl-$x_L$ proteins.

DESCRIPTION OF THE DRAWINGS

FIG. 2A, FIG. 2B, FIG. 2C, FIG. 2D and FIG. 2E show certain embodiments of E groups for compounds of Formula I.

DETAILED DESCRIPTION OF THE INVENTION

I. Definitions

Figure 1:
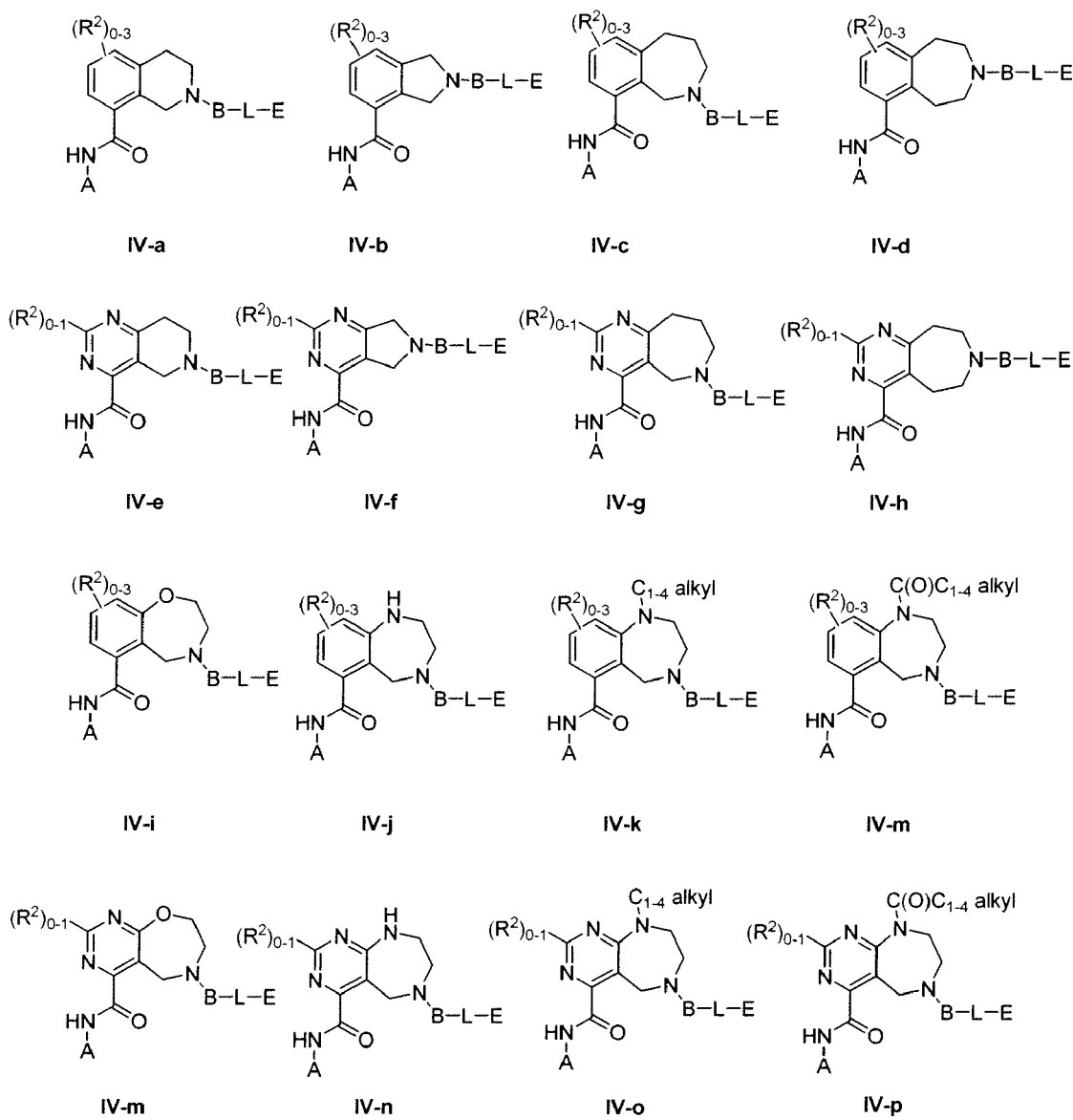
FIG. 1 shows certain subformulae of compounds of the invention, i.e., Subformulae IV-a, IV-b, IV-c, IV-d, IV-e, IV-f, IV-g, IV-h, IV-i, IV-k, IV-m, IV-n, IV-o and IV-p.

As used herein, the term "alkyl", by itself or as part of another substituent, means, unless otherwise stated, a straight or branched chain hydrocarbon radical, having the number of carbon atoms designated (i.e., $C_{1-6}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds and is meant to include mono- and poly-halogenated variants. Similarly, the term "alkynyl" refers to an unsaturated alkyl radical having one or more triple bonds and is meant to include mono- and poly-halogenated variants. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The terms "cycloalkyl," "carbocyclic," and "carbocycle," are used interchangeably and when used by itself or as part of another substituent refers to hydrocarbon rings having the indicated number of ring atoms (e.g., $C_{3-6}$ cycloalkyl) and being fully saturated or having no more than one double bond between ring vertices. As used herein, "cycloalkyl," "carbocyclic," or "carbocycle" is also meant to refer to bicyclic, polycyclic and spirocyclic hydrocarbon rings such as, for example, bicyclo[2.2.1]heptane, pinane, bicyclo[2.2.2]octane, adamantane, norborene, spirocyclic $C_{5-12}$ alkane, etc. A "cycloalkyl," "carbocyclic," or "carbocycle" ring can be attached to the remainder of a molecule through a ring carbon atoms, or, if stated as such, in the alternative, a "cycloalkyl," "carbocyclic," or "carbocycle" ring can be fused to the remainder of a molecule. Non-limiting examples of a "cycloalkyl," "carbocyclic," or "carbocycle" ring that is fused to, for example, a benzene ring include, 1,2,3,4-tetrahydronaphthalene, 2,3-dihydro-1H-indene, (Z)-6,9-dihydro-5H-benzo[7]annulene, and the like.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation (e.g., double and triple bonds), and also includes mono- and poly-halogenated variants, or combinations thereof. Examples of "heteroalkyl" include —$CH_2$—$CH_2$—O—$CH_3$, —$CH_2$—$CH_2$—O—$CF_3$, —$CH_2$—$CH_2$—NH—$CH_3$, —$CH_2$—$CH_2$—$N(CH_3)$—$CH_3$, —$CH_2$—S—$CH_2$—$CH_3$, —S(O)—$CH_3$, —$CH_2$—$CH_2$—S$(O)_2$—$CH_3$, —CH=CH—O—$CH_3$, —$Si(CH_3)_3$, —$CH_2$—CH=N—$OCH_3$, and —CH=CH=$N(CH_3)$—$CH_3$. Also, for "heteroalkyl" up to two heteroatoms can be consecutive, such as, for example, —$CH_2$—NH—$OCH_3$ and —$CH_2$—O—$Si(CH_3)_3$.

The terms "heterocycloalkyl," "heterocyclic," and "heterocycle" are used interchangeably and when as used by itself or as part of another substituent refers to a cycloalkyl group that contain from one to five heteroatoms selected from N, O, and S, wherein the nitrogen and sulfur atoms are optionally oxidized, and the nitrogen atom(s) are optionally quaternized. Those skilled in the art will understand, with respect to "heterocycloalkyl," "heterocyclic," and "heterocycle" having a designated number of carbon atoms (e.g., "$C_{3-7}$ heterocycloalkyl"), that at least one, and possibly up to five, if feasible, of the designated carbons are replaced with a heteroatom. For example, "$C_3$ heterocycloalkyl" includes, among other possibilities, oxiranyl, which has two carbon atoms plus one oxygen atom as ring members. Unless otherwise stated, "heterocycloalkyl," "heterocyclic," and "heterocycle" ring can be a monocyclic, a bicyclic, spirocyclic or a polycylic ring system. Non-limiting examples of "heterocycloalkyl," "heterocyclic," and "heterocycle" groups include pyrrolidine, piperidine, imidazolidine, pyrazolidine, butyrolactam, valerolactam, imidazolidinone, hydantoin, dioxolane, phthalimide, piperidine, pyrimidine-2,4(1H,3H)-dione, pyrimidin-4-one, pyrimidin-2-one, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, tropane and the like. A "heterocycloalkyl," "heterocyclic," or "heterocycle" group can be attached to the remainder of the molecule through a ring carbon, a heteroatom, or alternatively, if stated as such, a "heterocycloalkyl," "heterocyclic," or "heterocycle" group can be fused to the remainder of a molecule. Non-limiting examples of a "heterocycloalkyl," "heterocyclic," or "heterocycle" ring that is fused to, for example, a benzene ring include, isochroman, 2,3-dihydrobenzofuran, (Z)-4,5-dihydro-1H-benzo[b]azepine, and the like. Unless otherwise stated, "heterocycloalkyl," "heterocyclic," and "heterocycle" rings include mono- and poly-halogenated variants thereof.

The term "alkylene" by itself or as part of another substituent means a divalent radical derived from an alkane or haloalkane, as exemplified by —$CH_2CH_2CH_2CH_2$— and —$CF_2CF_2$—. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively, including mono and poly halogenated variants.

The term "heteroalkylene" by itself or as part of another substituent means a divalent radical derived from heteroalkyl, as exemplified by —O—CH$_2$—CH$_2$—CH$_2$—CH$_2$—O—, —O—CH$_2$, —CH$_2$—O—, —CH$_2$—CH$_2$—S—CH$_2$CH$_2$— and —CH$_2$—S—CH$_2$—CH$_2$—NH—CH$_2$—, —O—CH$_2$—CH═CH—, —CH$_2$—CH═C(H)CH$_2$—O—CH$_2$—, —O—CH$_2$—CH═CH—, —S—CH$_2$—C≡C—, —CF$_2$—O—. For heteroalkylene groups, a heteroatom can also occupy either or both of the chain termini (e.g., alkyleneoxy, alkylenedioxy, alkyleneamino, alkylenediamino, and the like). As used herein, the term "heteroalkylene" also refers to mono- and poly-halogenated variants.

The terms "alkoxy," "alkylamino" and "alkylthio" (or thio-alkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^i$R$^{ii}$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "C$_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group, which can be a single ring or multiple rings (up to three rings) which are fused together. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridinyl, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Optional substituents for each of the above noted aryl and heteroaryl ring systems can be selected from, but are not limited to, the group of acceptable substituents described further below.

As used herein, the term "arylene" generically refers to any aryl that is a divalent radical. For a more specific example, "phenylene" refers to a divalent phenyl ring radical. The terms "1,2-arylene," "1,3-arylene" or "1,4-arylene" refer to geometrical isomers of a particular arylene wherein, two groups attached to an aryl as depicted in a formula are situated in an ortho, meta or para geometrical relationship about the aryl, respectively.

As used herein, the term "heteroarylene" generically refers to any heteroaryl that is a divalent radical. For a more specific example, "pyridylene" refers to a divalent pyridyl ring radical.

Those skilled in the art will understand, with respect to the terms "heteroaryl" and "heteroarylene" having a designated number of carbon atoms (e.g., "C$_{5-6}$ heteroaryl" or "C$_{5-9}$ heteroarylene"), that at least one and, where feasible, up to five of the designated carbon atoms are replaced with a heteroatom. A C$_5$ heteroaryl, for example, can be pyrrolyl or, as another example, be thiazolyl, among other possibilities.

As used herein, the combination term of "arylene-heteroalkylene" generically refers to a divalent radical comprised of aryl group and heteroalkyl group that are covalently attached to each other, and wherein the aryl and alkyl group each comprises an additional radical center to which can be attached another group. Examples of arylene-heteroalkylene include, but are not limited to:

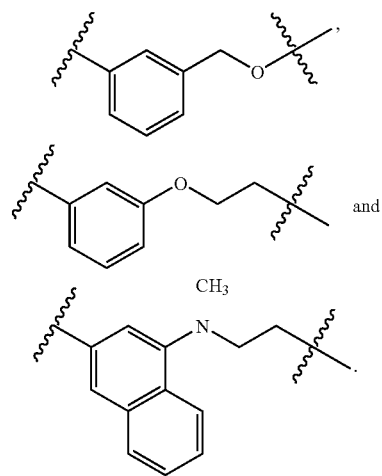

Similarly, the term "heteroarylene-heteroalkylene" refers to a divalent radical comprised of a heteroaryl group and heteroalkyl group that are covalently attached to each other, and wherein and wherein the heteroaryl and heteroalkyl group each comprises an additional radical center to which is attached another group. Examples of heteroarylene-heteroalkylene include, but are not limited to

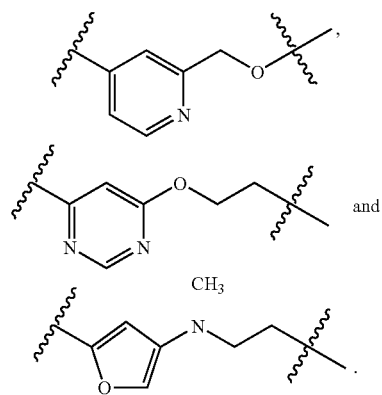

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkyl, heterocycloalkyl and cycloalkyl) can be a variety of groups including, but not limited to, -halogen, —OR', —NR'R", —SR', —SiR'R"R''', —OC(O)R', —C(O)R', —CO$_2$R', —CONR'R", —OC(O)NR'R", —NR"C(O)R', —NR'''C(O)NR'R", —NR"C(O)$_2$R', —NHC(NH$_2$)=NH, —NR'C(NH$_2$)=NH, —NHC(NH$_2$)=NR', —NR'''C(NR'R")=N—CN, —NR'''C(NR'R")=NOR', —NHC(NH$_2$)=NR', —S(O)R', —S(O)$_2$R', —S(O)$_2$NR'R", —NR'S(O)$_2$R", —NR'''S(O)$_2$NR'R", —CN, =O, =S, =N—OH and —NO$_2$ in a number ranging from zero to (2m'+1), where m' is the total number of carbon atoms in such radical. R', R" and R''' each independently refers to groups including, for example, hydrogen, unsubstituted C$_{1-6}$ alkyl, unsubstituted heteroalkyl, unsubstituted aryl, aryl substituted with 1-3 halogens, unsubstituted C$_{1-6}$ alkyl, C$_{1-6}$ alkoxy or C$_{1-6}$ thioalkoxy groups, or unsubstituted aryl-C$_{1-4}$ alkyl groups, unsubstituted heteroaryl, substituted heteroaryl, among others. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other substituents for alkyl radicals, including heteroalkyl, alkylene, include for example, =O, =NR', =N—OR', =N—CN, =NH, wherein R' include substituents as described above.

Similarly, substituents for the aryl and heteroaryl groups are varied and are generally selected from the group including, but not limited to, -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'C(O)NR"R''', —NHC(NH$_2$)=NH, —NR'C(NH$_2$)=NH, —NHC(NH$_2$)=NR', —S(O)R', —S(O)$_2$R', —S(O)$_2$NR'R", —NR'S(O)$_2$R", —N$_3$, perfluoro-C$_{1-4}$ alkoxy, and perfluoro-C$_{1-4}$ alkyl, in a number ranging from zero to the total number of open valences on the aromatic ring system; and where R', R" and R''' can be independently selected from hydrogen, C$_{1-6}$ alkyl, C$_{1-6}$ haloalkyl, C$_{3-6}$ cycloalkyl, C$_{2-6}$ alkenyl, C$_{2-6}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms.

As used herein, a wavy line, "～", that intersects a single, double or triple bond in any chemical structure depicted herein, represent the point attachment of the single, double, or triple bond to the remainder of the molecule.

As used herein, a "compound of the invention" refers to a compound of Formula I or any specific embodiment thereof; or to any stereoisomer, geometric isomer, tautomer, solvate, metabolites or pharmaceutically acceptable salt or prodrug of a compound of Formula I or an embodiment thereof.

To describe the number of times that a substituent (e.g., R$^{10}$) can be attached to a chemical structure shown in this application, the substituent (e.g., R$^{10}$) is written in parenthesis and the possible number of occurrences is noted as a subscript range. For example, "—(R$^{10}$)$_{0-4}$" means that the R$^{10}$ group can be absent or can be present for up to four occurrences.

As used herein, the term "heteroatom" is meant to include oxygen (O), nitrogen (N), sulfur (S) and silicon (Si).

II. Compounds

In one aspect, the present invention provides for a compound of Formula I

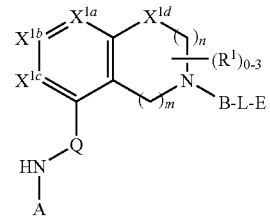

or a pharmaceutically acceptable salt thereof. In Formula I, Q is selected from the group consisting of —C(O)—, —CH$_2$—, —CH(R$^a$)— and —C(R$^a$)$_2$—, wherein R$^a$ is C$_{1-4}$ alkyl or C$_{1-4}$ haloalkyl. R$^1$, if present, is independently a member selected from the group consisting of halogen, =O, C$_{1-6}$ alkyl, C$_{1-6}$ heteroalkyl, C$_{2-6}$ alkenyl, C$_{2-6}$ alkynyl and C$_{1-6}$ haloalkyl. X$^{1a}$, X$^{1b}$ and X$^{1c}$ are each independently selected from the group consisting of C(H), C(R$^2$) and N, in which at least one of X$^{1a}$, X$^{1b}$ and X$^{1c}$ is C(H) or C(R$^2$). R$^2$ is independently selected from the group consisting of —OR$^b$, —NR$^b$R$^c$, —SR$^b$, —C(O)OR$^c$, —C(O)NR$^b$R$^c$, —NR$^b$C(O)R$^d$, —S(O)$_2$R$^d$, —S(O)R$^d$, —S(O)$_2$NR$^b$R$^c$, —R$^d$, halogen, —CN and —NO$_2$, in which R$^b$ and R$^c$ are each independently selected from the group consisting of hydrogen, C$_{1-4}$ alkyl, C$_{2-4}$ alkenyl, C$_{2-4}$ alkynyl, C$_{1-4}$ haloalkyl, or optionally R$^b$ and R$^c$, together with the atoms to which each is attached, are combined to form a 3- to 7-membered heterocyclic ring comprising 1 to 2 heteroatoms selected from N, O and S as ring vertices; and R$^d$ is selected from the group consisting of C$_{1-4}$ alkyl, C$_{2-4}$ alkenyl, C$_{2-4}$ alkynyl and C$_{1-4}$ haloalkyl. In Formula I, X$^{1d}$ is absent or is selected from the group consisting of —O—, —NH—, —N(C$_{1-4}$ alkyl)- and —N(C(O)C$_{1-4}$ alkyl)-, the subscript m is an integer from 1 to 2, and the subscript n is an integer from 1 to 3; in which if X$^{1d}$ is present, then the subscript n is 2 or 3. In Formula I, A is a member selected from the group consisting of:

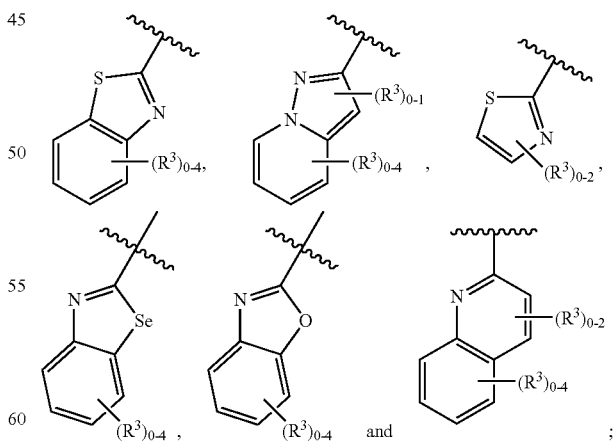

in which R$^3$, if present, is independently selected from the group consisting of —NR$^e$R$^f$, —OR$^e$, —CN, —NO$_2$, halogen, —C(O)OR$^e$, —C(O)NR$^e$R$^f$, —NR$^e$C(O)R$^f$, —NR$^e$S(O)$_2$R$^g$, —NR$^e$S(O)R$^g$, —S(O)$_2$R$^g$, —S(O)R$^g$ and —R$^g$. R$^e$ and R$^f$ at each occurrence are each independently selected from the group consisting of hydrogen, $C_{1-4}$ alkyl, $C_{2-4}$ alkenyl, $C_{2-4}$ alkynyl, $C_{1-4}$ haloalkyl and —$(CH_2)_{1-4}$ phenyl, or $R^e$ and $R^f$, or $R^e$ and $R^g$, together with the atom to which each is attached, are optionally combined to form a 3- to 7-membered heterocyclic ring comprising 1 to 2 heteroatoms selected from N, O and S as ring vertices; and $R^g$ is selected from the group consisting of $C_{1-4}$ alkyl, $C_{2-4}$ alkenyl, $C_{2-4}$ alkynyl and $C_{1-4}$ haloalkyl. In Formula I, B is a member selected from the group consisting of:

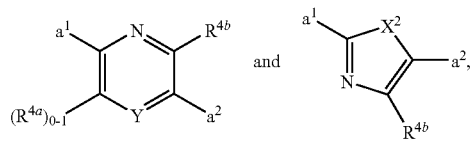

in which Y is N, C(H) or $C(R^{4a})$; $X^2$ is —N(H)—, —N($C_{1-3}$ alkyl)-, O or S. $R^{4a}$, if present, is independently selected from $C_{1-4}$ alkyl, $C_{1-4}$ haloalkyl, $C_{2-4}$ alkenyl, $C_{2-4}$ alkynyl, halogen and —CN; $R^{4b}$ is independently selected from the group consisting of —C(O)$OR^j$, —C(O)$NR^hR^i$, —C(O)$R^i$, —$NR^hC(O)R^i$, —$NR^hC(O)NR^hR^i$, —OC(O)$NR^hR^i$, —$NR^hC(O)OR^i$, —C(=$NOR^h$)$NR^hR^i$, —$NR^hC$(=NCN) $NR^hR^i$, —$NR^hS(O)_2NR^hR^i$, —$S(O)_2R^j$, —$S(O)_2NR^hR^i$, —N($R^h$)$S(O)_2R^i$, —$NR^hC$(=$NR^i$)$NR^hR^i$, —C(=S)$NR^hR^i$, —C(=$NR^h$)$NR^hR^i$, halogen, —$NO_2$, and —CN, in which $R^h$ and $R^i$ at each occurrence are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and —$(CH_2)_{1-4}$-phenyl. $R^j$ is selected from the group consisting of $C_{1-6}$ alkyl, $C_{2-6}$ alkenyl, $C_{2-6}$ alkynyl, $C_{1-6}$ haloalkyl, $C_{3-7}$ cycloalkyl, phenyl and —$(CH_2)_{1-4}$ phenyl. $R^h$ and $R^i$, or $R^h$ and $R^j$, together with the atom to which each is attached are optionally combined to form a 3- to 7-membered heterocyclic ring comprising 1 to 2 heteroatoms selected from N, O and S as ring vertices; or in the alternative, $R^{4b}$ is selected from the group consisting of:

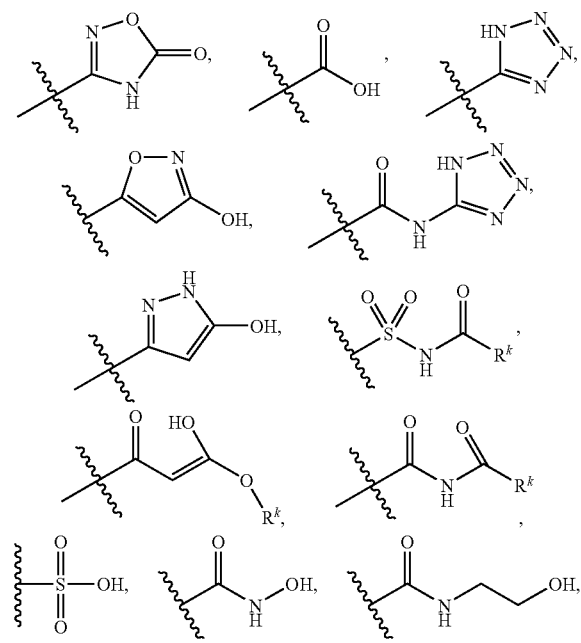

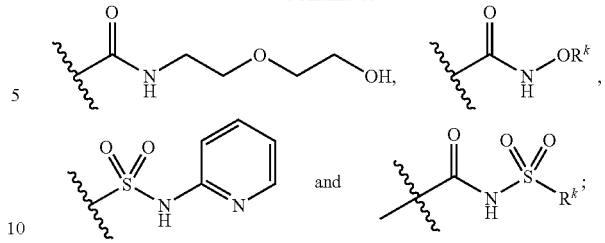

in which $R^k$ is selected from $C_{1-6}$ alkyl, $C_{2-6}$ alkenyl, $C_{2-6}$ alkynyl, $C_{3-7}$ cycloalkyl and $C_{1-6}$ haloalkyl. In certain embodiments, $R^{4b}$ is selected from the group consisting of:

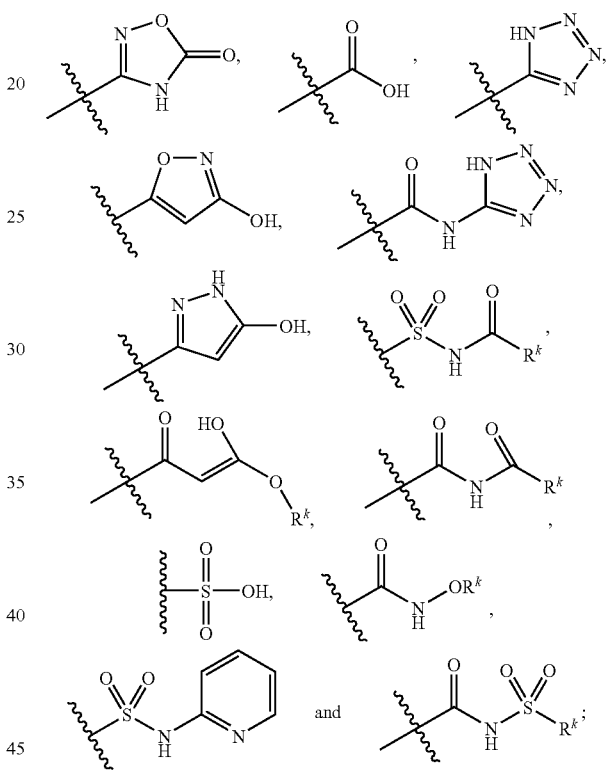

in which $R^k$ is selected from $C_{1-6}$ alkyl, $C_{2-6}$ alkenyl, $C_{2-6}$ alkynyl, $C_{3-7}$ cycloalkyl and $C_{1-6}$ haloalkyl. For the B group in Formula I, the group $a^1$ represents the point of attachment of the B group to the nitrogen atom in Formula I and $a^2$ represents the point of attachment of the B group to the L group in Formula I. In Formula I, L is absent or is a linker selected from the group consisting of $C_{6-10}$ arylene-$C_{1-6}$ heteroalkylene, $C_{5-9}$ heteroarylene-$C_{1-6}$ heteroalkylene, $C_{1-6}$ heteroalkylene, $C_{1-6}$ alkylene, $C_{1-6}$ haloalkylene, $C_{2-6}$ alkenylene, $C_{2-6}$ alkynylene, —NH—, —S— and —O—, wherein the alkylene, alkenylene, alkynylene or heteroalkylene portions of the L group is substituted with 0 to 4 $R^{5a}$ substituents selected from the group consisting of halogen, —$R^m$ and =O, and the aromatic portions of the L group is substituted with 0 to 4 $R^{5b}$ substituents selected from the group consisting of halogen, —$OR^n$, —$NR^nR^o$, —$R^n$, —$NO_2$, and CN; wherein $R^m$ is selected from the group consisting of $C_{1-6}$ alkyl, $C_{2-6}$ alkenyl, $C_{2-6}$ alkynyl, $C_{1-6}$ heteroalkyl, $C_{3-6}$ heterocycloalkyl-$C_{1-6}$ alkyl, $C_{3-7}$ heterocycloalkyl-$C_{1-6}$ heterocycloalkyl and $C_{1-6}$ haloalkyl. Optionally any two $R^{5a}$ substituents attached to the same or different atoms of L can be combined to form a 5- to 7-membered carbocyclic ring or a 5- to 7-membered heterocyclic ring comprising 1 to 2 heteroatoms selected from N, O and S as ring vertices; and in which $R^n$ and $R^o$, at each occurrence, is independently selected from the group consisting of hydrogen, $C_{1-6}$ alkyl, $C_{2-6}$ alkenyl, $C_{2-6}$ alkynyl and $C_{1-6}$ haloalkyl, and wherein optionally $R^n$ and $R^o$, together with the atoms to which each is attached, are combined to form a 3- to 7-membered heterocyclic ring comprising 1 to 2 heteroatoms selected from N, O and S as ring vertices. In Formula I, E is hydrogen or halogen; or in the alternative E is selected from the group consisting of phenyl, $C_{5-6}$ heteroaryl, $C_{3-7}$ heterocycloalkyl and $C_{3-7}$ cycloalkyl, and optionally fused to E is 1 or 2 rings independently selected from the group consisting of a 5- to 7-membered carbocyclic ring, a 5- to 7-membered heterocyclic ring, a benzene ring and a 5- to 6-membered heteroaromatic ring, wherein E and each ring optionally fused to E is independently substituted with 0 to 5 $R^6$ substituents selected from the group consisting of halogen, —$NR^pR^q$, —$SR^p$, —$OR^p$, —$C(O)OR^p$, —$C(O)NR^pR^q$, —$C(O)R^p$, —$NR^pC(O)R^q$, —$OC(O)R^r$, —$NR^pC(O)NR^pR^q$, —$OC(O)NR^pR^q$, —$NR^pC(O)OR^r$, —$C(=NOR^p)NR^pR^q$, —$NR^pC(=N—CN)NR^pR^q$, —$NR^pS(O)_2NR^pR^q$, —$S(O)_2R^r$, —$S(O)_2NR^pR^q$, —$R^r$, —$R^s$, —$NO_2$, —$N_3$, =O, —CN, —$Z^1$—$NR^pR^q$, —$Z^1$—$SR^p$, —$Z^1$—$OR^p$, —$Z^1$—$C(O)OR^p$, —$Z^1$—$C(O)NR^pR^q$, —$Z^1$—$C(O)R^p$, —$Z^1$—$NR^pC(O)R^q$, —$Z^1$—$OC(O)R^r$, —$Z^1$—$NR^pC(O)NR^pR^q$, —$Z^1$—$OC(O)NR^pR^q$, —$Z^1$—$NR^pC(O)OR^r$, —$Z^1$—$C(=NOR^p)NR^pR^q$, —$Z^1$—$NR^pC(=N—CN)NR^pR^q$, —$Z^1$—$NR^pS(O)_2NR^pR^q$, —$Z^1$—$S(O)_2R^r$, —$Z^1$—$S(O)_2NR^pR^q$, —$Z^1$—$NO_2$, —$Z^1$—$N_3$, —$Z^1$—$R^s$ and —$Z^1$—CN; in which $Z^1$ is selected from the group consisting of $C_{1-6}$ alkylene, $C_{2-6}$ alkenylene, $C_{2-6}$ alkynylene and $C_{1-6}$ heteroalkylene; $R^p$ and $R^q$ are each independently selected from the group consisting of hydrogen, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl, phenyl and —$(CH_2)_{1-4}$-phenyl; and $R^r$ is selected from the group consisting of $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ heterocycloalkyl, phenyl and —$(CH_2)_{1-4}$-phenyl. Optionally within each $R^6$ substituent $R^p$ and $R^q$ or $R^p$ and $R^r$, together with the atom to which each is attached, are optionally combined to form a 3- to 7-membered heterocyclic ring optionally comprising 1 to 2 heteroatoms selected from N, O and S as ring vertices; $R^s$ is selected from the group consisting of phenyl, $C_{5-6}$ heteroaryl, $C_{3-7}$ heterocycloalkyl, $C_{3-7}$ cycloalkyl, and optionally fused to $R^s$ is 1 or 2 rings each independently selected from the group consisting of a 5- to 7-membered carbocyclic ring, a 5- to 7-membered heterocyclic ring, a benzene ring and a 5- to 6-membered heteroaromatic ring, and wherein $R^s$ and each ring optionally fused to $R^s$ is each independently substituted with 0 to 5 $R^7$ substituents selected from the group consisting of halogen, —$NR^tR^u$, —$SR^t$, —$OR^t$, —$C(O)OR^t$, —$C(O)NR^tR^u$, —$C(O)R^t$, —$NR^tC(O)R^v$, —$OC(O)R^v$, —$NR^tC(O)NR^tR^u$, —$OC(O)NR^tR^u$, —$NR^tC(O)OR^v$, —$C(=NOR^t)NR^tR^u$, —$NR^tC(=N—CN)NR^tR^u$, —$NR^tS(O)_2NR^tR^u$, —$S(O)_2R^v$, —$S(O)_2NR^tR^u$, —$R^v$, —$NO_2$, —$N_3$, =O, —CN, —$Z^2$—$NR^tR^u$, —$Z^2$—$SR^t$, —$Z^2$—$OR^t$, —$Z^2$—$C(O)OR^t$, —$Z^2$—$C(O)NR^tR^u$, —$Z^2$—$C(O)R^v$, —$Z^2$—$NR^tC(O)R^u$, —$Z^2$—$OC(O)R^v$, —$Z^2$—$NR^tC(O)NR^tR^u$, —$Z^2$—$OC(O)NR^tR^u$, —$Z^2$—$NR^tC(O)OR^v$, —$Z^2$—$C(=NOR^t)NR^tR^u$, —$Z^2$—$NR^tC(=N—CN)NR^tR^u$, —$Z^2$—$NR^tS(O)_2NR^tR^u$, —$Z^2$—$S(O)_2R^v$, —$Z^2$—$S(O)_2NR^tR^u$, —$Z^2$—$NO_2$, —$Z^2$—$N_3$ and —$Z^2$—CN. $Z^2$ is selected from the group consisting of $C_{1-6}$ alkylene, $C_{2-6}$ alkenylene, $C_{2-6}$ alkynylene, $C_{1-6}$ heteroalkylene, $R^t$ and $R^u$ are each independently selected from the group consisting of hydrogen, $C_{1-6}$ alkyl, $C_{1-6}$ haloalkyl, $C_{2-6}$ alkenyl, $C_{2-6}$ alkynyl, —$(CH_2)_{1-4}$-phenyl, $C_{3-7}$ cycloalkyl and $C_{3-7}$ heterocycloalkyl; $R^v$ is selected from $C_{1-4}$ alkyl, $C_{1-4}$ haloalkyl, $C_{2-6}$ alkenyl, $C_{2-6}$ alkynyl, —$(CH_2)_{1-4}$-phenyl, $C_{3-7}$ cycloalkyl and $C_{3-7}$ heterocycloalkyl; and within each $R^7$ substituent, $R^t$ and $R^u$ or $R^t$ and $R^v$, together with the atom to which each is attached, optionally are combined to form a 3- to 7-membered heterocyclic ring having 1 to 2 heteroatoms selected from N, O and S as ring vertices.

In a first embodiment, in compounds of Formula I, A is

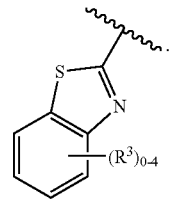

In a second embodiment, in compounds of Formula I or within the first embodiment thereof, the compound is has the Formula I-a

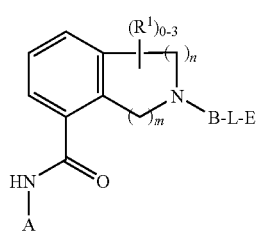

I-a

Within the second embodiment, $R^1$ is halogen, $C_{1-6}$ alkyl, $C_{1-6}$ heteroalkyl or =O. The subscript n is the integer 2 or 3; and the subscript m is an integer from 1 to 2. A is

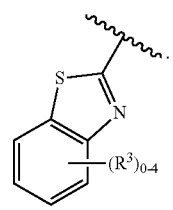

Also within this second embodiment, B is a member selected from the group consisting of:

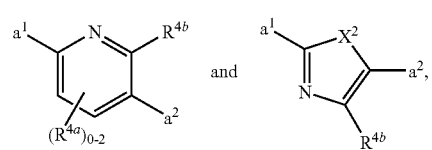

in which $R^{4b}$ is selected from the group consisting of

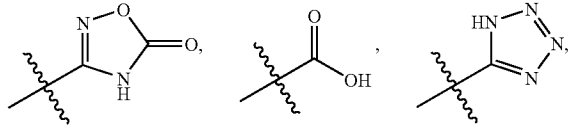

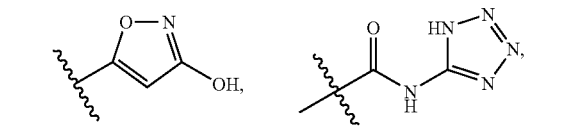

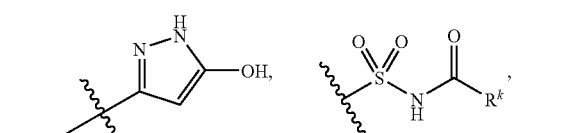

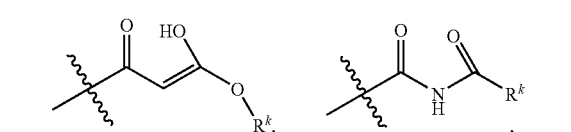

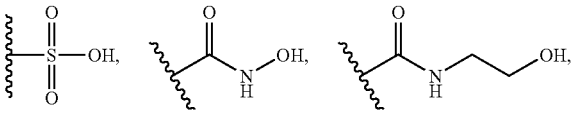


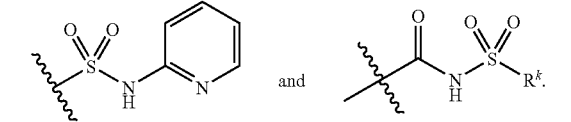

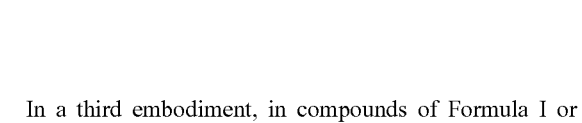

In a third embodiment, in compounds of Formula I or within the first embodiment thereof, the compound is of Formula I-a

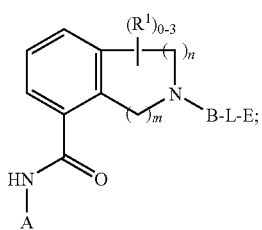

I-a in which $R^1$ is halogen, $C_{1-6}$ alkyl, $C_{1-6}$ heteroalkyl or =O; the subscript n is an integer from 2 to 3; and the subscript m is an integer from 1 to 2. In this third embodiment, A is

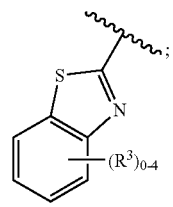

and B is a member selected from the group consisting of:

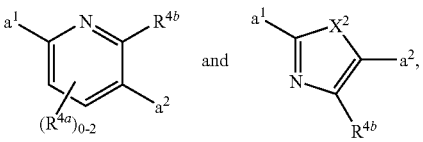

in which $R^{4b}$ is selected from the group consisting of —C(O)OR$^j$, —C(O)NR$^h$R$^i$, —C(O)R$^i$, —NR$^h$C(O)R$^i$, —NR$^h$C(O)NR$^h$R$^i$, —OC(O)NR$^h$R$^i$, —NR$^h$C(O)OR$^j$, —C(=NOR$^h$)NR$^h$R$^i$, —NR$^h$C(=NCN)NR$^h$R$^i$, —NR$^h$S(O)$_2$NR$^h$R$^i$, —S(O)$_2$R$^j$, —S(O)$_2$NR$^h$R$^i$, —N(R$^h$)S(O)$_2$R$^i$, —NR$^h$C(=NR$^i$)NR$^h$R$^i$, —C(=S)NR$^h$R$^i$, —C(=NR$^h$)NR$^h$R$^i$, —R$^j$, halogen, —NO$_2$, and —CN.

In a fourth embodiment, within certain aspects of the second and third embodiment of compounds of Formula I, the subscript n is 2 and the subscript m is 1.

In a fifth embodiment, within certain aspects of the second embodiment of compounds of Formula I, $R^1$ is absent; and B is

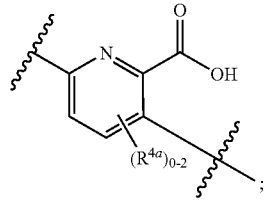

in which $R^{4a}$, if present is selected from halogen and $C_{1-4}$ alkyl; wherein the subscript n is 2 and the subscript m is 1.

In a sixth embodiment, within certain aspects of the second embodiment of compounds of Formula I, $R^1$ is absent; and B is

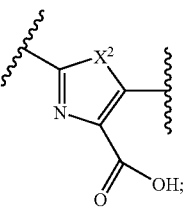

in which the subscript n is 2 and the subscript m is 1.

In a seventh embodiment, within compounds of Formula I, or with the first, second, or third embodiment thereof, a compound of the invention is of a Formula selected from the group consisting of

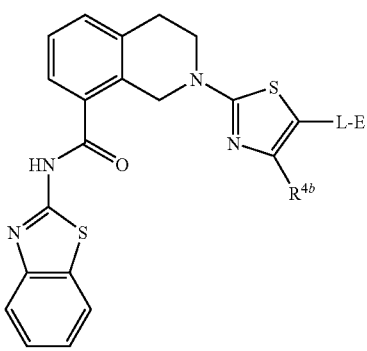

II-a

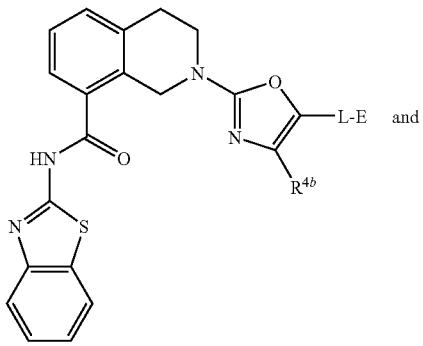

II-b and

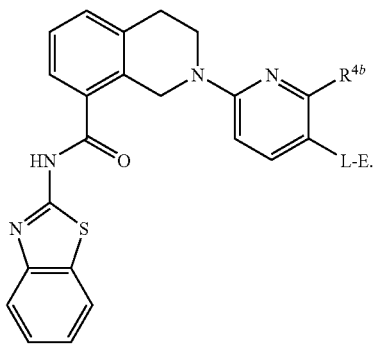

II-c

In an eighth embodiment, within certain aspects of the first, second, third fourth, fifth, sixth or seventh embodiment of compounds of the invention, L is absent or is an optionally substituted group selected from the group consisting of optionally substituted $C_{6-10}$ arylene-$C_{1-6}$ heteroalkylene and $C_{5-9}$ heteroarylene-$C_{1-6}$ heteroalkylene.

In a ninth embodiment within certain aspects of the eighth embodiment of compounds of Formula I, L is selected from the group consisting of

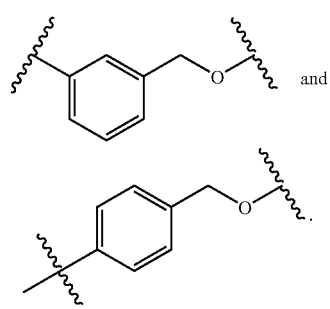

In a tenth embodiment, within certain aspects of the first, second, third, fourth, fifth, sixth or seventh embodiment of compounds of Formula I, L is an optionally substituted group selected from the group consisting of optionally substituted $C_{1-6}$ heteroalkylene, $C_{1-6}$ alkylene, $C_{2-6}$ alkenylene and $C_{2-6}$ alkynylene.

In an eleventh embodiment, within certain aspects of the tenth embodiment of compounds of Formula I, L is selected from the group consisting of optionally substituted $C_{1-4}$ alkyleneoxy, $C_{2-4}$ alkenyleneoxy, $C_{2-4}$ alkynyleneoxy and $C_{1-4}$ alkylene, in which L is substituted with 0 to 4 $R^m$ groups, and in which any two $R^m$ groups located on the same or different atom of L are optionally combined to form a 5- to 7-membered carbocyclic ring or a 5- to 7-membered heterocyclic ring comprising 1 to 2 heteroatoms selected from N, O and S as ring vertices.

In a twelfth embodiment, within certain aspects of the tenth embodiment of compounds of Formula I, L is selected from the group consisting of

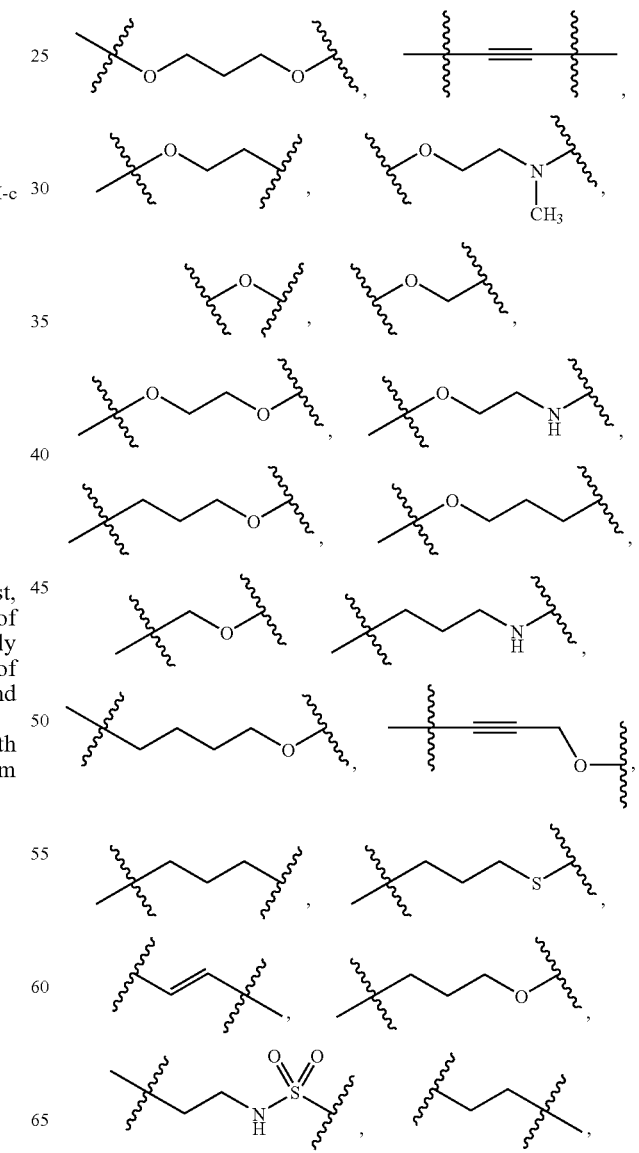

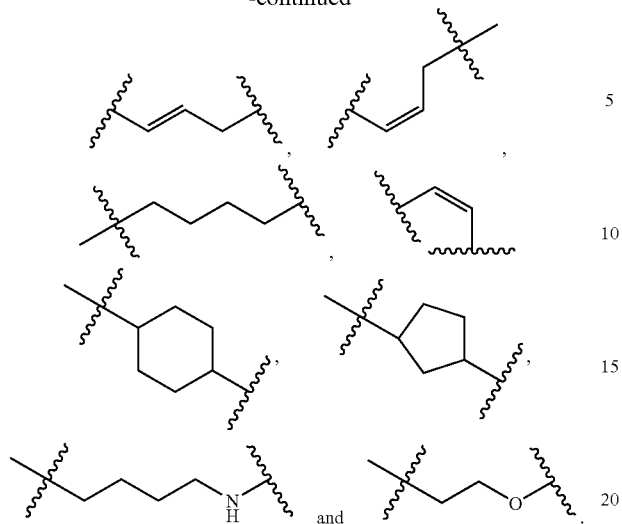

In a thirteenth embodiment, within certain aspects of the second, third, forth, fifth, sixth, seventh, eighth, ninth, tenth, eleventh or twelfth embodiment of compounds of Formula I, E is hydrogen.

In a fourteenth embodiment, and within certain aspects of the second, third, forth, fifth, sixth, seventh, eighth, ninth, tenth, eleventh, twelfth or thirteenth embodiment of compounds of Formula I, E is selected from the group consisting of phenyl, $C_{5-6}$ heteroaryl and $C_{3-7}$ heterocycloalkyl, and optionally fused to E is a ring independently selected from 5- to 7-membered carbocyclic ring, a 5- to 7-membered heterocyclic ring, a benzene ring and a 5- to 6-membered heteroaromatic ring, in which E and the ring optionally fused thereto are together substituted with a total of 1 to 3 $R^6$ substituents, wherein one $R^6$ substituent is —$NR^pR^q$, —$Z^1$—$NR^pR^q$, —$R^s$, or —$Z^1$—$R^s$.

In a fifteenth embodiment, within certain aspects of the fourteenth embodiment of compounds of Formula I, the said one $R^6$ substituent is —$NR^pR^q$ or —$Z^1$—$NR^pR^q$.

In a sixteenth embodiment, within certain aspects of the fifteenth embodiment of Formula I, 1 or 2 $R^6$ substituents is selected from the group consisting of fluorine and chlorine.

In a seventeenth embodiment, within certain aspects of the fourteenth embodiment of compounds of Formula I, the said one $R^6$ substituent is $R^s$ or —$Z^1$—$R^s$, wherein $R^s$ is of a formula selected from the group consisting of:

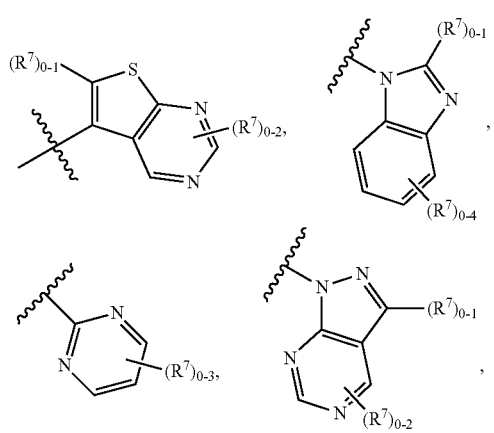

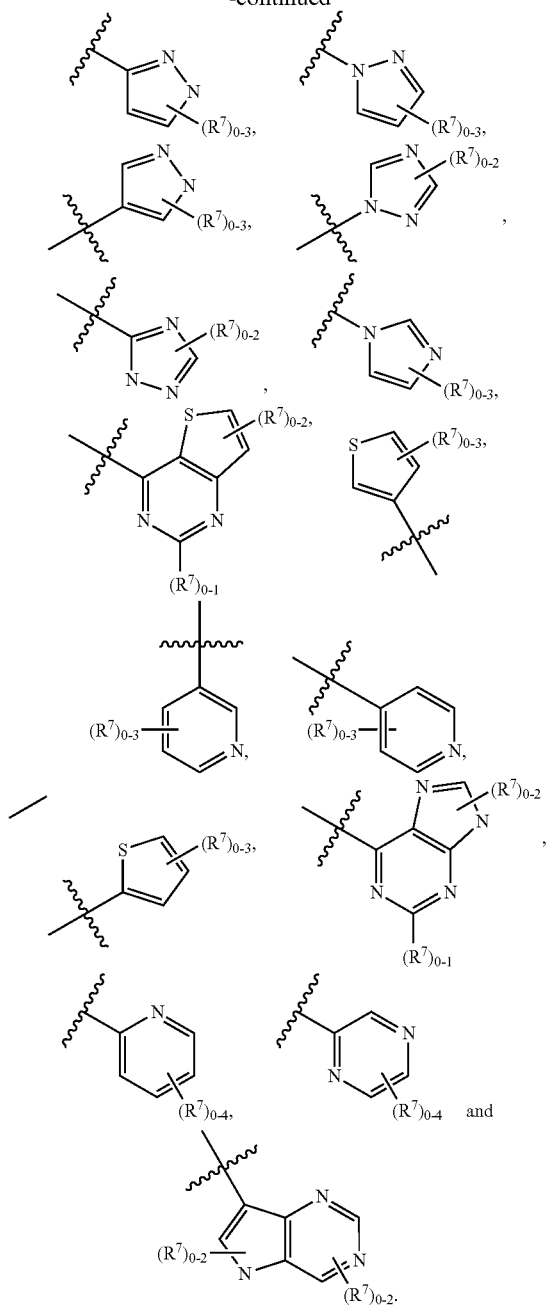

In an eighteenth embodiment, within certain aspects of the fourteenth, fifteenth, sixteenth or seventeenth embodiment of compounds of Formula I, $Z^1$ is selected from the group consisting of:

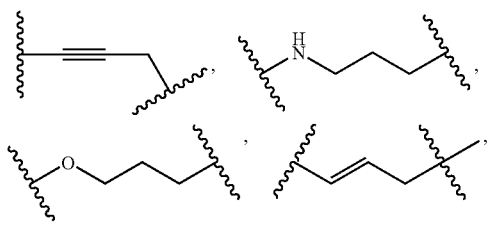

-continued

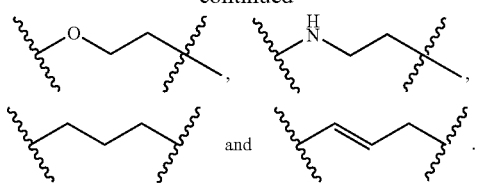

In a nineteenth embodiment, within certain aspects of the fourth, tenth, eleventh, or twelfth embodiment of compounds of Formula I, the compound is of a Formula selected from the group consisting of:

III-a

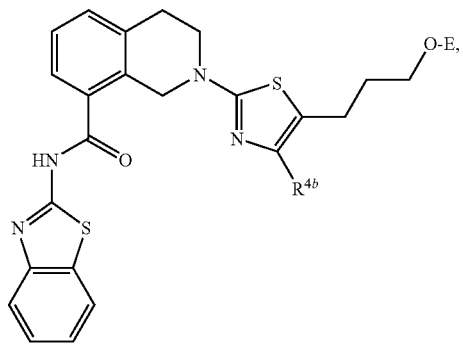

III-b

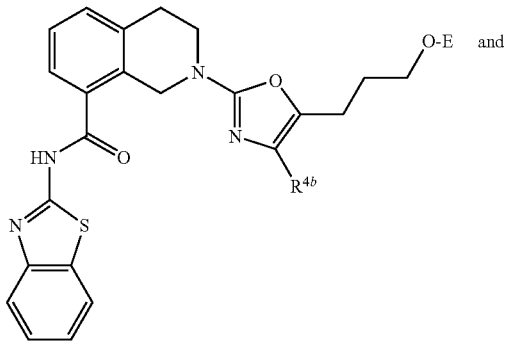

III-c

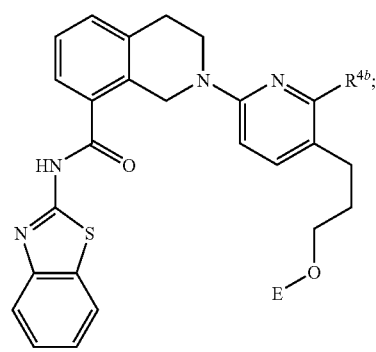

in which $R^{4b}$ is selected from the group consisting of

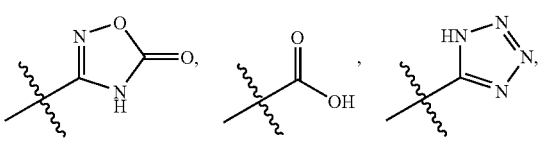

-continued

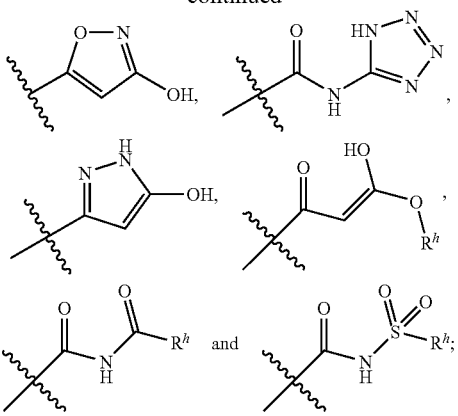

and E is phenyl, and is substituted with from 1 to 3 $R^6$ substituents.

In a twentieth embodiment, within certain aspects of the nineteenth embodiment of compound of Formula I, $R^{4b}$ is —C(O)OH.

In a twenty-first embodiment, within certain aspects of the first, second, third, fourth, seventh, or nineteenth embodiment of compounds of Formula I, E is -phenyl, in which the phenyl group is substituted at the meta or para position with an optionally substituted $R^s$ group is of a formula selected from the group consisting of:

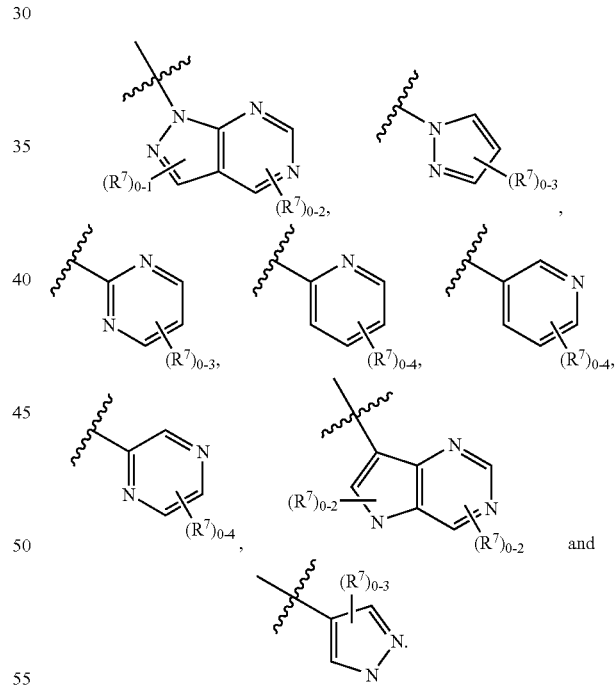

In a twenty-second embodiment, within certain aspects of the seventeenth, or twenty-first embodiments of compounds of Formula I, at least one $R^7$, if present, is selected from the group consisting of —NR'R$^u$ and —Z$^2$—NR'R$^u$.

In a twenty-third embodiment, within certain aspects of the twenty-second embodiment of compounds of Formula I, $Z^2$ is selected from $C_{1-4}$ alkylene, $C_{2-4}$ alkenylene, $C_{2-4}$ alkynylene and $C_{1-4}$ heteroalkylene.

In a twenty-fourth embodiment, within certain aspects of the twenty-third embodiment of compounds of Formula I, $Z^2$ is selected from the group consisting of

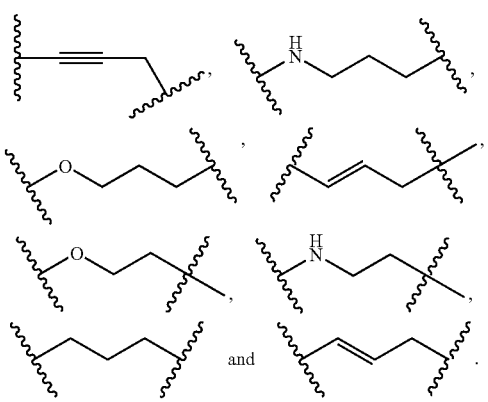

In a twenty-fifth embodiment, for compounds of Formula I, the compound is of a formula selected from the group set forth in FIG. 1.

In a twenty-sixth embodiment, for compounds of Formula I, the compound is of a formula selected from the group consisting of Formula IV-a, IV-b, IV-c, IV-e and IV-i in FIG. 1.

In a twenty-seventh embodiment, in compounds of Formula I or within certain aspects of the first, second, third, seventh or nineteenth embodiment thereof, E is selected from the group set forth on FIG. 2-A, FIG. 2-B, FIG. 2-C, FIG. 2-D or FIG. 2-E.

In a twenty-eighth embodiment, compounds of Formula I are selected from the group set forth in Table 1 (below).

TABLE 1

| No. | Structure | Name |
|---|---|---|
| 1 | 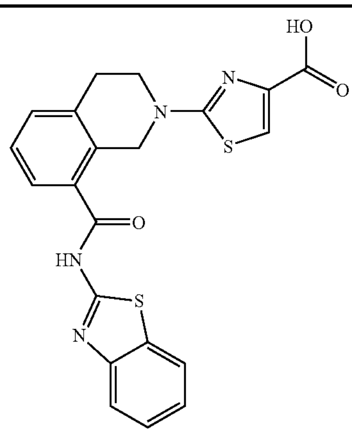 | 2-(8-(benzo[d]thiazol-2-ylcarbamoyl)-3,4-dihydroisoquinolin-2(1H)-yl)thiazole-4-carboxylic acid |
| 2 | 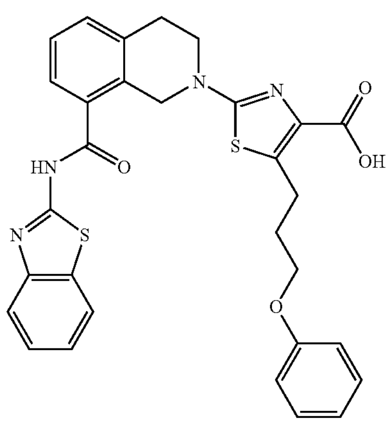 | 2-(8-(benzo[d]thiazol-2-ylcarbamoyl)-3,4-dihydroisoquinolin-2(1H)-yl)-5-(3-phenoxypropyl)thiazole-4-carboxylic acid |

TABLE 1-continued

| No. | Structure | Name |
|---|---|---|
| 3 | 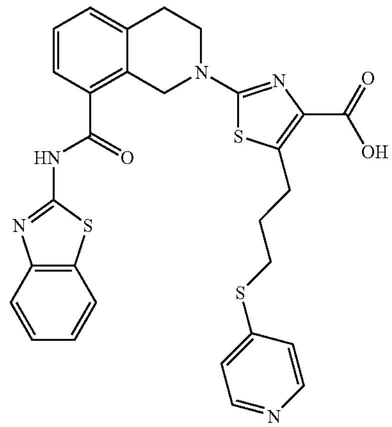 | 2-(8-(benzo[d]thiazol-2-ylcarbamoyl)-3,4-dihydroisoquinolin-2(1H)-yl)-5-(3-(pyridin-4-ylthio)propyl)thiazole-4-carboxylic acid |
| 4 | 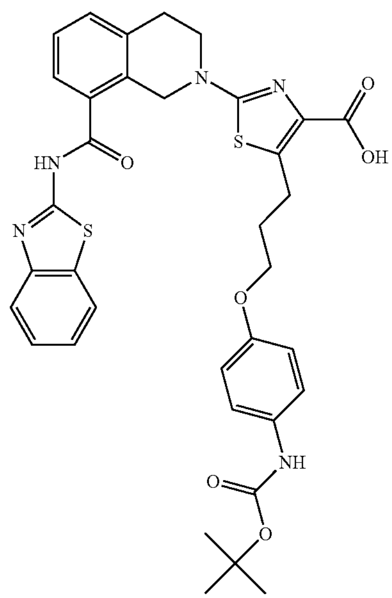 | 2-(8-(benzo[d]thiazol-2-ylcarbamoyl)-3,4-dihydroisoquinolin-2(1H)-yl)-5-(3-(4-(tert-butoxycarbonylamino)phenoxy)propyl)thiazole-4-carboxylic acid |
| 5 | 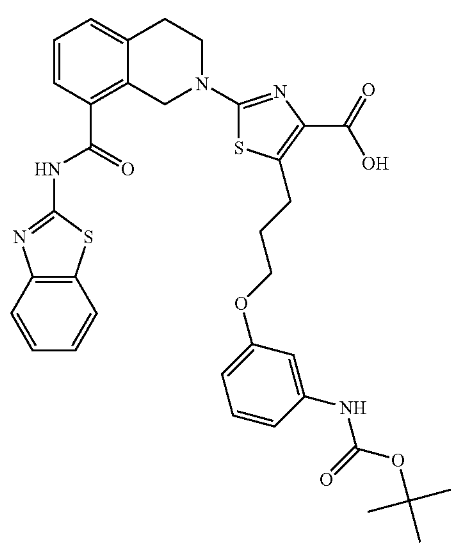 | 2-(8-(benzo[d]thiazol-2-ylcarbamoyl)-3,4-dihydroisoquinolin-2(1H)-yl)-5-(3-(3-(tert-butoxycarbonylamino)phenoxy)propyl)thiazole-4-carboxylic acid |

TABLE 1-continued

| No. | Structure | Name |
|---|---|---|
| 6 | 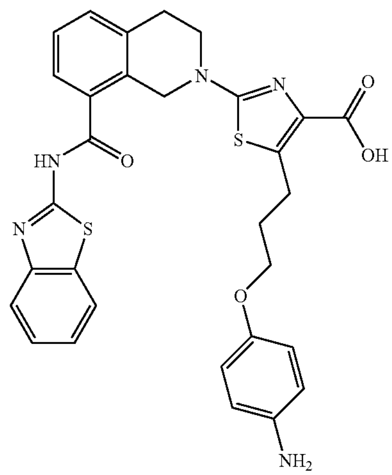 | 5-(3-(4-aminophenoxy)propyl)-2-(8-(benzo[d]thiazol-2-ylcarbamoyl)-3,4-dihydroisoquinolin-2(1H)-yl)thiazole-4-carboxylic acid |
| 7 | 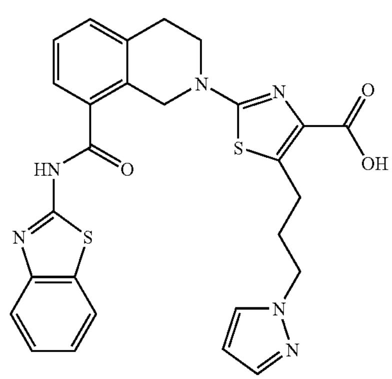 | 5-(3-(1H-pyrazol-1-yl)propyl)-2-(8-(benzo[d]thiazol-2-ylcarbamoyl)-3,4-dihydroisoquinolin-2(1H)-yl)thiazole-4-carboxylic acid |
| 8 | 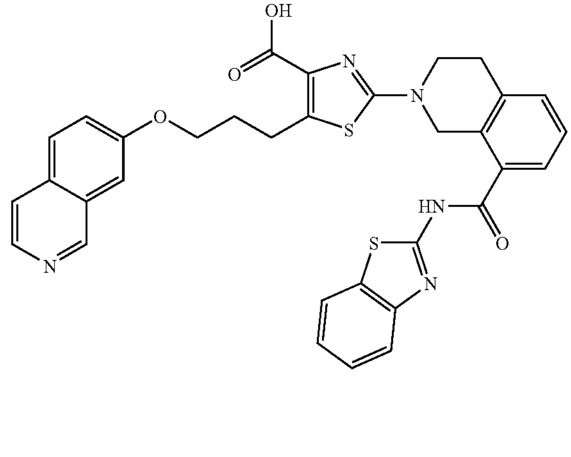 | 2-(8-(benzo[d]thiazol-2-ylcarbamoyl)-3,4-dihydroisoquinolin-2(1H)-yl)-5-(3-(isoquinolin-7-yloxy)propyl)thiazole-4-carboxylic acid |

TABLE 1-continued

| No. | Structure | Name |
|---|---|---|
| 9 | 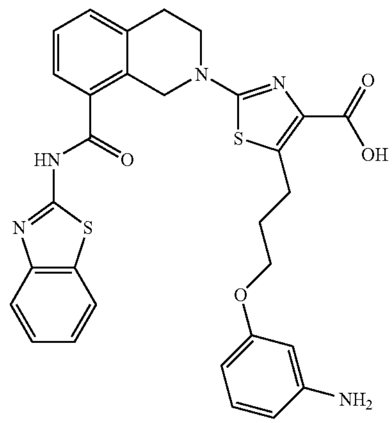 | 5-(3-(3-aminophenoxy)propyl)-2-(8-(benzo[d]thiazol-2-ylcarbamoyl)-3,4-dihydroisoquinolin-2(1H)-yl)thiazole-4-carboxylic acid |
| 10 | 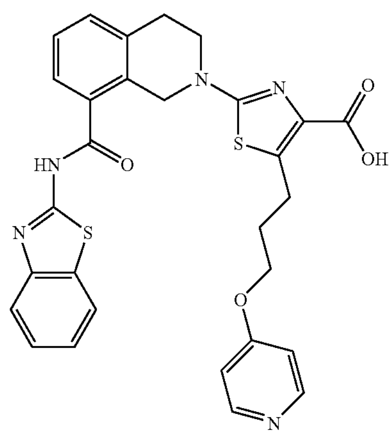 | 2-(8-(benzo[d]thiazol-2-ylcarbamoyl)-3,4-dihydroisoquinolin-2(1H)-yl)-5-(3-(pyridin-4-yloxy)propyl)thiazole-4-carboxylic acid |
| 11 | 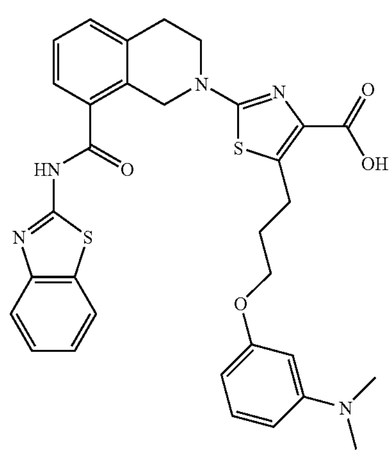 | 2-(8-(benzo[d]thiazol-2-ylcarbamoyl)-3,4-dihydroisoquinolin-2(1H)-yl)-5-(3-(3-(dimethylamino)phenoxy)propyl)thiazole-4-carboxylic acid |

TABLE 1-continued

| No. | Structure | Name |
|---|---|---|
| 12 | 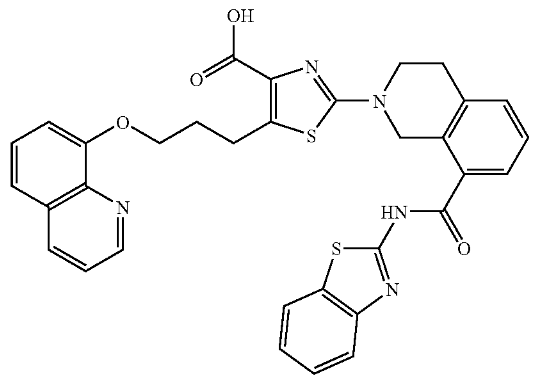 | 2-(8-(benzo[d]thiazol-2-ylcarbamoyl)-3,4-dihydroisoquinolin-2(1H)-yl)-5-(3-(quinolin-8-yloxy)propyl)thiazole-4-carboxylic acid |
| 13 | 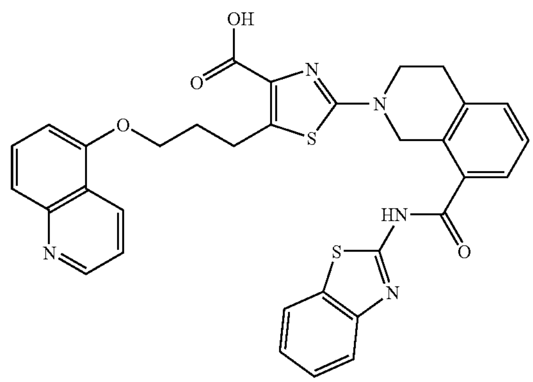 | 2-(8-(benzo[d]thiazol-2-ylcarbamoyl)-3,4-dihydroisoquinolin-2(1H)-yl)-5-(3-(quinolin-5-yloxy)propyl)thiazole-4-carboxylic acid |
| 14 | 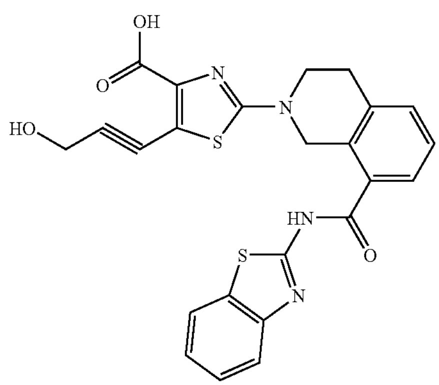 | 2-(8-(benzo[d]thiazol-2-ylcarbamoyl)-3,4-dihydroisoquinolin-2(1H)-yl)-5-(3-hydroxyprop-1-ynyl)thiazole-4-carboxylic acid |
| 15 | 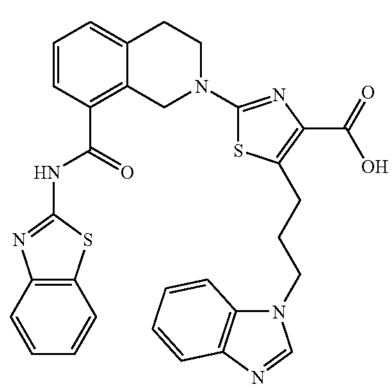 | 5-(3-(1H-benzo[d]imidazol-1-yl)propyl)-2-(8-(benzo[d]thiazol-2-ylcarbamoyl)-3,4-dihydroisoquinolin-2(1H)-yl)thiazole-4-carboxylic acid |

TABLE 1-continued

| No. | Structure | Name |
|---|---|---|
| 16 | 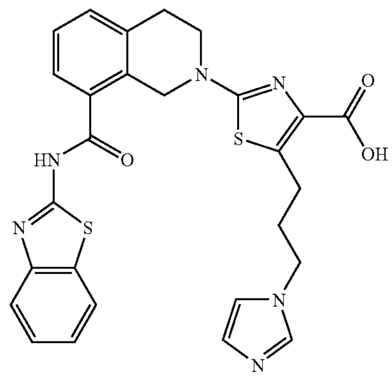 | 5-(3-(1H-imidazol-1-yl)propyl)-2-(8-(benzo[d]thiazol-2-ylcarbamoyl)-3,4-dihydroisoquinolin-2(1H)-yl)thiazole-4-carboxylic acid |
| 17 | 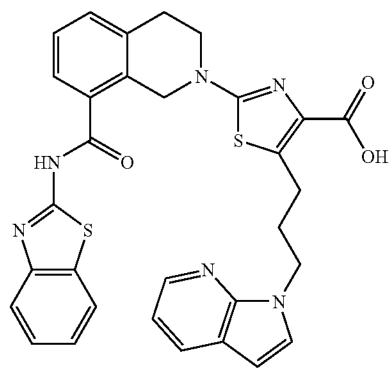 | 5-(3-(1H-pyrrolo[2,3-b]pyridin-1-yl)propyl)-2-(8-(benzo[d]thiazol-2-ylcarbamoyl)-3,4-dihydroisoquinolin-2(1H)-yl)thiazole-4-carboxylic acid |
| 18 | 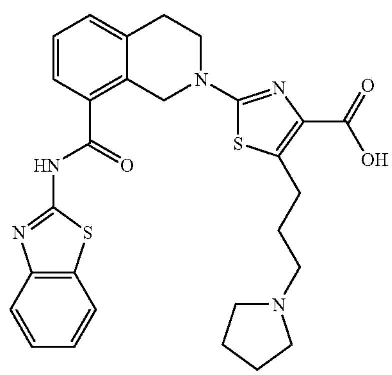 | 2-(8-(benzo[d]thiazol-2-ylcarbamoyl)-3,4-dihydroisoquinolin-2(1H)-yl)-5-(3-(pyrrolidin-1-yl)propyl)thiazole-4-carboxylic acid |
| 19 | 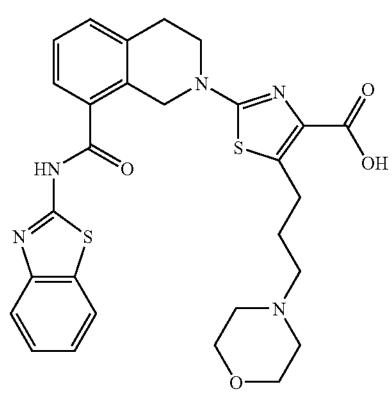 | 2-(8-(benzo[d]thiazol-2-ylcarbamoyl)-3,4-dihydroisoquinolin-2(1H)-yl)-5-(3-morpholinopropyl)thiazole-4-carboxylic acid |

TABLE 1-continued

| No. | Structure | Name |
|---|---|---|
| 20 | 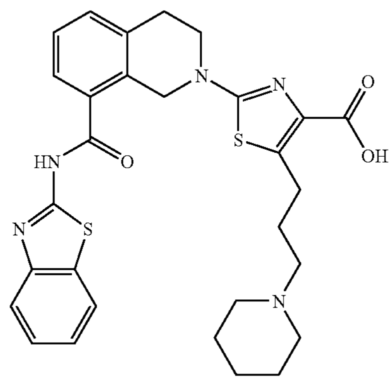 | 2-(8-(benzo[d]thiazol-2-ylcarbamoyl)-3,4-dihydroisoquinolin-2(1H)-yl)-5-(3-(piperidin-1-yl)propyl)thiazole-4-carboxylic acid |
| 21 | 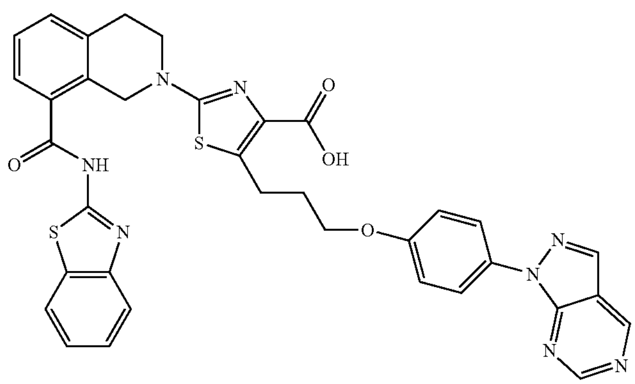 | 5-(3-(4-(1H-pyrazolo[3,4-d]pyrimidin-1-yl)phenoxy)propyl)-2-(8-(benzo[d]thiazol-2-ylcarbamoyl)-3,4-dihydroisoquinolin-2(1H)-yl)thiazole-4-carboxylic acid |
| 22 | 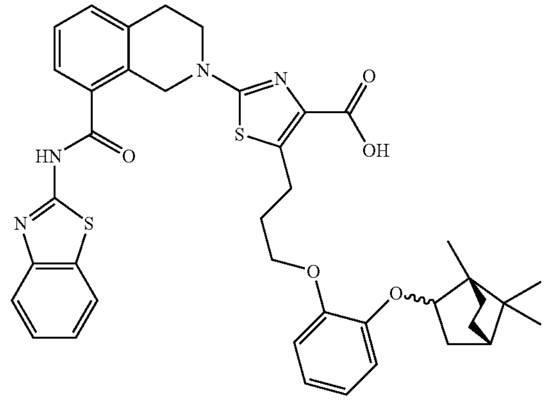 | 2-(8-(benzo[d]thiazol-2-ylcarbamoyl)-3,4-dihydroisoquinolin-2(1H)-yl)-5-(3-(2-((1S,4S)-1,7,7-trimethylbicyclo[2.2.1]heptan-2-yloxy)phenoxy)propyl)thiazole-4-carboxylic acid |

TABLE 1-continued

| No. | Structure | Name |
|---|---|---|
| 23 | 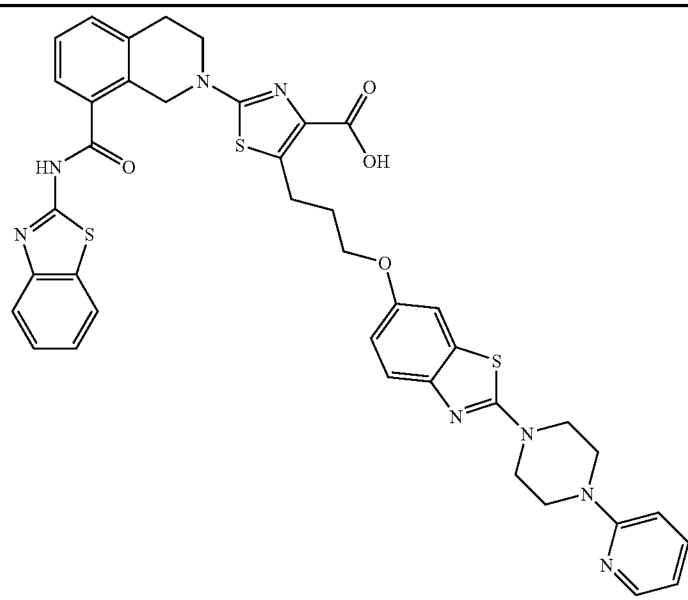 | 2-(8-(benzo[d]thiazol-2-ylcarbamoyl)-3,4-dihydroisoquinolin-2(1H)-yl)-5-(3-(2-(4-(pyridin-2-yl)piperazin-1-yl)benzo[d]thiazol-6-yloxy)propyl)thiazole-4-carboxylic acid |
| 24 | 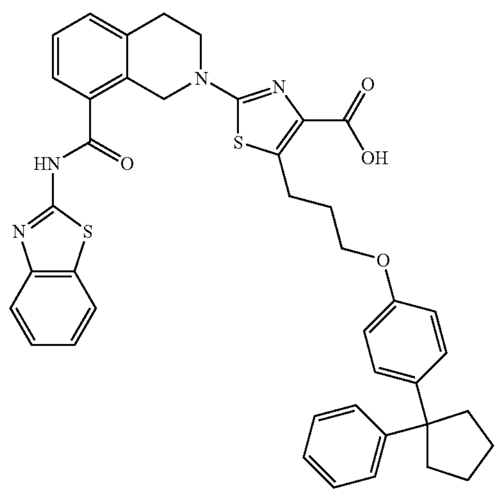 | 2-(8-(benzo[d]thiazol-2-ylcarbamoyl)-3,4-dihydroisoquinolin-2(1H)-yl)-5-(3-(4-(1-phenylcyclopentyl)phenoxy)propyl)thiazole-4-carboxylic acid |
| 25 | 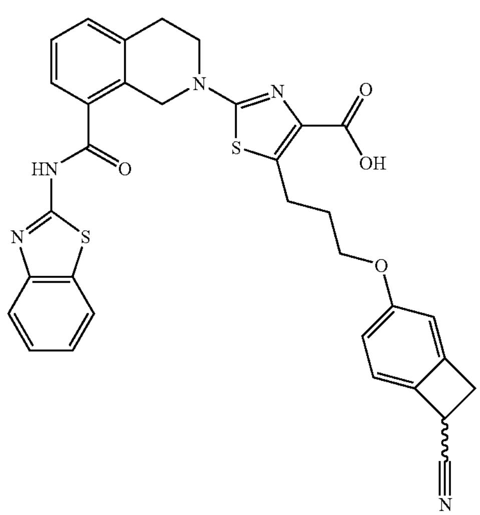 | 2-(8-(benzo[d]thiazol-2-ylcarbamoyl)-3,4-dihydroisoquinolin-2(1H)-yl)-5-(3-(1-cyano-1,2-dihydrocyclobutabenzen-4-yloxy)propyl)thiazole-4-carboxylic acid |

TABLE 1-continued

| No. | Structure | Name |
|---|---|---|
| 26 | 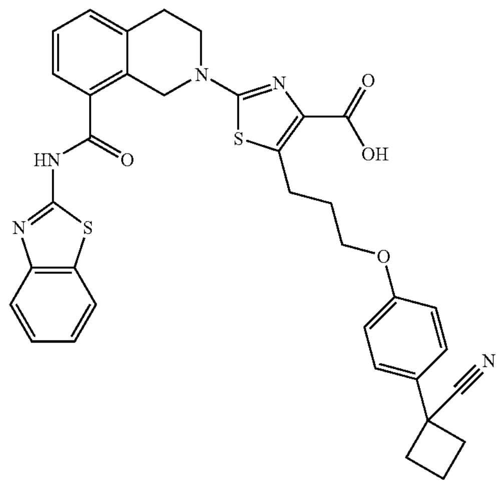 | 2-(8-(benzo[d]thiazol-2-ylcarbamoyl)-3,4-dihydroisoquinolin-2(1H)-yl)-5-(3-(4-(1-cyanocyclobutyl)phenoxy)propyl)thiazole-4-carboxylic acid |
| 27 | 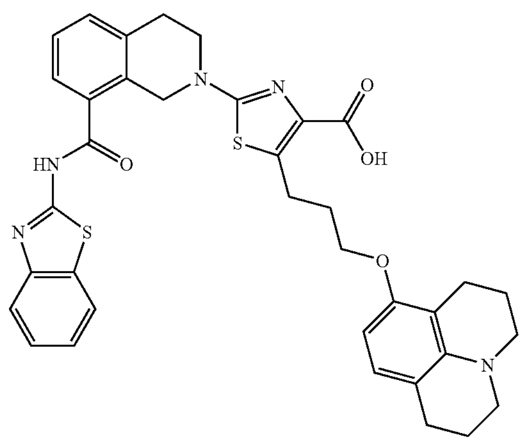 | 2-(8-(benzo[d]thiazol-2-ylcarbamoyl)-3,4-dihydroisoquinolin-2(1H)-yl)-5-(3-(1,2,3,5,6,7-hexahydropyrido[3,2,1-ij]quinolin-8-yloxy)propyl)thiazole-4-carboxylic acid |
| 28 | 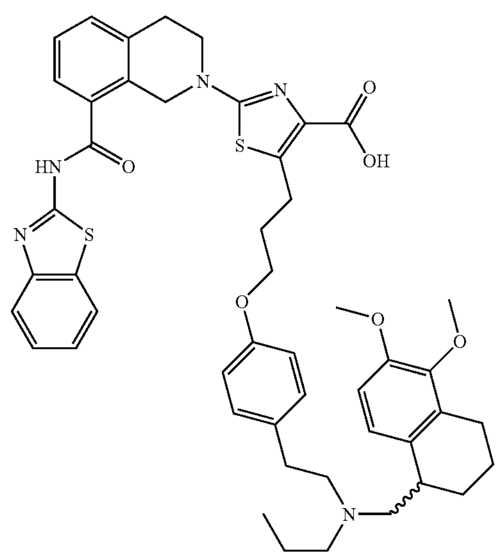 | 2-(8-(benzo[d]thiazol-2-ylcarbamoyl)-3,4-dihydroisoquinolin-2(1H)-yl)-5-(3-(4-(2-(((5,6-dimethoxy-1,2,3,4-tetrahydronaphthalen-1-yl)methyl)(propyl)amino)ethyl)phenoxy)propyl)thiazole-4-carboxylic acid |

TABLE 1-continued

| No. | Structure | Name |
|---|---|---|
| 29 | 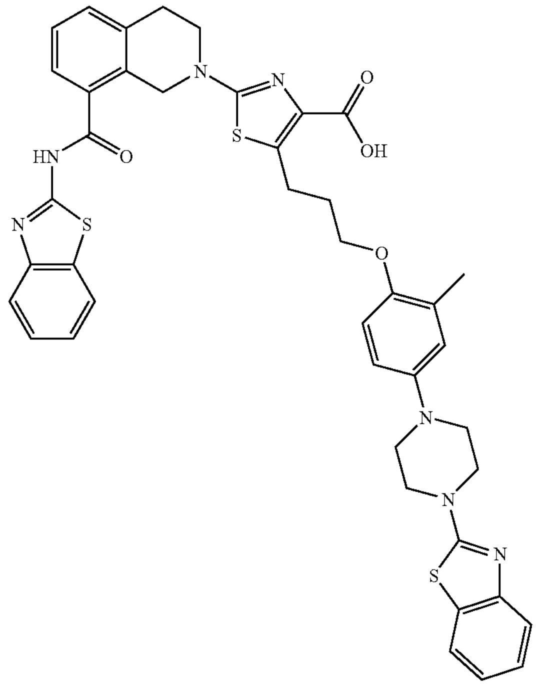 | 5-(3-(4-(4-(benzo[d]thiazol-2-yl)piperazin-1-yl)-2-methylphenoxy)propyl)-2-(8-(benzo[d]thiazol-2-ylcarbamoyl)-3,4-dihydroisoquinolin-2(1H)-yl)thiazole-4-carboxylic acid |
| 30 | 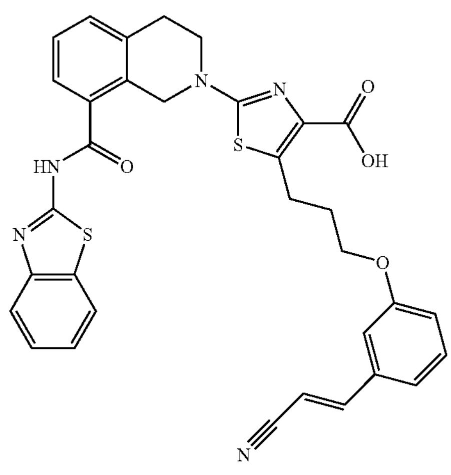 | (E)-2-(8-(benzo[d]thiazol-2-ylcarbamoyl)-3,4-dihydroisoquinolin-2(1H)-yl)-5-(3-(3-(2-cyanovinyl)phenoxy)propyl)thiazole-4-carboxylic acid |

TABLE 1-continued

| No. | Structure | Name |
|---|---|---|
| 31 | 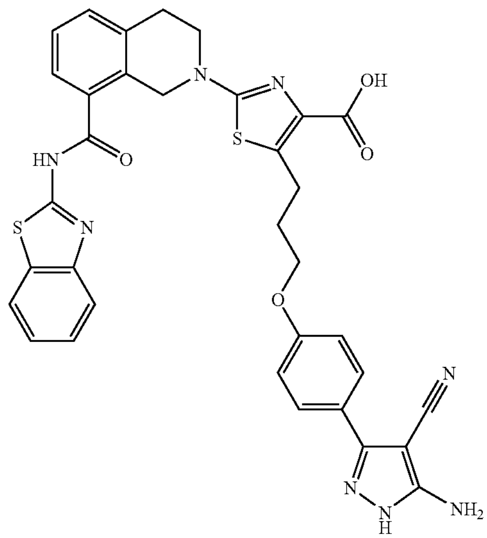 | 5-(3-(4-(5-amino-4-cyano-1H-pyrazol-3-yl)phenoxy)propyl)-2-(8-(benzo[d]thiazol-2-ylcarbamoyl)-3,4-dihydroisoquinolin-2(1H)-yl)thiazole-4-carboxylic acid |
| 32 | 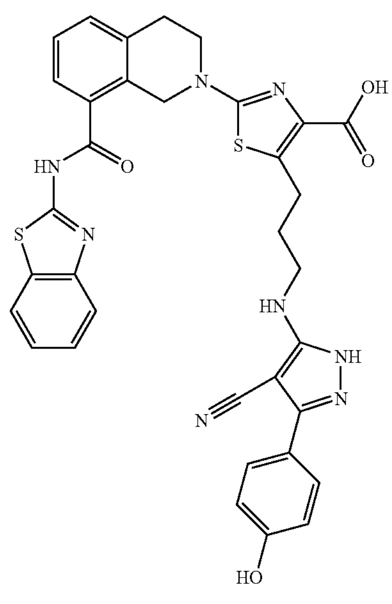 | 2-(8-(benzo[d]thiazol-2-ylcarbamoyl)-3,4-dihydroisoquinolin-2(1H)-yl)-5-(3-(4-cyano-3-(4-hydroxyphenyl)-1H-pyrazol-5-ylamino)propyl)thiazole-4-carboxylic acid |
| 33 | 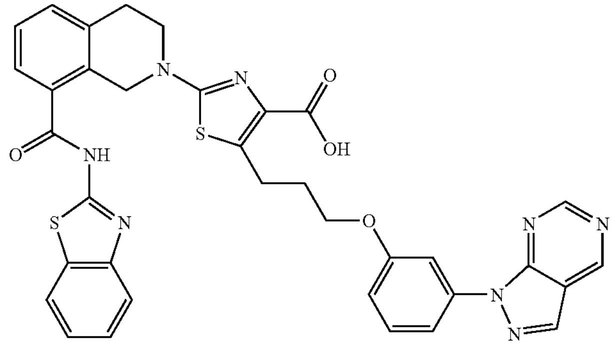 | 5-(3-(3-(1H-pyrazolo[3,4-d]pyrimidin-1-yl)phenoxy)propyl)-2-(8-(benzo[d]thiazol-2-ylcarbamoyl)-3,4-dihydroisoquinolin-2(1H)-yl)thiazole-4-carboxylic acid |

TABLE 1-continued

| No. | Structure | Name |
|---|---|---|
| 34 | 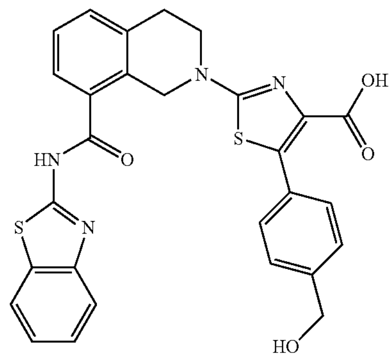 | 2-(8-(benzo[d]thiazol-2-ylcarbamoyl)-3,4-dihydroisoquinolin-2(1H)-yl)-5-(4-(hydroxymethyl)phenyl)thiazole-4-carboxylic acid |
| 35 | 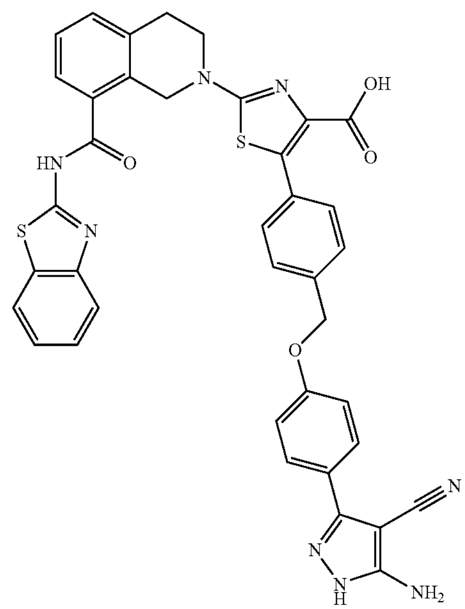 | 5-(4-((4-(5-amino-4-cyano-1H-pyrazol-3-yl)phenoxy)methyl)phenyl)-2-(8-(benzo[d]thiazol-2-ylcarbamoyl)-3,4-dihydroisoquinolin-2(1H)-yl)thiazole-4-carboxylic acid |
| 36 | 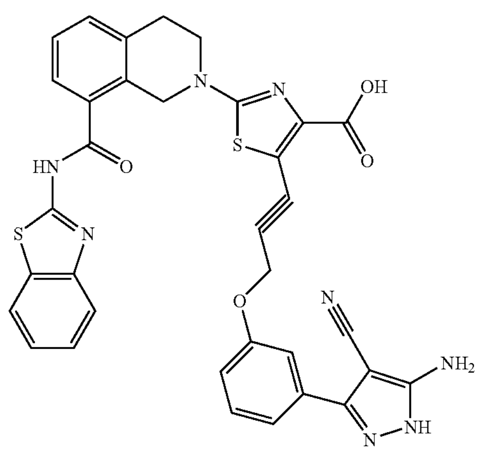 | 5-(3-(3-(5-amino-4-cyano-1H-pyrazol-3-yl)phenoxy)prop-1-ynyl)-2-(8-(benzo[d]thiazol-2-ylcarbamoyl)-3,4-dihydroisoquinolin-2(1H)-yl)thiazole-4-carboxylic acid |

TABLE 1-continued

| No. | Structure | Name |
| --- | --- | --- |
| 37 | 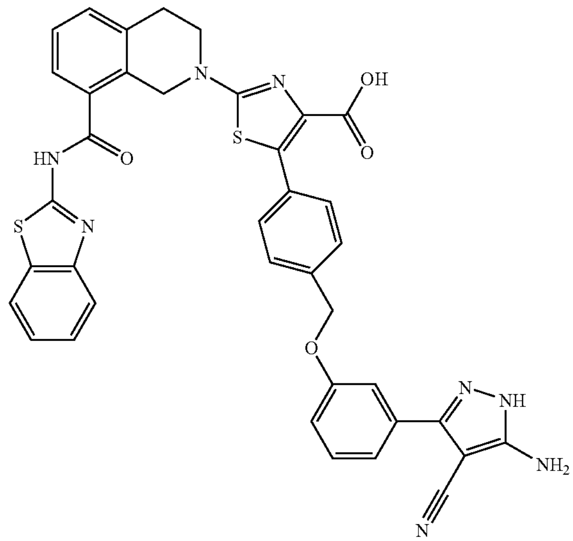 | 5-(4-((3-(5-amino-4-cyano-1H-pyrazol-3-yl)phenoxy)methyl)phenyl)-2-(8-(benzo[d]thiazol-2-ylcarbamoyl)-3,4-dihydroisoquinolin-2(1H)-yl)thiazole-4-carboxylic acid |
| 38 | 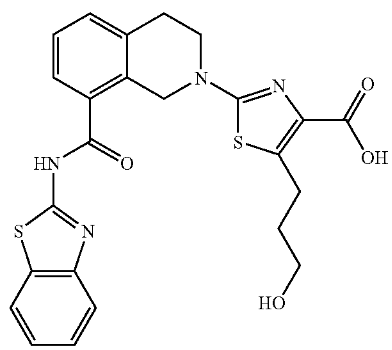 | 2-(8-(benzo[d]thiazol-2-ylcarbamoyl)-3,4-dihydroisoquinolin-2(1H)-yl)-5-(3-hydroxypropyl)thiazole-4-carboxylic acid |
| 39 | 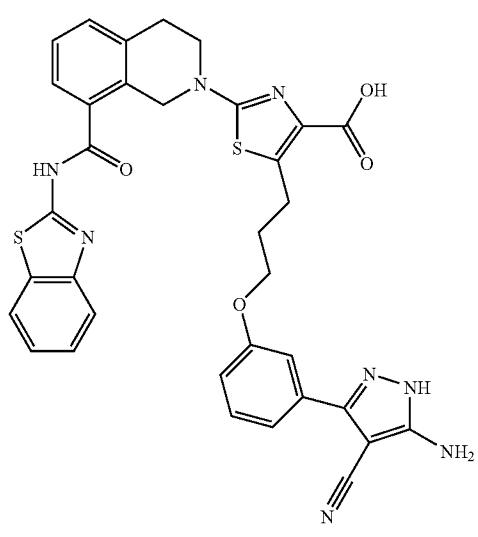 | 5-(3-(3-(5-amino-4-cyano-1H-pyrazol-3-yl)phenoxy)propyl)-2-(8-(benzo[d]thiazol-2-ylcarbamoyl)-3,4-dihydroisoquinolin-2(1H)-yl)thiazole-4-carboxylic acid |

TABLE 1-continued

| No. | Structure | Name |
| --- | --- | --- |
| 40 | 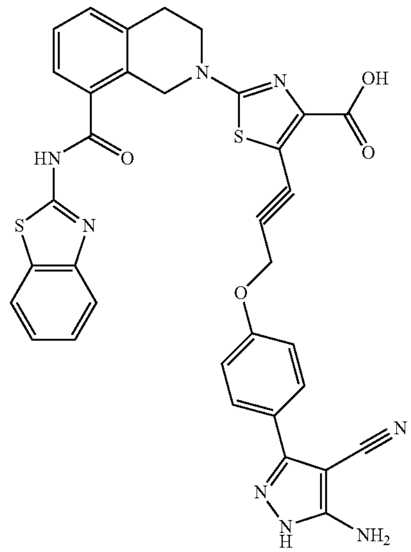 | 5-(3-(4-(5-amino-4-cyano-1H-pyrazol-3-yl)phenoxy)prop-1-ynyl)-2-(8-(benzo[d]thiazol-2-ylcarbamoyl)-3,4-dihydroisoquinolin-2(1H)-yl)thiazole-4-carboxylic acid |
| 41 | 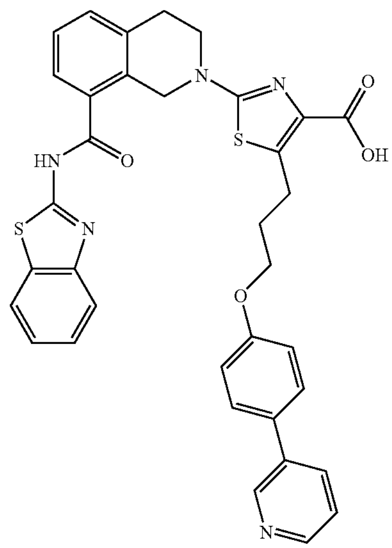 | 2-(8-(benzo[d]thiazol-2-ylcarbamoyl)-3,4-dihydroisoquinolin-2(1H)-yl)-5-(3-(4-(pyridin-3-yl)phenoxy)propyl)thiazole-4-carboxylic acid |
| 42 | 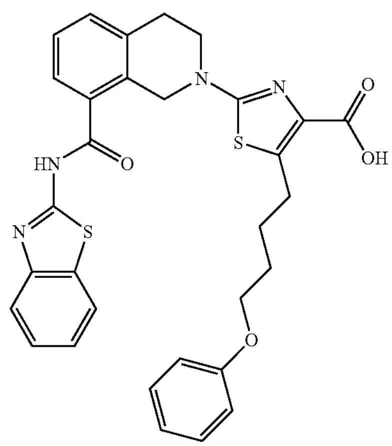 | 2-(8-(benzo[d]thiazol-2-ylcarbamoyl)-3,4-dihydroisoquinolin-2(1H)-yl)-5-(4-phenoxybutyl)thiazole-4-carboxylic acid |

TABLE 1-continued

| No. | Structure | Name |
|---|---|---|
| 43 | 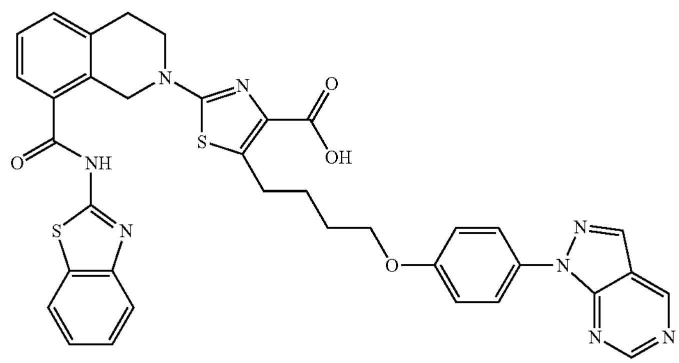 | 5-(4-(4-(1H-pyrazolo[3,4-d]pyrimidin-1-yl)phenoxy)butyl)-2-(8-(benzo[d]thiazol-2-ylcarbamoyl)-3,4-dihydroisoquinolin-2(1H)-yl)thiazole-4-carboxylic acid |
| 44 | 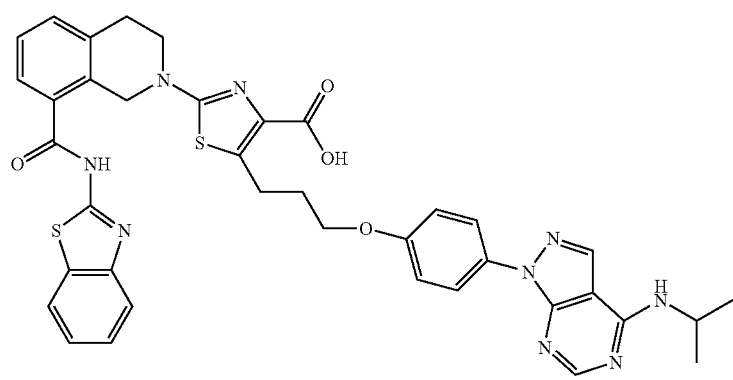 | 2-(8-(benzo[d]thiazol-2-ylcarbamoyl)-3,4-dihydroisoquinolin-2(1H)-yl)-5-(3-(4-(4-(isopropylamino)-1H-pyrazolo[3,4-d]pyrimidin-1-yl)phenoxy)propyl)thiazole-4-carboxylic acid |
| 45 | 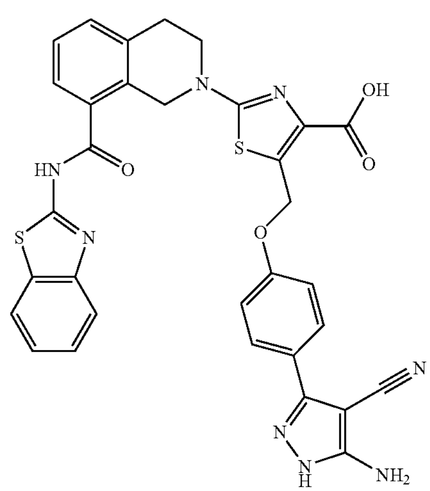 | 5-((4-(5-amino-4-cyano-1H-pyrazol-3-yl)phenoxy)methyl)-2-(8-(benzo[d]thiazol-2-ylcarbamoyl)-3,4-dihydroisoquinolin-2(1H)-yl)thiazole-4-carboxylic acid |
| 46 | 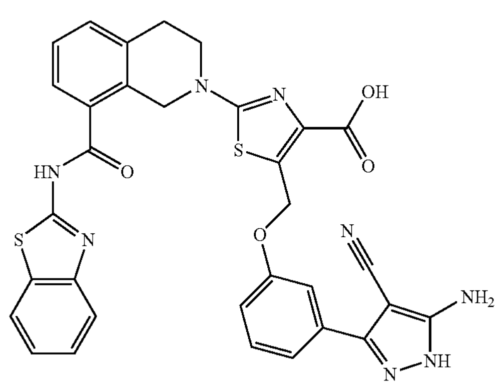 | 5-((3-(5-amino-4-cyano-1H-pyrazol-3-yl)phenoxy)methyl)-2-(8-(benzo[d]thiazol-2-ylcarbamoyl)-3,4-dihydroisoquinolin-2(1H)-yl)thiazole-4-carboxylic acid |

TABLE 1-continued

| No. | Structure | Name |
|---|---|---|
| 47 | 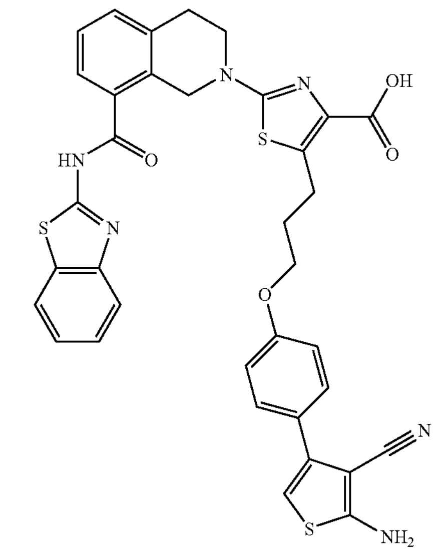 | 5-(3-(4-(5-amino-4-cyanothiophen-3-yl)phenoxy)propyl)-2-(8-(benzo[d]thiazol-2-ylcarbamoyl)-3,4-dihydroisoquinolin-2(1H)-yl)thiazole-4-carboxylic acid |
| 48 | 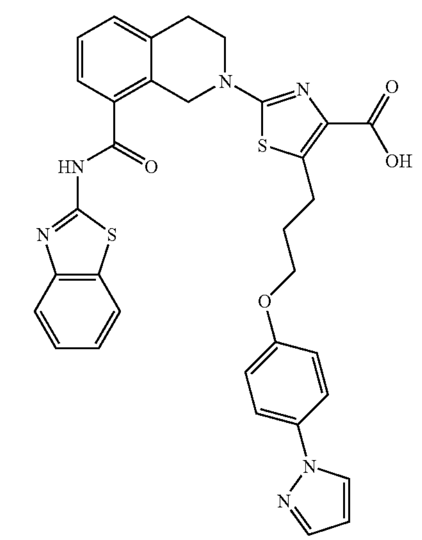 | 5-(3-(4-(1H-pyrazol-1-yl)phenoxy)propyl)-2-(8-(benzo[d]thiazol-2-ylcarbamoyl)-3,4-dihydroisoquinolin-2(1H)-yl)thiazole-4-carboxylic acid |
| 49 | 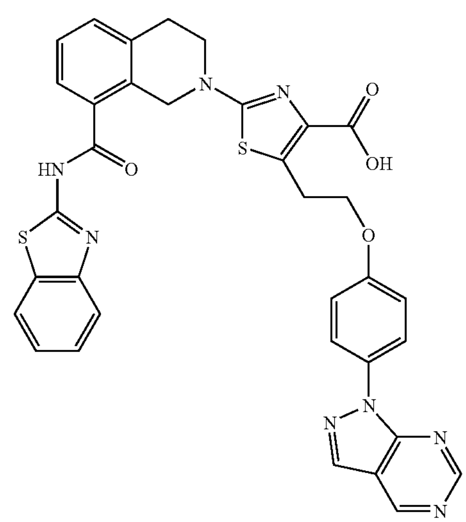 | 5-(2-(4-(1H-pyrazolo[3,4-d]pyrimidin-1-yl)phenoxy)ethyl)-2-(8-(benzo[d]thiazol-2-ylcarbamoyl)-3,4-dihydroisoquinolin-2(1H)-yl)thiazole-4-carboxylic acid |

TABLE 1-continued

| No. | Structure | Name |
|---|---|---|
| 50 | 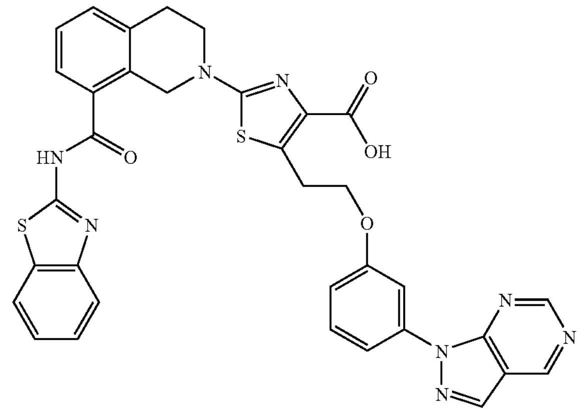 | 5-(2-(3-(1H-pyrazolo[3,4-d]pyrimidin-1-yl)phenoxy)ethyl)-2-(8-(benzo[d]thiazol-2-ylcarbamoyl)-3,4-dihydroisoquinolin-2(1H)-yl)thiazole-4-carboxylic acid |
| 51 | 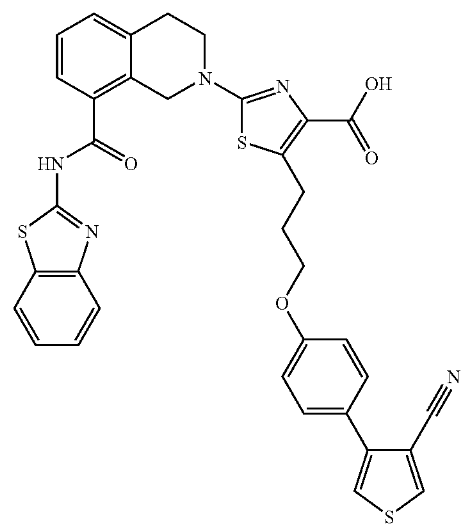 | 2-(8-(benzo[d]thiazol-2-ylcarbamoyl)-3,4-dihydroisoquinolin-2(1H)-yl)-5-(3-(4-(4-cyanothiophen-3-yl)phenoxy)propyl)thiazole-4-carboxylic acid |
| 52 | 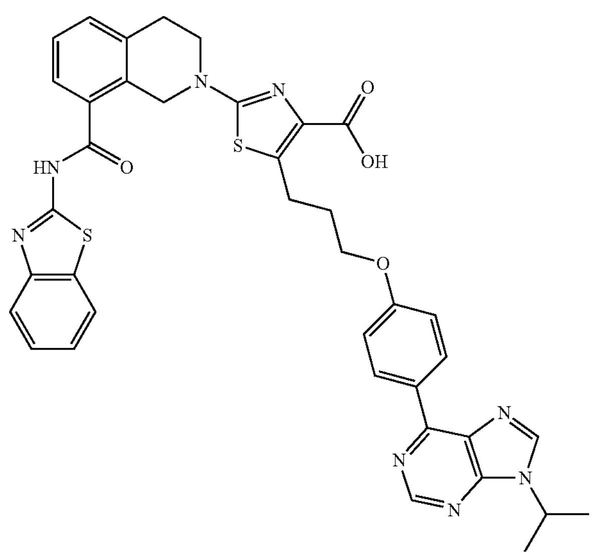 | 2-(8-(benzo[d]thiazol-2-ylcarbamoyl)-3,4-dihydroisoquinolin-2(1H)-yl)-5-(3-(4-(9-isopropyl-9H-purin-6-yl)phenoxy)propyl)thiazole-4-carboxylic acid |

TABLE 1-continued

| No. | Structure | Name |
|---|---|---|
| 53 | 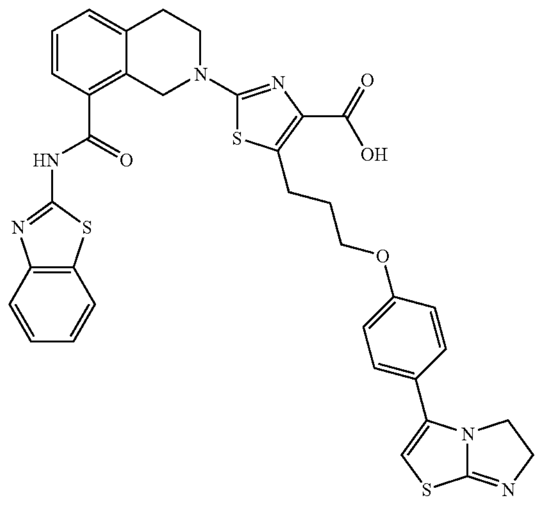 | 2-(8-(benzo[d]thiazol-2-ylcarbamoyl)-3,4-dihydroisoquinolin-2(1H)-yl)-5-(3-(4-(5,6-dihydroimidazo[2,1-b]thiazol-3-yl)phenoxy)propyl)thiazole-4-carboxylic acid |
| 54 | 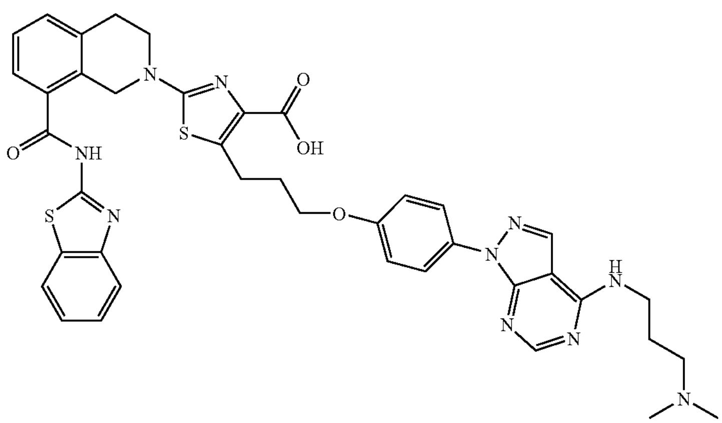 | 2-(8-(benzo[d]thiazol-2-ylcarbamoyl)-3,4-dihydroisoquinolin-2(1H)-yl)-5-(3-(4-(4-(3-(dimethylamino)propylamino)-1H-pyrazolo[3,4-d]pyrimidin-1-yl)phenoxy)propyl)thiazole-4-carboxylic acid |
| 55 | 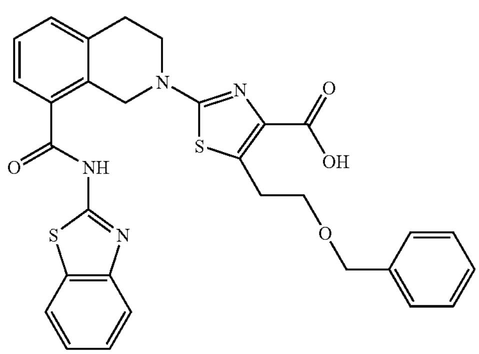 | 2-(8-(benzo[d]thiazol-2-ylcarbamoyl)-3,4-dihydroisoquinolin-2(1H)-yl)-5-(2-(benzyloxy)ethyl)thiazole-4-carboxylic acid |

TABLE 1-continued

| No. | Structure | Name |
|---|---|---|
| 56 | 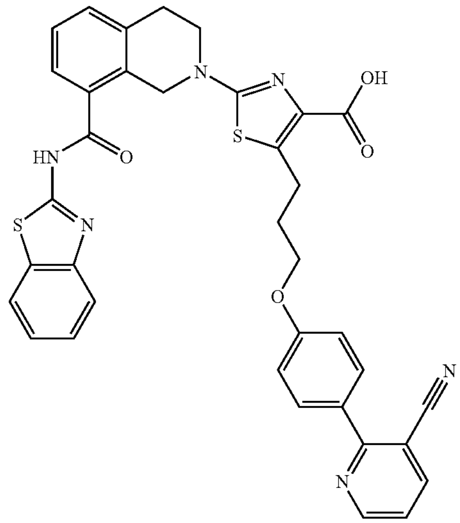 | 2-(8-(benzo[d]thiazol-2-ylcarbamoyl)-3,4-dihydroisoquinolin-2(1H)-yl)-5-(3-(4-(3-cyanopyridin-2-yl)phenoxy)propyl)thiazole-4-carboxylic acid |
| 57 | 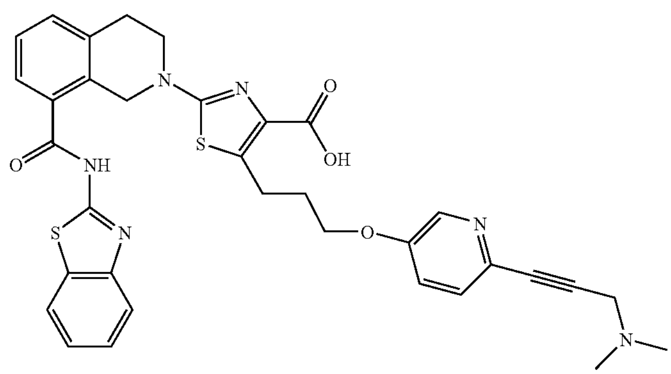 | 2-(8-(benzo[d]thiazol-2-ylcarbamoyl)-3,4-dihydroisoquinolin-2(1H)-yl)-5-(3-(6-(3-(dimethylamino)prop-1-ynyl)pyridin-3-yloxy)propyl)thiazole-4-carboxylic acid |
| 58 | 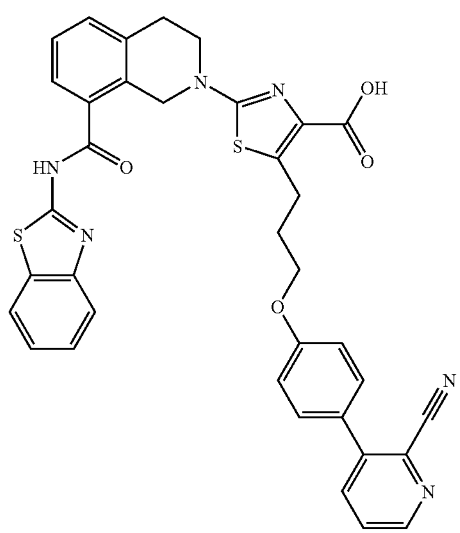 | 2-(8-(benzo[d]thiazol-2-ylcarbamoyl)-3,4-dihydroisoquinolin-2(1H)-yl)-5-(3-(4-(2-cyanopyridin-3-yl)phenoxy)propyl)thiazole-4-carboxylic acid |

TABLE 1-continued

| No. | Structure | Name |
|---|---|---|
| 59 | 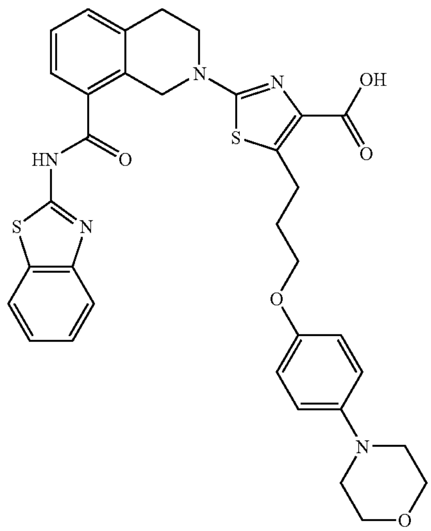 | 2-(8-(benzo[d]thiazol-2-ylcarbamoyl)-3,4-dihydroisoquinolin-2(1H)-yl)-5-(3-(4-morpholinophenoxy)propyl)thiazole-4-carboxylic acid |
| 60 | 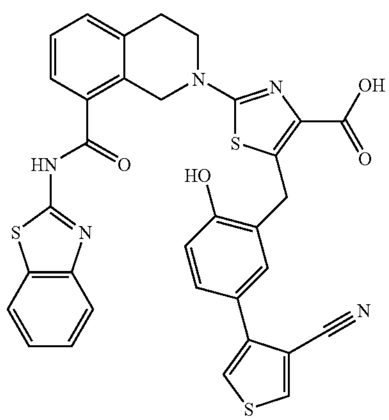 | 2-(8-(benzo[d]thiazol-2-ylcarbamoyl)-3,4-dihydroisoquinolin-2(1H)-yl)-5-(5-(4-cyanothiophen-3-yl)-2-hydroxybenzyl)thiazole-4-carboxylic acid |
| 61 | 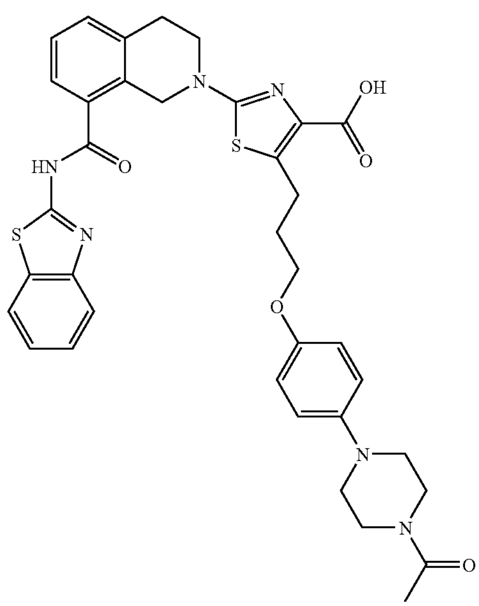 | 5-(3-(4-(4-acetylpiperazin-1-yl)phenoxy)propyl)-2-(8-(benzo[d]thiazol-2-ylcarbamoyl)-3,4-dihydroisoquinolin-2(1H)-yl)thiazole-4-carboxylic acid |

TABLE 1-continued

| No. | Structure | Name |
|---|---|---|
| 62 | 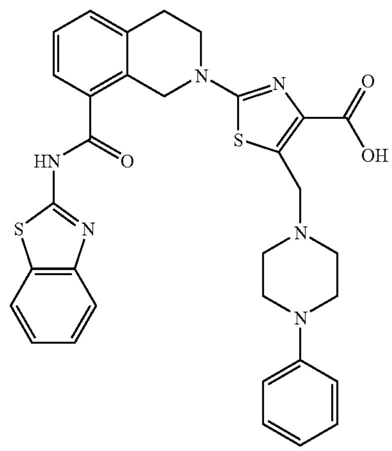 | 2-(8-(benzo[d]thiazol-2-ylcarbamoyl)-3,4-dihydroisoquinolin-2(1H)-yl)-5-((4-phenyl-piperazin-1-yl)methyl)thiazole-4-carboxylic acid |
| 63 | 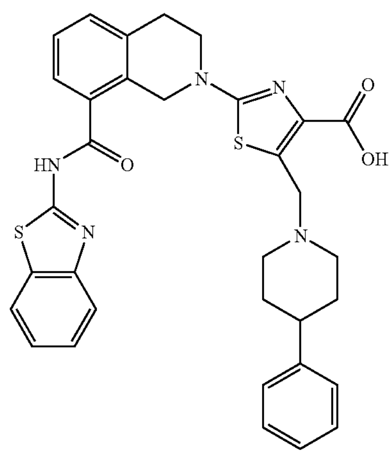 | 2-(8-(benzo[d]thiazol-2-ylcarbamoyl)-3,4-dihydroisoquinolin-2(1H)-yl)-5-((4-phenyl-piperidin-1-yl)methyl)thiazole-4-carboxylic acid |
| 64 | 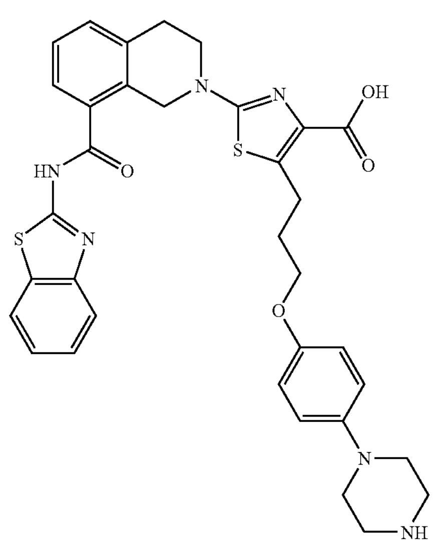 | 2-(8-(benzo[d]thiazol-2-ylcarbamoyl)-3,4-dihydroisoquinolin-2(1H)-yl)-5-(3-(4-(piperazin-1-yl)phenoxy)propyl)thiazole-4-carboxylic acid |

TABLE 1-continued

| No. | Structure | Name |
|---|---|---|
| 65 | 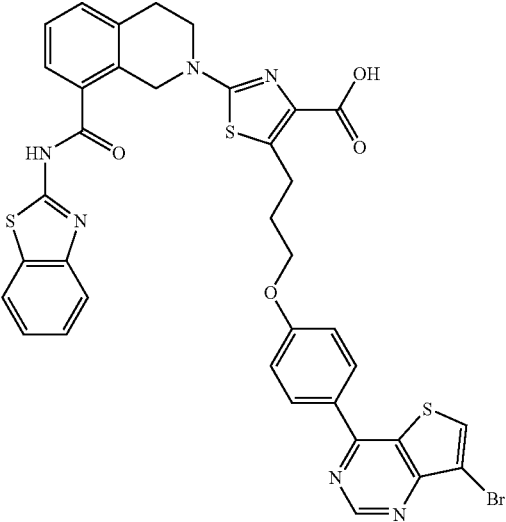 | 2-(8-(benzo[d]thiazol-2-ylcarbamoyl)-3,4-dihydroisoquinolin-2(1H)-yl)-5-(3-(4-(7-bromothieno[3,2-d]pyrimidin-4-yl)phenoxy)propyl)thiazole-4-carboxylic acid |
| 66 | 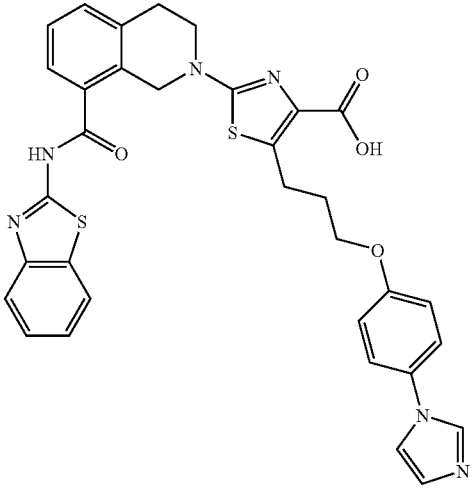 | 5-(3-(4-(1H-imidazol-1-yl)phenoxy)propyl)-2-(8-(benzo[d]thiazol-2-ylcarbamoyl)-3,4-dihydroisoquinolin-2(1H)-yl)thiazole-4-carboxylic acid |
| 67 | 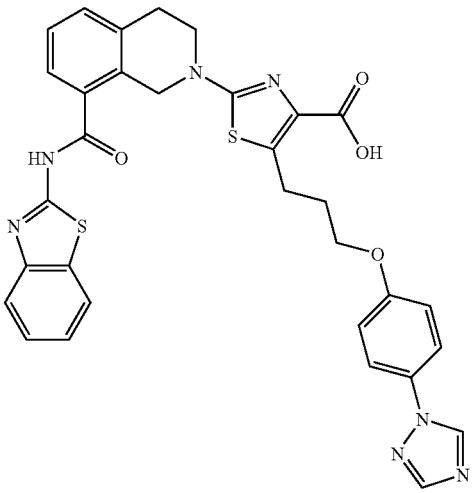 | 5-(3-(4-(1H-1,2,4-triazol-1-yl)phenoxy)propyl)-2-(8-(benzo[d]thiazol-2-ylcarbamoyl)-3,4-dihydroisoquinolin-2(1H)-yl)thiazole-4-carboxylic acid |

TABLE 1-continued

| No. | Structure | Name |
|---|---|---|
| 68 | 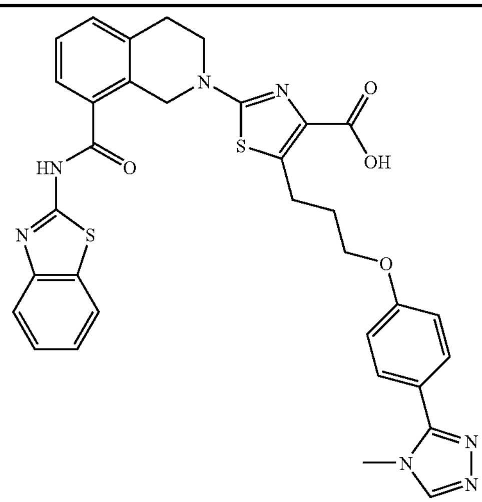 | 2-(8-(benzo[d]thiazol-2-ylcarbamoyl)-3,4-dihydroisoquinolin-2(1H)-yl)-5-(3-(4-(4-methyl-4H-1,2,4-triazol-3-yl)phenoxy)propyl)thiazole-4-carboxylic acid |
| 69 | 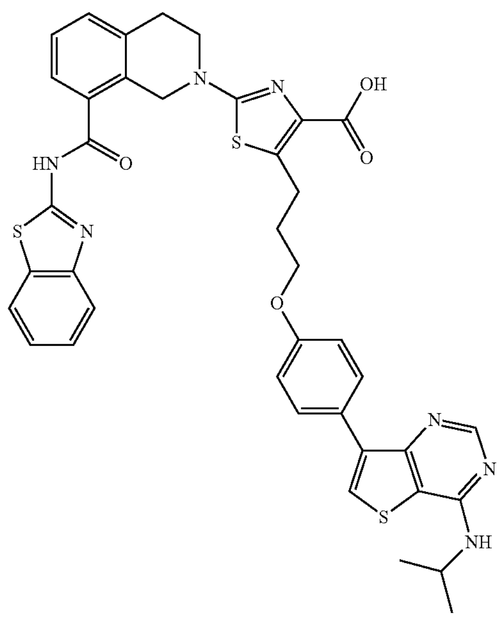 | 2-(8-(benzo[d]thiazol-2-ylcarbamoyl)-3,4-dihydroisoquinolin-2(1H)-yl)-5-(3-(4-(4-(isopropylamino)thieno[3,2-d]pyrimidin-7-yl)phenoxy)propyl)thiazole-4-carboxylic acid |
| 70 | 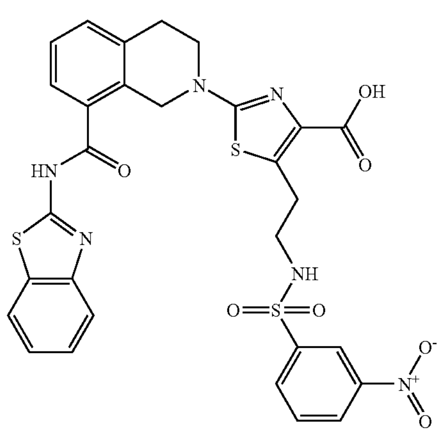 | 2-(8-(benzo[d]thiazol-2-ylcarbamoyl)-3,4-dihydroisoquinolin-2(1H)-yl)-5-(2-(3-nitrophenylsulfonamido)ethyl)thiazole-4-carboxylic acid |

| No. | Structure | Name |
|---|---|---|
| 71 | 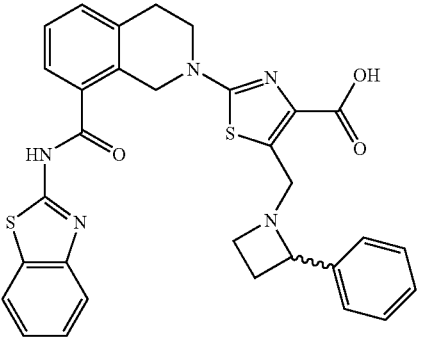 | 2-(8-(benzo[d]thiazol-2-ylcarbamoyl)-3,4-dihydroisoquinolin-2(1H)-yl)-5-((2-phenyl-azetidin-1-yl)methyl)thiazole-4-carboxylic acid |
| 72 | 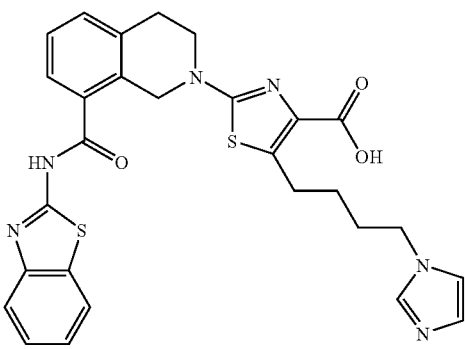 | 5-(4-(1H-imidazol-1-yl)butyl)-2-(8-(benzo[d]thiazol-2-ylcarbamoyl)-3,4-dihydroisoquinolin-2(1H)-yl)thiazole-4-carboxylic acid |
| 73 | 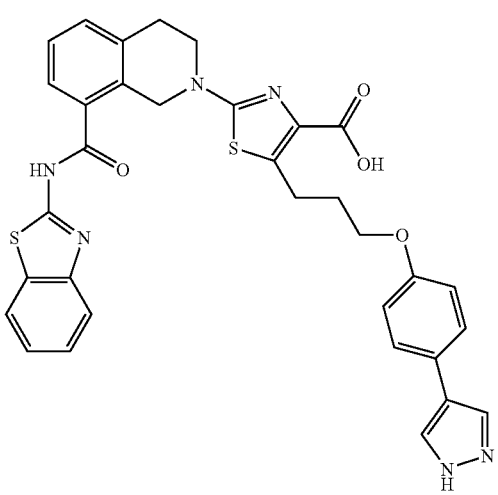 | 5-(3-(4-(1H-pyrazol-4-yl)phenoxy)propyl)-2-(8-(benzo[d]thiazol-2-ylcarbamoyl)-3,4-dihydroisoquinolin-2(1H)-yl)thiazole-4-carboxylic acid |

TABLE 1-continued

| No. | Structure | Name |
|---|---|---|
| 74 | 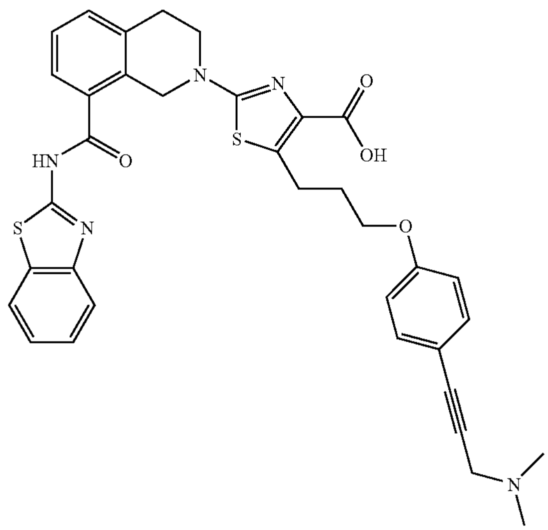 | 2-(8-benzo[d]thiazol-2-ylcarbamoyl)-3,4-dihydroisoquinolin-2(1H)-yl)-5-(3-(4-(3-(dimethylamino)prop-1-ynyl)phenoxy)propyl)thiazole-4-carboxylic acid |
| 75 | 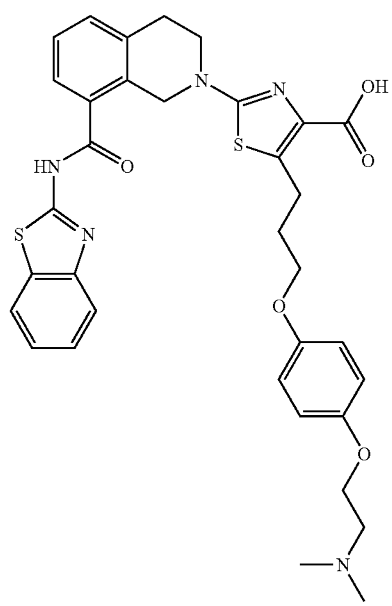 | 2-(8-(benzo[d]thiazol-2-ylcarbamoyl)-3,4-dihydroisoquinolin-2(1H)-yl)-5-(3-(4-(2-(dimethylamino)ethoxy)phenoxy)propyl)thiazole-4-carboxylic acid |
| 76 | 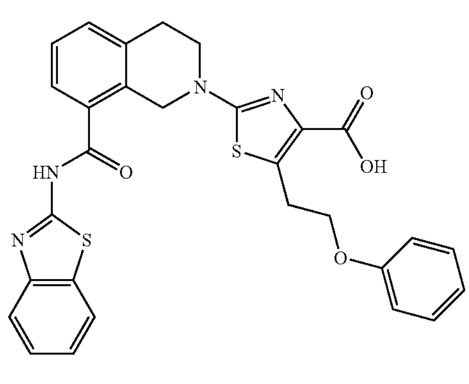 | 2-(8-(benzo[d]thiazol-2-ylcarbamoyl)-3,4-dihydroisoquinolin-2(1H)-yl)-5-(2-phenoxyethyl)thiazole-4-carboxylic acid |

TABLE 1-continued

| No. | Structure | Name |
|---|---|---|
| 77 | 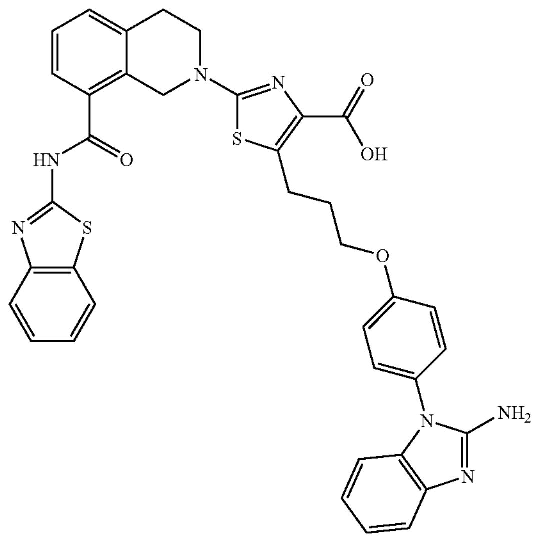 | 5-(3-(4-(2-amino-1H-benzo[d]imidazol-1-yl)phenoxy)propyl)-2-(8-(benzo[d]thiazol-2-ylcarbamoyl)-3,4-dihydroisoquinolin-2(1H)-yl)thiazole-4-carboxylic acid |
| 78 | 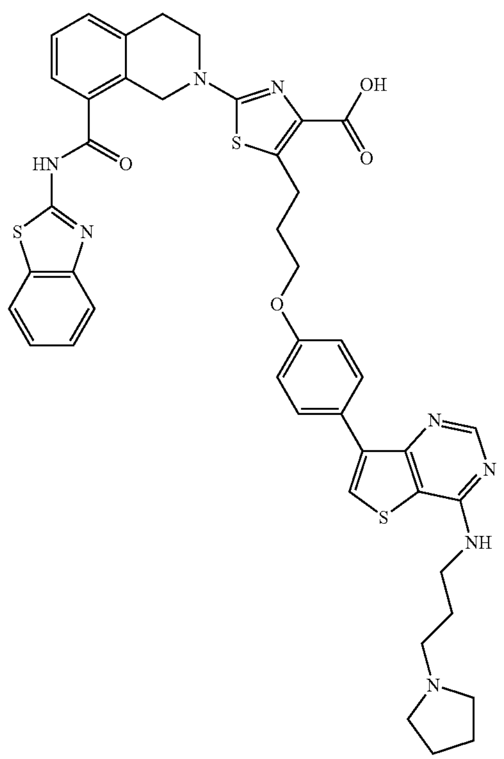 | 2-(8-(benzo[d]thiazol-2-ylcarbamoyl)-3,4-dihydroisoquinolin-2(1H)-yl)-5-(3-(4-(4-(3-(pyrrolidin-1-yl)propylamino)thieno[3,2-d]pyrimidin-7-yl)phenoxy)propyl)thiazole-4-carboxylic acid |

TABLE 1-continued
| No. | Structure | Name |
|---|---|---|
| 79 | 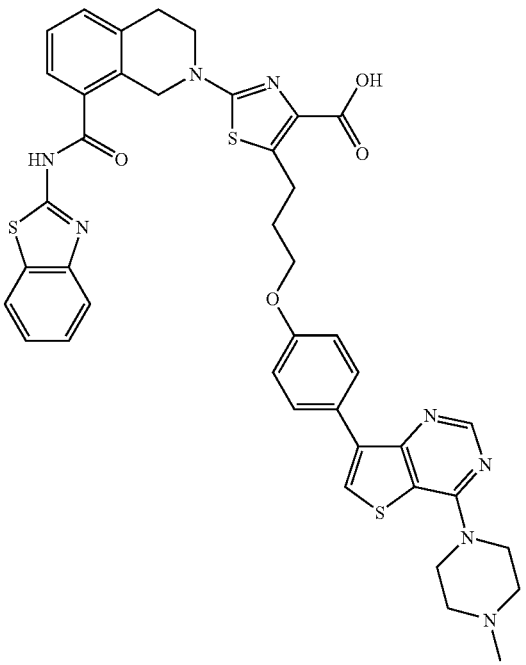 | 2-(8-(benzo[d]thiazol-2-ylcarbamoyl)-3,4-dihydroisoquinolin-2(1H)-yl)-5-(3-(4-(4-(4-methylpiperazin-1-yl)thieno[3,2-d]pyrimidin-7-yl)phenoxy)propyl)thiazole-4-carboxylic acid |
| 80 | 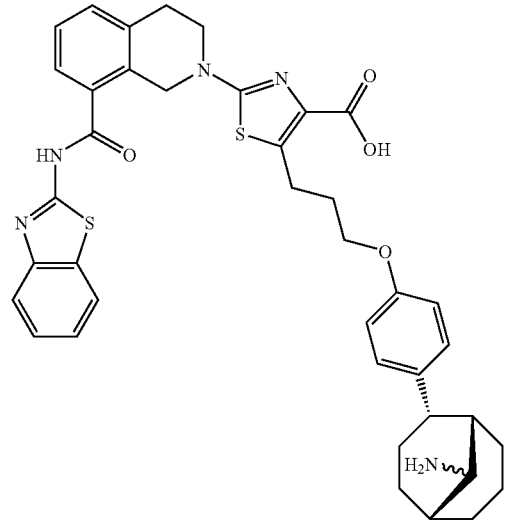 | 5-(3-(4-((1S,2S,5R)-9-aminobicyclo[3.3.1]nonan-2-yl)phenoxy)propyl)-2-(8-(benzo[d]thiazol-2-ylcarbamoyl)-3,4-dihydroisoquinolin-2(1H)-yl)thiazole-4-carboxylic acid |

TABLE 1-continued

| No. | Structure | Name |
| --- | --- | --- |
| 81 | 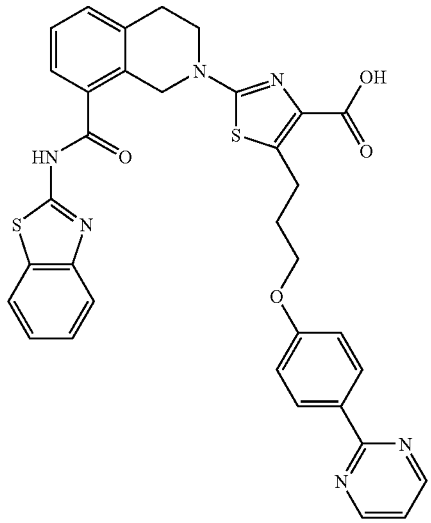 | 2-(8-(benzo[d]thiazol-2-ylcarbamoyl)-3,4-dihydroisoquinolin-2(1H)-yl)-5-(3-(4-(pyrimidin-2-yl)phenoxy)propyl)thiazole-4-carboxylic acid |
| 82 | 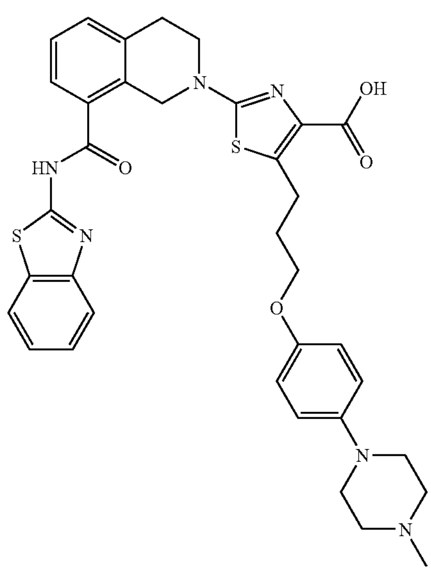 | 2-(8-(benzo[d]thiazol-2-ylcarbamoyl)-3,4-dihydroisoquinolin-2(1H)-yl)-5-(3-(4-(4-methylpiperazin-1-yl)phenoxy)propyl)thiazole-4-carboxylic acid |

TABLE 1-continued

| No. | Structure | Name |
|---|---|---|
| 83 | 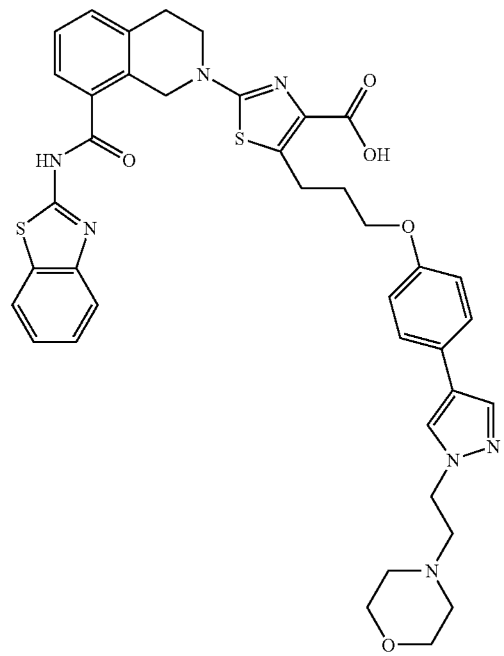 | 2-(8-(benzo[d]thiazol-2-ylcarbamoyl)-3,4-dihydroisoquinolin-2(1H)-yl)-5-(3-(4-(1-(2-morpholinoethyl)-1H-pyrazol-4-yl)phenoxy)propyl)thiazole-4-carboxylic acid |
| 84 | 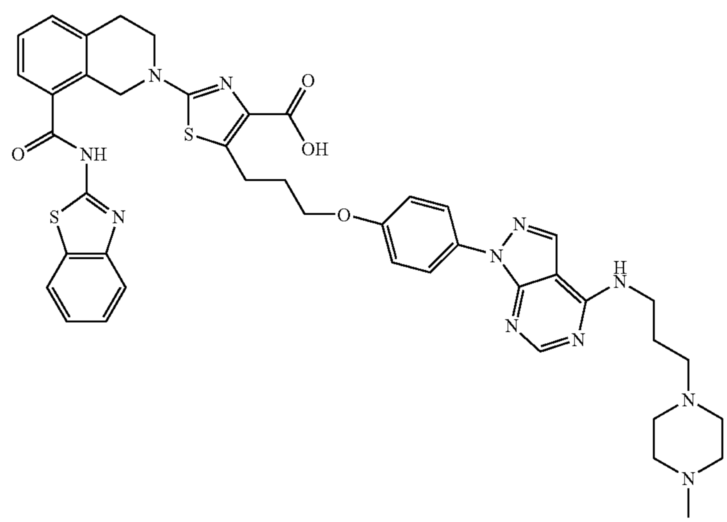 | 2-(8-(benzo[d]thiazol-2-ylcarbamoyl)-3,4-dihydroisoquinolin-2(1H)-yl)-5-(3-(4-(4-(3-(4-methylpiperazin-1-yl)propylamino)-1H-pyrazolo[3,4-d]pyrimidin-1-yl)phenoxy)propyl)thiazole-4-carboxylic acid |
| 85 | 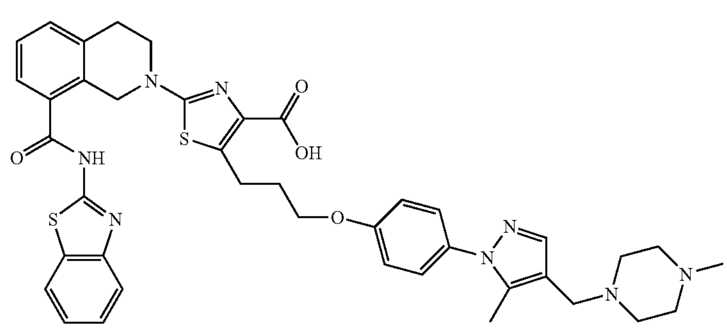 | 2-(8-(benzo[d]thiazol-2-ylcarbamoyl)-3,4-dihydroisoquinolin-2(1H)-yl)-5-(3-(4-(5-methyl-4-((4-methylpiperazin-1-yl)methyl)-1H-pyrazol-1-yl)phenoxy)propyl)thiazole-4-carboxylic acid |

TABLE 1-continued

| No. | Structure | Name |
|---|---|---|
| 86 | 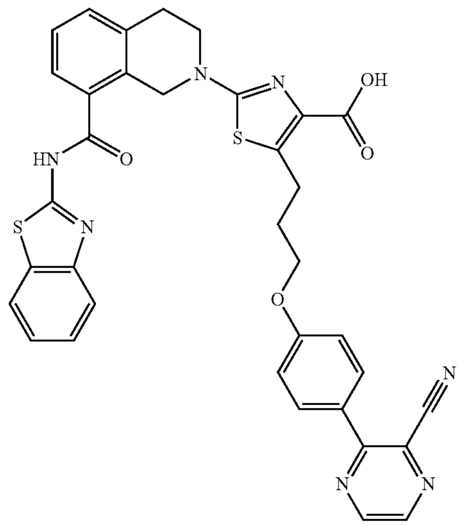 | 2-(8-(benzo[d]thiazol-2-ylcarbamoyl)-3,4-dihydroisoquinolin-2(1H)-yl)-5-(3-(4-(3-cyanopyrazin-2-yl)phenoxy)propyl)thiazole-4-carboxylic acid |
| 87 | 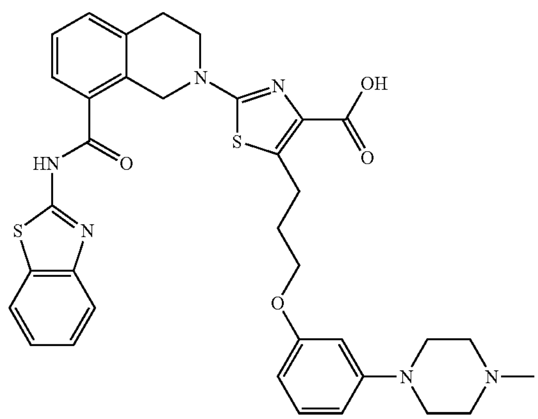 | 2-(8-(benzo[d]thiazol-2-ylcarbamoyl)-3,4-dihydroisoquinolin-2(1H)-yl)-5-(3-(3-(4-methylpiperazin-1-yl)phenoxy)propyl)thiazole-4-carboxylic acid |
| 88 | 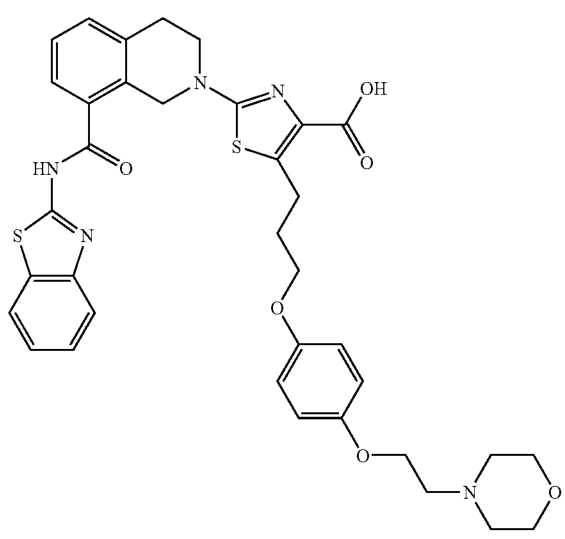 | 2-(8-(benzo[d]thiazol-2-ylcarbamoyl)-3,4-dihydroisoquinolin-2(1H)-yl)-5-(3-(4-(2-morpholinoethoxy)phenoxy)propyl)thiazole-4-carboxylic acid |

TABLE 1-continued

| No. | Structure | Name |
|---|---|---|
| 89 | 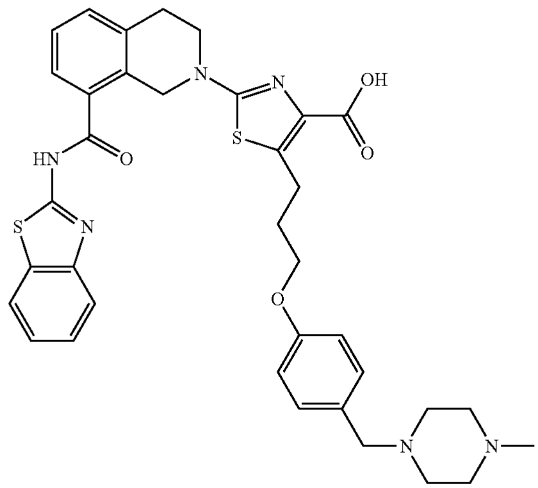 | 2-(8-(benzo[d]thiazol-2-ylcarbamoyl)-3,4-dihydroisoquinolin-2(1H)-yl)-5-(3-(4-((4-methylpiperazin-1-yl)methyl)phenoxy)propyl)thiazole-4-carboxylic acid |
| 90 | 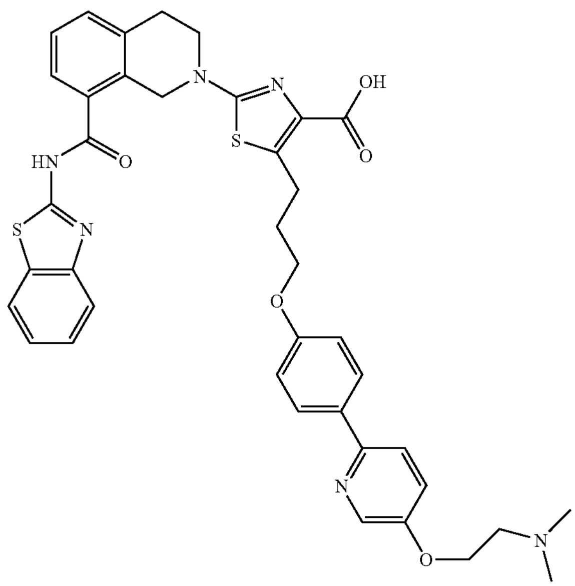 | 2-(8-(benzo[d]thiazol-2-ylcarbamoyl)-3,4-dihydroisoquinolin-2(1H)-yl)-5-(3-(4-(5-(2-(dimethylamino)ethoxy)pyridin-2-yl)phenoxy)propyl)thiazole-4-carboxylic acid |
| 91 | 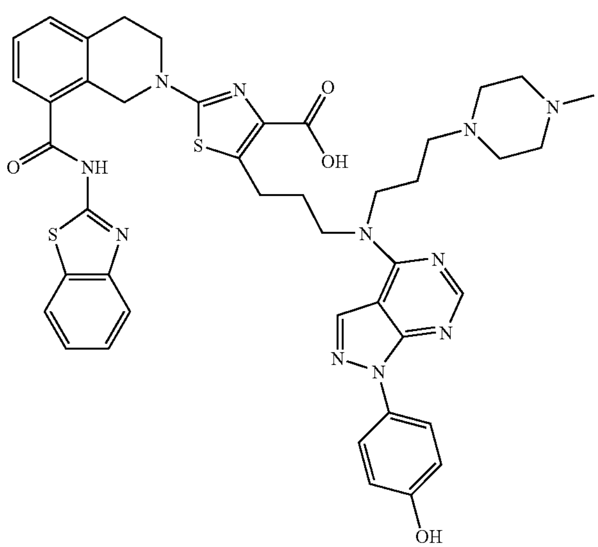 | 2-(8-(benzo[d]thiazol-2-ylcarbamoyl)-3,4-dihydroisoquinolin-2(1H)-yl)-5-(3-((1-(4-hydroxyphenyl)-1H-pyrazolo[3,4-d]pyrimidin-4-yl)(3-(4-methylpiperazin-1-yl)propyl)amino)propyl)thiazole-4-carboxylic acid |

TABLE 1-continued

| No. | Structure | Name |
|---|---|---|
| 92 | 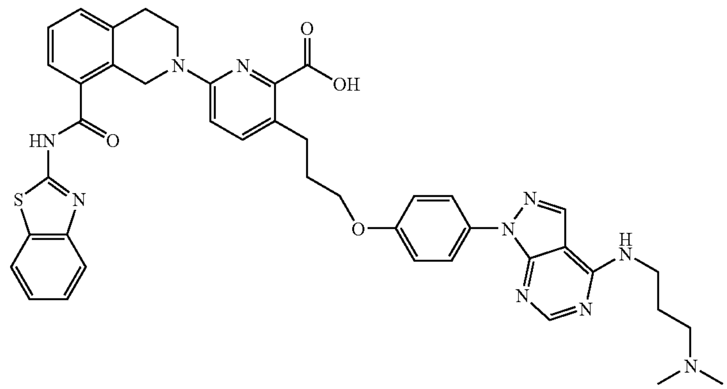 | 6-(8-(benzo[d]thiazol-2-ylcarbamoyl)-3,4-dihydroisoquinolin-2(1H)-yl)-3-(3-(4-(4-(3-(dimethylamino)propylamino)-1H-pyrazolo[3,4-d]pyrimidin-1-yl)phenoxy)propyl)picolinic acid |
| 93 | 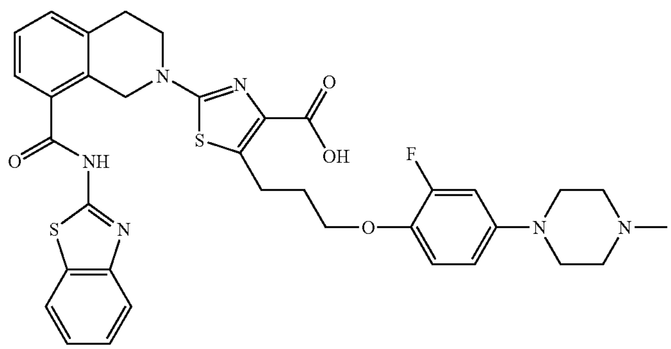 | 2-(8-(benzo[d]thiazol-2-ylcarbamoyl)-3,4-dihydroisoquinolin-2(1H)-yl)-5-(3-(2-fluoro-4-(4-methylpiperazin-1-yl)phenoxy)propyl)thiazole-4-carboxylic acid |
| 94 | 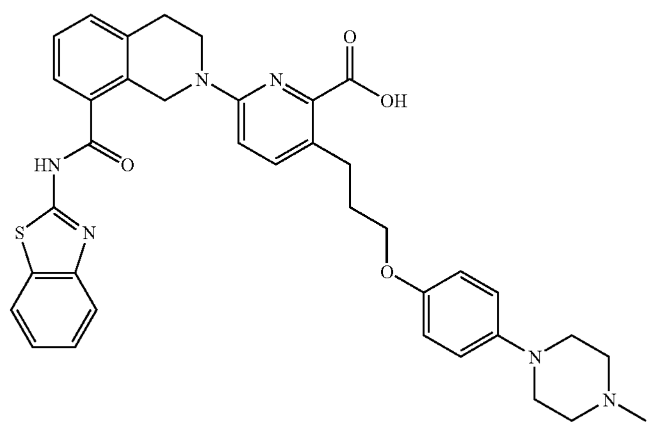 | 6-(8-(benzo[d]thiazol-2-ylcarbamoyl)-3,4-dihydroisoquinolin-2(1H)-yl)-3-(3-(4-(4-methyl-piperazin-1-yl)phenoxy)propyl)picolinic acid |
| 95 | 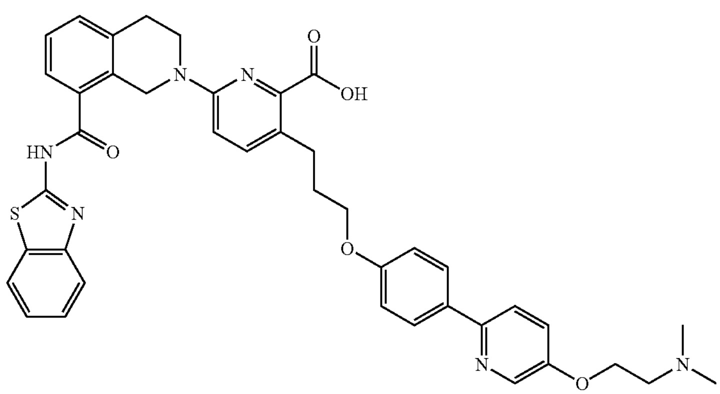 | 6-(8-(benzo[d]thiazol-2-ylcarbamoyl)-3,4-dihydroisoquinolin-2(1H)-yl)-3-(3-(4-(5-(2-(dimethylamino)ethoxy)pyridin-2-yl)phenoxy)propyl)picolinic acid |

TABLE 1-continued

| No. | Structure | Name |
|---|---|---|
| 96 | 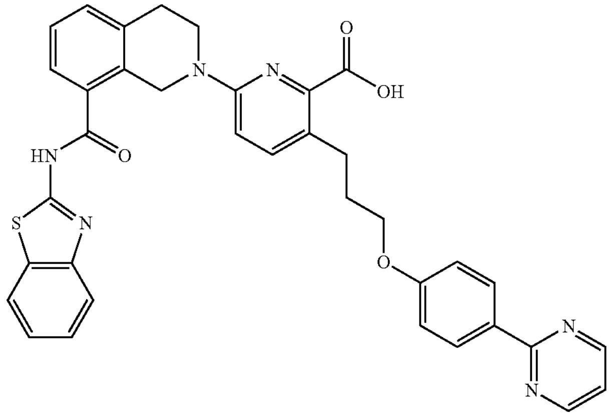 | 6-(8-(benzo[d]thiazol-2-ylcarbamoyl)-3,4-dihydroisoquinolin-2(1H)-yl)-3-(3-(4-(pyrimidin-2-yl)phenoxy)propyl)picolinic acid |
| 97 | 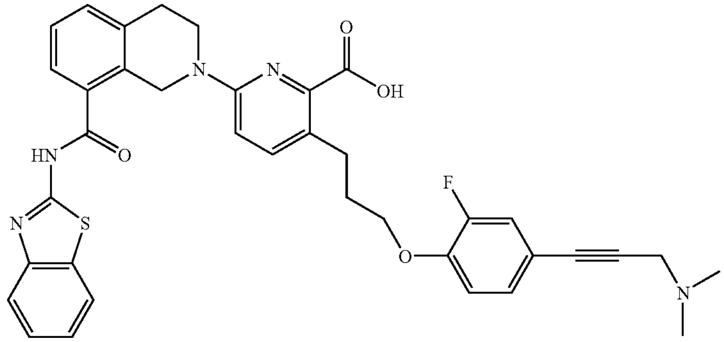 | 6-(8-(benzo[d]thiazol-2-ylcarbamoyl)-3,4-dihydroisoquinolin-2(1H)-yl)-3-(3-(4-(3-(dimethylamino)prop-1-ynyl)-2-fluorophenoxy)propyl)picolinic acid |
| 98 | 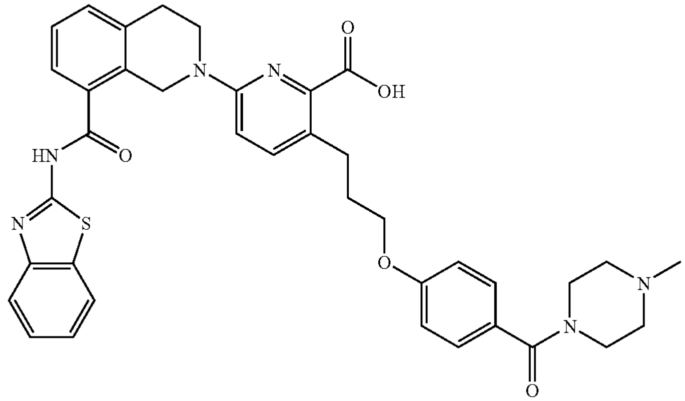 | 6-(8-(benzo[d]thiazol-2-ylcarbamoyl)-3,4-dihydroisoquinolin-2(1H)-yl)-3-(3-(4-(4-methylpiperazine-1-carbonyl)phenoxy)propyl)picolinic acid |
| 99 | 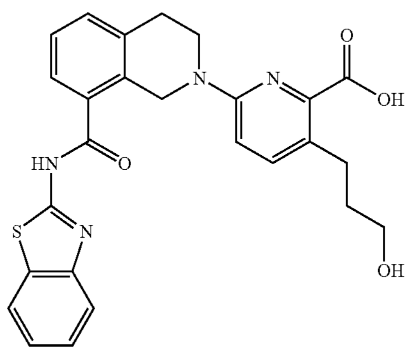 | 6-(8-(benzo[d]thiazol-2-ylcarbamoyl)-3,4-dihydroisoquinolin-2(1H)-yl)-3-(3-hydroxypropyl)picolinic acid |

TABLE 1-continued

| No. | Structure | Name |
|---|---|---|
| 100 | 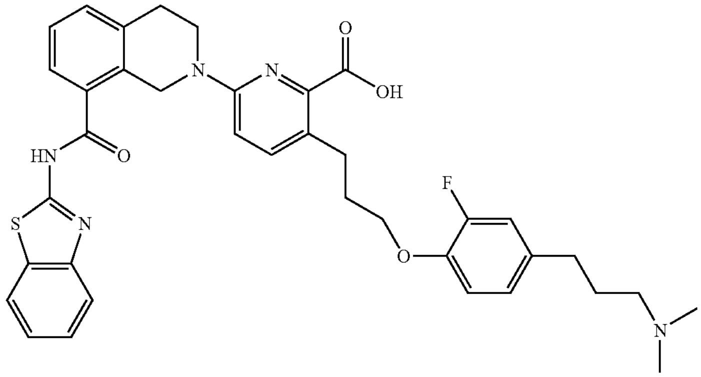 | 6-(8-(benzo[d]thiazol-2-ylcarbamoyl)-3,4-dihydroisoquinolin-2(1H)-yl)-3-(3-(4-(3-(dimethylamino)propyl)-2-fluorophenoxy)propyl)picolinic acid |
| 101 | 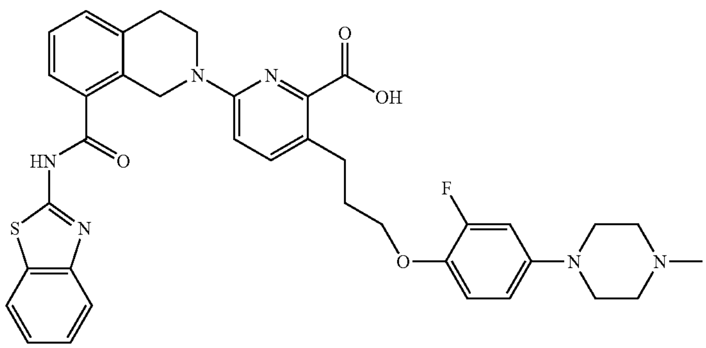 | 6-(8-(benzo[d]thiazol-2-ylcarbamoyl)-3,4-dihydroisoquinolin-2(1H)-yl)-3-(3-(2-fluoro-4-(4-methylpiperazin-1-yl)phenoxy)propyl)picolinic acid |
| 124 | 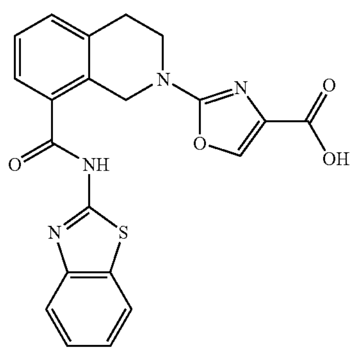 | 2-(8-(benzo[d]thiazol-2-ylcarbamoyl)-3,4-dihydroisoquinolin-2(1H)-yl)oxazole-4-carboxylic acid |
| 122 | 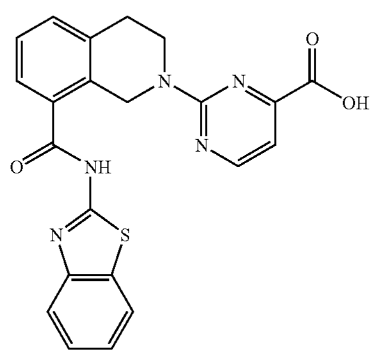 | 2-(8-(benzo[d]thiazol-2-ylcarbamoyl)-3,4-dihydroisoquinolin-2(1H)-yl)pyrimidine-4-carboxylic acid |

| No. | Structure | Name |
| --- | --- | --- |
| 123 | 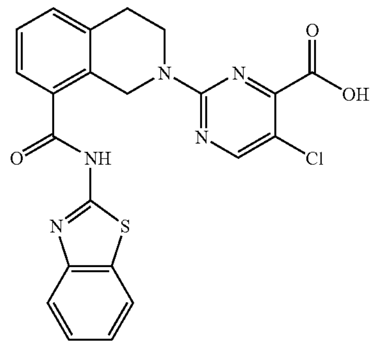 | 2-(8-(benzo[d]thiazol-2-ylcarbamoyl)-3,4-dihydroisoquinolin-2(1H)-yl)-5-chloropyrimidine-4-carboxylic acid |
| 120 | 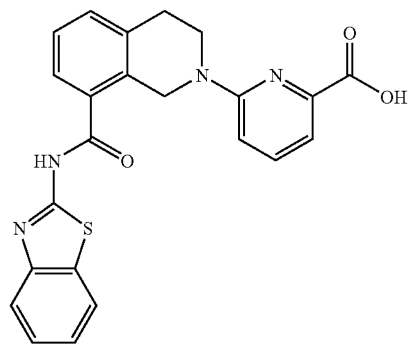 | 6-(8-(benzo[d]thiazol-2-ylcarbamoyl)-3,4-dihydroisoquinolin-2(1H)-yl)picolinic acid |
| 125 | 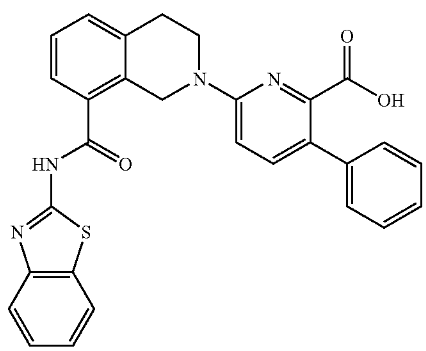 | 6-(8-(benzo[d]thiazol-2-ylcarbamoyl)-3,4-dihydroisoquinolin-2(1H)-yl)-3-phenylpicolinic acid |
| 126 | 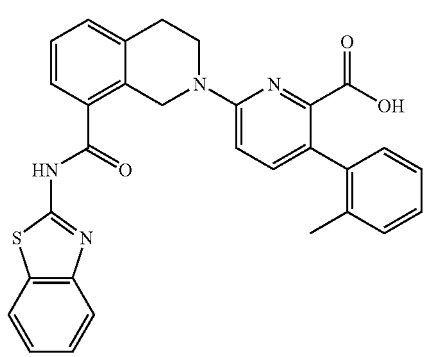 | 6-(8-(benzo[d]thiazol-2-ylcarbamoyl)-3,4-dihydroisoquinolin-2(1H)-yl)-3-o-tolylpicolinic acid |

TABLE 1-continued

| No. | Structure | Name |
|---|---|---|
| 127 | 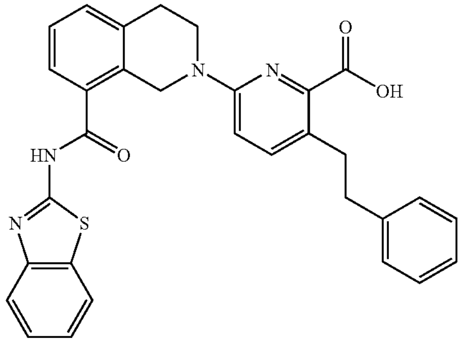 | 6-(8-(benzo[d]thiazol-2-ylcarbamoyl)-3,4-dihydroisoquinolin-2(1H)-yl)-3-phenethylpicolinic acid |
| 136 | 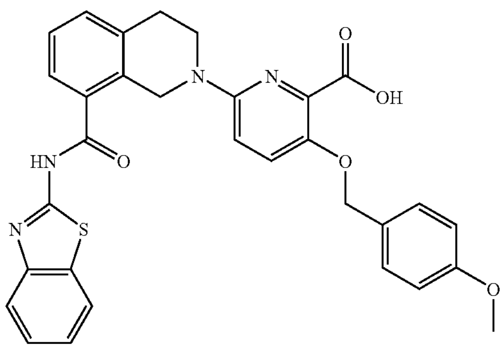 | 6-(8-(benzo[d]thiazol-2-ylcarbamoyl)-3,4-dihydroisoquinolin-2(1H)-yl)-3-(4-methoxybenzyloxy)picolinic acid |
| 137 | 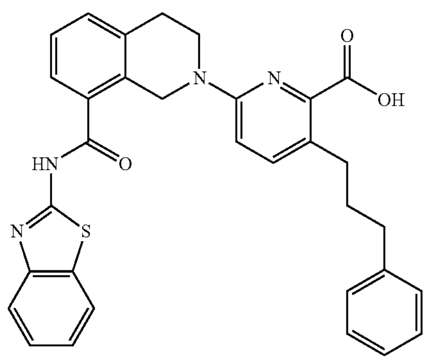 | 6-(8-(benzo[d]thiazol-2-ylcarbamoyl)-3,4-dihydroisoquinolin-2(1H)-yl)-3-(3-phenylpropyl)picolinic acid |
| 138 | 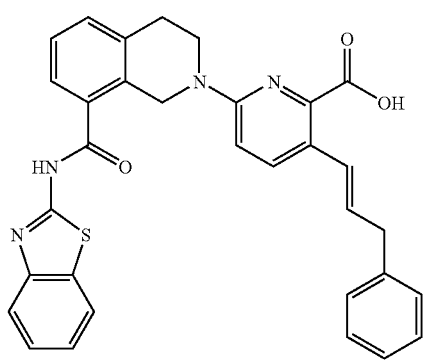 | (E)-6-(8-(benzo[d]thiazol-2-ylcarbamoyl)-3,4-dihydroisoquinolin-2(1H)-yl)-3-(3-phenylprop-1-enyl)picolinic acid |

TABLE 1-continued

| No. | Structure | Name |
|---|---|---|
| 121 | 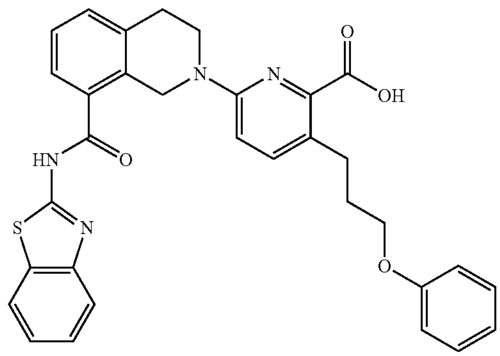 | 6-(8-(benzo[d]thiazol-2-ylcarbamoyl)-3,4-dihydroisoquinolin-2(1H)-yl)-3-(3-phenoxypropyl)picolinic acid |
| 131 | 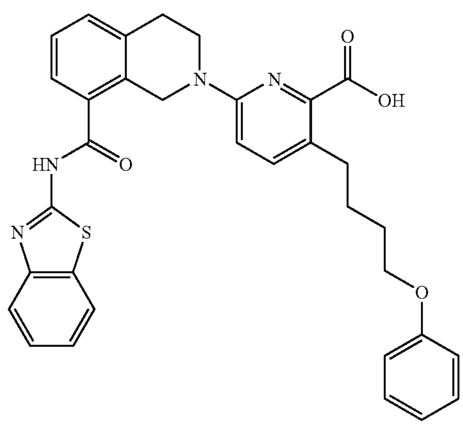 | 6-(8-(benzo[d]thiazol-2-ylcarbamoyl)-3,4-dihydroisoquinolin-2(1H)-yl)-3-(4-phenoxybutyl)picolinic acid |
| 132 | 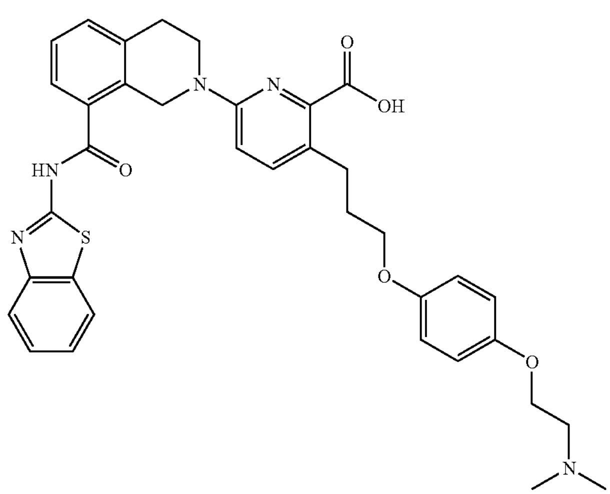 | 6-(8-(benzo[d]thiazol-2-ylcarbamoyl)-3,4-dihydroisoquinolin-2(1H)-yl)-3-(3-(4-(2-(dimethylamino)ethoxy)phenoxy)propyl)picolinic acid |

TABLE 1-continued

| No. | Structure | Name |
|---|---|---|
| 139 | 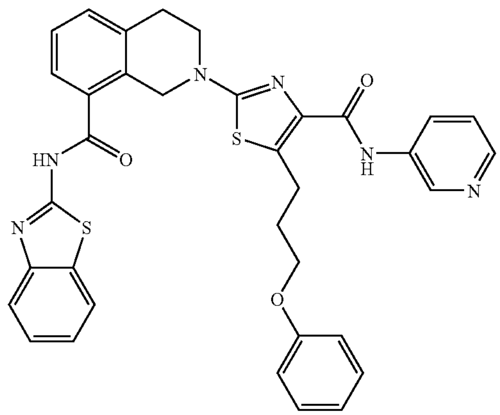 | 2-(8-(benzo[d]thiazol-2-ylcarbamoyl)-3,4-dihydroisoquinolin-2(1H)-yl)-5-(3-phenoxypropyl)-N-(pyridin-3-yl)thiazole-4-carboxamide |
| 134 | 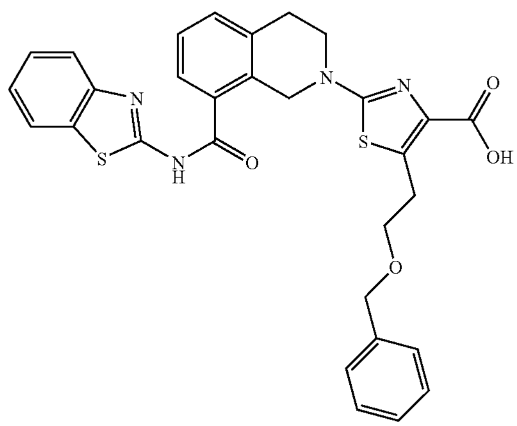 | 2-(8-(benzo[d]thiazol-2-ylcarbamoyl)-3,4-dihydroisoquinolin-2(1H)-yl)-5-(2-(benzyloxy)ethyl)thiazole-4-carboxylic acid |
| 107 | 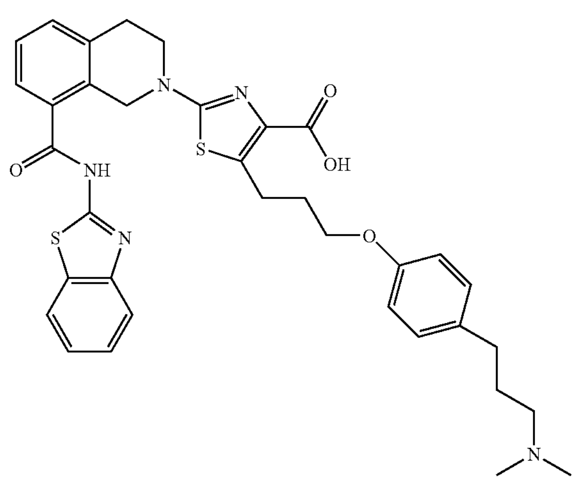 | 2-(8-(benzo[d]thiazol-2-ylcarbamoyl)-3,4-dihydroisoquinolin-2(1H)-yl)-5-(3-(4-(3-(dimethylamino)propyl)phenoxy)propyl)thiazole-4-carboxylic acid |

TABLE 1-continued

| No. | Structure | Name |
|---|---|---|
| 119 | 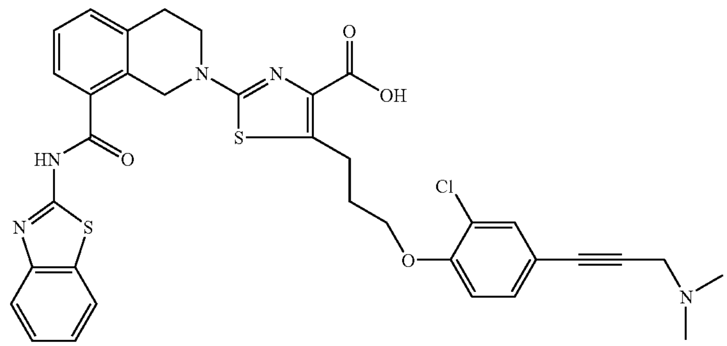 | 2-(8-(benzo[d]thiazol-2-ylcarbamoyl)-3,4-dihydroisoquinolin-2(1H)-yl)-5-(3-(2-chloro-4-(3-(dimethylamino)prop-1-ynyl)phenoxy)propyl)thiazole-4-carboxylic acid |
| 116 | 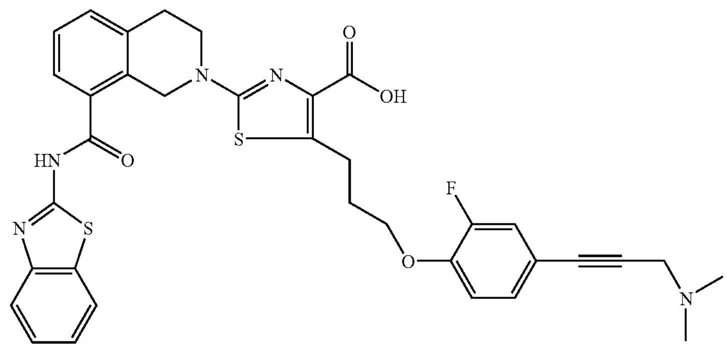 | 2-(8-(benzo[d]thiazol-2-ylcarbamoyl)-3,4-dihydroisoquinolin-2(1H)-yl)-5-(3-(4-(3-(dimethylamino)prop-1-ynyl)-2-fluorophenoxy)propyl)thiazole-4-carboxylic acid |
| 117 | 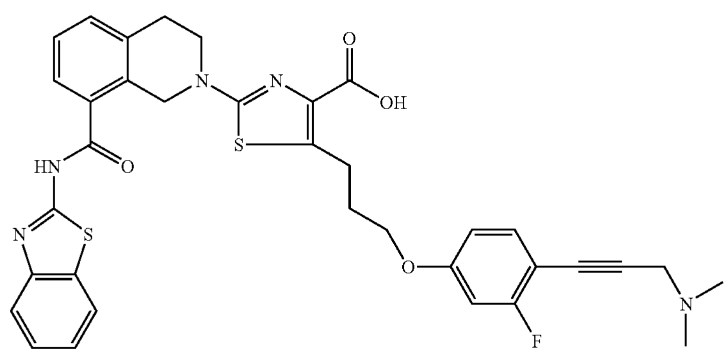 | 2-(8-(benzo[d]thiazol-2-ylcarbamoyl)-3,4-dihydroisoquinolin-2(1H)-yl)-5-(3-(4-(3-(dimethylamino)prop-1-ynyl)-3-fluorophenoxy)propyl)thiazole-4-carboxylic acid |
| 103 | 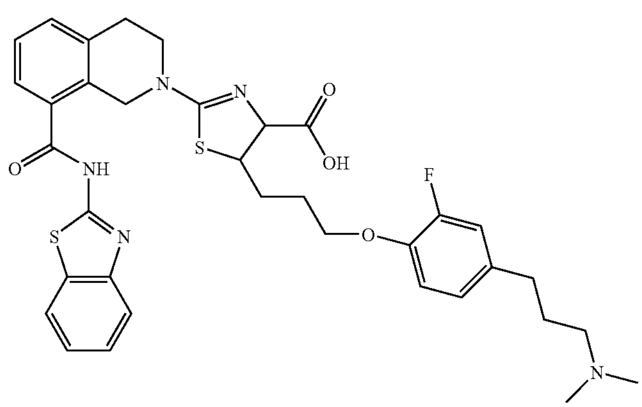 | 2-(8-(benzo[d]thiazol-2-ylcarbamoyl)-3,4-dihydroisoquinolin-2(1H)-yl)-5-(3-(4-(3-(dimethylamino)propyl)-2-fluorophenoxy)propyl)thiazole-4-carboxylic acid |

TABLE 1-continued

| No. | Structure | Name |
|---|---|---|
| 118 | 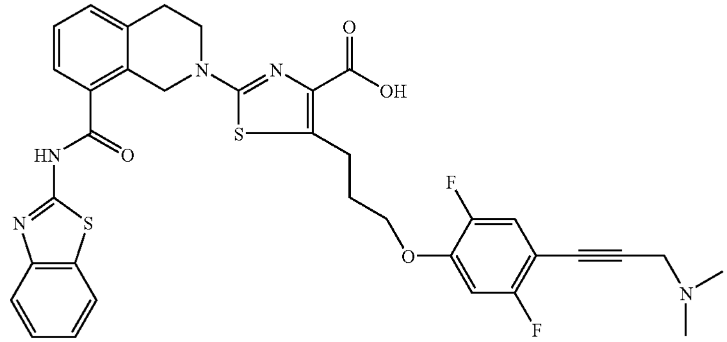 | 2-(8-(benzo[d]thiazol-2-ylcarbamoyl)-3,4-dihydroisoquinolin-2(1H)-yl)-5-(3-(4-(3-(dimethylamino)prop-1-ynyl)-2,5-difluorophenoxy)propyl)thiazole-4-carboxylic acid |
| 114 | 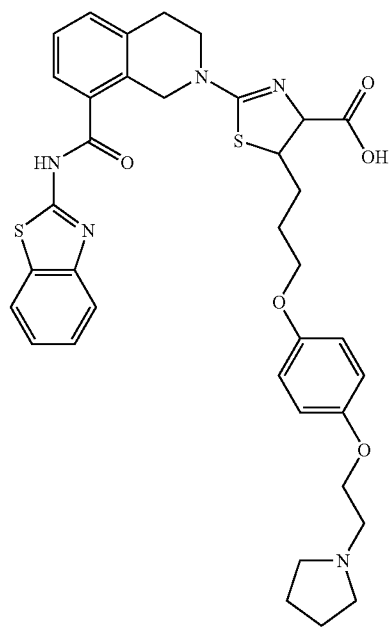 | 2-(8-(benzo[d]thiazol-2-ylcarbamoyl)-3,4-dihydroisoquinolin-2(1H)-yl)-5-(3-(4-(2-(pyrrolidin-1-yl)ethoxy)phenoxy)propyl)thiazole-4-carboxylic acid |
| 108 | 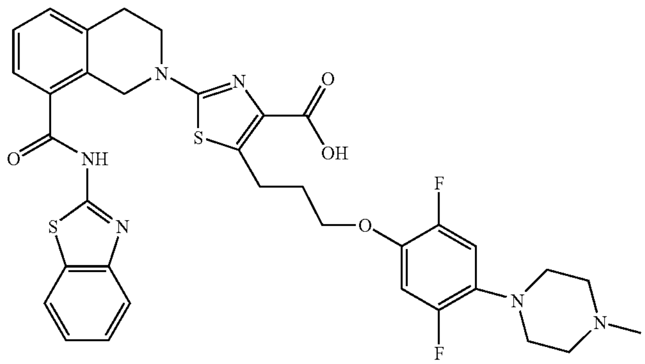 | 2-(8-(benzo[d]thiazol-2-ylcarbamoyl)-3,4-dihydroisoquinolin-2(1H)-yl)-5-(3-(2,5-difluoro-4-(4-methylpiperazin-1-yl)phenoxy)propyl)thiazole-4-carboxylic acid |

TABLE 1-continued

| No. | Structure | Name |
|---|---|---|
| 115 | 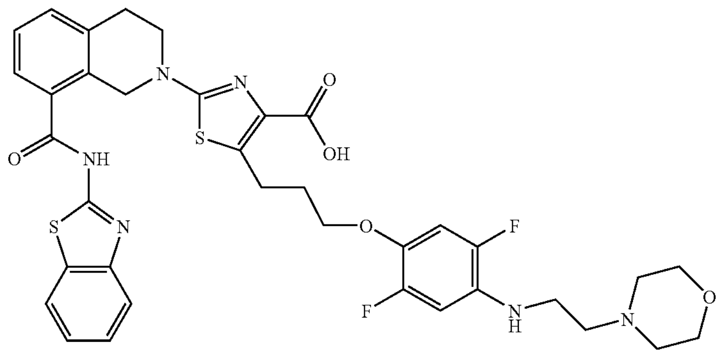 | 2-(8-(benzo[d]thiazol-2-ylcarbamoyl)-3,4-dihydroisoquinolin-2(1H)-yl)-5-(3-(2,5-difluoro-4-(2-morpholinoethylamino)phenoxy)propyl)thiazole-4-carboxylic acid |
| 135 | 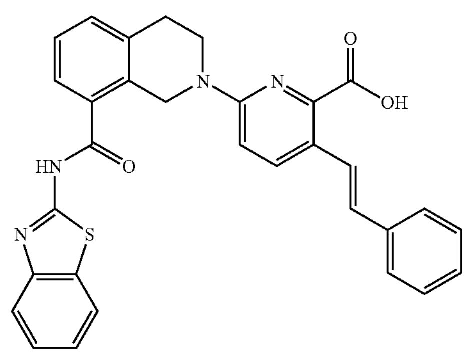 | (E)-6-(8-(benzo[d]thiazol-2-ylcarbamoyl)-3,4-dihydroisoquinolin-2(1H)-yl)-3-styrylpicolinic acid |
| 109 | 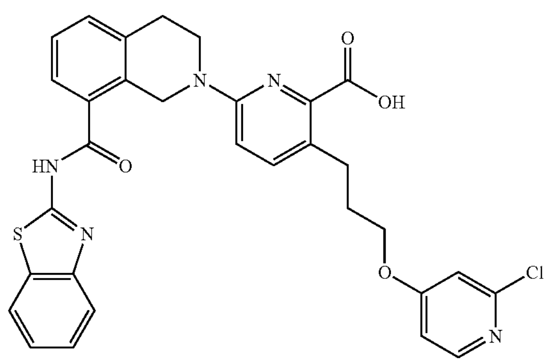 | 6-(8-(benzo[d]thiazol-2-ylcarbamoyl)-3,4-dihydroisoquinolin-2(1H)-yl)-3-(3-(2-chloropyridin-4-yloxy)propyl)picolinic acid |
| 128 | 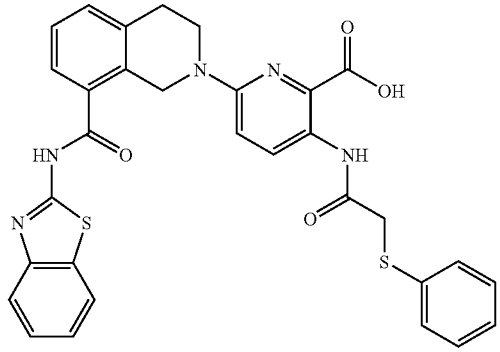 | 6-(8-(benzo[d]thiazol-2-ylcarbamoyl)-3,4-dihydroisoquinolin-2(1H)-yl)-3-(2-(phenylthio)acetamido)picolinic acid |

TABLE 1-continued

| No. | Structure | Name |
|---|---|---|
| 129 | 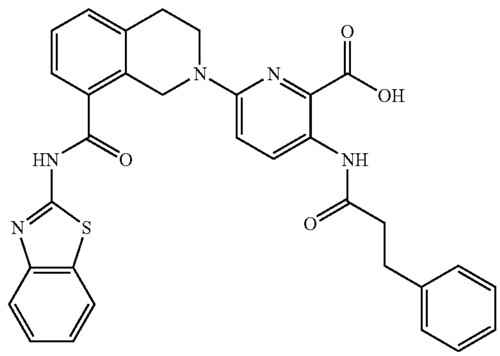 | 6-(8-(benzo[d]thiazol-2-ylcarbamoyl)-3,4-dihydroisoquinolin-2(1H)-yl)-3-(3-phenylpropanamido)picolinic acid |
| 130 | 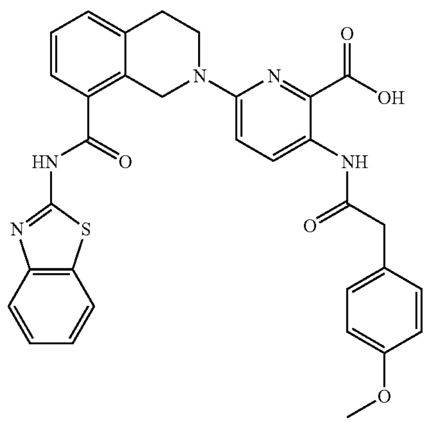 | 6-(8-(benzo[d]thiazol-2-ylcarbamoyl)-3,4-dihydroisoquinolin-2(1H)-yl)-3-(2-(4-methoxyphenyl)acetamido)picolinic acid |
| 102 | 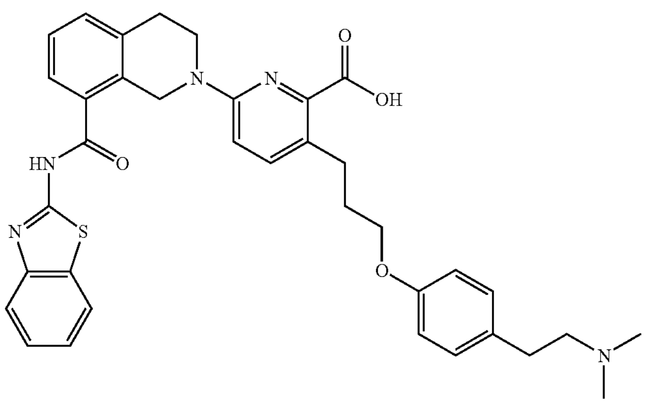 | 6-(8-(benzo[d]thiazol-2-ylcarbamoyl)-3,4-dihydroisoquinolin-2(1H)-yl)-3-(3-(4-(2-(dimethylamino)ethyl)phenoxy)propyl)picolinic acid |
| 113 | 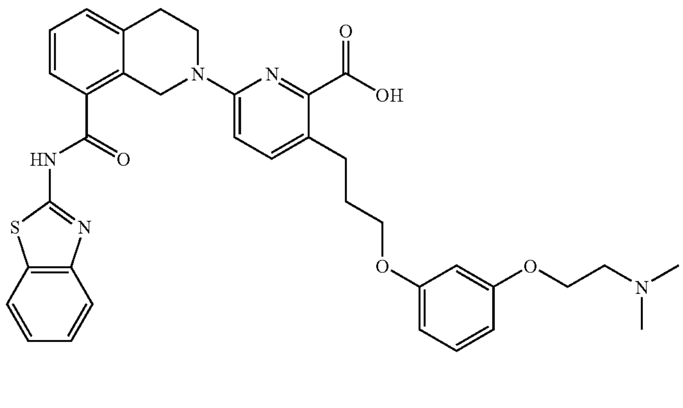 | 6-(8-(benzo[d]thiazol-2-ylcarbamoyl)-3,4-dihydroisoquinolin-2(1H)-yl)-3-(3-(3-(2-(dimethylamino)ethoxy)phenoxy)propyl)picolinic acid |

TABLE 1-continued

| No. | Structure | Name |
|---|---|---|
| 133 | 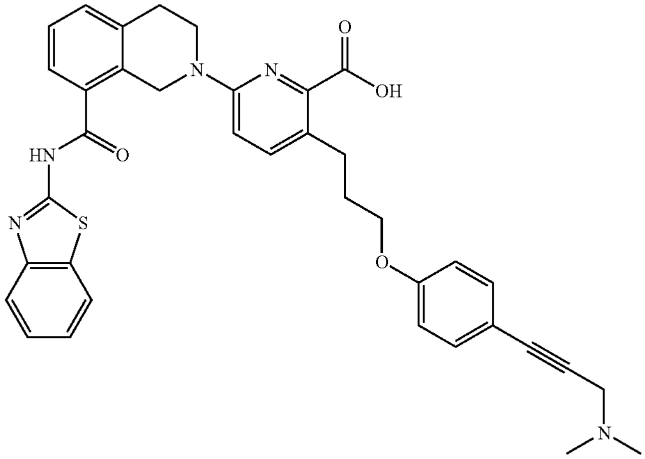 | 6-(8-(benzo[d]thiazol-2-ylcarbamoyl)-3,4-dihydroisoquinolin-2(1H)-yl)-3-(3-(4-(3-(dimethylamino)prop-1-ynyl)phenoxy)propyl)picolinic acid |
| 106 | 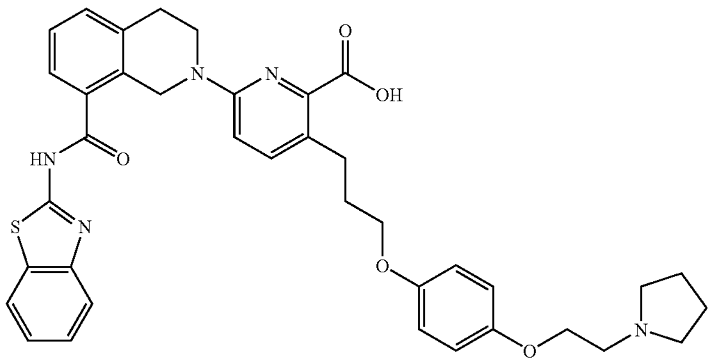 | 6-(8-(benzo[d]thiazol-2-ylcarbamoyl)-3,4-dihydroisoquinolin-2(1H)-yl)-3-(3-(4-(2-(pyrrolidin-1-yl)ethoxy)phenoxy)propyl)picolinic acid |
| 105 | 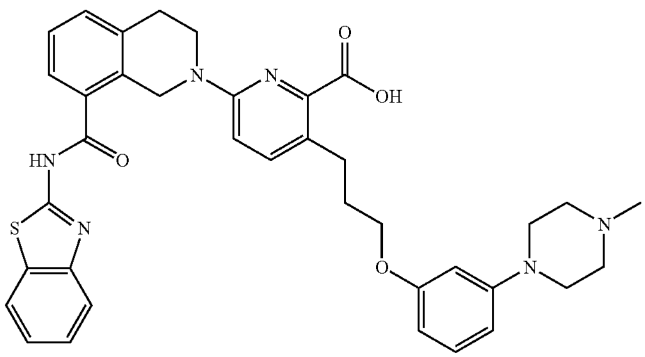 | 6-(8-(benzo[d]thiazol-2-ylcarbamoyl)-3,4-dihydroisoquinolin-2(1H)-yl)-3-(3-(3-(4-methylpiperazin-1-yl)phenoxy)propyl)picolinic acid |
| 104 | 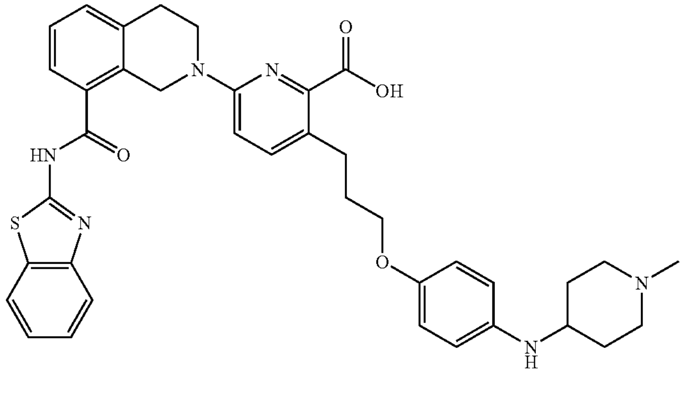 | 6-(8-(benzo[d]thiazol-2-ylcarbamoyl)-3,4-dihydroisoquinolin-2(1H)-yl)-3-(3-(4-(1-methylpiperidin-4-ylamino)phenoxy)propyl)picolinic acid |

TABLE 1-continued

| No. | Structure | Name |
|---|---|---|
| 112 | 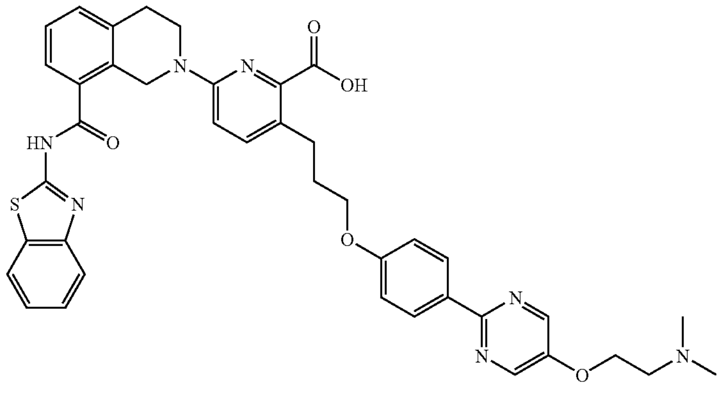 | 6-(8-(benzo[d]thiazol-2-ylcarbamoyl)-3,4-dihydroisoquinolin-2(1H)-yl)-3-(3-(4-(5-(2-(dimethylamino)ethoxy)pyrimidin-2-yl)phenoxy)propyl)picolinic acid |
| 110 | 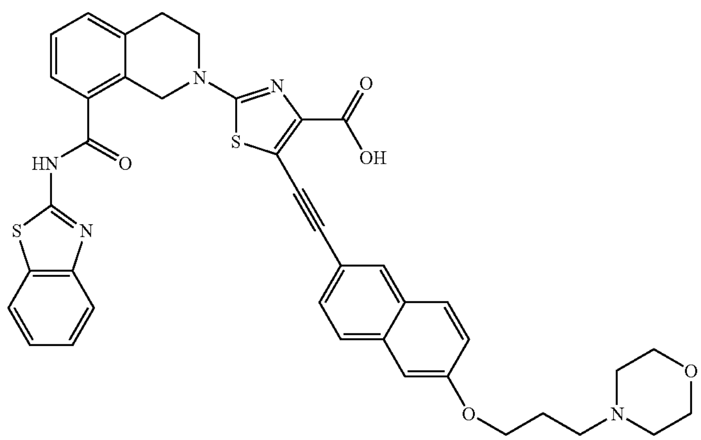 | 2-(8-(benzo[d]thiazol-2-ylcarbamoyl)-3,4-dihydroisoquinolin-2(1H)-yl)-5-((6-(3-morpholinopropoxy)naphthalen-2-yl)ethynyl)thiazole-4-carboxylic acid |
| 111 | 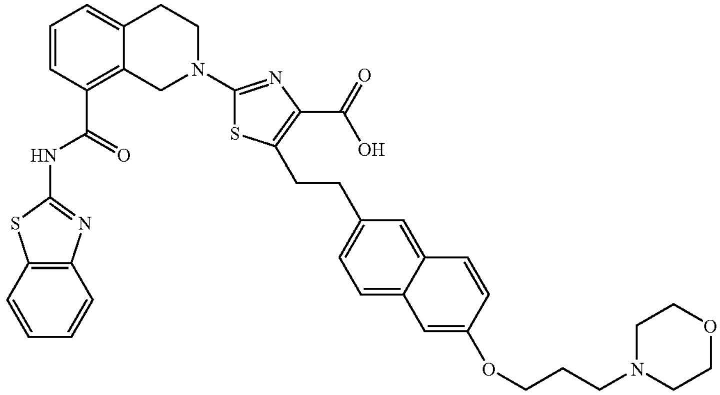 | 2-(8-(benzo[d]thiazol-2-ylcarbamoyl)-3,4-dihydroisoquinolin-2(1H)-yl)-5-(2-(6-(3-morpholinopropoxy)naphthalen-2-yl)ethyl)thiazole-4-carboxylic acid |

TABLE 1-continued

| No. | Structure | Name |
| --- | --- | --- |
| 140 | 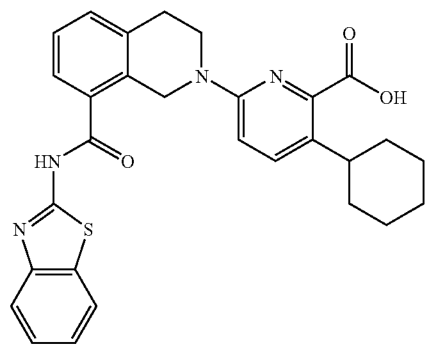 | 6-(8-(benzo[d]thiazol-2-ylcarbamoyl)-3,4-dihydroisoquinolin-2(1H)-yl)-3-cyclohexyl-picolinic acid |
| 141 | 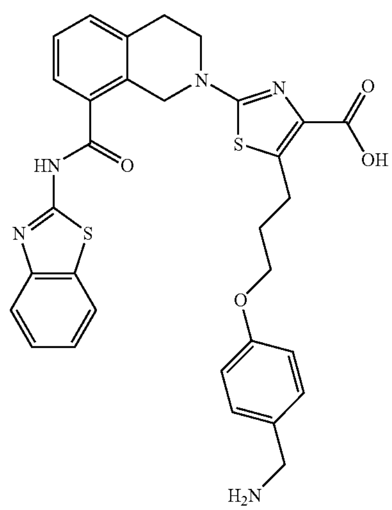 | 5-(3-(4-(aminomethyl)phenoxy)propyl)-2-(8-(benzo[d]thiazol-2-ylcarbamoyl)-3,4-dihydroisoquinolin-2(1H)-yl)thiazole-4-carboxylic acid |
| 142 | 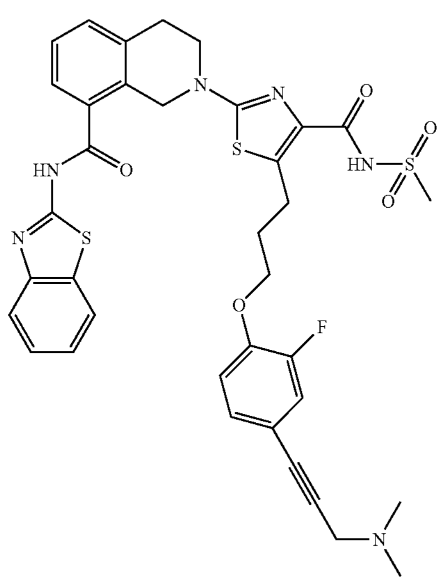 | 2-(8-(benzo[d]thiazol-2-ylcarbamoyl)-3,4-dihydroisoquinolin-2(1H)-yl)-5-(3-(4-(3-(dimethylamino)prop-1-ynyl)-2-fluorophenoxy)propyl)-N-(methylsulfonyl)thiazole-4-carboxamide |

… TABLE 1-continued
| No. | Structure | Name |
|---|---|---|
| 143 | 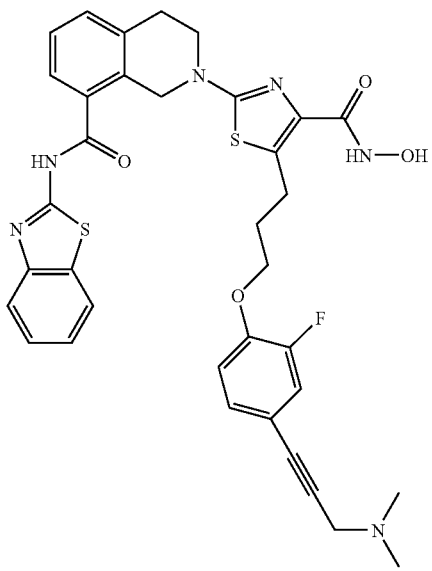 | 2-(8-(benzo[d]thiazol-2-ylcarbamoyl)-3,4-dihydroisoquinolin-2(1H)-yl)-5-(3-(4-(3-(dimethylamino)prop-1-ynyl)-2-fluorophenoxy)propyl)-N-hydroxythiazole-4-carboxamide |
| 144 | 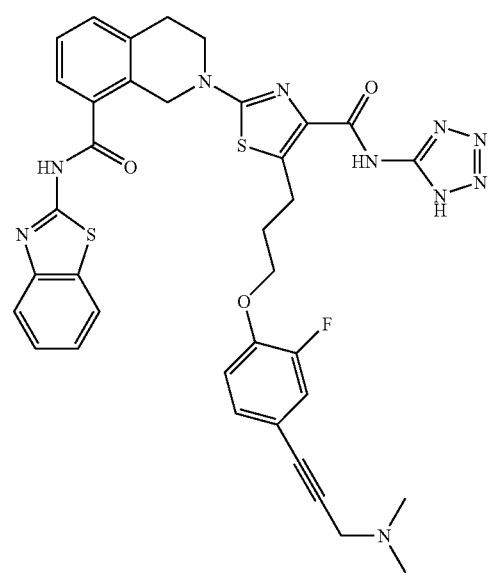 | 2-(8-(benzo[d]thiazol-2-ylcarbamoyl)-3,4-dihydroisoquinolin-2(1H)-yl)-5-(3-(4-(3-(dimethylamino)prop-1-ynyl)-2-fluorophenoxy)propyl)-N-(1H-tetrazol-5-yl)thiazole-4-carboxamide |

TABLE 1-continued

| No. | Structure | Name |
|---|---|---|
| 145 | 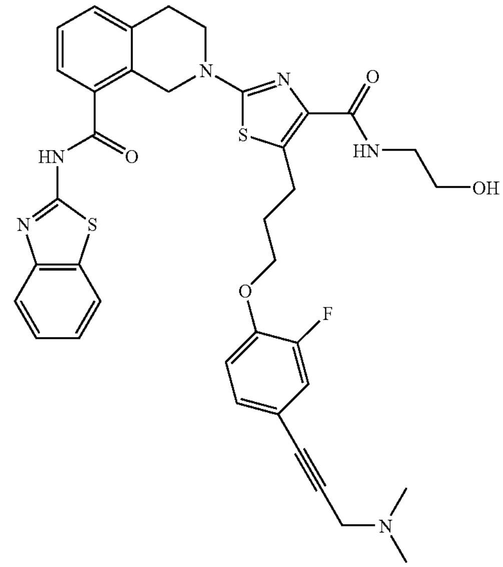 | 2-(8-(benzo[d]thiazol-2-ylcarbamoyl)-3,4-dihydroisoquinolin-2(1H)-yl)-5-(3-(4-(3-(dimethylamino)prop-1-ynyl)-2-fluorophenoxy)propyl)-N-(2-hydroxyethyl)thiazole-4-carboxamide |
| 146 | 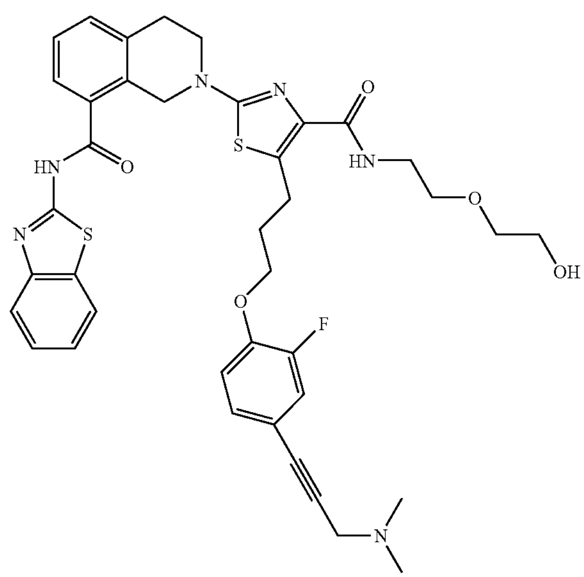 | 2-(8-(benzo[d]thiazol-2-ylcarbamoyl)-3,4-dihydroisoquinolin-2(1H)-yl)-5-(3-(4-(3-(dimethylamino)prop-1-ynyl)-2-fluorophenoxy)propyl)-N-(2-(2-hydroxyethoxy)ethyl)thiazole-4-carboxamide |

TABLE 1-continued

| No. | Structure | Name |
|---|---|---|
| 147 | 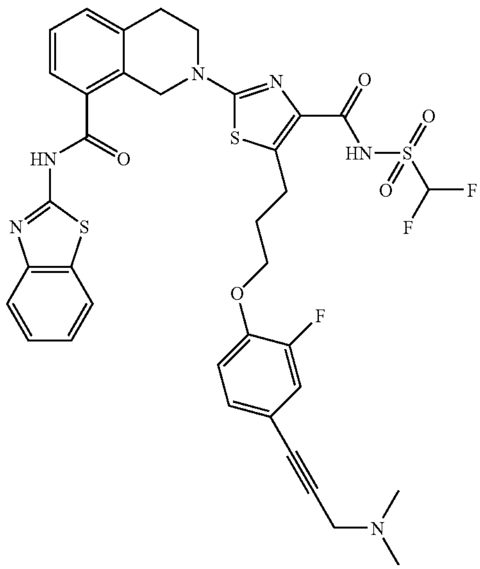 | 2-(8-(benzo[d]thiazol-2-ylcarbamoyl)-3,4-dihydroisoquinolin-2(1H)-yl)-N-(difluoromethylsulfonyl)-5-(3-(4-(3-(dimethylamino)prop-1-ynyl)-2-fluorophenoxy)propyl)thiazole-4-carboxamide |
| 148 | 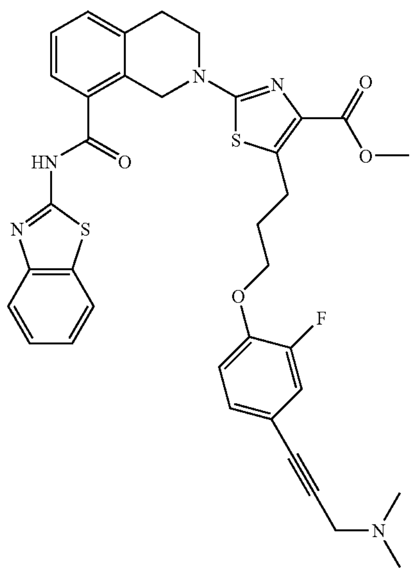 | methyl 2-(8-(benzo[d]thiazol-2-ylcarbamoyl)-3,4-dihydroisoquinolin-2(1H)-yl)-5-(3-(4-(3-(dimethylamino)prop-1-ynyl)-2-fluorophenoxy)propyl)thiazole-4-carboxylate |

General Synthetic Procedures

Compounds of the invention can be prepared by synthetic methods known in the art, some of which are described below for illustrative purposes. N-Boc-8-hydroxycarbonyl-1,2,3,4-tetrahydroisoquinoline has the CAS registry number 878798-87-9 and is commercially available from ASW MedChem Products Inc, New Brunswick, N.J., or can be prepared by following a modified procedure as described in *Helvetica Chimica Acta*, 68 (1985) 1828-1834 as shown in Scheme 1 below.

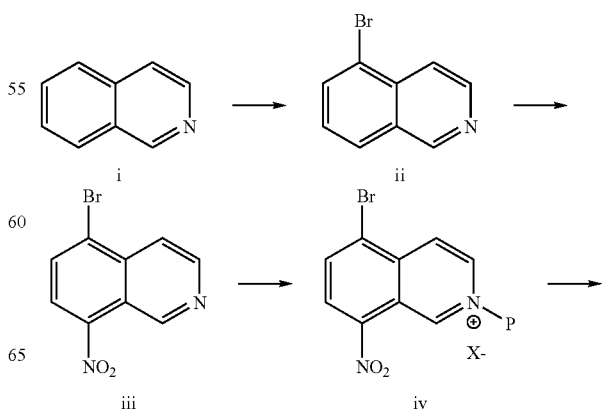

Scheme 1

-continued

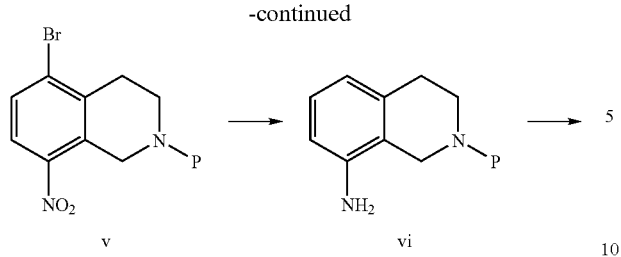

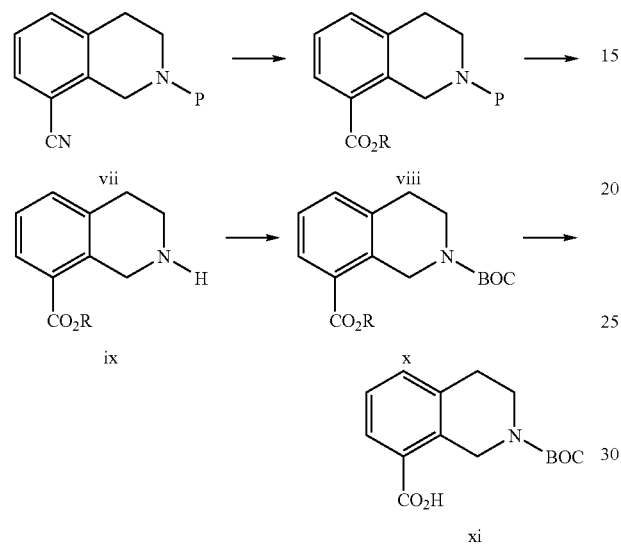

As shown in Scheme 1 above, compounds of Formula I having a tetrahydroisoquinoline core can be prepared starting with bromination of tetrahydroisoquinoline (i) with, for example, $Br_2$ in the presence of a Lewis acid, e.g., $AlCl_3$, to produce bromide compound ii, followed by nitration to form 5-bromo-8-nitroisoquinoline (iii). Substitution of the nitrogen atom of the isoquinoline ring with a protecting group (P), such as for example a benzyl, tosyl, trimethylsilylethoxymethyl (SEM) or 2-trimethylsilylethylsufonyl (SES) group, followed by reduction of the resultant pyridinium ring using a hydride reagent, such as for example, $NaBH_3CN$, can provide the tetrahydroisoquinoline compound v. Debromination and reduction of the nitro group on v can be accomplished using mild hydrogenation condition, e.g., $H_2$, Pd/C, to provide amino compound vi. Treatment of vi under Sandmeyer conditions, e.g., $HNO_2$, CuCN, can provide nitrile vii, which upon acidic hydrolysis (HCl aq.) in an alcoholic solvent (R—OH, e.g., methanol, ethanol) can provide ester viii. The conditions used to remove the protecting group (P) on compound viii, will depend on the nature of the protecting group. For example, hydrogenation conditions (e.g., $H_2$, $Pt_2O$) can be used to remove a benzyl protecting group; metal reduction conditions (Na, naphthalene) can be used to remove a tosyl group; and desilylation conditions (e.g., CsF) can be used to remove the SES or SEM group, to provide the secondary amine ix. Reprotection of ix with Boc anhydride followed by hydrolysis of the ester (—$CO_2R$) group under basic conditions (e.g., LiOH) can provide the tetrahydroisoquinoline core acid x.

Compounds of Formula I having a tetrahydropyridinopyrimidine core can be prepared as shown below in Scheme 2.

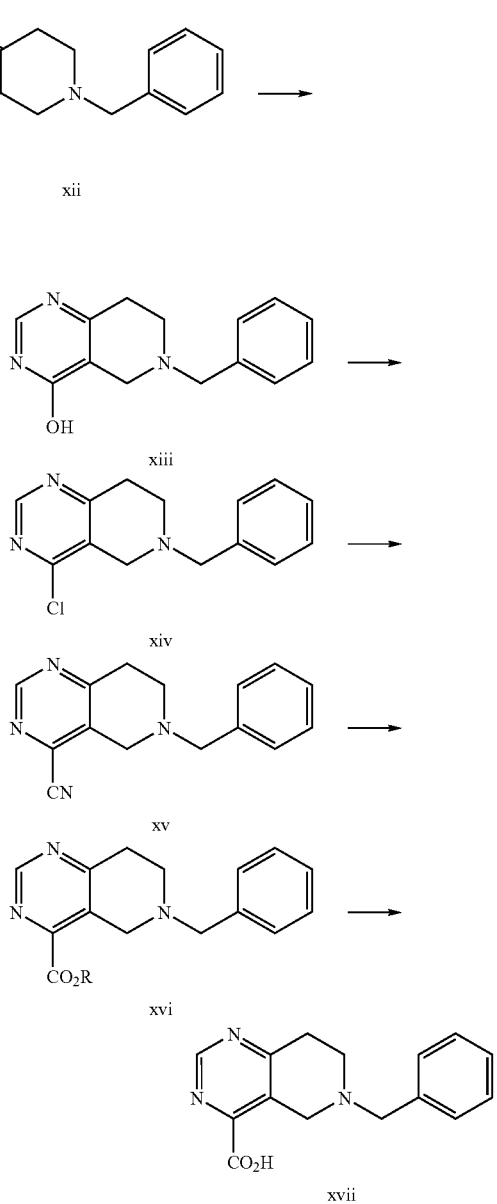

In Scheme 2, beta-ketoester xii is condensed with formamidine acetate to provide hydroxypyrimidine xiii. Conversion of the hydroxy group in xiii to a chloro group can be accomplished using $POCl_3$ to provide chloride xiv. Chloride xiv can be further converted to the corresponding nitrile xv by reaction with $Zn(CN)_2$ in the presence of a Pd(0) catalyst (e.g., $Pd(PPh_3)_4$. Hydrolysis of the nitrile product xv can be accomplished under acidic conditions (e.g., HCl/MeOH) to provide ester xvi, which can be hydrolyzed under basic conditions (e.g. NaOH, MeOH) to provide acid xvii.

Compounds of Formula I having a benzazepeine core can be prepare using a modified procedure as described in Scheme 3 below (see, Tetrahedron Letters, (1980), 1393; J Chem Soc Perkin Trans I, (1973), 782).

Scheme 3

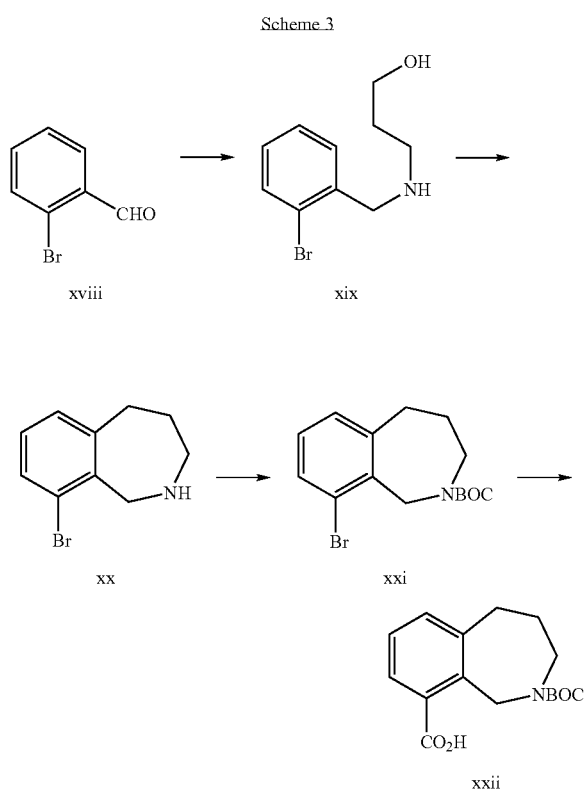

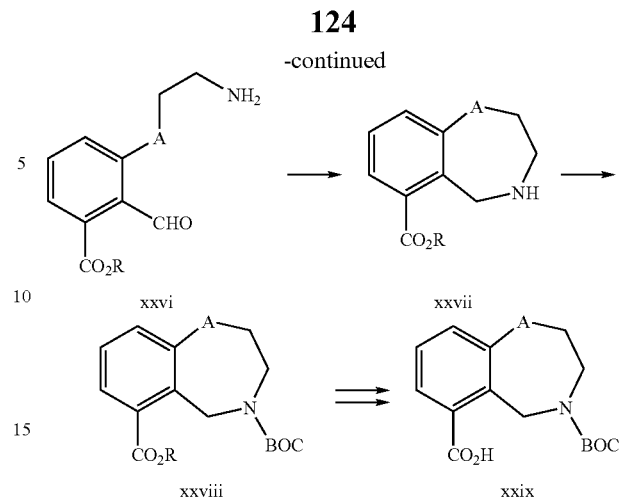

Bromobenzaldehyde xviii can be treated with 3-hydroxypropylamine under reductive amination conditions to provide the amine xix, which can be cyclized under Friedel-Crafts alkylation condition (e.g., AlCl$_3$) to provide benzoazepine xx. Protection of the secondary amine nitrogen atom on xx with BOC anhydride can provide xxi. Treatment of bromide xxi under lithium-halogen exchange conditions and quenching lithium anion of xxi with CO$_2$ can provide the desired benzoazepeine product xxii.

Compounds of Formula I having a benzooxazepeine, benzodiazepeine, or benzothiazepeine core can be prepare as described in Scheme 4 below.

Scheme 4

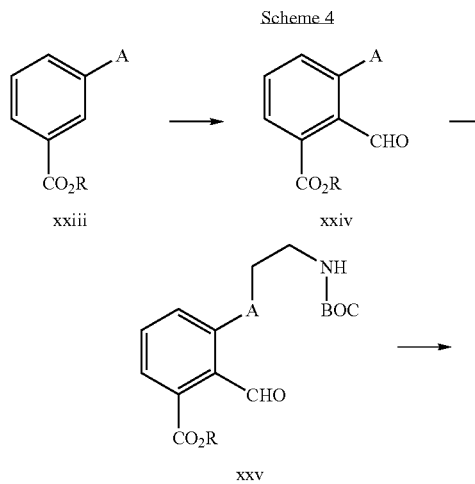

In Scheme 4, ester xxiii, in which R group is methyl or ethyl, can be formylated by treatment with hexamine and polyphosphoric acid to provide aldehyde xxiv. In Scheme 4, the symbol "A" represents a nucleophilic group, e.g., NH$_2$, SH, OH, NRH (wherein R is alkyl, acyl, etc). Alkylation of xxiv using tert-butyl 2-chloroethylcarbamate will provide xxv. Compound xxv can be treated with methanolic HCl to result in the removal of the Boc group xxvi. Intramolecular cyclization of xxvi in the presence of a reducing agent (e.g., NaBH$_4$) can provide compound xxvii, which is further reprotected with a Boc anhydride to provide the N-Boc compound xxviii. Hydrolysis of the ester group can provide the acid compound xxix.

As shown in Scheme 5, tetrahydroisoquinoline acid core xi can be further coupled to a suitable aryl amine (Ar—NH$_2$) using a number of standard amino acid coupling conditions, such as for example, 1-O-Benzotriazole-N,N,N',N'-tetramethyl-uronium-hexafluoro-phosphate and diethylisopropylamine, in DMF to provide amide xxx. The isoquinoline nitrogen atom can be deprotected under acidic conditions (e.g., 4N methanolic HCl) to provide free secondary amine xxxi.

Scheme 5

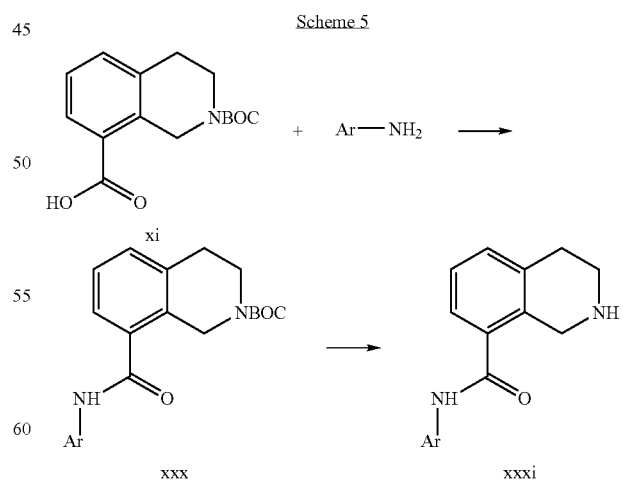

Further synthetic transformation that can be used to convert compound xxxi (and related compounds such as, for example, xvii, xxii and xxix) to compounds of Formula I described in detail throughout the Examples section.

III. Compositions

In addition to one or more of the compounds provided above (or stereoisomers, geometric isomers, tautomers, solvates, metabolites or pharmaceutically acceptable salts, or prodrugs thereof), compositions for modulating Bcl-2 protein family activity in humans and animals will typically contain a pharmaceutical carrier or diluent. In one embodiment, the invention provides for a pharmaceutical composition comprising a compound of Formula I and at least one pharmaceutically acceptable diluent, carrier or excipient.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In order to use a compound of this invention for the therapeutic treatment (including prophylactic treatment) of a patient, it is normally formulated in accordance with standard pharmaceutical practice as a pharmaceutical composition. A typical pharmaceutical composition is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300, etc.) and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations can be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

The pharmaceutical composition (or formulation) for application can be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container can also include a tamper-proof assemblage to prevent indiscreet access to the contents of the package. In addition, the container has deposited thereon a label that describes the contents of the container. The label can also include appropriate warnings.

Pharmaceutical compositions of a compound of the present invention can be prepared for various routes and types of administration. For example, a compound of the invention (e.g., a compound of Formula I) having the desired degree of purity can optionally be mixed with pharmaceutically acceptable diluents, carriers, excipients or stabilizers (see, Remington: The Science and Practice of Pharmacy: Remington the Science and Practice of Pharmacy (2005) $21^{st}$ Edition, Lippincott Williams & Wilkins, Philadelphia, Pa.), in the form of a lyophilized formulation, milled powder, or an aqueous solution. Compositions can be prepared by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but can range from about 3 to about 8. Formulation in an acetate buffer at pH 5 is a suitable embodiment.

A compound of this invention (e.g., compound of Formula I) for use herein is preferably sterile. In particular, compositions or formulations to be used for in vivo administration must be sterile. Such sterilization is readily accomplished by filtration through sterile filtration membranes.

A compound of the invention ordinarily can be stored as a solid composition, a lyophilized formulation or as an aqueous solution.

A pharmaceutical composition of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat diseases that can by characterized by the expression or overexpression of Bcl-$x_L$ proteins. Such amount is preferably below the amount that is toxic to the host.

As a general proposition, the initial pharmaceutically effective amount of an inhibitor compound of the invention administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). An active pharmaceutical ingredient of the invention (e.g., compound of Formula I) can also be entrapped in microcapsules prepared, for example, by coacervation techniques or by interfacial polymerization, for example, hydroxymethylcellulose or gelatin-microcapsules and poly-(methylmethacylate) microcapsules, respectively; in colloidal drug delivery systems, for example, liposomes, albumin microspheres, microemulsions, nano-particles and nanocapsules; or in macroemulsions. Such techniques are disclosed in Remington: The Science and Practice of Pharmacy: Remington the Science and Practice of Pharmacy (2005) $21^{st}$ Edition, Lippincott Williams & Wilkins, Philidelphia, Pa.

Sustained-release compositions of a compound of the invention (e.g., compound of Formula I) can be prepared. Suitable examples of sustained-release compositions include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid.

Pharmaceutical compositions include those suitable for the administration routes detailed herein. The compositions can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) $21^{st}$ Edition, Lippincott Williams & Wilkins, Philidelphia, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Pharmaceutical compositions of a compound of the invention (e.g., compound of Formula I) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient, which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include TWEEN® 60, SPAN® 80, cetostearyl alcohol, benzyl alcohol, myristyl alcohol, glyceryl mono-stearate and sodium lauryl sulfate.

Aqueous suspensions of a compound of the invention (e.g., compound of Formula I) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

A pharmaceutical composition of a compound of the invention (e.g., compound of Formula I) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable composition can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release composition intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Compositions suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Compositions suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Compositions suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Compositions for rectal administration can be presented as a suppository with a suitable base comprising for example cocoa butter or a salicylate.

Compositions suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment or prophylaxis disorders as described below.

Compositions suitable for vaginal administration can be presented as pessaries, tampons, creams, gels, pastes, foams or spray formulations containing in addition to the active ingredient such carriers as are known in the art to be appropriate.

The pharmaceutical compositions can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient (e.g., compound of Formula I) as above defined together with a veterinary carrier therefore. Veterinary carriers are materials useful for the purpose of administering the composition and can be solid, liquid or gaseous materials which are otherwise inert or acceptable in the veterinary art and are compatible with the active ingredient. These veterinary compositions can be administered parenterally, orally or by any other desired route.

IV. Methods of Use

The compounds of the invention (i.e., compounds of Formula I) (or stereoisomers, geometric isomers, tautomers, solvates, metabolites or pharmaceutically acceptable salts, or prodrugs thereof) bind to and inhibit the activity of anti-apoptotic Bcl-2 family proteins, and in certain aspects, of specifically anti-apoptotic Bcl-$x_L$ proteins; and therefore are useful in the treatment of diseases, conditions and/or disorders including, but not limited to, those diseases characterized by the expression or over-expression of anti-apoptotic Bcl-2 family protein members, and in certain embodiments those diseases characterized by the expression or the over-expression of Bcl-$x_L$ proteins. Accordingly, a certain aspect of this invention includes a method of treating diseases or conditions in a patient that can be characterized by the expression or over-expression of anti-apoptotic Bcl-2 protein family members. Within this aspect, in certain embodiments, the disease or condition is cancer. Compounds of the invention can selectively bind to a subgroup of anti-apoptotic Bcl-2 proteins, for example, of Bcl-$x_L$ over Bcl-2, Bcl-w or Mcl-1 proteins. In certain embodiments, compounds of the invention exhibit at least a 2-fold, 10-fold, 20-fold, 50-fold, 100-fold, 1000-fold, 10000-fold, 20000-fold, or 30000-fold selectivity for binding a Bcl-$x_L$ protein over a Bcl-2 protein. In certain embodiments, compounds of the invention exhibit at least a 2-fold, 10-fold, 20-fold, 50-fold, 100-fold, 1000-fold, 10000-fold, 20000-fold, or 30000-fold selectivity for binding a Bcl-$x_L$ protein over a Mcl-1 protein. In certain embodiments, compounds of the invention exhibit at least a 2-fold, 10-fold, 20-fold, 50-fold, 100-fold, 1000-fold, 10000-fold, 20000-fold, or 30000-fold selectivity for binding a Bcl-$x_L$ protein over a Bcl-w protein. In one embodiment, the method comprises administering to a patient in need thereof, a therapeutically effective amount of a compound of the invention, e.g., compound of Formula I, (or a stereoisomer, geometric isomer, tautomer, solvate, metabolite, or pharmaceutically acceptable salt or prodrug thereof). In another embodiment, the present invention provides for methods of treating diseases and conditions in a patient which is characterized by the expression or over-expression of an anti-apoptotic Bcl-$x_L$ protein, said methods comprising administering to the patient a therapeutically effective amount of a compound of Formula I, or a pharmaceutical composition thereof. In one aspect, said compositions for treating diseases and conditions during which are expressed or over-expressed an antiapoptotic Bcl-$x_L$ protein comprise an excipient and a therapeutically effective amount of the compound of Formula I.

Also provided in the invention is the use of a compound of the invention, e.g., of Formula I, (or stereoisomer, geometric isomer, tautomer, solvate, metabolite, or pharmaceutically acceptable salt, or prodrug thereof), in the preparation of a medicament for the treatment of the diseases and conditions described herein in a patient suffering from such disorder.

The compounds of the invention can be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds can be administered by intralesional administration, including perfusing or otherwise contacting the graft with the inhibitor before transplantation. It will be appreciated that the preferred route can vary with for example the condition of the recipient. Where the compound is administered orally, it can be formulated as a pill, capsule, tablet, etc. with a pharmaceutically acceptable carrier or excipient. Where the compound is administered parenterally, it can be formulated with a pharmaceutically acceptable parenteral vehicle and in a unit dosage injectable form, as detailed below.

A dose to treat human patients can range from about 10 mg to about 1000 mg of a Formula I compound. A typical dose can be about 100 mg to about 300 mg of the compound. A dose can be administered once a day (QID), twice per day (BID), or more frequently, depending on the pharmacokinetic and pharmacodynamic properties, including absorption, distribution, metabolism, and excretion of the particular compound. In addition, toxicity factors can influence the dosage and administration regimen. When administered orally, the pill, capsule, or tablet can be ingested daily or less frequently for a specified period of time. The regimen can be repeated for a number of cycles of therapy.

In another embodiment, the present invention provides for compositions comprising an pharmaceutically acceptable excipient and a therapeutically effective amount of a compound of Formula I for treating diseases or conditions of abnormal cell growth and/or dysregulated apoptosis, such as cancer, mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination thereof.

In another embodiment, the present invention provides for a method of treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination of one or more of the above cancers in a patient, said method comprising administering thereto a therapeutically effective amount of a compound of Formula I.

In yet another embodiment, the present invention provides for methods of treating autoimmune disease in a mammal comprising administering thereto a therapeutically acceptable amount of a compound having Formula I. The involvement of Bcl-2 proteins in immune and autoimmune diseases is described in Puck, J. M. et al. (2003), *Current Allergy and Asthma Reports*, 3, 378-384; Shimazaki, K. et al. (2000), *British Journal of Haematology*, 110(3), 584-90; Rengan, R. et al. (2000), *Blood*, 95(4), 1283-92; and Holzelova, E. et al. (2004), *New England Journal of Medicine*, 351(14), 1409-1418.

Autoimmune disorders include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcmia, microscopic vasculitis of the kidneys, migraine headache, mitochondrial multi-system disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, mycobacterium avium intracellulare, mycobacterium tuberculosis, myelodysplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, yersinia and salmonella-associated arthropathy and the like.

In one embodiment, a compound of the invention (e.g., compound of Formula I), or stereoisomer, geometric isomer, tautomer, solvate, metabolite, or pharmaceutically acceptable salt, prodrug thereof, is used as an anticancer agent or as an adjunct agent for the treatment of cancer in a combination therapy. One of ordinary skill in the art is readily able to determine whether or not a candidate compound treats a cancerous condition for any particular cell type, either alone or in combination. Within certain aspects of this embodiment, compounds of the invention are used in adjunct with other therapies, including conventional surgery, radiotherapy and chemotherapy, for the treatment of cancer.

Such therapies can include one or more of the following categories of anti-cancer agents: alkylating agents, angiogenesis inhibitors, antibodies, antimetabolites, antimitotics, antiproliferatives, aurora kinase inhibitors, apoptosis promoters (for example, Bcl-xL, Bcl-w and Bfl-1 inhibitors), activators of death receptor pathway, Bcr-Abl kinase inhibitors, BiTE (Bi-Specific T cell Engager) antibodies, biologic response modifiers, cyclin-dependent kinase inhibitors, cell cycle inhibitors, cyclooxygenase-2 inhibitors, dual variable domains binding proteins (DVDs), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAPs) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, combinations thereof and the like.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perform and granzyme B. In this regard, Bcl-2 has been shown to attenuate the induction of apoptosis by both perform and granzyme B. These data suggest that inhibition of Bcl-2 could enhance the cytotoxic effects elicited by T-cells when targeted to cancer cells (V. R. Sutton, D. L. Vaux and J. A. Trapani (1997) J. of Immunology. 158 (12): 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl) amino)-3-((trifluoromethyl)sulfonyl)benzenesulfonamide) or ABT-737 (i.e., N-(4-(4-((4'-chloro(1,1'-biphenyl)-2-yl) methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al (2008) Cancer Research. 68(9): 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Aurora kinase inhibitors include AZD-1152, MLN-8054, VX-680 and the like.

Bcl-2 family protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-((morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Activators of death receptor pathway include TRAIL, antibodies or other agents that target death receptors (e.g., DR4 and DR5) such as Apomab, conatumumab, ETR2-ST01, GDC0145, lexatumumab, HGS-1029, LBY-135, PRO-1762 and trastuzumab.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin), eptaplatin, lobaplatin, nedaplatin, PARAPLATIN® (carboplatin), satraplatin, picoplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzumab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula I may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zoledronic acid), zorubicin and the like.

The combination therapy can be administered as a simultaneous or sequential regimen. When administered sequentially, the combination can be administered in two or more administrations. The combined administration includes coadministration, using separate formulations or a single pharmaceutical formulation, and consecutive administration in either order, wherein preferably there is a time period while both (or all) active agents simultaneously exert their biological activities.

Accordingly, in another embodiment, the present invention provides for compositions for treating diseases in a patient during which is expressed or overexpressed an anti-apoptotic Bcl-$x_L$ protein, said compositions comprising an excipient and a therapeutically effective amount of the compound of Formula I and a therapeutically effective amount of one additional therapeutic agent or more than one additional therapeutic agent.

In another embodiment, the present invention provides for methods of treating diseases in a patient during which is expressed or overexpressed an anti-apoptotic Bcl-$x_L$ protein, said methods comprising administering to the patient a therapeutically effective amount of a compound of Formula I and a therapeutically effective amount of one additional therapeutic agent or more than one additional therapeutic agent.

In another embodiment, the present invention provides for methods of treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination of one or more of the above cancers in a patient, said methods comprising administering thereto therapeutically effective amounts of a compound of Formula I, or a pharmaceutical composition thereof and one or more than one of etoposide vincristine CHOP, rituximab, rapamycin, R-CHOP or bortezomib.

Suitable dosages for any of the above co-administered agents are those presently used and can be lowered due to the combined action (synergy) of the newly identified agent and other chemotherapeutic agents or treatments.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

In yet another embodiment, the present invention provides for methods of treating diseases or conditions caused, exacerbated by or resulting from an excess of, or undesired activation of, platelets in a patient comprising administering thereto a compound of Formula I, or a pharmaceutical composition thereof.

Diseases caused or exacerbated by an excess of, or undesired activation of, platelets include, but are not limited to, essential thrombocythemia, polycythemia vera, M7 acute myelogenous leukemia, restenosis, cardiovascular disease, perioperative antiplatelet therapy, device-associated thrombi and complications associated therewith, and the like. The involvement of platelets in essential thrombocythemia is reported in Seminars in Hematology (2005), 42(4), 230-238 and also in New Eng. J. Med., 2005, 353:1, 33-45. The involvement of platelets in polycythemia vera is reported in Seminars in Thrombosis and Hemostatis (2006), 32(3), 267-275. The involvement of platelets in restenosis is reported in Journal of Clinical Pathology (2006), 59(3), 232-239. The involvement of platelets in cardiovascular disease is reported in International Journal of Clinical Practice (2003), 57(10), 898-905. The involvement of platelets in perioperative antiplatelet therapy is reported in Journal of Thrombosis Thrombolysis. Diseases or conditions that result from elevated platelet levels include bleeding, thrombosis or other thromboembolic complication, initiation or worsening of other diseases or disorders of the blood, such as "sticky platelet" syndrome.

In one embodiment, the present invention provides for methods of reducing the number of platelets in a patient and treating pro-thrombotic conditions and diseases that are characterized by an excess of, or undesired activation of, platelets, by administering thereto a compound of Formula I.

In another embodiment, the present invention provides for methods of treating essential thrombocythemia in a patient comprising administering thereto a compound of Formula I. Within certain aspects of this embodiment, in one embodiment, the present invention provides for a method of reducing the number of platelets in a patient and treating essential thrombocythemia.

In another embodiment, the present invention provides methods of treating polycythemia vera in a patient comprising administering thereto a compound of Formula I which inhibits the activity of an Bcl-$x_L$ family protein member.

Within certain aspects of this embodiment, in one embodiment, the present invention provides methods of reducing the number of platelets in a patient and treating polycythemia vera.

In certain aspects, the present application provides a use of a compound as described herein (e.g., compound of Formula I), or stereoisomer, geometric isomer, tautomer, solvate, metabolite, or pharmaceutically acceptable salt, prodrug thereof, for treating a disease or condition. Exemplary diseases or conditions include, for example, any of the diseases or conditions caused, exacerbated by or resulting from an excess of, or undesired activation of, platelets discussed above, any of the cancers discussed above, or any of the autoimmune diseases discussed above. In certain embodiments of the uses provided, the compound (e.g., compound of Formula I), or stereoisomer, geometric isomer, tautomer, solvate, metabolite, or pharmaceutically acceptable salt, prodrug thereof, is used alone. In other embodiments, the compound (e.g., compound of Formula I), or stereoisomer, geometric isomer, tautomer, solvate, metabolite, or pharmaceutically acceptable salt, prodrug thereof, is used in as part of a combination therapy as discussed above.

In certain aspects, a compound or pharmaceutical composition used in each of the above described methods of the invention is a compound selected from Table 1, or pharmaceutical composition comprising a compound selected from Table 1.

The following examples are provided to illustrate the invention, but should not construed as to limit the invention in any way.

V. Examples

In the Examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters) or on an ISCO chromatography system (Manufacturer: Teledyne ISCO) having a silica gel column, or manually using a glass column as generally following the techniques described by W. C. Still (see, Still, W. C.; Kahn, M.; Mitra, A. *J. Org. Chem.* 1978, 43(14), 2923-2925). $^1$H NMR spectra were recorded on a Varian UNITY or Inova (500 MHz), Varian UNITY (400 MHz), or Varian UNITY plus or Mercury (300 MHz) or similar instrument operating at 300 or 400 MHz. Chemical shifts are reported as δ values (ppm) downfield relative to TMS as an internal standard. $^1$H NMR spectra were obtained in deuterated CDCl$_3$, d$_6$-DMSO, CH$_3$OD or d$_6$-acetone solutions (reported in ppm). Multiplicities reported in the usual manner, and when peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz). When possible, product formation in the reaction mixtures can be monitored by LC/MS, performed either on an Agilent 1200 Series LC coupled to a 6140 quadrupole mass spectrometer using a Supelco Ascentis Express C18 column with a linear gradient of 5%-95% acetonitrile/water (with 0.1% trifluoroacetic acid in each mobile phase) within 1.4 minutes and held at 95% for 0.3 minute, or on a PE Sciex API 150 EX using a Phenomenex DNYC monolithic C18 column with a linear gradient of 5%-95% acetonitrile/water (with 0.1% trifluoroacetic acid in each mobile phase) within 5 minutes and held at 95% for 1 minute, or similar system. Alternatively, analytical LC-MS was performed on a Finnigan Navigator mass spectrometer and Agilent 1100 HPLC system running Xcalibur 1.2 and Open-Access 1.3 software. The mass spectrometer was operated under positive APCI ionization conditions. The HPLC system comprised an Agilent Quaternary pump, degasser, column compartment, and autosampler and diode-array detector, with a SEDERE SEDEX 75 evaporative light-scattering detector. The column used was a Phenomenex Luna Combi-HTS C8(2) 5 µm 100 Å (2.1 mm×30 mm). TFA Method (Method A): A gradient of 10-100% acetonitrile (solvent 1) and 0.1% trifluoroacetic acid in water (solvent 2) was used, at a flow rate of 2 mL/min (0-0.1 min 10% solvent 1, 0.1-2.6 min 10-100% solvent 1, 2.6-2.9 min 100-10% solvent 1, 2.9-3.0 min 100-10% solvent 1). Ammonium Method (Method B): A gradient of 10-100% acetonitrile (solvent 1) and 10 mM NH4OAc in water (solvent 2) was used, at a flow rate of 1.5 mL/min (0-0.1 min 10% solvent 1, 0.1-3.1 min 10-100% solvent 1, 3.1-3.9 min 100-10% solvent 1, 3.9-4.0 min 100-10% solvent 1).

GC-MS mass spectral analyses were performed on a FINNIGAN SSQ7000 GC/MS mass spectrometer using different techniques, including electrospray ionization (ESI), and atmospheric pressure chemical ionization (APCI), as specified for individual compounds. Exact mass measurement was performed on a FINNIGAN FTMS NEWSTAR T70 mass spectrometer. The compound is determined to be "consistent" with the chemical formula if the exact mass measurement is within 5.0 ppm relative mass error (RME) of the exact monoisotopic mass.

Preparative reverse phase HPLC was performed on certain compounds and was accomplished on an automated Gilson HPLC system, using a SYMMETRYPREP SHIELD RP18 prep cartridge, 250 mm×21.20 mm i.d., 10 um, and a flow rate of 25 mL/min; =214, 245 nm; mobile phase A, 0.1% TFA in H2O; mobile phase B, CH$_3$CN; linear gradient 0-70% of B in 40 min.

All abbreviations used to described reagents, reaction conditions, or equipment used are consistent with the definitions set forth in the "List of standard abbreviations and acronyms" published yearly by the Journal of Organic Chemistry (an American Chemical Society journal). The following abbreviations used herein have the meaning as follows: rt=room temperature, DMAP=2,6-dimethylaminopyridine; EDCI, DCM=dichloromethane, THF=tetrahydrofuran, TEA=triethylamine, EtOAc=ethyl acetate, TFA=trifluoroacetic acid, LC/MS=liquid chromatography/mass spectrometry, APCI=atmospheric pressure chemical ionization, DCI=desporption chemical ioniziation, MS=mass spectrometry, MeOH=methanol, DMA=N,N-dimethylacetamide, EtOH=ethanol, Hex=hexane(s), NBS=N-bromosuccinimide, NIS=N-iodosuccinimide, SEMCl=2-(Trimethylsilyl)ethoxymethyl chloride, DME=dimethoxyethane, DBAD=dibenzylazodicarboxylate, DMF=N,N-dimethylformamide, DCE=dichloroethane and Et$_3$N=triethylamine.

Example 1

Synthesis of 2-(8-(Benzo[d]thiazol-2-ylcarbamoyl)-3,4-dihydroisoquinolin-2(1H)-yl)thiazole-4-carboxylic acid (1)

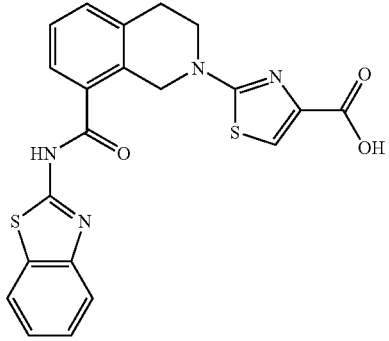

(1)

Step 1: Preparation of tert-butyl 8-(benzo[d]thiazol-2-ylcarbamoyl)-3,4-dihydroisoquinoline-2(1H)-carboxylate (1A)

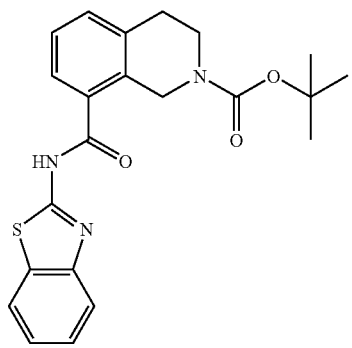

(1A)

To a solution of 2-(tert-butoxycarbonyl)-1,2,3,4-tetrahydroisoquinoline-8-carboxylic acid (6.8 g, 24.5 mmol) and benzo[d]thiazol-2-amine (5.52 g, 36.8 mmol) in DCM (80 mL) was added EDCI (9.4 g, 49.04 mmol) and DMAP (6 g, 49 mmol). The mixture was stirred at rt overnight. The reaction mixture was diluted with DCM (400 mL), washed with 5% aq. HCl, water, brine, dried over Na$_2$SO$_4$, and concentrated under reduced pressure to provide 8.5 g of the desired product tert-butyl 8-(benzo[d]thiazol-2-ylcarbamoyl)-3,4-dihydroisoquinoline-2(1H)-carboxylate (1A): $^1$H NMR (300 MHz, CDCl$_3$) δ ppm 7.83 (1H, m), 7.48 (1H, d), 7.34 (4H, m), 7.19 (1H, t), 4.91 (2H, m), 3.67 (2H, t), 2.92 (2H, t), 1.47 (9H, m). MS (ESI(+)): m/z 410 (M+H).

Step 2: Preparation of N-(benzo[d]thiazol-2-yl)-1,2,3,4-tetrahydroisoquinoline-8-carboxamide dihydrochloride (1B)

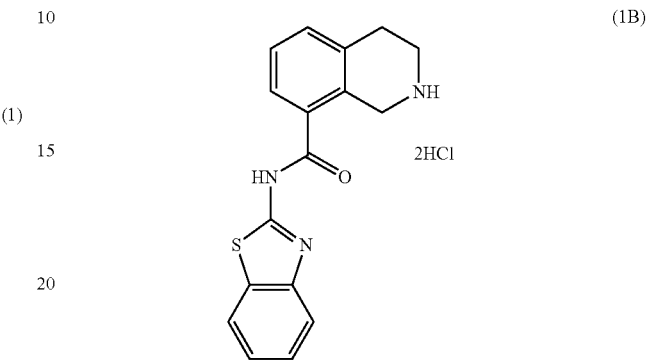

(1B)

To a solution of tert-butyl 8-(benzo[d]thiazol-2-ylcarbamoyl)-3,4-dihydroisoquinoline-2(1H)-carboxylate (1A) (8.5 g, 20.75 mmol) in DCM (80 mL) was added 2N HCl in ether (80 mL). The reaction mixture was stirred at rt overnight and concentrated under reduced pressure to provide the desired product N-(benzo[d]thiazol-2-yl)-1,2,3,4-tetrahydroisoquinoline-8-carboxamide dihydrochloride (1B): LC/MS (APCI): m/z 309.9 (M+H).

Step 3: Preparation of methyl 2-(8-(benzo[d]thiazol-2-ylcarbamoyl)-3,4-dihydroisoquinolin-2(1H)-yl)thiazole-4-carboxylate (1C)

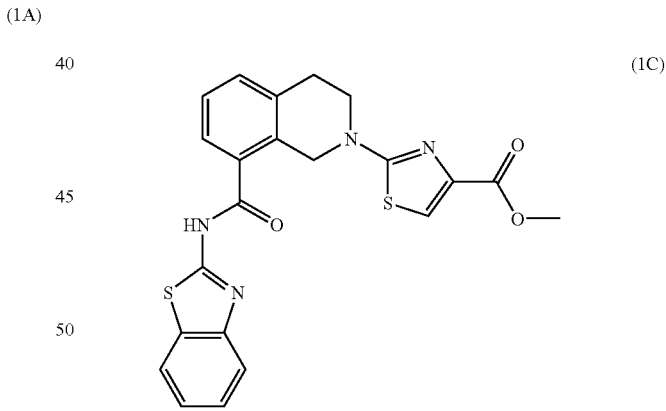

(1C)

To a solution of N-(benzo[d]thiazol-2-yl)-1,2,3,4-tetrahydroisoquinoline-8-carboxamide dihydrochloride (1B) (5.3 g, 13.86 mmol) and methyl 2-chlorothiazole-4-carboxylate (2.5 g, 14 mmol) in DMA (60 mL) was added Cs$_2$CO$_3$ (25 g, 70 mmol). The reaction mixture was stirred at 50° C. overnight. The reaction mixture was cooled to rt, acidified with 5% HCl, extracted with DCM, washed with water, brine, dried over Na$_2$SO$_4$, and concentrated under reduced pressure. The crude material was purified by column chromatography on silica gel eluting with 5% MeOH in DCM to provide 4.2 g (67%) of the desired product methyl 2-(8-(benzo[d]thiazol-2-ylcarbamoyl)-3,4-dihydroisoquinolin-2(1H)-yl)thiazole-4-carboxylate (1C): LC/MS (APCI): m/z 451.0 (M+H).

Step 4: Preparation of Title Compound 1

The title compound 2-(8-(Benzo[d]thiazol-2-ylcarbamoyl)-3,4-dihydroisoquinolin-2(1H)-yl)thiazole-4-carboxylic acid (1) was prepared by following procedure: To a solution of methyl 2-(8-(benzo[d]thiazol-2-ylcarbamoyl)-3,4-dihydroisoquinolin-2(1H)-yl)thiazole-4-carboxylate (1C) (180 mg, 4 mmol) in THF (4 mL) and MeOH (2 mL) was added 2N NaOH (2 mL). The reaction mixture was stirred at 50° C. for 4 hours and neutralized by slowly adding 5% aq. HCl. The precipitate was then filtered, dried, dissolved in DMSO/MeOH (1:1) and purified by column chromatography on silica gel to provide the desired product 2-(8-(Benzo[d]thiazol-2-ylcarbamoyl)-3,4-dihydroisoquinolin-2(1H)-yl)thiazole-4-carboxylic acid (1): $^1$H NMR (300 MHz, DMSO-D$_6$) δ ppm 7.99 (1H, d), 7.76 (1H, d), 7.69 (1H, dd), 7.52 (1H, s), 7.38 (4H, m), 4.91 (2H, s), 3.75 (2H, t), 3.05 (2H, t). MS (ESI(+)): m/z 437 (M+H).

Example 2

Synthesis of 2-(8-(benzo[d]thiazol-2-ylcarbamoyl)-3,4-dihydroisoquinolin-2(1H)-yl)-5-(3-phenoxypropyl)thiazole-4-carboxylic acid (2)

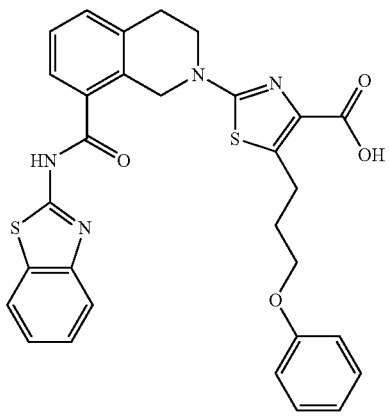

(2)

Step 1: Preparation of ethyl 3-bromo-6-chloro-2-oxohexanoate (2A)

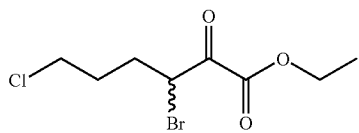

(2A)

To ethyl 6-chloro-2-oxohexanoate (2.9 g, 15 mmol) in carbon tetrachloride (30 mL) was added bromine (0.85 mL, 16.5 mmol) and stirred at rt for 1 hour. The reaction mixture was diluted with EtOAc, washed with Na$_2$S$_2$O$_3$ solution, water, brine, dried over MgSO$_4$, filtered, and concentrated under reduced pressure. The crude material was purified by column chromatography on silica gel eluting with a gradient of 0 to 10% EtOAc in hexanes to provide the desired product ethyl 3-bromo-6-chloro-2-oxohexanoate (2A) in 95% yield.

$^1$H NMR (300 MHz, DMSO-d$_6$) δ ppm 5.25 (1H, dd), 4.29 (2H, q), 3.71 (2H, t), 2.16 (1H, m), 1.91 (1H, m), 1.29 (3H, t).

Step 2: Preparation of ethyl 2-(8-(benzo[d]thiazol-2-ylcarbamoyl)-3,4-dihydroisoquinolin-2(1H)-yl)-5-(3-chloropropyl)thiazole-4-carboxylate (2B)

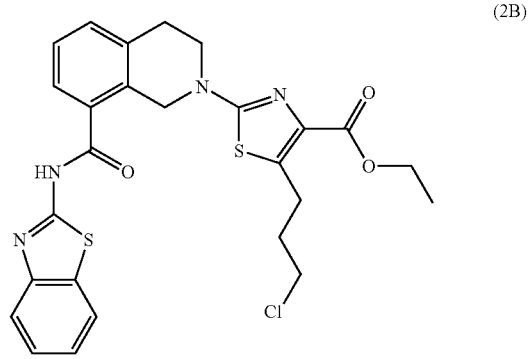

(2B)

To N-(benzo[d]thiazol-2-yl)-1,2,3,4-tetrahydroisoquinoline-8-carboxamide dihydrochloride (1B) (11.5 g, 30 mmol) in DMF (125 mL) was added TEA (16.7 mL, 120 mmol) and stirred at rt for 15 minutes. Di(1H-imidazol-1-yl)methanethione (6.53 g, 33 mmol) was added and the reaction mixture was stirred at rt for 1 hour. 7N Ammonia in MeOH (171 mL, 1.2 mol) was added and the mixture was stirred at rt overnight. The reaction mixture was concentrated to remove ammonia, TEA, and MeOH. To the concentrate was added a solution of ethyl 3-bromo-6-chloro-2-oxohexanoate (2A) (11.4 g, 42 mmol) in EtOH (40 mL). The reaction mixture was heated at 50° C. under nitrogen for 4.5 hours. Additional ethyl 3-bromo-6-chloro-2-oxohexanoate (2A) (0.815 g, 3 mmol) in EtOH (3 mL) was added and heating was continued for 1.5 hours. The reaction mixture was concentrated under reduced pressure to remove EtOH and then extracted with EtOAc. The combined organic extracts were washed with brine, dried over MgSO$_4$, filtered, and concentrated under reduced pressure. The concentrate was purified by column chromatography on silica gel eluting with a gradient of 30 to 50% EtOAc in hexanes to provide the desired product ethyl 2-(8-(benzo[d]thiazol-2-ylcarbamoyl)-3,4-dihydroisoquinolin-2(1H)-yl)-5-(3-chloropropyl)thiazole-4-carboxylate (2B) in 69% yield. $^1$H NMR (300 MHz, DMSO-d$_6$) δ ppm 12.89 (1H, s), 8.04 (1H, d), 7.79 (1H, d), 7.67 (1H, d), 7.42 (4H, m), 4.83 (2H, s), 4.19 (2H, q), 3.72 (2H, t), 3.64 (2H, t), 3.13 (2H, m), 3.04 (2H, t), 2.00 (2H, m), 1.21 (3H, t).

Step 3: Preparation of ethyl 2-(8-(benzo[d]thiazol-2-ylcarbamoyl)-3,4-dihydroisoquinolin-2(1H)-yl)-5-(3-iodopropyl)thiazole-4-carboxylate (2C)

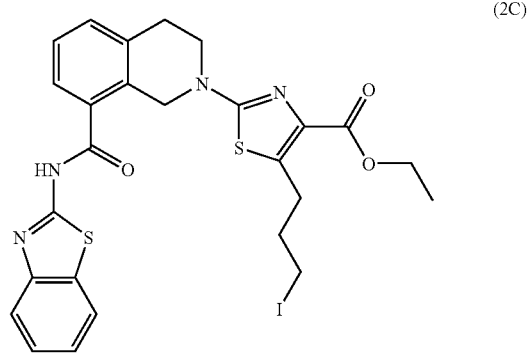

(2C)

To ethyl 2-(8-(benzo[d]thiazol-2-ylcarbamoyl)-3,4-dihydroisoquinolin-2(1H)-yl)-5-(3-chloropropyl)thiazole-4-carboxylate (2B) (9.3 g, 17.2 mmol) in acetonitrile (125 mL) was added sodium iodide (25.8 g, 172 mmol). The reaction mixture was purged with nitrogen twice. The reaction mixture was then heated at 90° C. for 5 hours, cooled to rt, and concentrated under reduced pressure. The concentrate was diluted with EtOAc, washed with water, brine, dried over MgSO$_4$, filtered, and concentrated under reduced pressure. The crude material was slurried in Et$_2$O, filtered, washed with additional Et$_2$O and dried under reduced pressure to provide the desired product ethyl 2-(8-(benzo[d]thiazol-2-ylcarbamoyl)-3,4-dihydroisoquinolin-2(1H)-yl)-5-(3-iodopropyl)thiazole-4-carboxylate (2C) in 93% yield. $^1$H NMR (300 MHz, DMSO-d$_6$) δ ppm 12.89 (1H, s), 8.04 (1H, d), 7.79 (1H, d), 7.66 (1H, d), 7.43 (4H, m), 4.83 (2H, s), 4.19 (2H, q), 3.72 (2H, t), 3.26 (2H, t), 3.06 (4H, m), 2.03 (2H, m), 1.21 (3H, t).

Step 4: Preparation of Title Compound 2

The title compound 2-(8-(benzo[d]thiazol-2-ylcarbamoyl)-3,4-dihydroisoquinolin-2(1H)-yl)-5-(3-phenoxypropyl)thiazole-4-carboxylic acid (2) was prepared by the following procedure: To phenol (22.6 mg, 0.24 mmol) in DMF (2 mL) was added NaH (60% oil dispersion) (24 mg, 0.6 mmol). After stirring at rt for 5 minutes, ethyl 2-(8-(benzo[d]thiazol-2-ylcarbamoyl)-3,4-dihydroisoquinolin-2(1H)-yl)-5-(3-iodopropyl)thiazole-4-carboxylate (2C) (127 mg, 0.2 mmol) was added and stirring was continued for 1 hour. The reaction mixture was acidified with 1N HCl and the precipitate was filtered and washed with water. The precipitate was slurried in Et$_2$O, filtered and washed with additional Et$_2$O. The resulting solid was purified by column chromatography on silica gel eluting with a gradient of 0 to 2% MeOH in DCM. To the purified material in DMF (1 mL) was added NaOH (4N aq) (0.5 mL, 2 mmol), heated at 50° C. for 5 hours, cooled to rt, and acidified with 1N HCl. The precipitate was filtered, washed with water, slurried in Et$_2$O, filtered, washed with Et$_2$O and dried in a vacuum oven to provide the desired product 2-(8-(benzo[d]thiazol-2-ylcarbamoyl)-3,4-dihydroisoquinolin-2(1H)-yl)-5-(3-phenoxypropyl)thiazole-4-carboxylic acid (2) in 37% yield. $^1$H NMR (300 MHz, DMSO-d$_6$) δ ppm 12.89 (s, 1H), 12.49 (1H, s), 8.04 (1H, d), 7.79 (1H, d), 7.67 (1H, d), 7.44 (4H, m), 7.25 (2H, m), 6.88 (3H, m), 4.82 (2H, s), 3.96 (2H, t), 3.72 (2H, t), 3.17 (2H, m), 3.03 (2H, t), 2.00 (2H, m). MS (ESI(+)): m/z 571 (M+H).

Example 3

Synthesis of 2-(8-(benzo[d]thiazol-2-ylcarbamoyl)-3,4-dihydroisoquinolin-2(1H)-yl)-5-(3-(pyridin-4-ylthio)propyl)thiazole-4-carboxylic acid (3)

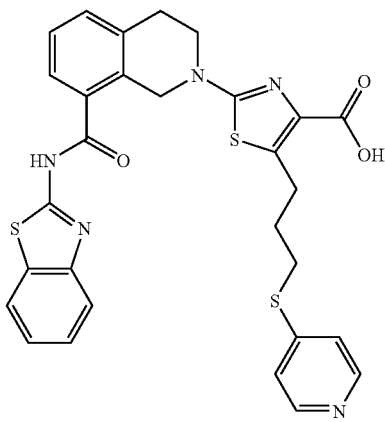

The title compound 2-(8-(benzo[d]thiazol-2-ylcarbamoyl)-3,4-dihydroisoquinolin-2(1H)-yl)-5-(3-(pyridin-4-ylthio)propyl)thiazole-4-carboxylic acid (3) was prepared by the following procedure: The title compound was prepared by substituting pyridine-4-thiol for phenol in step 4 of example 2. After precipitation of the desired product, the solid was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 0-90% of B in 40 minutes) to provide 2-(8-(benzo[d]thiazol-2-ylcarbamoyl)-3,4-dihydroisoquinolin-2(1H)-yl)-5-(3-(pyridin-4-ylthio)propyl)thiazole-4-carboxylic acid (3) in 30% yield. $^1$H NMR (300 MHz, DMSO-d$_6$) δ ppm 12.81 (1H, s), 8.48 (2H, d), 8.03 (1H, d), 7.79 (1H, d), 7.67 (1H, d), 7.59 (2H, m), 7.41 (4H, m), 4.83 (2H, s), 3.73 (2H, t), 3.18 (4H, m), 3.03 (2H, t), 1.95 (2H, m). MS (ESI(+)): m/z 588 (M+H).

Example 4

Synthesis of 2-(8-(benzo[d]thiazol-2-ylcarbamoyl)-3,4-dihydroisoquinolin-2(1H)-yl)-5-(3-(4-(tert-butoxycarbonylamino)phenoxy)propyl)thiazole-4-carboxylic acid (4)

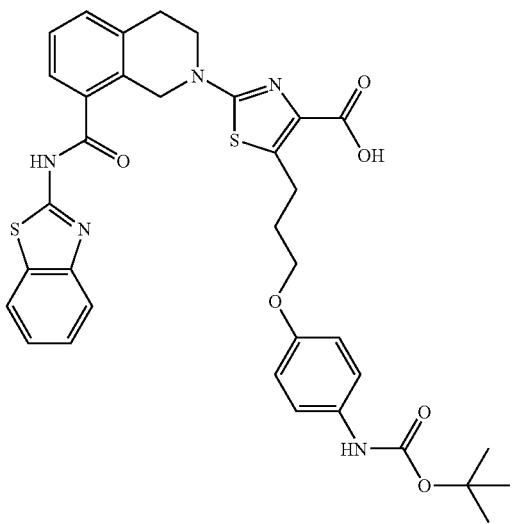

(4)

The title compound 2-(8-(benzo[d]thiazol-2-ylcarbamoyl)-3,4-dihydroisoquinolin-2(1H)-yl)-5-(3-(4-(tert-butoxycarbonylamino)phenoxy)propyl)thiazole-4-carboxylic acid (4) was prepared by the following procedure: The title compound was prepared by substituting tert-butyl 4-hydroxyphenylcarbamate for phenol in step 4 of example 2. As the addition of 1N HCl did not produce filterable solids for either the alkylation or hydrolysis steps, the reaction mixtures were extracted with EtOAc. The combined extracts were washed with brine, dried over MgSO$_4$, filtered, and concentrated under reduced pressure. Purification of each step followed as in example 2 with an additional MeOH wash of the final solid provided the desired compound 2-(8-(benzo[d]thiazol-2-ylcarbamoyl)-3,4-dihydroisoquinolin-2(1H)-yl)-5-(3-(4-(tert-butoxycarbonylamino)phenoxy)propyl)thiazole-4-carboxylic acid (4) in 58% yield. $^1$H NMR (300 MHz, DMSO-d$_6$) δ ppm 12.87 (1H, s), 12.52 (1H, s), 9.08 (1H, s), 8.03 (1H, d), 7.79 (1H, d), 7.67 (1H, d), 7.45 (2H, m), 7.35 (4H, m), 6.80 (2H, m), 4.83 (2H, s), 3.91 (2H, t), 3.72 (2H, t), 3.15 (2H, m), 3.03 (2H, t), 1.97 (2H, m), 1.45 (9H, s). MS (ESI(+)): m/z 686 (M+H).

Example 5

Synthesis of 2-(8-(benzo[d]thiazol-2-ylcarbamoyl)-3,4-dihydroisoquinolin-2(1H)-yl)-5-(3-(3-(tert-butoxycarbonylamino)phenoxy)propyl)thiazole-4-carboxylic acid (5)

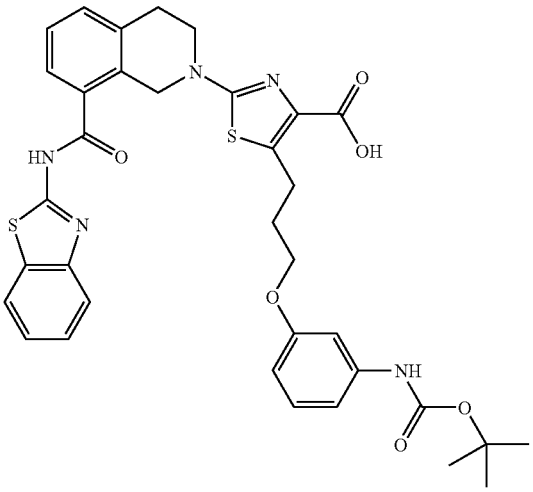

(5)

The title compound 2-(8-(benzo[d]thiazol-2-ylcarbamoyl)-3,4-dihydroisoquinolin-2(1H)-yl)-5-(3-(3-(tert-butoxycarbonylamino)phenoxy)propyl)thiazole-4-carboxylic acid (5) was prepared by the following procedure: The title compound was prepared by substituting tert-butyl 3-hydroxyphenylcarbamate for phenol in step 4 of example 2. The intermediate alkylation product was not isolated prior to ester hydrolysis. $^1$H NMR (400 MHz, DMSO-d$_6$) δ ppm 12.81 (1H, s), 9.24 (1H, s), 8.03 (1H, d), 7.79 (1H, d), 7.67 (1H, d), 7.46 (2H, m), 7.36 (2H, m), 7.09 (2H, m), 6.97 (1H, d), 6.50 (1H, dd), 4.84 (2H, s), 3.91 (2H, t), 3.72 (2H, t), 3.16 (2H, m), 3.03 (2H, t), 1.99 (2H, m), 1.45 (9H, s). MS (ESI(+)): m/z 686 (M+H).

Example 6

Synthesis of 5-(3-(4-aminophenoxy)propyl)-2-(8-(benzo[d]thiazol-2-ylcarbamoyl)-3,4-dihydroisoquinolin-2(1H)-yl)thiazole-4-carboxylic acid (6)

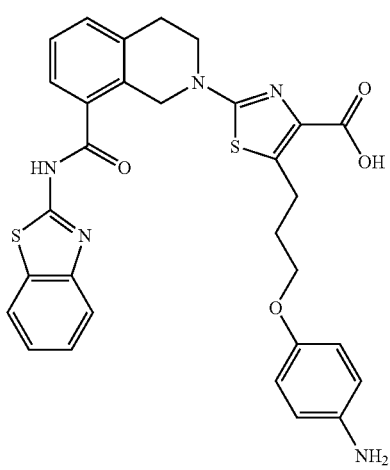

(6)

The title compound 5-(3-(4-aminophenoxy)propyl)-2-(8-(benzo[d]thiazol-2-ylcarbamoyl)-3,4-dihydroisoquinolin-2(1H)-yl)thiazole-4-carboxylic acid (6) was prepared by the following procedure: To 2-(8-(benzo[d]thiazol-2-ylcarbamoyl)-3,4-dihydroisoquinolin-2(1H)-yl)-5-(3-(4-(tert-butoxycarbonylamino)phenoxy)propyl)thiazole-4-carboxylic acid (4) (20 mg, 0.029 mmol) in MeOH (1 mL) was added TFA (1 mL, 13 mmol) and stirred at rt for 2 hours. The reaction mixture was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 0-70% of B in 40 minutes) to provide the desired product 5-(3-(4-aminophenoxy)propyl)-2-(8-(benzo[d]thiazol-2-ylcarbamoyl)-3,4-dihydroisoquinolin-2(1H)-yl)thiazole-4-carboxylic acid in 48% yield. $^1$H NMR (400 MHz, DMSO-d$_6$) δ ppm 12.77 (1H, s), 9.04 (1H, s), 8.03 (1H, d), 7.79 (1H, d), 7.67 (1H, d), 7.47 (2H, m), 7.37 (2H, m), 7.09 (2H, d), 6.92 (2H, m), 4.83 (2H, s), 3.95 (2H, t), 3.72 (2H, t), 3.17 (2H, m), 3.03 (2H, t), 1.99 (2H, m). MS (ESI(+)): m/z 586 (M+H).

Example 7

Synthesis of 5-(3-(1H-pyrazol-1-yl)propyl)-2-(8-(benzo[d]thiazol-2-ylcarbamoyl)-3,4-dihydroisoquinolin-2(1H)-yl)thiazole-4-carboxylic acid (7)

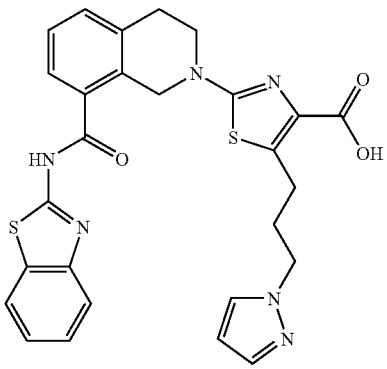

(7)

The title compound 5-(3-(1H-pyrazol-1-yl)propyl)-2-(8-(benzo[d]thiazol-2-ylcarbamoyl)-3,4-dihydroisoquinolin-2(1H)-yl)thiazole-4-carboxylic acid (7) was prepared by the following procedure: The title compound was prepared by substituting 1H-pyrazole for phenol in step 4 of example 2. The intermediate alkylation product was not isolated prior to ester hydrolysis. $^1$H NMR (400 MHz, DMSO-d6) δ ppm 12.85 (1H, s), 12.55 (1H, s), 8.03 (1H, d), 7.79 (1H, d), 7.68 (2H, m), 7.47 (2H, m), 7.37 (3H, m), 6.19 (1H, t), 4.83 (2H, s), 4.12 (2H, t), 3.73 (2H, t), 3.04 (2H, t), 2.99 (2H, m), 2.05 (2H, m). MS (ESI(+)): m/z 545 (M+H).

Example 8

Synthesis of 2-(8-(Benzo[d]thiazol-2-ylcarbamoyl)-3,4-dihydroisoquinolin-2(1H)-yl)-5-(3-(isoquinolin-6-yloxy)propyl)thiazole-4-carboxylic acid (8)

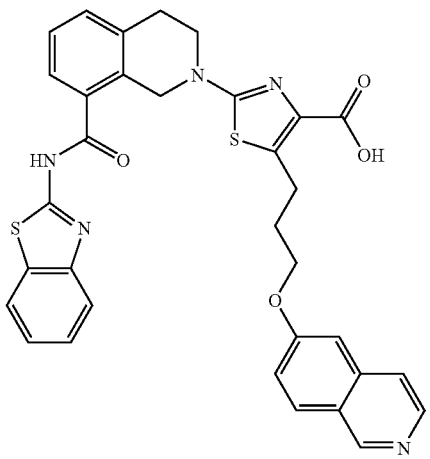

(8)

Step 1: Preparation of methyl 2-amino-5-iodothiazole-4-carboxylate (8A)

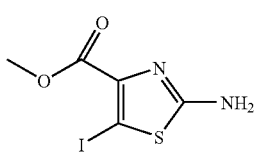

(8A)

To a solution of methyl 2-aminothiazole-4-carboxylate (5.6 g, 35.4 mmol) in DCM (60 mL) was added NIS (9.56 g, 42.5 mmol). The mixture was stirred at rt for 24 hours and then diluted with EtOAc (200 mL) and washed with water, brine, dried over $Na_2SO_4$, and concentrated under reduced pressure to provide 9.5 g (94%) of the desired product methyl 2-amino-5-iodothiazole-4-carboxylate (8A): LC/MS(APCI): m/z 284.9 (M+H).

Step 2: Preparation of methyl 2-chloro-5-iodothiazole-4-carboxylate (8B)

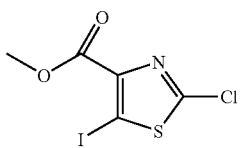

(8B)

To a solution of methyl 2-amino-5-iodothiazole-4-carboxylate (8A) (9 g, 31.7 mmol) in acetonitrile (60 mL) was added CuCl (4.75 g, 48 mmol) followed by t-butyl nitrite (6.19 g, 60 mmol). The mixture was stirred at rt for 2 hours. $NH_4Cl$ was then added slowly to the stirring mixture to quench the reaction. The mixture was extracted with EtOAc and the combined extracts were washed with water, brine, dried over $Na_2SO_4$, and concentrated under reduced pressure. The crude material was purified by column chromatography on silica gel eluting with 5% EtOAc in hexanes to provide 7.5 g (78%) of the desired product methyl 2-chloro-5-iodothiazole-4-carboxylate (88): LC/MS (APCI): m/z 304.0 (M+H).

Step 3: Preparation of methyl 2-(8-(benzo[d]thiazol-2-ylcarbamoyl)-3,4-dihydroisoquinolin-2(1H)-yl)-5-iodothiazole-4-carboxylate (8C)

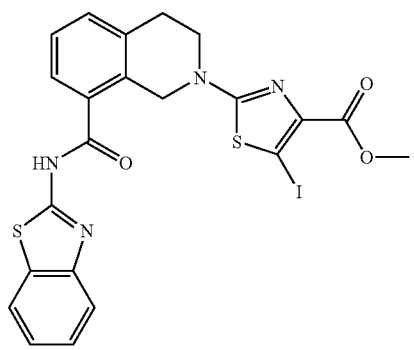

(8C)

To a solution of N-(benzo[d]thiazol-2-yl)-1,2,3,4-tetrahydroisoquinoline-8-carboxamide dihydrochloride (1B) (2 g, 5.23 mmol) and methyl 2-chloro-5-iodothiazole-4-carboxylate (8B) (1.66 g, 5.23 mmol) in DMA (10 mL) was added $Cs_2CO_3$ (8.52 g, 26.2 mmol). The reaction mixture was stirred at 60° C. overnight, cooled to rt, acidified with 5% HCl, extracted with DCM, washed with water, brine, dried over $Na_2SO_4$, and concentrated under reduced pressure. The crude material was purified by column chromatography on silica gel and eluted with 5% MeOH in DCM to provide 2.0 g (65%) of the desired product 2-(8-(benzo[d]thiazol-2-ylcarbamoyl)-3,4-dihydroisoquinolin-2(1H)-yl)-5-iodothiazole-4-carboxylate (8C): LC/MS (APCI): m/z 577.0 (M+H)

Step 4: Preparation of methyl 2-(8-(benzo[d]thiazol-2-ylcarbamoyl)-3,4-dihydroisoquinolin-2(1H)-yl)-5-(3-hydroxyprop-1-ynyl)thiazole-4-carboxylate (8D)

(8D)

To a solution of methyl 2-(8-(benzo[d]thiazol-2-ylcarbamoyl)-3,4-dihydroisoquinolin-2(1H)-yl)-5-iodothiazole-4-carboxylate (8C) (1.2 g, 2.03 mmol) and prop-2-yn-1-ol (336 mg, 6 mmol) in THF (20 mL) was added Pd(Ph$_3$P)$_4$ (231 mg, 0.2 mmol), CuI (76 mg, 0.121 mmol), DIEA (520 mg, 4 mmol). The mixture was stirred under nitrogen at rt overnight. The mixture was then diluted with DCM (400 mL) and washed with water, brine, dried over Na$_2$SO$_4$, and concentrated under reduced pressure. The crude material was purified by column chromatography on a silica gel column eluting with 5% MeOH in DCM to provide 0.76 g (73%) of the desired product methyl 2-(8-(benzo[d]thiazol-2-ylcarbamoyl)-3,4-dihydroisoquinolin-2(1H)-yl)-5-(3-hydroxyprop-1-ynyl)thiazole-4-carboxylate (8D): LC/MS (APCI): m/z 505.1 (M+H)

Step 5: Preparation of methyl 2-(8-(benzo[d]thiazol-2-ylcarbamoyl)-3,4-dihydroisoquinolin-2(1H)-yl)-5-(3-hydroxypropyl)thiazole-4-carboxylate (8E)

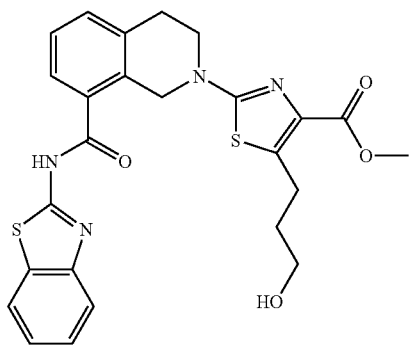

(8E)

To a solution of methyl 2-(8-(benzo[d]thiazol-2-ylcarbamoyl)-3,4-dihydroisoquinolin-2(1H)-yl)-5-(3-hydroxyprop-1-ynyl)thiazole-4-carboxylate (8D) (1.2 g, 2.31 mmol) in EtOAc (20 mL) was added PtO$_2$ (120 mg, 0.53 mmol). The mixture was stirred at rt under a hydrogen balloon overnight. After this time the mixture was filtered and the filtrate was concentrated to provide the desired product methyl 2-(8-(benzo[d]thiazol-2-ylcarbamoyl)-3,4-dihydroisoquinolin-2(1H)-yl)-5-(3-hydroxypropyl)thiazole-4-carboxylate (8E): LC/MS (APCI): m/z 509.2 (M+H).

Step 6: Preparation of methyl 2-(8-(benzo[d]thiazol-2-ylcarbamoyl)-3,4-dihydroisoquinolin-2(1H)-yl)-5-(3-(tosyloxy)propyl)thiazole-4-carboxylate (8F)

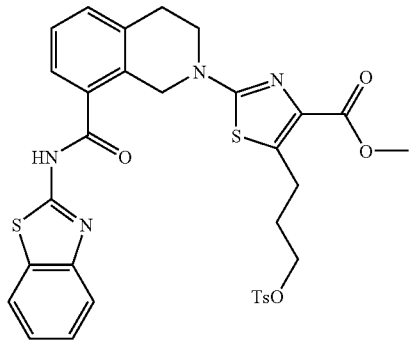

(8F)

To a solution of methyl 2-(8-(benzo[d]thiazol-2-ylcarbamoyl)-3,4-dihydroisoquinolin-2(1H)-yl)-5-(3-hydroxypropyl)thiazole-4-carboxylate (0.5 g, 0.96 mmol) in DCM (10 mL) was added TsCl (182 mg, 1 mmol), TEA (97 mg, 1 mmol), and catalytic amount of DMAP. The mixture was stirred at rt for 4 hours. The mixture was diluted with EtOAc and washed with water, brine, dried over Na$_2$SO$_4$, and concentrated under reduced pressure to provide the desired product methyl 2-(8-(benzo[d]thiazol-2-ylcarbamoyl)-3,4-dihydroisoquinolin-2(1H)-yl)-5-(3-(tosyloxy)propyl)thiazole-4-carboxylate (8F) which was used without further purification. LC/MS (APCI): m/z 663.0 (M+H)

Step 7: Preparation of Title Compound 8

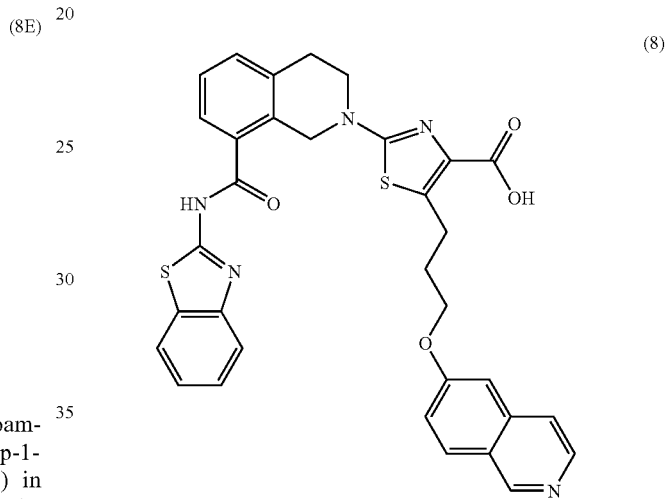

(8)

The title compound 2-(8-(benzo[d]thiazol-2-ylcarbamoyl)-3,4-dihydroisoquinolin-2(1H)-yl)-5-(3-(isoquinolin-6-yloxy)propyl)thiazole-4-carboxylic acid (8) was prepared by the following procedure: To a solution of methyl 2-(8-(benzo[d]thiazol-2-ylcarbamoyl)-3,4-dihydroisoquinolin-2(1H)-yl)-5-(3-(tosyloxy)propyl)thiazole-4-carboxylate (8F) (133 mg, 0.2 mmol) and 5-hydroxyisoquinoline (45 mg, 0.3 mmol) in DMA (3 mL) was added Cs$_2$CO$_3$ (50 mg, 0.3 mmol). The mixture was stirred at rt overnight and was diluted with 2N NaOH (4 mL) and stirred at 50° C. for 4 hours. The reaction mixture was neutralized with 5% HCl and the precipitate was filtered and dried. The residue was then dissolved in DMSO/MeOH (1:1) and purified by column chromatography on silica gel to provide the desired product 2-(8-(benzo[d]thiazol-2-ylcarbamoyl)-3,4-dihydroisoquinolin-2(1H)-yl)-5-(3-(isoquinolin-6-yloxy)propyl)thiazole-4-carboxylic acid (8): $^1$H NMR (300 MHz, DMSO-D$_6$) δ ppm 9.16 (1H, s), 8.34 (1H, d), 7.94 (1H, d), 7.85 (1H, d), 7.71 (4H, m), 7.38 (8H, m), 4.88 (2H, s), 4.14 (2H, t), 3.71 (2H, t), 3.00 (2H, t), 2.27 (1H, m), 2.09 (2H, m). LC/MS (APCI): m/z 622.2 (M+H).

Example 9

Synthesis of 5-(3-(3-aminophenoxy)propyl)-2-(8-(benzo[d]thiazol-2-ylcarbamoyl)-3,4-dihydroisoquinolin-2(1H)-yl)thiazole-4-carboxylic acid (9)

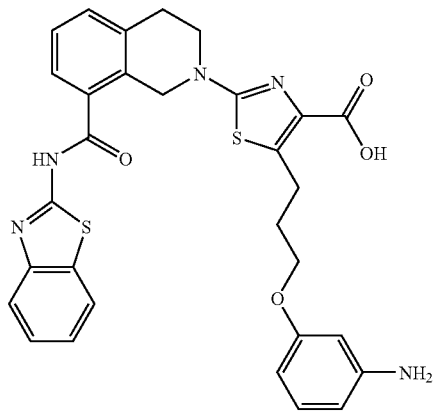

(9)

The title compound 9 was prepared by following the procedure set forth in Example 6 but substituting compound 4 in Example 6 with compound 5: $^1$H NMR (300 MHz, DMSO-d$_6$) δ ppm 12.89 (1H, s), 8.03 (1H, m), 7.79 (1H, d), 7.67 (1H, m), 7.42 (4H, m), 7.02 (1H, m), 6.33 (3H, m), 4.83 (2H, s), 3.90 (2H, t), 3.72 (2H, t), 3.16 (2H, m), 3.03 (2H, t), 1.98 (2H, m); MS (ESI(+)): m/z 586 (M+H).

Example 10

Synthesis of 2-(8-(benzo[d]thiazol-2-ylcarbamoyl)-3,4-dihydroisoquinolin-2(1H)-yl)-5-(3-(pyridin-4-yloxy)propyl)thiazole-4-carboxylic acid (10)

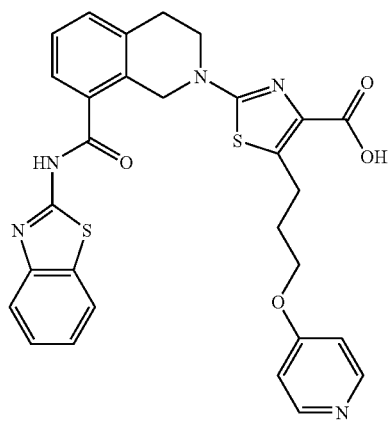

(10)

Compound 10 generally prepared as described in Example 2 by substituting 4-hydroxypyridine for phenol in step 4 of Example 2. The intermediate alkylation product was not isolated prior to ester hydrolysis: $^1$H NMR (400 MHz, DMSO-d$_6$) δ ppm 12.89 (1H, s), 12.55 (1H, s), 8.66 (1H, m), 8.44 (1H, d), 8.04 (1H, m), 7.79 (1H, d), 7.68 (1H, d), 7.43 (5H, m), 7.01 (1H, d), 4.82 (2H, s), 4.29 (2H, m), 3.74 (2H, m), 3.19 (2H, m), 3.04 (2H, m), 2.08 (2H, m); MS (ESI(+)): m/z 572 (M+H).

Example 11

Synthesis of 2-(8-(benzo[d]thiazol-2-ylcarbamoyl)-3,4-dihydroisoquinolin-2(1H)-yl)-5-(3-(3-(dimethylamino)phenoxy)propyl)thiazole-4-carboxylic acid (11)

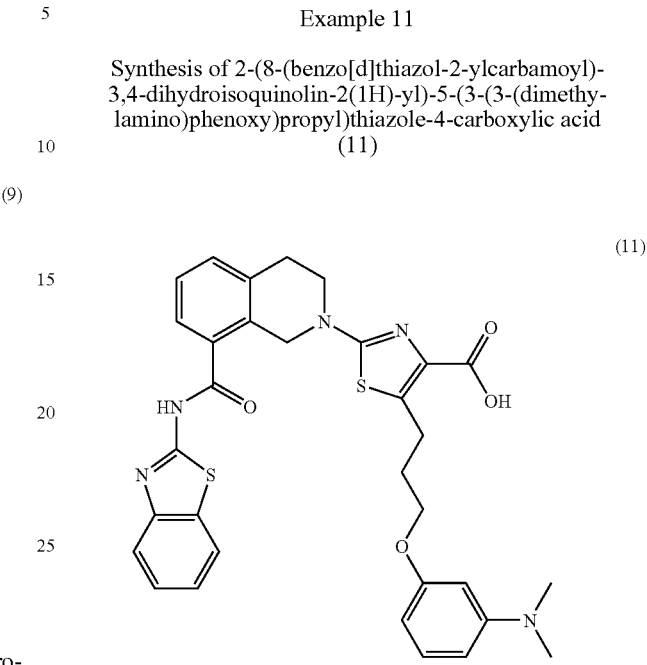

(11)

Compound 11 generally was prepared as described in Example 2 by substituting 3-(dimethylamino)phenol for phenol in step 4 of Example 2 with the modification that as the addition of 1N HCl did not produce filterable solids for the alkylation step, the reaction mixture was extracted with EtOAc (3×25 mL). The combined extracts were washed with brine, dried (MgSO$_4$), filtered and concentrated. Then the procedure continued as in step 4 of Example 2: $^1$H NMR (400 MHz, DMSO-d$_6$) δ ppm 7.93 (1H, d), 7.71 (2H, m), 7.37 (3H, m), 7.26 (1H, t), 7.02 (1H, t), 6.28 (1H, m), 6.19 (2H, m), 4.90 (2H, s), 3.93 (2H, t), 3.70 (2H, m), 3.17 (2H, m), 3.02 (2H, m), 2.83 (6H, s), 1.96 (2H, m); MS (ESI(+)): m/z 614 (M+H).

Example 12

Synthesis of 2-(8-(Benzo[d]thiazol-2-ylcarbamoyl)-3,4-dihydroisoquinolin-2(1H)-yl)-5-(3-(quinolin-5-yloxy)propyl)thiazole-4-carboxylic acid (12)

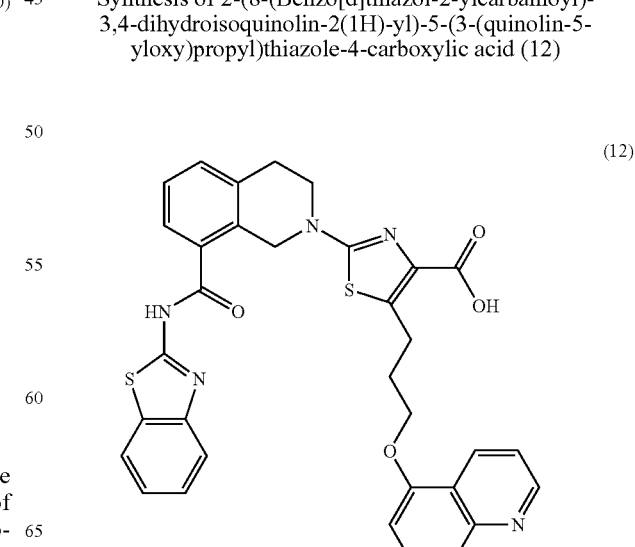

(12)

Compound 12 was prepared using the same procedure as described in Example 8 by substituting 4-hydroxyquinoline for 5-hydroxyisoquinoline in step 7 of Example 8: $^1$H NMR (300 MHz, DMSO-D$_6$) δ ppm 12.88 (1H, s), 8.85 (1H, d), 8.32 (1H, dd), 8.04 (1H, d), 7.78 (1H, d), 7.52 (11H, m), 7.19 (1H, d), 4.82 (2H, s), 4.20 (2H, t), 3.71 (2H, t), 3.02 (1H, m), 2.17 (2H, m). MS (ESI(+)): m/z 622 (M+H).

Example 13

Synthesis of 2-(8-(Benzo[d]thiazol-2-ylcarbamoyl)-3,4-dihydroisoquinolin-2(1H)-yl)-5-(3-(quinolin-8-yloxy)propyl)thiazole-4-carboxylic acid (13)

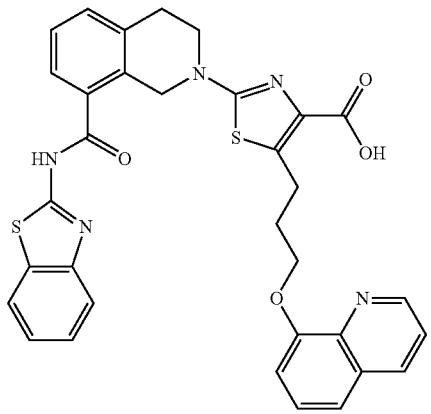
(13)

Compound 13 was prepared using the same procedure as described in Example 8 by substituting 8-hydroxyquinoline for 5-hydroxyisoquinoline in step 7 of Example 8: $^1$H NMR (300 MHz, DMSO-D$_6$) δ ppm 8.93 (1H, d), 8.63 (1H, d), 8.04 (1H, d), 7.79 (1H, d), 7.53 (12H, m), 7.08 (1H, d), 4.82 (2H, s), 4.22 (2H, t), 3.70 (2H, m), 3.31 (2H, t), 3.03 (2H, m), 2.17 (2H, m). MS (ESI(+)): m/z 622 (M+H).

Example 14

Synthesis of 2-(8-(Benzo[d]thiazol-2-ylcarbamoyl)-3,4-dihydroisoquinolin-2(1H)-yl)-5-(3-hydroxyprop-1-ynyl)thiazole-4-carboxylic acid (14)

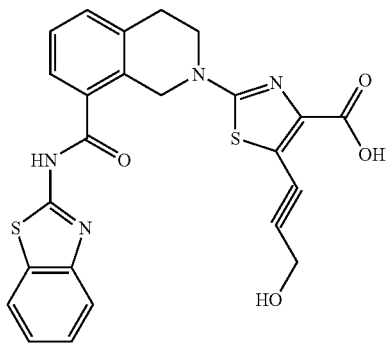
(14)

Compound 14 was prepared from compound 8D using the same hydrolysis and purification procedure as described in step 7 of Example 8: $^1$H NMR (300 MHz, DMSO-D$_6$) δ ppm 12.91 (1H, s), 8.04 (1H, d), 7.80 (1H, d), 7.52 (5H, m), 4.90 (2H, s), 4.30 (2H, m), 3.74 (2H, t), 3.06 (2H, t); MS (ESI(+)): m/z 491 (M+H).

Example 15

Synthesis of 5-(3-(1H-benzo[d]imidazol-1-yl)propyl)-2-(8-(benzo[d]thiazol-2-ylcarbamoyl)-3,4-dihydroisoquinolin-2(1H)-yl)thiazole-4-carboxylic acid (15)

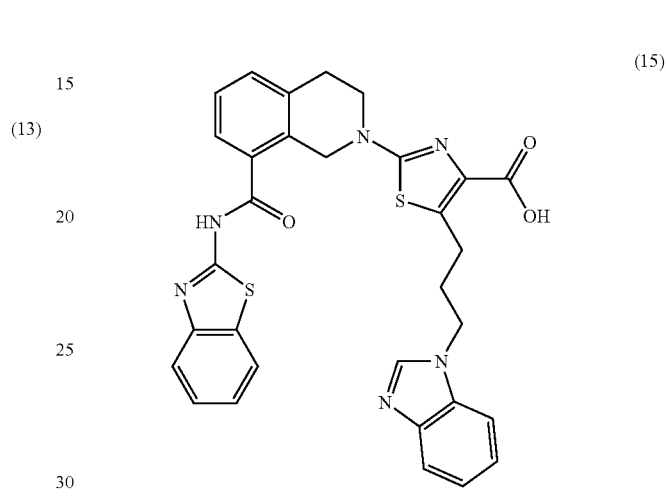
(15)

Compound 15 was prepared by substituting benzimidazole for phenol in step 4 of Example 2. The intermediate alkylation product was not isolated prior to ester hydrolysis: $^1$H NMR (300 MHz, DMSO-d$_6$) δ ppm 7.99 (1H, d), 7.75 (1H, d), 7.69 (1H, dd), 7.62 (1H, m), 7.56 (1H, m), 7.39 (5H, m), 7.19 (2H, m), 4.85 (2H, s), 4.27 (2H, t), 3.72 (2H, t), 3.04 (4H, m), 2.09 (2H, m). MS (ESI(+)): m/z 595 (M+H).

Example 16

Synthesis of 5-(3-(1H-imidazol-1-yl)propyl)-2-(8-(benzo[d]thiazol-2-ylcarbamoyl)-3,4-dihydroisoquinolin-2(1H)-yl)thiazole-4-carboxylic acid (16)

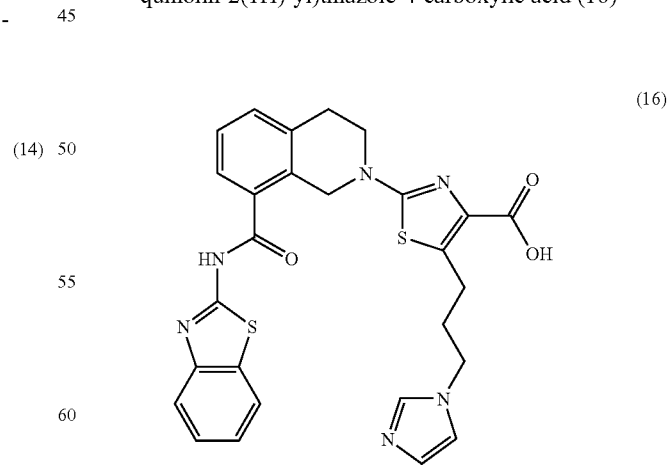
(16)

Compound 16 generally was prepared as described in Example 2 by substituting imidazole for phenol in step 4 of Example 2. The intermediate alkylation product was not isolated prior to ester hydrolysis: $^1$H NMR (300 MHz, DMSO-d$_6$) δ ppm 12.90 (1H, s), 12.53 (1H, s), 8.03 (1H, m), 7.86 (1H, s), 7.79 (1H, d), 7.67 (1H, m), 7.41 (4H, m), 7.26 (1H, s), 6.99 (1H, s), 4.83 (2H, s), 4.01 (2H, t), 3.73 (2H, t), 3.02 (4H, m), 2.01 (2H, t). MS (ESI(+)): m/z 545 (M+H).

Example 17

Synthesis of 5-(3-(1H-pyrrolo[2,3-b]pyridin-1-yl)propyl)-2-(8-benzo[d]thiazol-2-ylcarbamoyl)-3,4-dihydroisoquinolin-2(1H)-yl)thiazole-4-carboxylic acid (17)

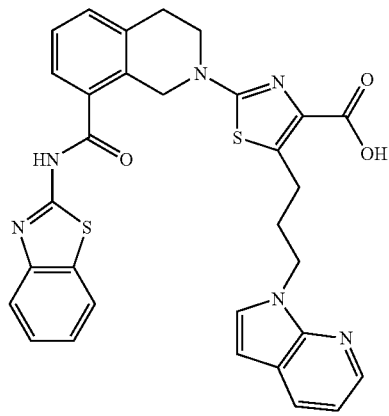

(17)

Compound 17 was prepared by substituting 7-azaindole for phenol in step 4 of Example 2. The intermediate alkylation product was not isolated prior to ester hydrolysis: $^1$H NMR (300 MHz, DMSO-d$_6$) δ ppm 12.87 (1H, s), 12.54 (1H, s), 8.20 (1H, dd), 8.03 (1H, m), 7.92 (1H, dd), 7.79 (1H, d), 7.67 (1H, m), 7.54 (1H, d), 7.44 (4H, m), 7.03 (1H, dd), 6.43 (1H, d), 4.81 (2H, s), 4.29 (2H, t), 3.72 (2H, t), 3.03 (4H, m), 2.10 (2H, m). MS (ESI(+)): m/z 595 (M+H).

Example 18

Synthesis of 2-(8-(benzo[d]thiazol-2-ylcarbamoyl)-3,4-dihydroisoquinolin-2(1H)-yl)-5-(3-(pyrrolidin-1-yl)propyl)thiazole-4-carboxylic acid (18)

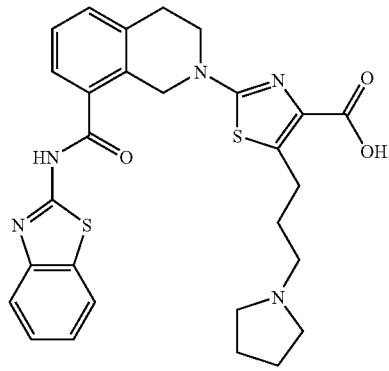

(18)

Compound 18 generally was prepared as described in Example 2 by substituting pyrrolidine for phenol in step 4 of Example 2. The intermediate alkylation product was not isolated prior to ester hydrolysis. After precipitation of the desired product, the solid was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 0-70% of B in 40 minutes) to provide the compound 18 in 18% yield: $^1$H NMR (300 MHz, DMSO-d$_6$) δ ppm 12.90 (1H, s), 12.66 (1H, s), 9.33 (1H, s), 8.04 (1H, d), 7.80 (1H, d), 7.68 (1H, d), 7.42 (4H, m), 4.83 (2H, s), 3.76 (2H, t), 3.53 (2H, m), 3.10 (6H, m), 2.96 (2H, m), 1.93 (4H, m), 1.82 (2H, m); MS (ESI(+)): m/z 548 (M+H).

Example 19

Synthesis of 2-(8-(benzo[d]thiazol-2-ylcarbamoyl)-3,4-dihydroisoquinolin-2(1H)-yl)-5-(3-morpholinopropyl)thiazole-4-carboxylic acid (19)

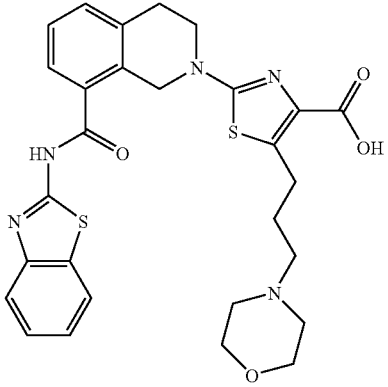

(19)

Compound 19 generally was prepared as described in Example 2 by substituting morpholine for phenol in step 4 of Example 2. The intermediate alkylation product was not isolated prior to ester hydrolysis. After precipitation of the desired product, the solid was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 0-70% of B in 40 minutes) to provide the compound 19 in 5% yield. $^1$H NMR (300 MHz, DMSO-d$_6$) δ ppm 12.90 (1H, s), 9.49 (1H, s), 8.04 (1H, d), 7.80 (1H, d), 7.68 (1H, d), 7.42 (4H, m), 4.83 (2H, s), 3.92 (2H, m), 3.76 (2H, t), 3.62 (2H, m), 3.07 (10H, m), 1.95 (2H, m); LCMS (APCI): m/z 564 (M+H).

Example 20

Synthesis of 2-(8-(benzo[d]thiazol-2-ylcarbamoyl)-3,4-dihydroisoquinolin-2(1H)-yl)-5-(3-(piperidin-1-yl)propyl)thiazole-4-carboxylic acid (20)

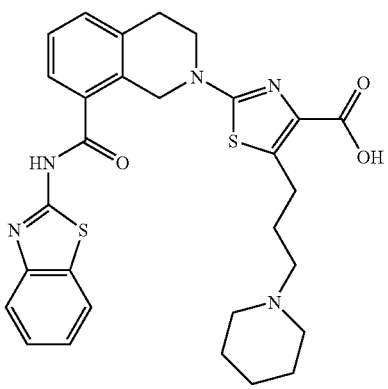

(20)

The title compound 20 generally was prepared as described in Example 2 by substituting piperidine for phenol in step 4 of Example 2. The intermediate alkylation product was not isolated prior to ester hydrolysis. After precipitation of the desired product, the solid was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 0-70% of B in 40 minutes) to provide the compound 20 in 17% yield: $^1$H NMR (300 MHz, DMSO-d$_6$) δ ppm 12.90 (1H, s), 8.85 (1H, s), 8.04 (1H, d), 7.80 (1H, m), 7.68 (1H, d), 7.43 (4H, m), 4.83 (2H, s), 3.76 (2H, t), 3.05 (7H, m), 2.82 (2H, m), 1.93 (2H, m), 1.77 (2H, m), 1.60 (3H, m), 1.34 (2H, m). MS (ESI(+)): m/z 562 (M+H).

Example 21

Synthesis of 5-(3-(4-(1H-pyrazolo[3,4-d]pyrimidin-1-yl)phenoxy)propyl)-2-(8-(benzo[d]thiazol-2-ylcarbamoyl)-3,4-dihydroisoquinolin-2(1H)-yl)thiazole-4-carboxylic acid (21)

(21)

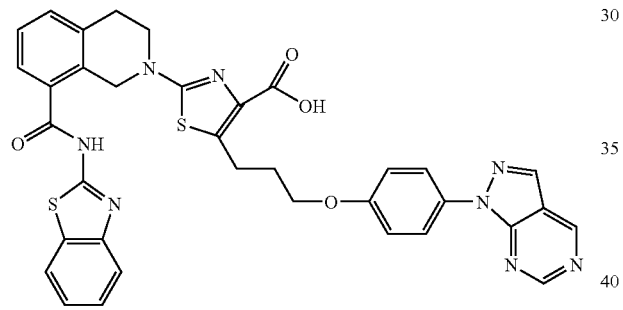

Step 1: Preparation of 5-amino-1-(4-bromophenyl)-1H-pyrazole-4-carboxylic acid (21A)

(21A)

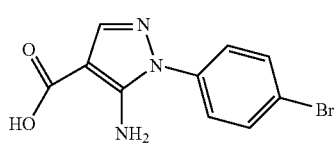

A mixture of (Z)-ethyl 2-cyano-3-ethoxyacrylate (2.099 g, 12.41 mmol), 4-bromophenylhydrazine hydrochloride (2.76 g, 12.41 mmol) and Na$_2$CO$_3$ (0.789 g, 7.44 mmol) in EtOH (30 mL) was refluxed for 5 h and slightly concentrated. The precipitate was collected by filtration, washed with ether and dried to provide the ester. The ester was dissolved in THF (5 mL) and MeOH (25 mL). 154 mL of 10% NaOH was added. The resulting mixture was stirred at 50° C. overnight and concentrated. A small amount of water was added and the resulting solution was neutralized with HCl to pH 6. A white precipitate was collected, washed with water and dried to provide compound 21A: $^1$H NMR (400 MHz, DMSO-D$_6$) ppm 12.09 (1H, s), 7.72 (2H, d), 7.52 (2H, d), 6.35 (2H, s).

Step 2: Preparation of 1-(4-bromophenyl)-1H-pyrazolo[3,4-d]pyrimidine (21B)

(21B)

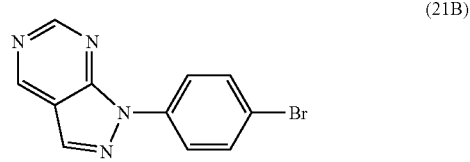

To a solution of 1,3,5-triazine (0.575 g, 7.09 mmol) and compound 21A (2 g, 7.09 mmol) in DMSO (30 mL) was added boron trifluoride etherate (1.078 mL, 8.51 mmol). The resulting mixture was heated at 120° C. for 20 h, cooled, diluted with EtOAc and washed with 1% NaOH and brine. The organic layer was dried over Na$_2$SO$_4$ and concentrated. The residue was triturated with small amount of EtOAc and the precipitate was collected to provide the desired product: $^1$H NMR (400 MHz, DMSO-D$_6$) δ ppm 9.47 (1H, s), 9.16 (1H, s), 8.68 (1H, s), 8.22 (2H, d), 7.80 (2H, d).

Step 3: Preparation of 1-(4-(4,4,5,5-tetramethyl-1,3,2-dioxaborolan-2-yl)phenyl)-1H-pyrazolo[3,4-d]pyrimidine (21C)

(21C)

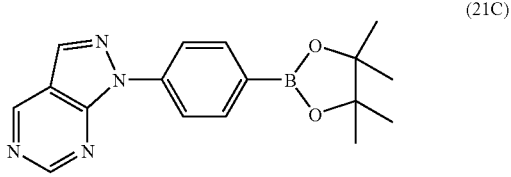

A mixture of compound 21B (500 mg, 1.817 mmol), 4,4,4',4',5,5,5',5'-octamethyl-2,2'-bi(1,3,2-dioxaborolane) (508 mg, 1.999 mmol), PdCl$_2$(dppt)-CH$_2$Cl$_2$ adduct (74.2 mg, 0.091 mmol) and potassium acetate (535 mg, 5.45 mmol) in DMSO (15 mL) was purged with nitrogen and then heated at 80° C. overnight. The reaction was diluted with ethyl acetate and washed with brine. The organic layer was dried over Na$_2$SO$_4$ and concentrated under reduced pressure. The crude material was purified by column chromatography on silica gel eluting with 0 to 20% EtOAc in DCM to provide the desired product 21C: $^1$H NMR (400 MHz, DMSO-D$_6$) δ ppm 9.49 (1H, s), 9.20 (1H, s), 8.70 (1H, s), 8.33 (2H, d), 7.90 (2H, d), 1.33 (12H, s).

Step 4: Preparation of 4-(1H-pyrazolo[3,4-d]pyrimidin-1-yl)phenol (21D)

(21D)

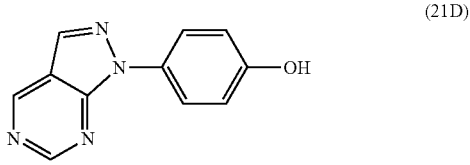

To a solution of compound 21C (100 mg, 0.31 mmol) in THF (5 mL) was added NaOH (0.248 mL, 0.621 mmol) and hydrogen peroxide (0.048 mL, 0.466 mmol). The mixture was stirred at 0° C. for 30 minutes. The reaction mixture was concentrated under reduced pressure and the concentrate was dissolved in 8 mL of water. The aqueous solution was acidified with diluted HCl. A white precipitate was collected, washed with water, and dried to provide the desired product 21D: $^1$H NMR (400 MHz, DMSO-$D_6$) δ ppm 9.75 (1H, s), 9.44 (1H, s), 9.09 (1H, s), 8.59 (1H, s), 7.82-7.99 (2H, m), 6.83-7.05 (2H, m).

Step 5: Preparation of the Title Compound 21

(21)

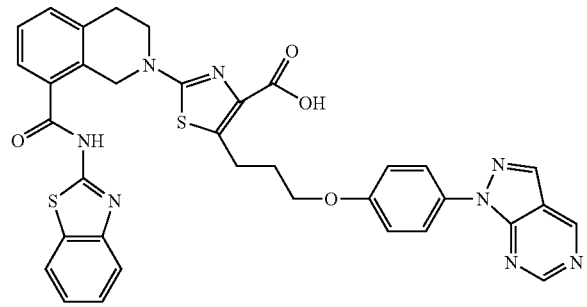

To a solution of compound 21D (106 mg, 0.498 mmol) in DMF (5 mL) was added sodium hydride (56.9 mg, 1.423 mmol). The resulting mixture was stirred at rt for 30 minutes and compound 2C (300 mg, 0.474 mmol) was added. The reaction mixture was stirred for 1 hour and 10% sodium hydroxide (1.897 mL, 4.74 mmol), THF (5 mL) and MeOH (3 mL) was added. The resulting mixture was stirred at 70° C. overnight, cooled, and filtered. The filtrate was acidified by HCl to pH 4. The precipitate was collected and dried to provide the desired product: $^1$H NMR (400 MHz, DMSO-$D_6$) δ ppm 12.85 (1H, s), 9.45 (1H, s), 9.10 (1H, s), 8.61 (1H, s), 7.98-8.06 (3H, m), 7.78 (1H, d), 7.67 (1H, d), 7.42-7.50 (2H, m), 7.32-7.40 (2H, m), 7.09-7.16 (2H, m), 4.84 (2H, s), 4.06 (2H, t), 3.73 (2H, t), 3.14-3.24 (2H, m), 3.03 (2H, t), 1.98-2.12 (2H, m); LCMS (APCI): m/z 687 (M+H).

Example 22

Synthesis of 2-(8-(benzo[d]thiazol-2-ylcarbamoyl)-3,4-dihydroisoquinolin-2(1H)-yl)-5-(3-(2-((1S,4S)-1,7,7-trimethylbicyclo[2.2.1]heptan-2-yloxy)phenoxy)propyl)thiazole-4-carboxylic acid (22)

(22)

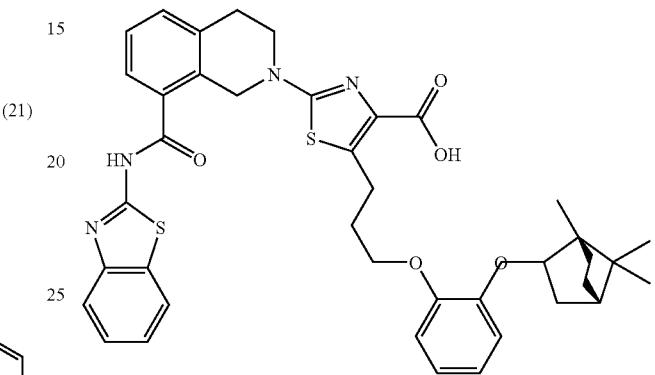

The title compound 22 generally was prepared as described in Example 2 by substituting 2-((1S,4S)-1,7,7-trimethylbicyclo[2.2.1]heptan-2-yloxy)phenol for phenol in step 4 of Example 2. The intermediate alkylation product was not isolated prior to ester hydrolysis. The final product underwent an additional MeOH wash providing the desired compound 22 in 76% yield: $^1$H NMR (300 MHz, DMSO-$d_6$) δ ppm 7.85 (1H, d), 7.76 (1H, dd), 7.64 (1H, d), 7.33 (3H, m), 7.20 (1H, m), 6.84 (4H, m), 4.93 (2H, s), 4.04 (1H, m), 3.91 (2H, t), 3.69 (2H, t), 3.18 (2H, m), 3.00 (2H, t), 1.96 (2H, m), 1.76 (2H, m), 1.62 (2H, m), 1.47 (1H, m), 1.07 (2H, m), 1.04 (3H, s), 0.93 (3H, s), 0.77 (3H, s); MS (ESI(+)): m/z 723 (M+H).

Example 23

Synthesis of 2-(8-(benzo[d]thiazol-2-ylcarbamoyl)-3,4-dihydroisoquinolin-2(1H)-yl)-5-(3-(2-(4-(pyridin-2-yl)piperazin-1-yl)benzo[d]thiazol-6-yloxy)propyl)thiazole-4-carboxylic acid (23)

(23)

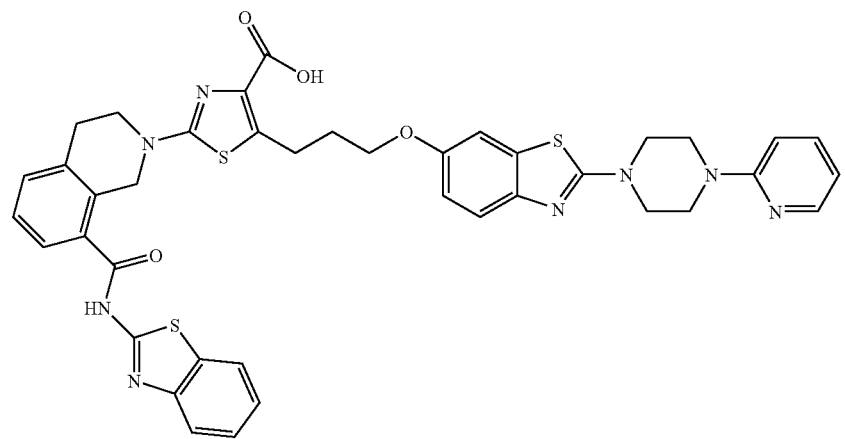

The title compound 23 generally was prepared as described in Example 2 by substituting 2-(4-(pyridin-2-yl)piperazin-1-yl)benzo[d]thiazol-6-ol for phenol in step 4 of Example 2. The alkylation intermediate was not isolated prior to ester hydrolysis. After precipitation with 1N HCl, the final product was further purified by column chromatography on silica gel eluting with a gradient of 0 to 10% MeOH in $CH_2Cl_2$ to provide the title compound 23 in 39% yield: $^1$H NMR (300 MHz, DMSO-$d_6$) δ ppm 12.87 (1H, s), 8.12 (1H, dd), 8.03 (1H, m), 7.72 (3H, m), 7.41 (6H, m), 7.08 (1H, d), 6.88 (1H, dd), 6.79 (1H, dd), 4.83 (2H, s), 3.98 (2H, m), 3.75 (6H, d), 3.69 (4H, m), 3.19 (2H, m), 3.03 (2H, t), 2.01 (2H, m); MS (ESI(+)): m/z 789 (M+H).

Example 24

Synthesis of 2-(8-(benzo[d]thiazol-2-ylcarbamoyl)-3,4-dihydroisoquinolin-2(1H)-yl)-5-(3-(4-(1-phenyl-cyclopentyl)phenoxy)propyl)thiazole-4-carboxylic acid (24)

(24)

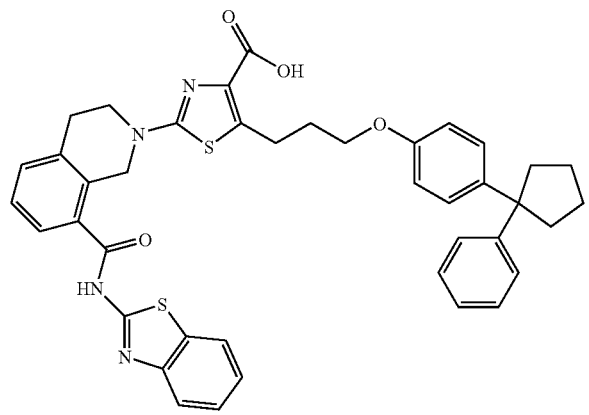

The title compound 24 generally was prepared as described in Example 2 by substituting 4-(1-phenylcyclopentyl)phenol for phenol in step 4 of Example 2. The alkylation intermediate was not isolated prior to ester hydrolysis. The final product underwent an additional MeOH wash providing the desired compound 24 in 67% yield: $^1$H NMR (300 MHz, DMSO-$d_6$) δ ppm 12.87 (1H, s), 12.56 (1H, s), 8.03 (1H, d), 7.79 (1H, d), 7.67 (1H, m), 7.42 (5H, m), 7.16 (6H, m), 6.77 (2H, m), 4.82 (2H, s), 3.91 (2H, t), 3.72 (2H, m), 3.14 (2H, m), 3.01 (2H, m), 2.20 (4H, m), 1.96 (2H, m), 1.59 (4H, m). MS (ESI(+)): m/z 715 (M+H).

Example 25

Synthesis of 2-(8-(benzo[d]thiazol-2-ylcarbamoyl)-3,4-dihydroisoquinolin-2(1H)-yl)-5-(3-(1-cyano-1,2-dihydrocyclobutabenzen-4-yloxy)propyl)thiazole-4-carboxylic acid (25)

(25)

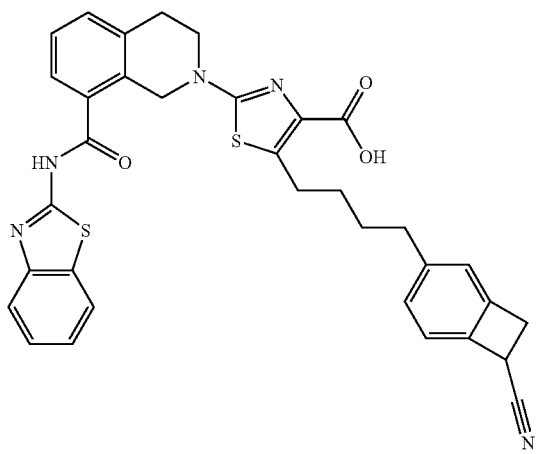

The title compound 25 was prepared by substituting 4-hydroxy-1,2-dihydrocyclobutabenzene-1-carbonitrile for phenol in step 4 of Example 2. The alkylation intermediate was not isolated. Ester hydrolysis was conducted at ambient temperature and the final product underwent an additional MeOH wash to provide the desired product 25 in 50% yield: $^1$H NMR (300 MHz, DMSO-$d_6$) δ ppm 12.89 (1H, s), 12.55 (1H, s), 8.03 (1H, m), 7.79 (1H, d), 7.67 (1H, d), 7.42 (4H, m), 7.16 (1H, d), 6.82 (2H, m), 4.83 (2H, s), 4.44 (1H, m), 3.95 (2H, t), 3.72 (2H, t), 3.58 (1H, dd), 3.37 (1H, m), 3.16 (2H, m), 3.03 (2H, t), 1.99 (2H, m); MS (ESI(+)): m/z 622 (M+H).

Example 26

Synthesis of 2-(8-(benzo[d]thiazol-2-ylcarbamoyl)-3,4-dihydroisoquinolin-2(1H)-yl)-5-(3-(4-(1-cyano-cyclobutyl)phenoxy)propyl)thiazole-4-carboxylic acid (26)

(26)

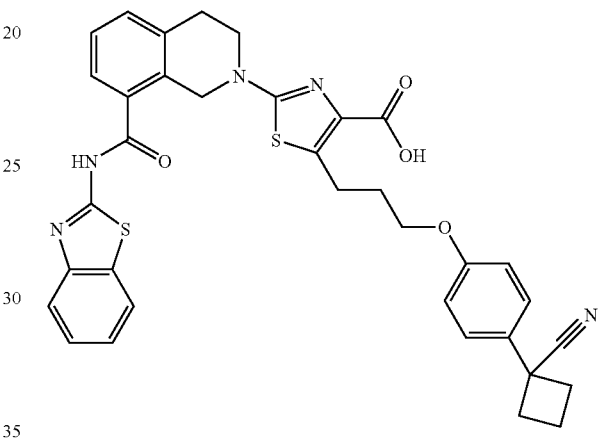

The title compound 26 generally was prepared as described in Example 2 by substituting 1-(4-hydroxyphenyl)cyclobutanecarbonitrile for phenol in step 4 of Example 2. The alkylation intermediate was not isolated. Ester hydrolysis was conducted at ambient temperature and the final product underwent an additional MeOH wash to provide the desired product 26 in 45% yield: $^1$H NMR (300 MHz, DMSO-$d_6$) δ ppm 12.72 (1H, s), 8.02 (1H, m), 7.78 (1H, d), 7.67 (1H, m), 7.41 (6H, m), 6.95 (2H, m), 4.84 (2H, s), 3.99 (2H, t), 3.72 (2H, t), 3.17 (2H, m), 3.03 (2H, t), 2.69 (2H, m), 2.56 (2H, m), 2.23 (2H, m), 1.97 (2H, m); MS (ESI(+)): m/z 650 (M+H).

Example 27

Synthesis of 2-(8-(benzo[d]thiazol-2-ylcarbamoyl)-3,4-dihydroisoquinolin-2(1H)-yl)-5-(3-(1,2,3,5,6,7-hexahydropyrido[3,2,1-ij]quinolin-8-yloxy)propyl)thiazole-4-carboxylic acid (27)

(27)

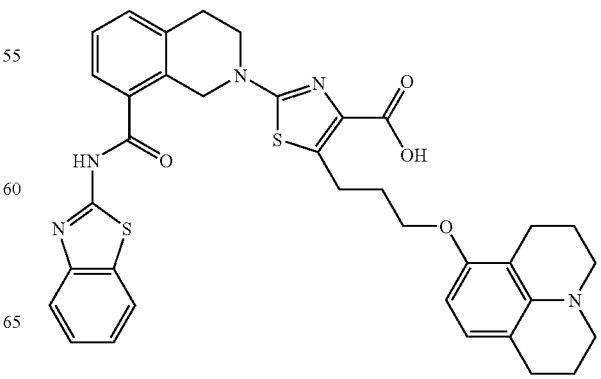

The title compound 27 generally was prepared as described in Example 2 by substituting 1,2,3,5,6,7-hexahydropyrido[3,2,1-ij]quinolin-8-ol for phenol in step 4 of Example 2. The alkylation intermediate was not isolated prior to ester hydrolysis. After precipitation with 1N HCl, the final product was further purified by column chromatography on silica gel eluting with a gradient of 0 to 12% MeOH in $CH_2Cl_2$ to provide the compound 27 in 20% yield: $^1H$ NMR (300 MHz, DMSO-$d_6$) δ ppm 12.90 (1H, s), 8.03 (1H, d), 7.79 (1H, d), 7.67 (1H, d), 7.43 (4H, m), 6.61 (1H, d), 6.09 (1H, d), 4.82 (2H, s), 3.86 (2H, t), 3.72 (2H, t), 3.17 (2H, t), 3.00 (6H, m), 2.58 (4H, m), 1.96 (2H, m), 1.81 (4H, m); MS (ESI(+)): m/z 666 (M+H).

Example 28

Synthesis of 2-(8-(benzo[d]thiazol-2-ylcarbamoyl)-3,4-dihydroisoquinolin-2(1H)-yl)-5-(3-(4-(2-(((5,6-dimethoxy-1,2,3,4-tetrahydronaphthalen-1-yl)methyl)(propyl)amino)ethyl)phenoxy)propyl)thiazole-4-carboxylic acid (28)

(28)

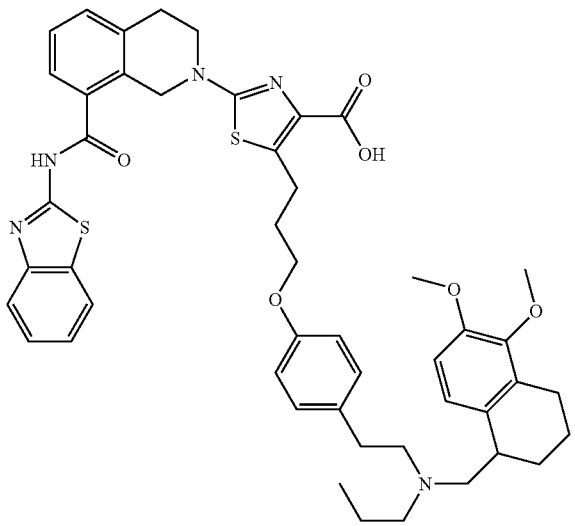

The title compound 28 generally was prepared as described in Example 2 by substituting 4-(2-4(5,6-dimethoxy-1,2,3,4-tetrahydronaphthalen-1-yl)methyl)(propyl)amino)ethyl)phenol, HCl for phenol in step 4 of Example 2. The alkylation intermediate was not isolated prior to ester hydrolysis. After precipitation of the desired product, the solid was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; A. 214, 245 nm; mobile phase A, 0.1% TFA in $H_2O$; mobile phase B, $CH_3CN$; linear gradient 0-90% of B in 40 minutes) to provide the title compound in 7% yield: $^1H$ NMR (400 MHz, DMSO-$d_6$) δ ppm 12.87 (1H, s), 8.91 (1H, s), 8.03 (1H, d), 7.79 (1H, d), 7.67 (1H, d), 7.47 (2H, m), 7.36 (2H, m), 7.25 (1H, d), 7.18 (1H, d), 6.97 (1H, m), 6.89 (3H, m), 4.83 (2H, s), 3.96 (2H, m), 3.77 (3H, d), 3.72 (2H, t), 3.67 (3H, d), 3.26 (6H, m), 3.16 (3H, m), 3.03 (2H, t), 2.91 (2H, m), 2.72 (1H, m), 2.58 (1H, m), 1.99 (2H, m), 1.74 (6H, m), 0.94 (3H, m). MS (ESI(+)): m/z 860 (M+H).

Example 29

Synthesis of 5-(3-(4-(4-(benzo[d]thiazol-2-yl)piperazin-1-yl)-2-methylphenoxy)propyl)-2-(8-(benzo[d]thiazol-2-ylcarbamoyl)-3,4-dihydroisoquinolin-2(1H)-yl)thiazole-4-carboxylic acid (29)

(29)

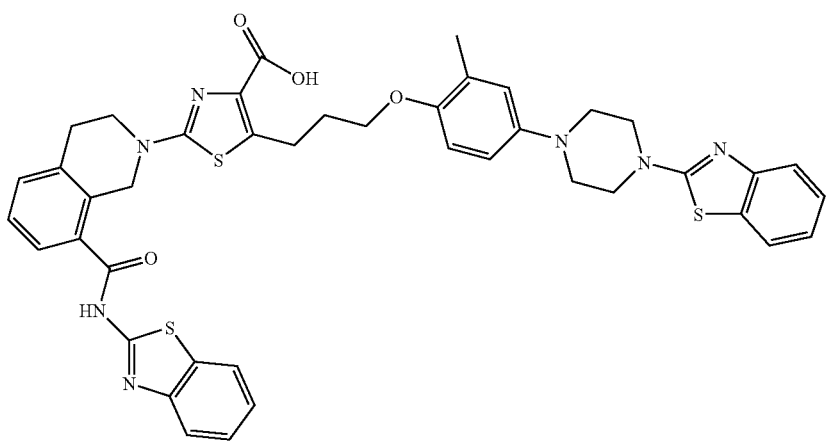

The title compound 29 generally was prepared as described in Example 2 by substituting 4-(4-(benzo[d]thiazol-2-yl)piperazin-1-yl)-2-methylphenol, 2HCl for phenol in step 4 of Example 2. The alkylation intermediate was not isolated prior to ester hydrolysis. After precipitation of the desired product, the solid was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 0-90% of B in 40 minutes) to provide the title compound 29 in 12% yield: $^1$H NMR (400 MHz, DMSO-d$_6$) δ ppm 12.87 (1H, s), 8.03 (1H, d), 7.78 (2H, t), 7.66 (1H, d), 7.47 (2H, m), 7.44 (1H, m), 7.36 (2H, m), 7.29 (1H, m), 7.08 (1H, m), 6.94 (1H, d), 6.54 (1H, d), 6.43 (1H, dd), 4.82 (2H, s), 3.99 (2H, t), 3.72 (2H, t), 3.68 (4H, m), 3.21 (6H, m), 3.02 (2H, t), 2.03 (3H, s), 2.00 (2H, m); MS (ESI(+)): m/z 802 (M+H).

Example 30

Synthesis of (E)-2-(8-(benzo[d]thiazol-2-ylcarbamoyl)-3,4-dihydroisoquinolin-2(1H)-yl)-5-(3-(3-(2-cyanovinyl)phenoxy)propyl)thiazole-4-carboxylic acid (30)

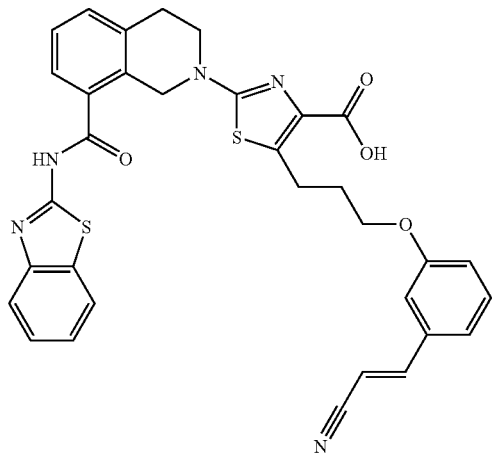

(30)

The title compound 30 generally was prepared as described in Example 2 by substituting (E)-3-(2-(1,2,4-oxadiazol-3-yl)vinyl)phenol for phenol in step 4 of Example 2. In addition to the desired alkylation, the NaH reacted with the oxadiazolyl moiety resulting in the formation of a cyano moiety in place of the oxadiazolyl moiety. This intermediate was not isolated prior to ester hydrolysis which was conducted at ambient temperature. After precipitation of the desired product, the solid was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 0-90% of B in 40 minutes) to provide the title compound 30 in 14% yield: $^1$H NMR (400 MHz, DMSO-d$_6$) δ ppm 12.87 (1H, s), 12.55 (1H, s), 8.03 (1H, d), 7.79 (1H, d), 7.67 (1H, d), 7.58 (1H, d), 7.47 (2H, m), 7.37 (2H, m), 7.30 (1H, d), 7.22 (1H, m), 7.18 (1H, d), 7.00 (1H, dd), 6.47 (1H, d), 4.82 (2H, s), 4.01 (2H, t), 3.72 (2H, t), 3.18 (2H, m), 3.03 (2H, t), 2.01 (2H, m). MS (ESI(+)): m/z 622 (M+H).

Example 31

Synthesis of 5-(3-(4-(5-amino-4-cyano-1H-pyrazol-3-yl)phenoxy)propyl)-2-(8-(benzo[d]thiazol-2-ylcarbamoyl)-3,4-dihydroisoquinolin-2(1H)-yl)thiazole-4-carboxylic acid (31)

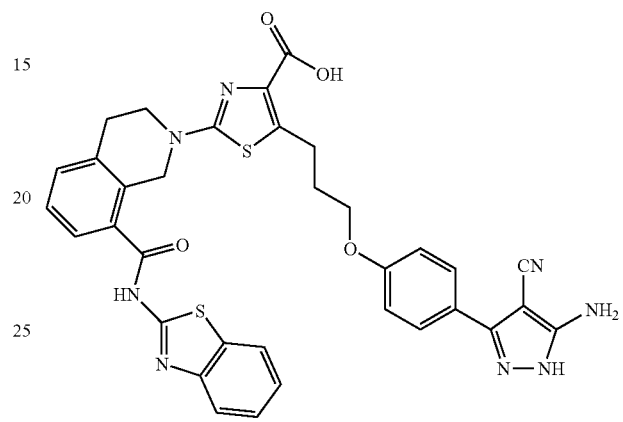

(31)

Step 1: Preparation of 4-(benzyloxy)benzoyl chloride (31A)

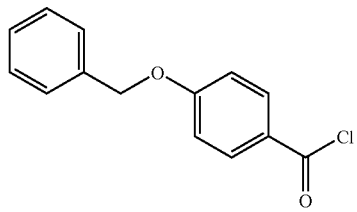

(31A)

4-(Benzyloxy)benzoic acid (4.73 g, 20.72 mmol) was suspended in CH$_2$Cl$_2$ (50 mL). The suspension was cooled to 0° C. To this suspension was added oxalyl chloride (3.63 mL, 41.4 mmol) followed by N,N-dimethylformamide (0.24 mL, 3.11 mmol) dropwise. The reaction was stirred for 16 hours. The reaction mixture was concentrated under reduced pressure, diluted with toluene, and concentrated under reduced pressure. The isolated solid was used directly for the next reaction without further purification.

Step 2: Preparation of 2-(4-(benzyloxy)benzoyl)malononitrile (31B)

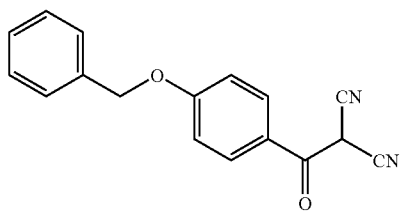

(31B)

NaH (1.657 g, 60%, 41.4 mmol) was suspended in THF (10 mL). To this suspension was added malononitrile (1.368 g, 20.71 mmol) in THF (10 mL) at 0° C. dropwise over 10 minutes. The suspension was stirred for additional 20 minutes. To this solution was added compound 31A (5.11 g, 20.71 mmol) in THF (40 mL) portion wise. Afterwards, the solution was warmed to rt and stirred for 30 minutes. The pH of the solvent was adjusted to 1 with concentrated HCl. The reaction mixture was concentrated, and partitioned between water and EtOAc. The aqueous layer was extracted with additional EtOAc. The combined organic layers were washed with brine, dried (MgSO$_4$), filtered, and concentrated under reduced pressure. The residue was triturated with 1:1 Hex/EtOAc (50 mL) to give a solid which was collected by filtration to provide 3.7 g of the desired product 31B: $^1$H NMR (DMSO-d$_6$): δ 7.60-7.63 (m, 2H), 7.32-7.47 (m, 5H), 7.03-7.07 (m, 2H), 5.16 (s, 2H). MS (DCI(+)): m/z 294 (M+NH$_4$).

Step 3: Preparation of 2-((4-(benzyloxy)phenyl)(methoxy)methylene)malononitrile (31C)

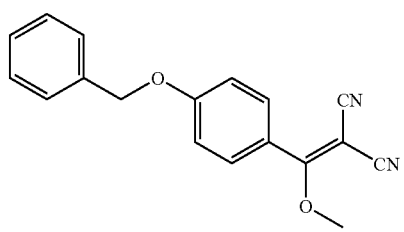

(31C)

Compound 31B (3.7 g, 13.39 mmol) was dissolved in 1,4-dioxane (30 mL) and water (5 mL). To this solution was added to sodium bicarbonate (9.0 g, 107 mmol) portionwise to control the gas formation. To the resulting suspension was added dimethyl sulfate (8.96 mL, 94 mmol). The reaction was heated under reflux for 2 hours. The reaction mixture was concentrated, and partitioned between water and EtOAc. The aqueous layer was extracted with additional EtOAc. The combined organic layers were washed with brine, dried (MgSO$_4$), filtered, and concentrated under reduced pressure. The residue was purified by flash column chromatography on silica gel eluting with 7:3/hexanes: EtOAc to provide 3.1 g of the desired product: $^1$H NMR (DMSO-d$_6$): δ 7.64-7.68 (m, 2H), 7.34-7.69 (m, 5H), 7.22-7.26 (m, 2H), 5.22 (s, 2H), 3.92 (s, 3H). MS (DCI(+)): m/z 308 (M+NH$_4$).

Step 4: Preparation of 5-amino-3-(4-(benzyloxy)phenyl)-1H-pyrazole-4-carbonitrile (31D)

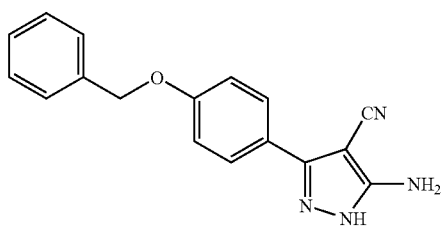

(31D)

Compound 31C (3.1 g, 10.68 mmol) was dissolved in EtOH (20 mL). To this solution was added hydrazine hydrate (0.622 mL, 12.81 mmol). The reaction was heated under reflux for 2 hours. The solvent was removed, and the residue was taken up into EtOAc. It was then washed with water, brine, dried over MgSO$_4$, and concentrated under reduced pressure to provide 2.72 g of the desired product: $^1$H NMR (DMSO-d$_6$): δ 12.64 and 11.99 (s, 1H), 7.71-7.74 (m, 2H), 7.32-7.48 (m, 5H), 7.09-7.10 (br, 2H), 6.38 (s, 2H), 5.15 (s, 2H). MS (DCI(+)): m/z 291 (M+H).

Step 5: Preparation of tert-butyl 5-amino-3-(4-(benzyloxy)phenyl)-4-cyano-1H-pyrazole-1-carboxylate (31E)

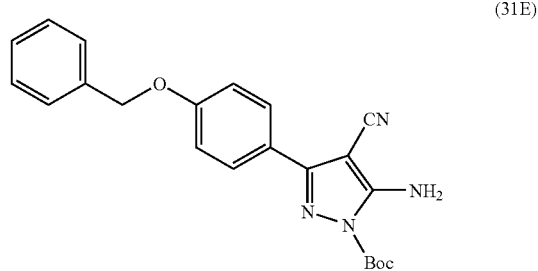

(31E)

To a mixture of compound 31D (1.6 g, 5.51 mmol) and di-tert-butyl dicarbonate (1.44 g, 6.61 mmol) in THF (15 mL) was added N,N-dimethylpyridin-4-amine (0.808 g, 6.61 mmol) at rt. The reaction mixture was stirred for 1 hour. The solvent was removed, and residue was purified by flash column chromatography on silica gel eluting with 5:1/hexanes: EtOAc to provide 2.03 g of the desired product: $^1$H NMR (DMSO-d$_6$): δ 7.78 (d, J=8.9 Hz, 2H), 7.68 (s, 2H), 7.32-7.48 (m, 5H), 7.15 (d, J=8.9 Hz, 2H), 5.17 (s, 2H), 1.59 (s, 9H). MS (DCI(+)): m/z 391 (M+H).

Step 6: Preparation of tert-butyl 5-amino-4-cyano-3-(4-hydroxyphenyl)-1H-pyrazole-1-carboxylate (31F)

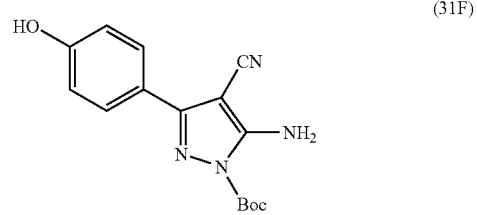

(31F)

A mixture of compound 31E (1.3 g, 3.33 mmol) and Pd/C (0.071 g) in EtOH (15 mL) was hydrogenated with a balloon of hydrogen at rt for 6 hours. The solvent was removed, and residue was purified by flash column chromatography on silica gel eluting with 1:1/hexanes:EtOAc to provide 0.85 g of the desired product 31F: $^1$H NMR (DMSO-d$_6$): δ 9.88 (s, 1H), 7.67 (d, J=8.9 Hz, 2H), 7.64 (s, 2H), 6.87 (d, J=8.9 Hz, 2H), 1.59 (s, 9H). MS (DCI(+)): m/z 301 (M+H).

Step 7: Preparation of Title Compound 31

To compound 31F (0.132 g, 0.44 mmol) in DMF (4 mL) was added 60% sodium hydride (0.048 g, 1.2 mmol) at 0° C.

The solution was stirred for 10 minutes. To this solution was added compound 2C. The solution was stirred at rt for 2 hours. The solution was diluted with conc. HCl (0.5 mL), and heated at 60° C. for 30 minutes. The mixture was diluted with DMSO (5 mL) and MeOH (9 mL). The solid was filtered off. The filtrate was then purified by Prep HPLC to provide 12 mg of the desired product: $^1$H NMR (DMSO-d$_6$): δ 8.03 (d, J=7.98 Hz, 1H), 7.79 (d, J=7.98 Hz, 1H), 7.67-7.71 (m, 4H), 7.33-7.49 (m, 5H), 7.00 (d, J=8.59 Hz, 2H), 4.84 (s, 2H), 4.03 (t, J=5.98 Hz, 2H), 3.71-3.74 (m, 2H), 3.17-3.20 (m, 2H), 3.01-3.05 (m, 2H), 2.02 (m, 2H). MS (ESI(+)): 677 (M+H).

Example 32

Synthesis of 2-(8-(benzo[d]thiazol-2-ylcarbamoyl)-3,4-dihydroisoquinolin-2(1H)-yl)-5-(3-(4-cyano-3-(4-hydroxyphenyl)-1H-pyrazol-5-ylamino)propyl)thiazole-4-carboxylic acid (32)

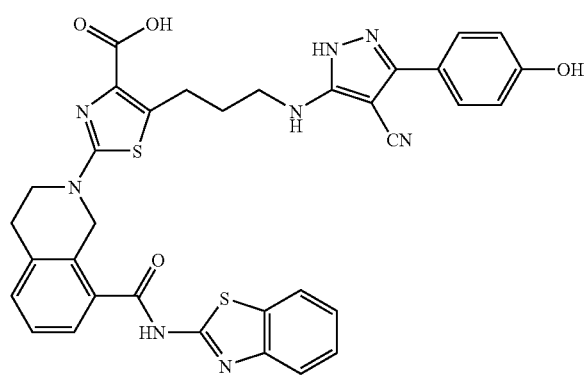

(32)

The title compound 32 was isolated as a by-product from the synthesis of compound 31: $^1$H NMR (DMSO-d$_6$): δ 8.02 (d, J=7.67 Hz, 1H), 7.79 (d, J=7.98 Hz, 1H), 7.67 (d, J=7.67 Hz, 1H), 7.59-7.61 (m, 2H), 7.33-7.49 (m, 5H), 6.80-6.82 (m, 2H), 4.84 (s, 2H), 4.03 (t, J=5.98 Hz, 2H), 3.93-3.95 (m, 2H), 3.71-3.74 (m, 2H), 3.02-3.08 (m, 4H), 1.94-1.98 (m, 2H). MS (ESI(+)): 677 (M+H).

Example 33

Synthesis of 5-(3-(4-(1H-pyrazolo[3,4-d]pyrimidin-1-yl)phenoxy)propyl)-2-(8-(benzo[d]thiazol-2-ylcarbamoyl)-3,4-dihydroisoquinolin-2(1H)-yl)thiazole-4-carboxylic acid (33)

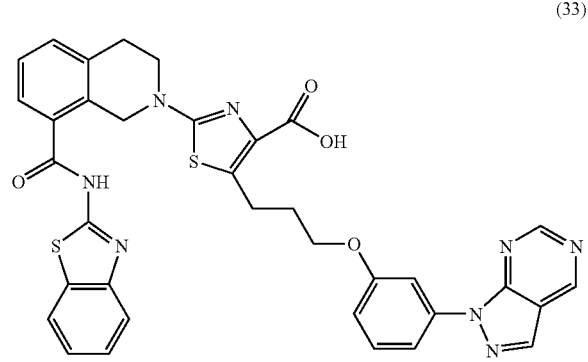

(33)

Step 1: Preparation of 5-amino-1-(3-bromophenyl)-1H-pyrazole-4-carboxylic acid (33A)

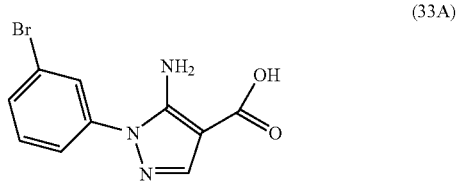

(33A)

The compound 33A was prepared using the same procedure described in step 1 of Example 21 by replacing 4-bromophenylhydrazine hydrochloride with 3-bromophenylhydrazine hydrochloride: $^1$H NMR (400 MHz, DMSO-D$_6$) δ ppm 12.13 (1H, s), 7.74 (1H, t), 7.70 (1H, s), 7.57-7.62 (2H, m), 7.49 (1H, t), 6.41 (2H, s).

Step 2: Preparation of 1-(3-bromophenyl)-1H-pyrazolo[3,4-d]pyrimidine (33B)

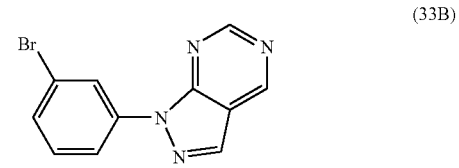

(33B)

The compound 33B was prepared using the same procedure described in step 2 of Example 21 by replacing compound 21A with compound 33A: $^1$H NMR (400 MHz, DMSO-D$_6$) δ ppm 9.49 (1H, s), 9.20 (1H, s), 8.71 (1H, s), 8.51 (1H, t), 8.25-8.30 (1H, m), 7.55-7.63 (2H, m).

Step 3: Preparation of 1-(3-(4,4,5,5-tetramethyl-1,3,2-dioxaborolan-2-yl)phenyl)-1H-pyrazolo[3,4-d]pyrimidine (33C)

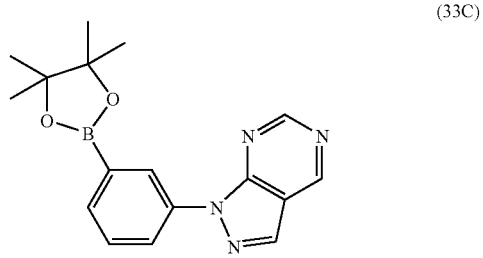

(33C)

The title compound 33C was prepared using the same procedure described in step 3 of Example 21 by replacing compound 21B with compound 33B: $^1$H NMR (400 MHz, DMSO-D$_6$) δ ppm 9.48 (1H, s), 9.18 (1H, s), 8.68 (1H, s), 8.47 (1H, d), 8.36-8.40 (1H, m), 7.68-7.71 (1H, m), 7.64 (1H, t), 1.34 (12H, s).

Step 4: Preparation of 3-(1H-pyrazolo[3,4-d]pyrimidin-1-yl)phenol (33D)

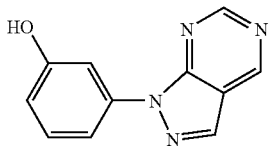

(33D)

The title compound 33D was prepared using the same procedure described in step 4 of Example 21 by replacing compound 21C with compound 33C: $^1$H NMR (400 MHz, DMSO-D$_6$) δ ppm 9.86 (1H, s), 9.46 (1H, s), 9.16 (1H, s), 8.64 (1H, s), 7.72 (1H, t), 7.67-7.70 (1H, m), 7.38 (1H, t), 6.80 (1H, dd).

Step 5: Preparation of the Title Compound 33

The title compound 33 was prepared using the same procedure described in step 5 of Example 21 by replacing compound 21D with compound 33D: $^1$H NMR (500 MHz, DMSO-D6) δ ppm 12.89 (1H, s), 12.53 (1H, s), 9.46 (1H, s), 9.15 (1H, s), 8.64 (1H, s), 8.02 (1H, d), 7.76-7.84 (3H, m), 7.66 (1H, d), 7.33-7.49 (5H, m), 6.93-6.97 (1H, m), 4.82 (2H, s), 4.09 (2H, t), 3.72 (2H, t), 3.18-3.26 (2H, m), 3.02 (2H, t), 2.01-2.13 (2H, m); LCMS (APCI): m/z 687 (M+H).

Example 34

Synthesis of 2-(8-(benzo[d]thiazol-2-ylcarbamoyl)-3,4-dihydroisoquinolin-2(1H)-yl)-5-(4-(hydroxymethyl)phenyl)thiazole-4-carboxylic acid (34)

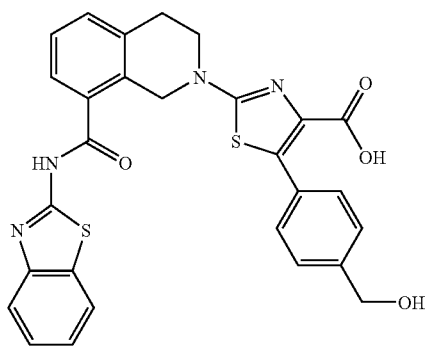

(34)

Step 1: Preparation of ethyl 2-(8-(benzo[d]thiazol-2-ylcarbamoyl)-3,4-dihydroisoquinolin-2(1H)-yl)thiazole-4-carboxylate (34A)

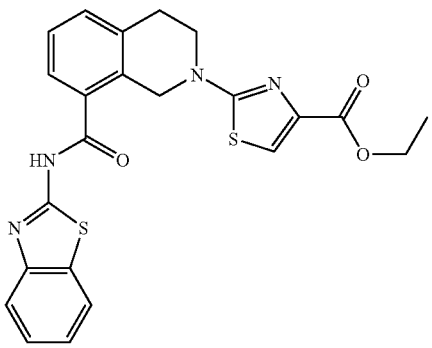

(34A)

Compound 34A was prepared in a similar manner to the synthesis of step 3 of Example 1 by substituting methyl 2-chlorothiazole-4-carboxylate with ethyl 2-chlorothiazole-4-carboxylate: MS (ESI(+)): 465 (M+H).

Step 2: Preparation of ethyl 2-(8-(benzo[d]thiazol-2-ylcarbamoyl)-3,4-dihydroisoquinolin-2(1H)-yl)-5-bromothiazole-4-carboxylate (34B)

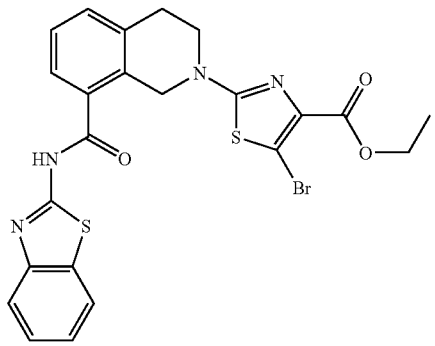

(34B)

To compound 34A in acetonitrile was added 1.05 eq of NBS. The reaction mixture was stirred at rt for 2 hours. The solvent was removed, and the residue was purified by column chromatography on silica gel eluting with 3:2 hexanes/EtOAc to provide the desired product: MS (ESI(+)): 544 (M+H).

Step 3: Preparation of ethyl 2-(8-(benzo[d]thiazol-2-yl((2-(trimethylsilyl)ethoxy)methyl)carbamoyl)-3,4-dihydroisoquinolin-2(1H)-yl)-5-bromothiazole-4-carboxylate (34C)

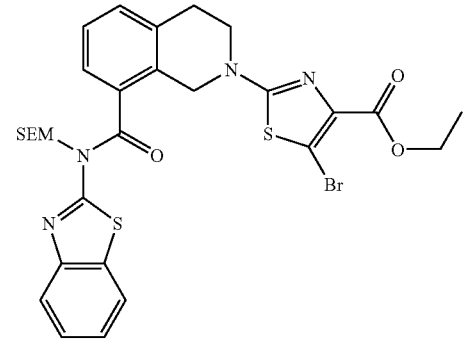

(34C)

To a mixture of compound 34B (0.815 g, 1.5 mmol) and SEMCl (0.318 mL, 1.8 mmol) in THF (6 mL) was added TEA (0.65 mL, 4.5 mmol) at rt. The reaction mixture was stirred for 20 minutes, concentrated under reduced pressure, and purified by column chromatography on silica gel eluting with 3:1/hexanes:EtOAc to provide 0.95 g of the desired product as a mixture of two inseparable isomers: MS (ESI(+)): m/z 657 (M+H).

Step 4: Preparation of ethyl 2-(8-(benzo[d]thiazol-2-yl((2-(trimethylsilyl)ethoxy)methyl)carbamoyl)-3,4-dihydroisoquinolin-2(1H)-yl)-5-(4-(hydroxymethyl)phenyl)thiazole-4-carboxylate (34D)

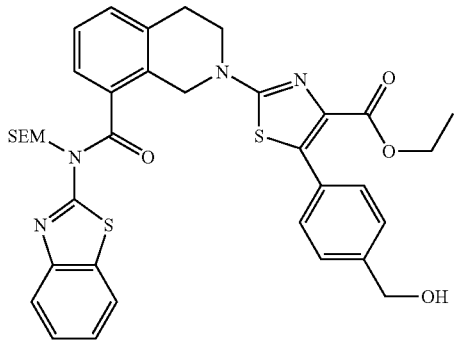

(34D)

A mixture of compound 34C (0.135 g, 0.2 mmol), 4-(hydroxymethyl)phenylboronic acid (0.033 g, 0.22 mmol), Pd(PPh$_3$)$_4$ (0.012 g, 0.01 mmol) and CsF (0.091 g, 0.6 mmol) in the DME (2 mL) and MeOH (1 mL) were heated under microwave conditions (110° C., 20 minutes). The reaction mixture was concentrated, and partitioned between water and EtOAc. The aqueous layer was extracted with additional EtOAc. The combined organic layers were washed with brine, dried (MgSO$_4$), filtered, and concentrated under reduced pressure. The residue was purified by flash column chromatography on silica gel eluting with 1:1/hexanes:EtOAc to provide 0.085 g of the desired product 34D, which was also a mixture of two regioisomers. MS (ESI(+)): m/z 701 (M+H).

Step 5: Preparation of Title Compound 34

To compound 34D (0.14 g) in 1,4-dioxane (2 mL) was added 4 N HCl in 1,4-dioxane (2 mL) and MeOH (0.5 mL). The solution was stirred for 1 hour at rt, concentrated under reduced pressure, and added 1.0 N LiOH (2 mL) in 1,4-dioxane (2 mL). The solution was stirred at 60° C. for 1 hour, concentrated under reduced pressure and purified by Prep HPLC to provide the desired product 34: $^1$H NMR (DMSO-d$_6$): δ 8.02 (d, J=7.98 Hz, 1H), 7.79 (d, J=7.98 Hz, 1H), 7.69 (d, J=7.36 Hz, 1H), 7.29-7.49 (m, 8H), 4.90 (s, 2H), 4.50 (s, 2H), 3.78 (t, J=5.98 Hz, 2H), 3.98 (t, J=5.98 Hz, 2H); MS (ESI(+)): m/z 543 (M+H).

Example 35

Synthesis of 5-(4-((4-(5-amino-4-cyano-1H-pyrazol-3-yl)phenoxy)methyl)phenyl)-2-(8-(benzo[d]thiazol-2-ylcarbamoyl)-3,4-dihydroisoquinolin-2(1H)-yl)thiazole-4-carboxylic acid (35)

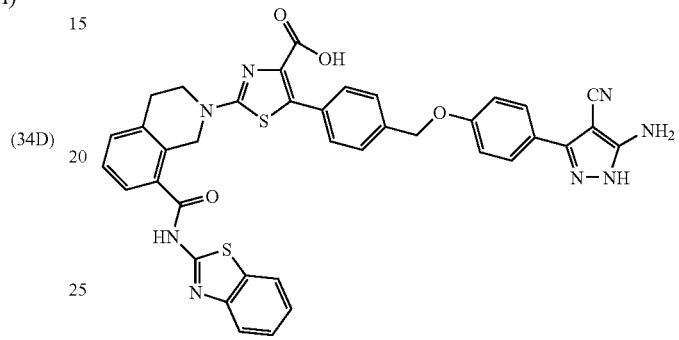

(35)

Step 1: Preparation of ethyl 5-(4-((4-(5-amino-1-(tert-butoxycarbonyl)-4-cyano-1H-pyrazol-3-yl)phenoxy)methyl)phenyl)-2-(8-(benzo[d]thiazol-2-yl((2-(trimethylsilyl)ethoxy)methyl)carbamoyl)-3,4-dihydroisoquinolin-2(1H)-yl)thiazole-4-carboxylate (35A)

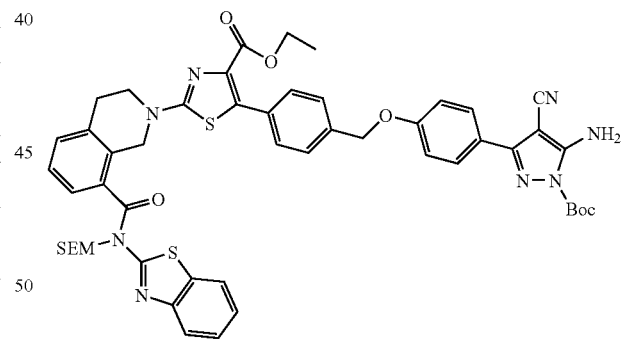

(35A)

A mixture of compound 34D (0.14 g, 0.2 mmol), PPh$_3$ (0.079 g, 0.3 mmol), and compound 31F (0.066 g, 0.022 mmol) was dissolved in THF (3 mL). The solution was cooled to 0° C. To this solution was added DBAD. The reaction mixture was stirred at rt for 2 hours. The solvent was removed, and the residue was purified by flash column chromatography on silica gel eluting with 2:1/hexanes:EtOAc to afford 0.13 g of the title compound as a mixture of two inseparable isomers. MS (ESI(+)): m/z 982 (M+NH$_4$—H$_2$O).

Step 2: Preparation of Title Compound 35

The title compound 35 was prepared in a similar manner to the synthesis of example 34 by substituting compound 34D with compound 35A: $^1$H NMR (DMSO-d$_6$): δ 8.02 (d, J=7.67 Hz, 1H), 7.79 (d, J=8.29 Hz, 1H), 7.68-7.74 (m, 3H), 7.37-7.49 (m, 9H), 7.12 (d, J=8.59 Hz, 2H), 4.90 (s, 2H), 5.16 (s, 2H), 4.91 (s, 2H), 3.79 (t, J=5.98 Hz, 2H), 3.08 (t, J=5.83 Hz, 2H). MS (ESI(+)): m/z 725 (M+H).

Example 36

Synthesis of 5-(3-(3-(5-amino-4-cyano-1H-pyrazol-3-yl)phenoxy)prop-1-ynyl)-2-(8-(benzo[d]thiazol-2-ylcarbamoyl)-3,4-dihydroisoquinolin-2(1H)-yl)thiazole-4-carboxylic acid (36)

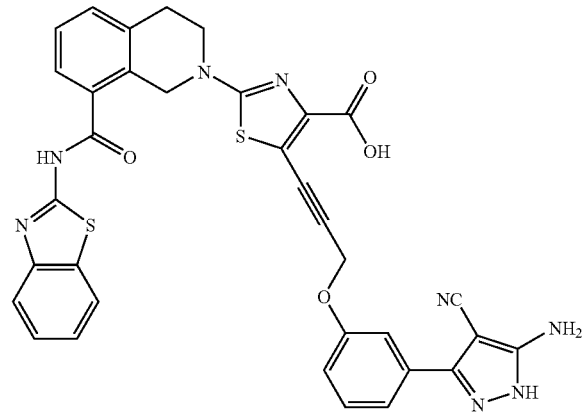

(36)

Step 1: Preparation of tert-butyl 5-amino-4-cyano-3-(3-hydroxyphenyl)-1H-pyrazole-1-carboxylate (36A)

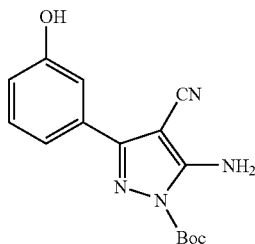

(36A)

Compound 36A was prepared in a similar manner to the synthesis of compound 31F by substituting 4-(benzyloxy) benzoic acid with 3-(benzyloxy)benzoic acid: $^1$H NMR (DMSO-d$_6$): δ 9.70 (s, 1H), 7.68 (s, 2H), 7.25-7.32 (m, 3H), 6.86-6.89 (m, 1H), 1.60 (s, 9H). MS (ESI(+)): m/z 322 (M+Na).

Step 2: Preparation of ethyl 2-(8-(benzo[d]thiazol-2-yl((2-(trimethylsilyl)ethoxy)methyl)carbamoyl)-3,4-dihydroisoquinolin-2(1H)-yl)-5-(3-hydroxyprop-1-ynyl)thiazole-4-carboxylate (36B)

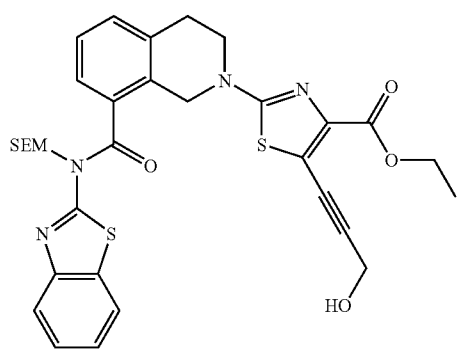

(36B)

A mixture of compound 34C (0.38 g, 0.564 mmol), prop-2-yn-1-ol (0.047 g, 0.846 mmol), CuI (0.011 g, 0.056 mmol), Et$_3$N (1.57 mL, 11 mmol) and Pd(PPh$_3$)$_2$Cl$_2$ (0.02 g, 0.028 mmol) in DMF (2 mL) was heated at 90° C. for 2 hours. After cooling, the reaction mixture was diluted with CH$_2$Cl$_2$. The solid was filtered off. The filtrate was concentrated. The residue was purified by flash column chromatography on silica gel eluting with 3:2/hexanes:EtOAc to provide 0.19 g of the desired product 36B as a mixture of two inseparable isomers: MS (ESI(+)): m/z 649 (M+H).

Step 3: Preparation of ethyl 5-(3-(3-(5-amino-1-(tert-butoxycarbonyl)-4-cyano-1H-pyrazol-3-yl)phenoxy) prop-1-ynyl)-2-(8-(benzo[d]thiazol-2-yl((2-(trimethylsilyl)ethoxy)methyl)carbamoyl)-3,4-dihydroisoquinolin-2(1H)-yl)thiazole-4-carboxylate (36C)

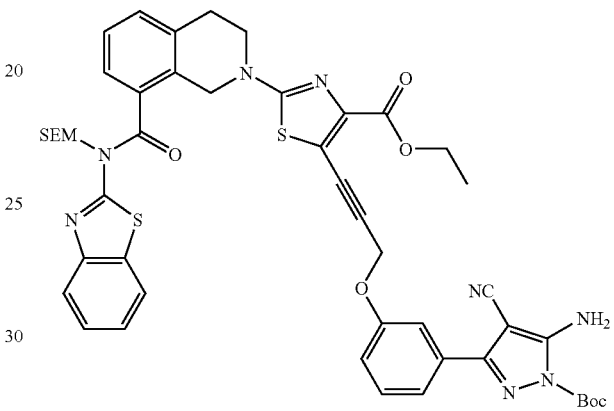

(36C)

Compound 36C was prepared in a similar manner to the synthesis of compound 35A by substituting compound 34D and compound 31F with compound 36B and compound 36A, respectively as a mixture of two inseparable isomers: MS (ESI(+)): m/z 932 (M+H).

Step 4: Preparation of Title Compound 36

Title compound 36 was prepared in a similar manner to the synthesis of compound 34 by substituting compound 34D with compound 36C in step 5 of Example 34: $^1$H NMR (DMSO-d$_6$): δ 8.03 (d, J=7.93 Hz, 1H), 7.79 (d, J=7.93 Hz, 1H), 7.66-7.68 (m, 1H), 7.35-7.48 (m, 8H), 5.08 (s, 2H), 4.91 (s, 2H), 3.70-3.73 (m, 2H), 3.46-3.49 (m, 2H), 3.05-3.07 (m, 2H). MS (ESI(+)): m/z 670 (M−H).

Example 37

Synthesis of 5-(4-((3-(5-amino-4-cyano-1H-pyrazol-3-yl)phenoxy)methyl)phenyl)-2-(8-(benzo[d]thiazol-2-ylcarbamoyl)-3,4-dihydroisoquinolin-2(1H)-yl) thiazole-4-carboxylic acid (37)

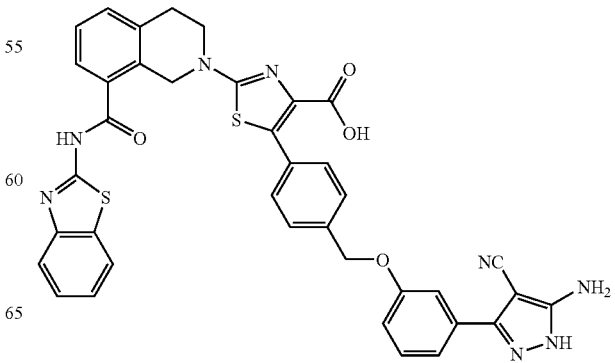

(37)

Step 1: Preparation of ethyl 5-(4-((3-(5-amino-1-(tert-butoxycarbonyl)-4-cyano-1H-pyrazol-3-yl)phenoxy)methyl)phenyl)-2-(8-(benzo[d]thiazol-2-yl((2-(trimethylsilyl)ethoxy)methyl)carbamoyl)-3,4-dihydroisoquinolin-2(1H)-yl)thiazole-4-carboxylate (37A)

(37A)

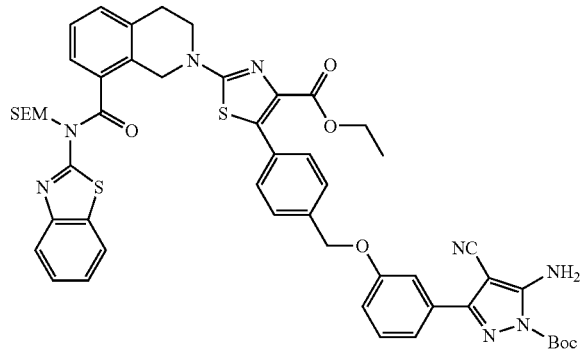

The title compound 37A was prepared in a similar manner to the synthesis of compound 35A by substituting compound 31F with compound 36A as a mixture of two inseparable isomers: MS (ESI(+)): m/z 984 (M+H).

Step 2: Preparation of Title Compound 37

The title compound 37 was prepared in a similar manner to the synthesis of compound 34 by substituting compound 34D with compound 37A: $^1$H NMR (DMSO-d$_6$): δ 8.02 (d, J=7.36 Hz, 1H), 7.78 (d, J=7.98 Hz, 1H), 7.33-7.49 (m, 11H), 7.05-7.08 (m, 1H), 5.15 (s, 2H), 4.91 (s, 2H), 3.78 (t, J=6.14 Hz, 2H), 3.08 (t, J=5.83 Hz, 2H). MS (ESI(+)): m/z 725 (M+H).

Example 38

Synthesis of 2-(8-(Benzo[d]thiazol-2-ylcarbamoyl)-3,4-dihydroisoquinolin-2(1H)-yl)-5-(3-hydroxypropyl)thiazole-4-carboxylic acid (38)

(38)

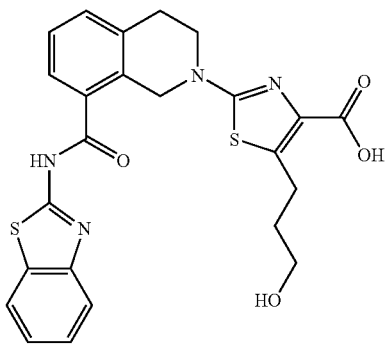

Step 1: Preparation of methyl 2-(8-(benzo[d]thiazol-2-yl((2-(trimethylsilyl)ethoxy)methyl)carbamoyl)-3,4-dihydroisoquinolin-2(1H)-yl)thiazole-4-carboxylate (38A)

(38A)

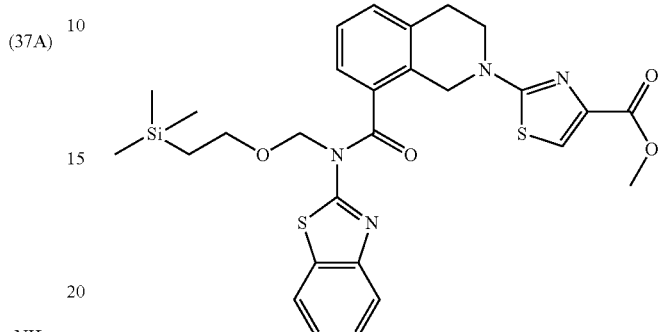

To a solution of methyl 2-(8-(benzo[d]thiazol-2-ylcarbamoyl)-3,4-dihydroisoquinolin-2(1H)-yl)thiazole-4-carboxylate (14 g, 31.1 mmol) in THF (150 mL) was added TEA (6.3 g, 62.1 mmol) and 2-(trimethylsilyl)ethoxymethyl chloride (7.77 g, 46.6 mmol). The mixture was stirred at r.t. for 4 h. The mixture was diluted with EtOAc (400 mL) and washed with 3% HCl, water and brine. Evaporation of solvent gave 18.2 g of product. LC/MS (APCI): m/z 580.9 (M+H).

Step 2: Preparation of tert-butyl 2-(8-(benzo[d]thiazol-2-yl((2-(trimethylsilyl)ethoxy)methyl)carbamoyl)-3,4-dihydroisoquinolin-2(1H)-yl)thiazole-4-carboxylate (38B)

(38B)

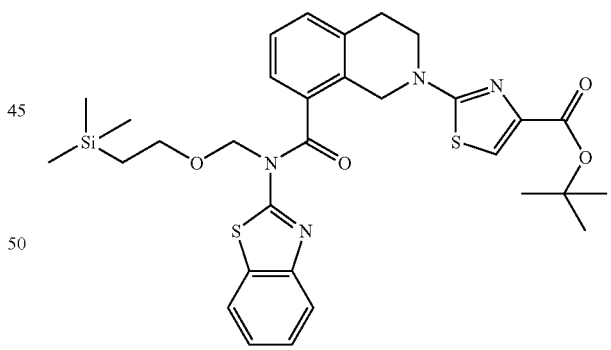

To a stirring solution of methyl 2-(8-(benzo[d]thiazol-2-yl((2-(trimethylsilyl)ethoxy)methyl)carbamoyl)-3,4-dihydroisoquinolin-2(1H)-yl)thiazole-4-carboxylate (38A) (14 g, 24.1 mmol) in t-butyl acetate (200 mL) was added 2 mL of t-BuOK in THF (2M) under vacuum. 3×2 mL t-BuOK were added to the stirring solution under vacuum to drive the reaction to complete. The mixture was then acidified to neutrality and washed with water, brine, dried over Na$_2$SO$_4$, and concentrated under reduced pressure. The crude material was purified by column chromatography on silica gel eluting with 5% EtOAc in hexanes to provide 3.5 g of the desired product 38B: $^1$H NMR (300 MHz, CDCl$_3$) δ ppm 8.29 (1H, m), 7.71

(1H, d), 7.62 (2H, m), 7.49 (2H, t), 7.34 (3H, m), 6.02 (2H, s), 5.20 (2H, s), 4.02 (2H, m), 3.71 (3H, m), 3.08 (2H, m), 1.59 (9H, t), 0.97 (2H, m), −0.09 (9H, m). MS (ESI(+)): m/z 623.0 (M+H).

Step 3: Preparation of tert-butyl 2-(8-(benzo[d]thiazol-2-yl((2-(trimethylsilyl)ethoxy)methyl)carbamoyl)-3,4-dihydroisoquinolin-2(1H)-yl)-5-iodothiazole-4-carboxylate (38C)

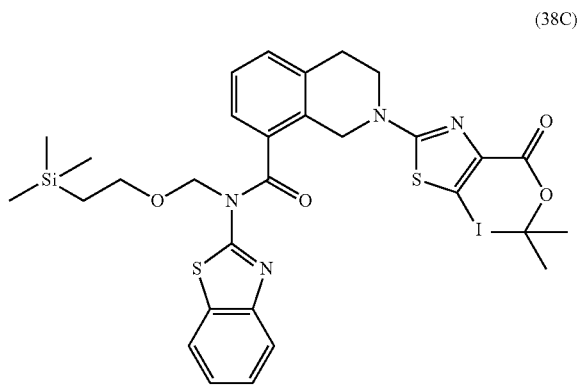

(38C)

To a solution of tert-butyl 2-(8-(benzo[d]thiazol-2-yl((2-(trimethylsilyl)ethoxy)methyl)carbamoyl)-3,4-dihydroisoquinolin-2(1H)-yl)thiazole-4-carboxylate (38B) (2.2 g, 3.53 mmol) in DCM (30 mL) was added NIS (0.795 g, 3.53 mmol). The mixture was stirred at r.t. overnight. The mixture was then diluted with EtOAc (300 mL) and washed with water, brine, dried over Na₂SO₄, and concentrated under reduced pressure. The crude material was purified by column chromatography on silica gel eluting with 5% EtOAc in hexanes to provide 2.6 g of the desired product. LC/MS (APCI): m/z 749.2 (M+H).

Step 4: Preparation of tert-butyl 2-(8-(benzo[d]thiazol-2-yl((2-(trimethylsilyl)ethoxy)methyl)carbamoyl)-3,4-dihydroisoquinolin-2(1H)-yl)-5-(3-hydroxyprop-1-ynyl)thiazole-4-carboxylate (38D)

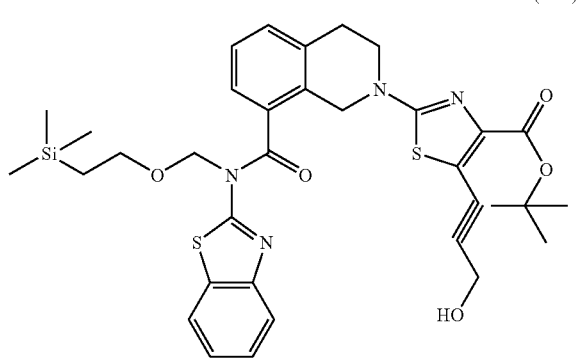

(38D)

To a solution of tent-butyl 2-(8-(benzo[d]thiazol-2-yl((2-(trimethylsilyl)ethoxy)methyl)carbamoyl)-3,4-dihydroisoquinolin-2(1H)-yl)-5-iodothiazole-4-carboxylate (38C) (2.5 g, 3.34 mmol) and prop-2-yn-1-ol (562 mg, 10 mmol) in THF (20 mL) was added Pd(Ph₃P)₄ (193 mg, 0.167 mmol), CuI (64 mg, 0.334 mmol), DIEA (863 mg, 6.7 mmol). The mixture was stirred under nitrogen at rt overnight. The mixture was then diluted with DCM (400 mL) and washed with water, brine, dried over Na₂SO₄, and concentrated under reduced pressure. The crude material purified by column chromatography on a silica gel column eluting with 5% MeOH in DCM to provide 2.0 g (88%) of the desired product: ¹H NMR (300 MHz, CDCl₃) δ ppm 8.31 (1H, m), 7.72 (1H, d), 7.59 (1H, m), 7.49 (1H, d), 7.34 (3H, m), 6.01 (2H, s), 5.18 (2H, s), 4.53 (2H, d), 4.00 (2H, t), 3.74 (2H, t), 3.07 (2H, t), 1.61 (9H, s), 0.98 (2H, t), 0.01 (9H, m). MS (ESI(+)): m/z 677 (M+H).

Step 5: Preparation of tert-butyl 2-(8-(benzo[d]thiazol-2-yl((2-(trimethylsilyl)ethoxy)methyl)carbamoyl)-3,4-dihydroisoquinolin-2(1H)-yl)-5-(3-hydroxypropyl)thiazole-4-carboxylate (38E)

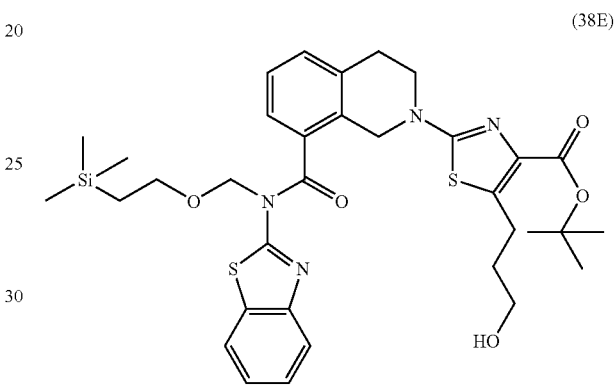

(38E)

To a solution of methyl 2-(8-(benzo[d]thiazol-2-ylcarbamoyl)-3,4-dihydroisoquinolin-2(1H)-yl)-5-(3-hydroxyprop-1-ynyl)thiazole-4-carboxylate (38D) (2.0 g, 3.96 mmol) in EtOAc (20 mL) was added PtO₂ (240 mg, 1.1 mmol). The mixture was stirred at rt under hydrogen (balloon) overnight. The mixture was then filtered and the filtrate was concentrated under reduced pressure to provide the desired product 38E: ¹H NMR (300 MHz, CDCl₃) δ ppm 8.30 (1H, m), 7.71 (1H, d), 7.59 (1H, m), 7.49 (1H, m), 7.35 (3H, m), 6.00 (2H, s), 5.14 (2H, s), 3.95 (2H, m), 3.75 (2H, t), 3.63 (2H, m), 3.17 (2H, t), 3.07 (2H, t), 2.40 (1H, t), 1.89 (2H, m), 1.58 (9H, d), 0.98 (2H, t), 0.01 (9H, m). MS (ESI(+)): m/z 681 (M+H).

Step 6: Preparation of Title Compound 38

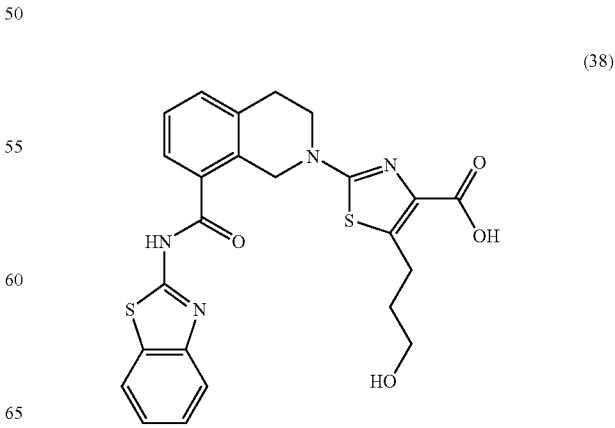

(38)

To a solution of tert-butyl 2-(8-(benzo[d]thiazol-2-yl((2-(trimethylsilyl)ethoxy)methyl)carbamoyl)-3,4-dihydroisoquinolin-2(1H)-yl)-5-(3-hydroxypropyl)thiazole-4-carboxylate (38E) (68 mg, 0.1 mmol) in DCM (2 mL) was added 2 mL of 2N HCl in ether. The mixture was stirred at rt overnight. MeOH (0.5 mL) was added to the mixture to dissolve the solid. The mixture was stirred at rt for another 2 hours. The reaction mixture was concentrated under reduced pressure to provide the desired product as an HCl salt: $^1$H NMR (300 MHz, DMSO-D$_6$) δ ppm 8.03 (1H, d), 7.79 (1H, d), 7.67 (1H, d), 7.41 (5H, m), 4.83 (2H, s), 3.73 (4H, t), 3.50 (2H, t), 3.41 (2H, t), 3.04 (4H, t), 1.69 (2H, m). MS (ESI(+)): m/z 495 (M+H).

Example 39

Synthesis of 5-(3-(3-(5-amino-4-cyano-1H-pyrazol-3-yl)phenoxy)propyl)-2-(8-(benzo[d]thiazol-2-ylcarbamoyl)-3,4-dihydroisoquinolin-2(1H)-yl)thiazole-4-carboxylic acid (39)

(39)

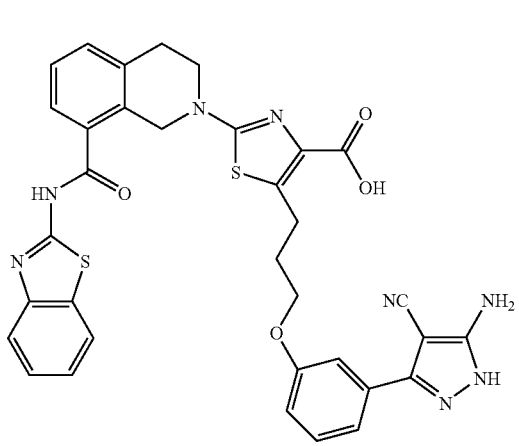

Step 1: Preparation of tert-butyl 5-(3-(3-(5-amino-1-(tert-butoxycarbonyl)-4-cyano-1H-pyrazol-3-yl)phenoxy)propyl)-2-(8-(benzo[d]thiazol-2-yl((2-(trimethylsilyl)ethoxy)methyl)carbamoyl)-3,4-dihydroisoquinolin-2(1H)-yl)thiazole-4-carboxylate (39A)

(39A)

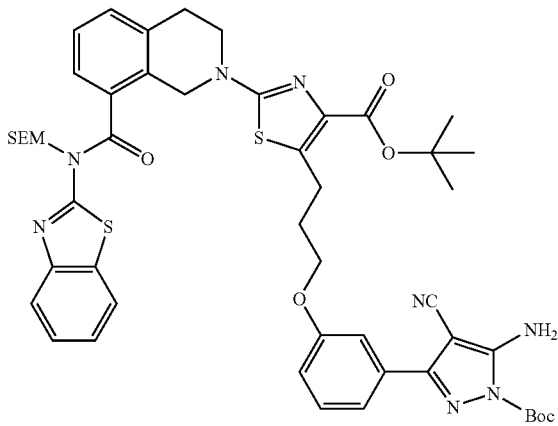

The title compound 39A was prepared in a similar manner to the synthesis of compound 35A by substituting compound 34D and compound 31F with compound 38E and compound 36A, respectively as a mixture of two inseparable isomers: MS (ESI(+)): 934 (M+H).

Step 2: Preparation of Title Compound 39

The title compound 39 was prepared in a similar manner to the procedure described in step 5 of Example 34 by substituting compound 34D with compound 39A: $^1$H NMR (DMSO-d$_6$): δ 8.03 (d, J=7.98 Hz, 1H), 7.79 (d, J=7.67 Hz, 1H), 7.65-7.67 (m, 2H), 7.32-7.49 (m, 6H), 6.94-6.96 (m, 1H), 4.84 (s, 2H), 4.01 (t, J=6.14 Hz, 2H), 3.70-3.73 (m, 4H), 3.19 (t, J=7.52 Hz, 2H), 3.01-3.03 (m, 2H), 2.01-2.05 (m, 2H). MS (ESI(+)): m/z 677 (M+H).

Example 40

Synthesis of 5-(3-(4-(5-amino-4-cyano-1H-pyrazol-3-yl)phenoxy)prop-1-ynyl)-2-(8-(benzo[d]thiazol-2-ylcarbamoyl)-3,4-dihydroisoquinolin-2(1H)-yl)thiazole-4-carboxylic acid (40)

(40)

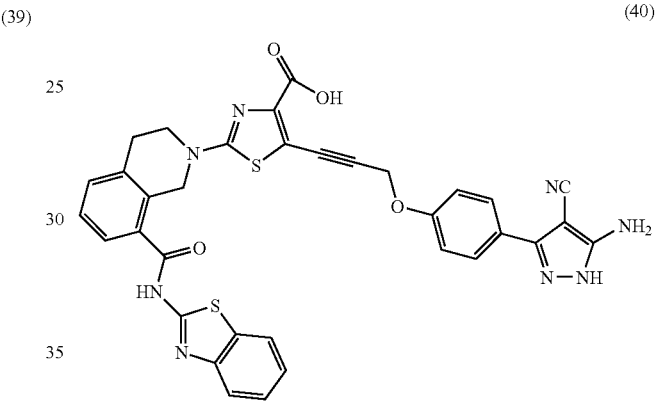

Step 1: Preparation of ethyl 5-(3-(4-(5-amino-1-(tert-butoxycarbonyl)-4-cyano-1H-pyrazol-3-yl)phenoxy)prop-1-ynyl)-2-(8-(benzo[d]thiazol-2-yl(tert-butoxycarbonyl)carbamoyl)-3,4-dihydroisoquinolin-2(1H)-yl)thiazole-4-carboxylate (40A)

(40A)

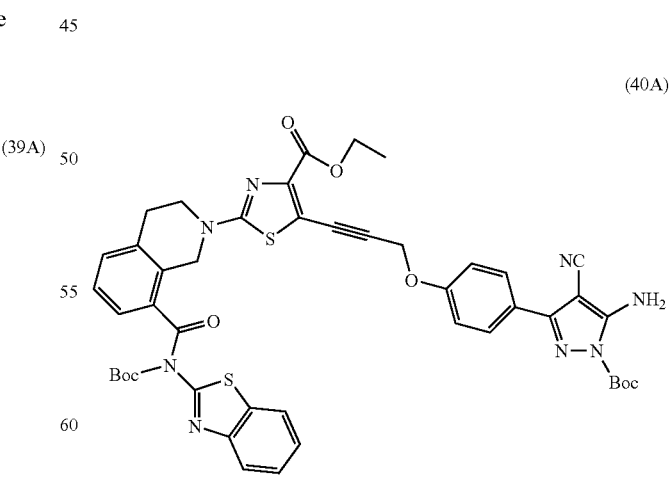

Compound 40A was prepared in a similar manner to the synthesis described in step 1 of Example 35 by substituting compound 34D with compound 36B as a mixture of two inseparable isomers: MS (ESI(+)): m/z 932 (M+H).

Step 2: Preparation of Title Compound 40

The title compound 40 was prepared in a similar manner to the synthesis of compound 34 by substituting compound 34D with compound 40A: $^1$H NMR (DMSO-$d_6$): δ 8.03 (d, J=7.98 Hz, 1H), 7.60-7.80 (m, 5H), 7.34-7.50 (m, 6H), 7.32-7.49 (m, 6H), 7.12 (d, J=8.9 Hz, 2H), 5.10 (s, 2H), 4.91 (s, 2H), 3.73-3.75 (m, 2H), 3.05-3.07 (m, 2H). MS (ESI(+)): m/z 673 (M+H).

Example 41

Synthesis of 2-(8-(Benzo[d]thiazol-2-ylcarbamoyl)-3,4-dihydroisoquinolin-2(1H)-yl)-5-(3-(4-(pyridin-3-yl)phenoxy)propyl)thiazole-4-carboxylic acid (41)

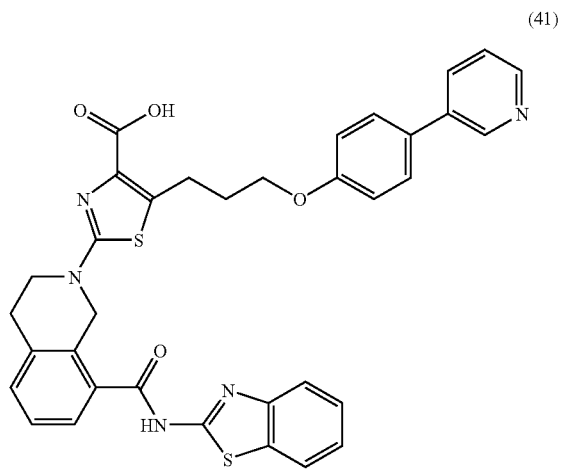

(41)

Step 1: Preparation of tert-butyl 2-(8-(benzo[d]thiazol-2-yl((2-(trimethylsilyl)ethoxy)methyl)carbamoyl)-3,4-dihydroisoquinolin-2(1H)-yl)-5-(3-(4-iodophenoxy)propyl)thiazole-4-carboxylate (41A)

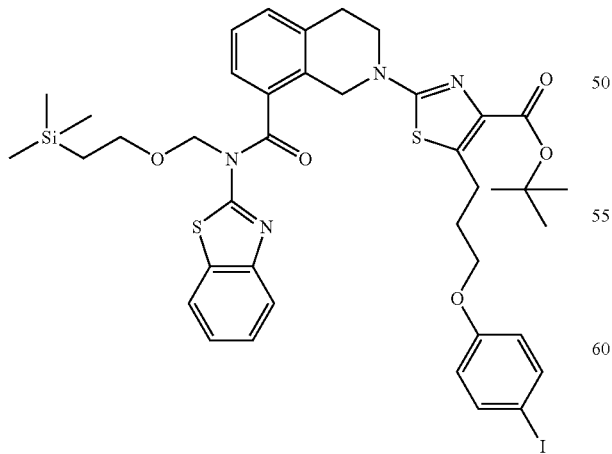

(41A)

To a solution of tert-butyl 2-(8-(benzo[d]thiazol-2-yl((2-(trimethylsilyl)ethoxy)methyl)carbamoyl)-3,4-dihydroisoquinolin-2(1H)-yl)-5-(3-hydroxypropyl)thiazole-4-carboxylate (92 mg, 0.135 mmol), triphenylphosphine (35.4 mg, 0.135 mmol) and 4-iodophenol (29.7 mg, 0.135 mmol) in THF (2 mL) was added DBAD (32 mg, 0.135 mmol). The mixture was stirred at rt for 4 hours. LC/MS showed the expected product as a single peak. The mixture was diluted with EtOAc and washed with water, brine, dried over $Na_2SO_4$, and concentrated under reduced pressure. The crude material was purified by column chromatography on silica gel eluting with 3% EtOAc in hexanes to provide 110 mg (92%) of the desired product: $^1$H NMR (300 MHz, $CDCl_3$) δ ppm 8.30 (1H, m), 7.72 (1H, d), 7.54 (4H, m), 7.34 (3H, m), 6.67 (2H, d), 6.00 (2H, s), 5.14 (2H, s), 3.96 (4H, m), 3.75 (2H, t), 3.22 (2H, t), 3.06 (2H, t), 2.13 (2H, m), 1.59 (9H, s), 0.97 (2H, t), 0.01 (9H, m). MS (ESI(+)): m/z 833 (M+H).

Step 2: Preparation of Title Compound 41

To a mixture of tert-butyl 2-(8-(benzo[d]thiazol-2-yl((2-(trimethylsilyl)ethoxy)methyl)carbamoyl)-3,4-dihydroisoquinolin-2(1H)-yl)-5-(3-(4-iodophenoxy)propyl)thiazole-4-carboxylate (20 mg, 0.023 mmol) and pyridine-3-boronic acid (41A) (2.83 mg, 0.23 mmol) in DME/MeOH (2:1, 3 mL) was added $Pd(Ph_3P)_4$ (1.37 mg, 0.115 umol), and CsF (12 mg, 0.069 mmol). The mixture was stirred at 100° C. for 30 minutes under microwave heating (Smith Synthesizer). The mixture was diluted with EtOAc (200 mL) and washed with water, brine, dried over $Na_2SO_4$, and concentrated under reduced pressure. The crude material was purified by column chromatography eluting with 5% EtOAc in hexanes to provide 17 mg (90%) of product, which was immediately deprotected using the same procedure described in Example 38 to afford the title compound 41: $^1$H NMR (300 MHz, DMSO-$D_6$) δ ppm 9.15 (1H, s), 8.77 (1H, d), 8.71 (1H, d), 8.02 (1H, d), 7.98 (1H, m), 7.80 (2H, d), 7.67 (1H, d), 7.41 (5H, m), 7.10 (2H, d), 4.84 (2H, m), 4.07 (2H, m), 3.73 (2H, m), 3.21 (4H, m), 3.04 (2H, t), 2.06 (2H, m). MS (ESI(+)): m/z 648 (M+H).

Example 42

Synthesis of 2-(8-(benzo[d]thiazol-2-ylcarbamoyl)-3,4-dihydroisoquinolin-2(1H)-yl)-5-(4-phenoxybutyl)thiazole-4-carboxylic acid (42A)

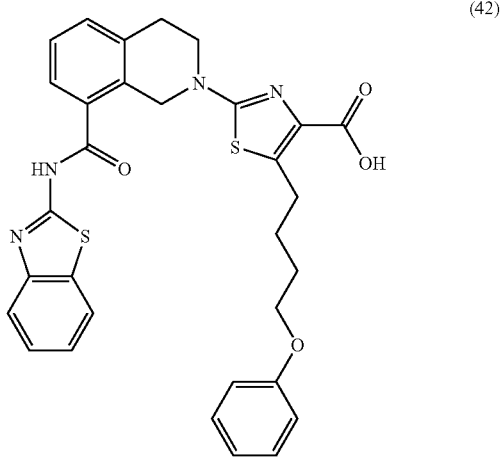

(42)

Step 1: Preparation of ethyl 3-bromo-7-chloro-2-oxoheptanoate (42A)

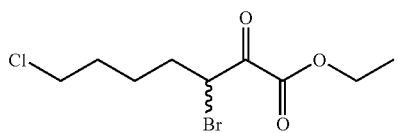

The title compound 42A was prepared by substituting ethyl 7-chloro-2-oxoheptanoate for ethyl 6-chloro-2-oxohexanoate in step 1 of Example 2: ¹H NMR (300 MHz, DMSO-d₆) δ ppm 5.18 (1H, dd), 4.29 (2H, q), 3.66 (2H, t), 2.03 (1H, m), 1.90 (1H, m), 1.78 (2H, m), 1.63 (1H, m), 1.48 (1H, m), 1.29 (3H, t).

Step 2: Preparation of ethyl 2-(8-(benzo[d]thiazol-2-ylcarbamoyl)-3,4-dihydroisoquinolin-2(1H)-yl)-5-(4-chlorobutyl)thiazole-4-carboxylate (42B)

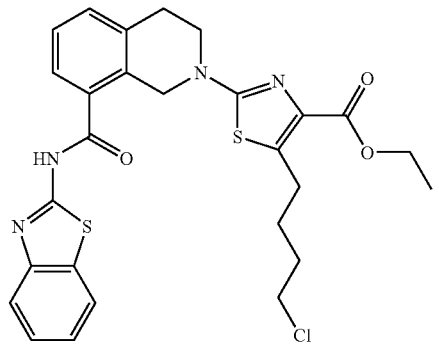

The title compound 42B was prepared by substituting compound 42A for compound 2A in step 2 of Example 2: ¹H NMR (300 MHz, DMSO-d₆) δ ppm 12.88 (1H, s), 8.03 (1H, d), 7.79 (1H, d), 7.66 (1H, d), 7.42 (4H, m), 4.82 (2H, s), 4.19 (2H, q), 3.72 (2H, t), 3.63 (2H, t), 3.03 (4H, m), 1.70 (4H, m), 1.20 (3H, t).

Step 3: Preparation of ethyl 2-(8-(benzo[d]thiazol-2-ylcarbamoyl)-3,4-dihydroisoquinolin-2(1H)-yl)-5-(4-iodobutyl)thiazole-4-carboxylate (42C)

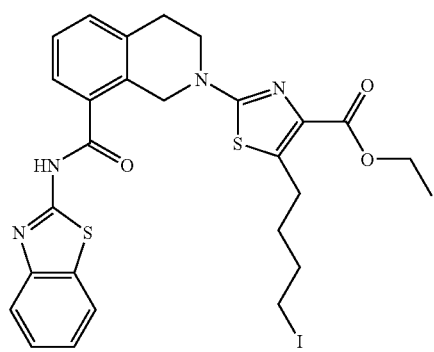

The title compound 42C was prepared by substituting compound 42B for compound 2B in step 3 of Example 2: ¹H NMR (300 MHz, DMSO-d₆) δ ppm 12.89 (1H, s), 8.04 (1H, d), 7.79 (1H, d), 7.66 (1H, d), 7.41 (4H, m), 4.82 (2H, s), 4.19 (2H, q), 3.72 (2H, t), 3.27 (2H, t), 3.03 (4H, m), 1.77 (2H, m), 1.63 (2H, m), 1.20 (3H, t).

Step 4: Preparation of Title Compound 42

The title compound 42 was prepared by substituting compound 42C for compound 2C in step 4 of Example 2: ¹H NMR (400 MHz, DMSO-d₆) δ ppm 12.86 (1H, s), 8.02 (1H, d), 7.78 (1H, d), 7.66 (1H, d), 7.46 (2H, m), 7.36 (2H, m), 7.23 (2H, t), 6.88 (3H, m), 4.81 (2H, s), 3.94 (2H, t), 3.72 (2H, t), 3.09 (2H, m), 3.02 (2H, t), 1.70 (4H, m). MS (ESI(+)): m/z 585 (M+H).

Example 43

Synthesis of 5-(4-(4-(1H-pyrazolo[3,4-d]pyrimidin-1-yl)phenoxy)butyl)-2-(8-(benzo[d]thiazol-2-ylcarbamoyl)-3,4-dihydroisoquinolin-2(1H)-yl)thiazole-4-carboxylic acid (43)

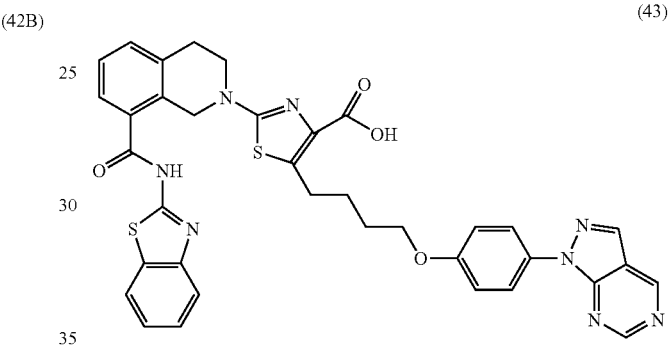

The title compound 43 was prepared using the same procedure described in Example 21 by replacing compound 2C with compound 42C: ¹H NMR (400 MHz, DMSO-D₆) δ ppm 12.87 (1H, s), 9.45 (1H, s), 9.10 (1H, s), 8.61 (1H, s), 7.92-8.10 (3H, m), 7.78 (1H, d), 7.67 (1H, d), 7.42-7.48 (2H, m), 7.31-7.41 (2H, m), 7.07-7.16 (2H, m), 4.83 (2H, s), 4.05 (2H, t), 3.73 (2H, t), 3.12 (2H, t), 3.03 (2H, t), 1.68-1.83 (4H, m). LCMS (APCI) 703 (M+H).

Example 44

Synthesis of 2-(8-(benzo[d]thiazol-2-ylcarbamoyl)-3,4-dihydroisoquinolin-2(1H)-yl)-5-(3-(4-(4-(isopropylamino)-1H-pyrazolo[3,4-d]pyrimidin-1-yl)phenoxy)propyl)thiazole-4-carboxylic acid (44)

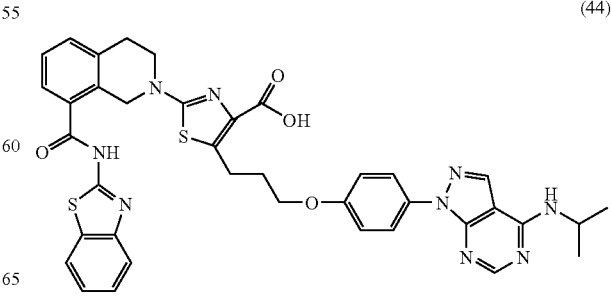

Step 1: Preparation of ethyl 5-amino-1-(4-methoxyphenyl)-1H-pyrazole-4-carboxylate (44A)

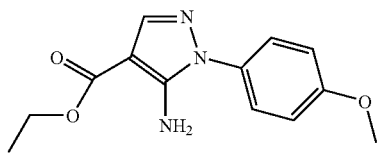
(44A)

A mixture of (Z)-ethyl 2-cyano-3-ethoxyacrylate (9.64 g, 57.0 mmol), 4-methoxyphenylhydrazine hydrochloride (9.95 g, 57.0 mmol) and Na$_2$CO$_3$ (6.04 g, 57.0 mmol) in EtOH (480 mL) was refluxed for 5 h and stirred overnight at rt. The insoluble material was filtered off and the filtrate was concentrated and solid precipitated. The precipitate was collected and washed with MeOH and washed with water extensively. The pale solid was dried to provide the desired product: $^1$H NMR (400 MHz, DMSO-D$_6$) δ ppm 7.65 (1H, s), 7.42 (2H, d), 7.07 (2H, d), 6.15 (2H, s), 4.14-4.26 (2H, m), 3.81 (3H, s), 1.27 (3H, t).

Step 2: Preparation of 1-(4-methoxyphenyl)-1H-pyrazolo[3,4-d]pyrimidin-4(3aH)-one (44B)

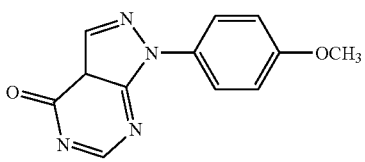
(44B)

A mixture of compound 44A (7 g, 26.8 mmol) and formamide (64.1 mL, 1607 mmol) was heated at 180° C. overnight and cooled. The precipitate was collected, washed with water and dried to provide the desired product: $^1$H NMR (400 MHz, DMSO-D6) δ ppm 12.35 (1H, s), 8.28 (1H, s), 8.15 (1H, s), 7.85-7.93 (2H, m), 7.09-7.14 (2H, m), 3.82 (3H, s).

Step 3: Preparation of 4-chloro-1-(4-methoxyphenyl)-1H-pyrazolo[3,4-d]pyrimidine (44C)

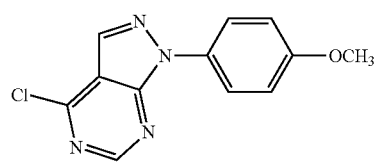
(44C)

A mixture of compound 44B (2 g, 8.26 mmol) and phosphoryl trichloride (11.51 mL, 124 mmol) was heated at 100° C. for 2 h and cooled. The reaction mixture was slowly poured onto ice. The precipitate was collected, washed with water and dried to provide the desired product. MS (APCI): m/z 261 (M+H).

Step 4: Preparation of 4-(4-(isopropylamino)-1H-pyrazolo[3,4-d]pyrimidin-1-yl)phenol (44D)

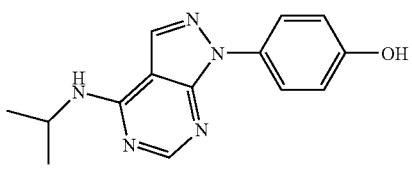
(44D)

To a mixture of compound 44C (388 mg, 1.48 mmol) and propan-2-amine (0.14 mL, 1.63 mmol) in THF (10 mL) was added TEA (0.456 mL, 3.27 mmol). The resulting mixture was stirred at 30° C. overnight and diluted with EtOAc. The organic layer was washed with brine, dried over Na$_2$SO$_4$, concentrated under reduced pressure, and dried. To the crude material was added iodotrimethylsilane (1.0 mL, 7.06 mmol) in tetramethylene sulfone (5 mL). The reaction mixture was heated at 80° C. overnight. The reaction was slowly poured into ice-water (5 mL). The precipitate was collected, washed with water, and purified by reverse phase HPLC (mobile phase: 0%-50% acetonitrile in 0.1% TFA aqueous solution during 40 minutes) to provide the title compound: $^1$H NMR (400 MHz, DMSO-D$_6$) δ ppm 9.68 (1H, s, br), 8.55 (1H, s, br), 8.39 (1H, s), 8.35 (1H, s), 7.82 (2H, d), 6.88-6.94 (2H, m), 4.34-4.46 (1H, m), 1.28 (6H, d)

Step 5: Preparation of Title Compound 44

The title compound 44 was prepared using the same procedure described in step 5 of Example 21 by replacing compound 21D with compound 44D: $^1$H NMR (400 MHz, DMSO-D$_6$) δ ppm 12.87 (1H, s), 8.45 (1H, s), 8.39 (1H, s), 8.34 (1H, s), 8.01 (1H, d), 7.98 (2H, d), 7.79 (1H, d), 7.65-7.73 (2H, m), 7.43-7.49 (2H, m), 7.32-7.41 (2H, m), 7.07 (2H, d), 4.84 (2H, s), 4.09-4.20 (1H, m), 4.04 (2H, t), 3.73 (2H, t), 3.20 (2H, t), 3.03 (2H, t), 2.00-2.08 (2H, m), 1.28 (3H, s), 1.27 (3H, s). LCMS (APCI): m/z 746 (M+H).

Example 45

Synthesis of 5-((4-(5-amino-4-cyano-1H-pyrazol-3-yl)phenoxy)methyl)-2-(8-(benzo[d]thiazol-2-ylcarbamoyl)-3,4-dihydroisoquinolin-2(1H)-yl)thiazole-4-carboxylic acid (45)

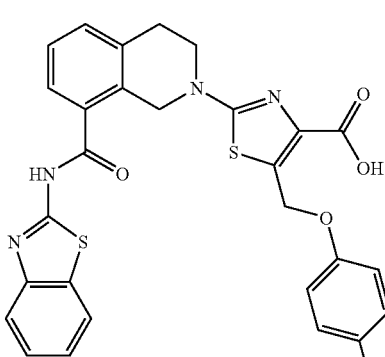
(45)

Step 1: Preparation of N-(benzo[d]thiazol-2-yl)-2-(4-chloro-5-formylthiazol-2-yl)-1,2,3,4-tetrahydroisoquinoline-8-carboxamide (45A)

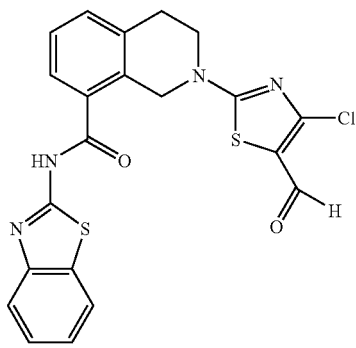

(45A)

A mixture of compound 1B (3.82 g, 10 mmol), 2,4-dichlorothiazole-5-carbaldehyde (1.82 g, 10 mmol), and $Cs_2CO_3$ (9.77 g, 30 mmol) in DMA (30 mL) was heated at 60° C. for 8 hours, cooled to rt and then poured into water (500 mL). The solid was collected by filtration and dried in a vacuum oven overnight (60° C.) to provide 4.2 g of the desired product (45A): $^1$H NMR (DMSO-$d_6$): δ 12.66 (s, 1H), 9.69 (s, 1H), 8.00 (d, J=7.82 Hz, 1H), 7.77 (d, J=8.06 Hz, 1H), 7.73 (d, J=7.58 Hz, 1H), 7.40-7.49 (m, 3H), 7.33-7.36 (m, 1H), 5.04 (s, 2H), 3.82 (t, J=5.92 Hz, 2H), 3.11 (t, J=6.16 Hz, 2H). MS (ESI(+)): m/z 455 (M+H).

Step 2: Preparation of (E)-2-(4-chloro-5-formylthiazol-2-yl)-N-(3-((2-(trimethylsilyl)ethoxy)methyl)benzo[d]thiazol-2(3H)-ylidene)-1,2,3,4-tetrahydroisoquinoline-8-carboxamide (45B)

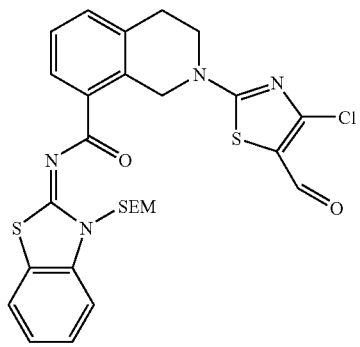

(45B)

Compound 45B was prepared in a similar manner to the synthesis of compound 34C by substituting compound 34B with compound 45A in step 3 of Example 34. Compound 45B was isolated as a white solid by trituration of the mixture of two isomers with 1:4 hexanes:EtOAc. The other isomer was isolated from the mother liquor: $^1$H NMR (DMSO-$d_6$): δ 9.71 (s, 1H), 8.24 (d, J=7.82 Hz, 1H), 7.92 (d, J=7.58 Hz, 1H), 7.70 (d, J=8.06 Hz, 1H), 7.53-7.56 (m, 1H), 7.36-7.46 (m, 3H), 6.01 (s, 2H), 5.35 (s, 2H), 3.85 (t, J=5.92 Hz, 2H), 3.72-3.75 (m, 2H), 3.11 (t, J=6.04 Hz, 2H). MS (ESI(+)): m/z 585 (M+H).

Step 3: (E)-methyl 5-formyl-2-(8-(3-((2-(trimethylsilyl)ethoxy)methyl)benzo[d]thiazol-2(3H)-ylidenecarbamoyl)-3,4-dihydroisoquinolin-2(1H)-yl)thiazole-4-carboxylate (45C)

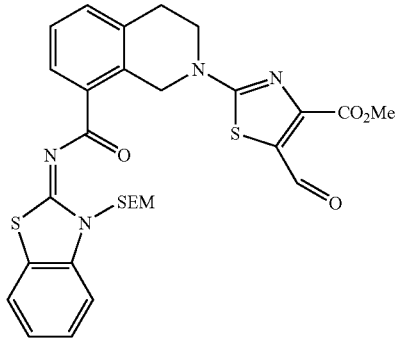

(45C)

Compound 45B (4.6 g, 7.86 mmol) in MeOH (50 mL) was added to Pd-dppf (0.288 g, 0.393 mmol) and $NEt_3$ (2.191 mL, 15.72 mmol) in a 250 mL SS pressure bottle. The mixture was pressurized with CO (60 psi), and stirred at 100° C. for 7 h. The solid was filtered off and the then filtrate was concentrated. The residue was purified by flash column chromatography on silica gel eluting with 3:1/hexanes:EtOAc to provide 4.45 g of the desired product 45C: $^1$H NMR (DMSO-$d_6$): δ 10.16 (s, 1H), 8.27 (d, J=6.74 Hz, 1H), 7.96 (d, J=7.14 Hz, 1H), 7.72 (d, J=8.33 Hz, 1H), 7.53-7.56 (m, 1H), 7.37-7.42 (m, 3H), 6.01 (s, 2H), 5.32 (s, 2H), 3.85-3.88 (m, 5H), 3.66-3.71 (m, 2H), 3.09 (t, J=5.95 Hz, 2H), 0.85-0.91 (m, 2H), −0.19 (s, 9H). MS (ESI(+)): m/z 609 (M+H).

Step 4: Preparation of (E)-methyl 5-(hydroxymethyl)-2-(8-(3-((2-(trimethylsilyl)ethoxy)methyl)benzo[d]thiazol-2(3H)-ylidenecarbamoyl)-3,4-dihydroisoquinolin-2(1H)-yl)thiazole-4-carboxylate (45D)

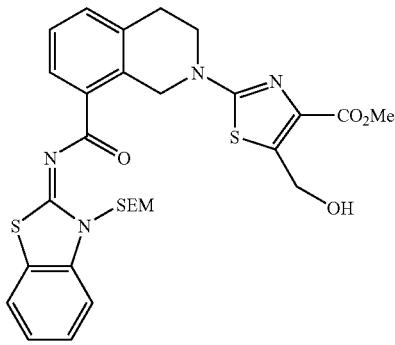

(45D)

To compound 45C (2.08 g, 3.42 mmol) in MeOH (50 mL) and THF (20 mL) was added $NaBH_4$ (0.259 g, 6.83 mmol). The reaction mixture was heated at 70° C. for 2 hours. The solvent was removed, and the residue was partitioned between EtOAc and water. The organic layer was isolated, and the aqueous layer was extracted with additional EtOAc. The combined organic layers were washed with brine, dried over MgSO$_4$, and concentrated under reduced pressure. The crude material was purified by column chromatography on silica gel eluting with 1:1/hexanes:EtOAc to provide 1.86 g of the desired product: $^1$H NMR (DMSO-d$_6$): δ 8.24-8.26 (m, 1H), 7.94 (d, J=7.67 Hz, 1H), 7.70 (d, J=8.20 Hz, 1H), 7.52-7.56 (m, 1H), 7.34-7.42 (m, 3H), 6.00 (s, 2H), 5.77 (t, J=5.52 Hz, 1H), 5.13 (s, 2H), 4.83 (d, J=5.52 Hz, 2H), 3.67-3.75 (m, 7H), 3.03 (t, J=5.98 Hz, 2H), 0.87-0.91 (m, 2H), −0.18 (s, 9H). MS (ESI(+)): m/z 611 (M+H).

Step 5: Preparation of (E)-methyl 5-((4-(5-amino-1-(tert-butoxycarbonyl)-4-cyano-1H-pyrazol-3-yl)phenoxy)methyl)-2-(8-(3-((2-(trimethylsilyl)ethoxy)methyl)benzo[d]thiazol-2(3H)-ylidenecarbamoyl)-3,4-dihydroisoquinolin-2(1H)-yl)thiazole-4-carboxylate (45E)

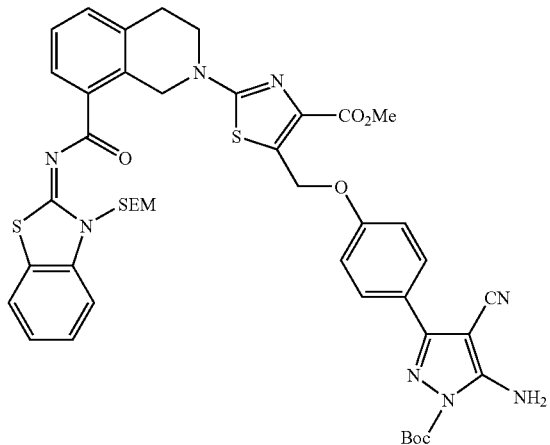

(45E)

Compound 45E was prepared in a similar manner to the synthesis of compound 35A by substituting compound 34D with compound 45D in step 1 of Example 35: $^1$H NMR (DMSO-d$_6$): δ 8.24 (dd, J=7.52, 1.38 Hz, 1H), 7.94 (d, J=7.67 Hz, 1H), 7.70 (d, J=7.98 Hz, 1H), 7.67 (s, 2H), 7.53-7.57 (m, 1H), 7.34-7.43 (m, 3H), 7.10-7.14 (m, 2H), 6.00 (s, 2H), 5.57 (s, 2H), 5.17 (s, 2H), 3.81 (s, 3H), 3.76 (t, J=5.98 Hz, 2H), 3.66-3.70 (m, 2H), 3.04 (t, J=6.14 Hz, 2H), 0.85-0.89 (m, 2H), −0.20 (s, 9H). MS (ESI(+)): m/z 892 (M+NH$_4$—H$_2$O).

Step 6: Preparation Title Compound 45

The title compound 45 was prepared in a similar manner to the synthesis of compound 34 by substituting compound 34D with compound 45E: $^1$H NMR (DMSO-d$_6$): δ 8.02 (d, J=7.67 Hz, 1H), 7.78 (d, J=7.98 Hz, 1H), 7.59-7.71 (m, 3H), 7.33-7.48 (m, 4H), 7.05 (d, J=7.59 Hz, 1H), 6.83 (d, J=7.67 Hz, 1H), 5.54 (s, 2H), 4.77-4.86 (m, 4H), 3.74 (t, J=5.68 Hz, 2H), 3.04 (t, J=5.83 Hz, 2H). MS (ESI(+)): m/z 647 (M−H).

Example 46

Synthesis of 5-[3-(5-Amino-4-cyano-1H-pyrazol-3-yl)-phenoxymethyl]-2-[8-(benzothiazol-2-ylcarbamoyl)-3,4-dihydro-1H-isoquinolin-2-yl]-thiazole-4-carboxylic acid (46)

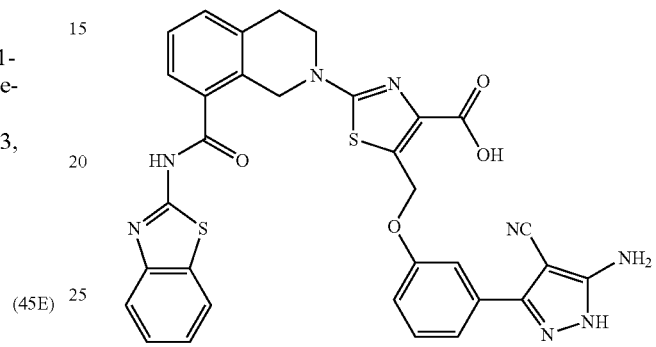

(46)

Step 1: Preparation of (E)-methyl 5-((3-(5-amino-1-(tert-butoxycarbonyl)-4-cyano-1H-pyrazol-3-yl)phenoxy)methyl)-2-(8-(3-((2-(trimethylsilyl)ethoxy)methyl)benzo[d]thiazol-2(3H)-ylidenecarbamoyl)-3,4-dihydroisoquinolin-2(1H)-yl)thiazole-4-carboxylate (46A)

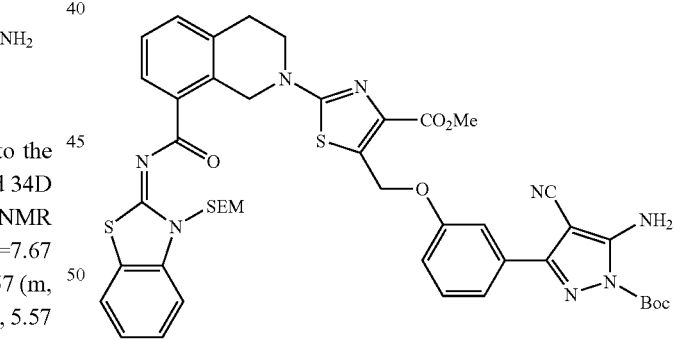

(46A)

The title compound (46A) was prepared in a similar manner to the synthesis of compound 35A by substituting compound 34D and compound 31F with compound 45D and compound 36A, respectively, in step 1 of Example 35: LCMS (ESI(+)): m/z 892 (M+NH$_4$—H$_2$O).

Step 2: Preparation of Title Compound 46

The title compound 46 was prepared in a similar manner to the synthesis of compound 34 by substituting compound 34D with compound 46A in step 5 of Example 34: $^1$H NMR (DMSO-d$_6$): δ 12.83 (s, 1H), 7.96 (d, J=7.93 Hz, 1H), 7.72 (d, J=7.93 Hz, 1H), 7.61 (d, J=7.32 Hz, 1H), 7.27-7.42 (m, 7H), 6.95 (d, J=7.93 Hz, 1H), 5.47 (s, 2H), 4.72-4.81 (m, 4H), 3.74 (t, J=5.68 Hz, 2H), 2.98 (t, J=5.65 Hz, 2H). MS (ESI(+)): m/z 649 (M+H).

Example 47

Synthesis of 5-{3-[4-(5-Amino-4-cyano-thiophen-3-yl)-phenoxy]-propyl}-2-[8-(benzothiazol-2-ylcarbamoyl)-3,4-dihydro-1H-isoquinolin-2-yl]-thiazole-4-carboxylic acid (47)

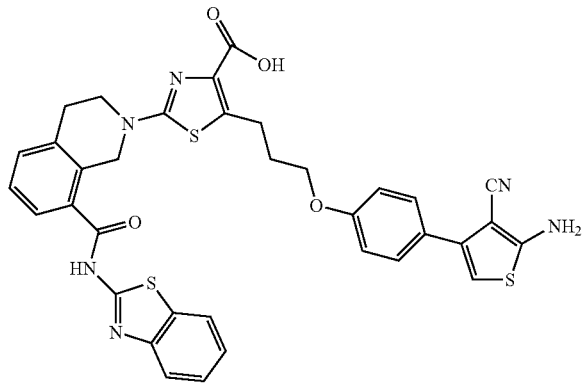

(47)

Step 1: Preparation 2-(1-(4-(benzyloxy)phenyl)ethylidene)malononitrile (47A)

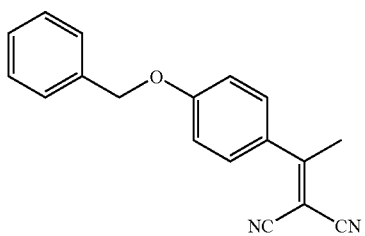

(47A)

Hexamethyldisilazane (2.50 mL, 1.937 g, 12.0 mmol) was added to 1-(4-(benzyloxy)phenyl)ethanone (2.263 g, 10 mmol) in acetic acid (6 mL) at a rate to maintain the internal temperature below 74° C. After the addition was over, malononitrile (1.32 g, 20 mmol) in acetic acid (6 mL) was added to the solution. The reaction was heated at 90 C.° for 12 hours. After cooling, the reaction was poured into ice/water, extracted with EtOAc, dried, and concentrated under reduced pressure to give the crude product. The solid was triturated with 1:9 EtOAc/hexanes to provide 2.74 g of the desired product. $^1$H NMR (DMSO-d$_6$): δ 7.72-7.75 (m, 2H), 7.35-7.49 (m, 5H), 7.18-7.21 (d, 2H), 5.22 (s, 2H), 2.61 (s, 3H). MS (ESI(+)): m/z 291 (M+NH$_4$).

Step 2: Preparation of 2-amino-4-(4-(benzyloxy)phenyl)thiophene-3-carbonitrile (47B)

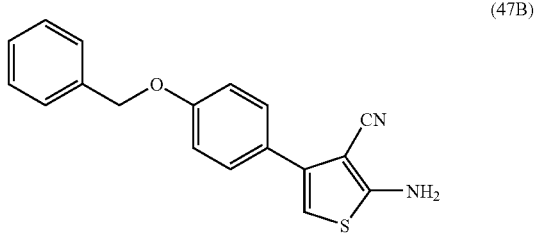

(47B)

To a mixture of compound 47A (2.74 g, 9.99 mmol) and sulfur (0.374 g, 11.99 mmol) in THF (20 mL) was added sodium bicarbonate (0.839 g, 9.99 mmol). The reaction mixture was heated under reflux for 2 hours and concentrated under reduced pressure. The residue was partitioned between EtOAc and water. The organic layer was isolated, and the aqueous layer was extracted with additional EtOAc. The combined organic layers were washed with brine, dried over MgSO$_4$, and concentrated under reduced pressure. The residue was purified by column chromatography on silica gel eluting with 3:1/hexanes:EtOAc to provide 2.42 g of the desired product: $^1$H NMR (DMSO-d$_6$): δ 7.33-7.48 (m, 7H), 7.19 (s, 2H), 7.07 (d, J=8.73 Hz, 2H), 6.42 (s, 1H), 5.14 (s, 2H). MS (ESI(+)): m/z 307 (M+H).

Step 3: Preparation of 2-amino-4-(4-hydroxyphenyl)thiophene-3-carbonitrile (47C)

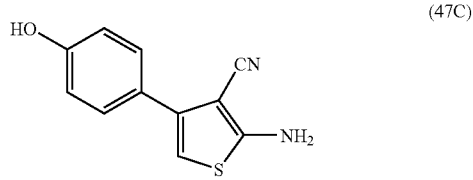

(47C)

To compound 47B (1.1 g, 3.59 mmol) in DCM (80 mL) was added 1.0 M BBr$_3$ (36 mL, 36 mmol) in DCM at rt. A precipitate formed upon addition and gradually disappeared after stirring at rt for 2 hours. The solvent was removed, and the residue was partitioned between water and EtOAc. The organic layer was isolated. The aqueous layer was extracted with EtOAc. The combined organic layers were washed with brine, dried over MgSO$_4$, filtered, and concentrated under reduced pressure. The crude material was purified by column chromatography on silica gel eluting with 3:2/hexanes: EtOAc to provide 0.65 g of the desired product 47C: $^1$H NMR (DMSO-d$_6$): δ 9.58 (s, 1H), 7.35 (d, J=8.73 Hz, 2H), 7.15 (s, 2H), 6.80 (d, J=8.73 Hz, 2H), 6.34 (s, 1H); MS (ESI(+)): m/z 217 (M+H).

Step 4: Preparation of methyl 2-(8-(benzo[d]thiazol-2-yl((2-(trimethylsilyl)ethoxy)methyl)carbamoyl)-3,4-dihydroisoquinolin-2(1H)-yl)-5-iodothiazole-4-carboxylate (47D)

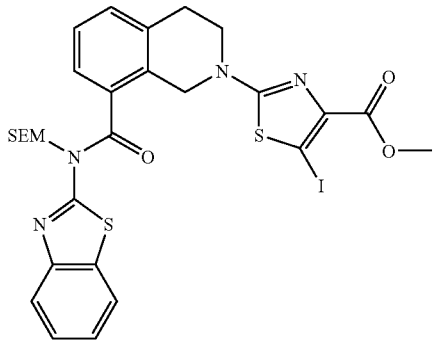

(47D)

Compound 47D was prepared in a similar manner to the synthesis of compound 34C by substituting compound 34B with compound 8C in step 3 of Example 34: APCI (+)/LC/MS: 707 (M+H).

Step 5: Preparation of methyl 2-(8-(benzo[d]thiazol-2-yl((2-(trimethylsilyl)ethoxy)methyl)carbamoyl)-3,4-dihydroisoquinolin-2(1H)-yl)-5-(3-hydroxyprop-1-ynyl)thiazole-4-carboxylate (47E)

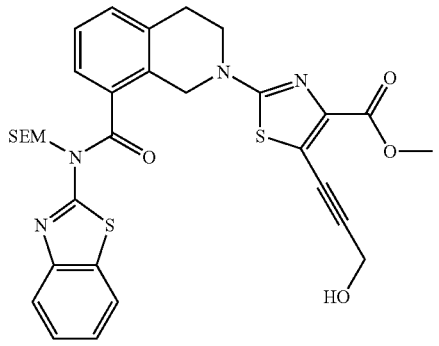

(47E)

Compound 47E was prepared in a similar manner to the synthesis of compound 36B by substituting compound 34C with compound 47D in step 2 of Example 34: LCMS (APCI): m/z 635 (M+H).

Step 6: Preparation of methyl 2-(8-(benzo[d]thiazol-2-yl((2-(trimethylsilyl)ethoxy)methyl)carbamoyl)-3,4-dihydroisoquinolin-2(1H)-yl)-5-(3-hydroxypropyl)thiazole-4-carboxylate (47F)

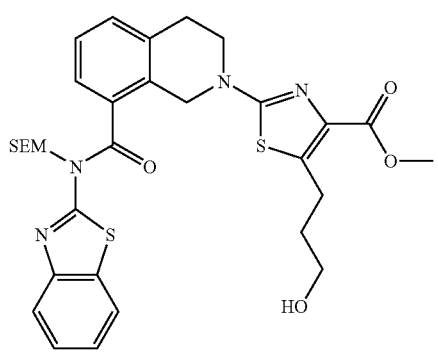

(47F)

The title compound (47F) was prepared in a similar manner to the synthesis of compound 8E by substituting compound 8D with compound 47E: LC/MS (APCI): m/z 639 (M+H).

Step 7: Preparation of methyl 5-(3-(4-(5-amino-4-cyanothiophen-3-yl)phenoxy)propyl)-2-(8-(benzo[d]thiazol-2-yl((2-(trimethylsilyl)ethoxy)methyl)carbamoyl)-3,4-dihydroisoquinolin-2(1H)-yl)thiazole-4-carboxylate (47G)

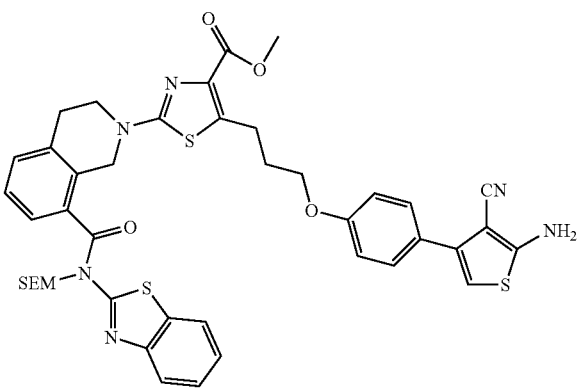

(47G)

Compound 47G was prepared in a similar manner to the synthesis of compound 35A by substituting compound 34B and compound 31F with compound 47F and compound 47C, respectively: MS (ESI(+)): m/z 838 (M+H).

Step 8: Preparation of Title Compound 47H

The title compound 47H was prepared in a similar manner to the synthesis of compound 34 by substituting compound 34D with compound 47G: $^1$H NMR (DMSO-d$_6$): δ 7.95 (d, J=7.98 Hz, 1H), 7.72 (d, J=7.67 Hz, 1H), 7.60 (d, J=6.75 Hz, 1H), 7.26-7.44 (m, 6H), 6.87-6.90 (m, 2H), 6.32 (s, 1H), 4.77 (s, 2H), 3.94 (t, J=6.14 Hz, 2H), 3.64-3.67 (m, 2H), 3.10-3.13 (m, 2H), 2.96 (t, J=5.83 Hz, 2H), 1.93-1.96 (m, 2H). MS (ESI(+)): m/z 693 (M+H).

Example 48

Synthesis of 5-(3-(4-(1H-pyrazol-1-yl)phenoxy)propyl)-2-(8-(benzo[d]thiazol-2-ylcarbamoyl)-3,4-dihydroisoquinolin-2(1H)-yl)thiazole-4-carboxylic acid (48)

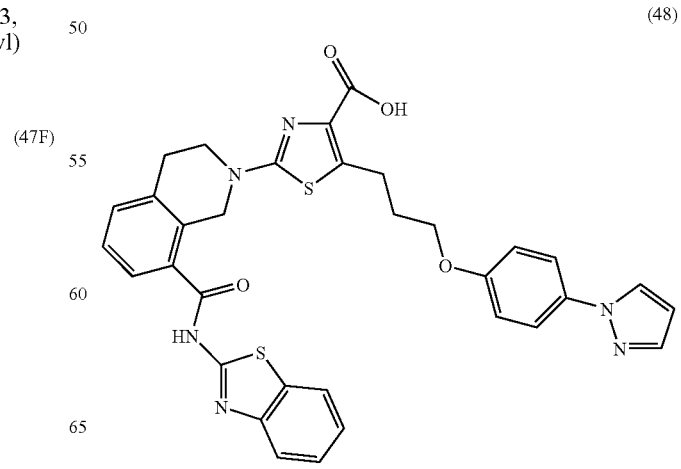

(48)

The title compound 48 was prepared by substituting 4-(1H-pyrazol-1-yl)phenol for phenol in step 4 in Example 2. The alkylation intermediate was not isolated prior to ester hydrolysis. After precipitation of the desired product, the solid was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 0-90% of B in 40 minutes) to provide the title compound 48 in 29% yield: $^1$H NMR (300 MHz, DMSO-d$_6$) δ ppm 12.89 (1H, s), 8.35 (1H, d), 8.03 (1H, d), 7.79 (1H, d), 7.69 (4H, m), 7.42 (4H, m), 7.02 (2H, m), 6.49 (1H, m), 4.84 (2H, s), 4.02 (2H, t), 3.72 (2H, t), 3.19 (2H, t), 3.03 (2H, t), 2.02 (2H, m). MS (ESI(+)): m/z 637 (M+H).

Example 49

Synthesis of 5-(2-(4-(1H-pyrazolo[3,4-d]pyrimidin-1-yl)phenoxy)ethyl)-2-(8-(benzo[d]thiazol-2-ylcarbamoyl)-3,4-dihydroisoquinolin-2(1H)-yl)thiazole-4-carboxylic acid (49)

(49)

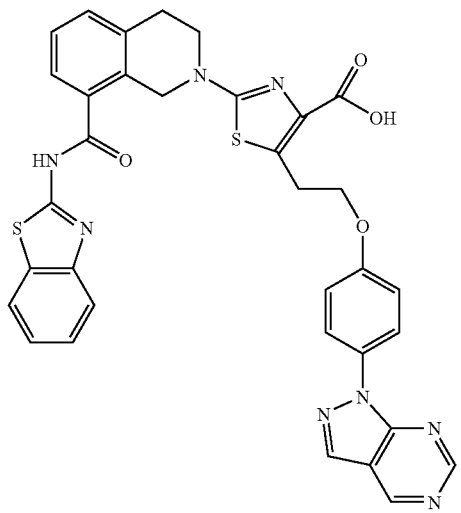

Step 1: Preparation of N-(benzo[d]thiazol-2-yl)-2-carbamothioyl-1,2,3,4-tetrahydroisoquinoline-8-carboxamide (49A)

(49A)

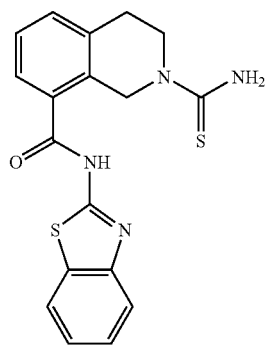

To a mixture of compound 1B (3.25 g, 8.50 mmol) in DMF (50 mL) was added TEA (4.71 mL, 34.0 mmol). The resulting mixture was stirred for 10 minutes and di(1H-imidazol-1-yl)methanethione (1.818 g, 10.20 mmol) was added. The reaction mixture was stirred at rt for 30 minutes. Ammonia (7 N in MeOH) (48.6 mL, 340 mmol) was added and the resulting mixture was stirred overnight. The reaction mixture was concentrated to remove the ammonia and MeOH. The DMF solution was directly used for the next step without further purification. LCMS (APCI): m/z 369 (M+H).

Step 2: Preparation of ethyl 2-(8-(benzo[d]thiazol-2-ylcarbamoyl)-3,4-dihydroisoquinolin-2(1H)-yl)-5-(2-(tert-butyldimethylsilyloxy)ethyl)thiazole-4-carboxylate (49B)

(49B)

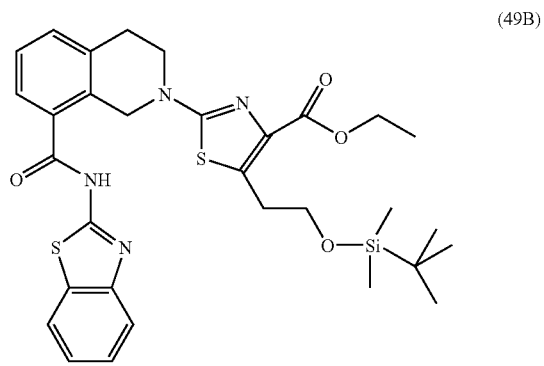

To a solution of 3-(tert-butyldimethylsilyloxy)propanal (1 g, 5.31 mmol) and ethyl 2,2-dichloroacetate (0.651 mL, 5.31 mmol) in Et$_2$O (4 mL) at 0° was dropwise added sodium ethanolate (0.397 g, 5.84 mmol) in EtOH (4 mL). The reaction mixture was stirred at 0° C. for 1.5 h and diluted with Et$_2$O. The resulting mixture was washed with brine and the organic layer was dried over Na$_2$SO$_4$ and concentrated under reduced pressure. The residue was dried in vacuo and dissolved in EtOH (8 mL). To the resulting solution was added Example 49A (1 eq) in DMF. The reaction mixture was heated at 50° C. for 8 hours and concentrated under reduced pressure. The residue was dissolved in DCM and purified by column chromatography on silica gel eluting with 0% to 17% EtOAc in hexanes, then with 0% to 15% EtOAc in DCM to provide the desired product 49B: LCMS (APCI): m/z 623 (M+H).

Step 3: Preparation of ethyl 2-(8-(benzo[d]thiazol-2-yl((2-(trimethylsilyl)ethoxy)methyl)carbamoyl)-3,4-dihydroisoquinolin-2(1H)-yl)-5-(2-(tert-butyldimethylsilyloxy)ethyl)thiazole-4-carboxylate (49C$^1$); and (Z)-ethyl 5-(2-(tert-butyldimethylsilyloxy)ethyl)-2-(8-(3-((2-(trimethylsilyl)ethoxy)methyl)benzo[d]thiazol-2(3H)-ylidenecarbamoyl)-3,4-dihydroisoquinolin-2(1H)-yl)thiazole-4-carboxylate (49C$^2$)

49C$^1$

49C$^2$

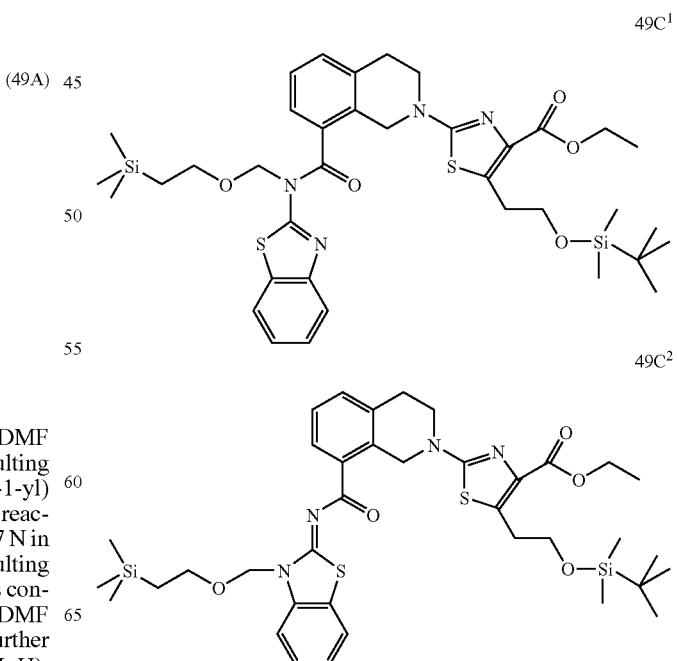

To a mixture of Example 49B (365 mg, 0.586 mmol) and (2-(chloromethoxy)ethyl)trimethylsilane (0.109 mL, 0.615 mmol) in DMF (5 mL) was added TEA (0.163 mL, 1.172 mmol) dropwise. The reaction mixture was stirred at rt for 10 minutes. The desired product presented as two regioisomers (49C$^1$ and 49C$^2$). The reaction was diluted with EtOAc, washed with brine, dried over Na$_2$SO$_4$, and concentrated under reduced pressure. The crude material was used in the next step without further purification.

Step 4: Preparation of ethyl 2-(8-(benzo[d]thiazol-2-yl((2-(trimethylsilyl)ethoxy)methyl)carbamoyl)-3,4-dihydroisoquinolin-2(1H)-yl)-5-(2-hydroxyethyl)thiazole-4-carboxylate (49D$^1$); and (Z)-ethyl 5-(2-hydroxyethyl)-2-(8-(3-((2-(trimethylsilyl)ethoxy)methyl)benzo[d]thiazol-2(3H)-ylidenecarbamoyl)-3,4-dihydroisoquinolin-2(1H)-yl)thiazole-4-carboxylate (49D$^2$)

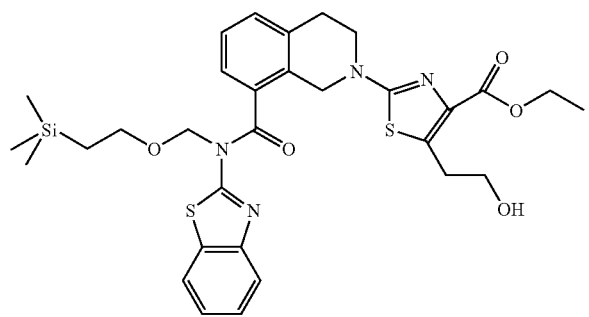

49D$^1$

49D$^2$

To a solution of Example 49C$^1$ and 49C$^2$ (400 mg, 0.531 mmol) in DCM (2 mL) was added MeOH (50 mL). 1% HCl in MeOH (3.87 mL, 1.062 mmol) was added dropwise. The reaction mixture was stirred at rt for 5 hours and was diluted with EtOAc (250 mL) and washed with 50% NaCl. The organic layer was dried over Na$_2$SO$_4$ and concentrated under reduced pressure. The residue was dissolved in DCM and purified by column chromatography on silica gel eluting with a gradient of 0% to 25% EtOAc in DCM to provide the desired compounds 49D$^1$ and 49D$^2$: LCMS (APCI): m/z 639 (M+H).

Step 5: Preparation of ethyl 5-(2-(4-(1H-pyrazolo[3,4-d]pyrimidin-1-yl)phenoxy)ethyl)-2-(8-(benzo[d]thiazol-2-yl((2-(trimethylsilyl)ethoxy)methyl)carbamoyl)-3,4-dihydroisoquinolin-2(1H)-yl)thiazole-4-carboxylate (49E$^1$); and (Z)-ethyl 5-(2-(4-(1H-pyrazolo[3,4-d]pyrimidin-1-yl)phenoxy)ethyl)-2-(8-(3-((2-(trimethylsilyl)ethoxy)methyl)benzo[d]thiazol-2(3H)-ylidenecarbamoyl)-3,4-dihydroisoquinolin-2(1H)-yl)thiazole-4-carboxylate (49E$^2$)

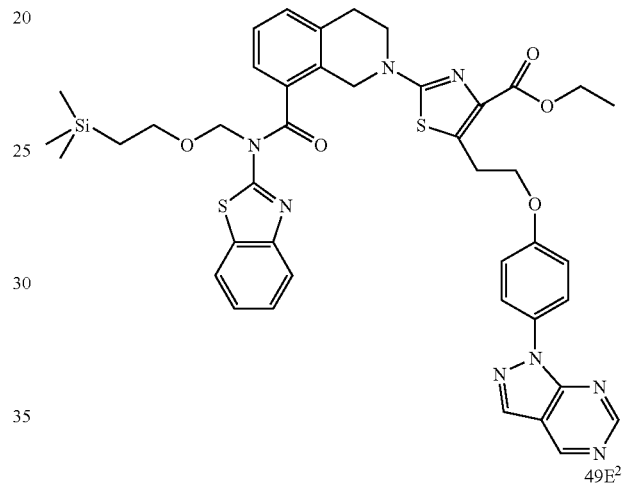

49E$^1$

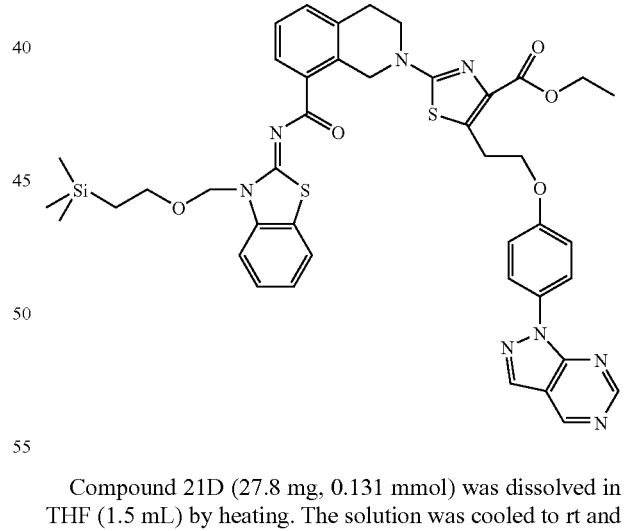

49E$^2$

Compound 21D (27.8 mg, 0.131 mmol) was dissolved in THF (1.5 mL) by heating. The solution was cooled to rt and then compounds 49D$^1$ and 49D$^2$ (55.7 mg, 0.087 mmol) and triphenylphosphine (11.43 mg, 0.044 mmol) were added, followed by the addition of (E)-di-tert-butyl diazene-1,2-dicarboxylate (10.04 mg, 0.044 mmol). The reaction mixture was stirred for 3 hours. The reaction mixture was diluted with EtOAc and washed with 2% NaOH, 5% HCl, and water. The organic layer was dried over Na$_2$SO$_4$ and concentrated under reduced pressure. The residue was purified by column chromatography on silica gel eluting with a gradient of 0 to 25%

EtOAc in DCM to provide the desired compounds 49E$^1$ and 49E$^2$: LCMS (APCI): m/z 834 (M+H).

Step 6: Preparation of 5-(2-(4-(1H-pyrazolo[3,4-d]pyrimidin-1-yl)phenoxy)ethyl)-2-(8-(benzo[d]thiazol-2-ylcarbamoyl)-3,4-dihydroisoquinolin-2(1H)-yl)thiazole-4-carboxylic acid (49)

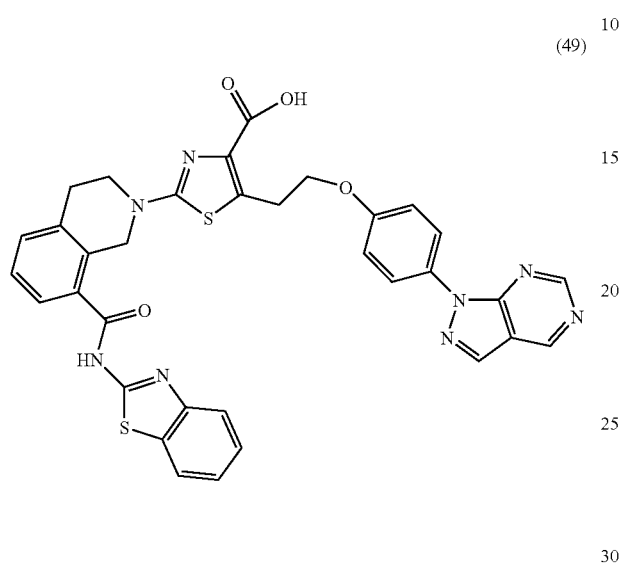

(49)

To a solution compound 49E$^1$ and compound 49E$^2$ (100 mg, 0.120 mmol) in DCM (5 mL) was added 2 N HCl in ether (0.60 mL, 1.20 mmol). The reaction was stirred 15 minutes and concentrated under reduced pressure. To the crude material was added 10% NaOH (0.17 mL, 0.427 mmol) and water (5 mL) in THF (5 mL) and MeOH (5 mL) and heated to 50° C. for 2 hours. The reaction mixture was cooled and filtered. The filtrate was acidified with HCl and the precipitate was collected by filtration, washed with water, and dried to provide the desired product 49: $^1$H NMR (400 MHz, DMSO-D$_6$) δ ppm 12.87 (1H, s), 9.44 (1H, s), 9.09 (1H, s), 8.60 (1H, s), 7.97-8.02 (3H, m), 7.77 (1H, d), 7.66 (1H, d), 7.28-7.47 (4H, m), 7.13-7.17 (2H, m), 4.84 (2H, s), 4.23 (2H, t), 3.75 (2H, t), 3.53 (2H, t), 3.04 (2H, t). LCMS (APCI): m/z 675 (M+H).

Example 50

Synthesis of 5-(2-(3-(1H-pyrazolo[3,4-d]pyrimidin-1-yl)phenoxy)ethyl)-2-(8-(benzo[d]thiazol-2-ylcarbamoyl)-3,4-dihydroisoquinolin-2(1H)-yl)thiazole-4-carboxylic acid (50)

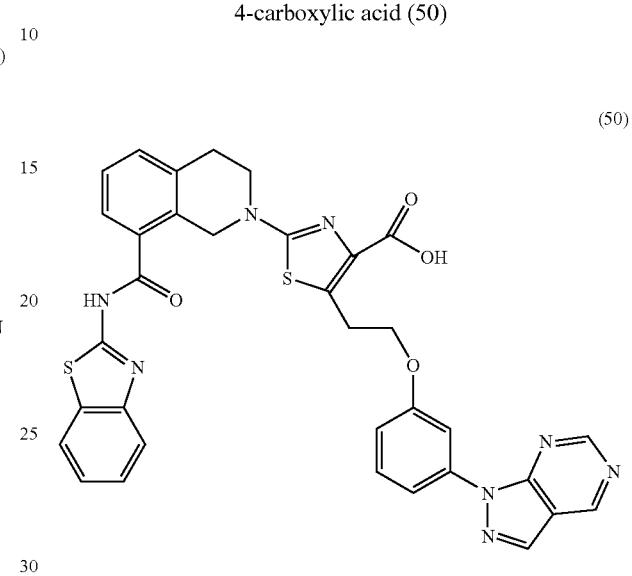

(50)

Step 1: Preparation of ethyl 5-(2-(3-(1H-pyrazolo[3,4-d]pyrimidin-1-yl)phenoxy)ethyl)-2-(8-(benzo[d]thiazol-2-yl((2-(trimethylsilyl)ethoxy)methyl)carbamoyl)-3,4-dihydroisoquinolin-2(1H)-yl)thiazole-4-carboxylate (50A$^1$); and (Z)-ethyl 5-(2-(3-(1H-pyrazolo[3,4-d]pyrimidin-1-yl)phenoxy)ethyl)-2-(8-(3-((2-(trimethylsilyl)ethoxy)methyl)benzo[d]thiazol-2(3H)-ylidenecarbamoyl)-3,4-dihydroisoquinolin-2(1H)-yl)thiazole-4-carboxylate (50A$^2$)

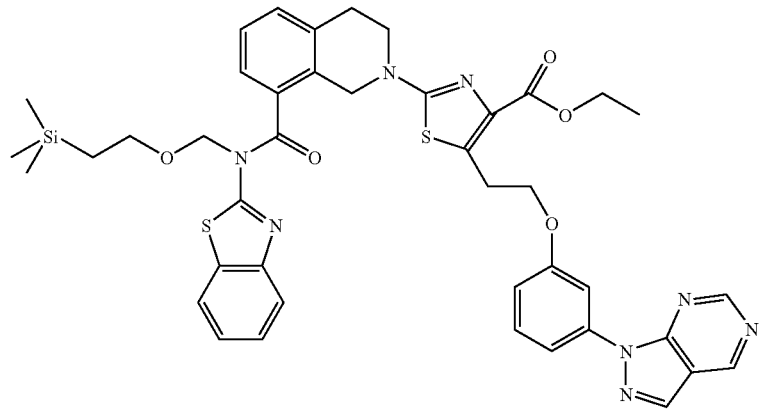

50A$^1$

-continued

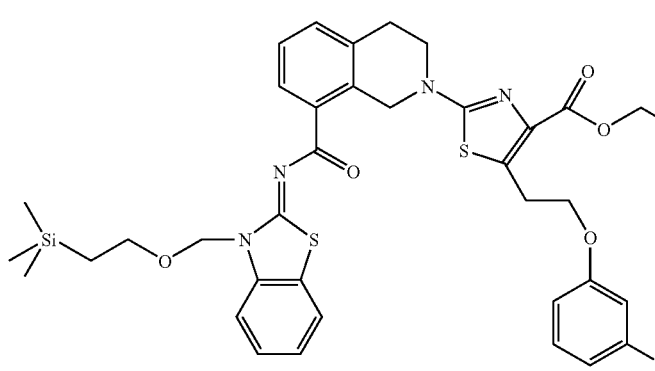

50A²

Compounds 50A¹ and 50A² was prepared using the same procedure described in step 5 of Example 49 by replacing compound 21D with compound 33D: LCMS (APCI): m/z 834 (M+H).

Step 2: Preparation of 5-(2-(3-(1H-pyrazolo[3,4-d]pyrimidin-1-yl)phenoxy)ethyl)-2-(8-(benzo[d]thiazol-2-ylcarbamoyl)-3,4-dihydroisoquinolin-2(1H)-yl)thiazole-4-carboxylic acid (50)

Compound 50 was prepared using the same procedure described in step 5 of Example 49 by replacing compound 49E¹ and compound 49E² with compound 50A¹ and compound 50A²: ¹H NMR (400 MHz, DMSO-D$_6$) δ ppm 12.84 (1H, s), 9.44 (1H, s), 9.14 (1H, s), 8.62 (1H, s), 8.01 (1H, d), 7.76-7.84 (3H, m), 7.66 (1H, d), 7.32-7.50 (5H, m), 6.98 (1H, dd), 4.84 (2H, s), 4.25 (2H, t), 3.73 (2H, t), 3.54 (2H, t), 3.03 (2H, t). LCMS (APCI): m/z 675 (M+H).

Example 51

Synthesis of 2-[8-(Benzothiazol-2-ylcarbamoyl)-3,4-dihydro-1H-isoquinolin-2-yl]-5-{3-[4-(4-cyano-thiophen-3-yl)-phenoxy]-propyl}-thiazole-4-carboxylic acid (51)

Step 1: Preparation of 4-(4-hydroxyphenyl)thiophene-3-carbonitrile (51A)

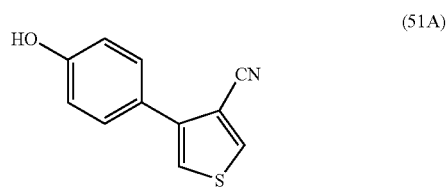

(51A)

Compound 51A was prepared in a similar manner to the synthesis of compound 34D by substituting compound 34C and 4-(hydroxymethyl)phenylboronic acid with 4-bromothiophene-3-carbonitrile and 4-(4,4,5,5-tetramethyl-1,3,2-dioxaborolan-2-yl)phenol, respectively: ¹H NMR (DMSO-d$_6$): δ 9.68 (s, 1H), 8.62 (d, J=3.38 Hz, 1H), 7.73 (d, J=3.07 Hz, 1H), 7.44 (d, J=8.59 Hz, 2H), 6.86 (d, J=8.59 Hz, 2H). MS (ESI(+)): m/z 200 (M−H).

(51)

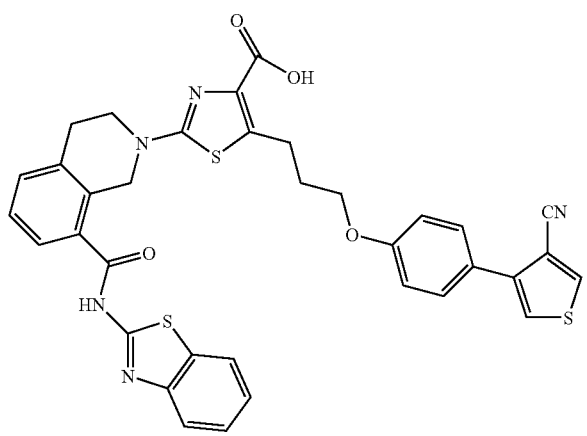

Step 2: Preparation of Title Compound 51

To compound 51A (0.095 g, 0.015 mmol) in DMF (4 mL) was added 60% sodium hydride (0.036 g, 0.9 mmol) at 0° C. The solution was stirred for 10 minutes. To this solution was added compound 2C. The solution was stirred at rt for 2 hours. The reaction was quenched with MeOH (1 mL). Conc. HCl (0.5 mL) was added, and the solution was filtered through a syringe filter. The filtrate was then purified by Prep HPLC to provide the desired product 51: ¹H NMR (DMSO-d$_6$): δ 8.57 (d, J=3.38 Hz, 1H), 7.95 (d, J=7.98 Hz, 1H), 7.71-7.72 (m, 2H), 7.60 (d, J=7.36 Hz, 1H), 7.45-7.48 (m, 2H), 7.26-7.41 (m, 4H), 6.95-6.97 (m, 214), 4.77 (s, 2H), 3.97

(t, J=6.29 Hz, 2H), 3.66 (t, J=5.98 Hz, 2H), 3.11-3.14 (m, 2H), 2.96 (t, J=5.98 Hz, 2H), 1.93-2.00 (m, 2H); MS (ESI(+)): m/z 678 (M+H).

Example 52

Synthesis of 2-(8-(benzo[d]thiazol-2-ylcarbamoyl)-3,4-dihydroisoquinolin-2(1H)-yl)-5-(3-(4-(9-isopropyl-9H-purin-6-yl)phenoxy)propyl)thiazole-4-carboxylic acid (52)

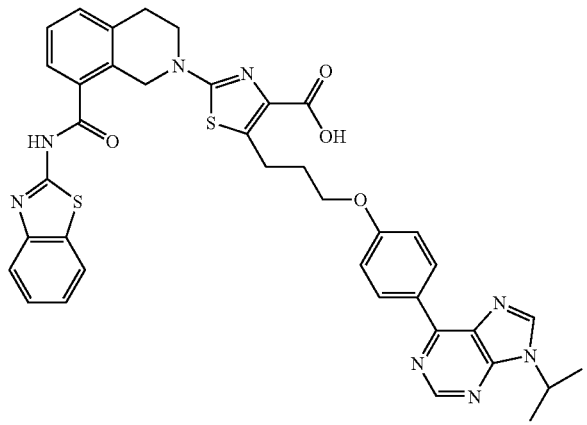

Step 1: Preparation of 6-chloro-N4-isopropylpyrimidine-4,5-diamine (52A)

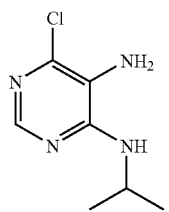

4,6-Dichloropyrimidin-5-amine (492 mg, 3 mmol), propan-2-amine (284 µl, 3.3 mmol) and Et₃N (836 µl, 6 mmol) were combined and heated at reflux. The mixture was refluxed for 5 days and each day additional isopropylamine (0.77 mL, 9 mmol) was added. The reaction mixture was cooled to room temperature, concentrated, slurried in water, filtered, rinsed with additional water and dried under reduced pressure to provide the title compound 52A as a tan solid: $^1$H NMR (300 MHz, DMSO-$d_6$) δ ppm 7.72 (1H, s), 6.53 (1H, d), 5.02 (2H, s), 4.20 (1H, octet), 1.18 (6H, d).

Step 2: Preparation of 6-chloro-9-isopropyl-9H-purine (52B)

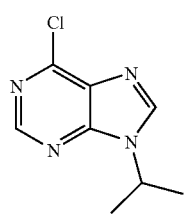

Compound 52A (268 mg, 1.44 mmol), triethyl orthoformate (2.4 ml, 14.36 mmol) and para-toluenesulfonic acid (27.3 mg, 0.144 mmol) were combined and heated at 115° C. overnight. Precipitation occurred upon cooling to room temperature. The precipitate was collected via filtration, rinsed with diethyl ether and dried under reduced pressure to yield the title compound 52B: $^1$H NMR (300 MHz, DMSO-$d_6$) δ ppm 8.81 (1H, s), 8.78 (1H, s), 4.89 (1H, m), 1.58 (6H, d).

Step 3: Preparation of 9-isopropyl-6-(4-(tetrahydro-2H-pyran-2-yloxy)phenyl)-9H-purine (52C):

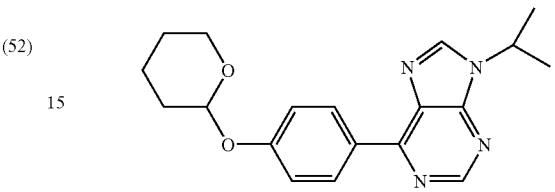

Compound 52B (165 mg, 0.84 mmol) in toluene (5 ml) was treated sequentially with 4-(tetrahydro-2H-pyran-2-yloxy)phenylboronic acid (280 mg, 1.26 mmol), tetrakis(triphenylphosphine)palladium(0) (48.6 mg, 0.042 mmol) and sodium carbonate (2N aq.) (1.26 ml, 2.52 mmol). The reaction vessel was purged with nitrogen and heated at reflux overnight. The reaction mixture was cooled to room temperature, diluted with EtOAc, washed with water and brine, dried (MgSO₄), filtered and concentrated. The concentrate was purified by column chromatography on silica gel eluting with a gradient of 0 to 5% MeOH in CH₂Cl₂: $^1$H NMR (300 MHz, DMSO-$d_6$) δ ppm 8.92 (1H, s), 8.83 (2H, m), 8.74 (1H, s), 7.22 (2H, m), 5.63 (1H, t), 4.92 (1H, septet), 3.79 (1H, ddd), 3.60 (1H, m), 1.82 (4H, m), 1.60 (6H, d), 1.55 (2H, m).

Step 4: Preparation of 4-(9-isopropyl-9H-purin-6-yl)phenol (52D)

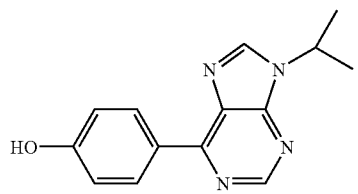

Compound 52C (149 mg, 0.44 mmol) in dioxane (3 ml) was treated with HCl (4N in dioxane) (0.55 ml, 2.2 mmol) and stirred at ambient temperature for 1 hour. The reaction mixture was concentrated and dried to give a light gray solid 52D in 94% yield: $^1$H NMR (300 MHz, DMSO-$d_6$) δ ppm 10.16 (1H, s), 8.90 (1H, s), 8.76 (1H, m), 8.73 (2H, m), 6.97 (2H, m), 4.91 (1H, septet), 1.60 (6H, d).

Step 5: Preparation of Title Compound 52

The title compound 52 was prepared by substituting compound 52D for phenol in step 4 of Example 2. The alkylation intermediate was purified by column chromatography on silica gel eluting with a gradient of 0 to 60% EtOAc in CH₂Cl₂. The remainder of the procedure followed step 4 of Example 2: $^1$H NMR (500 MHz, DMSO-$d_6$) δ ppm 12.89 (1H, s), 8.89 (1H, s), 8.81 (2H, d), 8.72 (1H, s), 8.00 (1H, d), 7.77 (1H, d), 7.65 (1H, d), 7.45 (2H, m), 7.35 (2H, m), 7.11 (2H, d), 4.90 (1H, m), 4.83 (2H, s), 4.09 (2H, m), 3.71 (2H, m), 3.20 (2H, m), 3.02 (2H, m), 2.04 (2H, m), 1.59 (6H, d). MS (ESI(+)) m/e 731 (M+H).

Example 53

Synthesis of 2-(8-(benzo[d]thiazol-2-ylcarbamoyl)-3,4-dihydroisoquinolin-2(1H)-yl)-5-(3-(4-(5,6-dihydroimidazo[2,1-b]thiazol-3-yl)phenoxy)propyl)thiazole-4-carboxylic acid (53)

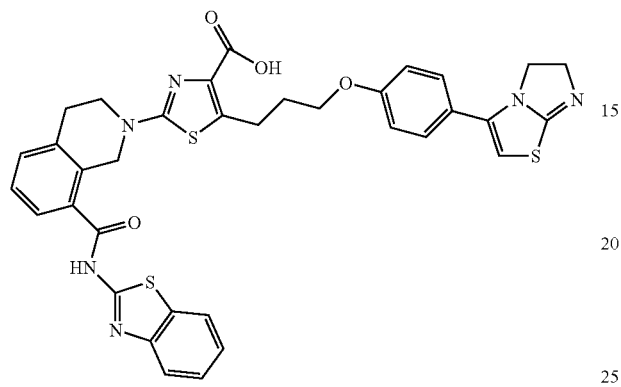

The title compound 53 was prepared by substituting 4-(5,6-dihydroimidazo[2,1-b]thiazol-3-yl)phenol, HBr for phenol in step 4 of Example 2. The alkylation intermediate was purified by column chromatography on silica gel eluting with a gradient of 5 to 60% EtOAc in hexanes. The procedure was followed as described in step 4 of Example 2 except that the ester hydrolysis was conducted at ambient temperature: $^1$H NMR (300 MHz, DMSO-d$_6$) δ ppm 12.89 (1H, s), 12.57 (1H, s), 8.03 (1H, d), 7.79 (1H, d), 7.68 (1H, d), 7.42 (6H, m), 7.03 (2H, d), 6.75 (1H, s), 4.83 (2H, s), 4.39 (2H, m), 4.23 (2H, m), 4.04 (2H, t), 3.73 (2H, t), 3.19 (2H, t), 3.03 (2H, t), 2.03 (2H, m). MS (ESI(+)) m/e 695 (M+H).

Example 54

Synthesis of 2-(8-(benzo[d]thiazol-2-ylcarbamoyl)-3,4-dihydroisoquinolin-2(1H)-yl)-5-(3-(4-(4-(3-(dimethylamino)propylamino)-1H-pyrazolo[3,4-d]pyrimidin-1-yl)phenoxy)propyl)thiazole-4-carboxylic acid (54)

Step 1: Preparation of 4-(4-(3-(dimethylamino)propylamino)-1H-pyrazolo[3,4-d]pyrimidin-1-yl)phenol (54A)

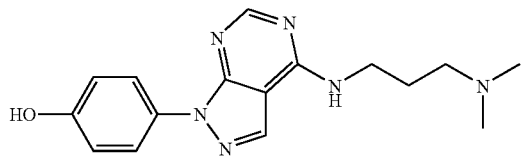

The title compound 54A was prepared using the same procedure described in step 4 of Example 44 by replacing isopropylamine with dimethylaminopropylamine: $^1$H NMR (500 MHz, DMSO-D$_6$) δ ppm 9.54 (1H, s), 8.63 (1H, t), 8.36 (1H, s), 8.31 (1H, s), 7.85 (2H, d), 6.92 (2H, d), 3.60 (2H, q), 3.12-3.18 (2H, m), 2.80 (6H, s), 1.95-2.03 (2H, m).

Step 2: Preparation of Title Compound 54

To a solution of compound 54A (160 mg, 0.512 mmol) in DMF (5 ml) was added sodium hydride (102 mg, 2.56 mmol) (60%). The reaction mixture was stirred for 10 min and Example 2C (194 mg, 0.307 mmol) was added. The resulting mixture was stirred for 1 hour and methanol (3 ml), 10% NaOH (3 ml) and water (1 ml) were added. The resulting mixture was stirred overnight, acidified with TFA and concentrated. The residue was dissolved in a mixture of DMSO-methanol and purified by reverse phase HPLC (mobile phase: 0%-55% acetonitrile in 0.1% TFA aqueous solution during 60 min) to provide the title compound: $^1$H NMR (400 MHz, DMSO-D$_6$) δ ppm 12.84 (1H, s), 9.34 (1H, s), 8.53 (1H, t), 8.36 (1H, s), 8.32 (1H, s), 7.96-8.03 (3H, m), 7.78 (1H, d), 7.67 (1H, d), 7.42-7.49 (2H, m), 7.32-7.41 (2H, m), 7.05-7.10 (2H, m), 4.84 (2H, s), 4.04 (2H, t), 3.73 (2H, t), 3.60 (2H, q),

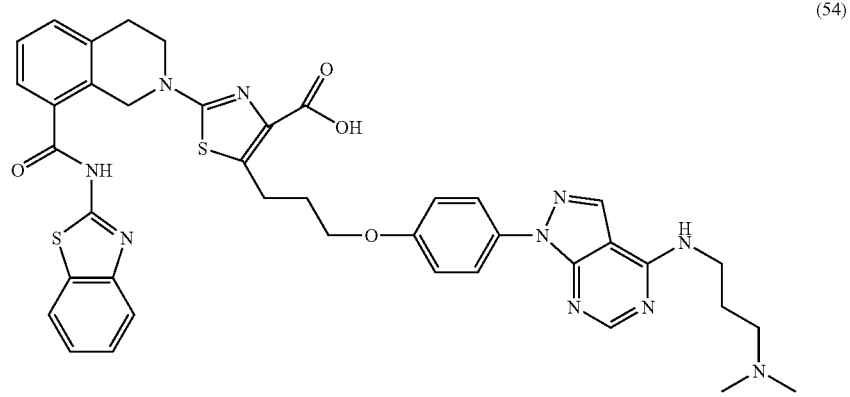

3.12-3.26 (4H, m), 3.03 (2H, t), 2.80 (6H, s), 1.93-2.08 (4H, m). LCMS (APCI) m/e 789 (M+H).

Example 55

Synthesis of 2-(8-(benzo[d]thiazol-2-ylcarbamoyl)-3,4-dihydroisoquinolin-2(1H)-yl)-5-(2-(benzyloxy)ethyl)thiazole-4-carboxylic acid (55)

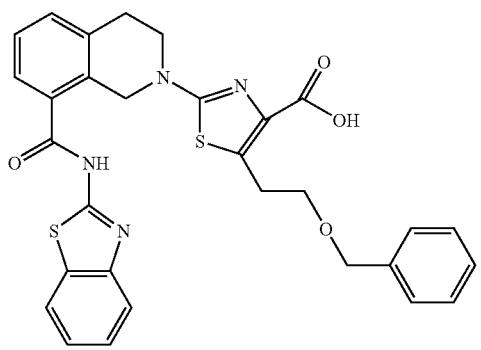

(55)

Step 1: Preparation of ethyl 2-(8-(benzo[d]thiazol-2-ylcarbamoyl)-3,4-dihydroisoquinolin-2(1H)-yl)-5-(2-(benzyloxy)ethyl)thiazole-4-carboxylate (55A)

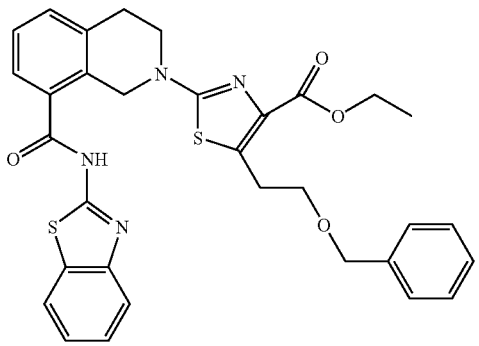

(55A)

Compound 55A was prepared using the same sequence described for step 2 of Example 49 by replacing 3-(tert-butyldimethylsilyloxy)propanal with 3-(benzyloxy)propanal: $^1$H NMR (400 MHz, DMSO-D$_6$) δ ppm 12.88 (1H, s), 8.03 (1H, d), 7.79 (1H, d), 7.66 (1H, d), 7.43-7.51 (2H, m), 7.33-7.41 (2H, m), 7.26-7.30 (4H, m), 7.16-7.23 (1H, m), 4.82 (2H, s), 4.46 (2H, s), 4.17 (2H, q), 3.73 (2H, t), 3.61 (2H, t), 3.26-3.30 (2H, m), 3.04 (2H, t), 1.18 (3H, t); LCMS (APCI) m/e 599 (M+H).

Step 2: Preparation of Title Compound 55

To compound 55A (138 mg, 0.230 mmol) in THF (3 ml) and MeOH (3 ml) was treated with 10% sodium hydroxide (0.46 ml, 1.152 mmol) for 1 day. The reaction mixture was concentrated and acidified by conc. HCl. The precipitate was collected by filtration and dried to provide the title compound: $^1$H NMR (500 MHz, DMSO-D$_6$) δ ppm 12.89 (2H, s), 8.03 (1H, d), 7.80 (1H, d), 7.67 (1H, d), 7.42-7.51 (2H, m), 7.33-

7.42 (2H, m), 7.25-7.31 (4H, m), 7.17-7.21 (1H, m), 4.82 (2H, s), 4.46 (2H, s), 3.74 (2H, t), 3.60 (2H, t), 3.28-3.35 (2H, m), 3.03 (2H, t); LCMS (APCI) m/e 571.

Example 56

Synthesis of 2-[8-(Benzothiazol-2-ylcarbamoyl)-3,4-dihydro-1H-isoquinolin-2-yl]-5-{3-[4-(3-cyano-pyridin-2-yl)-phenoxy]-propyl}-thiazole-4-carboxylic acid (56)

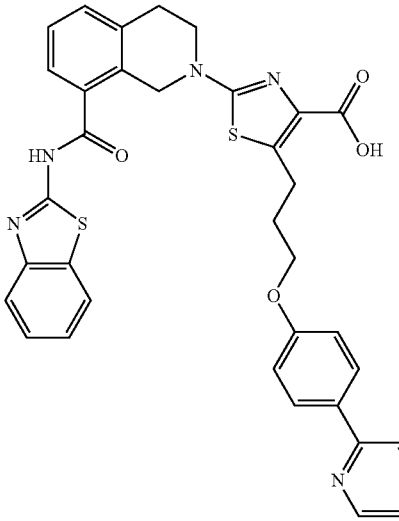

(56)

Step 1: Preparation of 2-(4-hydroxyphenyl)nicotinonitrile (56A)

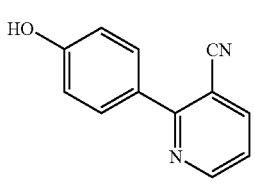

(56A)

Compound 56A was prepared in a similar manner to the synthesis of compound 34D by substituting compound 34C and 4-(hydroxymethyl)phenylboronic acid with 2-chloronicotinonitrile and 4-(4,4,5,5-tetramethyl-1,3,2-dioxaborolan-2-yl)phenol, respectively: ESI (+)/LC/MS: 197 (M+H)$^+$.

Step 2: Preparation of Title Compound 56

Title compound 56 was prepared in a similar manner to the synthesis of compound 51 by substituting compound 51A with compound 56A in step 2 of Example 51: $^1$H NMR (DMSO-d$_6$): δ 8.86 (dd, J=4.76, 1.69 Hz, 1H), 8.34 (dd, J=7.82, 1.69 Hz, 1H), 8.01 (d, J=7.67 Hz, 1H), 7.82 (d, J=8.9 Hz, 2H), 7.77 (d, J=7.98 Hz, 1H), 7.66 (d, J=7.36 Hz, 1H), 7.32-7.53 (m, 5H), 7.07 (d, J=8.9 Hz, 2H), 4.83 (s, 2H), 4.07

(t, J=6.14 Hz, 2H), 3.70-3.73 (m, 2H), 3.18-3.22 (m, 2H), 3.01-3.03 (m, 2H), 2.00-2.08 (m, 2H). ESI (+)/MS: 673 (M+H)⁺.

Example 57

Synthesis of 2-(8-(benzo[d]thiazol-2-ylcarbamoyl)-3,4-dihydroisoquinolin-2(1H)-yl)-5-(3-(6-(3-(dimethylamino)prop-1-ynyl)pyridin-3-yloxy)propyl)thiazole-4-carboxylic acid (57)

(57)

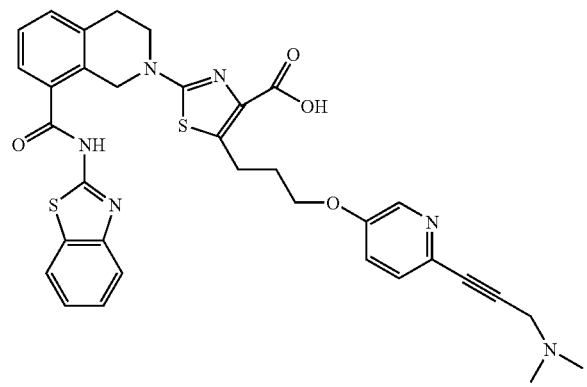

Step 1: Preparation of 2-chloro-5-((2-(trimethylsilyl)ethoxy)methoxy)pyridine (57A)

(57A)

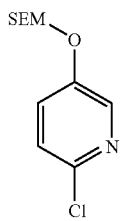

The title compound 57A was prepared using the same procedure described in step 3 of Example 49 by replacing compound 49B with 6-chloropyridin-3-ol: LCMS (APCI) m/e 260 (M+H).

Step 2: Preparation of N,N-dimethyl-3-(5-((2-(trimethylsilyl)ethoxy)methoxy)pyridin-2-yl)prop-2-yn-1-amine (57B)

(57B)

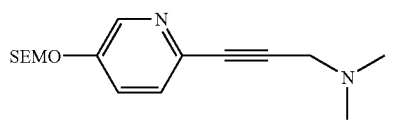

To a mixture of compound 57A (154 mg, 0.593 mmol), N,N-dimethylprop-2-yn-1-amine (0.190 ml, 1.778 mmol), (PPh₃)₂PdCl₂ (62.4 mg, 0.089 mmol), TEA (0.413 ml, 2.96 mmol) in DMF (3 ml) was added copper(I) iodide (11.29 mg, 0.059 mmol). The resulting mixture was heated at 150° C. in a Smith microwave synthesizer for 30 min and purified by flash chromatography to provide the desired compound 57B; LCMS (APCI) m/e 307.

Step 3: Preparation of 6-(3-(dimethylamino)prop-1-ynyl)pyridin-3-ol (57C)

(57C)

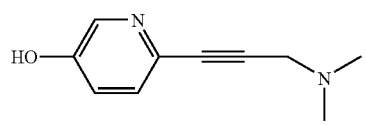

Compound 57B (40 mg, 0.131 mmol) in MeOH (3 ml) was treated with 2 N hydrogen chloride in ether (0.1 ml, 0.200 mmol) for 1 h and the mixture was concentrated to provide the title compound 57C. LCMS (APCI) m/e 177 (M+H).

Step 4: Preparation of the Title Compound (57)

(57)

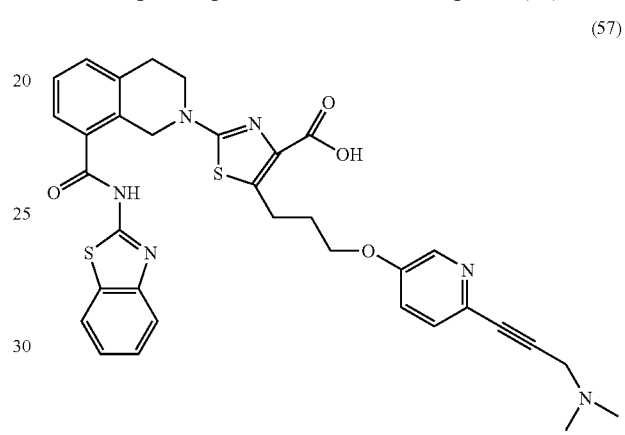

The title compound 57 was prepared using the same procedure described in step 2 of Example 54 by replacing compound 54A with compound 57C: ¹H NMR (500 MHz, DMSO-D₆) δ ppm 12.90 (1H, s), 10.25 (1H, s), 8.28 (1H, d), 8.04 (1H, d), 7.79 (1H, d), 7.67 (1H, d), 7.58 (1H, d), 7.43-7.50 (2H, m), 7.34-7.43 (3H, m), 4.83 (2H, s), 4.34 (2H, s), 4.10 (2H, t), 3.69-3.76 (2H, m), 3.16-3.24 (2H, m), 3.03 (2H, t), 2.73 (6H, s), 1.98-2.07 (2H, m); LCMS (APCI) m/e 654 (M+H).

Example 58

Synthesis of 2-[8-(Benzothiazol-2-ylcarbamoyl)-3,4-dihydro-1H-isoquinolin-2-yl]-5-{3-[4-(2-cyano-pyridin-3-yl)-phenoxy]-propyl}-thiazole-4-carboxylic acid (58)

(58)

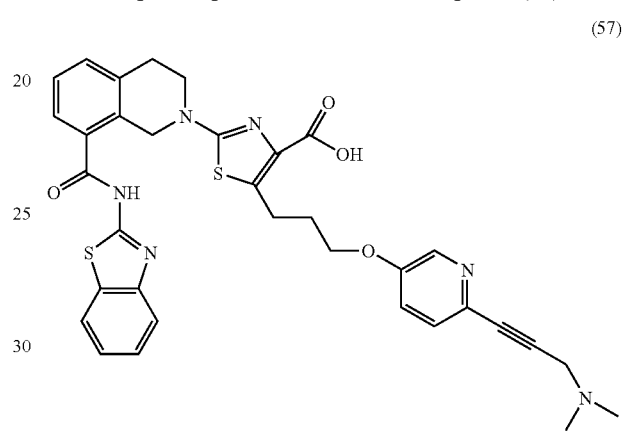

Step 1: Preparation of 3-(4-hydroxyphenyl)picolinonitrile (58A)

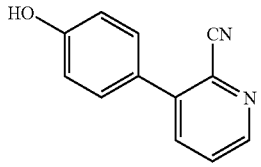

The title compound 58A was prepared in a similar manner to the synthesis of compound 34D by substituting compound 34C and 4-(hydroxymethyl)phenylboronic acid with 3-chloropicolinonitrile and 4-(4,4,5,5-tetramethyl-1,3,2-dioxaborolan-2-yl)phenol, respectively. ESI (+)/LC/MS: 197 (M+H)$^+$.

Step 2: Preparation of Title Compound 58

The title compound 58 was prepared in a similar manner to the synthesis of compound 51 by substituting compound 51A with compound 58A in step 2 of Example 51: $^1$H NMR (DMSO-d$_6$): δ 8.84 (dd, J=4.6, 1.53 Hz, 1H), 7.98 (dd, J=7.98, 1.53 Hz, 1H), 7.95 (d, J=7.67 Hz, 1H), 7.27-7.7 (m, 9H), 7.01-7.03 (m, 2H), 4.77 (s, 2H), 4.01 (t, J=6.29 Hz, 2H), 3.66 (t, J=5.98 Hz, 2H), 3.12-3.16 (m, 2H), 2.97 (t, J=5.98 Hz, 2H), 1.95-2.02 (m, 2H). ESI (+)/MS: 673 (M+H)$^+$.

Example 59

Synthesis of 2-[8-(Benzothiazol-2-ylcarbamoyl)-3,4-dihydro-1H-isoquinolin-2-yl]-5-[3-(4-morpholin-4-yl-phenoxy)-propyl]-thiazole-4-carboxylic acid (59)

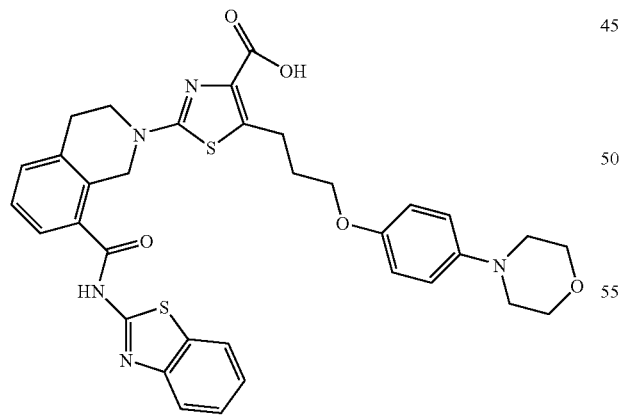

The title compound was prepared in a similar manner to the synthesis of compound 51 by substituting compound 51A with 4-morpholinophenol in step 2 of Example 51: $^1$H NMR (DMSO-d$_6$): δ 7.96 (d, J=7.67 Hz, 1H), 7.72 (d, J=7.98 Hz, 1H), 7.60 (d, J=7.06 Hz, 1H), 7.27-7.42 (m, 4H), 6.88 (d, J=8.9 Hz, 2H), 6.75-6.79 (m, 2H), 4.76 (s, 2H), 3.85 (t, J=6.29 Hz, 2H), 3.64-3.68 (m, 6H), 3.07-3.11 (m, 2H), 2.95-2.98 (m, 6H), 1.87-1.94 (m, 2H). ESI (+)/MS: 656 (M+H)$^+$.

Example 60

Synthesis 2-[8-(Benzothiazol-2-ylcarbamoyl)-3,4-dihydro-1H-isoquinolin-2-yl]-5-[5-(4-cyano-thiophen-3-yl)-2-hydroxy-benzyl]-thiazole-4-carboxylic acid (60)

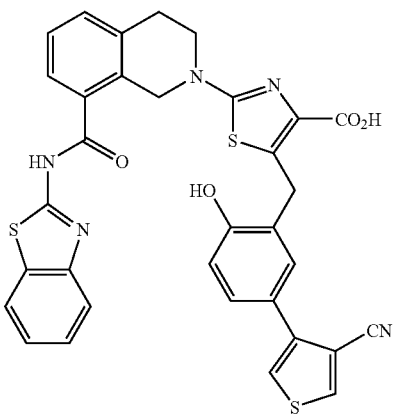

Step 1: Preparation of (E)-methyl 5-(5-(4-cyanothiophen-3-yl)-2-hydroxybenzyl)-2-(8-(3-((2-(trimethylsilyl)ethoxy)methyl)benzo[d]thiazol-2(3H)-ylidenecarbamoyl)-3,4-dihydroisoquinolin-2(1H)-yl)thiazole-4-carboxylate (60A)

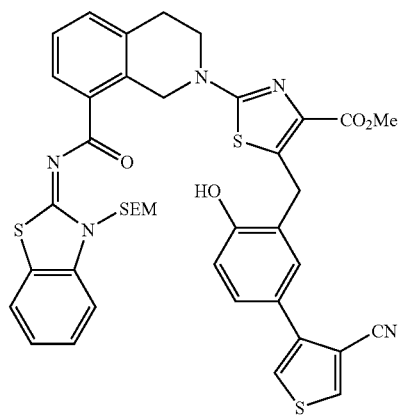

The title compound 60A was prepared in a similar manner to the synthesis of compound 35A by substituting compound 34D and compound 31F with compound 45D and compound 51A, respectively: ESI (+)/LC/MS: 892 (M+NH$_4$—H$_2$O)$^+$: $^1$H NMR (DMSO-d$_6$): δ 9.99 (s, 1H), 8.58 (s, 1H), 8.21 (d, J=6.71 Hz, 1H), 7.92 (d, J=7.32 Hz, 1H), 7.66-7.68 (m, 2H), 7.52-7.55 (m, 1H), 7.32-7.41 (m, 5H), 6.92 (d, J=8.24 Hz, 1H), 5.97 (s, 2H), 5.08 (s, 2H), 4.35 (s, 2H), 3.78 (s, 3H), 3.64-3.68 (m, 2H), 2.98 (t, J=5.8 Hz, 2H), 0.84-0.87 (m, 2H), −0.22 (s, 9H). ESI (+)/MS: 794 (M+H)$^+$.

Step 2: Preparation of Title Compound 60

The title compound 60 was prepared in a similar manner to the synthesis of compound 34 by substituting compound 34D with compound 60A: $^1$H NMR (DMSO-d$_6$): δ 9.92 (s, 1H), 8.55 (d, J=3.07 Hz, 1H), 8.00 (d, J=7.98 Hz, 1H), 7.77 (d, J=8.29 Hz, 1H), 7.63-7.66 (m, 2H), 7.29-7.48 (m, 6H), 6.90 (d, J=8.29 Hz, 1H), 4.79 (s, 2H), 4.34 (s, 2H), 3.66 (d, J=5.98 Hz, 2H), 2.99 (t, J=5.83 Hz, 2H). ESI (+)/MS: 650 (M+H)$^+$.

Example 61

Synthesis of 5-{3-[4-(4-Acetyl-piperazin-1-yl)-phenoxy]-propyl}-2-[8-(benzothiazol-2-ylcarbamoyl)-3,4-dihydro-1H-isoquinolin-2-yl]-thiazole-4-carboxylic acid (61)

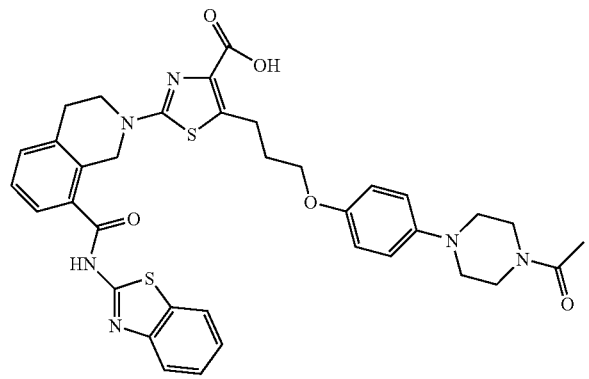

(61)

The title compound 61 was prepared in a similar manner to the synthesis of compound 51 by substituting compound 51A with 1-(4-(4-hydroxyphenyl)piperazin-1-yl)ethanone in step 2 of Example 51: $^1$H NMR (DMSO-d$_6$): δ 8.02 (d, J=7.36 Hz, 1H), 7.78 (d, J=8.29 Hz, 1H), 7.66 (d, J=7.06 Hz, 1H), 7.33-7.49 (m, 4H), 6.90-6.92 (m, 2H), 6.80-6.82 (m, 2H), 4.82 (s, 2H), 3.90 (t, J=6.29 Hz, 2H), 3.71 (t, J=6.29 Hz, 2H), 3.53-3.56 (m, 2H), 3.13-3.17 (m, 2H), 3.02 (t, J=5.37 Hz, 4H), 2.94-2.96 (m, 2H), 2.02 (s, 3H), 1.92-1.99 (m, 2H). ESI (+)/MS: 697 (M+H)$^+$.

Example 62

Synthesis of 2-(8-(benzo[d]thiazol-2-ylcarbamoyl)-3,4-dihydroisoquinolin-2(1H)-yl)-5-((4-phenylpiperazin-1-yl)methyl)thiazole-4-carboxylic acid (62A)

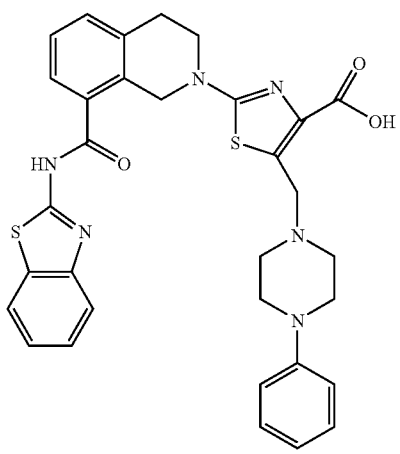

(62)

Step 1: Preparation of methyl 2-(8-(benzo[d]thiazol-2-yl((2-(trimethylsilyl)ethoxy)methyl)carbamoyl)-3,4-dihydroisoquinolin-2(1H)-yl)-5-((4-phenylpiperazin-1-yl)methyl)thiazole-4-carboxylate (62A)

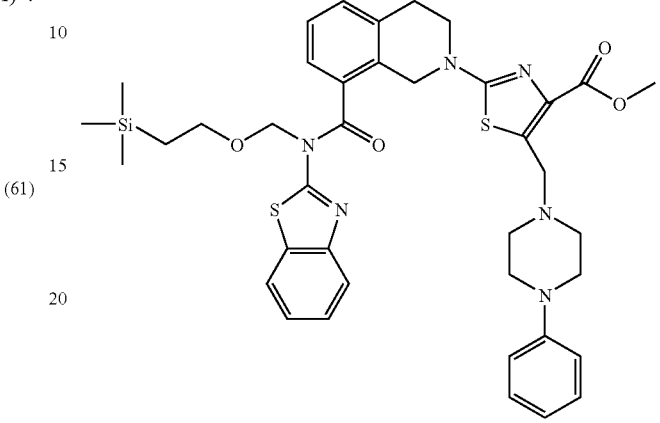

(62A)

To a solution of compound 45C (55 mg, 0.090 mmol) in DCE (3.5 ml) was added 1-phenylpiperazine (14.57 mg, 0.090 mmol) and sodium triacetoxyborohydride (28.7 mg, 0.136 mmol). The reaction was stirred for 2 days and concentrated. The residue was triturated with methanol and white precipitate was collected to give the title compound: LCMS (APCI) m/e 756 (M+H).

Step 2: Preparation of Title Compound 62

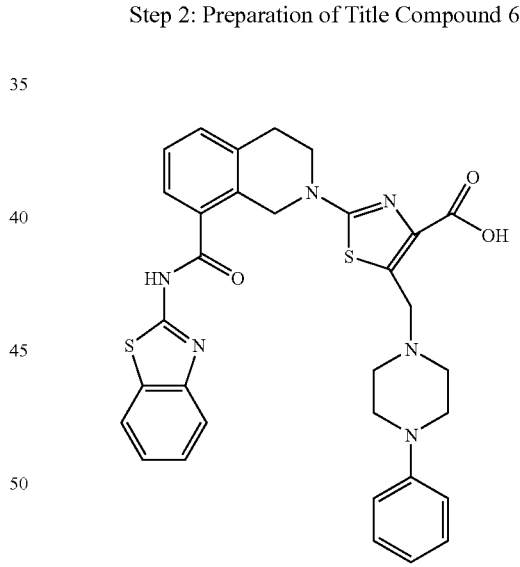

(62)

Compound 62A (50 mg, 0.066 mmol) in DCM (3.5 ml) was treated with 2 N hydrogen chloride in ether (3.31 ml, 6.62 mmol) for 30 min. The reaction was concentrated and the residue was dissolved in THF (3 ml) and methanol (3 ml). NaOH (10% aq., 1 ml) was added. The resulting mixture was stirred overnight and concentrated. The residue was purified by purified by reverse phase HPLC (mobile phase: 0%-70% acetonitrile in 0.1% TFA aqueous solution during 40 min) to provide the title compound: $^1$H NMR (400 MHz, DMSO-D$_6$) δ ppm 12.91 (1H, s), 8.02 (1H, d), 7.78 (1H, d), 7.70 (1H, d), 7.44-7.50 (2H, m), 7.41 (1H, t), 7.35 (1H, t), 7.20-7.27 (2H, m), 6.96 (2H, d), 6.84 (1H, t), 4.89 (2H, s), 4.73 (2H, s), 3.82 (2H, t), 3.45 (8H, s), 3.07 (2H, t). LCMS (APCI) m/e 611 (M+H).

Example 63

Synthesis of 2-(8-(benzo[d]thiazol-2-ylcarbamoyl)-3,4-dihydroisoquinolin-2(1H)-yl)-5-((4-phenylpiperidin-1-yl)methyl)thiazole-4-carboxylic acid (63)

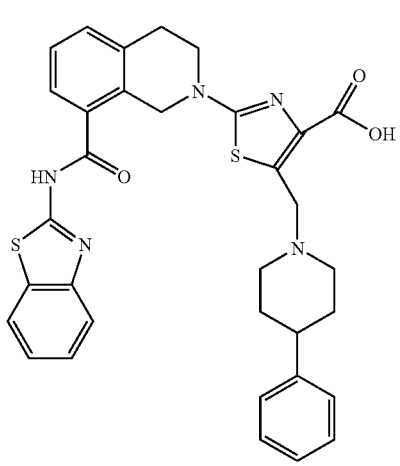

(63)

Step 1: Preparation of methyl 2-(8-(benzo[d]thiazol-2-yl((2-(trimethylsilyl)ethoxy)methyl)carbamoyl)-3,4-dihydroisoquinolin-2(1H)-yl)-5-((4-phenylpiperidin-1-yl)methyl)thiazole-4-carboxylate (63A)

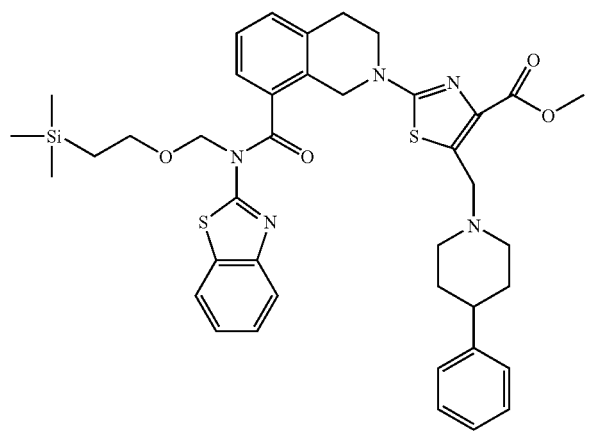

(63A)

The compound was prepared using the same procedure described in step 1 of Example 62 by replacing 1-phenylpiperazine with 4-phenylpiperidine. LCMS (APCI) m/e 755 (M+H).

Step 2: Preparation of Title Compound 63

The title compound 63 was prepared using the same procedure described in step 2 of Example 62 by replacing compound 62A with compound 63A: $^1$H NMR (400 MHz, DMSO-D$_6$) δ ppm 12.94 (1H, s), 9.32 (1H, s), 8.03 (1H, d), 7.78 (1H, d), 7.71 (1H, d), 7.45-7.50 (2H, m), 7.41 (1H, t), 7.29-7.38 (3H, m), 7.21 (3H, t), 4.89 (2H, s), 4.76 (2H, s), 3.83 (2H, t), 3.48-3.59 (2H, m), 3.11-3.21 (2H, m), 3.07 (2H, t), 2.78-2.90 (1H, m), 1.76-2.02 (4H, m).); LCMS (APCI) m/e 610 (M+H).

Example 64

Synthesis of 2-[8-(Benzothiazol-2-ylcarbamoyl)-3,4-dihydro-1H-isoquinolin-2-yl]-5-[3-(4-piperazin-1-yl-phenoxy)-propyl]-thiazole-4-carboxylic acid (64)

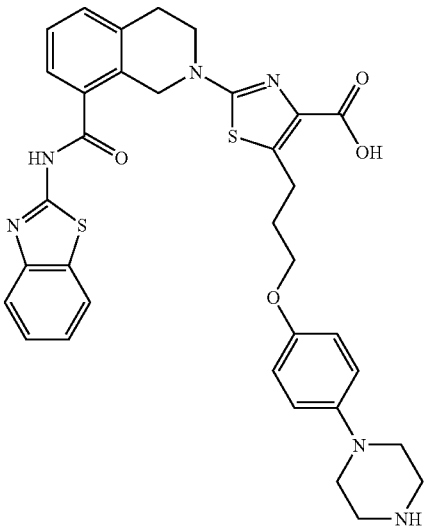

(64)

Compound 61 (25 mg) in dioxane (2 mL) and MeOH (2 mL) was treated with 1.0 N LiOH (2 mL). The reaction mixture was heated under reflux until compound 61 was consumed as monitored by TLC. The solvents were removed, and the residue was purified with Prep HPLC to give the title compound 64 as a TFA salt: $^1$H NMR (DMSO-d$_6$): δ 8.56 (s, 2H), 7.96 (d, J=7.67 Hz, 1H), 7.72 (d, J=7.98 Hz, 1H), 7.60 (d, J=7.36 Hz, 1H), 7.27-7.43 (m, 4H), 6.92-6.95 (m, 2H), 6.75-6.77 (m, 2H), 4.76 (s, 2H), 3.84 (t, J=6.14 Hz, 2H), 3.65 (t, J=5.98 Hz, 2H), 3.07-3.14 (m, 8H), 2.96 (t, J=5.98 Hz, 2H), 1.86-1.94 (m, 2H). ESI (+)/MS: 655 (M+H)$^+$.

Example 65

Synthesis of 2-[8-(Benzothiazol-2-ylcarbamoyl)-3,4-dihydro-1H-isoquinolin-2-yl]-5-{3-[4-(5-bromo-thieno[2,3-d]pyrimidin-4-yl)-phenoxy]-propyl}-thiazole-4-carboxylic acid (65)

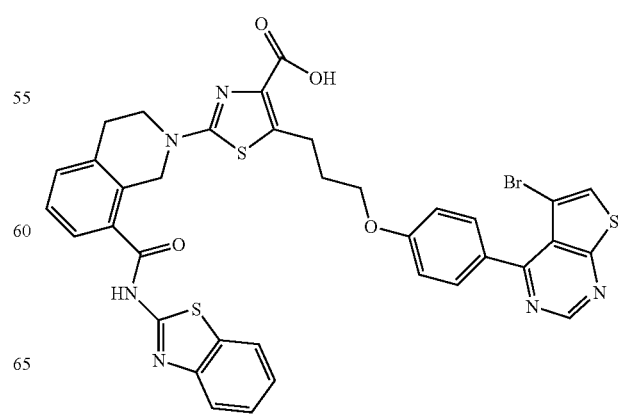

(65)

Step 1: Preparation of 7-bromo-4-chlorothieno[3,2-d]pyrimidine (65A)

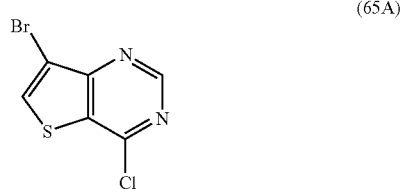

(65A)

7-Bromothieno[3,2-d]pyrimidin-4(3H)-one (0.9 g, 3.89 mmol) in POCl$_3$ was heated under reflux for 2 hours and excess of POCl$_3$ was removed under reduced pressure. The residue was partitioned between water and EtOAc. The organic layer was separated, and the aqueous layer was extracted with additional EtOAc. The combined organic layers were washed with brine, dried (MgSO4), filtered, and concentrated to give 0.91 g of the compound 65A: $^1$H NMR (DMSO-d$_6$): δ 9.15 (s, 1H), 8.78 (s, 1H). ESI (+)/MS: 248 (M–H)$^+$.

Step 2: Preparation of 4-(7-bromothieno[3,2-d]pyrimidin-4-yl)phenol (65B)

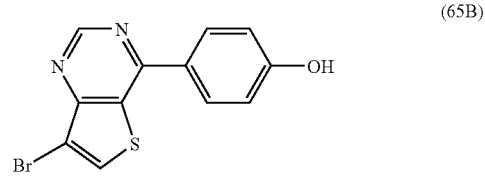

(65B)

The title compound was prepared using similar conditions as described for the synthesis of compound 34D by substituting compound 34C and 4-(hydroxymethyl)phenylboronic acid with compound 65A and 4-(4,4,5,5-tetramethyl-1,3,2-dioxaborolan-2-yl)phenol, respectively: $^1$H NMR (DMSO-d$_6$): δ 9.27 (s, 1H), 8.73 (s, 1H), 8.08-8.10 (m, 2H), 7.01-7.03 (m, 2H); ESI (–)/MS: 308 (M–H)$^-$.

Step 3: Preparation of the Title Compound 65

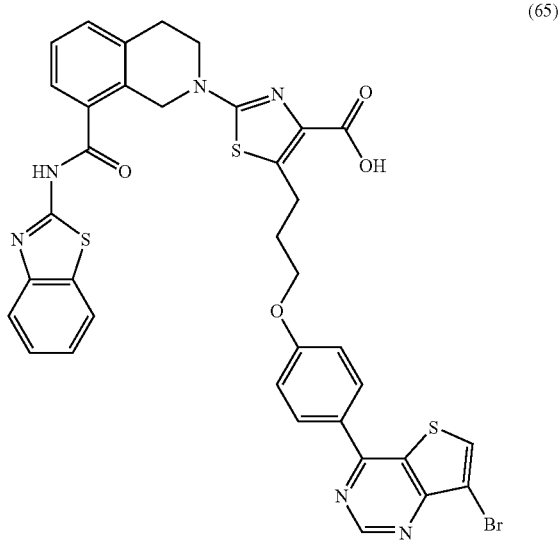

(65)

The title compound 65 was prepared in a similar manner to the synthesis of compound 51 by substituting compound 51A with compound 65B: $^1$H NMR (DMSO-d$_6$): δ 9.29 (s, 1H), 8.73 (s, 1H), 8.13 (d, J=8.59 Hz, 2H), 7.99 (d, J=7.98 Hz, 1H), 7.76 (d, J=7.98 Hz, 1H), 7.66 (d, J=7.06 Hz, 1H), 7.31-7.47 (m, 4H), 7.17 (J=8.9 Hz, 2H), 4.82 (s, 2H), 4.11 (t, J=6.14 Hz, 2H), 3.71-3.74 (m, 2H), 3.19-3.22 (m, 2H), 3.02 (t, J=5.37 Hz, 2H), 2.05-2.07 (m, 2H). ESI (+)/MS: 527 (M+H)$^+$.

Example 66

Synthesis of 5-(3-(4-(1H-imidazol-1-yl)phenoxy)propyl)-2-(8-(benzo[d]thiazol-2-ylcarbamoyl)-3,4-dihydroisoquinolin-2(1H)-yl)thiazole-4-carboxylic acid (66)

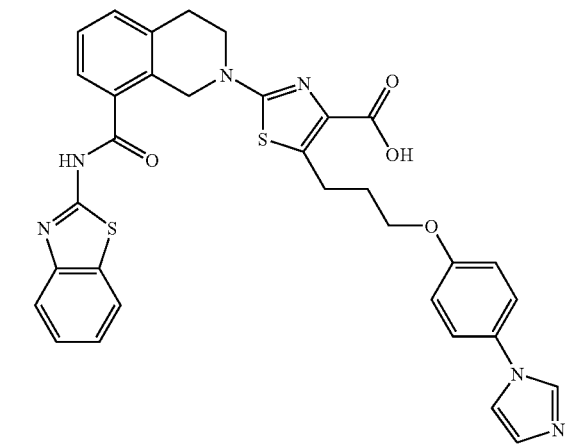

(66)

The title compound 66 was prepared by substituting 4-(1H-imidazol-1-yl)phenol for phenol in step 4 of Example 2. The alkylation intermediate was not isolated prior to ester hydrolysis. After precipitation of the desired product, the solid was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 20-90% of B in 40 min) to provide the title compound in 45% yield: $^1$H NMR (300 MHz, DMSO-d$_6$) δ ppm 12.88 (1H, s), 12.52 (1H, s), 9.34 (1H, s), 8.10 (1H, d), 8.02 (1H, m), 7.78 (2H, m), 7.66 (3H, m), 7.42 (4H, m), 713 (2H, m), 4.83 (2H, s), 4.07 (2H, t), 3.73 (2H, t), 3.20 (2H, m), 3.03 (2H, t), 2.04 (2H, m); MS (ESI(+)) m/e 637 (M+H).

Example 67

Synthesis of 5-(3-(4-(1H-1,2,4-triazol-1-yl)phenoxy)propyl)-2-(8-(benzo[d]thiazol-2-ylcarbamoyl)-3,4-dihydroisoquinolin-2(1H)-yl)thiazole-4-carboxylic acid (67)

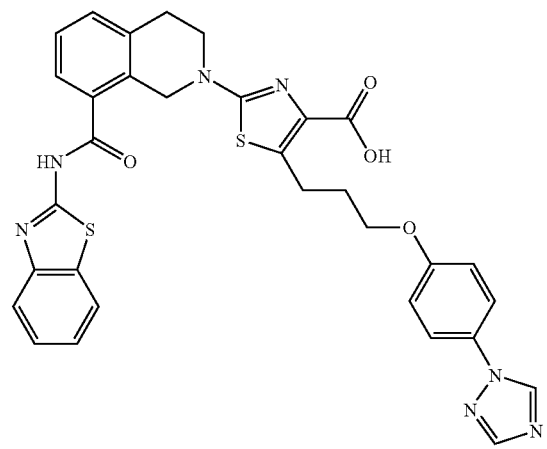

(67)

The title compound was prepared by substituting 4-(1H-1,2,4-triazol-1-yl)phenol for phenol in step 4 of Example 2. The alkylation intermediate was not isolated prior to ester hydrolysis. After precipitation of the desired product, the solid was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 20-90% of B in 40 min) to provide the title compound 67 in 43% yield: $^1$H NMR (300 MHz, DMSO-d$_6$) δ ppm 12.88 (1H, s), 9.14 (1H, s), 8.17 (1H, s), 8.03 (1H, d), 7.79 (1H, d), 7.72 (2H, m), 7.66 (1H, d), 7.42 (5H, m), 7.07 (2H, m), 4.83 (2H, s), 4.04 (2H, t), 3.72 (2H, t), 3.19 (2H, m), 3.03 (2H, t), 2.02 (2H, m). MS (ESI)(+)) m/e 638 (M+H).

Example 68

Synthesis of 2-(8-(benzo[d]thiazol-2-ylcarbamoyl)-3,4-dihydroisoquinolin-2(1H)-yl)-5-(3-(4-(4-methyl-4H-1,2,4-triazol-3-yl)phenoxy)propyl)thiazole-4-carboxylic acid (68):

(68)

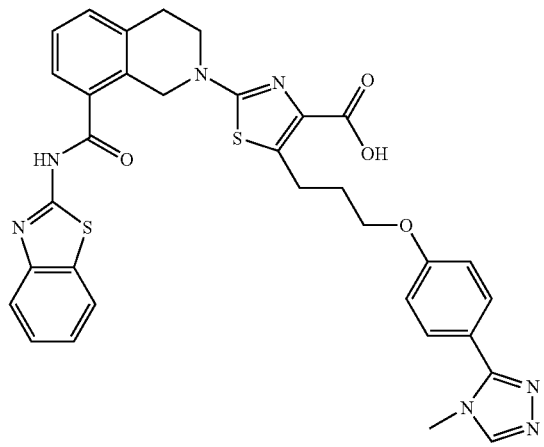

The title compound 68 was prepared by substituting 4-(4-methyl-4H-1,2,4-triazol-3-yl)phenol for phenol in step 4 of Example 2. The alkylation intermediate was not isolated prior to ester hydrolysis. After precipitation of the desired product, the solid was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 20-90% of B in 40 min) to provide the title compound 68 in 56% yield: $^1$H NMR (300 MHz, DMSO-d$_6$) δ ppm 12.89 (1H, s), 8.73 (1H, s), 8.03 (1H, d), 7.79 (1H, d), 7.66 (3H, m), 7.42 (4H, m), 7.09 (2H, m), 4.83 (2H, s), 4.07 (2H, t), 3.73 (5H, m), 3.20 (2H, m), 3.03 (2H, t), 2.04 (2H, m). MS (ESI(+)) m/e 652 (M+H).

Example 69

Synthesis of 2-[8-(Benzothiazol-2-ylcarbamoyl)-3,4-dihydro-1H-isoquinolin-2-yl]-5-{3-[4-(4-isopropylamino-thieno[3,2-d]pyrimidin-7-yl)-phenoxy]-propyl}-thiazole-4-carboxylic acid (69):

(69)

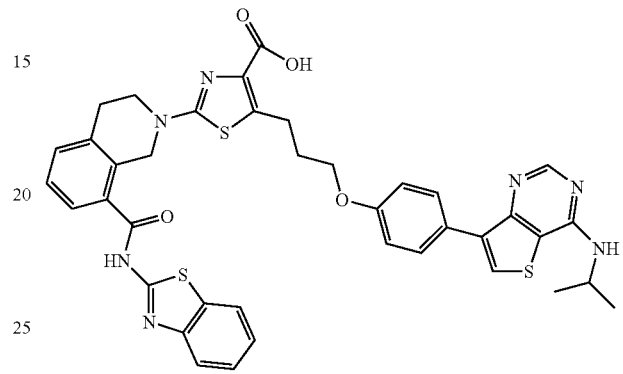

Step 1: Preparation of 7-bromo-N-isopropylthieno[3,2-d]pyrimidin-4-amine (69A)

(69A)

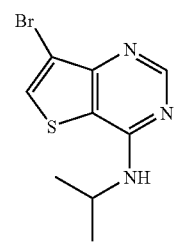

A mixture of compound 65A (0.125 g, 0.5 mmol), and propan-2-amine (0.148 g, 2.5 mmol) in ethanol (10 mL) was heated under reflux for 15 hours. The solvent was removed, and the residue was purified by flash column chromatography on silica gel eluting with 1:1 EtOAc/hexanes to give 0.13 g of the title compound: $^1$H NMR (DMSO-d$_6$): δ 8.50 (s, 1H), 8.28 (s, 1H), 7.87 (d, J=7.46 Hz, 1H), 4.40-4.51 (m, 1H), 1.23 (d, J=6.78 Hz, 6H). ESI (+)/MS: 273 (M−H)$^+$.

Step 2: Preparation of 4-(4-(isopropylamino)thieno[3,2-d]pyrimidin-7-yl)phenol (69B)

(69B)

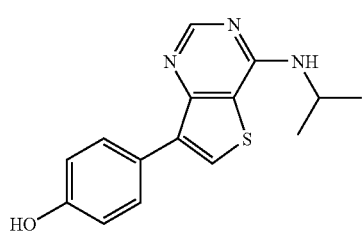

The title compound 69B was prepared in a similar manner to the synthesis of compound 34D by substituting compound 34C and 4-(hydroxymethyl)phenylboronic acid with compound 69A and 4-(4,4,5,5-tetramethyl-1,3,2-dioxaborolan-2-yl)phenol, respectively: 1H NMR (DMSO-$d_6$): δ 9.49 (s, 1H), 8.50 (s, 1H), 8.10 (s, 1H), 7.88-7.91 (m, 2H), 7.57 (d, J=7.67 Hz, 1H), 6.83-6.86 (m, 2H), 4.44-4.53 (m, 1H), 1.25 (d, J=6.75 Hz, 6H). ESI (+)/MS: 286 (M−H)$^+$.

Step 3: Preparation of Title Compound 69

The title compound 69 was prepared in a similar manner to the synthesis of compound 51 by substituting compound 51A with compound 69B: $^1$H NMR (DMSO-$d_6$): δ 8.59 (s, 1H), 8.25 (s, 1H), 8.00 (d, J=7.67 Hz, 1H), 7.66-7.79 (m, 4H), 7.32-7.48 (m, 4H), 7.03 (d, J=8.59 Hz, 2H), 4.84 (s, 2H), 4.41-4.47 (m, 1H), 4.05 (t, J=6.14 Hz, 2H), 3.72-3.75 (m, 2H), 3.19-3.22 (m, 2H), 3.03 (t, J=5.98 Hz, 2H), 2.00-2.08 (m, 2H), 1.28 (d, J=6.44 Hz, 6H). ESI (+)/MS: 762 (M+H)$^+$.

Example 70

Synthesis of 2-[8-(Benzothiazol-2-ylcarbamoyl)-3,4-dihydro-1H-isoquinolin-2-yl]-5-[2-(3-nitro-benzene-sulfonylamino)-ethyl]thiazole-4-carboxylic acid (70)

(70)

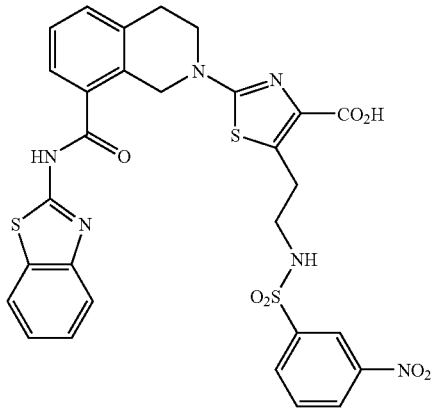

Step 1: Preparation of (E)-ethyl 5-(2-(3-nitrophenyl-sulfonamido)ethyl)-2-(8-(2-(3-((2-(trimethylsilyl)ethoxy)methyl)benzo[d]thiazol-2(3H)-ylidene)acetyl)-3,4-dihydroisoquinolin-2(1H)-yl)thiazole-4-carboxylate (70A)

(70A)

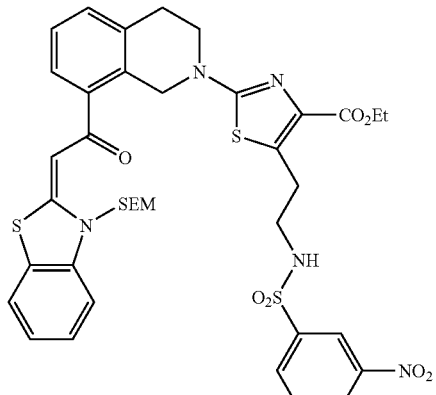

The title compound 70A was prepared in a similar manner to the synthesis of compound 35A by substituting compound 34D and compound 31F with compound 49D and 3-nitrobenzenesulfonamide, respectively: ESI (+)/LC/MS: 823 (M+H)$^+$.

Step 2: Preparation of Title Compound 70

The title compound 70 was prepared in a similar manner to the synthesis of compound 51 by substituting compound 51A with compound 70A: $^1$H NMR (DMSO-$d_6$): δ 8.39-8.44 (m, 2H), 8.11-8.15 (m, 2H), 8.04 (d, J=7.98 Hz, 1H), 7.78-7.84 (m, 2H), 7.68 (d, J=7.36 Hz, 1H), 7.34-7.50 (m, 4H), 6.90 (d, J=8.29 Hz, 1H), 4.79 (s, 2H), 3.69 (d, J=5.98 Hz, 2H), 3.06-3.10 (m, 4H), 3.03 (t, J=5.98 Hz, 2H). ESI (+)/MS: 665 (M+H)$^+$.

Example 71

Synthesis of 2-[8-(Benzothiazol-2-ylcarbamoyl)-3,4-dihydro-1H-isoquinolin-2-yl]-5-(2-phenyl-azetidin-1-ylmethyl)-thiazole-4-carboxylic acid (71)

(71)

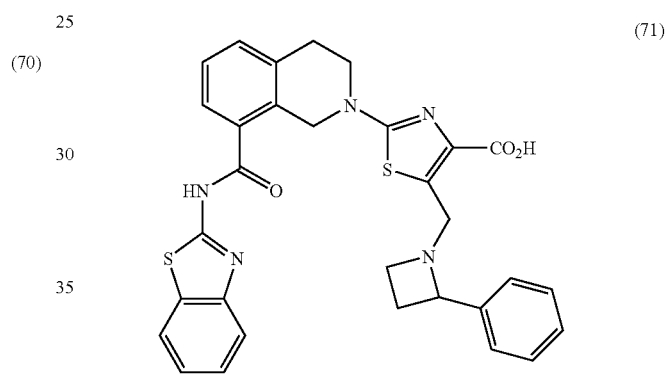

Step 1: Preparation of (E)-methyl 5-((2-phenylazetidin-1-yl)methyl)-2-(8-(2-(3-((2-(trimethylsilyl)ethoxy)methyl)benzo[d]thiazol-2(3H)-ylidene)acetyl)-3,4-dihydroisoquinolin-2(1H)-yl)thiazole-4-carboxylate (71A)

(71A)

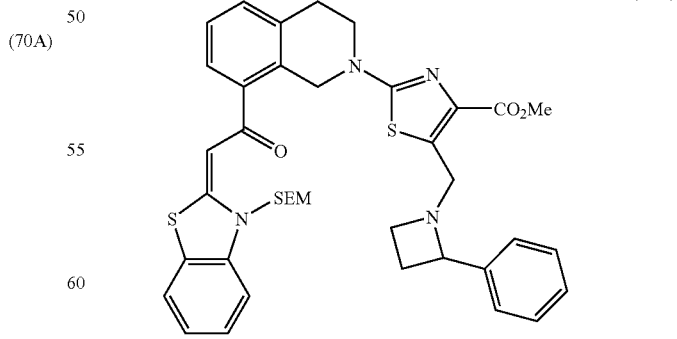

The title compound 71A was prepared in a similar manner to the synthesis of compound 62A by substituting phenylepiperazine with 2-phenylazetidine: ESI (+)/LC/MS: 726 (M+H)$^+$.

Step 2: Preparation of Title Compound 71

The title compound was prepared in a similar manner to the synthesis of compound 51 by substituting compound 51A with compound 71A: $^1$H NMR (DMSO-d$_6$): δ 12.89 (s, 1H), 8.04 (d, J=7.36 Hz, 1H), 7.80 (d, J=7.98 Hz, 1H), 7.70 (d, J=7.37 Hz, 1H), 7.34-7.54 (m, 9H), 5.47 (br, 1H), 4.70-4.95 (m, 4H), 4.40 (br, s, 1H), 3.88 (br, 1H), 3.76 (d, J=5.83 Hz, 2H), 2.60-2.8 (br, s, 2H). ESI (+)/MS: 582 (M+H)$^+$.

Example 72

Synthesis of 5-(4-(1H-imidazol-1-yl)butyl)-2-(8-(benzo[d]thiazol-2-ylcarbamoyl)-3,4-dihydroisoquinolin-2(1H)-yl)thiazole-4-carboxylic acid (72)

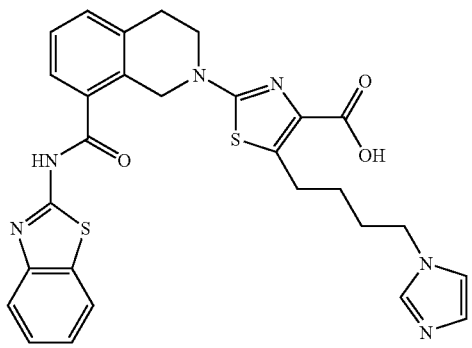

(72)

The title compound 72 was prepared by substituting compound 42C for compound 2C and imidazole for phenol in step 4 of Example 2. The alkylation intermediate was not isolated prior to ester hydrolysis. After precipitation of the desired product, the solid was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 20-90% of B in 40 min) to provide the title compound in 34% yield: $^1$H NMR (300 MHz, DMSO-d$_6$) δ ppm 12.91 (1H, s), 12.55 (1H, s), 9.06 (1H, s), 8.04 (1H, d), 7.77 (2H, m), 7.66 (2H, m), 7.43 (4H, m), 4.19 (2H, t), 3.73 (2H, t), 3.05 (4H, m), 1.83 (2H, m), 1.53 (2H, m). MS (ESI(+)) m/e 559 (M+H).

Example 73

Synthesis of 5-(3-(4-(1H-pyrazol-4-yl)phenoxy)propyl)-2-(8-(benzo[d]thiazol-2-ylcarbamoyl)-3,4-dihydroisoquinolin-2(1H)-yl)thiazole-4-carboxylic acid (73)

(73)

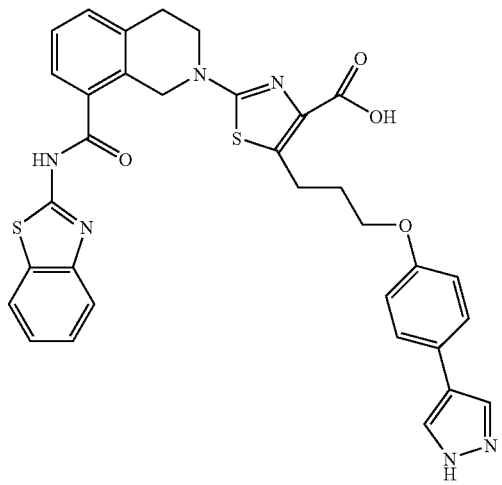

Step 1: Preparation of tert-butyl 5-(3-(4-(1H-pyrazol-4-yl)phenoxy)propyl)-2-(8-(benzo[d]thiazol-2-yl((2-(trimethylsilyl)ethoxy)methyl)carbamoyl)-3,4-dihydroisoquinolin-2(1H)-yl)thiazole-4-carboxylate (73A)

(73A)

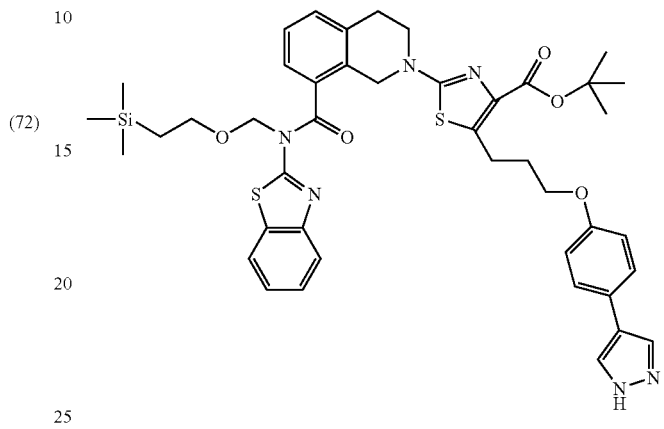

A mixture of compound 41A (90 mg, 0.102 mmol), 4-(4,4,5,5-tetramethyl-1,3,2-dioxaborolan-2-yl)-1H-pyrazole (29.7 mg, 0.153 mmol), Na$_2$CO$_3$ (108 μl, 0.102 mmol) (1M) and (Ph$_3$P)$_2$Cl$_2$Pd (7.15 mg, 10.19 μmol) in EtOH-DME-H$_2$O (7:3:2, 4 ml) was in a Smith microwave synthesizer at 120° C. for 30 min and then concentrated. The residue was purified by flash chromatography to give the compound 73A. LCMS (APCI) m/e 824 (M+H).

Step 2: Preparation of Title Compound 73

Compound 73A (30 mg) in DCM (1 ml) was treated with HCl 2 N in ether (5 ml) for 2 days. The precipitate was collected and dried to give the title compound 73: $^1$H NMR (400 MHz, DMSO-D$_6$) δ ppm 8.09 (2H, s), 8.02 (1H, d), 7.79 (1H, d), 7.68 (1H, d), 7.51 (2H, d), 7.44-7.48 (2H, m), 7.33-7.42 (2H, m), 6.91 (2H, d), 4.87 (2H, s), 3.99 (2H, t), 3.75 (2H, t), 3.19 (2H, t), 3.04 (2H, t); LCMS (APCI) m/e 637 (M+H).

Example 74

Synthesis of 2-[8-(Benzothiazol-2-ylcarbamoyl)-3,4-dihydro-1H-isoquinolin-2-yl]-5-{3-[4-(3-dimethylamino-prop-1-ynyl)-phenoxy]-propyl}-thiazole-4-carboxylic acid (74)

(74)

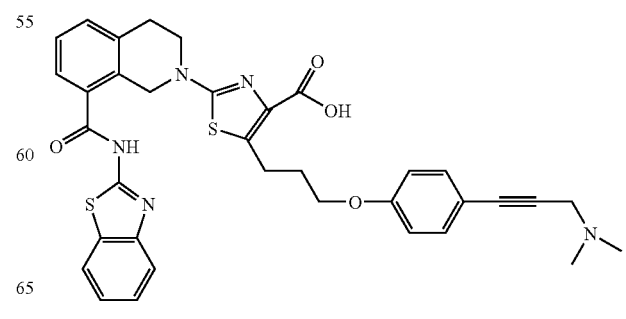

Step 1 Preparation of 2-(8-(benzo[d]thiazol-2-ylcarbamoyl)-3,4-dihydroisoquinolin-2(1H)-yl)-5-(3-(4-(3-(dimethylamino)prop-1-ynyl)phenoxy)propyl)thiazole-4-carboxylic acid (74)

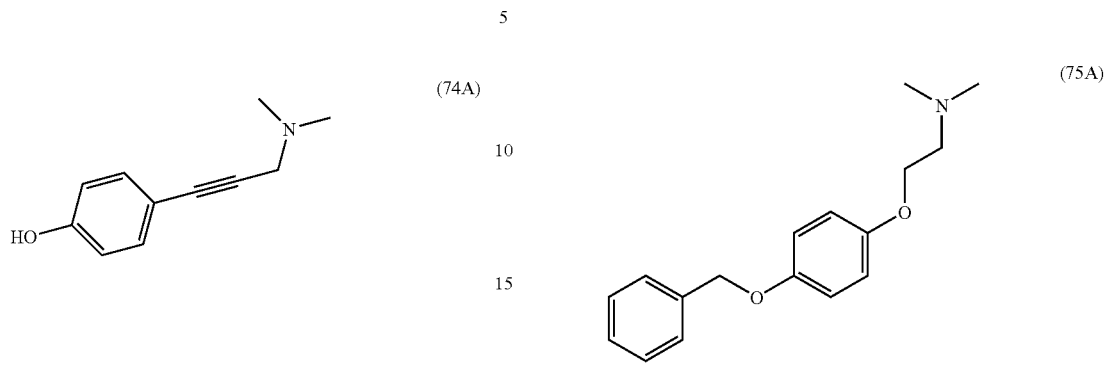

(74A)

To a mixture of 4-iodophenol (750 mg, 3.41 mmol), N,N-dimethylprop-2-yn-1-amine (1.090 ml, 10.23 mmol), (PPh$_3$)$_4$ Pd (192 mg, 0.166 mmol), TEA (1.425 ml, 10.23 mmol) in DMF (12 ml) was added copper(I) iodide (97 mg, 0.511 mmol). The resulting mixture was heated in a Smith microwave synthesizer at 100° C. for 25 min and then concentrated. The residue was purified by reverse phase HPLC (mobile phase: 0%-30% acetonitrile in 0.1% TFA aqueous solution during 30 min) to provide the compound as a TFA salt: $^1$H NMR (400 MHz, DMSO-D$_6$) δ ppm 10.06 (1H, s), 7.35 (2H, d), 6.80 (2H, d), 4.25 (2H, s), 2.85 (6H, s).

Step 2: Preparation of Title Compound 74

The title compound 74 was prepared using the same procedure described for Example 54 by replacing compound 54A with compound 74A in step 2 of Example 54: $^1$H NMR (400 MHz, DMSO-D$_6$) δ ppm 12.86 (1H, s), 10.19 (1H, s), 8.03 (1H, d), 7.79 (1H, d), 7.67 (1H, d), 7.33-7.50 (6H, m), 6.95 (2H, d), 4.83 (2H, s), 4.29 (2H, t), 3.72 (2H, t), 3.11-3.21 (2H, m), 3.03 (2H, t), 2.87 (6H, s), 1.96-2.07 (2H, m); LCMS (APCI) m/e 652 (M+H).

Example 75

Synthesis of 2-[8-(Benzothiazol-2-ylcarbamoyl)-3,4-dihydro-1H-isoquinolin-2-yl]-5-{3-[4-(2-dimethylamino-ethoxy)-phenoxy]-propyl}-thiazole-4-carboxylic acid (75)

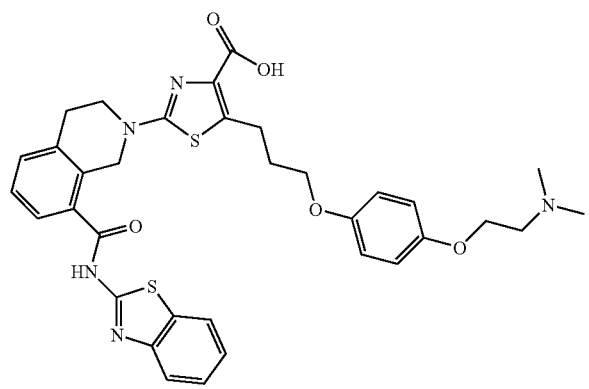

(75)

Step 1: Preparation of 2-(4-(benzyloxy)phenoxy)-N,N-dimethylethanamine (75A)

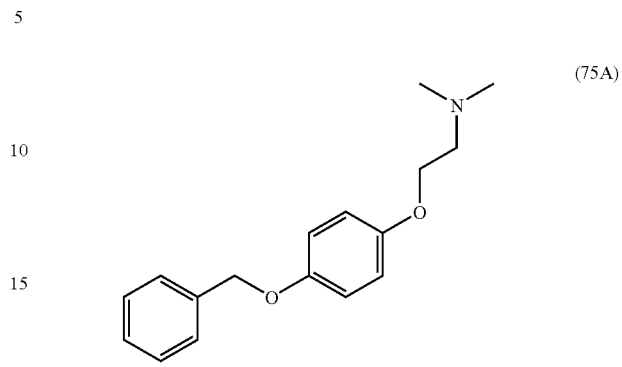

(75A)

Compound 75A was prepared in a similar manner to the synthesis of compound 35A by substituting compound 34D and compound 31F with 2-(dimethylamino)ethanol and 4-(benzyloxy)phenol, respectively: $^1$H NMR (DMSO-d$_6$): δ 7.31-7.44 (m, 5H), 6.84-6.94 (m, 4H), 5.03 (s, 2H), 3.94-3.98 (m, 2H), 2.57 (d, J=5.93 Hz, 2H), 2.19 (s, 6H). ESI (+)/MS: 272 (M+H)$^+$.

Step 2: Preparation of 4-(2-(dimethylamino)ethoxy)phenol (75B)

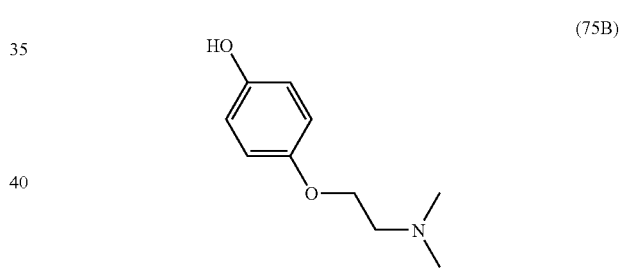

(75B)

Compound 75B was prepared in a similar manner to the synthesis of compound 31F by substituting compound 31E with compound 75A: $^1$H NMR (DMSO-d$_6$): δ 8.86 (s, 1H), 6.72-6.76 (m, 2H), 6.64-6.68 (m, 2H), 3.92 (d, J=5.83 Hz, 2H), 2.56 (d, J=5.83 Hz, 2H), 2.19 (s, 6H). ESI (+)/MS: 182 (M+H)$^+$.

Step 3: Preparation of Title Compound 75

The title compound 75 was prepared as a TFA salt in a similar manner to the synthesis of compound 51 by substituting compound 51A with compound 75B: $^1$H NMR (DMSO-d$_6$): δ 12.85 (s, 1H), 9.58 (s, 1H), 8.03 (d, J=7.67 Hz, 1H), 7.79 (d, J=7.67 Hz, 1H), 7.67 (d, J=7.06 Hz, 1H), 7.33-7.50 (m, 4H), 6.86-6.93 (m 4H), 4.83 (s, 2H), 4.21-4.24 (m, 2H), 3.92 (t, J=6.29 Hz, 2H), 3.73 (t, J=5.98 Hz, 2H), 3.15-3.18 (m, 2H), 3.03 (t, J=5.98 Hz, 2H), 2.85 (s, 6H), 1.94-2.01 (m, 2H). ESI (+)/MS: 658 (M+H)$^+$.

Example 76

Synthesis of 2-(8-(benzo[d]thiazol-2-ylcarbamoyl)-3,4-dihydroisoquinolin-2(1H)-yl)-5-(2-phenoxyethyl)thiazole-4-carboxylic acid (76)

(76)

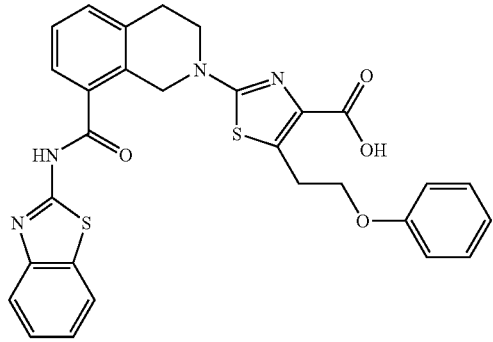

Compound 49D (51 mg, 0.08 mmol), phenol (11 mg, 0.12 mmol) and triphenylphosphine (31 mg, 0.12 mmol) were combined with THF (2 ml) and stirred at ambient temperature for 20 minutes. Di-tert-butyl azodicarboxylate (21 mg, 0.092 mmol) was added and stirring was continued overnight. The reaction mixture was diluted with EtOAc, washed with water and brine, dried (MgSO$_4$), filtered and concentrated. The concentrate was purified by column chromatography on silica gel eluting with a gradient of 10-50% EtOAc in hexanes. The resulting material was taken up in dioxane (2 ml), treated with HCl (4N in dioxane) (0.4 ml, 1.6 mmol) and heated at 70° C. for several hours. The reaction mixture was cooled to room temperature and concentrated. The concentrate was taken up in dioxane (2 ml), treated with NaOH (4N aqueous) (0.2 ml, 0.8 mmol) and heated at 50° C. for four hours. The reaction mixture was cooled to room temperature and treated with 1N HCl (aq.) to induce precipitation of the product. The solid was filtered, rinsed with water, slurried in Et$_2$O, filtered, rinsed with Et$_2$O, slurried in 1:1 DMSO/MeOH, filtered and rinsed with MeOH to provide the title compound as a white solid. $^1$H NMR (300 MHz, DMSO-d$_6$) δ ppm 12.88 (1H, s), 12.66 (1H, s), 8.04 (1H, d), 7.80 (1H, d), 7.66 (1H, d), 7.43 (4H, m), 7.22 (2H, m), 6.90 (3H, m), 4.83 (2H, s), 4.13 (2H, t), 3.73 (2H, t), 3.47 (2H, t), 3.03 (2H, t). MS (ESI(+)) m/e 557 (M+H).

Example 77

Synthesis of 5-(3-(4-(2-amino-1H-benzo[d]imidazol-1-yl)phenoxy)propyl)-2-(8-(benzo[d]thiazol-2-ylcarbamoyl)-3,4-dihydroisoquinolin-2(1H)-yl)thiazole-4-carboxylic acid (77)

(77)

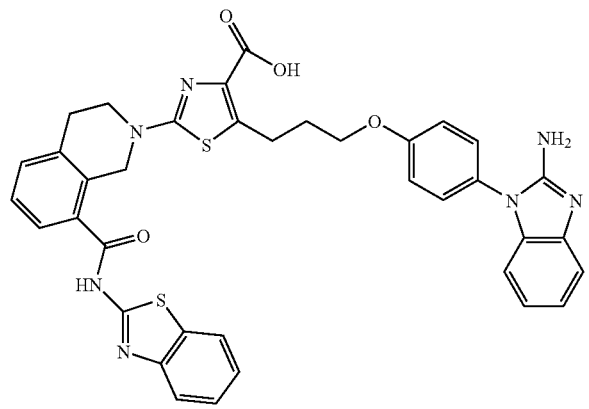

Step 1: Preparation of 4-(2-(N-acetylacetamido)-1H-benzo[d]imidazol-1-yl)phenyl acetate (77A)

(77A)

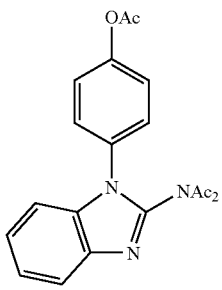

4-(2-Amino-1H-benzo[d]imidazol-1-yl)phenol (0.113 g, 0.5 mmol) in a mixture of dichloromethane (2 ml) and THF (1 ml) was treated with acetic anhydride (0.47 ml, 5 mmol) and DMAP (0.031 g, 0.25 mmol) and stirred at ambient temperature for 3 hours. The reaction mixture was diluted with EtOAc, washed with water and brine, dried (MgSO$_4$), filtered and concentrated to provide the desired product: LCMS m/e 352 (M+H).

Step 2: Preparation of N-(1-(4-hydroxyphenyl)-1H-benzo[d]imidazol-2-yl)acetamide (77B)

(77B)

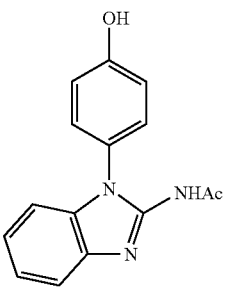

Compound 77A (176 mg, 0.5 mmol) in MeOH (4 ml) was treated with K$_2$CO$_3$ (69.1 mg, 0.5 mmol) and stirred at ambient temperature for about 40 minutes. The reaction mixture was concentrated to remove MeOH, diluted with EtOAc and acidified to pH 5 with 1N HCl solution. The mixture was poured into a separatory funnel and the layers were separated. The aqueous layer was extracted with EtOAc (2×40 mL). The combined organic layers were dried (MgSO$_4$), filtered and concentrated to provide the title compound 77B as an off-white solid in 67% yield: $^1$H NMR (300 MHz, DMSO-d$_6$) δ ppm 10.26 (1H, s), 9.84 (1H, s), 7.63 (1H, m), 7.20 (5H, m), 6.93 (2H, m), 1.94 (3H, s).

Step 3: Preparation Title Compound 77

Compound 77B (32 mg, 0.12 mmol) in DMF (1 ml) was treated with NaH (60% oil dispersion) (12 mg, 0.3 mmol). After stirring at ambient temperature for 5 minutes, compound 2C (63 mg, 0.1 mmol) was added and stirring was continued for 1 hour. Additional NaH (60% oil dispersion) (12 mg, 0.3 mmol) was added and the mixture was stirred at ambient temperature overnight. NaOH (4 N aq.) (0.25 ml, 1 mmol) was added and the mixture was stirred at ambient temperature for 4 hours. HCl (4N in dioxane) (2.5 ml, 10 mmol) was added and the mixture was heated at 70° C. for several hours. When the reaction was shown to be complete by LCMS, the reaction mixture was concentrated, 1N HCl was added to induce any further precipitation of the product. The solid was filtered and rinsed with water. The solid was slurried in Et$_2$O, filtered and rinsed with additional Et$_2$O. The solid was dissolved in 1:1 DMSO/MeOH, filtered via syringe filter to remove undissolved salts and impurities and purified by HPLC (Preparative reverse phase HPLC was performed on an automated Gilson HPLC system, using a SymmetryPrep Shield RP 18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 20-90% of B in 40 min) to provide the title compound 77 in 31% yield as an off-white solid: $^1$H NMR (300 MHz, DMSO-d$_6$) δ ppm 12.90 (1H, s), 12.83 (1H, s), 8.44 (2H, s), 8.02 (1H, d), 7.79 (1H, d), 7.68 (1H, d), 7.41 (8H, m), 7.17 (3H, m), 6.93 (1H, d), 4.84 (2H, s), 4.10 (2H, t), 3.74 (2H, t), 3.23 (2H, m), 3.04 (2H, t), 2.07 (2H, m). MS (ESI(+)) m/e 702 (M+H).

Example 78

Synthesis of 2-[8-(Benzothiazol-2-ylcarbamoyl)-3,4-dihydro-1H-isoquinolin-2-yl]-5-(3-{4-[4-(3-pyrrolidin-1-yl-propylamino)-thieno[3,2-d]pyrimidin-7-yl]-phenoxy}-propyl)-thiazole-4-carboxylic acid (78):

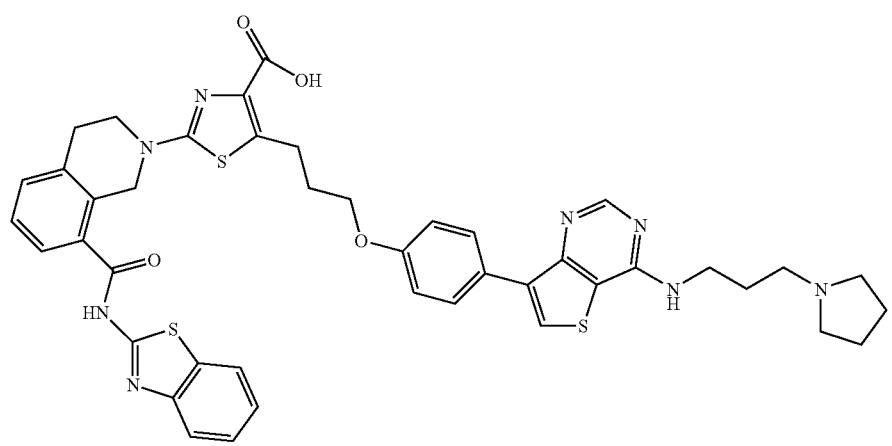

(78)

Step 1: Preparation of 7-bromo-N-(3-(pyrrolidin-1-yl)propyl)thieno[3,2-d]pyrimidin-4-amine (78A)

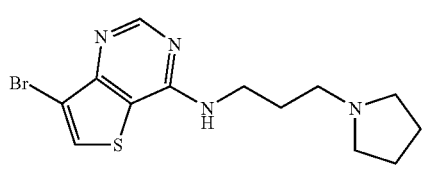

(78A)

Compound 78A was prepared in a similar manner to the synthesis of compound 69A by substituting propan-2-amine with 3-(pyrrolidin-1-yl)propan-1-amine: APCI (+)LC/MS: 342 (M+H)$^+$.

Step 2: Preparation of 4-(4-(3-(pyrrolidin-1-yl)propylamino)thieno[3,2-d]pyrimidin-7-yl)phenol (78B)

(78B)

Compound 78B was prepared in a similar manner to the synthesis of compound 34D by substituting compound 34C and 4-(hydroxymethyl)phenylboronic acid with compound 77A and 4-(4,4,5,5-tetramethyl-1,3,2-dioxaborolan-2-yl)phenol, respectively: $^1$H NMR (DMSO-d$_6$): δ 9.53 (s, 1H), 8.54 (s, 1H), 8.14 (s, 1H), 7.96 (d, J=5.68 Hz, 1H), 7.88-7.92 (m, 2H), 6.84-6.87 (m, 2H), 3.58-3.63 (m, 2H), 3.15-3.19 (m, 2H), 1.99-2.09 (m, 2H), 1.91-1.93 (m, 4H). ESI (+)/MS: 355 (M+H)$^+$.

Step 3: Preparation of Title Compound 78

(78)

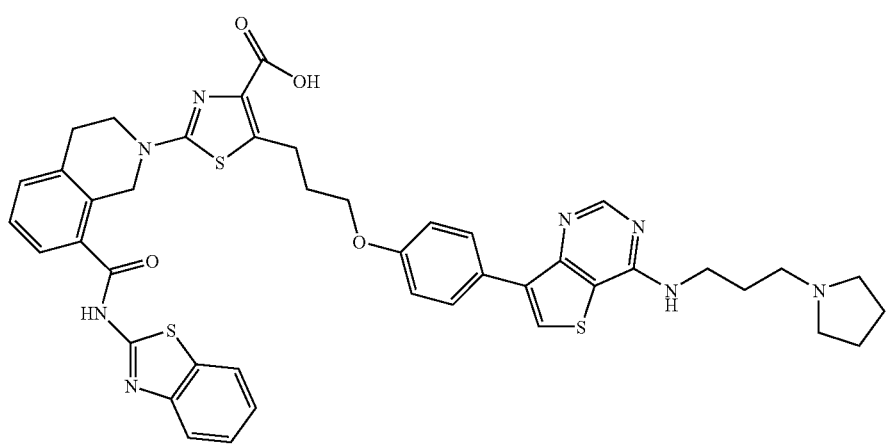

The title compound 78 was prepared as a TFA salt in a similar manner to the synthesis of compound 51 by substituting compound 51A with compound 78B: $^1$H NMR (DMSO-$d_6$): δ 12.82 (s, 1H), 9.53 (s, 1H), 8.52 (s, 1H), 8.22 (s, 1H), 8.03-8.07 (m, 1H), 8.01 (d, J=7.98 Hz, 1H), 7.69 (d, J=8.59 Hz, 1H), 7.79 (d, J=7.98 Hz, 1H), 7.67 (d, J=7.36 Hz, 1H), 7.32-7.49 (m, 4H), 7.01 (d, J=8.9 Hz, 2H), 4.84 (s, 2H), 4.04 (t, J=6.29 Hz, 2H), 3.73 (t, J=5.83 Hz, 2H), 3.18-3.24 (m, 4H), 3.01-3.05 (m, 4H), 1.78-2.07 (m, 6H). ESI (+)/MS: 831 (M+H)$^+$.

Example 79

Synthesis of 2-[8-(Benzothiazol-2-ylcarbamoyl)-3,4-dihydro-1H-isoquinolin-2-yl]-5-(3-{4-[4-(4-methyl-piperazin-1-yl)-thieno[3,2-d]pyrimidin-7]-phenoxy}-propyl)-thiazole-4-carboxylic acid (79):

(79)

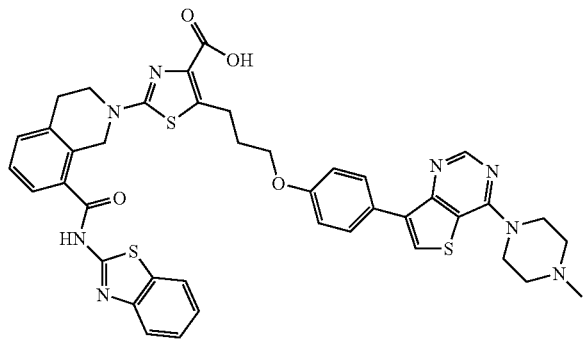

Step 1: Preparation of 7-bromo-4-(4-methylpiper-azin-1-yl)thieno[3,2-d]pyrimidine (79A)

(79A)

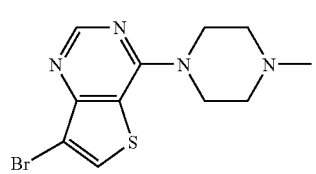

The compound 79A was prepared in a similar manner to the synthesis described in step 1 of example 69 by substituting propan-2-amine with 1-methylpiperazine: ESI (+)LC/MS: 314 (M+H)$^+$.

Step 2: Preparation of 4-(4-(4-methylpiperazin-1-yl) thieno[3,2-d]pyrimidin-7-yl)phenol (79B)

(79B)

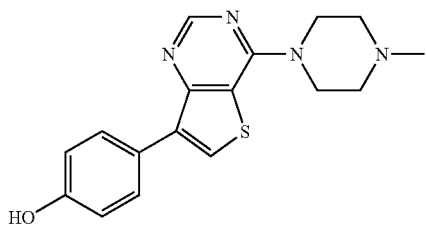

The compound 79B was prepared in a similar manner to the synthesis of compound 34D by substituting compound 34C and 4-(hydroxymethyl)phenylboronic acid with compound 79A and 4-(4,4,5,5-tetramethyl-1,3,2-dioxaborolan-2-yl) phenol, respectively: $^1$H NMR (DMSO-$d_6$): δ 9.56 (s, 1H), 8.63 (s, 1H), 8.28 (s, 1H), 7.85-7.89 (m, 2H), 6.48-6.88 (m, 2H), 4.06 (br, 4H), 2.91 (br, 4H), 2.53 (s, 3H). ESI (+)/MS: 327 (M+H)$^+$.

Step 3: Preparation of Title Compound 79

The title compound 79 was prepared as a TFA salt in a similar manner to the synthesis of compound 51 by substituting compound 51A with compound 79B: $^1$H NMR (DMSO-$d_6$): δ 12.86 (s, 1H), 9.98 (s, 1H), 8.69 (s, 1H), 8.40 (s, 1H), 8.01 (d, J=7.36 Hz, 1H), 7.69 (d, J=8.9 Hz, 2H), 7.79 (d, J=7.98 Hz, 1H), 7.67 (d, J=7.36 Hz, 1H), 7.32-7.49 (m, 4H), 7.02 (d, J=8.9 Hz, 2H), 4.78-4.84 (m, 4H), 4.05 (t, J=6.29 Hz, 2H), 3.73 (t, J=6.14 Hz, 2H), 3.57 (br, 6H), 3.18-3.22 (m, 2H), 3.03 (t, J=5.83 Hz, 2H), 2.87 (s, 3H), 2.00-2.09 (m, 2H). ESI (+)/MS: 803 (M+H)$^+$.

Example 80

Synthesis of 5-(3-(4-((1S,2S,5R,9S)-9-aminobicyclo[3.3.1]nonan-2-yl)phenoxy)propyl)-2-(8-(benzo[d]thiazol-2-ylcarbamoyl)-3,4-dihydroisoquinolin-2(1H)-yl)thiazole-4-carboxylic acid (80)

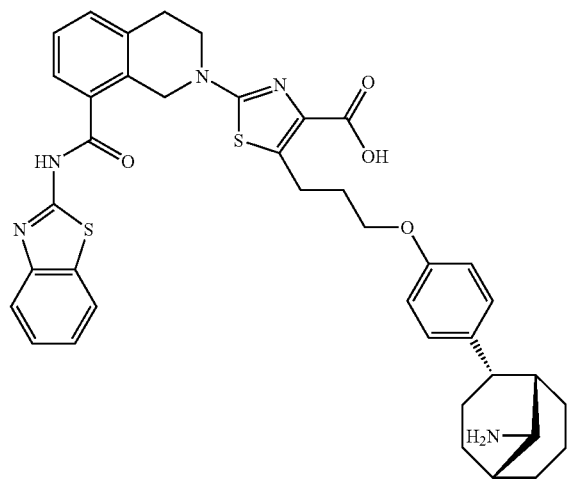

(80)

Step 1: Preparation of tert-butyl (1S,2S,5R,9S)-2-(4-hydroxyphenyl)bicyclo[3.3.1]nonan-9-ylcarbamate (80A)

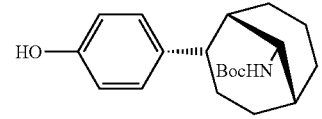

(80A)

4-((1S,2S,5R,9S)-9-aminobicyclo[3.3.1]nonan-2-yl)phenol HCl salt (92 mg, 0.344 mmol) in THF (2 ml) was treated with di-tert-butyl dicarbonate (0.088 ml, 0.38 mmol) and Et$_3$N (0.19 ml, 1.37 mmol) and stirred at ambient temperature for three hours. The reaction mixture was diluted with EtOAc, washed with water and brine, dried (MgSO$_4$), filtered and concentrated. The concentrate was purified by column chromatography on silica gel eluting with a gradient of 0 to 5% MeOH in CH$_2$Cl$_2$: $^1$H NMR (300 MHz, DMSO-$d_6$) δ ppm 9.09 (1H, s), 7.01 (2H, m), 6.68 (2H, m), 3.53 (1H, m), 3.01 (1H, m), 2.09 (3H, m), 1.69 (10H, m), 1.42 (9H, s).

Step 2: Preparation of Title Compound 80

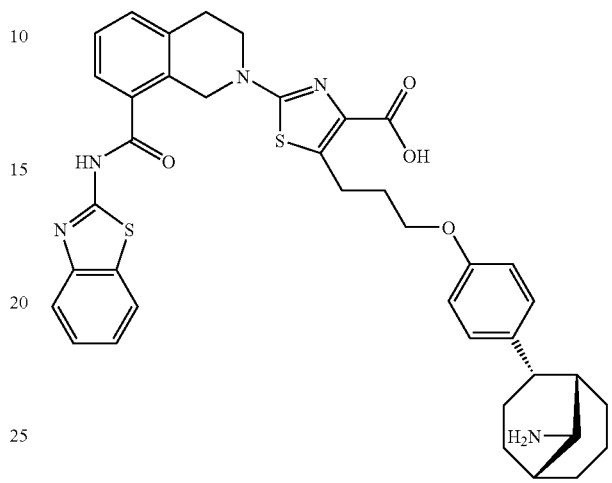

(80)

Tert-butyl (1S,2S,5R,9S)-2-(4-hydroxyphenyl)bicyclo[3.3.1]nonan-9-ylcarbamate 80A (40.5 mg, 0.11 mmol) in DMF (1 ml) was treated with NaH (12 mg, 0.3 mmol). After stirring at ambient temperature for 5 minutes, compound 2C (63 mg, 0.1 mmol) was added and stirring was continued for 1.5 hours. HCl (4N HCl in dioxane) (2.5 ml, 10 mmol) was added and the mixture was stirred overnight at room temperature and then at 60° C. for 6 hours. The reaction mixture was cooled to room temperature and concentrated. The residue was slurried with 1N HCl, filtered, rinsed with water, slurried in Et$_2$O, filtered and rinsed with additional Et$_2$O. The solid was purified by column chromatography on silica gel using a gradient of 0 to 5% MeOH in CH$_2$Cl$_2$. The solid was dissolved in dioxane (2 ml), treated with NaOH (4N aqueous) (0.25 mL, 1 mmol) and stirred overnight at rt. The reaction mixture was acidified with 1N HCl to induce precipitation of the product. The solid was filtered, rinsed with water, slurried in Et$_2$O, filtered and rinsed with additional Et$_2$O. The solid was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H$_2$O; mobile phase B, CH$_3$CN; linear gradient 20-90% of B in 40 min) to provide the title compound 80 in 7% yield as an off-white solid: $^1$H NMR (400 MHz, DMSO-$d_6$) δ ppm 12.85 (1H, s), 12.50 (1H, s), 8.03 (1H, d), 7.97 (2H, d), 7.97 (1H, d), 7.47 (2H, m), 7.37 (2H, m), 7.13 (2H, d), 6.88 (2H, m), 4.83 (2H, s), 3.95 (2H, t), 3.72 (2H, t), 3.17 (2H, m), 3.02 (2H, m), 2.19 (2H, m), 1.98 (5H, m), 1.80 (5H, m), 1.59 (2H, m), 1.40 (3H, m). MS (ESI(+)) m/e 708 (M+H).

Example 81

Synthesis of 2-[8-(Benzothiazol-2-ylcarbamoyl)-3,4-dihydro-1H-isoquinolin-2-yl]-5-[3-(4-pyrimidin-2-yl-phenoxy)-propyl]-thiazole-4-carboxylic acid (81)

(81)

Step 1: Preparation of 4-(pyrimidin-2-yl)phenol (81A)

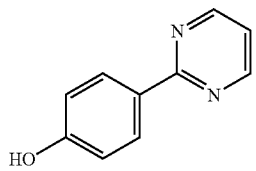

(81A)

Compound 81A was prepared in a similar manner to the synthesis of compound 34D by substituting compound 34C and 4-(hydroxymethyl)phenylboronic acid with 2-bromopyrimidine and 4-(4,4,5,5-tetramethyl-1,3,2-dioxaborolan-2-yl)phenol, respectively: $^1$H NMR (DMSO-$d_6$): δ 9.92 (s, 1H), 8.80 (d, J=4.6 Hz, 2H), 8.22-8.26 (m, 2H), 7.31 (t, J=4.6 Hz, 1H), 6.89-6.89 (m, 2H).

Step 2: Preparation of Title Compound 81

The title compound 81 was prepared as a TFA salt in a similar manner to the synthesis of compound 51 by substituting compound 51A with compound 81A: $^1$H NMR (DMSO-$d_6$): δ 8.83 (d, J=4.88 Hz, 2H), 8.32 (d, J=8.85 Hz, 2H), 8.03 (d, J=4.88 Hz, 1H), 7.79 (d, J=8.85 Hz, 1H), 7.67 (d, J=7.63 Hz, 1H), 7.34-7.49 (m, 5H), 7.04 (d, J=8.85 Hz, 2H), 4.84 (s, 2H), 4.07 (t, J=6.26 Hz, 2H), 3.72 (t, J=5.95 Hz, 2H), 3.18-3.12 (m, 2H), 3.03 (t, J=5.64 Hz, 2H), 2.01-2.07 (m, 2H). ESI (+)/MS: 649 (M+H)$^+$.

Example 82

Synthesis of 2-[8-(Benzothiazol-2-ylcarbamoyl)-3,4-dihydro-1H-isoquinolin-2-yl]-5-{3-[4-(4-methyl-piperazin-1-yl)-phenoxy]-propyl}-thiazole-4-carboxylic acid (82)

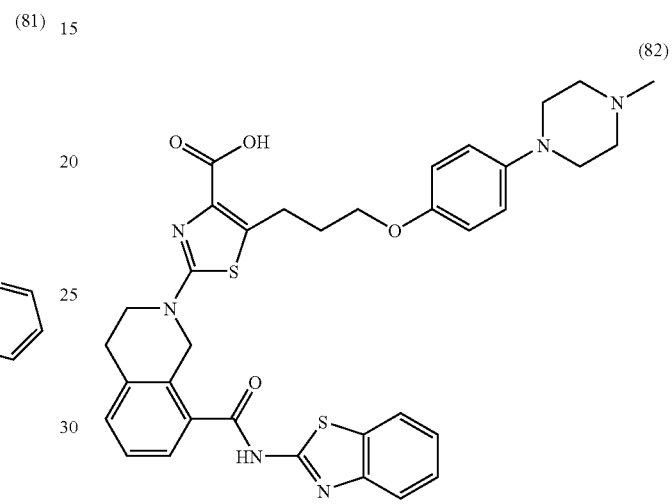

Step 1: Preparation of 4-(4-methylpiperazin-1-yl)phenol (82A)

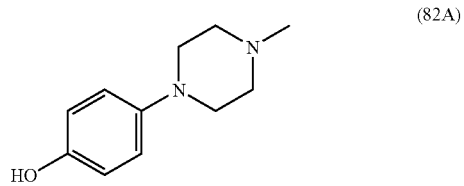

Compound 82A was prepared in a similar manner to the synthesis of compound 62A by substituting compound 42C and phenylpiperazine with paraformahyde and 4-(piperazin-1-yl)phenol, respectively: $^1$H NMR (DMSO-$d_6$): δ 6.74-6.78 (m, 2H), 6.61-6.65 (m, 2H), 2.93-2.95 (m, 4H), 2.41-2.44 (m, 4H), 2.22 (s, 3H). ESI (+)/MS: 193 (M+H)$^+$.

Step 2: Preparation of Title Compound 82

The title compound 82 was prepared as a TFA salt in a similar manner to the synthesis of compound 51 by substituting compound 51A with compound 82A: $^1$H NMR (DMSO-$d_6$): δ 12.90 (s, 1H), 9.58 (s, 1H), 8.04 (d, J=7.63 Hz, 2H), 7.80 (d, J=7.93 Hz, 2H), 7.67 (d, J=7.63 Hz, 1H), 7.35-7.50 (m, 4H), 6.90-6.92 (m, 2H), 6.82-6.85 (m, 2H), 4.83 (s, 2H), 3.91 (t, J=6.26 Hz, 2H), 3.14-3.17 (m, 2H), 3.03 (t, J=5.95 Hz, 2.82-2.86 (m, 5H), 1.94-2.00 (m, 2H). ESI (+)/MS: 669 (M+H)+.

Example 83

Synthesis of 2-(8-(benzo[d]thiazol-2-ylcarbamoyl)-3,4-dihydroisoquinolin-2(1H)-yl)-5-(3-(4-(1-(2-morpholinoethyl)-1H-pyrazol-4-yl)phenoxy)propyl)thiazole-4-carboxylic acid (83):

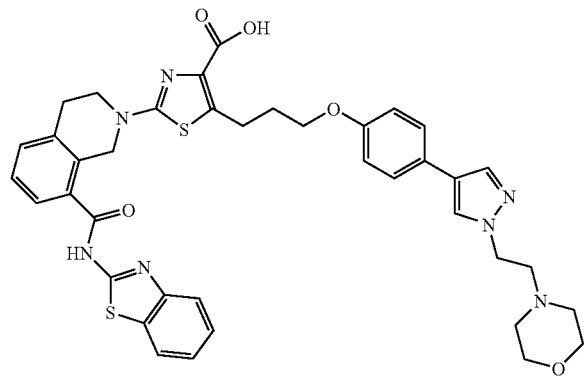

(83)

Step 1: Preparation of tert-butyl 2-(8-(benzo[d]thiazol-2-yl((2-(trimethylsilyl)ethoxy)methyl)carbamoyl)-3,4-dihydroisoquinolin-2(1H)-yl)-5-(3-(4-(1-(2-morpholinoethyl)-1H-pyrazol-4-yl)phenoxy)propyl)thiazole-4-carboxylate (83A):

Compound 83A was prepared using the same procedure described in step 1 of Example 73 by replacing 4-(4,4,5,5-tetramethyl-1,3,2-dioxaborolan-2-yl)-1H-pyrazole with 4-(2-(4-(4,4,5,5-tetramethyl-1,3,2-dioxaborolan-2-yl)-1H-pyrazol-1-yl)ethyl)morpholine: LCMS (APCI) m/e 936 (M+H).

Step 2: Preparation of Title Compound 83

The title compound 83 was prepared using the same procedure described in step 2 of Example 73 by replacing compound 73A with compound 83A: $^1$H NMR (400 MHz, DMSO-D$_6$) δ ppm 12.87 (1H, s), 8.12 (1H, s), 8.02 (1H, d), 7.89 (1H, s), 7.79 (1H, d), 7.67 (1H, d), 7.33-7.50 (6H, m), 6.91 (2H, d), 4.84 (2H, s), 4.52 (2H, t), 3.98 (2H, t), 3.77-3.93 (2H, m), 3.73 (2H, t), 3.51-3.65 (2H, m), 3.40-3.50 (2H, m), 3.13-3.25 (6H, m), 3.03 (2H, t), 1.95-2.07 (2H, m); LCMS (APCI) 751 (M+H).

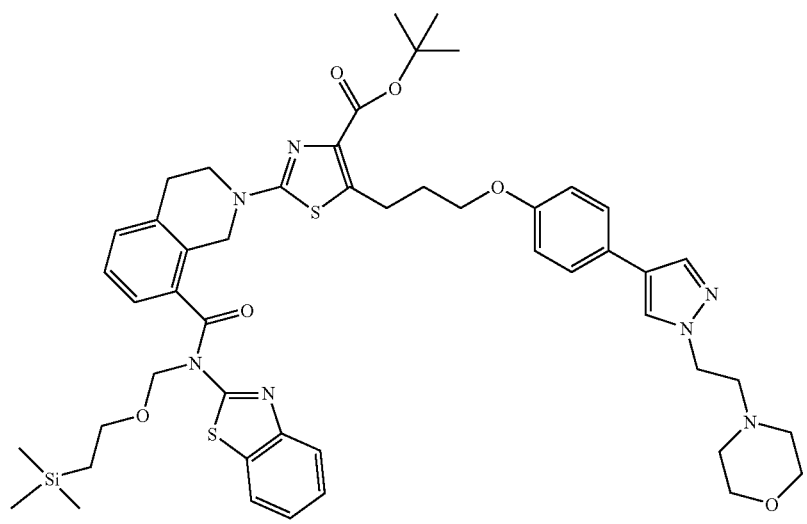

(83A)

Example 84

Synthesis of 2-(8-(benzo[d]thiazol-2-ylcarbamoyl)-3,4-dihydroisoquinolin-2(1H)-yl)-5-(3-(4-(4-(3-(4-methylpiperazin-1-yl)propylamino)-1H-pyrazolo[3,4-d]pyrimidin-1-yl)phenoxy)propyl)thiazole-4-carboxylic acid (84):

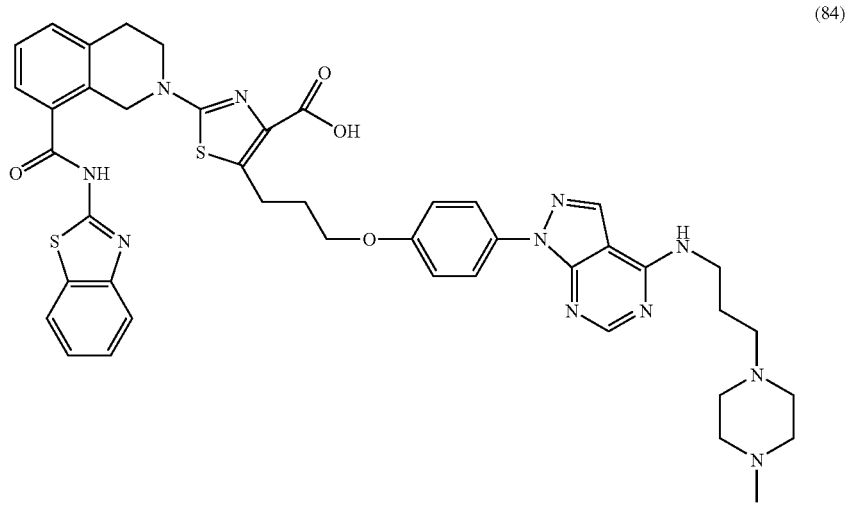

(84)

Step 1: Preparation of 4-(4-(3-(4-methylpiperazin-1-yl)propylamino)-1H-pyrazolo[3,4-d]pyrimidin-1-yl)phenol (84A)

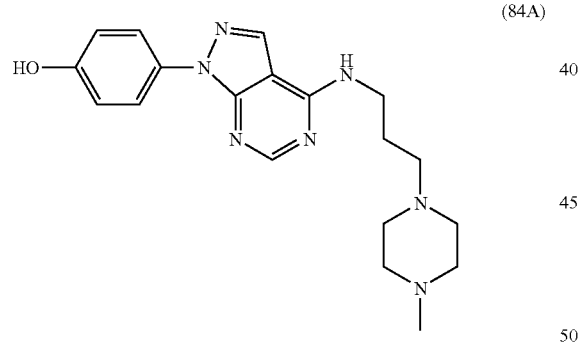

(84A)

The title compound 84A was prepared using the same procedure described in step 4 of Example 44 by replacing isopropylamine with 3-(4-methylpiperazin-1-yl)propan-1-amine; LCMS (APCI) m/e 368 (M+H).

Step 2: Preparation of Title Compound 84

The title compound 84 was prepared using the same procedure described in step 2 of Example 54 by replacing compound 54A with compound 84A. $^1$H NMR (500 MHz, PYRIDINE-D$_5$) δ ppm 8.69 (1H, s), 8.44-8.50 (1H, m), 8.41 (2H, d), 8.31 (1H, s), 7.95 (1H, d), 7.89 (1H, d), 7.78 (1H, dd), 7.43 (1H, t), 7.25-7.31 (3H, m), 7.14 (2H, d), 5.12 (2H, s), 4.09 (2H, t), 3.76-3.84 (4H, m), 3.48 (2H, t), 2.90 (2H, t), 2.71 (8H, dd), 2.61 (2H, t), 2.38 (3H, s), 2.14-2.23 (2H, m), 1.93-2.00 (2H, m).

Example 85

Synthesis of 2-(8-(benzo[d]thiazol-2-ylcarbamoyl)-3,4-dihydroisoquinolin-2(1H)-yl)-5-(3-(4-(5-methyl-4-((4-methylpiperazin-1-yl)methyl)-1H-pyrazol-1-yl)phenoxy)propyl)thiazole-4-carboxylic acid (85):

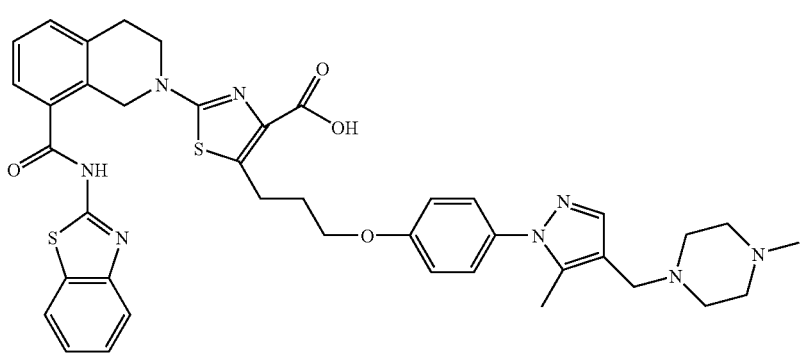

(85)

Step 1: Preparation of 4-(5-methyl-4-((4-methylpiperazin-1-yl)methyl)-1H-pyrazol-1-yl)phenol (85A)

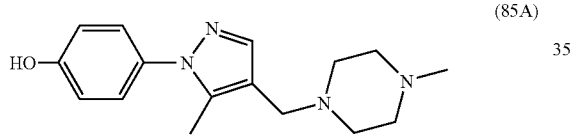

(85A)

To a solution of 1-(4-methoxyphenyl)-3-methyl-1H-pyrazole-4-carbaldehyde (232 mg, 1.073 mmol) in DCE (3.5 ml) was added 1-methylpiperazine (0.119 ml, 1.073 mmol) and sodium triacetoxyborohydride (455 mg, 2.146 mmol). The reaction was stirred overnight and diluted with ethyl acetate, washed with brine, dried over $Na_2SO_4$ and concentrated. The residue in tetramethylene sulfone (5 ml) was treated with iodotrimethylsilane (1.327 ml, 9.32 mmol) at 80° C. overnight and cooled. The reaction mixture was diluted with methanol and purified by reverse phase HPLC (mobile phase: 0%-30% acetonitrile in 0.1% TFA aqueous solution during 30 min) to provide the title compound as a TFA salt; LCMS (APCI) m/e 287 (M+H).

Step 2: Preparation of Title Compound 85

The title compound 85 was prepared using the same procedure described in step 2 of Example 54 by replacing compound 54A with compound 85A: $^1$H NMR (400 MHz, DMSO-$D_6$) δ ppm 12.87 (1H, s), 8.02 (1H, d), 7.79 (1H, d), 7.67 (1H, d), 7.57 (1H, d), 7.43-7.51 (2H, m), 7.33-7.41 (4H, m), 7.01-7.07 (2H, m), 4.84 (2H, t), 3.97 (2H, s), 3.68-3.79 (4H, m), 3.46-3.53 (2H, m), 3.12-3.26 (7H, m), 3.04 (4H, t), 2.76 (2H, s), 2.25 (3H, s).

Example 86

Synthesis of 2-[8-(Benzothiazol-2-ylcarbamoyl)-3,4-dihydro-1H-isoquinolin-2-yl]-5-{3-[4-(3-cyano-pyrazin-2-yl)-phenoxy]-propyl}-thiazole-4-carboxylic acid (86)

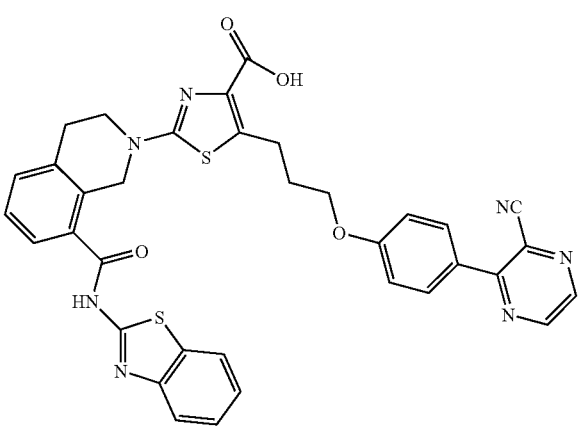

(86)

Step 1: Preparation of 3-(4-hydroxyphenyl)pyrazine-2-carbonitrile (86A)

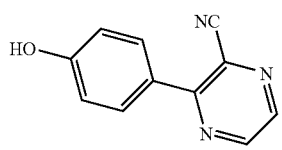

(86A)

Compound 86A was prepared in a similar manner to the synthesis of compound 34D by substituting compound 34C and 4-(hydroxymethyl)phenylboronic acid with 3-chloropyrazine-2-carbonitrile and 4-(4,4,5,5-tetramethyl-1,3,2-dioxaborolan-2-yl)phenol, respectively: $^1$H NMR (DMSO-d$_6$): δ 10.14 (s, 1H), 8.95 (d, J=2.45 Hz, 1H), 8.73 (d, J=2.45 Hz, 1H), 7.83-7.85 (m, 2H), 6.95-6.99 (m, 2H). ESI (+)/MS: 211 (M+H)$^+$.

Step 2: Preparation of Title Compound 86

The title compound 86 was prepared as a TFA salt in a similar manner to the synthesis of compound 51 by substituting compound 51A with compound 86A: $^1$H NMR (DMSO-d$_6$): δ 8.96 (d, J=2.45 Hz, 1H), 8.76 (d, J=2.45 Hz, 1H), 8.02 (d, J=7.98 Hz, 2H), 7.90-7.93 (d, J=7.98 Hz, 2H), 7.78 (d, J=7.98 Hz, 1H), 7.67 (d J=7.67 Hz, 1H), 7.33-7.49 (m, 4H), 7.11-7.15 (m, 2H), 4.84 (s, 2H), 4.1 (t, J=6.29 Hz, 2H), 3.70-3.74 (m, 2H), 3.19-3.23 (m, 2H), 3.03 (t, J=5.83 Hz, 2H), 2.02-2.09 (m, 2H). ESI (+)/MS: 674 (M+H)$^+$.

Example 87

Synthesis of 2-[8-(Benzothiazol-2-ylcarbamoyl)-3,4-dihydro-1H-isoquinolin-2-yl]-5-{3-[3-(4-methyl-piperazin-1-yl)-phenoxy]-propyl}-thiazole-4-carboxylic acid (87)

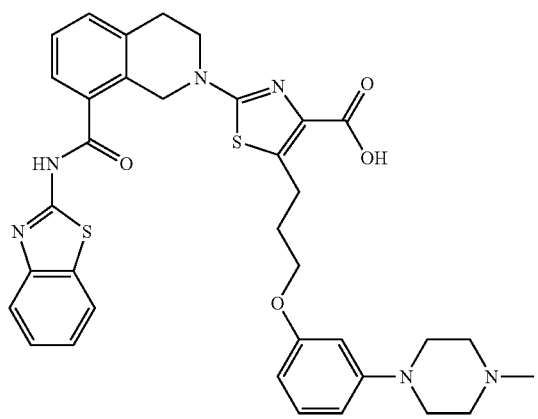
(87)

Step 1: Preparation of 3-(4-methylpiperazin-1-yl)phenol (87A)

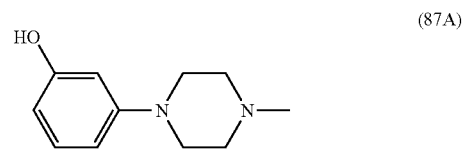
(87A)

Compound 87A was prepared in a similar manner to the synthesis of compound 62A by substituting compound 45C and phenylpiperazine with paraformahyde and 3-(piperazin-1-yl)phenol, respectively: $^1$H NMR (DMSO-d$_6$): δ 9.07 (s, 1H), 6.94-6.98 (m, 1H), 6.36 (d, J=8.13, 2.4 Hz, 2H), 8.28-8.29 (m, 1H), 6.18-6.21 (m, 1H), 3.04-3.07 (m, 4H), 2.41-2.43 (m, 4H), 2.21 (s, 3H). ESI (+)/MS: 193 (M+H)$^+$.

Step 2: Preparation of Title Compound 87

The title compound 87 was prepared as a TFA salt in a similar manner to the synthesis of compound 51 by substituting compound 51A with compound 87A: $^1$H NMR (DMSO-d$_6$): δ 12.85 (s, 1H), 9.65 (s, 1H), 8.03 (d, J=7.67 Hz, 1H), 7.79 (d, J=7.98 Hz, 2H), 7.67 (d, J=7.67 Hz, 1H), 7.34-7.50 (m, 4H), 7.12 (t, J=8.13 Hz, 1H), 6.54 (dd, J=8.13, 2.3 Hz, 1H), 6.50 (t, J=2.15 Hz, 1H), 6.42 (dd, J=8.29, 2.15 Hz, 1H), 4.83 (s, 2H), 3.96 (t, J=6.29 Hz, 2H), 3.73 (t, J=5.83 Hz, 2H), 3.10-3.18 (m, 5H), 3.03 (t, J=5.98 Hz, 2H), 2.90-2.98 (m, 2H), 2.85 (s, 3H), 1.95-2.02 (m, 2H). ESI (+)/MS: 669 M+H)$^+$.

Example 88

Synthesis of 2-[8-(Benzothiazol-2-ylcarbamoyl)-3,4-dihydro-1H-isoquinolin-2-yl]-5-{3-[4-(2-morpholin-4-yl-ethoxy)-phenoxy]-propyl}-thiazole-4-carboxylic acid (88)

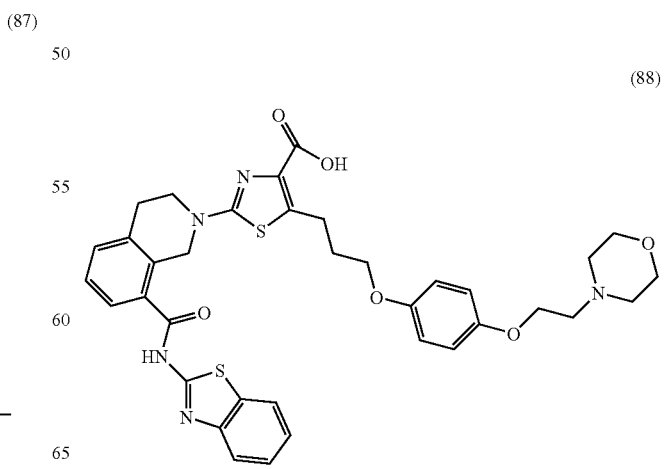
(88)

Step 1: Preparation of 4-(2-(4-(benzyloxy)phenoxy)ethyl)morpholine (88A)

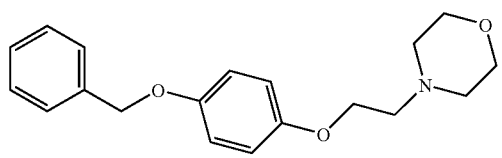

(88A)

Compound 88A was prepared in a similar manner to the synthesis of compound 35A by substituting compound 34B and compound 31F with 2-morpholinoethanol and 4-(benzyloxy)phenol, respectively: ESI (+)LC/MS: 314 (M+H)$^+$.

Step 2: Preparation of 4-(2-morpholinoethoxy)phenol (88B)

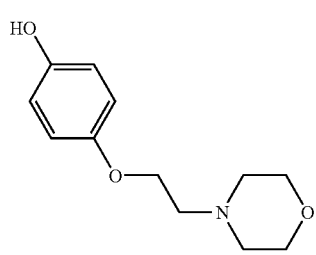

(88B)

Compound 88B was prepared in a similar manner to the synthesis of compound 31F by substituting compound 31E with compound 88A: $^1$H NMR (DMSO-d$_6$): δ 8.84 (s, 1H), 6.72-6.75 (m, 2H), 6.64-6.67 (m, 2H), 3.96 (d, J=5.83 Hz, 2H), 3.55-3.58 (m 4H), 2.63 (d, J=5.83 Hz, 2H), 2.42-2.46 (m, 4H). ESI (+)/MS: 224 (M+H)$^+$.

Step 3: Preparation of Title Compound 88

The title compound 88 was prepared as a TFA salt in a similar manner to the synthesis of compound 51 by substituting compound 51A with compound 88B: $^1$H NMR (DMSO-d$_6$): δ 12.86 (s, 1H), 9.96 (s, 1H), 8.03 (d, J=7.98 Hz, 1H), 7.79 (d, J=7.98 Hz, 2H), 7.67 (d, J=7.36 Hz, 1H), 6.86-6.94 (m, 4H), 4.83 (s, 2H), 4.25-4.27 (m, 2H), 3.91-4.02 (m, 4H), 3.73 (t, J=5.98 Hz, 2H), 3.14-3.22 (m, 4H), 3.03 (t, J=5.98 Hz, 2H), 1.94-2.01 (m, 2H). ESI (+)/MS: 700 (M+H)$^+$.

Example 89

Synthesis of 2-[8-(Benzothiazol-2-ylcarbamoyl)-3,4-dihydro-1H-isoquinolin-2-yl]-5-{3-[4-(4-methylpiperazin-1-ylmethyl)-phenoxy]-propyl}-thiazole-4-carboxylic acid (89)

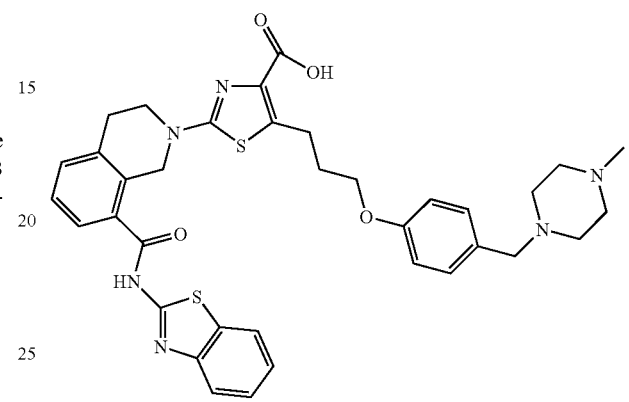

(89)

Step 1: Preparation of 4-((4-methylpiperazin-1-yl)methyl)phenol (89A)

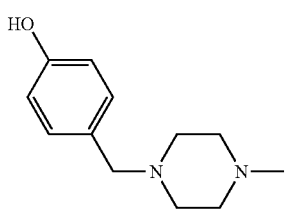

(89A)

Compound 89A was prepared in a similar manner to the synthesis of compound 62A by substituting compound 45C and phenylpiperazine with 4-hydroxybenzaldehyde and 1-methylpiperazine, respectively: ESI (+)/MS: 207 (M+H)$^+$.

Step 2: Preparation of Title Compound 89

The title compound 89 was prepared as a TFA salt in a similar manner to the synthesis of compound 51 by substituting compound 51A with compound 89A: $^1$H NMR (DMSO-d$_6$): δ 8.03 (d, J=7.67 Hz, 1H), 7.79 (d, J=7.98 Hz, 1H), 7.67 (d, J=7.06 Hz, 1H), 7.34-7.50 (m, 4H), 7.28 (d, J=8.59 Hz, 2H), 6.93 (d, J=8.59 Hz, 2H), 4.83 (s, 2H), 3.98 (d, J=6.29 Hz, 2H), 3.16-3.19 (m, 4H), 3.03 (t, J=5.83 Hz, 2H), 2.76 (s, 3H), 1.97-2.03 (m, 2H). ESI (+)/MS: 683 (M+H)$^+$.

Example 90

Synthesis of 2-[8-(Benzothiazol-2-ylcarbamoyl)-3,4-dihydro-1H-isoquinolin-2-yl]-5-(3-{4-[5-(2-dimethylamino-ethoxy)-pyridin-2-yl]-phenoxy}-propyl)-thiazole-4-carboxylic acid (90):

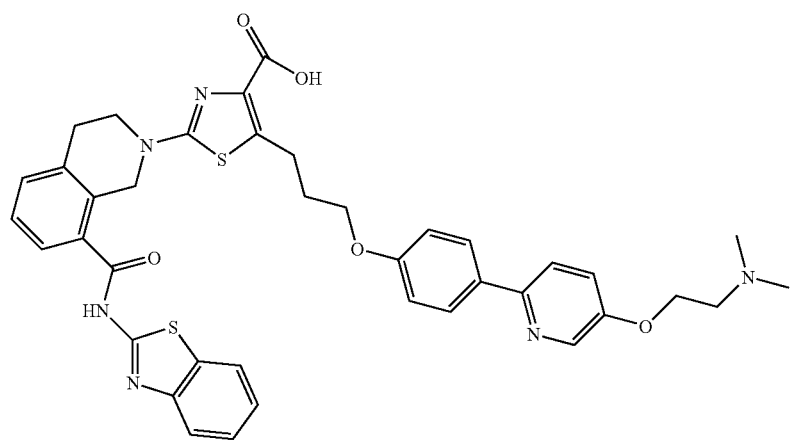

(90)

Step 1: Preparation of 2-(6-chloropyridin-3-yloxy)-N,N-dimethylethanamine (90A)

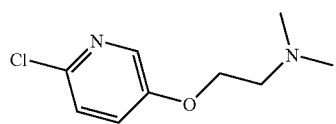

(90A)

Compound 90 was prepared in a similar manner to the synthesis of compound 35A by substituting compound 34C and compound 31F with 2-(dimethylamino)ethanol and 6-chloropyridin-3-ol, respectively.

Step 2: 4-(5-(2-(dimethylamino)ethoxy)pyridin-2-yl)phenol (90B)

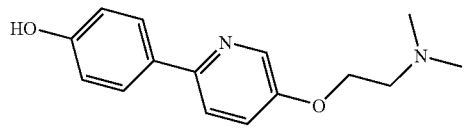

(90B)

Compound 90B was prepared in a similar manner to the synthesis of compound 34D by substituting compound 34C and 4-(hydroxymethyl)phenylboronic acid with compound 90A and 4-(4,4,5,5-tetramethyl-1,3,2-dioxaborolan-2-yl)phenol, respectively: ¹H NMR (DMSO-d₆): δ 9.56 (s, 1H), 8.29 (d, J=2.76 Hz, 1H), 7.83 (d, J=8.59 Hz, 1H), 7.74 (d, J=8.59 Hz, 2H), 7.41 (dd, J=8.59, 2.76 Hz, 2H), 6.82 (d, J=8.29 Hz, 2H), 4.14 (t, J=5.68 Hz, 2H), 2.64 (t, J=5.68 Hz, 2H), 2.22 (s, 6H). ESI (+)/MS: 258 (M+H)⁺.

Step 3: Preparation of Title Compound 90

The title compound 90 was prepared as a TFA salt in a similar manner to the synthesis of compound 51 by substituting compound 51A with compound 90B: ¹H NMR (DMSO-d₆): δ 9.60 (s, 1H), 8.09 (d, J=2.76 Hz, 1H), 8.02 (d, J=7.37 Hz, 1H), 7.93 (d, J=8.9 Hz, 2H), 7.85 (d, J=8.9 Hz, 1H), 7.79 (d, J=8.29 Hz, 1H), 7.67 (d, J=7.67 Hz, 1H), 7.33-7.51 (m, 5H), 6.99 (d, J=8.9 Hz, 2H), 4.84 (s, 2H), 4.42-4.45 (m, 2H), 4.04 (d, J=6.29 Hz, 2H), 3.83 (d, J=5.83 Hz, 1H), 3.55 (br, 2H), 3.16-3.21 (m, 2H), 3.03 (t, J=5.83 Hz, 2H), 2.89 (s, 6H), 1.99-2.07 (m, 2H). ESI (+)/MS: 735 (M+H)⁺.

Example 91

Synthesis of 2-(8-(benzo[d]thiazol-2-ylcarbamoyl)-3,4-dihydroisoquinolin-2(1H)-yl)-5-(3-((1-(4-hydroxyphenyl)-1H-pyrazolo[3,4-d]pyrimidin-4-yl)(3-(4-methylpiperazin-1-yl)propyl)amino)propyl)thiazole-4-carboxylic acid (91):

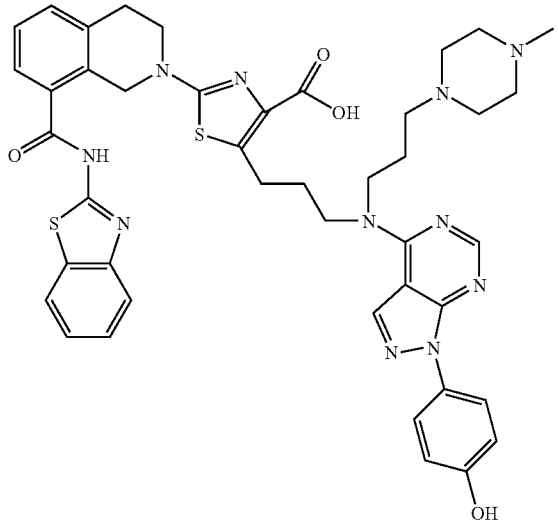

(91)

To a solution compound 84A (50 mg, 0.136 mmol) in DMF (5 ml) was added sodium hydride (27.2 mg, 0.680 mmol) (60%). The reaction mixture was stirred for 10 min and compound 2C (77 mg, 0.122 mmol) was added. The resulting mixture was stirred for 1 hour and methanol (3 ml), 10% NaOH and water (1 ml) were added. The mixture was stirred overnight, acidified with TFA and concentrated. The residue was dissolved in a mixture of DMSO-methanol and purified by reverse phase HPLC (mobile phase: 0%-60% acetonitrile in 0.1% TFA aqueous solution during 60 min) to provide the title compound 91 as a TFA salt: $^1$H NMR (500 MHz, PYRIDINE-D$_5$) δ ppm 8.62 (1H, s), 8.41 (1H, s), 8.35 (2H, d), 7.94 (1H, d), 7.89 (1H, d), 7.77-7.81 (1H, m), 7.43 (1H, t), 7.24-7.33 (5H, m), 5.15 (2H, s), 3.93-4.01 (2H, m), 3.87 (2H, d), 3.81 (2H, t), 3.45 (2H, t), 2.92 (2H, t), 2.79-2.85 (4H, m), 2.62-2.69 (4H, m), 2.42-2.47 (5H, m), 2.18-2.28 (2H, m), 1.89-1.98 (2H, m); LCMS (APCI) m/e 844 (M+H).

Example 92

Synthesis of 6-(8-(benzo[d]thiazol-2-ylcarbamoyl)-3,4-dihydroisoquinolin-2(1H)-yl)-3-(3-(4-(4-(3-(dimethylamino)propylamino)-1H-pyrazolo[3,4-d]pyrimidin-1-yl)phenoxy)propyl)picolinic acid (92):

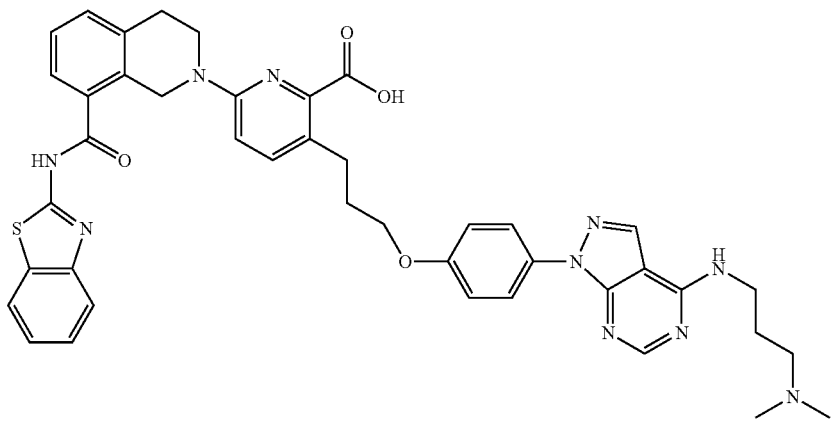

(92)

Step 1: Preparation of tert-butyl 6-(8-(benzo[d]thiazol-2-ylcarbamoyl)-3,4-dihydroisoquinolin-2(1H)-yl)-3-(3-(4-(4-(3-(dimethylamino)propylamino)-1H-pyrazolo[3,4-d]pyrimidin-1-yl)phenoxy)propyl)picolinate (92A)

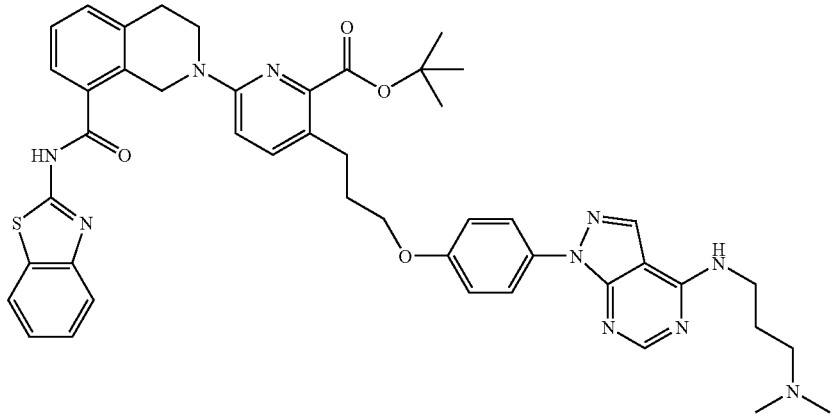

(92A)

To a solution of compound 54A (100 mg, 0.320 mmol) in DMF (5 ml) was added sodium hydride (60%, 38.4 mg, 0.960 mmol). The reaction was stirred for 10 min and compound 96D (168 mg, 0.256 mmol) was added. The resulting mixture was stirred for 1 hour and purified by reverse phase HPLC (mobile phase: 0%-70% acetonitrile in 0.1% TFA aqueous solution during 70 min) to provide the title compound 92A as a TFA salt. LCMS (APCI) m/e 839 (M+H).

Step 2: Preparation of Title Compound 92

Compound 92A (90 mg, 0.107 mmol) and triethylsilane (37.4 mg, 0.322 mmol) in DCM (1 ml) was treated with TFA (3 ml, 38.9 mmol) for 4 h. The mixture was concentrated and the residue was purified by reverse phase HPLC (mobile phase: 0%-60% acetonitrile in 0.1% TFA aqueous solution during 70 min) to provide the title compound as a TFA salt: $^1$H NMR (400 MHz, DMSO-D$_6$) δ ppm 12.82 (1H, s), 9.37 (1H, s), 8.55 (1H, t) 8.34 (1H, d), 8.03 (1H, d), 7.96-8.01 (2H, m), 7.79 (1H, d), 7.55-7.63 (2H, m), 7.44-7.50 (2H, m), 7.39-7.43 (1H, m), 7.35 (2H, t), 7.05-7.09 (2H, m), 6.97 (1H, d), 4.93 (2H, s), 3.99 (2H, q), 3.87 (2H, t), 3.43-3.70 (2H, m), 3.12-3.18 (2H, m), 2.99 (2H, t), 2.82-2.87 (2H, m), 2.80 (6H, s), 1.91-2.05 (4 FI, m). LCMS (APCI) 783 (M+H).

Example 93

Synthesis of 2-[8-(Benzothiazol-2-ylcarbamoyl)-3,4-dihydro-1H-isoquinolin-2-yl]-5-{3-[2-fluoro-4-(4-methyl-piperazin-1-yl)-phenoxy]-propyl}-thiazole-4-carboxylic acid (93)

(93)

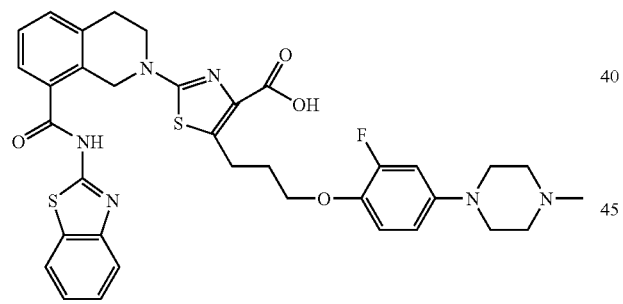

Step 1: Preparation of
1-(benzyloxy)-4-bromo-2-fluorobenzene (93A)

(93A)

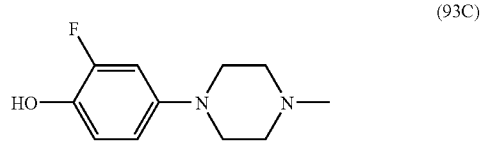

4-bromo-2-fluorophenol (2.557 g, 13.39 mmol) and (bromomethyl)benzene (1.590 ml, 13.39 mmol) in DMF (20 ml) were treated with K$_2$CO$_3$ (3.70 g, 26.8 mmol) overnight. The reaction was then diluted with ethyl acetate and washed with water. The organic layer was dried over Na$_2$SO$_4$ and concentrated to provide the title compound. LCMS (APCI) m/e 282 (M+H).

Step 2: Preparation of 1-(4-(benzyloxy)-3-fluorophenyl)-4-methylpiperazine (93B)

(93B)

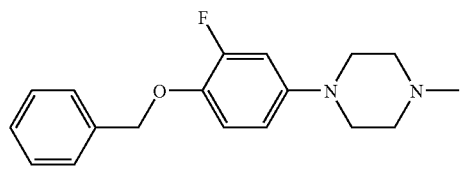

An oven-dried vial was charged with t-BuONa (360 mg, 3.75 mmol), Pd$_2$(dba)$_3$ (51.5 mg, 0.056 mmol) and (S)-BINAP (105 mg, 0.169 mmol). Toluene (5 ml), Example 93A (527 mg, 1.875 mmol) and 1-methylpiperazine (416 μl, 3.75 mmol) were added. The resulting mixture was purged with nitrogen and the vial was sealed and heated at 80° C. overnight. The reaction was concentrated and the residue was purified by reverse phase HPLC (mobile phase: 0%-50% acetonitrile in 0.1% TFA aqueous solution during 40 min) to provide the title compound as a TFA salt: LCMS (APCI) m/e 301 (M+H).

Step 3: Preparation of
2-fluoro-4-(4-methylpiperazin-1-yl)phenol (93C)

(93C)

Compound 93B (230 mg, 0.766 mmol) in MeOH (5 ml) was treated with 10% Pd/C (48 mg, 0.045 mmol) under H$_2$ atmosphere overnight. The insoluble material was removed by filtration through Celite and the filtrate was concentrated. The residue was purified by reverse phase HPLC (mobile phase: 0%-30% acetonitrile in 0.1% TFA aqueous solution during 30 min) to provide the title compound as a TFA salt: LCMS (APCI) m/e 211 (M+H).

Step 4: Preparation of Title Compound 93

The title compound 92 was prepared using the same procedure described in step 2 of Example 54 by replacing compound 54A with compound 93: $^1$H NMR (400 MHz, DMSO-D$_6$) δ ppm 12.85 (1H, s), 9.64 (1H, s), 8.03 (1H, d), 7.79 (1H, d), 7.67 (1H, d), 7.43-7.51 (2H, m), 7.33-7.42 (2H, m), 7.03 (1H, t), 6.92 (1H, dd), 6.70 (1H, dd), 4.83 (2H, s), 3.98 (2H, t), 3.72 (2H, t), 3.40-3.55 (2H, m), 3.33-3.39 (2H, m), 3.09-

3.20 (4H, m), 3.03 (2H, t), 2.85-2.95 (2H, m), 2.84 (3H, s), 1.93-2.02 (2H, m). LCMS (APCI) m/e 687 (M+H).

Example 94

Synthesis of 6-[8-(Benzothiazol-2-ylcarbamoyl)-3,4-dihydro-1H-isoquinolin-2-yl]-3-{3-[4-(4-methyl-piperazin-1-yl)-phenoxy]-propyl}-pyridine-2-carboxylic acid (94)

(94)

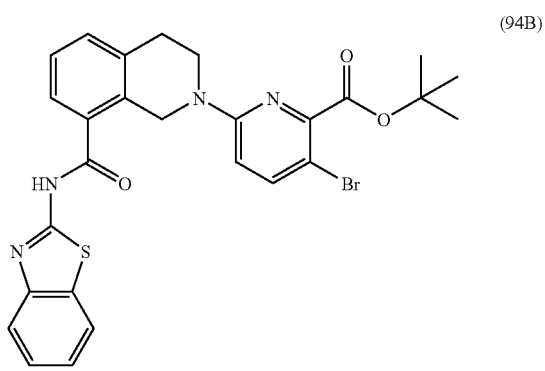

Step 1: Preparation of tert-butyl 3-bromo-6-chloropicolinate (94A)

(94A)

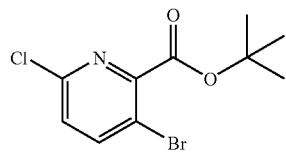

Tosyl chloride (7.7 g, 40.4 mmol) was added to a solution of 2-chloro-5-bromo picolinic acid (4 g, 17 mmol) and pyridine (9.2 mL, 114 mmol) in 33 mL of t-BuOH at 0° C. The reaction was then stirred at room temperature for 12 hours. NaHCO₃ (sat.) was then added and the mixture was extracted with ethyl acetate (3 times). The combined organic phases were washed with brine and dried over Na₂SO₄. Evaporation of the organic solvent afforded the desired compound 94A, which is used in the next step without further purification: ¹H NMR (300 MHz, DMSO-d₆) δ ppm 8.27 (1H, d), 7.63 (1H, d), 1.57 (9H, s).

Step 2: Preparation of tert-butyl 6-(8-(benzo[d]thiazol-2-ylcarbamoyl)-3,4-dihydroisoquinolin-2(1H)-yl)-3-bromopicolinate (94B)

(94B)

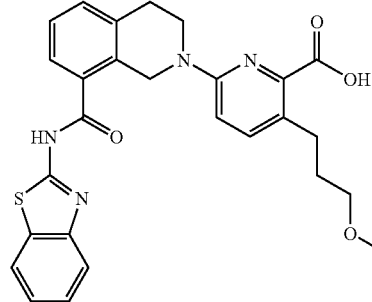

Cs₂CO₃ (4.1 g, 12.6 mmol) and 4A sieves were dried under high vacuum at 150° C. for 6 to 10 hours before the start of the reaction. After cooling to room temperature, compound 94A (0.736 g, 2.53 mmol) and compound 1B (1.62 g, 3 mmol) were transferred to the reaction vessel and the atmosphere was purged with nitrogen. 12 mL of anhydrous DMA were then added and the reaction was stirred at 120° C. for 12 hours. The cooled reaction mixture was then diluted with ethyl acetate and 10% citric acid. The organic phase was washed three times with citric acid, once with water and brine, and dried over Na₂SO₄. Concentration afforded an orange film/foam. Purification on Flash Master (SiO₂, ethyl acetate/petroleum ether 0:100 to 40:60) afforded a white solid (1.15 g, 80% yield): ¹H NMR (300 MHz, DMSO-d₆) δ ppm 12.84 (1H, s), 8.03 (1H, d), 7.77 (2H, m), 7.58 (1H, d), 7.40 (4H, m), 6.86 (1H, d), 4.92 (2H, s), 3.78 (2H, t), 3.01 (2H, t), 1.34 (9H, s).

Step 3: Preparation of (Z)-tert-butyl 3-bromo-6-(8-(3-((2-(trimethylsilyl)ethoxy)methyl)benzo[d]thiazol-2(3H)-ylidenecarbamoyl)-3,4-dihydroisoquinolin-2(1H)-yl)picolinate (94C)

(94C)

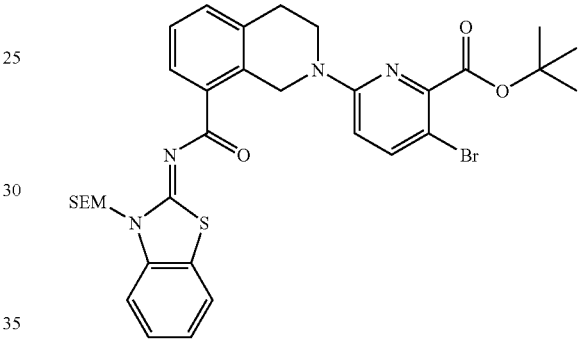

Compound 94B (350 mg, 0.62 mmol) was dissolved in THF. NEt₃ (127 µL, 0.91 mmol) and SEMCl (135 µL, 0.74 mmol) were added successively. The reaction was stirred at room temperature for 1 hour. It was then concentrated. The residue was taken into ethyl acetate and water. The aqueous layer was extracted three times with ethyl acetate. The combined organic layers were washed with brine and dried over Na₂SO₄. After concentration, the residue was purified by flash chromatography using the flash master: SiO₂, ethyl acetate/petroleum ether 0:100 to 30:70. A pale yellow foamy solid 94B was obtained as a mixture of two inseparable isomers (276 mg, 64%).

Step 4: Preparation of (Z)-tert-butyl 3-(2-(1,3-dioxolan-2-yl)ethyl)-6-(8-(3-((2-(trimethylsilyl)ethoxy)methyl)benzo[d]thiazol-2(3H)-ylidenecarbamoyl)-3,4-dihydroisoquinolin-2(1H)-yl)picolinate (94D)

(94D)

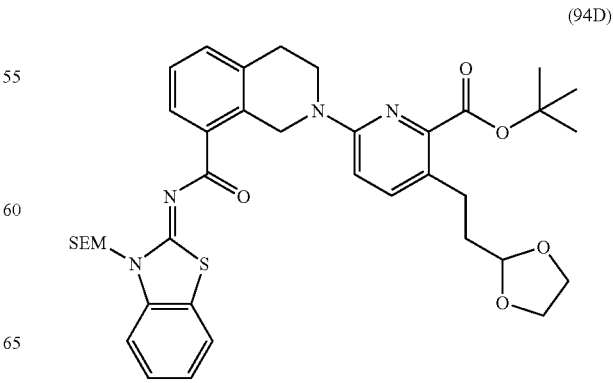

A mixture of compound 94C (2.97 g, 4.27 mmol), dicyclohexyl(2',6'-dimethoxybiphenyl-2-yl)phosphine (0.35 g, 0.854 mmol) and palladium acetate (0.096 g, 0.427 mmol) in THF (20 mL) was stirred at room temperature for 5 min. To this solution was added 0.5 M (2-(1,3-dioxolan-2-yl)ethyl)zinc(II) bromide (17.08 mL, 8.54 mmol) dropwise at room temperature. The reaction was stirred overnight. To the solution were added 2',6'-dimethoxybiphenyl-2-yl)phosphine (170 mg), palladium acetate (42 mg) and (2-(1,3-dioxolan-2-yl)ethyl)zinc(II) bromide (15 mL). The resulting mixture was stirred for another 6 hours and concentrated. The residue was loaded on a silica gel column and eluted with 7:3/hexanes:EtOAc to afford 2.75 g of desired product 94D which is a mixture of two isomers. APCI (+) LC/MS: 717 (M+H)$^+$.

Step 5: Preparation of (Z)-tert-butyl 3-(3-oxopropyl)-6-(8-(3-((2-(trimethylsilyl)ethoxy)methyl)benzo[d]thiazol-2(3H)-ylidenecarbamoyl)-3,4-dihydroisoquinolin-2(1H)-yl)picolinate (94E):

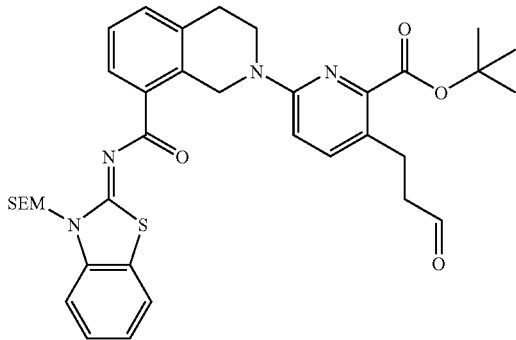

(94E)

Compound 94D (1.47 g) was dissolved in THF (30 mL). To this solution was added 5% HCl (10 mL). The reaction mixture was heated at 48° C. for 90 min. After cooling to room temperature, the reaction mixture was quenched with sat. NaHCO$_3$ solution until no more CO$_2$ was released. The solution was concentrated under vacuum. The residue was re-dissolved in EtOAc, and treated with water (100 mL). The organic layer was separated, and the aqueous layer was extracted with additional EtOAc (three times). The combined organic layers were washed with brine, dried (MgSO$_4$), filtered and concentrated under vacuum. The residue was purified with flash column chromatography on silica gel eluting with 7:3/Hex:EtOAc to give 1.10 g of the title compound 94E (80%): APCI (+)LC/MS: 673 (M+H)$^+$.

Step 6: Preparation of (Z)-tert-butyl 3-(3-hydroxypropyl)-6-(8-(3-((2-(trimethylsilyl)ethoxy)methyl)benzo[d]thiazol-2(3H)-ylidenecarbamoyl)-3,4-dihydroisoquinolin-2(1H)-yl)picolinate (94F):

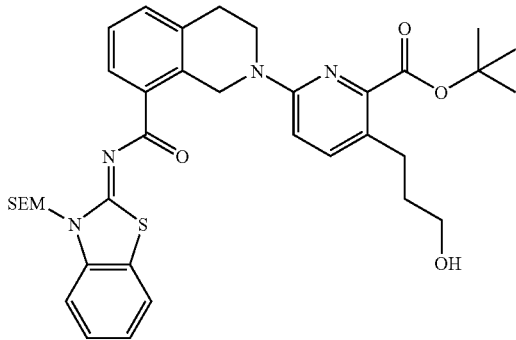

(94F)

Compound 94E (0.91 g, 1.351 mmol) in THF (30 mL) and methanol (5 mL) was treated with NaBH$_4$ (0.102 g, 2.7 mmol). The reaction mixture was heated under reflux for 1 hour. The solvents were removed under vacuum. The residue was re-dissolved in EtOAc and treated with water. The organic layer was separated, and the aqueous layer was extracted with additional EtOAc. The combined organic layers were washed with brine, dried (MgSO$_4$), filtered, and concentrated. The residue was purified by flash chromatography to give 0.75 g of the title compound 94F (82%): APCI (+)LC/MS: 675 (M+H)$^+$.

Step 7: Preparation of tert-butyl 6-(8-(benzo[d]thiazol-2-yl((2-(trimethylsilyl)ethoxy)methyl)carbamoyl)-3,4-dihydroisoquinolin-2(1H)-yl)-3-(3-(4-(4-methylpiperazin-1-yl)phenoxy)propyl)picolinate (94G):

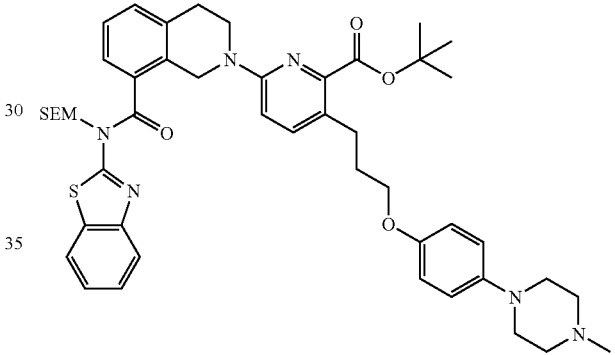

(94G)

The title compound 94G was prepared in a similar manner to the synthesis of compound 35A by substituting compound 34D and compound 31F with compound 94F and compound 82A, respectively: ESI (+)LC/MS: 849 (M+H$_2$O—NH$_4$)$^+$.

Step 7: Preparation of Title Compound 94

Compound 94G (0.012 g) in dioxane (2 mL) was treated with 4 N HCl in dioxane (2 mL) and methanol (0.5 mL). The solution was stirred at 60° C. for 6 hours. The solvent was removed, and the residue was purified by Prep HPLC to give the title compound 94 as a TFA salt: $^1$H NMR (DMSO-d$_6$): δ 12.85 (d, J=7.02 Hz, 1H), 9.70 (d, J=9.46 Hz, 1H), 8.04 (d, J=7.63 Hz, 1H), 7.79 (d, J=7.93 Hz, 1H), 7.60 (d, J=7.63 Hz, 1H), 7.55 (d, J=8.85 Hz, 1H), 7.34-7.50 (m, 4H), 6.96 (d, J=8.54 Hz, 1H), 6.90-6.93 (m, 2H), 6.81-6.84 (m, 2H), 4.92 (s, 2H), 3.85-3.87 (m, 4H), 3.62-3.64 (m, 2H), 3.12-3.18 (m, 2H), 2.98 (t, J=5.8 Hz, 2H), 2.79-2.86 (m, 7H), 1.86-1.93 (m, 2H), 1.26-1.28 (m, 2H). ESI (+)LC/MS: 663 (M+H)$^+$.

Example 95

Synthesis of 6-[8-(Benzothiazol-2-ylcarbamoyl)-3,4-dihydro-1H-isoquinolin-2-yl]-3-(3-{4-[5-(2-dimethylamino-ethoxy)-pyridin-2-yl]-phenoxy}-propyl)-pyridine-2-carboxylic acid (95)

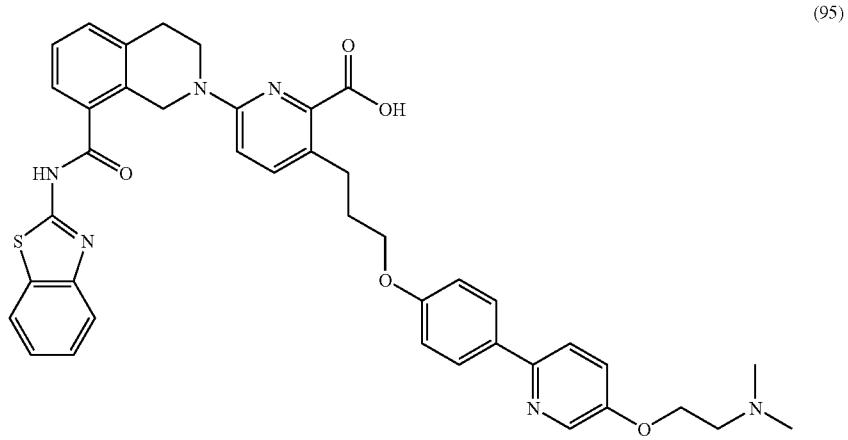

(95)

Step 1: Preparation of tert-butyl 6-(8-(benzo[d]thiazol-2-yl((2-(trimethylsilyl)ethoxy)methyl)carbamoyl)-3,4-dihydroisoquinolin-2(1H)-yl)-3-(3-(4-(5-(2-(dimethylamino)ethoxy)pyridin-2-yl)phenoxy)propyl)picolinate (95A):

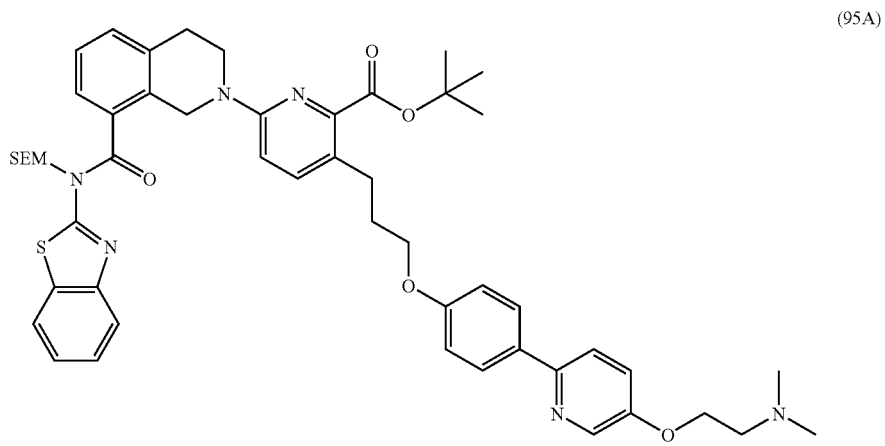

(95A)

Compound 95A was prepared in a similar manner to the synthesis of compound 35A by substituting compound 34D and compound 31F with compound 94F and compound 90B, respectively: ESI (+)LC/MS: 915 (M+H$_2$O—NH$_4$)$^+$.

Step 2: Preparation of Title Compound 95

The title compound 95 was prepared in a similar manner to the synthesis of Example 94 by substituting compound 94G with compound 95A: NMR (DMSO-d$_6$): δ 12.80 (s, 1H), 9.69 (s, 1H), 8.39 (d, J=3.07 Hz, 1H), 8.03 (d, J=7.67 Hz, 1H), 7.93 (d, J=8.59 Hz, 2H), 7.86 (d, J=8.59 Hz, 1H), 7.79 (d, J=7.98 Hz, 1H), 7.33-7.61 (m, 7H), 6.96-7.00 (m, 1H), 4.93 (s, 2H), 4.43-4.45 (m, 2H), 3.99 (d, J=6.6 Hz, 2H), 3.69 (d, J=5.98 Hz, 2H), 2.98 (t, J=5.83 Hz, 2H), 2.82-2.89 (m, 8H), 1.93-2.01 (m, 2H). ESI (+)/MS: 729 (M+H)$^+$.

Example 96

Synthesis of 6-[8-(Benzothiazol-2-ylcarbamoyl)-3,4-dihydro-1H-isoquinolin-2-yl]-3-[3-(4-pyrimidin-2-yl-phenoxy)-propyl]-pyridine-2-carboxylic acid (96)

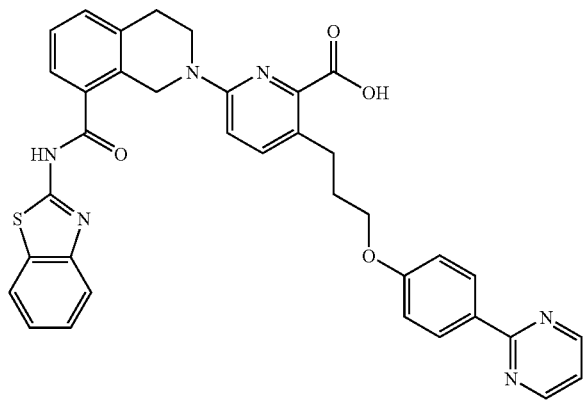

(96)

Step 1: Preparation of tert-butyl 3-(2-(1,3-dioxolan-2-yl)ethyl)-6-(8-(benzo[d]thiazol-2-ylcarbamoyl)-3,4-dihydroisoquinolin-2(1H)-yl)picolinate (96A)

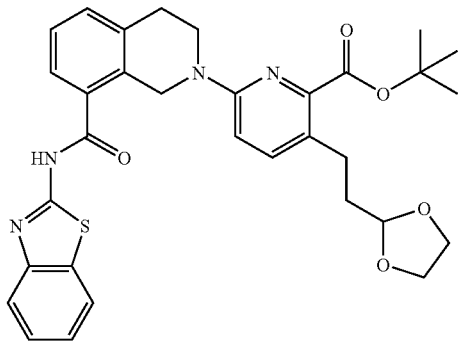

(96A)

A mixture of compound 94B (8.0 g, 14.15 mmol), dicyclohexyl(2',6'-dimethoxybiphenyl-2-yl)phosphine (1.162 g, 2.83 mmol) and palladium acetate (0.318 g, 1.415 mmol) in THF (60 mL) was stirred at room temperature for 5 min. To this solution was added 0.5 M (2-(1,3-dioxolan-2-yl)ethyl)zinc(II) bromide (56.6 mL, 28.3 mmol) via an additional funnel drop wise at room temperature. The reaction was stirred overnight. The solvent was removed, and residue was loaded on a silica column and eluted with 7:3/hexanes:EtOAc to give 7.58 g of desired product 96A: APCI (+)LC/MS: 587 (M+H)$^+$.

Step 2: Preparation of tert-butyl 6-(8-(benzo[d]thiazol-2-ylcarbamoyl)-3,4-dihydroisoquinolin-2(1H)-yl)-3-(3-oxopropyl)picolinate (96B)

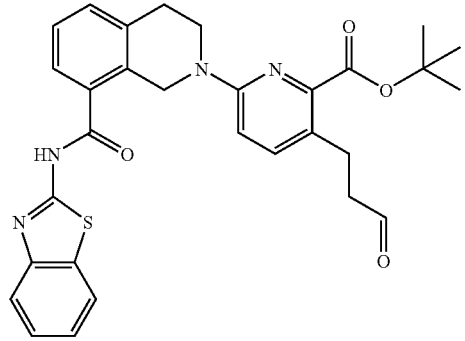

(96B)

Compound 96A (7.58 g) was dissolved in THF (120 mL). To this solution was added 5% aq. HCl (100 mL). The reaction mixture was heated at 48° C. for 90 min. After cooling to room temperature, the reaction mixture was quenched with sat. NaHCO$_3$ solution until no more CO$_2$ was released. The solution was concentrated under vacuum. The residue was re-dissolved in EtOAc, and treated with water (500 mL). The organic layer was separated, and the aqueous layer was extracted with additional EtOAc (three times). The combined organic layers were washed with brine, dried (MgSO$_4$), filtered and concentrated under vacuum. The residue was purified with flash column chromatography on silica gel eluting with 7:3/Hex:EtOAc to give 5.5 g of the title compound 96B (78%): APCI (+)LC/MS: 543 (M+H)$^+$.

Step 3: Preparation of tert-butyl 6-(8-(benzo[d]thiazol-2-ylcarbamoyl)-3,4-dihydroisoquinolin-2(1H)-yl)-3-(3-hydroxypropyl)picolinate (96C)

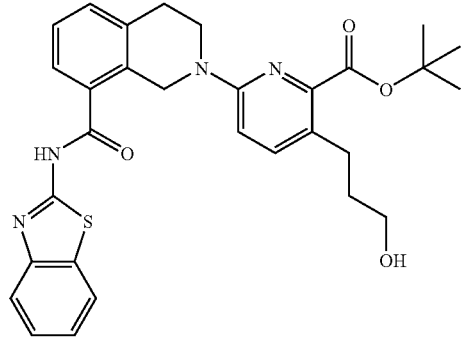

(96C)

Compound 96B (5.5 g, 10.14 mmol) in THF (100 mL) and methanol (20 mL) was treated NaBH$_4$ (0.767 g, 20.28 mmol). The reaction mixture was heated under reflux for 1 hour. The solvents were removed under vacuum. The residue was re-dissolved in EtOAc and treated with water. The organic layer was separated, and the aqueous layer was extracted with additional EtOAc. The combined organic layers were washed with brine, dried (MgSO$_4$), filtered, and concentrated. The residue was purified by flash chromatography to give 5.13 g of the title compound 96C (93%): APCI (+)LC/MS: 545 (M+H)$^+$.

Step 4: Preparation of tert-butyl 6-(8-(benzo[d]thiazol-2-ylcarbamoyl)-3,4-dihydroisoquinolin-2(1H)-yl)-3-(3-iodopropyl)picolinate (96D)

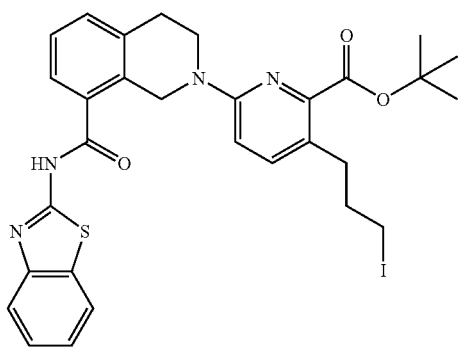

(96D)

The compound 96D was prepared in a similar manner to the synthesis of compound 98A by substituting compound 94F with compound 96C; APCI (+)LC/MS: 655 (M+H)$^+$.

Step 5: Preparation Title Compound 96

The title compound 96 was prepared as a TFA salt in a similar manner to the synthesis of compound 51 by substituting compound 51A with compound 96D: ESI (+)/MS: 643 (M+H)$^+$; $^1$H NMR (DMSO-d$_6$): δ 12.84 (s, 1H), 8.863 (d, J=4.48, 2H), 8.32 (d, J=8.85 Hz, 2H), 8.03 (d, J=7.93 Hz, 1H), 7.79 (d, J=7.93 Hz, 1H), 7.57-7.61 (m, 2H), 7.46-7.49 (m, 1H), 7.34-7.37 (m, 3H), 7.03 (d, J=9.15 Hz, 2H), 6.98 (d, J=8.54 Hz, 1), 4.93 (s, 2H), 4.01-4.04 (m, 2H), 3.87 (d, J=5.95 Hz, 2H), 2.99 (d, J=5.65 Hz, 2H), 2.83-2.86 (m, 2H), 1.95-2.01 (m, 2H). ESI (+)/MS: 643 (M+H)$^+$.

Example 97

Synthesis of 6-(8-(benzo[d]thiazol-2-ylcarbamoyl)-3,4-dihydroisoquinolin-2(1H)-yl)-3-(3-(4-(3-(dimethylamino)prop-1-ynyl)-2-fluorophenoxy)propyl) picolinic acid (97)

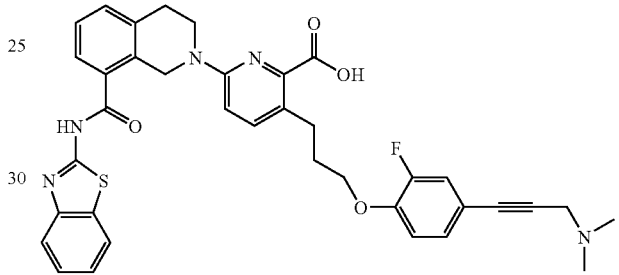

(97)

Step 1: Preparation of tert-butyl 6-(8-(benzo[d]thiazol-2-yl((2-(trimethylsilyl)ethoxy)methyl)carbamoyl)-3,4-dihydroisoquinolin-2(1H)-yl)-3-(3-(4-bromo-2-fluorophenoxy)propyl)picolinate (97A$^1$); and (Z)-tert-butyl 3-(3-(4-bromo-2-fluorophenoxy)propyl)-6-(8-(3-((2-(trimethylsilyl)ethoxy)methyl)benzo[d]thiazol-2(3H)-ylidenecarbamoyl)-3,4-dihydroisoquinolin-2(1H)-yl)picolinate (97A$^2$):

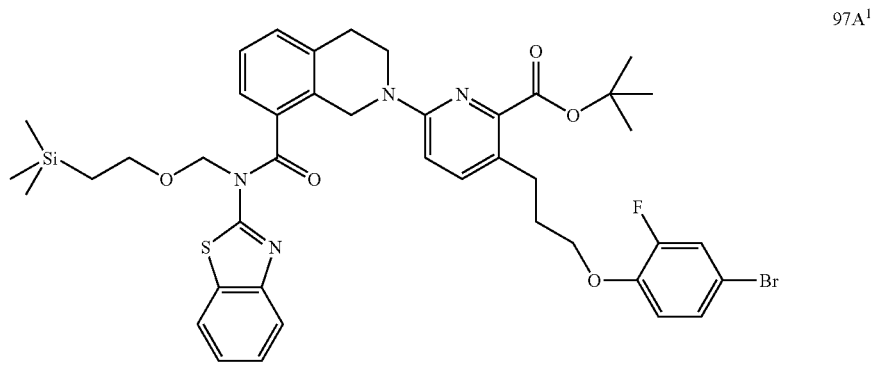

97A$^1$

97A²

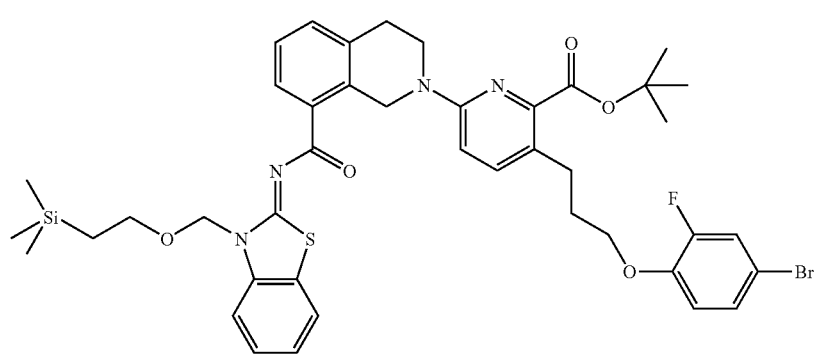

To a solution of Compound 94F (110 mg, 0.163 mmol), 4-bromo-2-fluorophenol (62.3 mg, 0.326 mmol) and triphenylphosphine (64.1 mg, 0.244 mmol) in THF (3 ml) was added (E)-di-tert-butyl diazene-1,2-dicarboxylate (56.3 mg, 0.244 mmol). The reaction was stirred for 2 h and water (0.5 ml) was added. The mixture was concentrated and the residue was purified by flash chromatography, eluting with DCM to provide the compounds 97A¹ and compound 97A²; LCMS (APCI) m/e 848 (M+H).

Step 2: Preparation of (Z)-tert-butyl 3-(3-(4-(3-(dimethylamino)prop-1-ynyl)-2-fluorophenoxy)propyl)-6-(8-(3-((2-(trimethylsilyl)ethoxy)methyl)benzo[d]thiazol-2(3H)-ylidenecarbamoyl)-3,4-dihydroisoquinolin-2(1H)-yl)picolinate (97B¹); and tert-butyl 6-(8-(benzo[d]thiazol-2-yl((2-(trimethylsilyl)ethoxy)methyl)carbamoyl)-3,4-dihydroisoquinolin-2(1H)-yl)-3-(3-(4-(3-(dimethylamino)prop-1-ynyl)-2-fluorophenoxy)propyl)picolinate (97B²)

97B¹

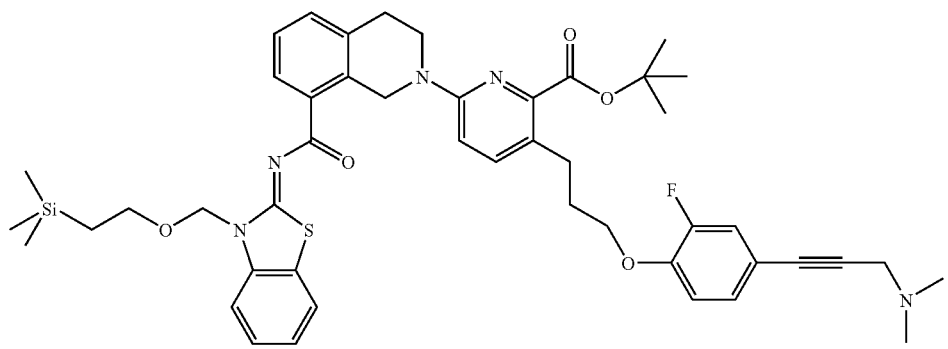

97B²

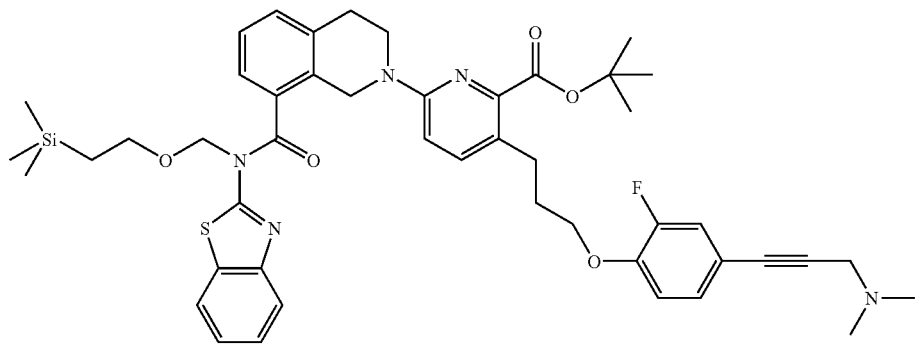

To a mixture of compound 97A[1] and compound 97A[2] (90 mg, 0.106 mmol), N,N-dimethylprop-2-yn-1-amine (0.034 ml, 0.318 mmol), (PPh$_3$)$_2$PdCl$_2$ (22.35 mg, 0.032 mmol), TEA (0.074 ml, 0.531 mmol) in DMF (2 ml) was added copper(I) iodide (2.022 mg, 0.01 mmol). The resulting mixture was heated at 100° C. in oil bath overnight and purified by reverse phase HPLC (mobile phase: 10%-95% acetonitrile in 0.1% TFA aqueous solution during 60 min) to provide the compounds 97B[1] and 97B[2] as TFA salts: LCMS (APCI) m/e 850 (M+H).

Step 3: Preparation of Title Compound 97

Compound 97B[1] and compound 97B[2] (60 mg, 0.071 mmol) in DCM (2 ml) were treated with 2 N hydrogen chloride in ether (0.15 ml), 0.423 mmol) for 2 h and the reaction mixture was concentrated. The residue in THF (2 mL) and MeOH (2 mL) was treated with 10% sodium hydroxide (256 μl, 0.639 mmol) at 70° C. overnight and concentrated. The residue was purified by reverse phase HPLC (mobile phase: 0%-70% acetonitrile in 0.1% TFA aqueous solution during 60 min) to provide the title compound 97 as a TFA salt: $^1$H NMR (400 MHz, DMSO-D$_6$) δ ppm 12.79 (1H, s), 10.17 (1H, s), 8.03 (1H, d), 7.79 (1H, d), 7.53-7.63 (2H, m), 7.45-7.50 (1H, m), 7.39-7.44 (2H, m), 7.28-7.38 (3H, m), 7.17 (1H, t), 6.96 (1H, d), 4.93 (2H, s), 4.30 (2H, s), 4.06 (2H, t), 3.87 (2H, t), 2.99 (2H, t), 2.78-2.90 (8H, m), 1.91-2.05 (2H, m); LCMS (APCI) m/e 664 (M+H).

Example 98

Synthesis of 6-(8-(benzo[d]thiazol-2-ylcarbamoyl)-3,4-dihydroisoquinolin-2(1H)-yl)-3-(3-(4-(4-methylpiperazine-1-carbonyl)phenoxy)propyl)picolinic acid (98)

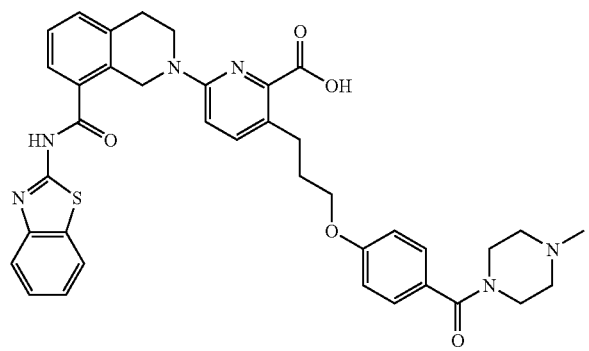

(98)

Step 1: Preparation of tert-butyl 6-(8-(benzo[d]thiazol-2-yl((2-(trimethylsilyl)ethoxy)methyl)carbamoyl)-3,4-dihydroisoquinolin-2(1H)-yl)-3-(3-iodopropyl)picolinate (98A[1]); and (Z)-tert-butyl 3-(3-iodopropyl)-6-(8-(3-((2-(trimethylsilyl)ethoxy)methyl)benzo[d]thiazol-2(3H)-ylidenecarbamoyl)-3,4-dihydroisoquinolin-2(1H)-yl)picolinate (98A[2])

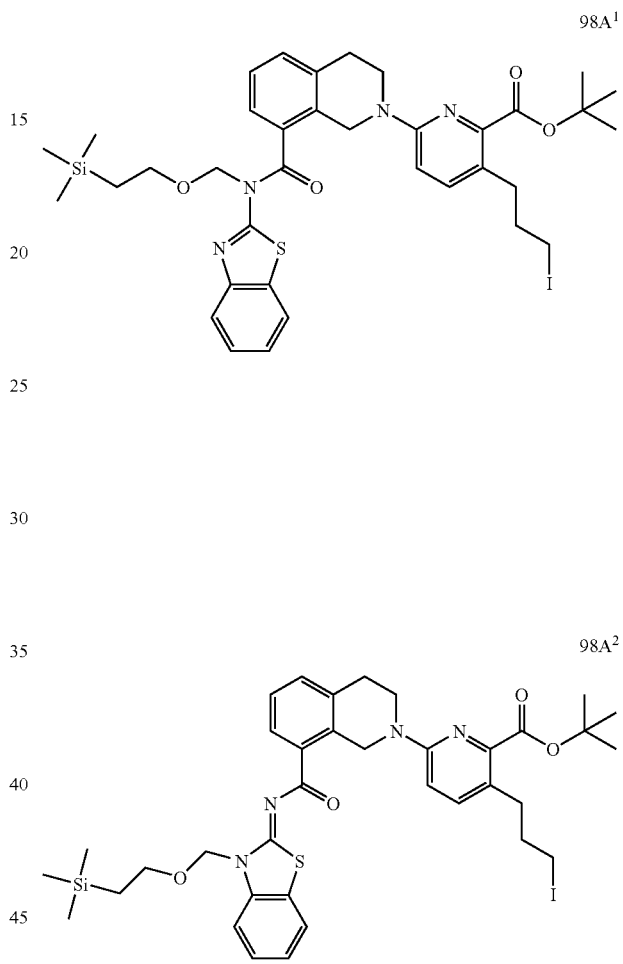

Compound 94F (874 mg, 1.3 mmol) in diethyl ether (6.5 ml) and acetonitrile (2.2 ml) was treated sequentially with imidazole (203 mg, 2.98 mmol), triphenylphosphine (509 mg, 1.94 mmol) and iodine (493 mg, 1.94 mmol). The reaction mixture was stirred for five minutes between each addition to allow the added reagent to completely dissolve. When all of the reagents had been added, the reaction mixture was stirred at ambient temperature for 45 minutes, diluted with EtOAc, washed with water and brine, dried (MgSO$_4$), filtered and concentrated. The concentrate was purified by column chromatography on silica gel eluting with a gradient of 5 to 30% EtOAc in hexanes providing the desired compounds in 89% yield as an off-white solid: $^1$H NMR (300 MHz, DMSO-d$_6$) δ ppm 8.12 (1H, dd), 7.95 (1H, d), 7.70 (1H, d), 7.54 (2H, m), 7.37 (3H, m), 6.90 (1H, d), 5.98 (2H, s), 5.20 (2H, s), 3.82 (2H, t), 3.68 (2H, m), 3.23 (2H, t), 2.98 (2H, t), 2.61 (2H, dd), 1.97 (2H, m), 1.45 (9H, s), 0.88 (2H, m), −0.19 (9H, s).

Step 2: Preparation of tert-butyl 6-(8-(benzo[d]thiazol-2-yl((2-(trimethylsilyl)ethoxy)methyl)carbamoyl)-3,4-dihydroisoquinolin-2(1H)-yl)-3-(3-(4-(4-methylpiperazine-1-carbonyl)phenoxy)propyl)picolinate (98B¹); and (Z)-tert-butyl 3-(3-(4-(4-methylpiperazine-1-carbonyl)phenoxy)propyl)-6-(8-(3-((2-(trimethylsilyl)ethoxy)methyl)benzo[d]thiazol-2(3H)-ylidenecarbamoyl)-3,4-dihydroisoquinolin-2(1H)-yl)picolinate (98B²)

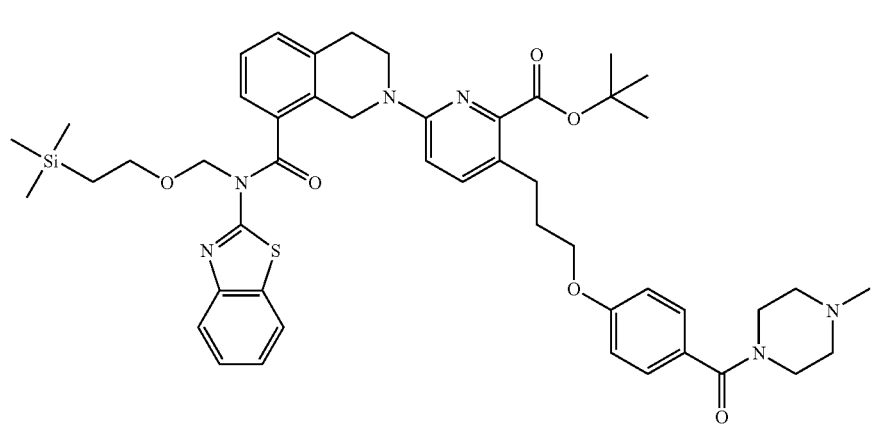

98B¹

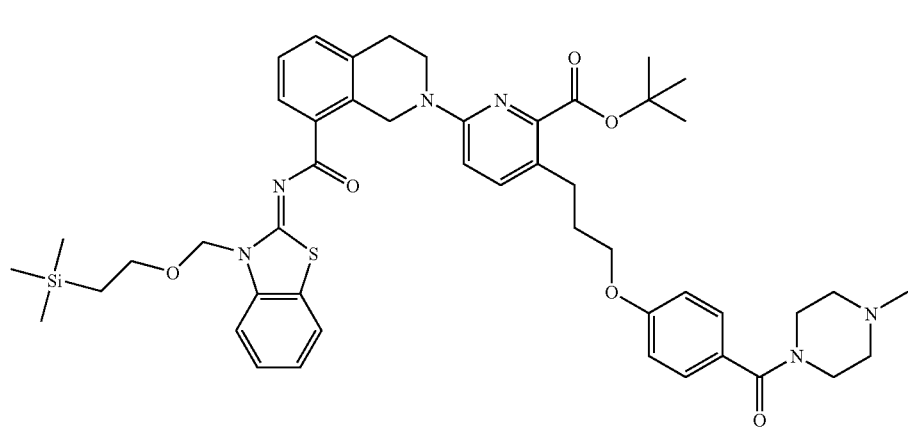

98B²

(4-Hydroxyphenyl)(4-methylpiperazin-1-yl)methanone (66.1 mg, 0.3 mmol) in DMF (2 ml) was treated with NaH (24 mg, 0.6 mmol). After stirring at ambient temperature for 15 minutes, compounds 98A¹ and 98A² (157 mg, 0.2 mmol) was added and stirring was continued for 3 hours. The reaction mixture was diluted with EtOAc, washed with water and brine, dried (MgSO₄), filtered and concentrated. The concentrate was purified by column chromatography on silica gel eluting with a gradient of 0 to 5% MeOH in CH₂Cl₂ providing 97.5 mg (56% yield) of desired products 98B¹ and 98B²: LCMS m/e 877 (M+H).

Step 3: Preparation of Title Compound 98

Compound 98B¹ and compound 98B² were treated sequentially with triethylsilane (0.177 ml, 1.1 mmol) and TFA (1.5 ml, 19.5 mmol). A minimal amount of dichloromethane (0.1 ml) was added to make the reaction mixture homogeneous. The reaction mixture was stirred at ambient temperature for 6 hours. The material was purified by HPLC (Preparative reverse phase HPLC was performed on an automated Gilson HPLC system, using a SymmetryPrep Shield RP18 prep cartridge, 250 mm×21.20 mm i.d., 10 um, and a flow rate of 25 mL/min; λ=214, 245 nm; mobile phase A, 0.1% TFA in H₂O; mobile phase B, CH₃CN; linear gradient 10-70% of B in 40 min) to provide the title compound 98 in 63% yield as an off-white solid: $^1$H NMR (300 MHz, DMSO-d$_6$) δ ppm 12.84 (1H, s), 9.70 (1H, s), 8.04 (1H, d), 7.79 (1H, d), 7.59 (2H, t), 7.41 (6H, m), 6.97 (3H, m), 4.93 (2H, s), 4.18 (2H, m), 3.99

(2H, t), 3.87 (2H, t), 3.24 (4H, m), 3.08 (2H, m), 2.99 (2H, t) 2.82 (5H, m), 1.96 (2H, m). MS (ESI(+)) m/e 691 (M+H).

Example 99

Synthesis of 6-[8-(Benzothiazol-2-ylcarbamoyl)-3,4-dihydro-1H-isoquinolin-2-yl]-3-(3-hydroxy-propyl)-pyridine-2-carboxylic acid (99)

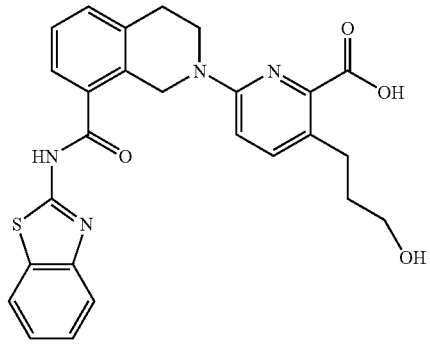

(99)

To a solution of compound 84A (60 mg, 0.163 mmol) in DMF (5 ml) was added sodium hydride (32.7 mg, 0.816 mmol)(60%). The reaction was stirred for 10 min and compound 96D (107 mg, 0.163 mmol) was added. The resulting mixture was stirred for 3 hour and purified by reverse phase HPLC (mobile phase: 0%-50% acetonitrile in 0.1% TFA aqueous solution during 70 min) to provide the title compound 99: $^1$H NMR (400 MHz, DMSO-D$_6$) δ ppm 12.81 (1H, s), 8.04 (1H, dd), 7.79 (1H, d), 7.60 (1H, d), 7.53 (1H, d), 7.45-7.50 (1H, m), 7.39-7.43 (1H, m), 7.32-7.38 (2H, m), 6.95 (1H, d), 4.92 (2H, s), 3.86 (2H, t), 3.37 (2H, t), 2.99 (2H, t), 2.63-2.70 (2H, m), 1.58-1.69 (2H, m), LCMS (APCI) 489 (M+H).

Example 100

Synthesis of 6-[8-(Benzothiazol-2-ylcarbamoyl)-3,4-dihydro-1H-isoquinolin-2-yl]-3-{3-[4-(3-dimethylamino-propyl)-2-fluoro-phenoxy]-propyl}-pyridine-2-carboxylic acid (100)

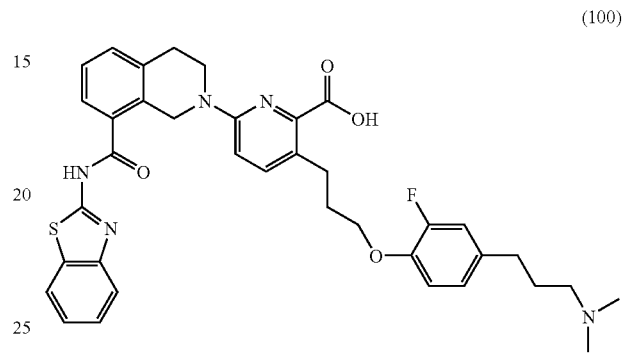

(100)

Step 1: Preparation of tert-butyl 6-(8-(benzo[d]thiazol-2-yl((2-(trimethylsilyl)ethoxy)methyl)carbamoyl)-3,4-dihydroisoquinolin-2(1H)-yl)-3-(3-(4-(3-(dimethylamino)propyl)-2-fluorophenoxy)propyl) picolinate (100A$^1$); and (Z)-tert-butyl 3-(3-(4-(3-(dimethylamino)propyl)-2-fluorophenoxy)propyl)-6-(8-(3-((2-(trimethylsilyl)ethoxy)methyl)benzo[d]thiazol-2(3H)-ylidenecarbamoyl)-3,4-dihydroisoquinolin-2(1H)-yl)picolinate (100A$^2$)

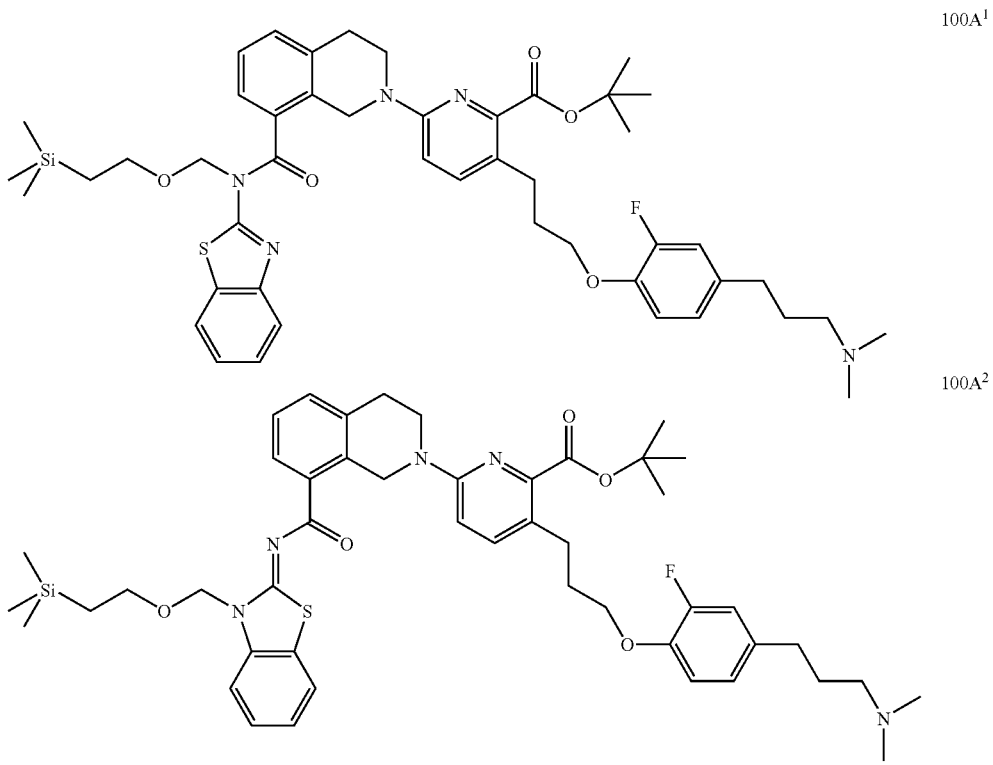

100A$^1$

100A$^2$

Compounds 97B¹ and 97B² (25 mg, 0.029 mmol) in MeOH (5 ml) were treated with platinum(IV) oxide (5.34 mg, 0.024 mmol) overnight. The insoluble material was filtered off through Celite and the filtrate was concentrated to provide the compounds 100A¹ and 100A²: LCMS (APCI) m/e 854 (M+H).

Step 2: Preparation of Title Compound 100

Compound 99 (20 mg, 0.023 mmol) in DCM (0.5 ml) and MeOH (0.5 ml) was treated with 2 N HCl in ether (5 ml). The resulting mixture was stirred at room temperature for 3 days and concentrated. The residue was purified by purified by reverse phase HPLC (mobile phase: 0%-70% acetonitrile in 0.1% TFA aqueous solution during 60 min) to provide the title compound 100 as a TFA salt: $^1$H NMR (400 MHz, DMSO-D$_6$) δ ppm 12.82 (1H, s), 9.34 (1H, s), 8.03 (1H, d), 7.79 (1H, d), 7.60 (1H, d), 7.56 (1H, d), 7.45-7.51 (1H, m), 7.39-7.43 (1H, m), 7.33-7.38 (2H, m), 7.01-7.11 (2H, m), 6.92-6.97 (2H, m), 4.93 (2H, s), 3.94-4.01 (2H, m), 3.87 (2H, t), 2.95-3.04 (4H, m), 2.79 (2H, m), 2.76 (3H, s), 2.75 (3H, s), 2.52-2.58 (2H, m), 1.84-1.98 (4H, m). LCMS (APCI) m/e 668 (M+H).

Example 101

Synthesis of 6-(8-(benzo[d]thiazol-2-ylcarbamoyl)-3,4-dihydroisoquinolin-2(1H)-yl)-3-(3-(2-fluoro-4-(4-methylpiperazin-1-yl)phenoxy)propyl)picolinic acid (101)

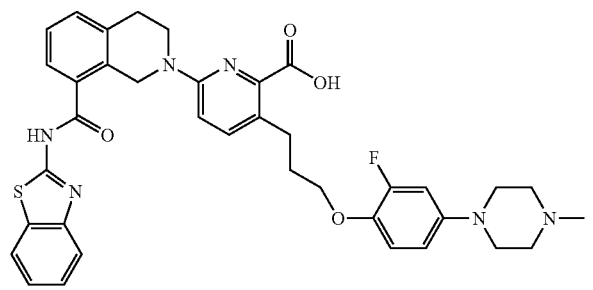

(101)

The title compound 101 was prepared using the same procedure described in step 2 of Example 54 by replacing compound 54A and compound 2C with compound 93 and compound 96D, respectively: $^1$H NMR (400 MHz, DMSO-D$_6$) δ ppm 12.80 (1H, s), 9.61 (1H, s), 8.03 (1H, d), 7.79 (1H, d), 7.60 (1H, d), 7.55 (1H, d), 7.44-7.51 (1H, m), 7.39-7.43 (1H, m), 7.33-7.38 (2H, m), 7.02 (1H, t), 6.90-6.98 (2H, m), 6.70 (1H, dd), 4.93 (2H, s), 3.93 (2H, t), 3.86 (2H, t), 3.67-3.75 (2H, m), 3.26-3.37 (2H, m), 3.06-3.20 (2H, m), 2.99 (2H, t), 2.76-2.93 (7H, m), 1.86-1.99 (2H, m); LCMS (APCI) m/e 681 (M+H).

Example 102

Synthesis of 6-(8-(benzo[d]thiazol-2-ylcarbamoyl)-3,4-dihydroisoquinolin-2(1H)-yl)-3-(3-(4-(2-(dimethylamino)ethyl)phenoxy)propyl)picolinic acid (102)

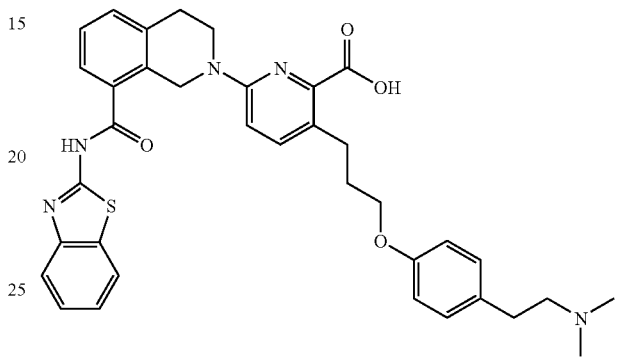

(102)

4-(2-(Dimethylamino)ethyl)phenol hydrochloric acid (60.5 mg, 0.300 mmol) in DMF (2 ml) was treated with Et$_3$N (84 µl, 0.60 mmol), stirred for 10 minutes, and then treated with NaH (24.0 mg, 0.60 mmol). After stirring for 15 minutes, the reaction mixture was treated with compound 98A¹ and 98A² (157 mg, 0.2 mmol) and stirred for 5 hours. After this time the reaction mixture was diluted with EtOAc, washed with water and brine, dried (MgSO$_4$), filtered and concentrated. The concentrate was purified by column chromatography on silica gel eluting with a gradient of 0 to 6% MeOH in CH$_2$Cl$_2$. The chromatographed material was treated successively with triethylsilane (220 µl, 1.377 mmol) and TFA (1 mL, 12.98 mmol). Dichloromethane (0.3 mL) was added dropwise until the reaction mixture became homogeneous. The reaction mixture was stirred under N$_2$ at ambient temperature for 6 hours. After this time the solvents were evaporated and the compound was purified by HPLC (Preparative reverse phase HPLC was performed on an automated Waters HPLC system, using a SunFire C18 prep cartridge, 250 mm×50 mm i.d., 10 um, and a flow rate of 25 mL/min; λ=214, 245 nm; mobile phase A, 0.1% TFA in H$_2$O; mobile phase B, CH$_3$CN; linear gradient 0-70% of B in 30 min) to provide the product as a light yellow solid in 10% yield: $^1$H NMR (300 MHz, DMSO-d$_6$) δ ppm 12.84 (1H, s), 9.29 (1H, s), 8.04 (1H, d), 7.79 (1H, d), 7.61 (1H, m), 7.56 (1H, d), 7.48 (1H, m), 7.42 (1H, m), 7.36 (2H, m), 7.17 (2H, m), 6.96 (1H, d), 6.88 (2H, m), 4.92 (2H, s), 3.89 (4H, m), 3.24 (4H, m), 2.98 (2H, m), 2.87 (2H, m), 2.81 (6H, d), 1.93 (2H, m). MS (ESI(+)) m/e 636 (M+H).

Example 103

Synthesis of 2-(8-(benzo[d]thiazol-2-ylcarbamoyl)-3,4-dihydroisoquinolin-2(1H)-yl)-5-(3-(4-(3-(dimethylamino)propyl)-2-fluorophenoxy)propyl)thiazole-4-carboxylic acid (103)

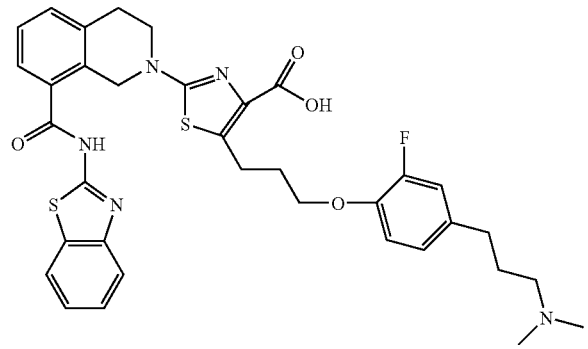

(103)

Step 1: Preparation of 3-(4-(benzyloxy)-3-fluorophenyl)-N,N-dimethylprop-2-yn-1-amine (103A)

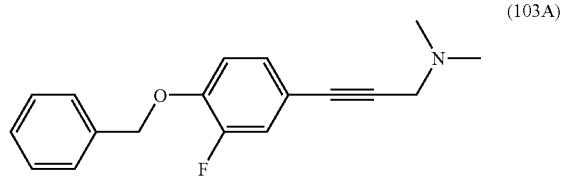

(103A)

The title compound 103A was prepared using the same procedure described in step 2 with Example 97 by replacing compound 97A with compound 93A: LCMS (APCI) 284 (M+H).

Step 2: Preparation of 4-(3-(dimethylamino)propyl)-2-fluorophenol (103B)

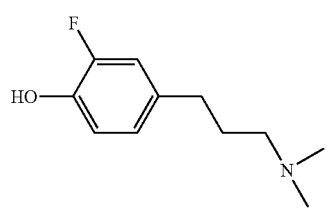

(103B)

The title compound 103B was prepared using the same procedure described in step 3 of Example 93 by replacing compound 93B with compound 103A: LCMS (APCI) 198 (M+H).

Step 3: Preparation of Title Compound 103

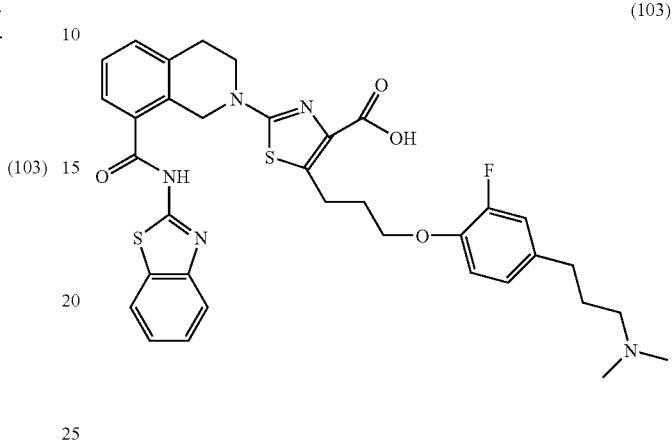

(103)

The title compound 103 was prepared using the same procedure described in step 2 of Example 54 by replacing compound 54A with compound 103B. The title compound 103 was obtained as a TFA salt: $^1$H NMR (500 MHz, DMSO-D$_6$) δ ppm 12.90 (2H, br, s), 9.43 (1H, s), 8.04 (1H, d), 7.80 (1H, d), 7.67 (1H, d), 7.43-7.50 (2H, m), 7.34-7.42 (2H, m), 7.02-7.10 (2H, m), 6.94 (1H, d), 4.83 (2H, s), 4.02 (2H, t), 3.68-3.76 (2H, m), 3.14-3.20 (2H, m), 2.96-3.06 (4H, m), 2.76 (3H, s), 2.75 (3H, s), 2.51-2.58 (2H, m), 1.97-2.04 (2H, m), 1.84-1.91 (2H, m). LCMS (APCI) 674 (M+H).

Example 104

Synthesis of 6-(8-(Benzo[d]thiazol-2-ylcarbamoyl)-3,4-dihydroisoquinolin-2(1H)-yl)-3-(3-(4-(1-methylpiperidin-4-ylamino)phenoxy)propyl)picolinic acid (104)

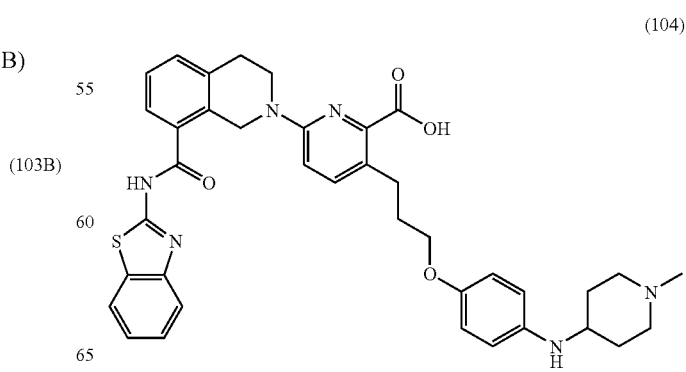

(104)

Step 1: Preparation of 4-(1-methylpiperidin-4-ylamino)phenol (104A)

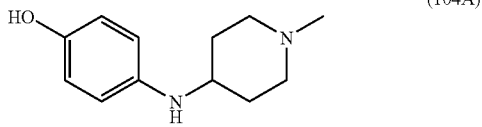

(104A)

The compound 104A was prepared in a similar manner to the synthesis of compound 62A by substituting 1-phenylpiperazine and compound 45C with 4-aminophenol and 1-methylpiperidin-4-one, respectively: ESI (+)/LC/MS: 207 (M+H)⁺.

Step 2: Preparation of tert-butyl 6-(8-(benzo[d]thiazol-2-ylcarbamoyl)-3,4-dihydroisoquinolin-2(1H)-yl)-3-(3-(4-(1-methylpiperidin-4-ylamino)phenoxy)propyl)picolinate (104B)

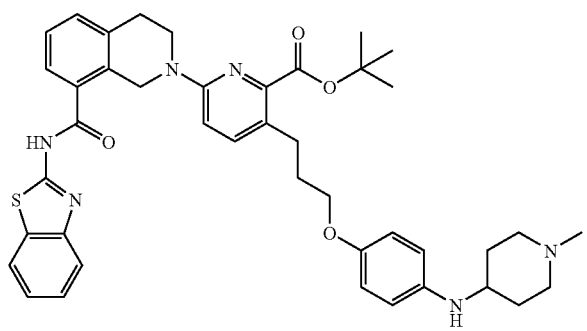

(104B)

The compound 104B was prepared as a TFA salt in a similar manner to the synthesis of step 2 of Example 51 by substituting compound 51A and compound 2C with compound 104A and compound 96D, respectively: APCI (+)/LC/MS: 733 (M+H)⁻.

Step 3: Preparation of Title Compound 104

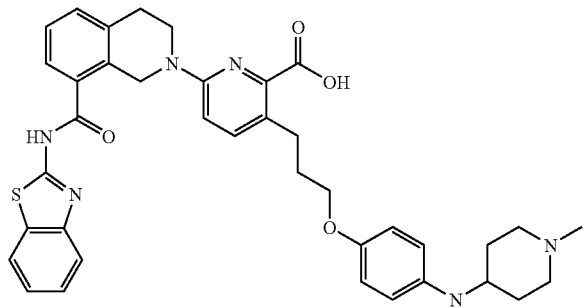

(104)

The title compound 104 was prepared in a similar manner to the synthesis of compound 94 by substituting compound 94G with compound 104B: ¹H NMR (DMSO-d₆): δ 12.84 (s, 1H), 9.40 (s, 1H), 8.04 (d, J=7.63 Hz, 1H), 7.79 (d, J=8.24 Hz, 1H), 7.60 (d, J=7.32 Hz, 1H), 7.55 (d, J=8.85 Hz, 1H), 7.34-7.49 (m, 4H), 6.96 (d, J=8.85 Hz, 1H), 6.60-6.79 (m, 1H), 4.92 (s, 2H), 3.81-3.88 (m, 4H), 2.97-3.00 (m, 4H), 2.74-2.80 (m, 4H), 2.10-2.13 (m, 2H), 1.87-1.92 (m, 4H) ESI (+)/MS: 677 (M+H)⁺.

Example 105

Synthesis of 6-(8-(benzo[d]thiazol-2-ylcarbamoyl)-3,4-dihydroisoquinolin-2(1H)-yl)-3-(3-(3-(4-methylpiperazin-1-yl)phenoxy)propyl)picolinic acid (105)

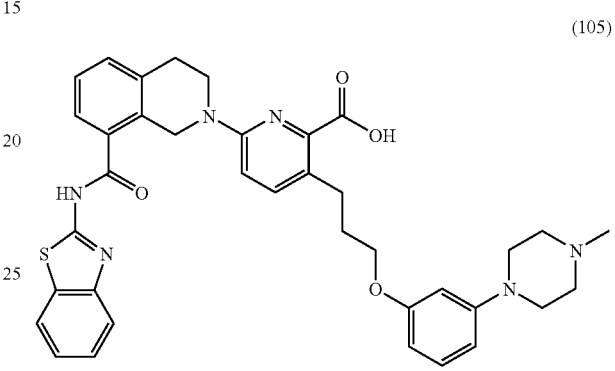

(105)

Compound 87A (0.032 g, 0.017 mmol) in DMF (3 mL) was treated with 60% sodium hydride (0.018 g, 0.46 mmol) at 0° C. The solution was stirred for 10 min. To this solution was added compound 96D (0.10 g, 0.15 mmol). The solution was stirred at room temperature for 2 hours. The reaction was then heated at 60° C. for 4 hours. It was then quenched with methanol (1 mL). Conc. HCl (0.5 mL) was added, and the solution was filtered through a syringe filter. The filtrate was then purified by Prep HPLC to give the title compound 105 as a TFA salt: ¹H NMR (DMSO-d₆): δ 12.85 (s, 1H), 9.61 (s, 1H), 8.04 (d, J=7.63 Hz, 1H), 7.79 (d, J=7.93 Hz, 1H), 7.60 (d, J=7.32 Hz, 1H), 7.55 (d, J=8.85 Hz, 1H), 7.34-7.49 (m, 4H), 7.13 (t, J=8.24 Hz, 1H), 6.97 (d, J=8.24 Hz, 1H), 6.55 (dd, J=8.39, 1.98 Hz, 1H), 6.50 (s, 1H), 6.42 (d, J=8.24, 2.14 Hz, 1H), 4.93 (s, 2H), 3.82-3.92 (m, 6H), 3.09-3.13 (m, 2H), 2.99 (t, J=5.64 Hz, 1H), 2.90-2.94 (m, 2H), 2.79-2.85 (m, 4H), 1.89-1.95 (m, 2H) ESI (+)/MS: 663 (M+H)⁺.

Example 106

Synthesis of 6-(8-(benzo[d]thiazol-2-ylcarbamoyl)-3,4-dihydroisoquinolin-2(1H)-yl)-3-(3-(4-(2-(pyrrolidin-1-yl)ethoxy)phenoxy)propyl)picolinic acid (106)

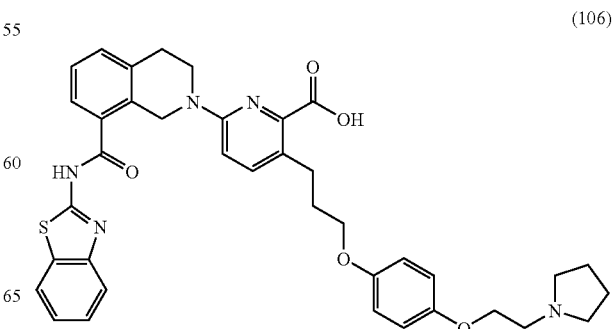

(106)

Step 1: Preparation of 1-(2-(4-(benzyloxy)phenoxy)ethyl)pyrrolidine (106A)

(106A)

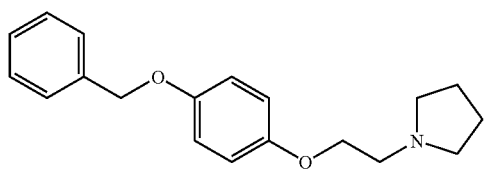

Compound 106A was prepared in a similar manner to the synthesis of compound 35A by substituting compound 34D and compound 31F with 2-(pyrrolidin-1-yl)ethanol and 4-(benzyloxy)phenol, respectively: DCI (+)MS: 298 (M+H)$^+$.

Step 2: Preparation of 4-(2-(pyrrolidin-1-yl)ethoxy)phenol (106B)

(106B)

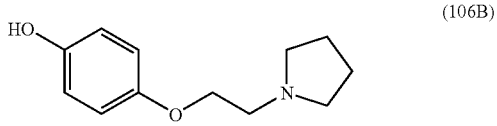

Compound 106B was prepared in a similar manner to the synthesis of compound 31F by substituting compound 31E with compound 106A: $^1$H NMR (DMSO-d$_6$): δ 8.88 (s, 1H), 6.72-6.75 (m, 2H), 6.64-6.67 (m, 2H), 3.94 (d, J=6.1 Hz, 2H), 2.72 (d, J=5.95 Hz, 2H), 2.48-2.51 (m, 4H), 1.65-1.68 (m, 4H) ESI (+)/MS: 208 (M+H)$^+$.

Step 3: Preparation of title compound 106

(106)

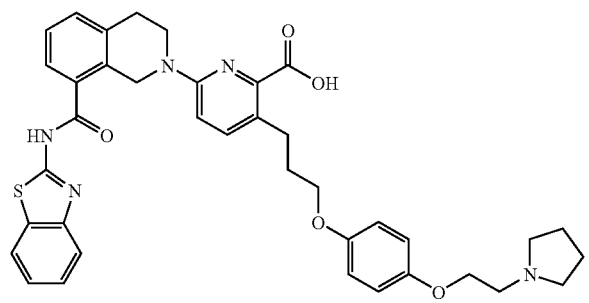

The title compound 106 was prepared in a similar manner to the synthesis of compound 105 by substituting compound 87C with compound 106B: $^1$H NMR (DMSO-d$_6$): δ 12.84 (s, 1H), 9.68 (s, 1H), 8.04 (d, J=7.93 Hz, 1H), 7.79 (d, J=8.24 Hz, 1H), 7.60 (d, J=7.32 Hz, 1H), 7.56 (d, J=8.54 Hz, 1H), 7.34-7.50 (m, 4H), 6.86-6.97 (m, 6H), 4.92 (s, 2H), 4.19-4.21 (m, 2H), 3.86-3.89 (m, 6H), 3.08-3.13 (m, 4H), 2.98 (t, J=5.8 Hz, 1H), 2.79-2.82 (m, 2H), 1.87-2.05 (m, 6H) ESI (+)/MS: 678 (M+H)$^+$.

Example 107

Synthesis of 2-(8-(benzo[d]thiazol-2-ylcarbamoyl)-3,4-dihydroisoquinolin-2(1H)-yl)-5-(3-(4-(3-(dimethylamino)propyl)phenoxy)propyl)thiazole-4-carboxylic acid (107)

(107)

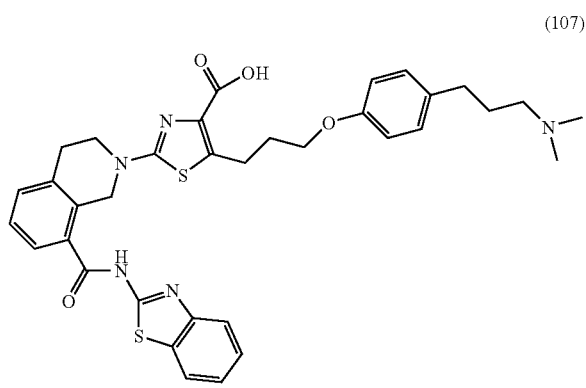

Step 1: Preparation of 4-(3-(dimethylamino)propyl)phenol (107A)

(107A)

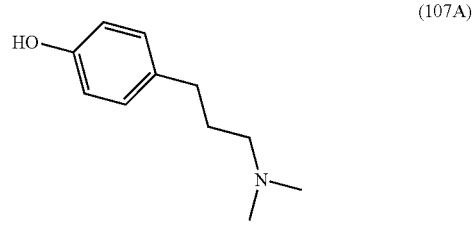

Compound 107A was prepared using the same procedure described in step 1 of Example 100 by replacing compound 97B$^1$ and compound 97B$^2$ with compound 74A: LCMS (APCI) 180 (M+H).

Step 2: Preparation of Title Compound 107

The title compound 107 was prepared using the same procedure described in step 2 of Example 54 by replacing compound 54A with compound 107A. The title compound 107 was obtained as a TFA salt: $^1$H NMR (500 MHz, DMSO-D$_6$) δ ppm 12.90 (2H, br, s), 9.41 (1H, s), 8.04 (1H, d), 7.80 (1H, d), 7.67 (1H, d), 7.44-7.50 (2H, m), 7.34-7.41 (2H, m), 7.10 (2H, d), 6.84 (2H, d), 4.83 (2H, s), 3.94 (2H, t), 3.72 (2H, t), 3.17 (2H, t), 2.96-3.06 (4H, m), 2.76 (3H, s), 2.75 (3H, s), 2.51-2.56 (2H, m), 1.96-2.02 (2H, m), 1.83-1.90 (2H, m); LCMS (APCI) 656 (M+H).

Example 108

Synthesis of 2-(8-(benzo[d]thiazol-2-ylcarbamoyl)-3,4-dihydroisoquinolin-2(1H)-yl)-5-(3-(2,5-difluoro-4-(4-methylpiperazin-1-yl)phenoxy)propyl)thiazole-4-carboxylic acid (108)

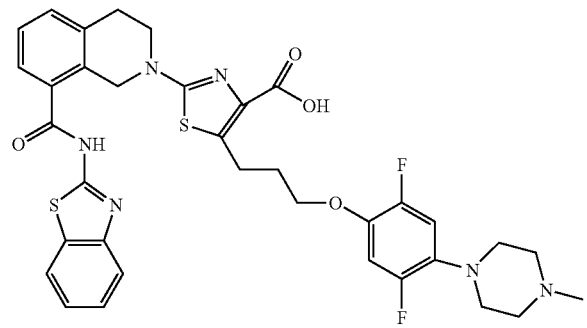

(108)

Step 1: Preparation of 1-(benzyloxy)-4-bromo-2,5-difluorobenzene (108A)

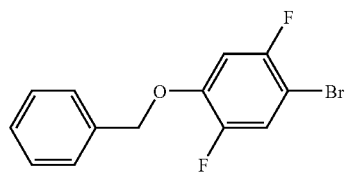

(108A)

Compound 108A was prepared using the same procedure described in step 1 of Example 93 by replacing 4-bromo-2-fluorophenol with 4-bromo-2,5-difluorophenol.

Step 2: Preparation of 1-(4-(benzyloxy)-2,5-difluorophenyl)-4-methylpiperazine (108B)

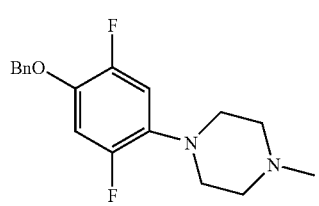

(108B)

Compound 108B was prepared using the same procedure described in step 2 of Example 93 by replacing compound 93A with compound 108A: LCMS (APCI) 319 (M+H).

Step 3: Preparation of 2,5-difluoro-4-(4-methylpiperazin-1-yl)phenol (108C)

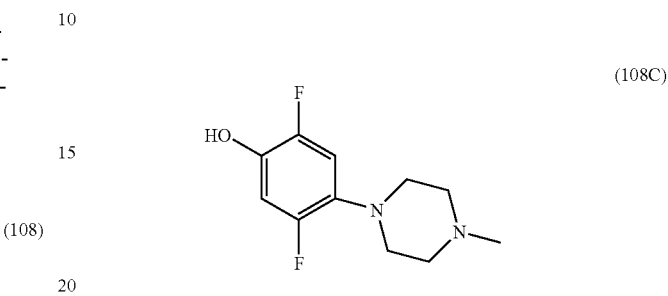

(108C)

Compound 108C was prepared using the same procedure described in step 3 of Example 93 by replacing compound 93B with compound 108B: LCMS (APCI) 229 (M+H).

Step 4: Preparation of Title Compound 108

The title compound 108 was prepared using the same procedure described in step 2 of Example 54 by replacing compound 54A with compound 108C. The title compound 108 was obtained as a TFA salt: $^1$H NMR (500 MHz, DMSO-D$_6$) δ ppm 12.89 (2H, s), 9.64 (1H, s), 8.03 (1H, d), 7.79 (1H, d), 7.67 (1H, d), 7.43-7.50 (2H, m), 7.33-7.41 (2H, m), 7.05-7.16 (2H, m), 4.83 (2H, s), 4.02 (2H, t), 3.72 (2H, t), 3.45-3.56 (2H, m), 3.34-3.48 (2H, m), 3.11-3.24 (4H, m), 3.03 (2H, t), 2.87-2.98 (2H, m), 2.85 (3H, d), 1.94-2.03 (2H, m). LCMS (APCI) 705 (M+H).

Example 109

Synthesis of tert-butyl 6-(8-(benzo[d]thiazol-2-ylcarbamoyl)-3,4-dihydroisoquinolin-2(1H)-yl)-3-(3-(2-chloropyridin-4-yloxy)propyl)picolinate (109)

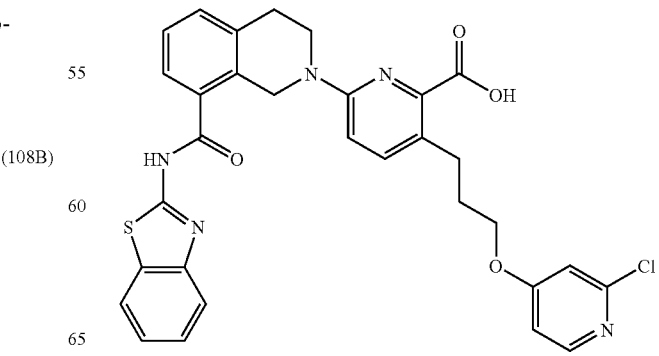

(109)

Step 1: Preparation of tert-butyl 6-(8-(benzo[d]thiazol-2-ylcarbamoyl)-3,4-dihydroisoquinolin-2(1H)-yl)-3-(3-(2-chloropyridin-4-yloxy)propyl)picolinate (109A)

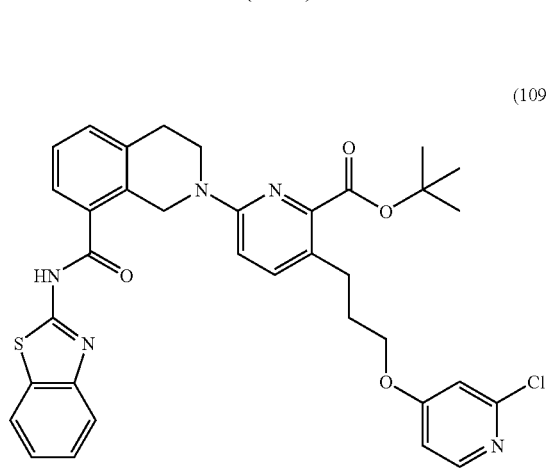

Compound 109A was prepared as a TFA salt in a similar manner to the synthesis of compound 51 by substituting compound 51A and compound 2C with compound 96D and 2-chloropyridin-4-ol, respectively: APCI (+)/LC/MS: 657 (M+H)$^+$.

Step 2: Preparation of Title Compound 109B

The title compound 109 was prepared in a similar manner to the synthesis of compound 94 by substituting compound 94G with compound 109A: $^1$H NMR (DMSO-d$_6$): δ 12.85 (s, 1H), 8.17 (d, J=5.8 Hz, 1H), 8.04 (d, J=7.93 Hz, 1H), 7.79 (d, J=8.24 Hz, 1H), 7.60 (d, J=7.32 Hz, 1H), 7.56 (d, J=8.85 Hz, 1H), 7.34-7.49 (m, 4H), 7.09 (d, J=2.44 Hz, 1H), 6.94-6.97 (m, 2H), 4.93 (s, 2H), 4.06 (t, J=6.26 Hz, 2H), 3.87 (t, J=5.95 Hz, 2H), 2.98 (t, J=5.8 Hz, 2H), 2.78-2.82 (m, 2H), 1.92-1.98 (m, 2H); ESI (+)/MS: 600 (M+H)$^+$.

Example 110

Step 1: 2-(8-(benzo[d]thiazol-2-ylcarbamoyl)-3,4-dihydroisoquinolin-2(1H)-yl)-5-((6-(3-morpholinopropoxy)naphthalen-2-yl)ethynyl)thiazole-4-carboxylic acid (110)

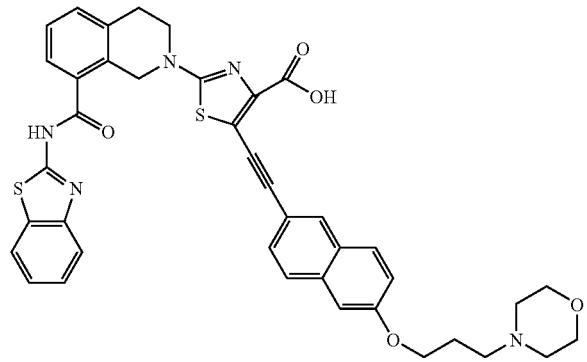

Step 1: Preparation of 6-((trimethylsilyl)ethynyl)naphthalen-2-ol (110A)

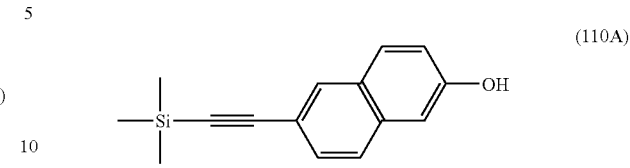

To a mixture of 6-bromonaphthalen-2-ol (3.8 g, 17.04 mmol), ethynyltrimethylsilane (7.08 ml, 51.1 mmol), (PPh$_3$)$_2$PdCl$_2$ (1.79 g, 2.56 mmol), TEA (12 ml, 85 mmol) in THF (12 ml) was added copper(I) iodide (0.324 g, 1.70 mmol). The resulting mixture was heated at 70° C. in oil bath overnight and cooled. To the mixture was added silica gel (40 g) and the resulting mixture was dried on vacuum. The gel powder was loaded on a silica gel column, eluted with DCM to provide compound 110A.

Step 2: Preparation of 6-ethynylnaphthalen-2-ol (110B)

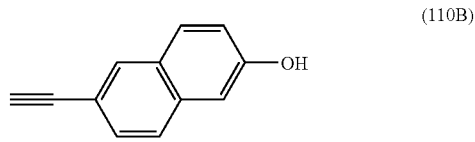

Compound 110A (770 mg, 3.20 mmol) in MeOH (5 ml) and THF (10 ml) was treated with K$_2$CO$_3$ (885 mg, 6.41 mmol) at room temperature for 3 h. The reaction was diluted with ethyl acetate and washed with water. The organic layer was concentrated and the residue was purified by flash chromatography, eluted with DCM to provide the compound 110B.

Step 3: Preparation of 4-(3-(6-ethynylnaphthalen-2-yloxy)propyl)morpholine (110C)

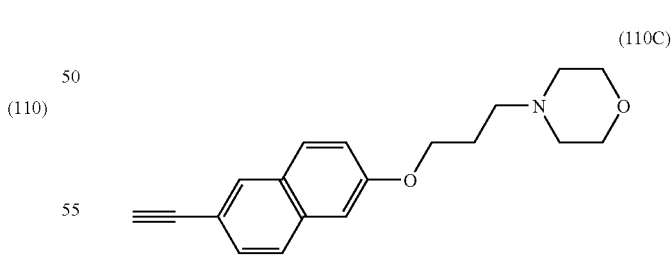

To a mixture of compound 110B (57 mg, 0.34 mmol), 3-morpholinopropan-1-ol (98 mg, 0.68 mmol) and triphenylphosphine (133 mg, 0.508 mmol) in THF (1.5 ml) was added (E)-di-tert-butyl diazene-1,2-dicarboxylate (117 mg, 0.508 mmol). The reaction mixture was stirred for 1 h and insoluble material was filtered off The filtrate was concentrated and the residue was purified by reverse phase HPLC (gradient: 0-55% acetonitrile in 0.1% TFA water/40 min) to provide compound 110C: LCMS (APCI) 296 (M+H).

Step 4: Preparation of methyl 2-(8-(benzo[d]thiazol-2-yl((2-(trimethylsilyl)ethoxy)methyl)carbamoyl)-3,4-dihydroisoquinolin-2(1H)-yl)-5-((6-(3-morpholinopropoxy)naphthalen-2-yl)ethynyl)thiazole-4-carboxylate (110D)

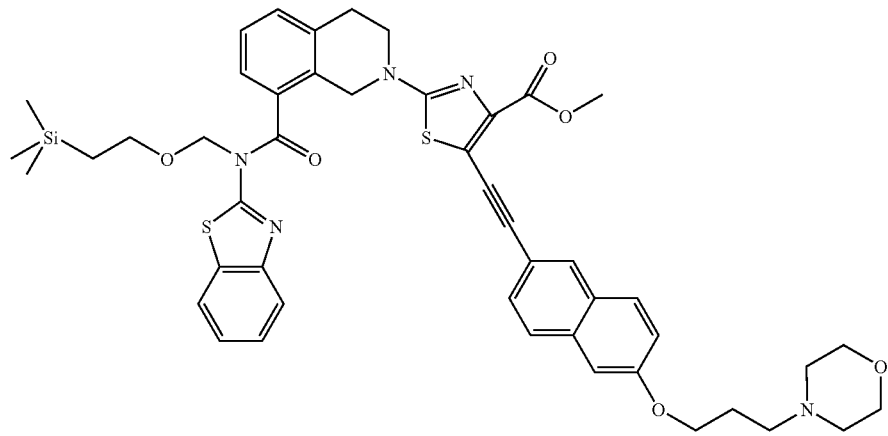

(110D)

To a mixture of compound 47D (200 mg, 0.283 mmol), compound 110C, (PPh₃)₂PdCl₂ (49.7 mg, 0.071 mmol), TEA (0.394 ml, 2.83 mmol) in DMF (5 ml) was added copper (I) iodide (5.40 mg, 0.028 mmol). The resulting mixture was heated at 120° C. in oil bath for 5 h. The reaction mixture was concentrated and purified by RP HPLC, eluting with 10-95% acetonitrile in 0.1% TFA water over 70 min to provide compound 110D: LCMS (APCI) 875 (M+H).

Step 5: Preparation of title compound 110

The title compound 110 was prepared using the same procedure described in step 3 of Example 97 by replacing compound 97B¹ and compound 97B² with compound 110D. The title compound 110 was obtained as a TFA salt: ¹H NMR (500 MHz, DMSO-d₆) δ ppm 12.88-13.12 (s, br, 1H), 12.94 (s, 1H), 9.64-9.69 (bs, 1H), 8.04-8.06 (m, 2H), 7.88 (d, J=9.0 Hz, 1H), 7.83 (d, J=8.8 Hz, 1H), 7.78-7.83 (m, 1H), 7.69-7.72 (m, 1H), 7.46-7.52 (m, 3H), 7.43 (t, J=7.6 Hz, 1H), 7.35-7.38 (m, 2H), 7.22 (dd, J=8.9, 2.4 Hz, 1H), 4.94-4.95 (bs, 2H), 4.21 (t, J=5.9 Hz, 2H), 3.98-4.06 (m, 2H), 3.78-3.81 (m, 2H), 3.62-3.68 (m, 2H), 3.48-3.54 (m, 2H), 3.01-3.15 (m, 6H), 2.17-2.24 (m, 2H); LCMS (APCI); 730 (M+H).

Example 111

Synthesis of 2-(8-(benzo[d]thiazol-2-ylcarbamoyl)-3,4-dihydroisoquinolin-2(1H)-yl)-5-(2-(6-(3-morpholinopropoxy)naphthalen-2-yl)ethyl)thiazole-4-carboxylic acid (111)

(111)

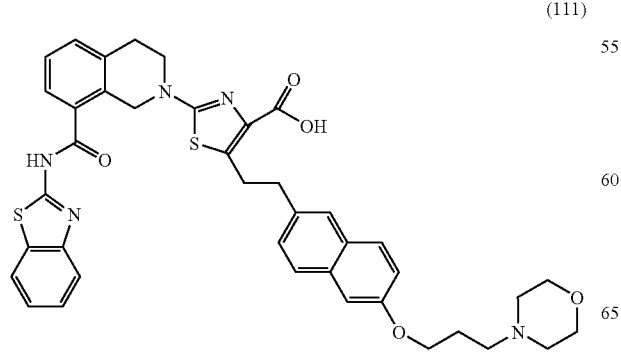

Step 1: Preparation of 2-(8-(benzo[d]thiazol-2-yl((2-(trimethylsilyl)ethoxy)methyl)carbamoyl)-3,4-dihydroisoquinolin-2(1H)-yl)-5-(2-(6-(3-morpholinopropoxy)naphthalen-2-yl)ethyl)thiazole-4-carboxylic acid (111A)

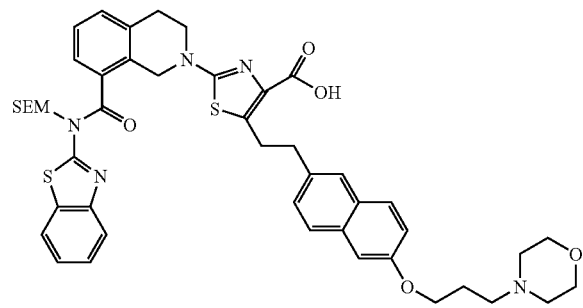

(111A)

The title compound 111A was prepared using the same procedure described in step 1 of Example 100 by replacing compounds 97B[1] and compound 97B[2] with compound 110D: LCMS (APCI) 879 (M+H).

Step 2: Preparation of Title Compound 111

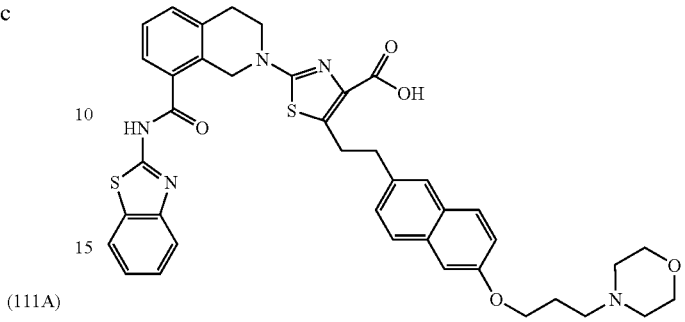

(111)

The title compound 111 was prepared using the same procedure described in step 3 of Example 97 by replacing compound 97B[1] and compound 97B[2] with compound 111A. The title compound 111 was obtained as a TFA salt: $^1$H NMR (500 MHz, DMSO-$d_6$) δ ppm 12.87-12.94 (s, br, 1H), 12.27-12.80 (s, br, 1H), 9.65-9.71 (s, br, 1H), 8.05 (d, J=7.7 Hz, 1H), 7.80 (d, J=7.8 Hz, 1H), 7.74 (d, J=9.2 Hz, 1H), 7.72 (d, J=8.5 Hz, 1H), 7.67 (d, J=6.7 Hz, 1H), 7.63-7.64 (m, 1H), 7.46-7.50 (m, 1H), 7.43-7.46 (m, 1H), 7.34-7.42 (m, 3H), 7.28 (d, J=2.6 Hz, 1H), 7.12 (dd, J=8.9, 2.5 Hz, 1H), 4.81 (s, 2H), 4.16 (t, J=5.8 Hz, 2H), 4.01 (d, J=12.2 Hz, 2H), 3.71 (t, J=6.0 Hz, 2H), 3.65 (t, J=12.1 Hz, 2H), 3.50 (d, J=11.9 Hz, 2H), 3.07-3.16 (m, 2H), 2.96-3.04 (m, 3H), 2.15-2.22 (m, 2H). LCMS (APCI) 734 (M+H).

Example 112

Synthesis of 6-(8-(benzo[d]thiazol-2-ylcarbamoyl)-3,4-dihydroisoquinolin-2(1H)-yl)-3-(3-(4-(5-(2-(dimethylamino)ethoxy)pyrimidin-2-yl)phenoxy)propyl)picolinic acid (112)

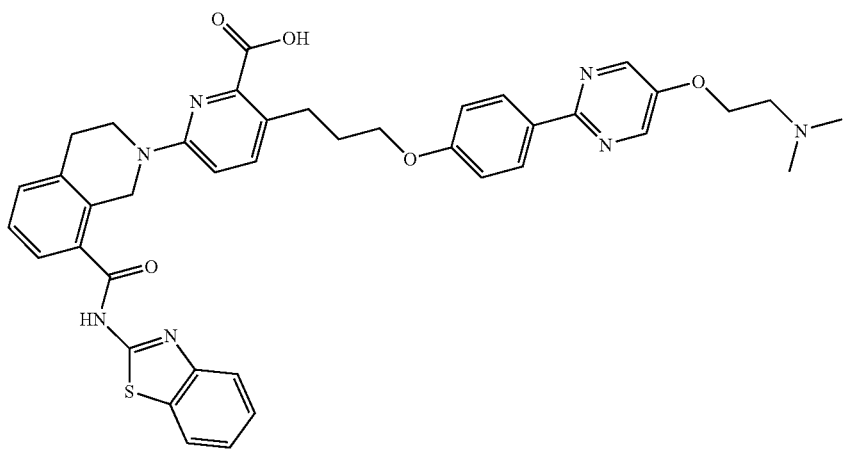

(112)

Step 1: Preparation of 2-chloropyrimidin-5-ol (112A)

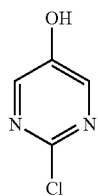

(112A)

2-Chloro-5-methoxypyrimidine (0.46 g, 3.18 mmol) in methylene chloride (10 mL) was treated with 1.0 N boron tribromide (16 mL, 16 mmol) at room temperature. The solution was stirred overnight. After this time the reaction was partitioned between saturated NaHCO$_3$ and DCM. The aqueous layer was extracted with additional DCM. The combined organic layers were dried (MgSO4), filtered, and concentrated. The residue was purified by flash column chromatography on silica gel to give 0.26 g of compound 112A (62%): $^1$H NMR (DMSO-d$_6$): δ 10.03 (s, 1H), 8.30 (s, 2H), ESI (−)/MS: 129 (M−H)$^-$.

Step 2: Preparation of 2-(2-chloropyrimidin-5-yloxy)-N,N-dimethylethanamine (112B)

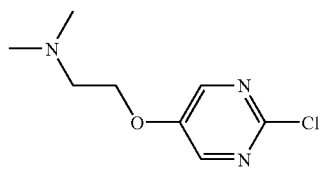

(112B)

Compound 112B was prepared in a similar manner to the synthesis of step 1 of Example 35 by substituting compound 34D and compound 31F with 2-(dimethylamino)ethanol and compound 112A, respectively: ESI (+)MS: 201 (M+H)$^-$.

Step 3: Preparation of 4-(5-(2-(dimethylamino)ethoxy)pyrimidin-2-yl)phenol (112C)

(112C)

Compound 112C was prepared in a similar manner to the synthesis of compound 34D by substituting compound 34C and 4-(hydroxymethyl)phenylboronic acid with compound 112B and 4-(4,4,5,5-tetramethyl-1,3,2-dioxaborolan-2-yl)phenol, respectively: $^1$H NMR (DMSO-d$_6$): δ 9.80 (s, 1H), 8.56 (s, 2H), 8.12-8.15 (m, 1H), 6.83-6.86 (m, 2H), 4.23 (t, J=5.8 Hz, 2H), 2.65 (t, J=5.65 Hz, 2H), 2.22 (s, 6H); ESI (+)/MS: 259 (M+H)$^+$.

Step 4: Preparation of 6-(8-(benzo[d]thiazol-2-ylcarbamoyl)-3,4-dihydroisoquinolin-2(1H)-yl)-3-(3-(4-(5-(2-(dimethylamino)ethoxy)pyrimidin-2-yl)phenoxy)propyl)picolinic acid (112D)

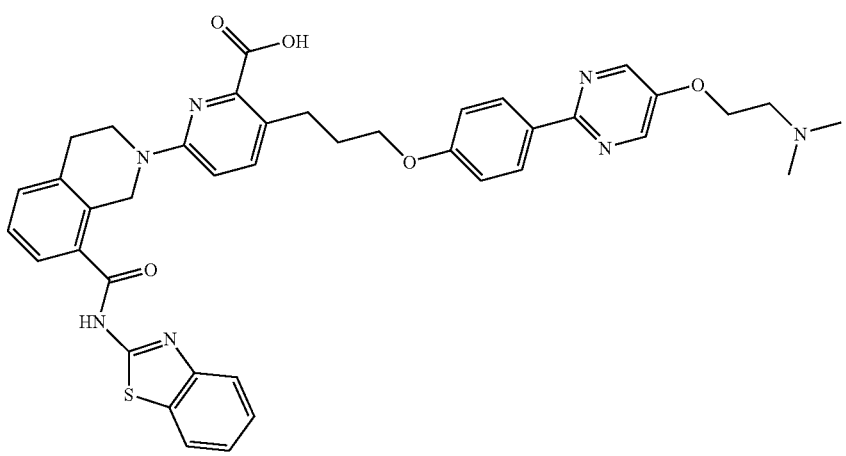

(112D)

The title compound 112D was prepared in a similar manner to the synthesis of compound 105 by substituting compound 87A with compound 112C: $^1$H NMR (DMSO-d$_6$): δ 12.84 (s, 1H), 9.70 (s, 1H), 8.64 (s, 2H), 8.23 (d, J=8.85 Hz, 2H), 8.04 (d, J=7.93 Hz, 1H), 7.79 (d, J=8.24 Hz, 1H), 7.57-7.61 (m, 2H), 7.34-7.49 (m, 4H), 7.02 (t, J=8.85 Hz, 2H), 6.97 (d, J=8.85 Hz, 1H), 4.93 (s, 2H), 4.52-4.54 (m, 2H), 4.01 (t, J=6.41 Hz, 2H), 3.87 (t, J=5.95 Hz, 2H), 2.95 (t, J=5.8 Hz, 2H), 2.82-2.85 (m, 2H), 1.95-2.00 (m, 2H): ESI (+)/MS: 730 (M+H)$^+$.

Example 113

Synthesis of 6-(8-(benzo[d]thiazol-2-ylcarbamoyl)-3,4-dihydroisoquinolin-2(1H)-yl)-3-(3-(3-(2-(dimethylamino)ethoxy)phenoxy)propyl)picolinic acid (113)

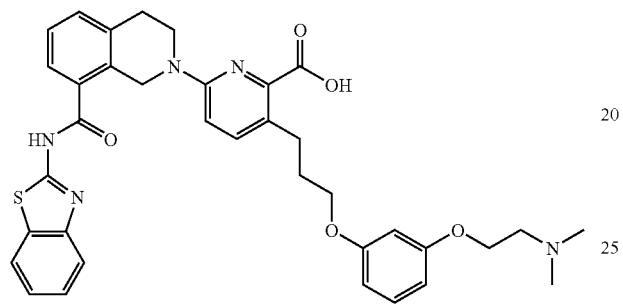

Step 1: Preparation of 2-(3-(benzyloxy)phenoxy)-N,N-dimethylethanamine (113A)

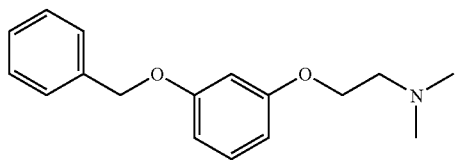

Compound 113A was prepared in a similar manner to the synthesis of step 1 of Example 35 by substituting compound 34D and compound 31F with 2-(dimethylamino)ethanol and 3-(benzyloxy)phenol, respectively: DCI (+)MS: 272 (M+H)$^+$.

Step 2: Preparation of 3-(2-(dimethylamino)ethoxy)phenol (113B)

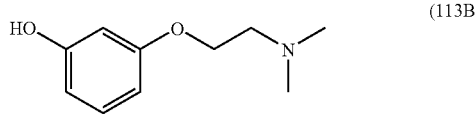

Compound 113B was prepared in a similar manner to the synthesis of compound 31F by substituting compound 31E with compound 113A: $^1$H NMR (DMSO-d$_6$): δ 9.34 (s, 1H), 7.03 (t, J=8.03 Hz, 1H), 6.30-6.36 (m, 3H), 3.96 (d, J=5.95 Hz, 2H), 2.58 (d, J=5.8 Hz, 2H), 2.20 (s, 2H) ESI (+)/MS: 182 (M+H)$^+$.

Step 3: Preparation of Title Compound 113

The title compound 113 was prepared in a similar manner to the synthesis of compound 105 by substituting compound 87A with compound 113C: $^1$H NMR (DMSO-d$_6$): δ 12.85 (s, 1H), 9.59 (s, 1H), 8.64 (s, 2H), 8.04 (d, J=7.63 Hz, 1H), 7.80 (d, J=8.24 Hz, 1H), 7.61 (d, J=7.32 Hz, 1H), 7.56 (d, J=8.54 Hz, 1H), 7.34-7.49 (m, 4H), 7.19 (t, J=8.09 Hz, 1H), 6.96 (d, J=8.85 Hz, 1H), 4.93 (s, 2H), 4.27-4.29 (m, 2H), 3.92 (t, J=6.56 Hz, 2H). 3.87 (t, J=5.95 Hz, 2H), 2.99 (t, J=5.8 Hz, 2H), 2.79-2.82 (m, 2H), 1.91-1.97 (m, 2H); ESI (+)/MS: 652 (M+H)$^+$.

Example 114

Synthesis of 2-(8-(benzo[d]thiazol-2-ylcarbamoyl)-3,4-dihydroisoquinolin-2(1H)-yl)-5-(3-(4-(2-(pyrrolidin-1-yl)ethoxy)phenoxy)propyl)thiazole-4-carboxylic acid (114)

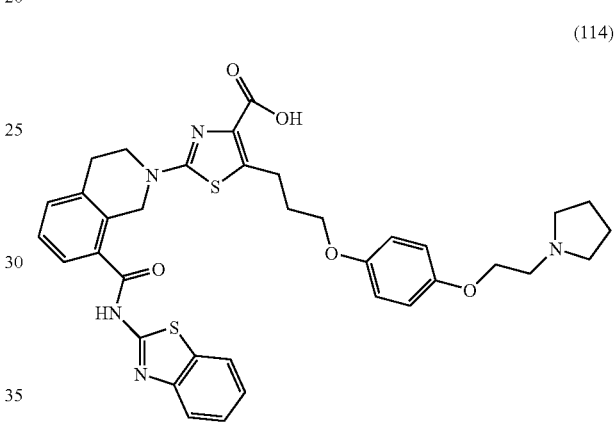

The title compound 114 was prepared as a TFA salt in a similar manner to the synthesis of compound 51 by substituting compound 51A with compound 106B: $^1$H NMR (DMSO-d$_6$): δ 12.90 (s, 1H), 9.75 (s, 1H), 8.04 (d, J=7.93 Hz, 1H), 7.80 (d, J=7.93 Hz, 1H), 7.68 (d, J=7.32 Hz, 2H), 7.35-7.50 (m, 4H), 6.86-6.93 (m, 4H), 4.83 (s, 2H), 4.19-4.21 (m, 2H), 3.92 (d, J=6.26 Hz, 2H), 3.72 (d, J=5.95 Hz, 1H), 3.55 (br, 4H), 3.10-3.18 (m, 4H), 3.03 (t, J=5.8 Hz, 2H), 1.85-2.02 (m, 6H). ESI (+)/MS: 684 (M+H)$^+$.

Example 115

Synthesis of 2-(8-(benzo[d]thiazol-2-ylcarbamoyl)-3,4-dihydroisoquinolin-2(1H)-yl)-5-(3-(2,5-difluoro-4-(2-morpholinoethylamino)phenoxy)propyl)thiazole-4-carboxylic acid (115)

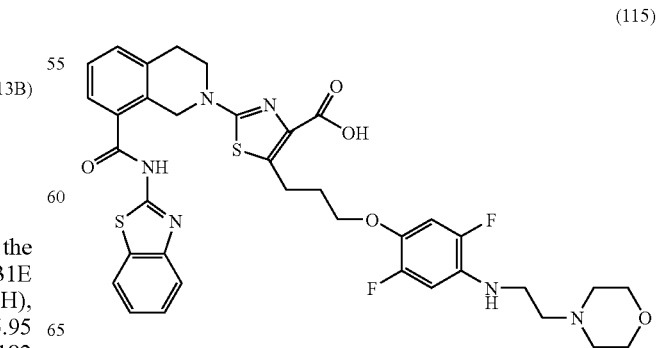

The title compound 115 was prepared using the same procedure described for Example 108 by replacing 1-methylpiperazine with 2-morpholinoethanamine. The title compound was obtained as a TFA salt: $^1$H NMR (500 MHz, PYRIDINE-D$_5$) δ ppm 8.05 (1H, d), 7.98 (1H, d), 7.85 (1H, d), 7.50 (1H, t), 7.26-7.38 (3H, m), 7.12 (1H, dd), 6.81 (1H, dd), 5.20 (2H, s), 4.11 (2H, t), 3.83 (1H, s), 3.79 (2H, t), 3.65-3.73 (4H, m), 3.52-3.59 (2H, m), 3.21 (2H, t), 2.88 (2H, t), 2.58 (2H, t), 2.42 (4H, br, s), 2.18-2.27 (2H, m), LCMS (APCI) 735 (M+H).

Example 116

Synthesis of 2-(8-(benzo[d]thiazol-2-ylcarbamoyl)-3,4-dihydroisoquinolin-2(1H)-yl)-5-(3-(4-(3-(dimethylamino)prop-1-ynyl)-2-fluorophenoxy)propyl)thiazole-4-carboxylic acid (116):

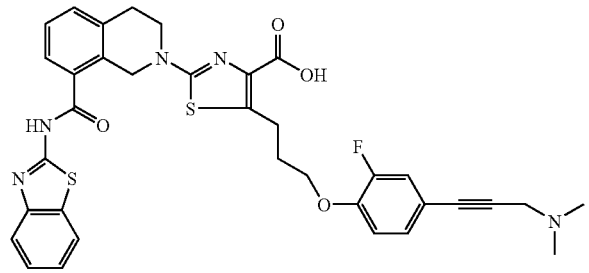

(116)

The title compound 116 was prepared using the same procedure described for step 3 of example 97 by replacing compound 94F with compound 47F. The title compound was obtained as a TFA salt: $^1$H NMR (500 MHz, DMSO-D$_6$) δ ppm 12.90 (1H, s), 10.12 (1H, s), 8.04 (1H, d), 7.80 (1H, d), 7.67 (1H, d), 7.34-7.50 (5H, m), 7.31 (1H, d), 7.18 (1H, t), 4.83 (2H, s), 4.30 (2H, s), 4.10 (2H, t), 3.72 (2H, t), 3.12-3.23 (2H, m), 3.03 (2H, t), 2.87 (6H, s), 1.97-2.09 (2H, m); LCMS (APCI) 670 (M+H).

Example 117

Synthesis of 2-(8-(benzo[d]thiazol-2-ylcarbamoyl)-3,4-dihydroisoquinolin-2(1H)-yl)-5-(3-(4-(3-(dimethylamino)prop-1-ynyl)-3-fluorophenoxy)propyl)thiazole-4-carboxylic acid (117):

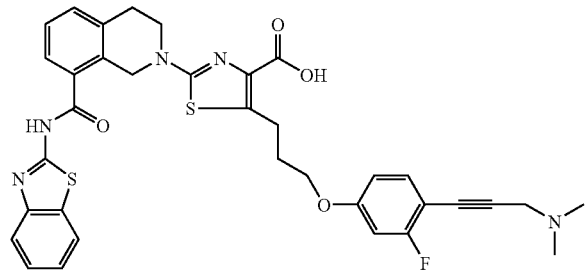

(117)

The title compound 117 was prepared using the same procedure described in Example 97 by replacing 4-bromo-2-fluorophenol and compound 94F with 4-bromo-3-fluorophenol and compound 47F, respectively. The title compound was obtained as a TFA salt: $^1$H NMR (500 MHz, DMSO-D$_6$) δ ppm 12.91 (1H, s), 10.13 (1H, s), 8.04 (1H, d), 7.80 (1H, d), 7.68 (1H, d), 7.44-7.51 (3H, m), 7.34-7.42 (2H, m), 7.03 (1H, dd), 6.77-6.82 (1H, m), 4.83 (2H, s), 4.32 (2H, s), 4.08 (2H, t), 3.72 (2H, t), 3.15-3.24 (2H, m), 3.03 (2H, t), 2.86 (6H, s), 1.98-2.08 (2H, m). LCMS (APCI) 670 (M+H).

Example 118

Synthesis of 2-(8-(benzo[d]thiazol-2-ylcarbamoyl)-3,4-dihydroisoquinolin-2(1H)-yl)-5-(3-(4-(3-(dimethylamino)prop-1-ynyl)-2,5-difluorophenoxy)propyl)thiazole-4-carboxylic acid (118):

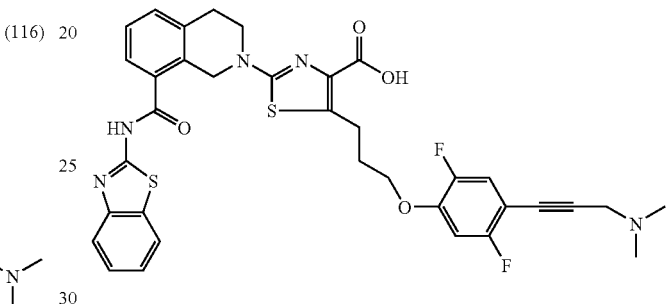

(118)

The title compound 118 was prepared using the same procedure described in Example 97 by replacing 4-bromo-2-fluorophenol and compound 94F with 4-bromo-2,5-difluorophenol and compound 47F, respectively. The title compound 118 was obtained as a TFA salt: $^1$H NMR (500 MHz, DMSO-D$_6$) δ ppm 12.90 (1H, s), 10.19 (1H, s), 8.04 (1H, d), 7.80 (1H, d), 7.67 (1H, d), 7.53 (1H, dd), 7.43-7.50 (2H, m), 7.34-7.42 (2H, m), 7.26 (1H, dd), 4.83 (2H, s), 4.35 (2H, s), 4.12 (2H, t), 3.72 (2H, t), 3.12-3.21 (2H, m), 3.03 (2H, t), 2.87 (6H, s), 1.96-2.10 (2H, m); LCMS (APCI) 688 (M+H).

Example 119

Synthesis of 2-(8-(benzo[d]thiazol-2-ylcarbamoyl)-3,4-dihydroisoquinolin-2(1H)-yl)-5-(3-(2-chloro-4-(3-(dimethylamino)prop-1-ynyl)phenoxy)propyl)thiazole-4-carboxylic acid (119):

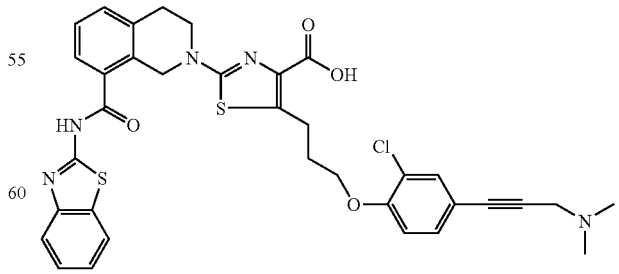

(119)

The title compound (119) was prepared using the same procedure described for Example 97 by replacing 4-bromo-2-fluorophenol and compound 94F with 4-bromo-2-chlorophenol and compound 47F, respectively. The title compound 119 was obtained as a TFA salt: ¹H NMR (500 MHz, DMSO-D₆) δ ppm 12.90 (1H, s), 10.09 (1H, s), 8.04 (1H, d), 7.80 (1H, d), 7.67 (1H, d), 7.62 (1H, d), 7.44-7.50 (3H, m), 7.35-7.41 (2H, m), 7.15 (1H, d), 4.83 (2H, s), 4.30 (2H, s), 4.11 (2H, t), 3.72 (2H, t), 3.17-3.23 (2H, m), 3.03 (2H, t), 2.88 (6H, s), 2.00-2.10 (2H, m); LCMS (APCI) 686 (M+H).

Example 120

Synthesis of 6-(8-(benzo[d]thiazol-2-ylcarbamoyl)-3,4-dihydroisoquinolin-2(1H)-yl)picolinic acid (120)

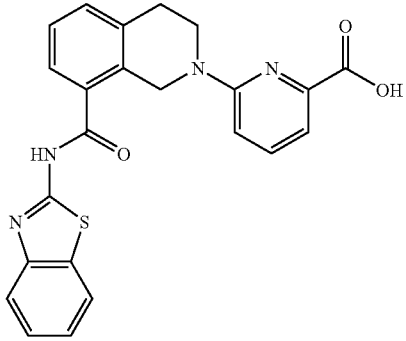

(120)

Step 1: Preparation of tert-butyl 6-fluoropicolinate (120A)

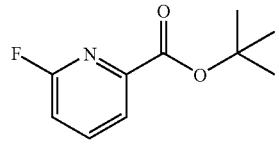

(120A)

Tosyl chloride (915 mg, 4.8 mmol) was added to a solution of 2-fluoro-picolinic acid (254 mg, 2 mmol) and pyridine (1.08 mL, 13.4 mmol) in 3.6 mL of t-BuOH at 0° C. The reaction was then stirred at room temperature for 12 hours. An aqueous solution of NaHCO₃ was then added and the mixture was extracted with ethyl acetate (3 times). The combined organic phases were washed with brine and dried over Na₂SO₄. The crude compound was purified by flash chromatography using SiO₂ (Petroleum Ether/EtOAc 100:0 to 90:10). The product 120A was obtained as a white solid (m=326 mg, 83%): ¹HNMR (ppm, CDCl₃) 1.6 (s, 9H), 7.05-7.11 (m, 1H), 7.85-7.93 (m, 2H).

Step 2: Preparation of tert-butyl 6-(8-(benzo[d]thiazol-2-ylcarbamoyl)-3,4-dihydroisoquinolin-2(1H)-yl)picolinate (120B)

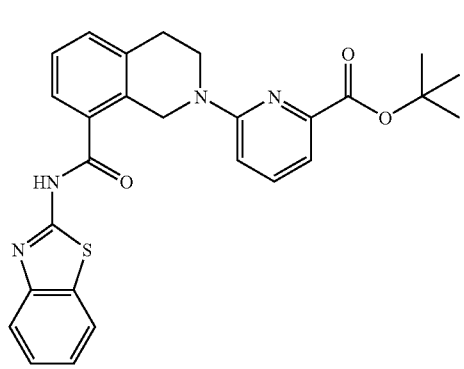

(120B)

Cs₂CO₃ (831 mg, 2.55 mmol) and 500 mg of 4 Å sieves were dried under high vacuum at 150° C. for 6 hours before the start of the reaction. Once cooled down, compound 120A (100 mg, 0.51 mmol) and compound 1B (327 mg, 0.61 mmol) were transferred to the reaction vessel and the atmosphere was purged with nitrogen. 1.5 mL of anhydrous DMA was then added and the reaction was stirred at 90° C. for 3 hours and then 100° C. for 2 hours. The cooled reaction mixture was then diluted with ethyl acetate and citric acid 10%. The organic phase was washed three times with citric acid, once with water and brine, and dried over Na₂SO₄. Concentration of the organic phase afforded an orange film/foam. This residue was purified by flash chromatography using SiO₂ (AcOEt/Pet. Eth. 0:100 to 40:60). to provide a white solid (72 mg, 29% yield): ¹HNMR (ppm, CDCl₃) 1.54 (s, 9H), 3.01 (t, J=5.85 Hz, 2H), 4.05 (t, J=6 Hz, 2H), 5.04 (s, 2H), 6.92 (dd, J=8.55 and 0.63 Hz, 1H), 7.09-7.29 (m, 5H), 7.34 (dd, J=7.32 and 0.63 Hz, 1H), 7.60-7.51 (m, 2H), 7.81 (d, J=9 Hz, 1H).

Step 3: Preparation of Title Compound 120

Compound 1B (71 mg, 0.15 mmol) was dissolved in 2 mL of EtOH. Two milliliters of water were then added followed by 2 mL of concentrated HCl. The reaction was stirred at room temperature for 72 hours until LCMS indicated complete conversion. Nitrogen gas was bubbled through the mixture to remove HCl and EtOH; a white solid precipitated. It was collected by filtration, rinsed with water and a small amount of Et₂O and dried under vacuum to provide the product as a white solid (42 mg, 67%): ¹HNMR (ppm, DMSO) 2.98 (t, J=6.15 Hz, 2H), 3.92 (t, J=6.06 Hz, 2H), 4.95 (s, 2H), 7.02 (d, J=8.5 Hz, 1H), 7.27 (d, J=7.3 Hz, 7.31-7.49 (m, 4H), 758 (d, J=7.5 Hz, 1H), 7.66-7.71 (m, 1H), 7.77 (d, J=8.0 Hz, 1H), 8.02 (d, J=7.9 Hz); LCMS m/z 431.0 (M+1).

Example 121

Synthesis of 6-(8-(benzo[d]thiazol-2-ylcarbamoyl)-3,4-dihydroisoquinolin-2(1H)-yl)-3-(3-phenoxypropyl)picolinic acid (121)

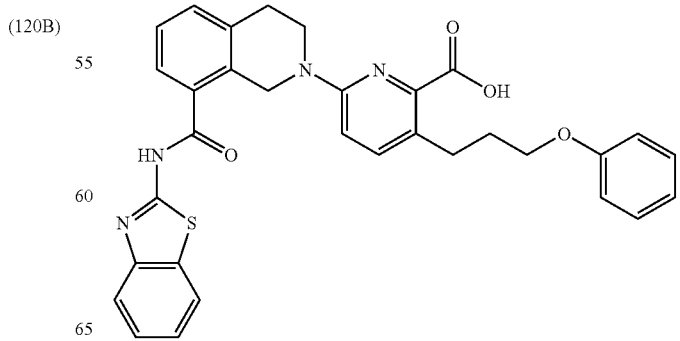

(121)

Step 1: Preparation of tert-butyl 2-bromo-5-chlorobenzoate (121A)

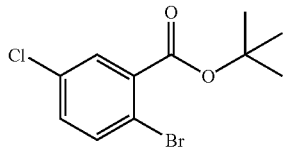

Tosyl chloride (7.7 g, 40.4 mmol) was added to a solution of 2-chloro-5-bromo picolinic acid (4 g, 17 mmol) and pyridine (9.2 mL, 114 mmol) in 33 mL of t-BuOH at 0° C. The reaction was then stirred at room temperature for 12 hours. NaHCO$_{3sat}$ was then added and the mixture was extracted with ethyl acetate (3 times). The combined organic phases were washed with brine and dried over Na$_2$SO$_4$. Concentration afforded the desired compound 121A (quantitative). It was used in the next step without further purification: $^1$H NMR (300 MHz, CDCl$_3$) δ 7.85 (d, 1H), 7.26 (d, 1H), 1.63 (s, 9H).

Step 2: Preparation of tert-butyl 6-(8-(benzo[d]thiazol-2-ylcarbamoyl)-3,4-dihydroisoquinolin-2(1H)-yl)-3-bromopicolinate (121B)

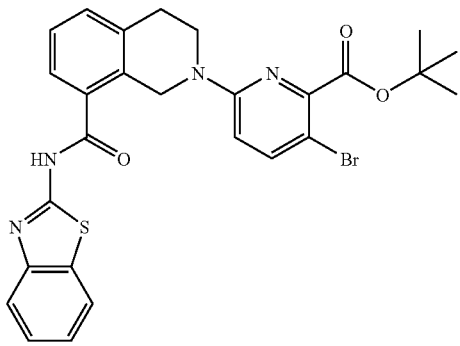

Cs$_2$CO$_3$ (4.1 g, 12.6 mmol) and 4 Å sieves were dried under high vacuum at 150° C. for 6 to 10 hours before the start of the reaction. Once cooled down, compound 121A (0.736 g, 2.53 mmol) and compound 1B (1.62 g, 3 mmol) were transferred to the reaction vessel and the atmosphere was purged with nitrogen. 12 mL of anhydrous DMA were then added and the reaction was stirred at 120° C. for 12 hours. The cooled reaction mixture was then diluted with ethyl acetate and citric acid 10%. The organic phase was washed three times with citric acid, once with water and brine, and dried over Na$_2$SO$_4$. Concentration of the organic phase afforded an orange film/foam. Purification on Flash Master (SiO$_2$, ethyl acetate/petroleum ether 0:100 to 40:60) afforded a the product 121B as a white solid (1.15 g, 80% yield): $^1$H NMR (300 MHz, CDCl$_3$) δ 7.86 (m, 1H), 7.71 (d, 1H), 7.60 (d, 1H), 7.50 (m, 1H), 7.42-7.22 (m, 5H), 6.67 (d, 1H), 4.99 (s, 2H), 3.95 (t, 2H), 3.01 (t, 2H), 1.56 (s, 9H).

Step 3: Preparation of tert-butyl 6-(8-(benzo[d]thiazol-2-yl((2-(trimethylsilyl)ethoxy)methyl)carbamoyl)-3,4-dihydroisoquinolin-2(1H)-yl)-3-bromopicolinate (121C):

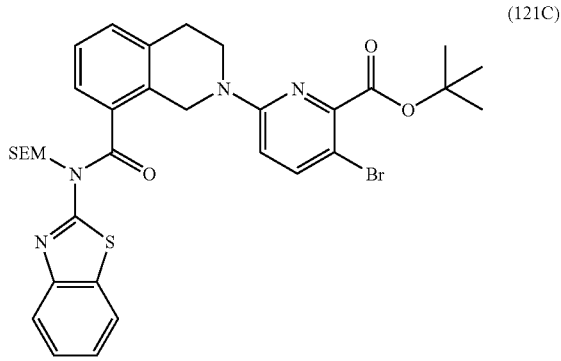

Compound 121B (350 mg, 0.62 mmol) was dissolved in THF. NEt$_3$ (127 μL, 0.91 mmol) and SEMCl (135 μL, 0.74 mmol) were added successively. The reaction was stirred at room temperature for 1 hour. It was then concentrated. The residue was taken into ethyl acetate and water. The aqueous layer was extracted three times with ethyl acetate. The combined organic layers were washed with brine and dried over Na$_2$SO$_4$. After concentration, the residue was purified by flash chromatography using the flash master: SiO$_2$, ethyl acetate/petroleum ether 0:100 to 30:70. A pale yellow foamy solid compound 121C was obtained (276 mg, 64%). NMR shows two N-SEM products: $^1$H NMR (300 MHz, CDCl$_3$), mixture of isomers (1:0.6) δ 8.28 (d, 1H), 7.86 (d, 1H), 7.71 (d, 1H), 7.62-7.42 (m, 5H), 7.38-7.26 (m, 5H), 6.80 (d, 1H), 6.55 (d, 0.6H), 5.98 (s, 2H), 5.53 (s, 1H), 5.19 (s, 2H), 4.67 (s, 1H), 4.00 (t, 2H), 3.93 (t, 1H), 3.75 (t, 2H), 3.61 (t, 1H), 3.02 (m, 3H), 1.61 (s, 9H), 1.53 (s, 5H), 0.98 (t, 2H), 0.82 (t, 1H), −0.09 (s, 9H).

Step 4: Synthesis of tert-butyl 6-(8-(benzo[d]thiazol-2-yl((2-(trimethylsilyl)ethoxy)methyl)carbamoyl)-3,4-dihydroisoquinolin-2(1H)-yl)-3-(3-phenoxyprop-1-ynyl)picolinate (121D)

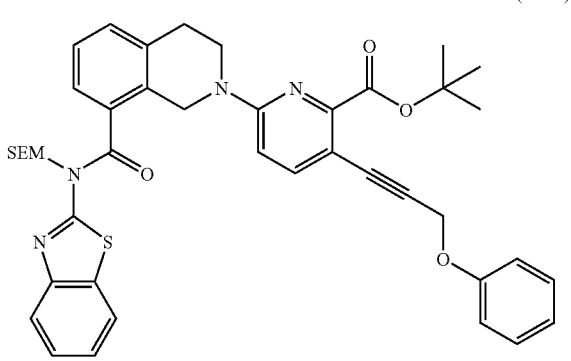

To pre-dried Cs₂CO₃ (378 mg, 1.16 mmol) was added compound 121C (180 mg, 0.26 mmol), 2-dicyclohexylphosphino-2',4',6'-tri-iso-propyl-1,1'-biphenyl (18 mg, 0.04 mmol) and bis(acetonitrile)dichloropalladium(II) (3.2 mg, 0.012 mmol). The atmosphere was purged with nitrogen and following the addition of propionitrile (3.0 mL) the mixture was stirred at room temperature for 10 min. before phenyl propargyl ether (205 mg, 1.54 mmol) was added. The mixture was heated at 105° C. for 1 hr, cooled to room temperature, concentrated, diluted with saturated NH₄Cl and extracted with EtOAc (3×). The organic phases were washed with brine (1×), dried (Na₂SO₄), filtered, and concentrated. The crude material was purified by flash column chromatography on silica gel using a gradient of PE:EtOAc 100:0-85:15, to give the product (90 mg, 47%): ¹H NMR (300 MHz, CDCl₃) δ 8.28 (d, 1H), 7.69 (d, 1H), 7.57 (m, 2H), 7.47 (t, 1H), 7.38-7.26 (m, 5H), 6.99 (m, 3H), 6.82 (d, 1H), 5.98 (s, 2H), 5.24 (s, 2H), 4.92 (s, 2H), 4.07 (t, 2H), 3.74 (t, 2H), 1.60 (s, 9H), 0.97 (t, 2H), −0.09 (s, 9H).

Step 5: Preparation of tert-butyl 6-(8-(benzo[d]thiazol-2-yl((2-(trimethylsilyl)ethoxy)methyl)carbamoyl)-3,4-dihydroisoquinolin-2(1H)-yl)-3-(3-phenoxypropyl)picolinate (121E):

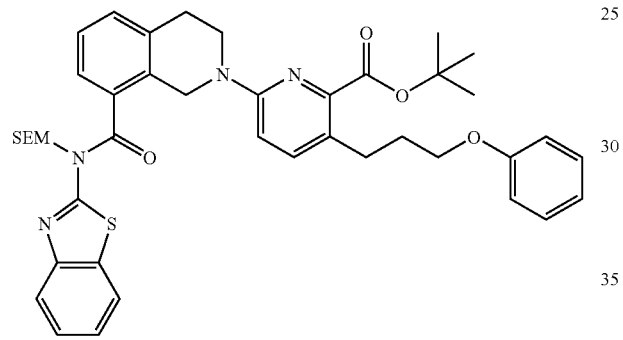

(121E)

PtO₂ (4.8 mg, 0.020 mmol) was added to a solution of compound 2D (60 mg, 0.080 mmol) in EtOAc (2.0 mL) and the mixture was stirred under H₂ atmosphere for 2 hrs. The mixture was filtered, washed with EtOAc and concentrated to give the product 121D (55 mg, 92%): ¹H NMR (300 MHz, CDCl₃) δ 8.26 (d, 1H), 7.69 (d, 1H), 7.57 (d, 1H), 7.48 (t, 1H), 7.40-7.23 (m, 6H), 6.97-6.82 (m, 4H), 5.97 (s, 2H), 5.20 (s, 2H), 4.03 (t, 2H), 3.96 (t, 2H), 3.75 (t, 2H), 3.04 (t, 2H), 2.88 (t, 2H), 2.06 (m, 2H), 1.62 (s, 9H), 0.97 (t, 2H), −0.09 (s, 9H).

Step 5: Preparation of Title Compound 121

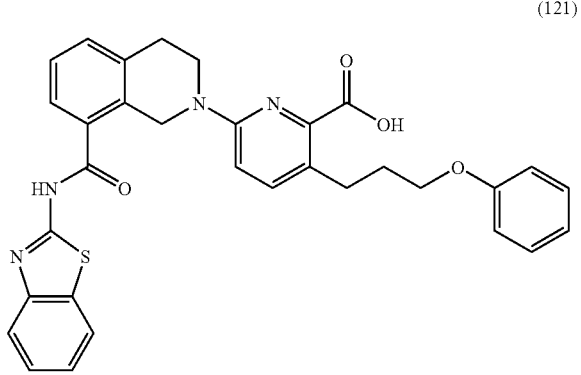

(121)

Compound 121E (55 mg, 0.073 mmol) was dissolved in 1 mL of EtOH. Water (1 mL) was added followed by 1 mL of concentrated HCl. The reaction was stirred at 50° C. for 12 hours. The solids that precipitated were collected by filtration and rinsed with water. The solid was purified by preparative HPLC to give a white solid: ¹H NMR (300 MHz, DMSO-d₆) δ2.09 (t, 2H), 3.06 (t, 2H), 3.21 (t, 2H), 3.91 (t, 2H), 3.97 (t, 2H), 5.21 (s, 2H), 6.87-6.94 (m, 4H), 7.25-7.42 (m, 5H), 7.46-7.50 (m, 2H), 7.56 (m, 1H), 8.01 (m, 1H); LCMS m/z 565.7 (M+1).

Example 122

Synthesis of 2-(8-(benzo[d]thiazol-2-ylcarbamoyl)-3,4-dihydroisoquinolin-2(1H)-yl)pyrimidine-4-carboxylic acid (122)

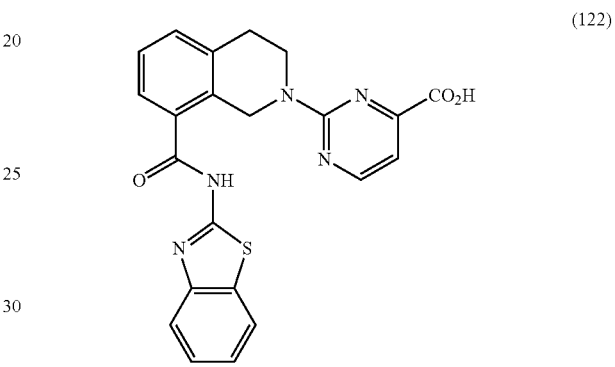

(122)

A mixture of compound 1B (309 mg, 1 mmol), 2-chloropyrimidine-4-carboxylic acid (134.5 mg, 1 mmol) cesium carbonate (975 mg, 3 mmol) in 2 ml of DMSO was heated to 60° C. for 6 h. The product was poured into water and precipitated out of solution and was collected by filtration. The crude material was chromatographed (SiO₂, 20% methanol in dichloromethane) to afford 37 as a white powder: LCMS (97% purity); retention time=8.70 min, 432.0 [M+H]; ¹H NMR (300 MHz, DMSO): 8.60 (1H, d), 8.25 (1H, d), 7.80 (1H, m), 7.60 (1H, d), 7.45 (1H, d), 7.1-7.2 (2H, m), 7.0 (1H, t), 6.75 (1H, d), 5.25 (2H, s), 3.95 (2H, t), 2.85 (2H, t).

Example 123

Synthesis of 2-(8-(benzo[d]thiazol-2-ylcarbamoyl)-3,4-dihydroisoquinolin-2(1H)-yl)-5-chloropyrimidine-4-carboxylic acid (123)

A mixture of compound 1B (309 mg, 1 mmol), 5-chloro-2-methanesulfonyl-pyrimidine-4-carboxylic acid (236 mg, 1 mmol) and cesium carbonate (975 mg, 3 mmol) in 2 ml of DMSO was heated to 60° C. for 6 h. The product was precipitated out of solution by addition to water and collected by filtration. The crude material was chromatographed (SiO₂, 20% methanol in dichloromethane) to afford title compound 123 as a white powder: LCMS (96% purity): m/z 465.9 [M+H].

Example 124

The measurement of competition of compounds of the invention with F-Bak for a Bcl-2 family protein (Bcl-x$_L$) binding site using a Time Resolved Fluorescence Resonance Energy Transfer (TR-FRET) binding assay:

Test compounds were serially diluted in DMSO starting at 50 μM (2× starting concentration; 10% DMSO) and 10 μt transferred into a 384-well plate. Then 10 μL, of a protein/probe/antibody mix is added to each well at final concentrations listed in Table 2.

TABLE 2

| Protein | Probe | Protein (nM) | Probe (nM) | Antibody | Antibody (nM) |
|---|---|---|---|---|---|
| GST-Bcl-$x_L$ | F-Bak (GQVGRQLAIIGDK(6-FAM)INR-amide) (SEQ ID NO: 1) | 1 | 100 | Tb-anti-GST | 1 |

The samples are then mixed on a shaker for 1 minute then incubated for an additional 2 hours at room temperature. For each assay plate, a probe/antibody and protein/antibody/probe mixture were included as a negative and a positive control, respectively. Fluorescence was measured on the Envision (Perkin Elmer) using a 340/35 nm excitation filter and 520/525 (F-Bak) and 495/510 nm (Tb-labeled anti-his antibody) emission filters. Dissociation constants ($K_i$) were determined using Wang's equation (see, Wang, Z. X. *An exact mathematical expression for describing competitive binding of two different ligands to a protein molecule*. FEBS Lett. 1995 360:111-114). The TR-FRET assay can be performed in the presence of varying concentrations of human serum (HS) or fetal bovine serum (FBS).

For comparison, the measurement of the competition of compounds of the invention for other Bcl-2 family protein binding sites (e.g., Bcl-2, Mcl-1) using the TR-FRET binding assay was accomplish by substituting GST-Bcl-$x_L$ in the TR-FRET assay with other GST-labeled protein, e.g., GST-Bcl-2, GST-Mcl-1, prepared in-house.

TR-FRET assay results ($K_i$ in micromolar) for representative compounds of the invention set forth in Table 1 are provided below in the order as they appear in Table 1: 0.077, 0.0002, 0.0002, 0.0003, 0.001, 0.0002, 0.007, 0.00006, 0.00007, 0.0001, 0.0001, 0.0003, 0.0007, 0.006, 0.003, 0.006, 0.004, 0.004, 0.009, 0.003, 0.00005, 0.019, 0.002, 0.007, 0.0003, 0.003, 0.001, 0.001, 0.023, 0.0004, 0.0001, 0.017, 0.0003, 0.004, 0.004, 0.005, 0.004, 0.005, 0.0002, 0.0004, 0.0001, 0.002, 0.005, 0.00007, 0.001, 0.001, 0.0001, 0.00005, 0.012, 0.002, 0.0003, 0.00005, 0.00005, 0.00005, 0.0006, 0.00005, 0.00007 (w/1% HS), 0.0005, 0.0003, 0.176, 0.0003, 0.13, 0.248, 0.00005, 0.00007, 0.0001, 0.00005, 0.0002, 0.0005, 0.040, 0.174, 0.003, 0.00008, 0.00005, 0.00005, 0.008, 0.007, 0.00005, 0.0001, 0.0005, 0.00005, 0.00005, 0.00005, 0.00005, 0.00005, 0.00007, 0.00005, 0.00005, 0.0001, 0.00005, 0.0007, 0.00005, 0.00005, 0.002, 0.00005, 0.0001, 0.00005, 0.010, 0.125, 0.0005, 0.0007, NA, NA, NA, 0.15, 0.0662, 0.197, 0.66, NA, NA, NA, 0.0106, 0.0189, 0.00018, NA, 0.0006, 0.00015, 0.00004, 0.000004, 0.003, 0.000006 (w/1% HS), 0.00001, 0.00004, 0.00002, 0.00005, NA, 0.0006, NA, NA, NA, 0.002, 0.0002, 0.000023, NA, 0.0003, 0.001, 0.0002, 0.00007, 0.00002, NA, 0.000487, 0.000088, NA, NA, NA, NA, >0.66 and NA. As used herein, the abbreviation "NA" means that the data for the compound is not available.

In one embodiment, compounds of the invention selectively inhibit the Bcl-2 family protein, Bcl-$x_L$, over other Bcl-2 family proteins, such as Bcl-2 and Mcl-1. For comparison, data ($K_i$ in micromolar) from the measurement of the competition by certain compounds of the invention (i.e., compounds 52, 58, 64, 70, 74, 76, 81, 82, 84, 88, 93, 94, 97, and 100 in Table 1) with F-Bak for the Bcl-2 binding site using the TR-FRET binding assay are 0.13, 0.31, 0.09, 0.5, 0.06, 0.35, 0.11, 0.12, 0.14, 0.3, 0.155, 0.572, 0.272 and 0.219, respectively.

Example 125

The measurement of competition of compounds of the invention with Bim26-mer for a Bcl-2 family protein binding site using an Alpha Screen Bcl-$x_L$ binding assay:

The BH3 proteins AlphaScreen™ assay was used to identify active small molecules Bcl-2 family protein screen, e.g., Bcl-xL, hmMcl-1 screen. To determine an accurate estimation of the $IC_{50}$, the compounds were routinely tested at starting concentrations, 100 μM and/or 1 μM and serially titrated 3 fold over 11 dilutions.

The assay uses Alphascreen™ technology that relies on hydrogel coated acceptor and donor beads which have functional groups for conjugation to a protein (e.g., GST-hmMcl-1, GST-Bcl-xL or GST-Biotin) and a peptide (Biotin-Bak, Biotin-Bim) respectively. The beads come in close proximity when the protein and the peptides interact. Donor beads contain a photosensitiser that converts oxygen to an excited form of $O_2$ at an excitation of 680 nm. Energy is transformed from the singlet oxygen and reacts with chemiluminescers on the acceptor bead, resulting in light emission at 520-620 nm. Compounds of the invention when added to the reaction, can reduce the intensity of the luminescence, dependent on the inhibition of proximity of the acceptor and donor beads. With this information, the $IC_{50}$ of each compound was calculated Materials GST-Bcl-xL, GST-hmMcl-1 and biotinylated GST proteins were prepared in-house and were stored as stock solutions at −80° C. The biotinylated-Bak, and biotinylated-Bim peptides were purchased from Auspep and were stored as 500 μM stock solutions in 100% DMSO at −80° C. The ALPHASCREEN™ GST (Glutathione-S-Transferase) Detection Kit was obtained from Perkin Elmer Lifesciences (Cat #6760603R). The Proxiplates, white 384 well flat-Bottom plates were purchased from Interpath Services, Melbourne (Cat #784075). The seals to cover the plates were purchased from Proscience, Melbourne (Cat#784075). DMSO was purchased from AnalaR. The 384 deep well plates and the Polypropylene 50 μV bottom polypropylene compound plates were purchased from Matrical.

Preparation of Compounds

Compounds of the invention were prepared as 10 mM stocks with 100% DMSO on the day prior to performing the assay. 12 μL of 100% DMSO and 6 μL of 10 mM compound (i.e. 3.333 mM, final 100 μM) was added to columns 1 and 12 in the Polypropylene 50 μV bottom compound plates. To achieve a final compound concentration of 1 μM, in a separate matrical plate, 28 μL of 100% DMSO and 2 μL of 10 mM compound was added to a well, mixed well, 2 μL of this solution was taken and added to 38 μL of 100% DMSO. 20 μL of this solution was added to the test matrical plate. Several control compounds were included in the test plates. For the control wells 15 μL 100% DMSO only was added to the appropriate wells of each plate. The compound plates were then serially diluted 2 fold using the MiniTrak. Once titrations were complete, the compound plate was immediately covered with a foil seal to prevent evaporation.

Buffer Preparation

The assay and bead buffers were prepared fresh. Each titrated compound plate was assayed in duplicate. The following volumes were sufficient to run 12 Proxiplates (4 assay plates run in duplicate in each of Bclxl, hmMcl and counter assays)

| [Stock] | [Final] | [Volume for 100 mL] |
|---|---|---|
| Assay Buffer | | |
| 1 M Hepes pH 7.4 | 50 mM | 5 mL |
| 1 M DTT | 10 mM | 1 mL |
| 4 M NaCl | 100 mM | 2.5 mL |
| 10% Tween-20 | 0.05% | 0.5 mL |
| 10 mg/mL Casein | 0.1 mg/mL | 1 mL |
| Milli-Q H$_2$O | | 90 mL |
| Bead Buffer | | |
| 1 M Tris-HCL pH 7.5 | 50 mM | 5 mL |
| 10% Tween-20 | 0.01% | 0.1 mL |
| 10 mg/mL Casein | 0.1 mg/mL | 1 mL |
| Milli-Q H$_2$O | | 93.9 mL |

Protein and Peptide Preparation; and Assay Performance

1. The assay and bead buffers were used to prepare the acceptor and donor solutions. ALPHASCREEN™ beads are light sensitive and therefore prepared in a darkened room. 2.5 μL of beads were added per 1 mL of buffer.
2. The volume of protein or peptide to add was calculated using the following formula:

$$\frac{C1}{C2} \times V1 \times 2 = V2$$

$C_1$=Final Concentration of protein/peptide
$C_2$=Stock Concentration of protein/peptide
$V_1$=Total Volume of Acceptor/Donor Solution
$V_2$=Volume of stock protein/Peptide to add to Acceptor/Donor solution 3. The assay components were prepared as separate Acceptor and Donor Solutions. The Acceptor Solution contained Acceptor beads and target protein, while the Donor Solution contained Donor beads and biotinylated peptide.

| [Acceptor Solution] | [mL] | [Donor Solution] | [mL] |
|---|---|---|---|
| hmMcl-1 | | | |
| Assay buffer | 10 mL | Assay buffer | 10 mL |
| Bead buffer | 10 mL | Bead buffer | 10 mL |
| Acceptor Beads | 50 μL | Donor Beads | 50 μL |
| 11.1 μM hmMcl-1 | 2.9 μL | 500 μM B-Bak | 0.32 μL |
| Final Protein | [0.8 nM] | Final Peptide | [4 nM] |
| Bcl-xL | | | |
| Assay buffer | 10 mL | Assay buffer | 10 mL |
| Bead buffer | 10 mL | Bead buffer | 10 mL |
| Acceptor Beads | 50 μL | Donor Beads | 50 μL |
| 23.5 μM Bcl-XL | 1.02 μL | 500 μM B-Bim | 0.16 μL |
| Final Protein | [0.6 nM] | Final Peptide | [2 nM] |
| Counter-GST | | | |
| Assay buffer | 10 mL | Assay buffer | 8 mL |
| Bead buffer | 10 mL | Bead buffer | 8 mL |
| Acceptor Beads | 50 μL | Donor Beads | 50 μL |
| 77 μM B-GST | 1.04 μL | | |
| Final Protein | [2 nm] | | |

4. After the solutions were prepared, they were left to incubate for 30 minutes at room temperature to allow the beads to bind to the protein and the peptide.
5. 50 μL of Bcl-xL solution, 50 μL of hmMcl-1 solution and 50 μL of biotinylated-GST were added into separate deep wells on an assay plate. A control 50 μL Assay/Bead buffer was added separate well plates (no protein).
6. 50 μL of Bim solution and 50 μL of Bak solution were added into separate deep well plates.
7. Transfer 0.3 μL it of sample from the compound plate into each assay plate.
8. Incubated for 30 mins at RT, then add 5 μL of the Donor solution. After addition of the Donor solution, tapped plates gently and sealed individually with adhesive film.
9. The plates were then loaded on the Envision 2103 plate reader to for analysis.

Data Analysis

The percent inhibition was calculated using the following equation:

$$\% \text{ Inhibition} = 100 * \left(1 - \left[\frac{(x - \mu^-)}{(\mu^+ - \mu^-)}\right]\right)$$

x=RFU obtained after compound treatment
$\mu^-$=RFU obtained for the negative controls (no protein controls)
$\mu^+$=RFU obtained for the positive controls (DMSO vehicle controls)

IC$_{50}$ values were obtained by non-linear least squares fitting of the above data, e.g., to XLfit3 equation 205: y=A+((B−A)/(1+((C/x)^D))).

The quality of the assay results were monitored by determination of the Z Prime factor for each assay plate, where Z Prime=>0.5 for the results was considered as reliable (Zhang et al, J Biomol Screening, 4:67-73, 1999).

Alphascreen results (IC$_{50}$ in micromolar) for exemplary compounds of the invention, that is compounds in Table 1, against the Bcl-x$_L$ protein are provided below in the order as they appear in Table 1: 0.10, 0.001, 0.001, 0.0008, 0.002, 0.002, 0.025, 0.0005, 0.0008, 0.001, 0.002, 0.004, 0.010, 0.020, 0.010, 0.010, 0.020, 0.006, NA, 0.008, 0.0003, 0.050, 0.001, 0.027, 0.0009, 0.005, 0.007, 0.008, 0.117, 0.0003, 0.0003, 0.050, NA, 0.005, 0.010, NA, NA, 0.005, NA, NA, 0.0007, 0.007, NA, NA, 0.004, NA, NA, 0.0003, 0.080, 0.010, 0.006, NA, NA, NA, NA, NA, NA, NA, NA, NA, NA, 1.6, 0.574, NA, NA, NA, NA, NA, NA, 0.26, 0.57, NA, NA, NA, 0.0001, 0.086, 0.034, NA, NA, NA, NA, NA, NA, NA, NA, NA, NA, NA, NA, NA, NA, NA, NA, NA, NA, 0.14, NA, NA, NA, 0.865, 7.5, 4, 0.31, 0.124, 0.0776, 0.598, 19, 0.030, 0.003, 0.136, 0.041, 0.0009, NA, NA, NA, 0.0002, 0.0002, 0.017, 0.0004, 0.0003, 0.00014, 0.0004, NA, 0.0924, 0.0106, 0.34, NA, 0.020, 0.0009, 0.0012, 0.0011, 0.0022, 0.0096, 0.00045, NA, NA, NA, 3.8, NA, NA, NA, NA, NA, NA, NA and NA. As used herein, the abbreviation "NA" means that the data for the compound is not available.

Example 126

Cell Viability Assay:

General:

The efficacy of the compounds of the present invention can also be determined in cell-based killing assays using a variety of cell lines and mouse tumor models. For example, their activity on cell viability can be assessed on a panel of cultured tumorigenic and non-tumorigenic cell lines, as well as primary mouse or human cell populations. In one exemplary set of conditions, 5,000-20,000 cells are cultured at 37° C. and 10% $CO_2$ in appropriate growth media (e.g., 100 μL Dulbecco's Modified Eagle's medium supplemented with 10% fetal calf serum, asparaginase, and 2-mercaptoethanol in the case of pre-B Eμ-Myc mouse tumors) in 96 well plates. Cell viability and total cell numbers can be monitored after several hours to several days of incubation with 1 nM-100 μM of the compounds to identify those that kill at $EC_{50}$<10 μM. Cell viability can be determined by the ability of the cells to exclude propidium iodide (10 μg/mL by immunofluorescence analysis of emission wavelengths of 660-675 nm on a flow cytometer (BD FACScan) or by luminescent detection after incubation with CELL TITER-GLO®. Alternatively, a high throughput colorimetric assay such as the CELLTITER® 96 Aqueous Non-Radioactive Cell Proliferation Assay (Promega) may be used. Cell death by apoptosis is confirmed by pre-incubation of the cells with 50 μM of a caspase inhibitor such as zVAD-fmk.

a. Cell Viability Assay for Mcl-1$^{-/-}$ Mouse Embryonic Fibroblasts (MEF):

Neutralization of both Bcl-$x_L$ and Mcl-1 anti-apoptotic proteins in normal cells is required before a cell undergoes apoptosis via the downstream Bax/Bak pathway See, Chen, L. et al. *Mol. Cell* (2005) 17, 393-403; Willis, S. N. et al. *Genes Dev.* (2005) 19, 1294-1305. A compound that only targets Bcl-$x_L$ should not affect normal cells, but could kill certain cancer cells if they rely more on Bcl-$x_L$ and less on other anti-apoptotic proteins, e.g., Mcl-1, for survival. To mirror this, compounds of the invention were tested for its effect on survival of wild type (wt) mouse embryo fibroblasts (MEFs), Bax/Bak double knockout (BB DKO) MEFs, MEFs that expressed Noxa, and MEFs that expressed Bad. Noxa specifically neutralizes Mcl-1. Hence, MEFs that express Noxa mirror cancer cell types that are reliant on Bcl-$x_L$ for survival and should be much more sensitive to killing by a Bcl-$x_L$ targeting compound than MEFs where both Bcl-$x_L$ and Mcl-1 are protective.

In this assay, Mcl-1$^{(-/-)}$ cells were used to confirm that cell apoptosis in the presence of BH3 mimetic small molecules was due to predominantly Bcl-$x_L$ inactivation. This inactivation leaves Bax/Bak unconstrained and results in apoptosis. The CELLTITER-GLO Luminescent Cell Viability Assay is a homogeneous method of determining the number of viable cells in culture based on quantitation of the ATP present. The amount of ATP correlates with the presence of metabolically active cells such that following cell lysis the amount of ATP present is proportional to the amount of luminescence measured.

Materials

Mcl-1$^{(-/-)}$ mouse embryonic fibroblasts (MEFs) are an adherent cell line prepared in house. MEFs were grown in Iwaki 75 cm$^2$ tissue culture flasks (cat #3123-075) with FMA media which consists of
  89% DME Kelso
  10% heat-inactivated foetal calf serum (FCS) (Hyclone cat #SH30396.03)
  1% 10 mM asparagine (Fluka cat #11149)
  275 μl of a 1:2000 dilution of 2-mercaptoethanol is added to the final 500 ml volume of FMA (Sigma cat #M7522; diluted in MT-PBS)

FMA was stored at 4° C. and used at 37° C. MEFs were cultured in FMA media and harvested in MT-PBS and trypsin. For MEF cell viability assays, cells were seeded separately in plates with 10% FCS-FMA and 1% FCS-FMA.
  1% FCS-FMA consists of:
  98% DME Kelso
  1% heat-inactivated foetal calf serum (FCS) (Hyclone cat #SH30396.03)
  1% 10 mM asparagine (Fluka cat #11149)
  275 μl of a 1:2000 dilution of 2-mercaptoethanol is added to the final 500 ml volume (Sigma cat #M7522; diluted in MT-PBS)

Assays were performed using white, flat clear-bottom Greiner 384-well tissue culture grade (Interpath #781098) plates. The compounds were made up in Matrical 384-well, 25 μl V-bottomed plates (cat #MP101-2-PP), sealed with aluminium foil from Beckman Coulter (cat #538619) and stored at 12° C. overnight. Compound preparation and titrations were performed in AnalaR grade DMSO (Merck cat #1.02952.2500). The cell viability detection assay used was CELLTITRE-GLO™ which is commercially available from Promega (cat #G7572), stored at −20° C. and used at 37° C.

Automated Systems that can be used in this assay include: 1) Multidrop—The MULTIDROP 384 (ThermoLabsystems) dispenser was used to dispense cells aseptically into the assay plates; 2) MiniTrak—The MINITRAK system from Perkin Elmer was used for titration of the compound plates; 3) Zymark—The ZYMARK SCICLONE ALH3000 System with 100 nL pintool head was used for compound addition to the cells; 4) EnVision—The ENVISION plate reader was used to measure the viability via the detection of the luminescence.

Compounds of the invention were prepared as 10 mM solution in 100% DMSO and stored at −20° C. Compounds were thawed to room temperature and dispensed into a 384 well Matrical plate. Standard control compounds, e.g. 32.3 mM Etoposide, were added to the plate as controls.

The plates can be sealed with foil seals and stored at 12° C. overnight. The compound plates were left to thaw at room temperature and the compounds titrated 1:3 in 100% DMSO on the MiniTrak (see methods section below—day 3).

Method

1. Day One—Cell Splitting

The media was aspirated and the Mcl-1$^{(-/-)}$ cells washed with 10 mls of warmed MT-PBS. MT-PBS was aspirated and 1 ml of trypsin was added. The T75 flasks were incubated at 37° C. until the cells became detached. 4 ml of 10% FCS FMA media was added to the trypsinized cells and the entire volume was transferred to a 50 ml centrifuge tube and centrifuged for 3 minutes at 250 g. The supernatant was aspirated and the pellet resuspended in 10 ml of 10% FCS FMA. 3 ml of this cell suspension was added to a clean 75 cm$^2$ flask containing 17 ml of 10% FCS FMA media, thus performing a 3:10 split. The remaining cell suspension was used to perform a 1:50 split into another 75 cm$^2$ flask for further culturing.

2. Day Two—Seeding Assay Plates and Setting Up Compound Plates

Cells were harvested as per method step 1 and the pellet resuspended in 3 mls 10% FCS FMA. Cell number was determined by counting in a Neubauer haemocytometer and the dilution calculated to achieve a density of $1\times10^4$ cells $ml^{-1}$ (500 cells per well in 50 µl media). Separate dilutions were prepared in 50 ml 10% FCS FMA and 50 ml 1% FCS FMA solutions respectively.

Four assay plates were set up per compound plate. Two 384 well plates containing Mcl-1$^{(-/-)}$ cells in 10% FCS FMA and the other two plates containing Mcl-1$^{(-/-)}$ cells in 1% FCS FMA.

Using the Multidrop, 25 µl cells were dispensed aseptically into all 384 wells of the assay plates. Plates were left to rest in a non-stacked layer at room temperature for approximately 30 minutes (minimizes edge-effects) and then were placed as a single layer in the 37° C. incubator. The plates were left to incubate overnight.

3. Day Three—Titrating Compound Plates and Treating the Cells

The compound plates were titrated by performing a 3-fold 11-point dilution series using 100% DMSO on the MiniTrak. Following titration of the compounds, 100 nl of compounds were added to the cell plates using the Zymark Sciclone Pintool. This was a 1:250 dilution of the compound so the highest final concentration of compound was 40 µM. The plates were then returned to 37° C. incubator and left to incubate overnight.

4. Day Four—Viability Analysis

The CELLTITRE-GLO™ solution was prepared according to the manufacturer's instructions by the reconstitution of CELLTITRE-GLO™ Substrate with CELLTITRE-GLO™ Buffer and stored after use at −80° C. Plates were removed from incubator and left to equilibrate to room temperature for 15 mins. 24 µl of diluted CELLTITRE-GLO™ was added to each well of the assay plates using the Multidrop. The plates were mixed on a plate shaker for 15 mins before being read on the Envision using the luminescence protocol.

Data Analysis

The percent inhibition was calculated using the following equation:

$$\% \text{ Inhibition} = 100 * \left(1 - \left[\frac{(x - \mu^-)}{(\mu^+ - \mu^-)}\right]\right)$$

x=CPS obtained after sample compound treatment

µ⁻=CPS obtained for the negative controls

µ⁺=CPS obtained for the positive controls $IC_{50}$ values were obtained by non-linear least squares fitting of the data, of the data using, e.g, the 4-parameter logistic fit (XLFit 4 eqn #205; y=A+((B−A)/(1+((C/x)^D))).

The quality of the assay results were monitored by determination of the Z' factor for each assay plate, where Z'≧0.5 for the results was considered as robust (Zhang et al, J Biomol Screening, 4:67-73, 1999).

MEF Mcl-1$^{-/-}$ KO cell viability results (i.e. $EC_{50}$ in micromolar and assay performed in the presence of 10% Fetal Bovine Serum) for certain compounds of the invention, i.e., compounds 58, 64, 74, 81, 82, 84, 88, 94, 97 and 100 in Table 1, are 1.3, 0.31, 0.007, 0.010, 0.030, 0.022, 0.028, 0.448, 0.026 and 0.399, respectively.

b. Cell Viability Assay for Platelets

Platelet rich plasma (PRP) was incubated with a compound of the invention for approximately 4 hours at 37° C. After incubation, platelets were equilibrated to room temperature for 20 minutes and then and equal volume of CELL TITER-GLO™ reagent (Promega Corporation) was added. Samples were mixed for two minutes and then allowed to equilibrate for an additional 10 minutes at room temperature. The luminescence generated from the samples was quantitated using a LJL Analyst plate reader. Data analysis was performed using GraphPad Prism 4.0. Platelet viability results (i.e. $EC_{50}$ in micromolar) for certain compounds of the invention, i.e., compounds 54, 74, 75, 78, 79, 86, 87, 88, 90, 95, 96 and 97 in Table 1, are 0.132, 0.021, 0.009, 0.003, 0.003, 0.010, 0.003, 0.003, 0.003, 0.003, 0.354 and 0.003, respectively.

c. Cellular Viability of Human Tumor Cell Line NCI-H146

NCI-H146 (ATCC, Manassas, Va.) human small cell lung carcinoma cells were plated 50,000 cells per well in 96-well tissue culture plates in a total volume of 100 µL tissue culture medium supplemented with 10% human serum (Invitrogen, Carlsbad, Calif.) and treated with a 2-fold serial dilution of the compounds of interest from 10 µM to 0.020 µL.

Each concentration was tested in duplicate at least 3 separate times. The number of viable cells following 48 hours of compound treatment was determined using the CELLTITER 96® Aqueous non-radioactive cell proliferation MTS assay according to manufacturer's recommendations (Promega Corp., Madison, Wis.). NCI-H146 cell viability results (i.e. $EC_{50}$ in micromolar) for certain compounds of the invention, i.e., compounds 74, 82, 84, 93 and 97 in Table 1, are 0.71, 2.5, 0.61, 3.2 and 2.4 respectively.

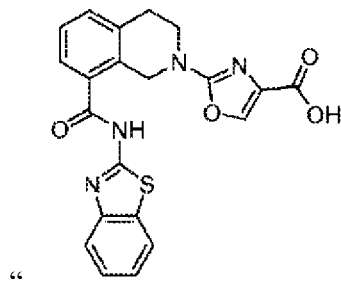

We claim:

1. A compound of Formula I

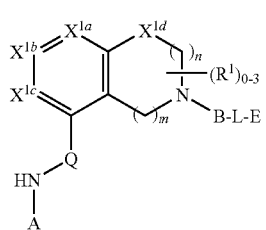

or a pharmaceutically acceptable salt thereof, wherein

Q is selected from the group consisting of —C(O)—, —CH$_2$—, —CH(R$^a$)— and —C(R$^a$)$_2$—, wherein R$^a$ is C$_{1-4}$ alkyl or C$_{1-4}$ haloalkyl;

R$^1$, if present, is independently a member selected from the group consisting of halogen, =O, C$_{1-6}$ alkyl, C$_{1-6}$ heteroalkyl, C$_{2-6}$ alkenyl, C$_{2-6}$ alkynyl and C$_{1-6}$ haloalkyl;

X$^{1a}$, X$^{1b}$ and X$^{1c}$ are each independently selected from the group consisting of C(H), C(R$^2$) and N, wherein at least one of X$^{1a}$, X$^{1b}$ and X$^{1c}$ is C(H) or C(R$^2$); wherein R$^2$ is independently selected from the group consisting of —OR$^b$, —NR$^b$R$^c$, —SR$^b$, —C(O)OR$^c$, —C(O)NR$^b$R$^c$, —NR$^b$C(O)R$^d$, —S(O)$_2$R$^d$, —S(O)R$^d$, —S(O)$_2$NR$^b$R$^c$, —R$^d$, halogen, —CN and —NO$_2$, wherein R$^b$ and R$^c$ are each independently selected from the group consisting of hydrogen, C$_{1-4}$ alkyl, C$_{2-4}$ alkenyl, C$_{2-4}$ alkynyl, C$_{1-4}$ haloalkyl, or optionally R$^b$ and R$^c$, together with the atoms to which each is attached, are combined to form a 3- to 7-membered heterocyclic ring comprising 1 to 2 heteroatoms selected from N, O and S as ring vertices; and R$^d$ is selected from the group consisting of C$_{1-4}$ alkyl, C$_{2-4}$ alkenyl, C$_{2-4}$ alkynyl and C$_{1-4}$ haloalkyl;

X$^{1d}$ is absent or is selected from the group consisting of —O—, —NH—, —N(C$_{1-4}$ alkyl)- and —N(C(O)C$_{1-4}$ alkyl)-;

the subscript m is an integer from 1 to 2, and the subscript n is an integer from 1 to 3; wherein if X$^{1d}$ is present, then the subscript n is 2 or 3;

A is a member selected from the group consisting of:

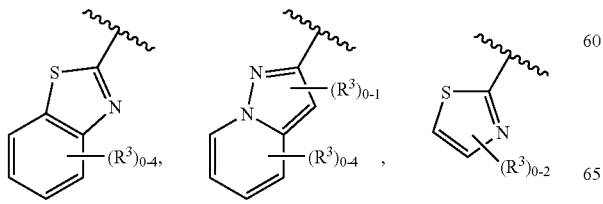

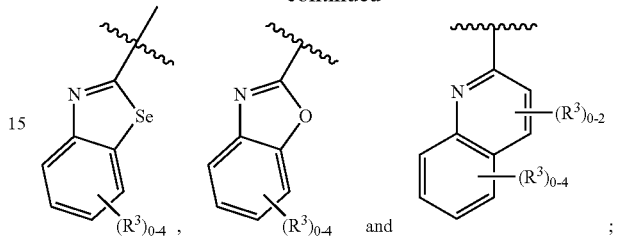

wherein R$^3$, if present, is independently selected from the group consisting of —NR$^e$R$^f$, —OR$^e$, —CN, —NO$_2$, halogen, —C(O)OR$^e$, —C(O)NR$^e$R$^f$, —NR$^e$C(O)R$^f$, —NR$^e$S(O)$_2$R$^g$, —NR$^e$S(O)R$^g$, —S(O)$_2$R$^g$, —S(O)R$^g$ and —R$^g$, wherein R$^e$ and R$^f$ at each occurrence are each independently selected from the group consisting of hydrogen, C$_{1-4}$ alkyl, C$_{2-4}$ alkenyl, C$_{2-4}$ alkynyl, C$_{1-4}$ haloalkyl and —(CH$_2$)$_{1-4}$ phenyl, or R$^e$ and R$^f$, or R$^e$ and R$^g$, together with the atom to which each is attached, are optionally combined to form a 3- to 7-membered heterocyclic ring comprising 1 to 2 heteroatoms selected from N, O and S as ring vertices; and R$^g$ is selected from the group consisting of C$_{1-4}$ alkyl, C$_{2-4}$ alkenyl, C$_{2-4}$ alkynyl and C$_{1-4}$ haloalkyl;

B is a member selected from the group consisting of:

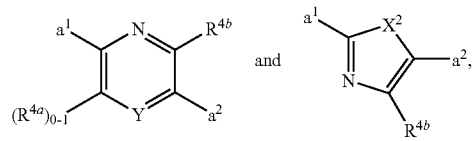

wherein Y is N, C(H) or C(R$^{4a}$); X$^2$ is —N(H)—, —N(C$_{1-3}$ alkyl)-, O or S; R$^{4a}$, if present, is independently selected from C$_{1-4}$ alkyl, C$_{1-4}$ haloalkyl, C$_{2-4}$ alkenyl, C$_{2-4}$ alkynyl, halogen and —CN; R$^{4b}$ is independently selected from the group consisting of —C(O)OR$^j$, —C(O)NR$^h$R$^i$, —C(O)R$^i$, —NR$^h$C(O)R$^i$, —NR$^h$C(O)NR$^h$R$^i$, —OC(O)NR$^h$R$^i$, —NR$^h$C(O)OR$^j$, —C(=NOR$^h$)NR$^h$R$^i$, —NR$^h$C(=NCN)NR$^h$R$^i$, —NR$^h$S(O)$_2$NR$^h$R$^i$, —S(O)$_2$R$^j$, —S(O)$_2$NR$^h$R$^i$, —N(R$^h$)S(O)$_2$R$^i$, —NR$^h$C(=NR$^i$)NR$^h$R$^i$, —C(=S)NR$^h$R$^i$, —C(=NR$^h$)NR$^h$R$^i$, halogen, —NO$_2$, and —CN, wherein R$^h$ and R$^i$ at each occurrence are each independently selected from the group consisting of hydrogen, C$_{1-6}$ alkyl, C$_{2-6}$ alkenyl, C$_{2-6}$ alkynyl, C$_{3-6}$ cycloalkyl, C$_{1-6}$ haloalkyl, phenyl and —(CH$_2$)$_{1-4}$-phenyl; R$^j$ is selected from the group consisting of C$_{1-6}$ alkyl, C$_{2-6}$ alkenyl, C$_{2-6}$ alkynyl, C$_{1-6}$ haloalkyl, C$_{3-7}$ cycloalkyl, phenyl and —(CH$_2$)$_{1-4}$ phenyl; R$^h$ and R$^i$, or R$^h$ and R$^j$, together with the atom to which each is attached are optionally combined to form a 3- to 7-membered heterocyclic ring comprising 1 to 2 heteroatoms selected from N, O and S as ring vertices; or in the alternative, $R^{4b}$ is selected from the group consisting of:

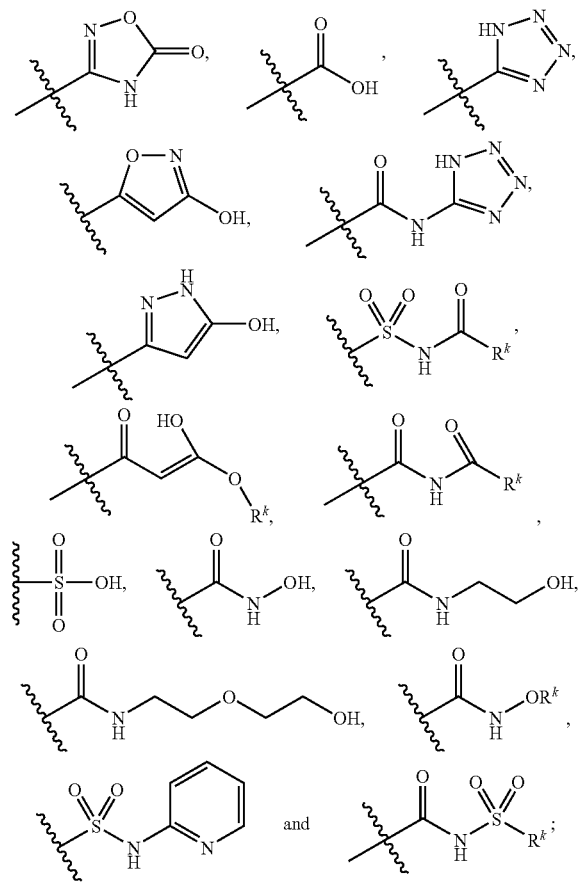

wherein $R^k$ is selected from $C_{1-6}$ alkyl, $C_{2-6}$ alkenyl, $C_{2-6}$ alkynyl, $C_{3-7}$ cycloalkyl and $C_{1-6}$ haloalkyl; $a^1$ denotes the point of attachment of the B group to the nitrogen atom in Formula I and $a^2$ denotes the point of attachment of the B group to the L group in Formula I;

L is absent or is a linker selected from the group consisting of $C_{6-10}$ arylene-$C_{1-6}$ heteroalkylene, $C_{5-9}$ heteroarylene-$C_{1-6}$ heteroalkylene, $C_{1-6}$ heteroalkylene, $C_{1-6}$ alkylene, $C_{1-6}$ haloalkylene, $C_{2-6}$ alkenylene, $C_{2-6}$ alkynylene, —NH—, —S— and —O—, wherein the alkylene, alkenylene, alkynylene or heteroalkylene portions of the L group is substituted with 0 to 4 $R^{5a}$ substituents selected from the group consisting of halogen, —$R^m$ and =O, and the aromatic portions of the L group is substituted with 0 to 4 $R^{5b}$ substituents selected from the group consisting of halogen, —$OR^n$, —$NR''R^o$, —$R^n$, —$NO_2$, and CN; wherein $R^m$ is selected from the group consisting of $C_{1-6}$ alkyl, $C_{2-6}$ alkenyl, $C_{2-6}$ alkynyl, $C_{1-6}$ heteroalkyl, $C_{3-6}$ heterocycloalkyl-$C_{1-6}$ alkyl, $C_{3-7}$ heterocycloalkyl-$C_{1-6}$ heterocycloalkyl and $C_{1-6}$ haloalkyl, and optionally any two $R^{5a}$ substituents attached to the same or different atoms of L can be combined to form a 5- to 7-membered carbocyclic ring or a 5- to 7-membered heterocyclic ring comprising 1 to 2 heteroatoms selected from N, O and S as ring vertices; and wherein $R^n$ and $R^o$, at each occurrence, is independently selected from the group consisting of hydrogen, $C_{1-6}$ alkyl, $C_{2-6}$ alkenyl, $C_{2-6}$ alkynyl and $C_{1-6}$ haloalkyl, and wherein optionally $R^n$ and $R^o$, together with the atoms to which each is attached, are combined to form a 3- to 7-membered heterocyclic ring comprising 1 to 2 heteroatoms selected from N, O and S as ring vertices;

E is hydrogen or halogen; or in the alternative E is selected from the group consisting of phenyl, $C_{5-6}$ heteroaryl, $C_{3-7}$ heterocycloalkyl and $C_{3-7}$ cycloalkyl, and optionally fused to E is 1 or 2 rings independently selected from the group consisting of a 3- to 7-membered carbocyclic ring, a 3- to 7-membered heterocyclic ring, a benzene ring and a 5- to 6-membered heteroaromatic ring, wherein E and each ring optionally fused to E is independently substituted with 0 to 5 $R^6$ substituents selected from the group consisting of halogen, —$NR^pR^q$, —$SR^p$, —$OR^p$, —$C(O)OR^p$, —$C(O)NR^pR^q$, —$C(O)R^p$, —$NR^pC(O)R^q$, —$OC(O)R^r$, —$NR^pC(O)NR^pR^q$, —$OC(O)NR^pR^q$, —$NR^pC(O)OR^r$, —$C(=NOR^p)NR^pR^q$, —$NR^pC(=N-CN)NR^pR^q$, —$NR^pS(O)_2NR^pR^q$, —$S(O)_2R^r$, —$S(O)_2NR^pR^q$, —$R^r$, —$R^s$, —$NO_2$, —$N_3$, =O, —CN, —$Z^1$—$NR^pR^q$, —$Z^1$—$SR^p$, —$Z^1$—$OR^p$, —$Z^1$—$C(O)OR^p$, —$Z^1$—$C(O)NR^pR^q$, —$Z^1$—$C(O)R^p$, —$Z^1$—$NR^pC(O)R^q$, —$Z^1$—$OC(O)R^r$, —$Z^1$—$NR^pC(O)NR^pR^q$, —$Z^1$—$OC(O)NR^pR^q$, —$Z^1$—$NR^pC(O)OR^r$, —$Z^1$—$C(=NOR^p)NR^pR^q$, —$Z^1$—$NR^pC(=N—CN)NR^pR^q$, —$Z^1$—$NR^pS(O)_2NR^pR^q$, —$Z^1$—$S(O)_2R^r$, —$Z^1$—$S(O)_2NR^pR^q$, —$Z^1$—$NO_2$, —$Z^1$—$N_3$, —$Z^1$—$R^s$ and —$Z^1$—CN; wherein $Z^1$ is selected from the group consisting of $C_{1-6}$ alkylene, $C_{2-6}$ alkenylene, $C_{2-6}$ alkynylene, $C_{1-6}$ heteroalkylene, $C_{3-7}$ heterocycloalkyl and $C_{3-7}$ cycloalkyl; $R^p$ and $R^q$ are each independently selected from the group consisting of hydrogen, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl, phenyl and —$(CH_2)_{1-4}$-phenyl; $R^r$ is selected from the group consisting of $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ heterocycloalkyl, phenyl and —$(CH_2)_{1-4}$- phenyl; optionally within each $R^6$ substituent $R^p$ and $R^q$ or $R^p$ and $R^r$, together with the atom to which each is attached, are optionally combined to form a 3- to 7-membered heterocyclic ring optionally comprising 1 to 2 heteroatoms selected from N, O and S as ring vertices; $R^s$ is selected from the group consisting of phenyl, $C_{5-6}$ heteroaryl, $C_{3-7}$ heterocycloalkyl, $C_{3-7}$ cycloalkyl, and optionally fused to $R^s$ is 1 or 2 rings each independently selected from the group consisting of a 5- to 7-membered carbocyclic ring, a 5- to 7-membered heterocyclic ring, a benzene ring and a 5- to 6-membered heteroaromatic ring, and wherein $R^s$ and each ring optionally fused to $R^s$ is each independently substituted with 0 to 5 $R^7$ substituents selected from the group consisting of halogen, —$NR^tR^u$, —$SR^t$, —$OR^t$, —$C(O)OR^t$, —$C(O)NR^tR^u$, —$C(O)R^t$, —$NR^tC(O)R^v$, —$OC(O)R^v$, —$NR^tC(O)NR^tR^u$, —$OC(O)NR^tR^r$, —$NR^tC(O)OR^v$, —$C(=NOR^t)NR^tR^u$, —$NR^tC(=N—CN)NR^tR^u$, —$NR^tS(O)_2NR^tR^u$, —$S(O)_2R^v$, —$S(O)_2NR^tR^u$, —$R^v$, —$NO_2$, —$N_3$, =O, —CN, —$Z^2$—$NR^tR^u$, —$Z^2$—$SR^t$, —$Z^2$—$OR^t$, —$Z^2$—$C(O)OR^t$, —$Z^2$—$C(O)NR^tR^u$, —$Z^2$—$C(O)R^v$, —$Z^2$—$NR^tC(O)R^u$, —$Z^2$—$OC(O)R^v$, —$Z^2$—$NR^tC(O)NR^tR^u$, —$Z^2$—$OC(O)NR^tR^u$, —$Z^2$—$NR^tC(O)OR^v$, —$Z^2$—$C(=NOR^t)NR^tR^u$, —$Z^2$—$NR^tC(=N—CN)NR^tR^u$, —$Z^2$—$NR^tS(O)_2NR^tR^u$, —$Z^2$—S (O)₂Rᵛ, —Z²—S(O)₂NRʳRᵘ, —Z²—NO₂, —Z²—N₃ and —Z²—CN; wherein Z² is selected from the group consisting of $C_{1-6}$ alkylene, $C_{2-6}$ alkenylene, $C_{2-6}$ alkynylene, $C_{1-6}$ heteroalkylene, Rʳ and Rᵘ are each independently selected from the group consisting of hydrogen, $C_{1-6}$ alkyl, $C_{1-6}$ haloalkyl, $C_{2-6}$ alkenyl, $C_{2-6}$ alkynyl, —(CH₂)₁₋₄-phenyl, $C_{3-7}$ cycloalkyl and $C_{3-7}$ heterocycloalkyl; Rᵛ is selected from $C_{1-4}$ alkyl, $C_{1-4}$ haloalkyl, $C_{2-6}$ alkenyl, $C_{2-6}$ alkynyl, —(CH₂)₁₋₄-phenyl, $C_{3-7}$ cycloalkyl and $C_{3-7}$ heterocycloalkyl; and within each R⁷ substituent, Rʳ and Rᵘ or Rʳ and Rᵛ, together with the atom to which each is attached, optionally are combined to form a 3- to 7-membered heterocyclic ring having 1 to 2 heteroatoms selected from N, O and S as ring vertices.

2. The compound of claim 1, or pharmaceutically acceptable salt thereof, wherein A is

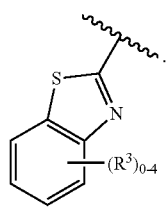

3. The compound of claim 1, or pharmaceutically acceptable salt thereof, wherein the compound is of Formula

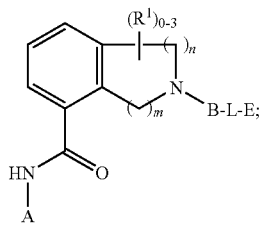

I-a wherein R¹ is halogen, $C_{1-6}$ alkyl, $C_{1-6}$ heteroalkyl or =O; the subscript n is the integer 2 or 3; and the subscript m is an integer from 1 to 2

A is

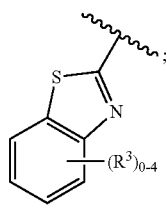

and B is a member selected from the group consisting of:

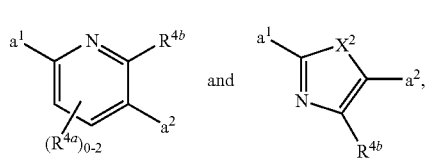

wherein R⁴ᵇ is selected from the group consisting of

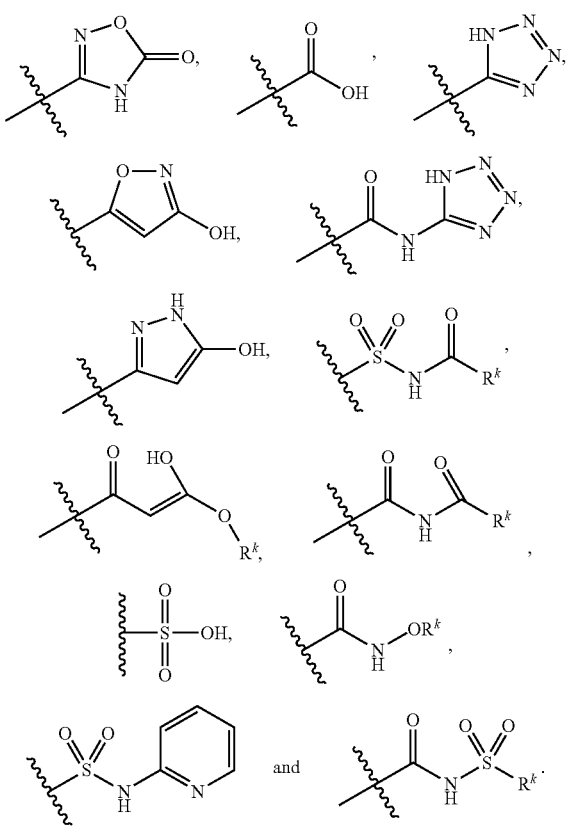

4. The compound of claim 1, or pharmaceutically acceptable salt thereof, wherein the compound is of the Formula

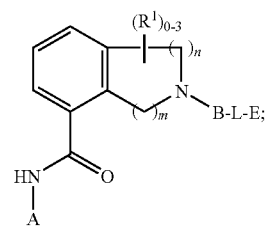

I-a wherein R¹ is halogen, $C_{1-6}$ alkyl, $C_{1-6}$ heteroalkyl or =O; the subscript n is an integer from 2 to 3; and the subscript m is an integer from 1 to 2;

A is

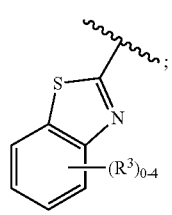

and B is a member selected from the group consisting of:

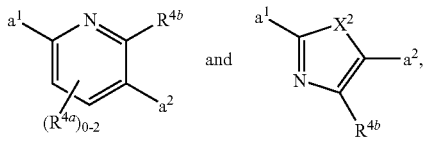
and wherein $R^{4b}$ is selected from the group consisting of —C(O)OR$^j$, —C(O)NR$^h$R$^i$, —C(O)R$^i$, —NR$^h$C(O)R$^i$, —NR$^h$C(O)NR$^i$R$^i$, —OC(O)NR$^h$R$^i$, —NR$^h$C(O)OR$^j$, —C(=NOR$^h$)NR$^h$R$^i$, —NR$^h$C(=NCN)NR$^h$R$^i$, —NR$^h$S(O)$_2$NR$^h$R$^i$, —S(O)$_2$R$^j$, —S(O)$_2$NR$^h$R$^i$, —N(R$^h$)S(O)$_2$R$^i$, —NR$^h$C(=NR$^i$)NR$^h$R$^i$, —C(=S)NR$^h$R$^i$, —C(=NR$^h$)NR$^h$R$^i$, —R$^j$, halogen, —NO$_2$, and —CN.

5. The compound of claim 3 or 4, or pharmaceutically acceptable salt thereof, wherein the subscript n is 2 and the subscript m is 1.

6. The compound of claim 3, or pharmaceutically acceptable salt thereof, wherein R$^1$ is absent; and B is

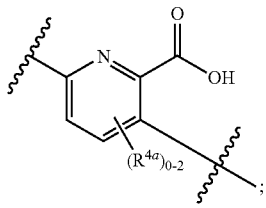

wherein $R^{4a}$, if present is selected from halogen and $C_{1-4}$ alkyl; wherein the subscript n is 2 and the subscript m is 1.

7. The compound of claim 3, or pharmaceutically acceptable salt thereof, wherein R$^1$ is absent; and B is

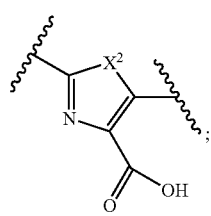

wherein the subscript n is 2 and the subscript m is 1.

8. The compound of claim 1, 3 or 4, or pharmaceutically acceptable salt thereof, wherein the compound is of a Formula selected from the group consisting of II-a

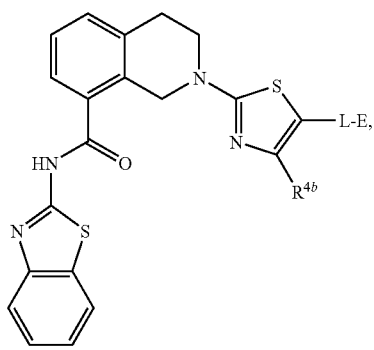

II-b

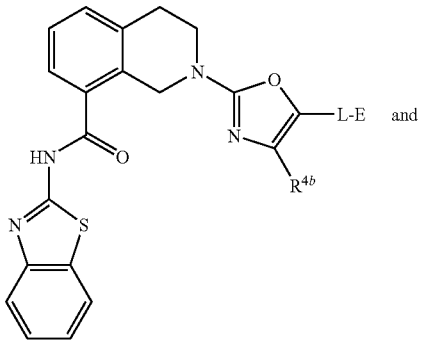
and

II-c

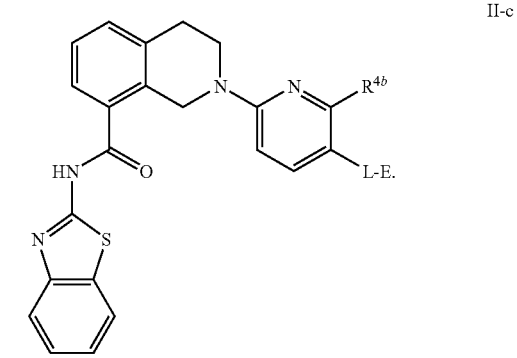

9. The compound of claim 3 or 4, or pharmaceutically acceptable salt thereof, wherein L is absent or is an optionally substituted group selected from the group consisting of optionally substituted $C_{6-10}$ arylene-$C_{1-6}$ heteroalkylene and $C_{5-9}$ heteroarylene-$C_{1-6}$ heteroalkylene.

10. The compound of claim 9, or pharmaceutically acceptable salt thereof, wherein L is selected from the group consisting of

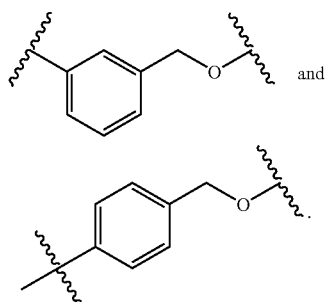

11. The compound of claim 3 or 4, or pharmaceutically acceptable salt thereof, wherein L is an optionally substituted group selected from the group consisting of optionally substituted $C_{1-6}$ heteroalkylene, $C_{1-6}$ alkylene, $C_{2-6}$ alkenylene and $C_{2-6}$ alkynylene.

12. The compound of claim 11, or pharmaceutically acceptable salt thereof, wherein L is selected from the group consisting of optionally substituted $C_{1-4}$ alkyleneoxy, $C_{2-4}$ alkenyleneoxy, $C_{2-4}$ alkynyleneoxy and $C_{1-4}$ alkylene, wherein L is substituted with 0 to 4 R$^m$ groups, wherein any two R$^m$ groups located on the same or different atom of L are optionally combined to form a 5- to 7-membered carbocyclic ring or a 5- to 7-membered heterocyclic ring comprising 1 to 2 heteroatoms selected from N, O and S as ring vertices.

13. The compound of claim 1, or pharmaceutically acceptable salt thereof, wherein L is selected from the group consisting of

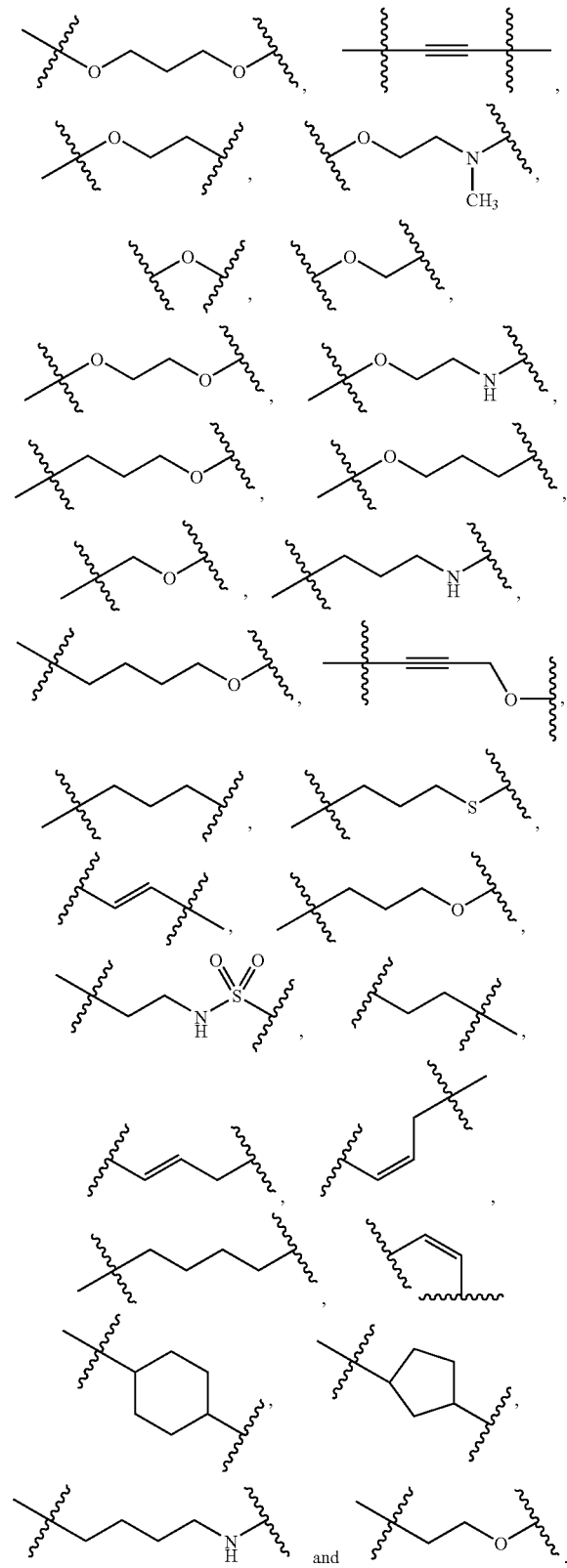

14. The compound of claim 3 or 4, or pharmaceutically acceptable salt thereof, wherein E is hydrogen.

15. The compound of claim 3 or 4, or pharmaceutically acceptable salt thereof, wherein E is selected from the group consisting of phenyl, $C_{5-6}$ heteroaryl and $C_{3-7}$ heterocycloalkyl, and optionally fused to E is a ring independently selected from the group consisting of a 5- to 7-membered carbocyclic ring, a 5- to 7-membered heterocyclic ring, a benzene ring and a 5- to 6-membered heteroaromatic ring, wherein E and the ring optionally fused thereto are together substituted with a total of 1 to 3 $R^6$ substituents, wherein one $R^6$ substituent is —$NR^pR^q$, —$Z^1$—$NR^pR^q$, —$R^s$, or —$Z^1$—$R^s$.

16. The compound of claim 15, or pharmaceutically acceptable salt thereof, wherein the said one $R^6$ substituent is —$NR^pR^q$ or —$Z^1$—$NR^pR^q$.

17. The compound of claim 16, or pharmaceutically acceptable salt thereof, wherein 1 or 2 $R^6$ substituents is selected from the group consisting of fluorine and chlorine.

18. The compound of claim 15, or pharmaceutically acceptable salt thereof, wherein the said one $R^6$ substituent is $R^s$ or —$Z^1$—$R^s$, wherein $R^s$ is of a formula selected from the group consisting of:

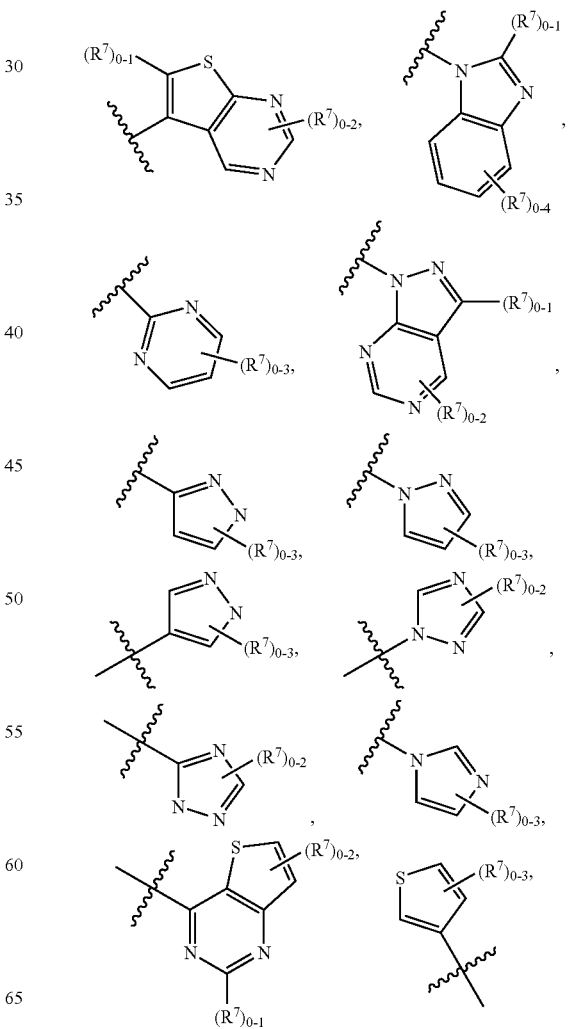

-continued
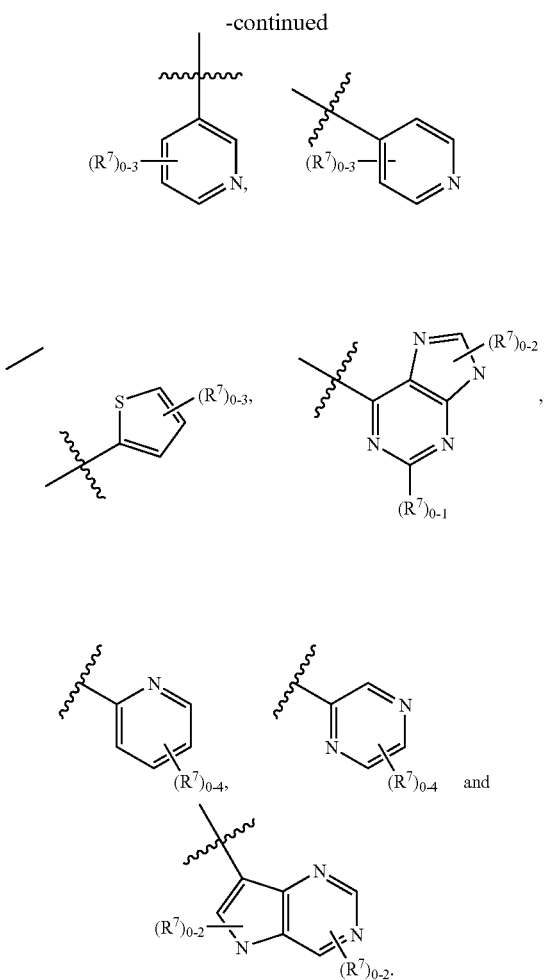
19. The compound of claim 15, or pharmaceutically acceptable salt thereof, wherein $Z^1$ is selected from the group consisting of:
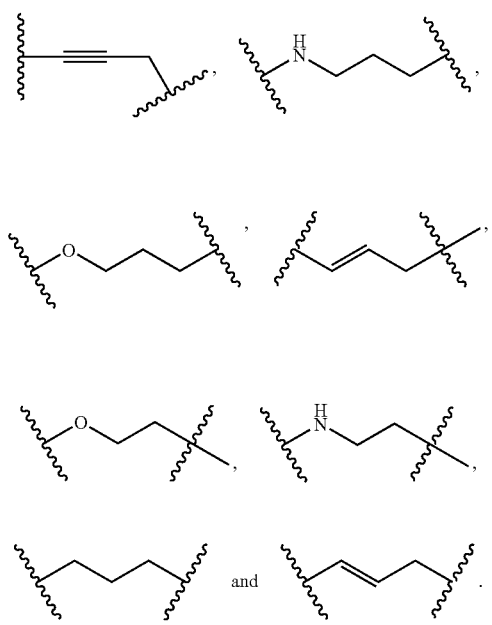
20. The compound of claim 5, or pharmaceutically acceptable salt thereof, wherein the compound is of a Formula selected from the group consisting of:
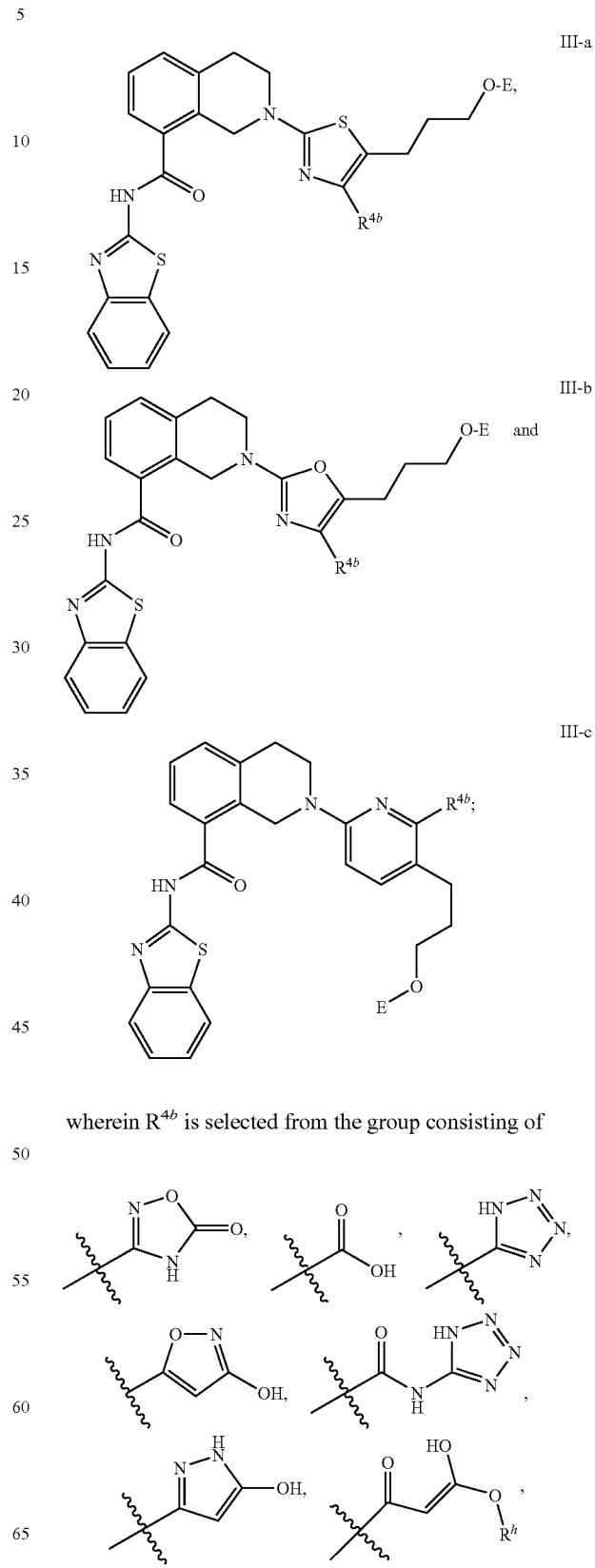
wherein $R^{4b}$ is selected from the group consisting of

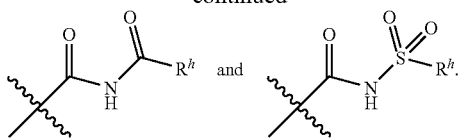 and and E is phenyl, and is substituted with from 1 to 3 $R^6$ substituents.

21. The compound of claim 20, or pharmaceutically acceptable salt thereof, wherein $R^{4b}$ is —C(O)OH.

22. The compound of claim 3 or 4, or pharmaceutically acceptable salt thereof, wherein E is -phenyl, wherein the phenyl group is substituted at the meta or para position with an optionally substituted $R^s$ group is of a formula selected from the group consisting of:

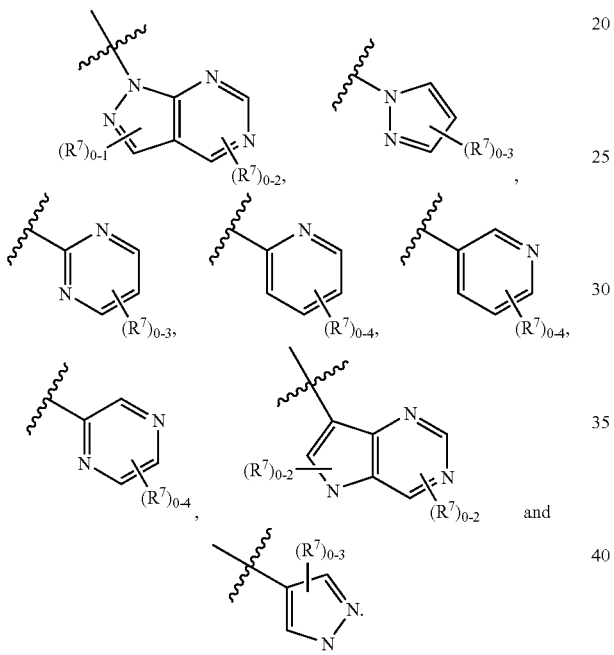

23. The compound of claim 22, or pharmaceutically acceptable salt thereof, wherein at least one $R^7$, if present, is selected from the group consisting of —$NR'R''$ and —$Z^2$—$NR'R''$.

24. The compound of claim 23, or pharmaceutically acceptable salt thereof, wherein $Z^2$ is selected from $C_{1-4}$ alkylene, $C_{2-4}$ alkenylene, $C_{2-4}$ alkynylene and $C_{1-4}$ heteroalkylene.

25. The compound of claim 24, or pharmaceutically acceptable salt thereof, wherein $Z^2$ is selected from the group consisting of

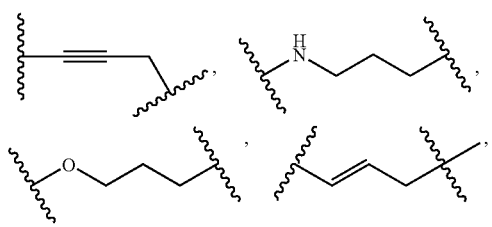

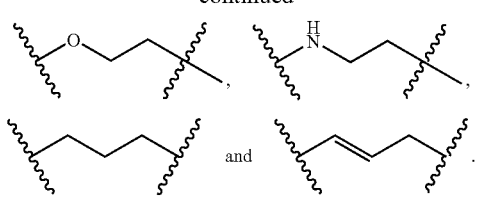 and

26. The compound of claim 1, or pharmaceutically acceptable salt thereof, wherein said compound is selected from the group consisting of:

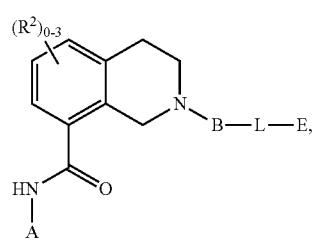
IV-a

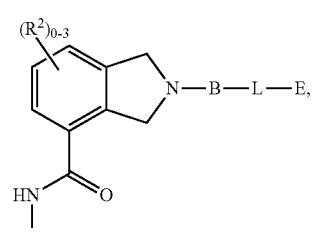
IV-b

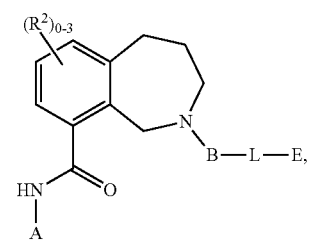
IV-c

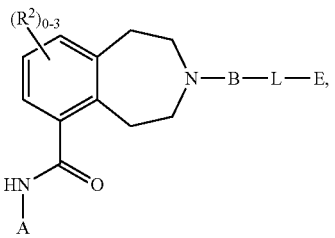
IV-d

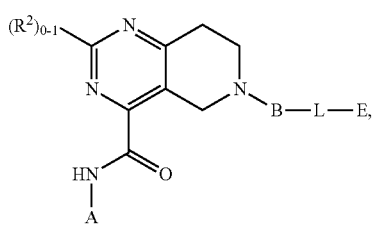
IV-e

-continued
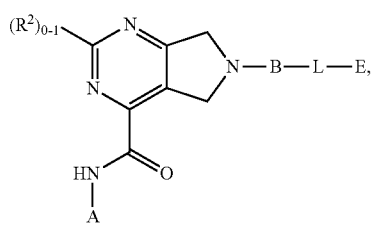
IV-f
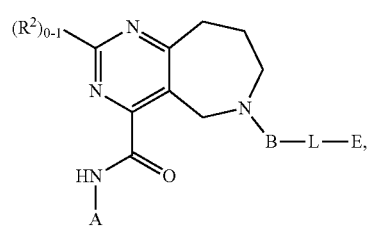
IV-g
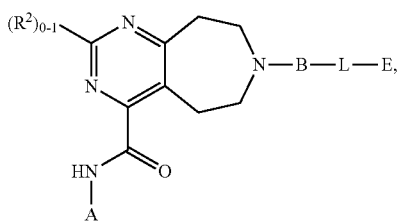
IV-h
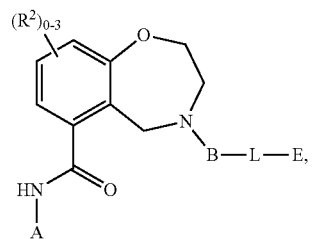
IV-i
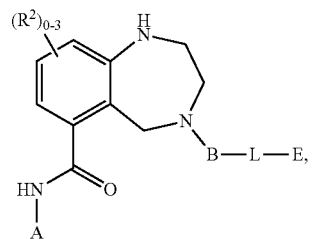
IV-j
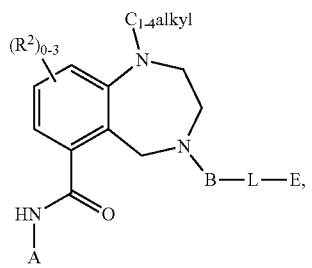
IV-k
-continued
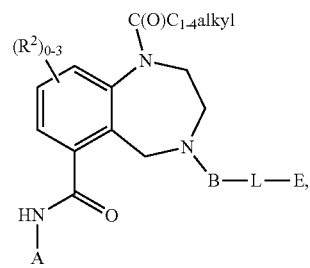
IV-l
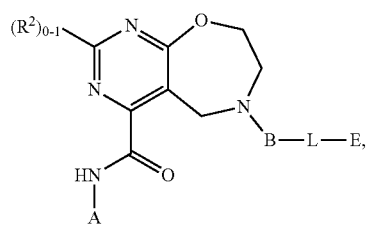
IV-m
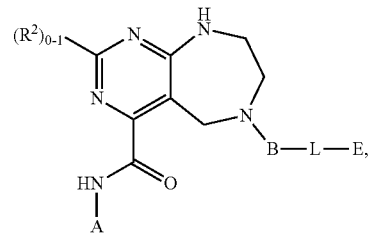
IV-n
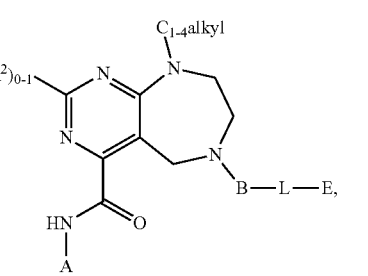
IV-o
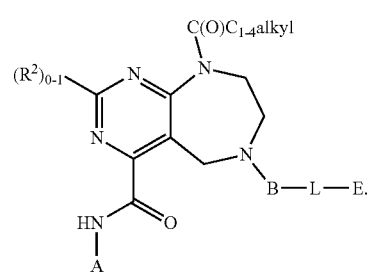
IV-p
27. The compound of claim 1, or pharmaceutically acceptable salt thereof, wherein said compound is selected from the group consisting of:
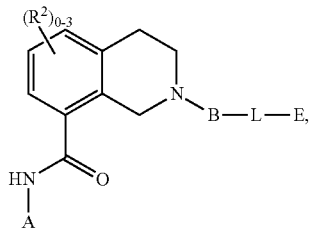
IV-a

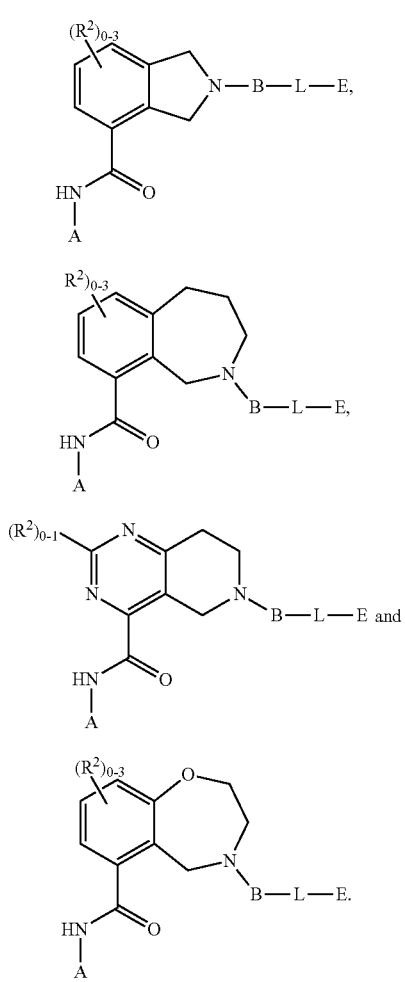
28. The compound of claim 1, or pharmaceutically acceptable salt thereof, wherein E is selected from the group consisting of:
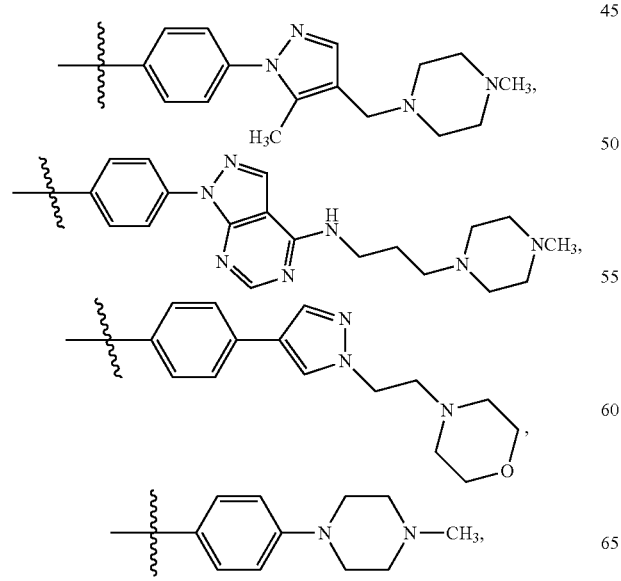
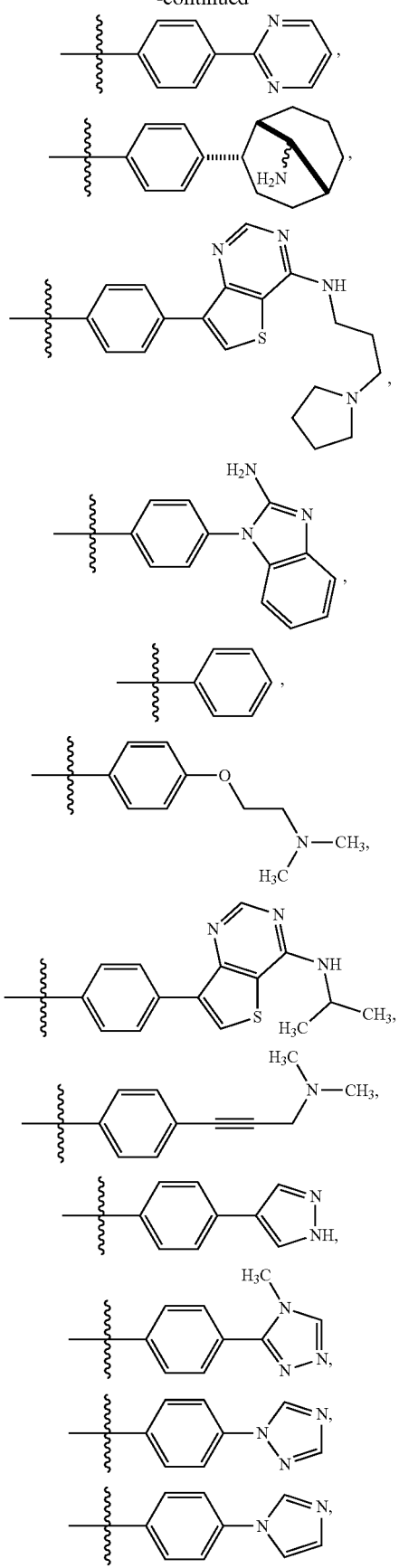

333
-continued
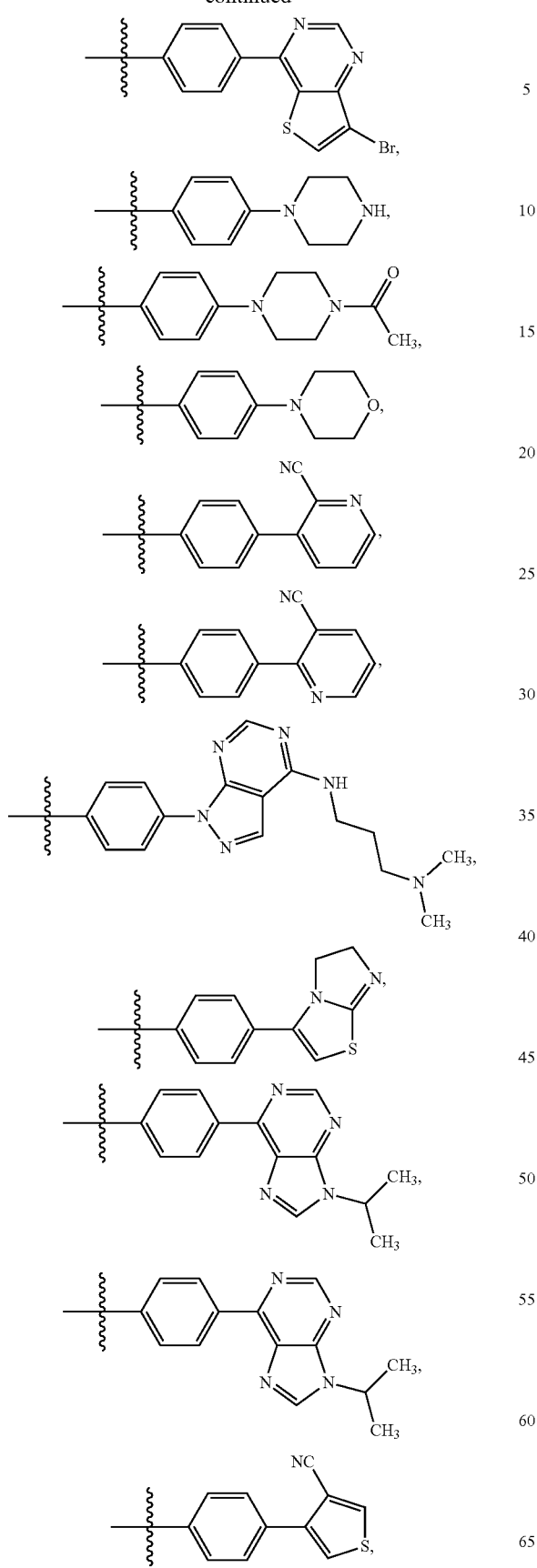
334
-continued
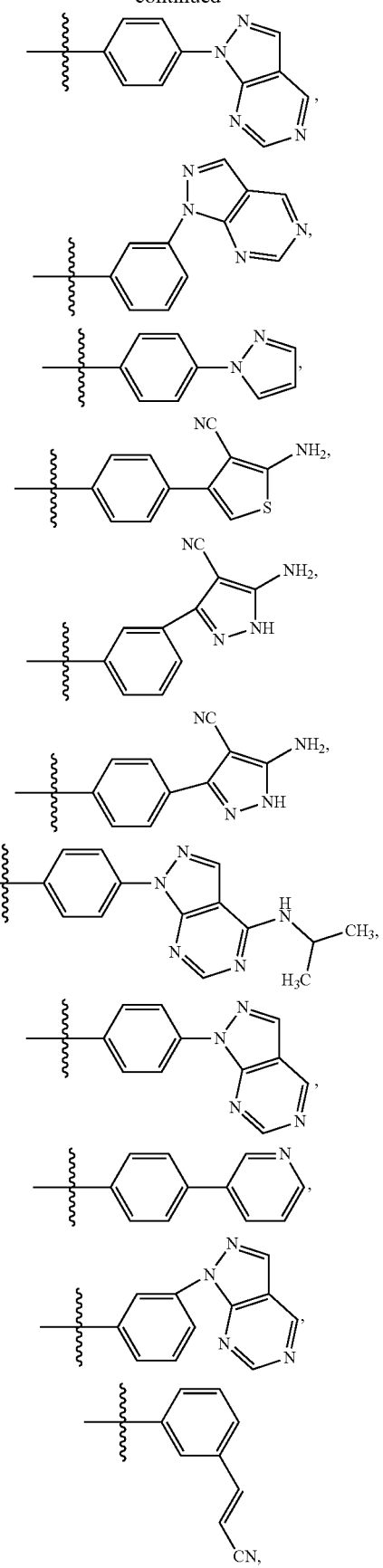

335
-continued
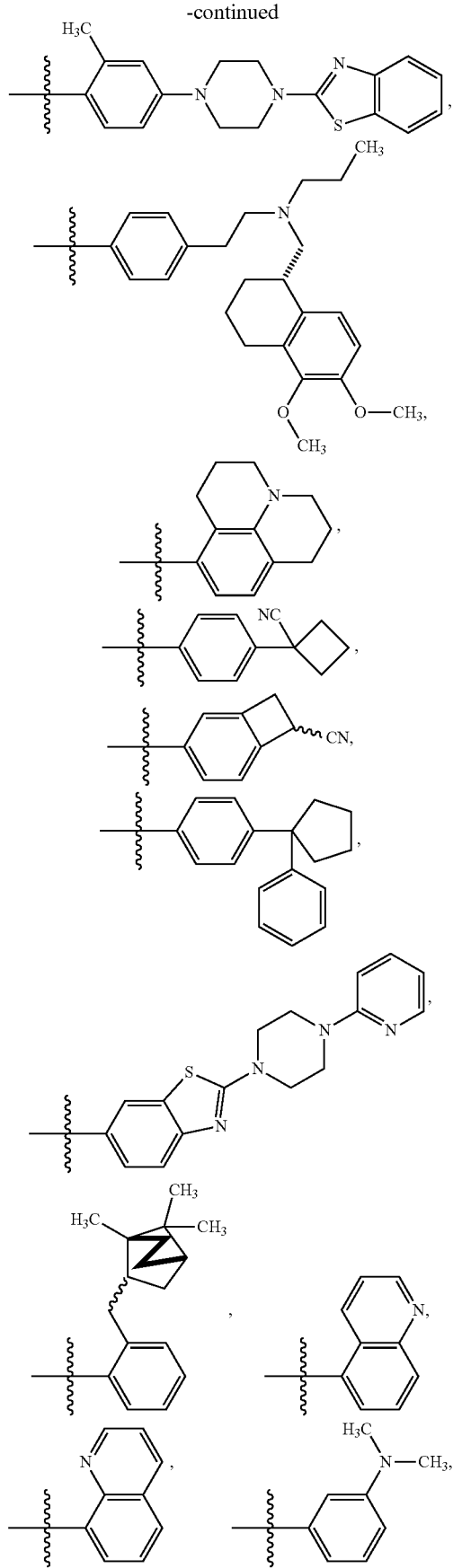
336
-continued
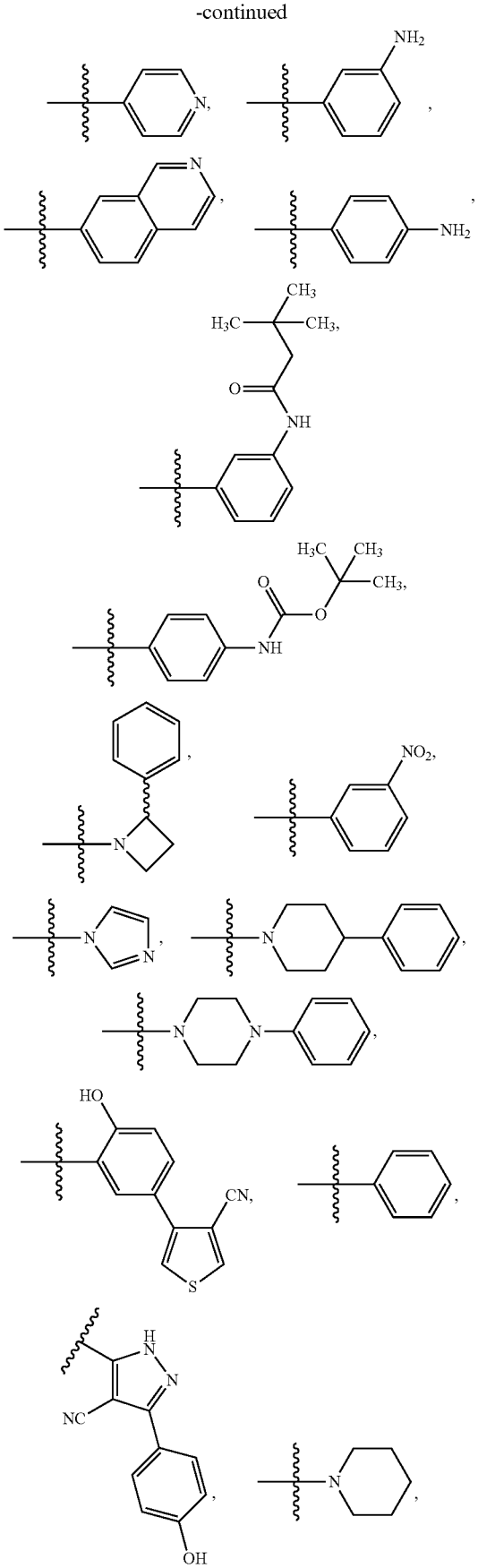

337
-continued
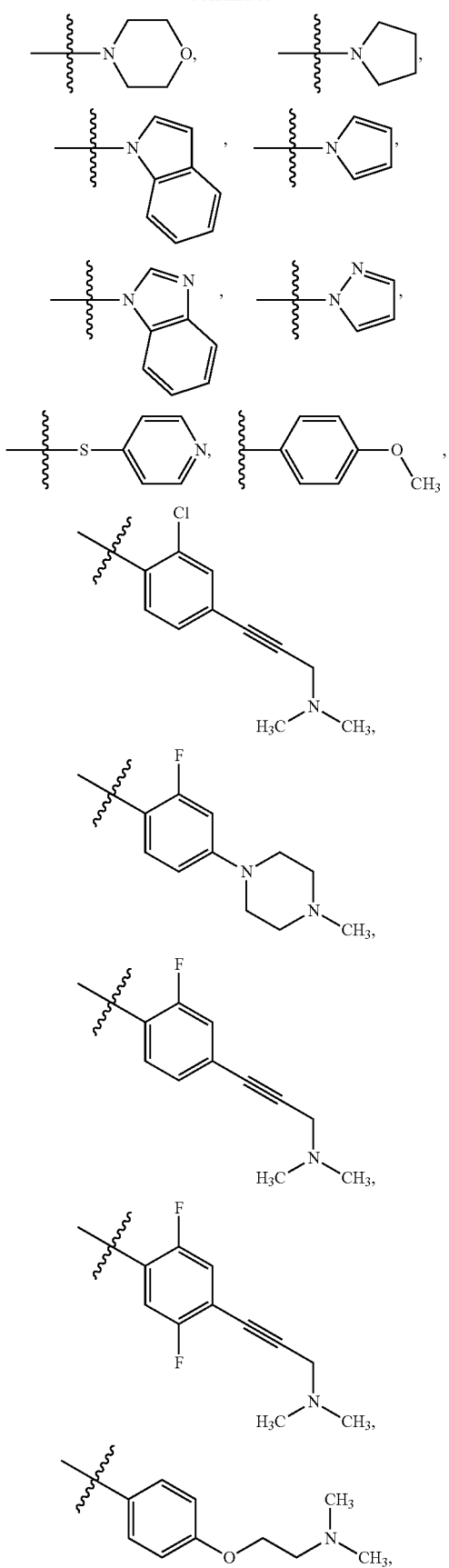
338
-continued
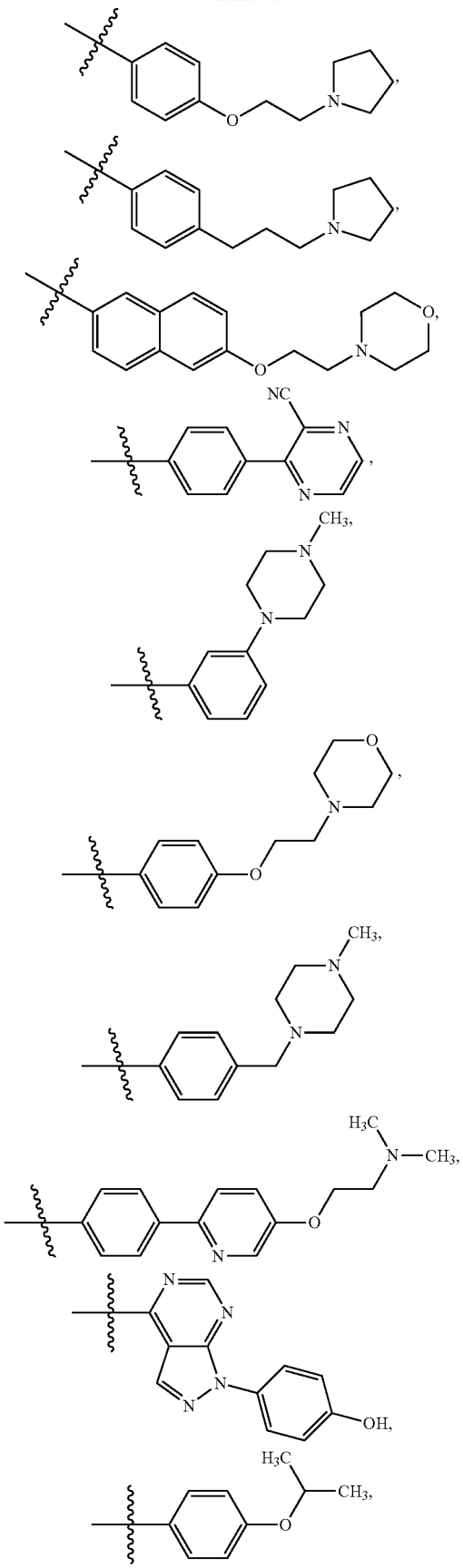

339
-continued
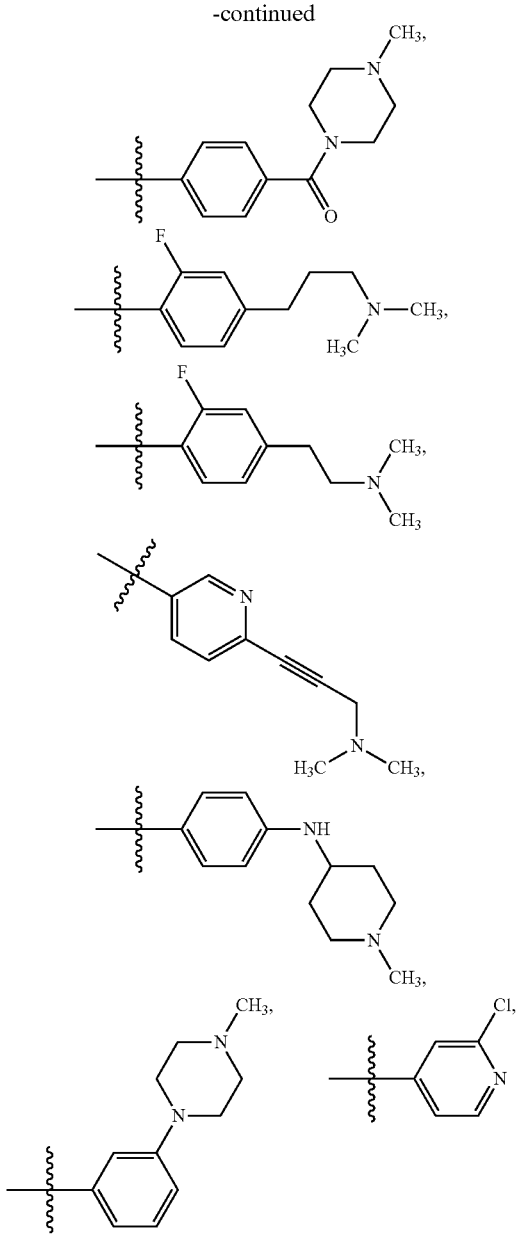
340
-continued
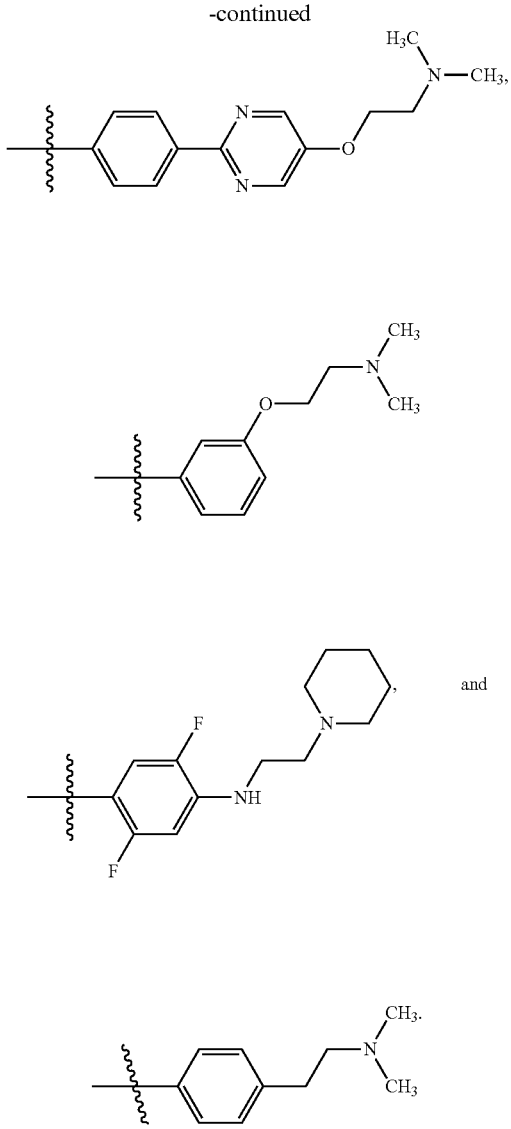
29. The compound of claim 1, or pharmaceutically acceptable salt thereof, wherein said compound is selected from the group consisting of:
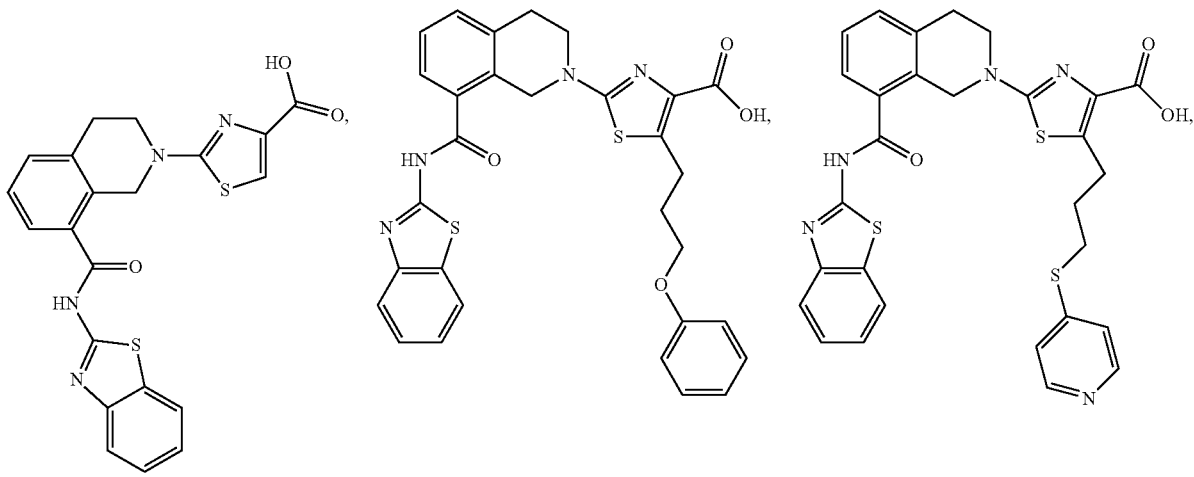

341
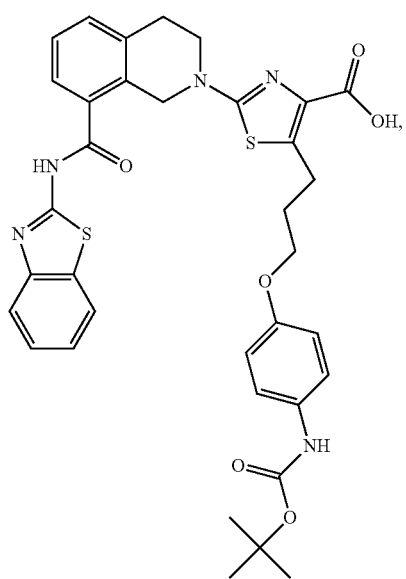
342
-continued
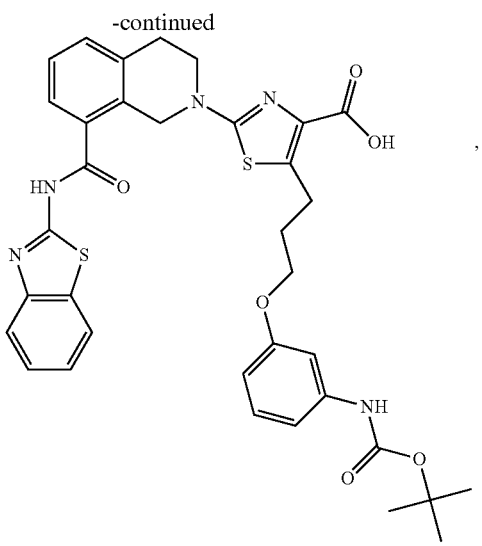
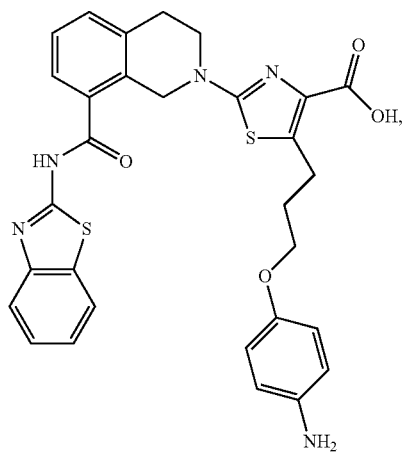
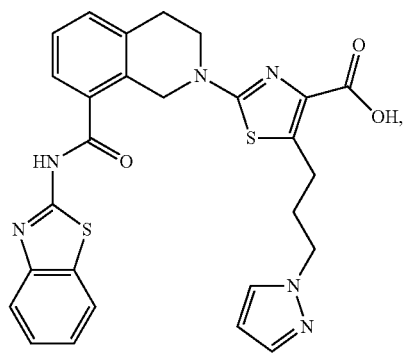
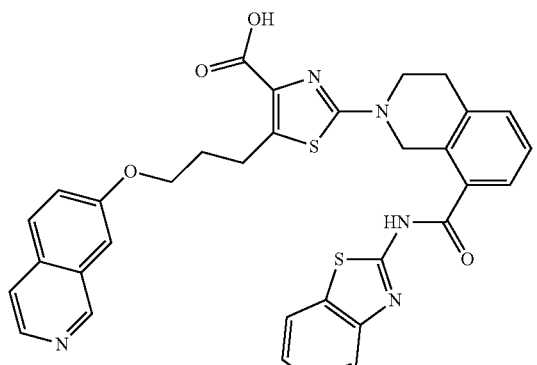
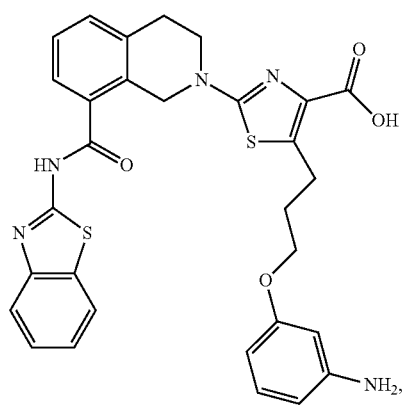

343
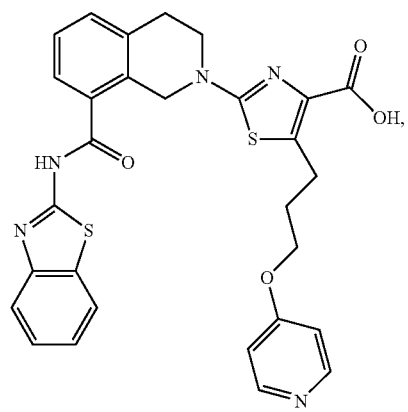
344
-continued
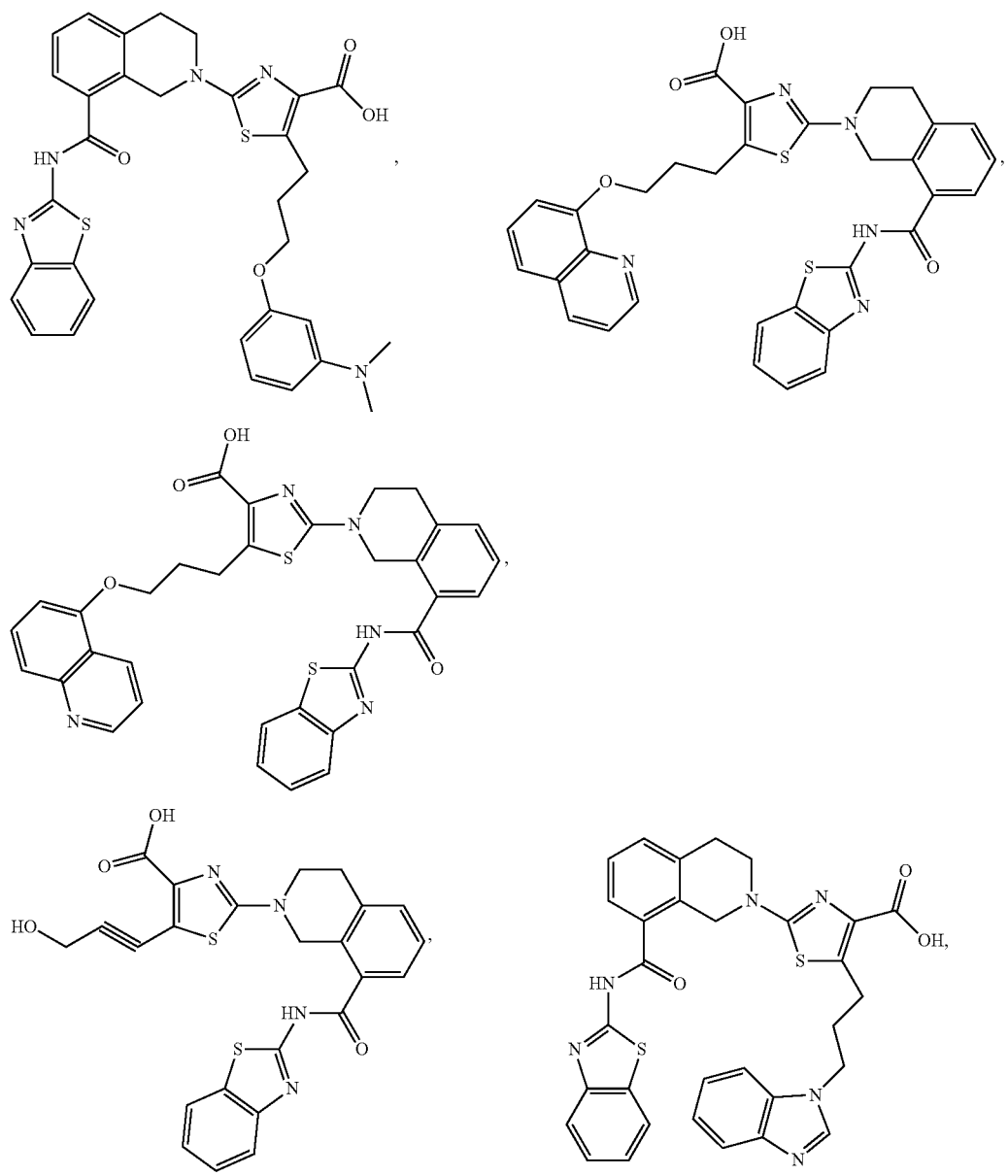

345
-continued
346
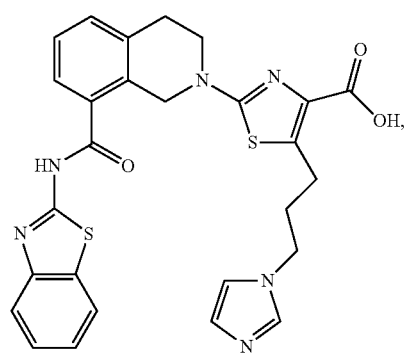
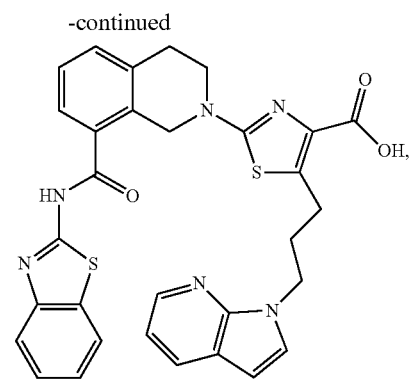
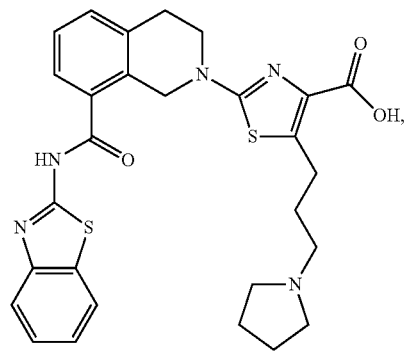
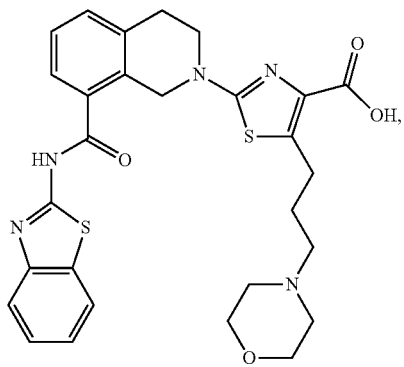
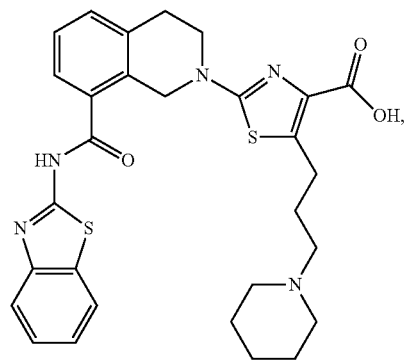
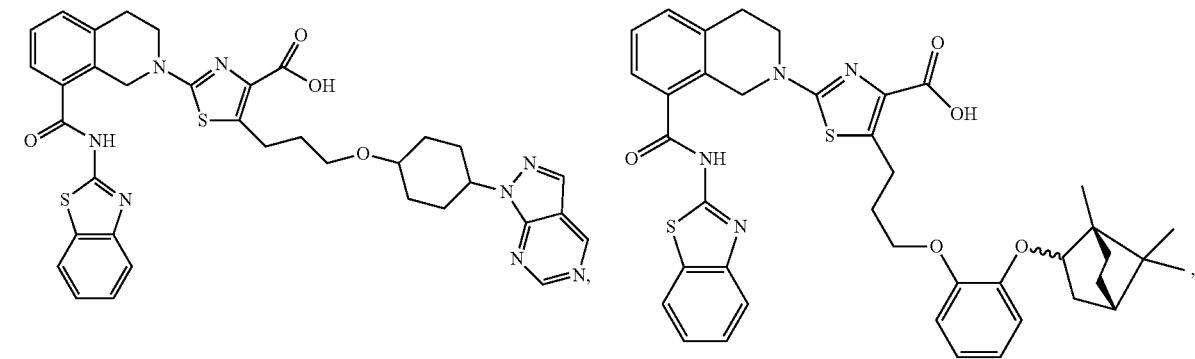

347
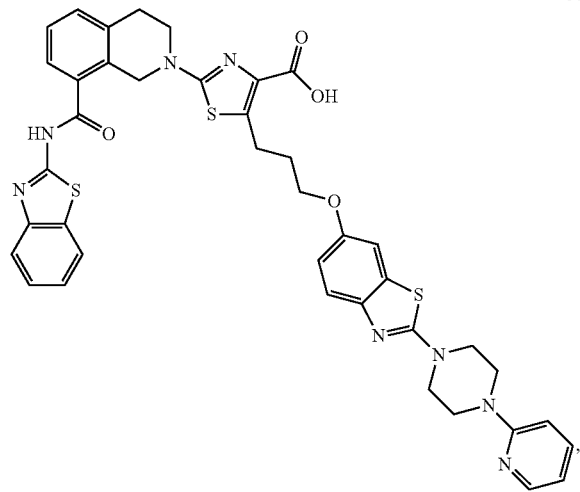
348
-continued
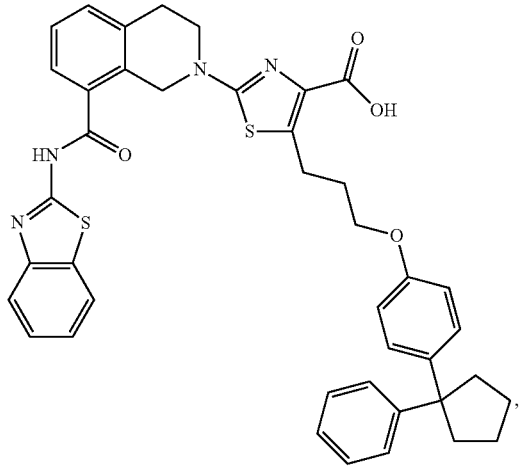
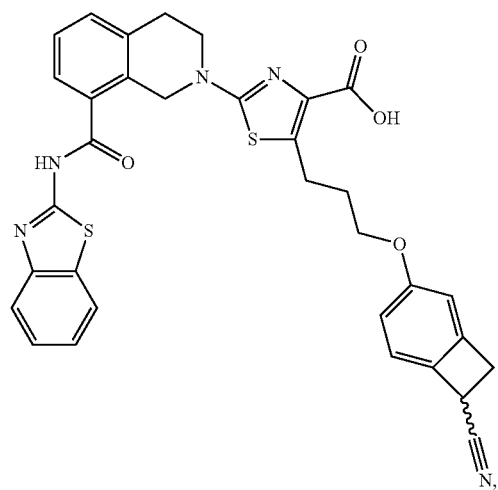
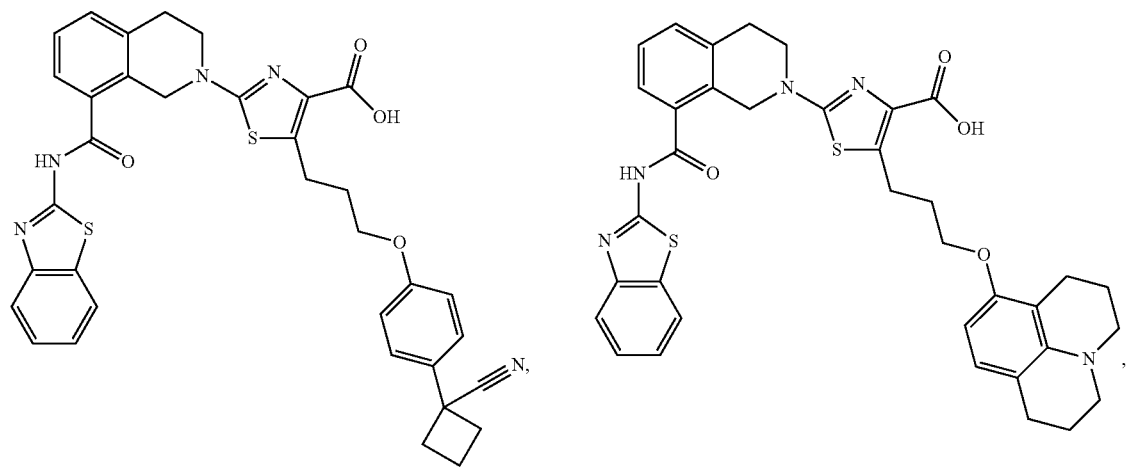

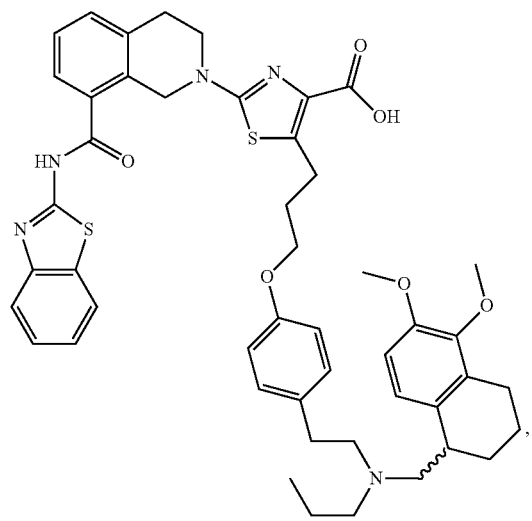
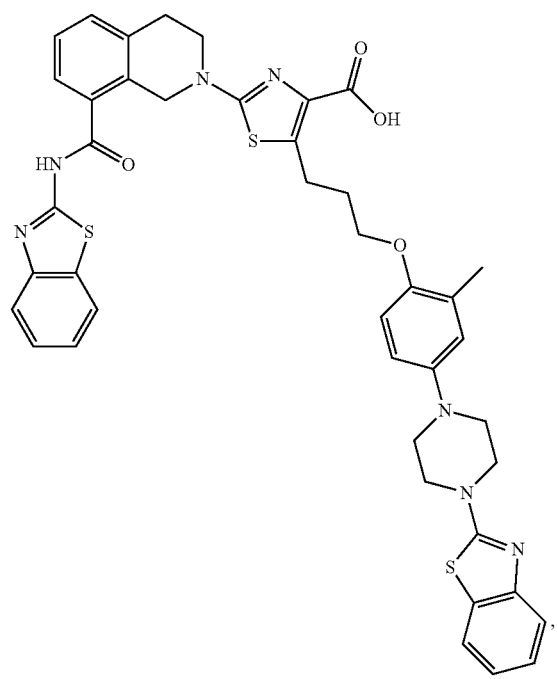
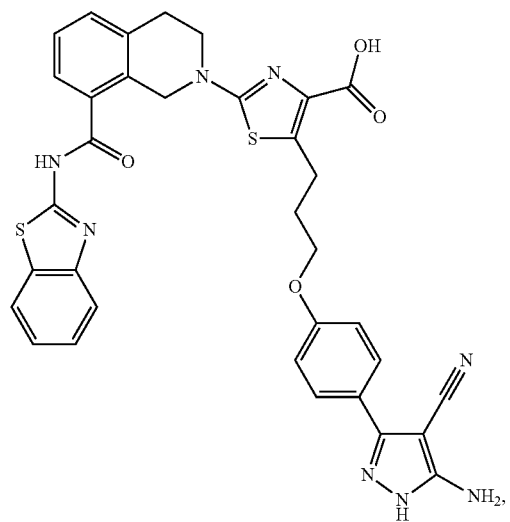

351
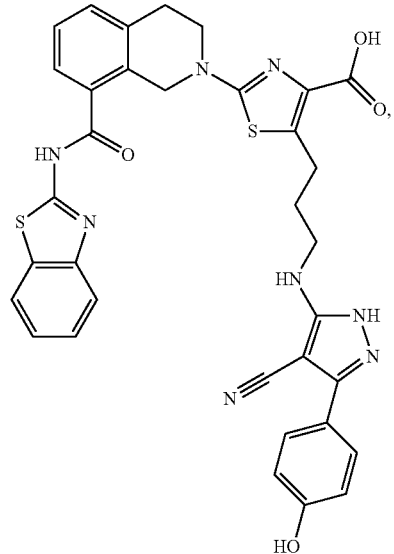
352
-continued
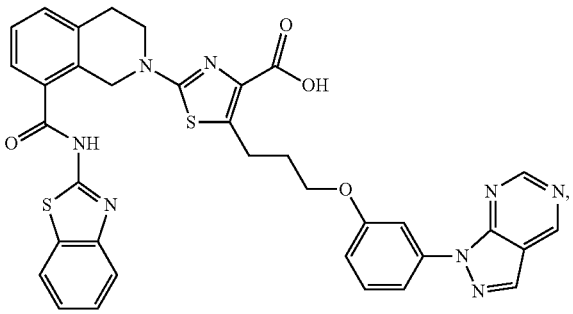
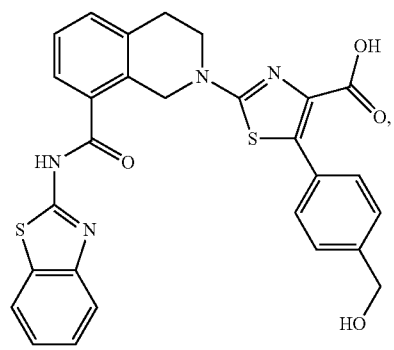
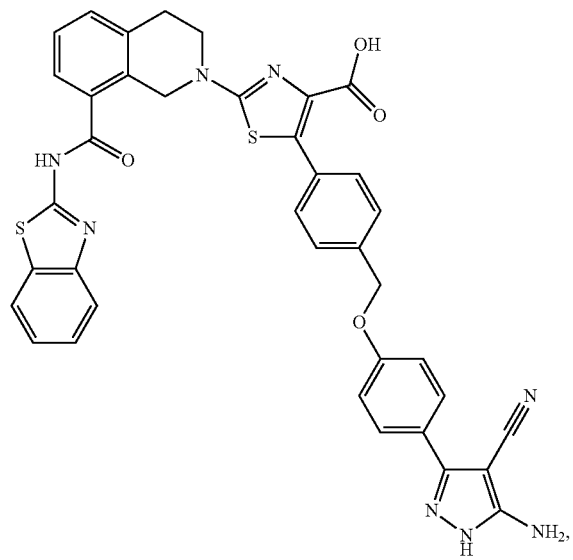
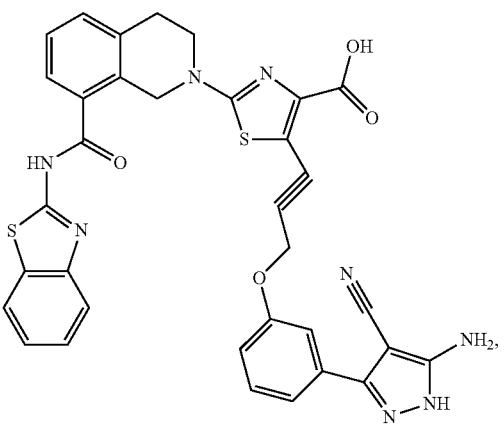

353
354
-continued
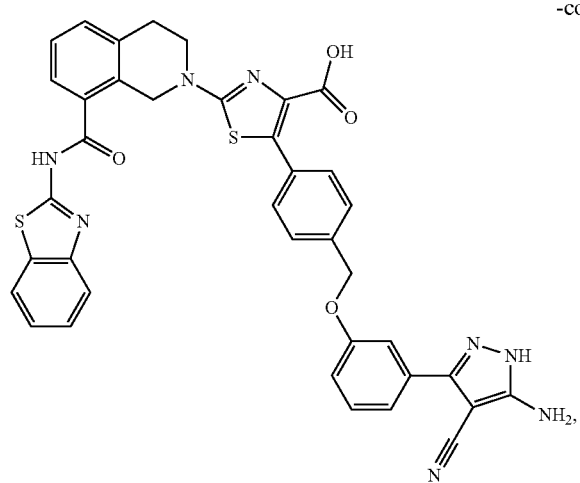
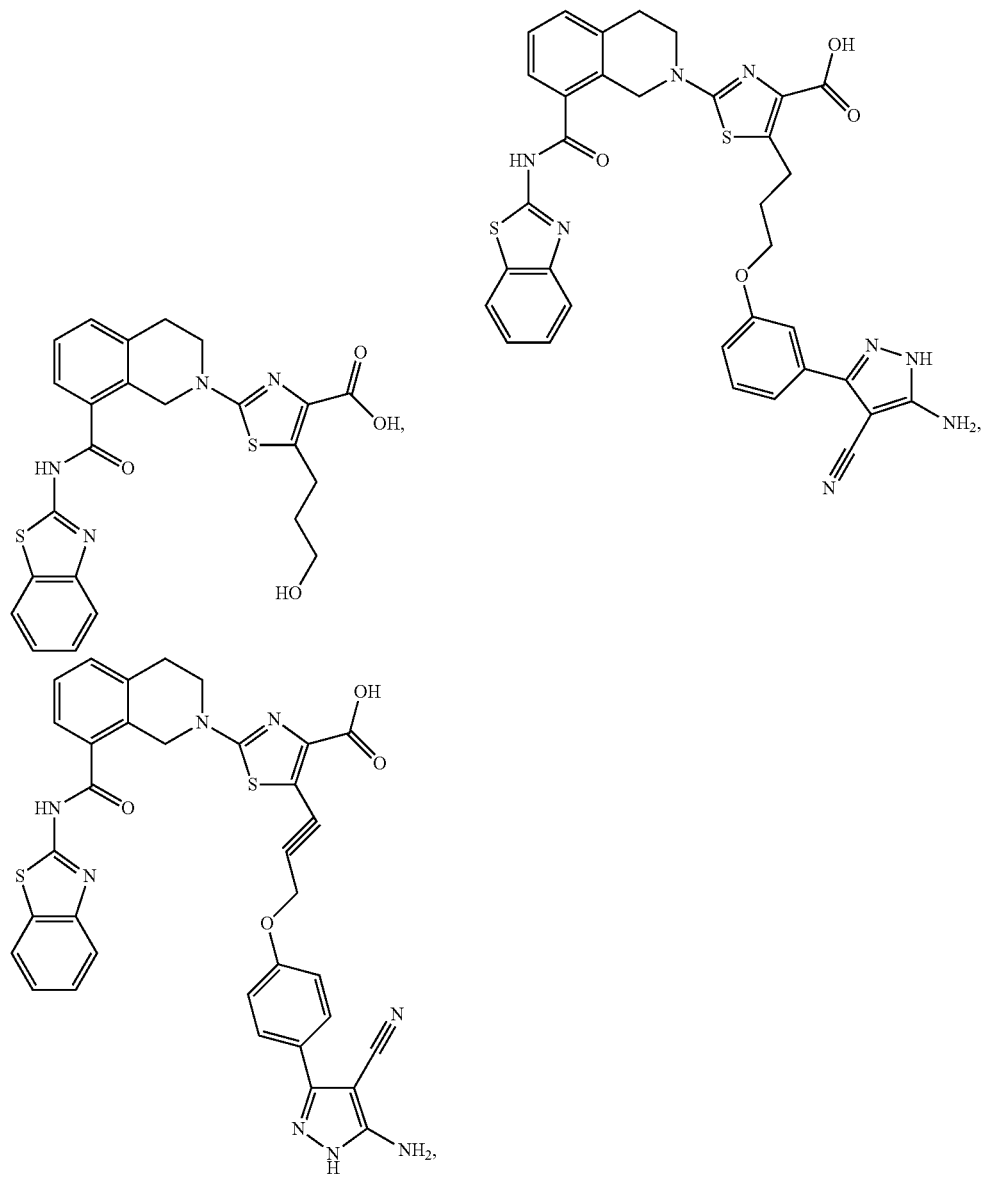

355
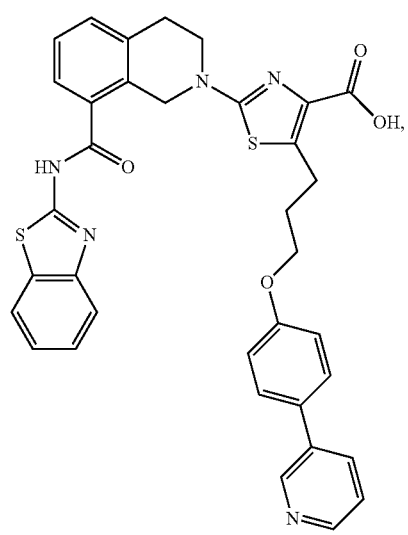
356
-continued
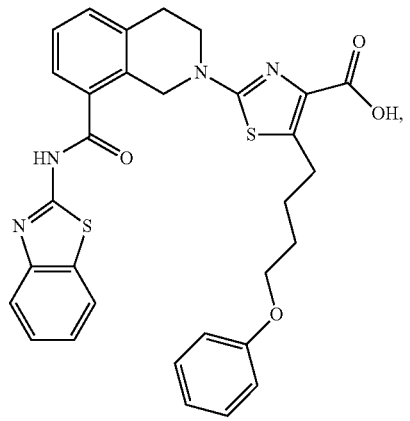
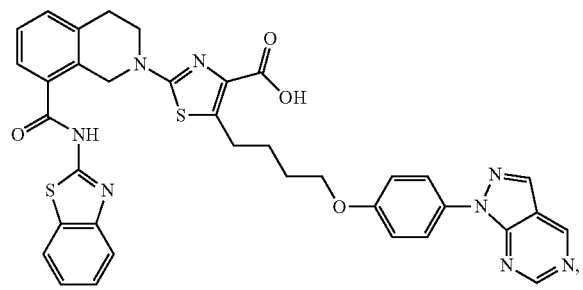
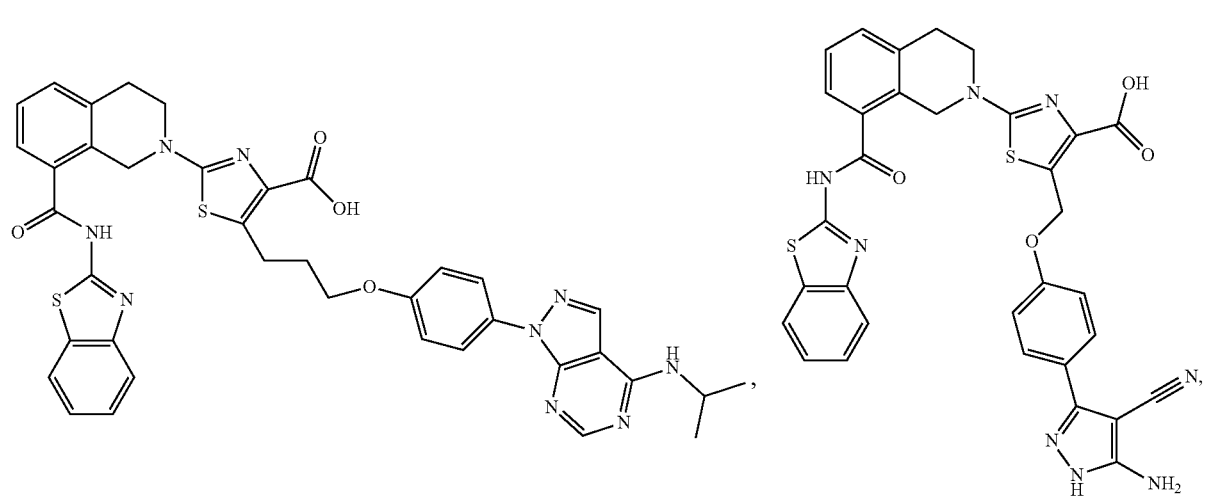

357
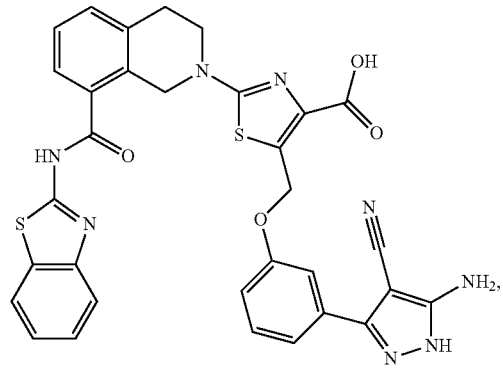
358
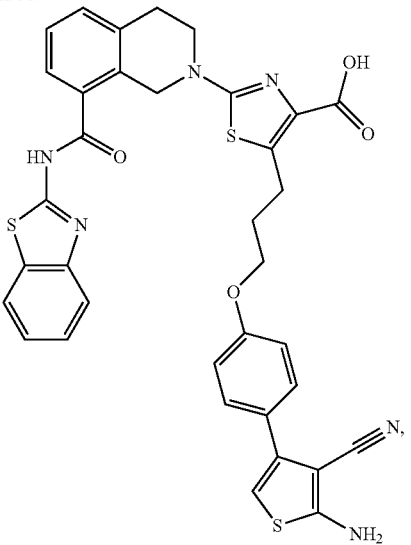
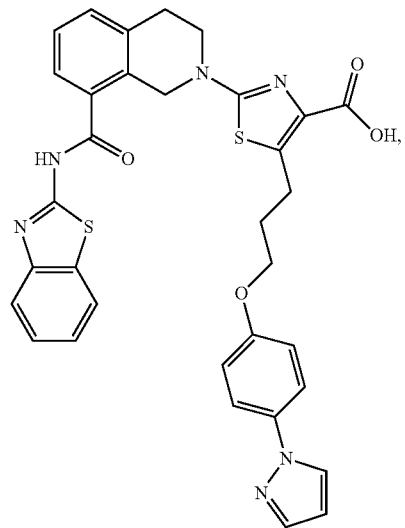
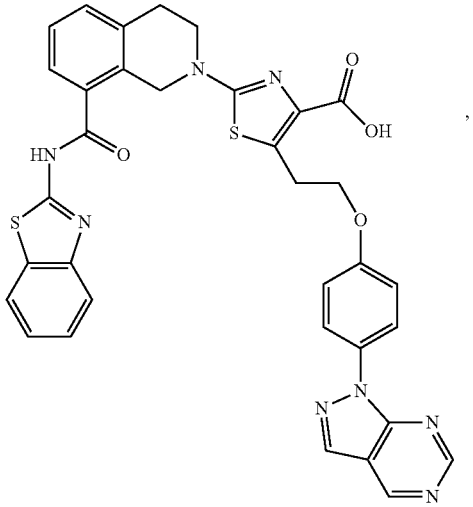
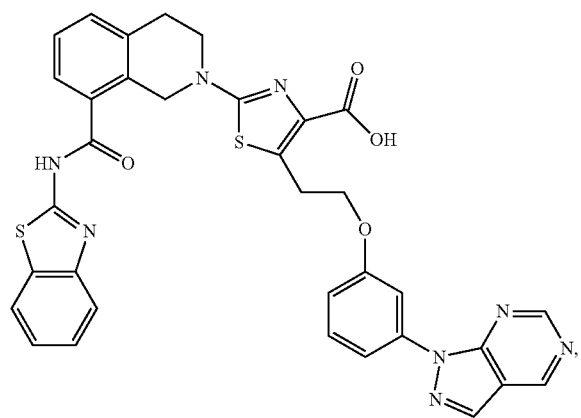

359
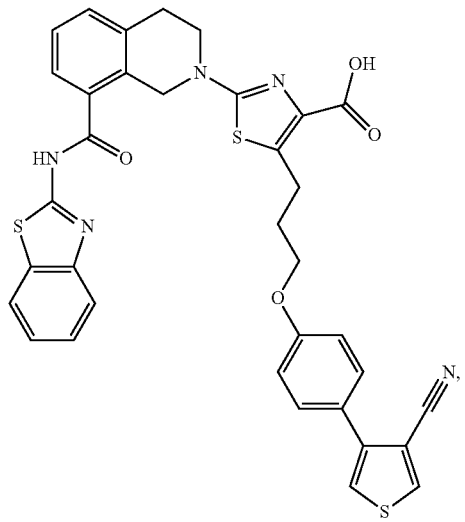
360
-continued
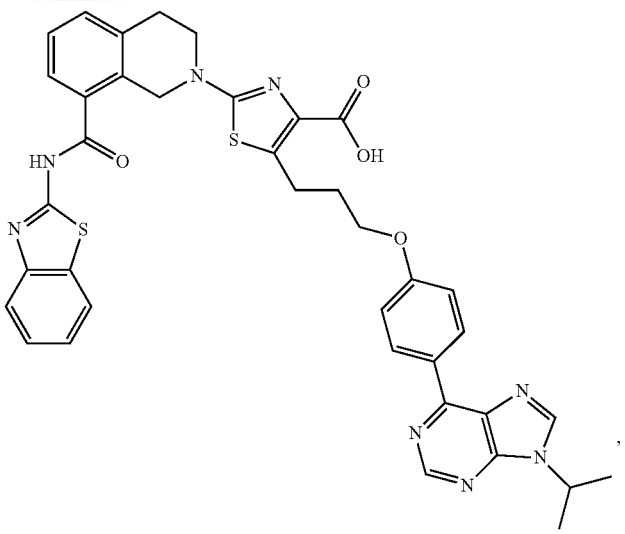
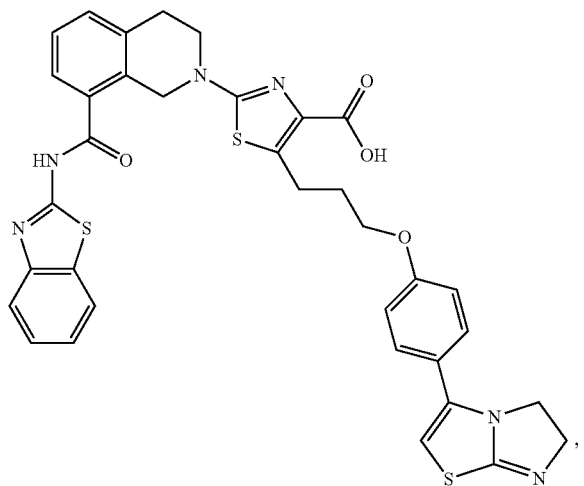
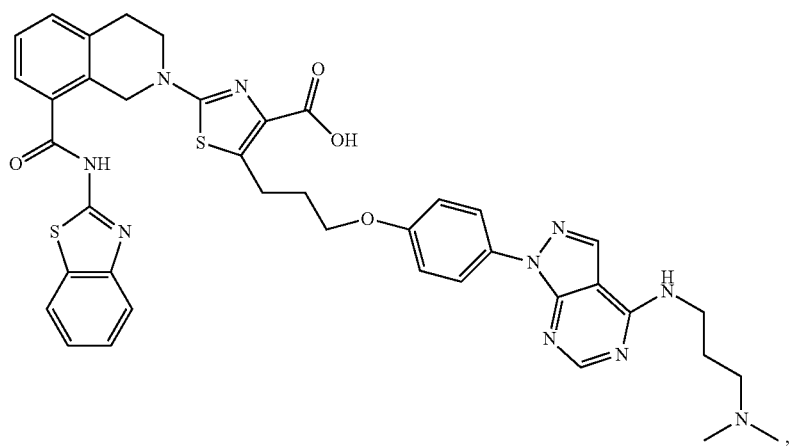

361
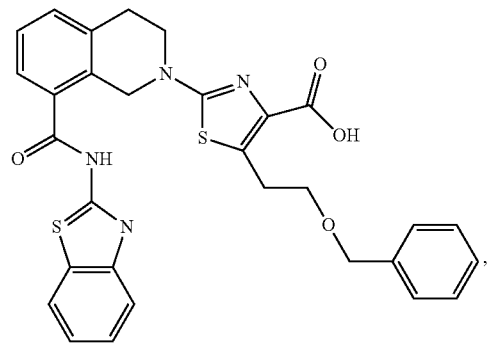
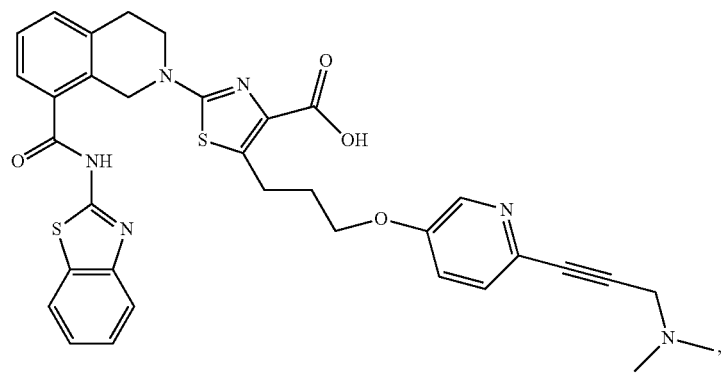
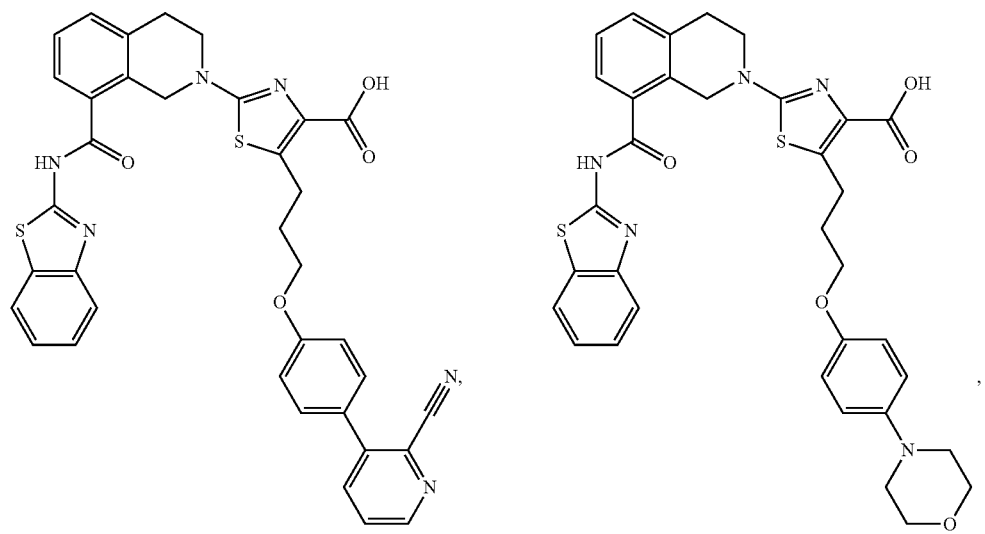
362
-continued
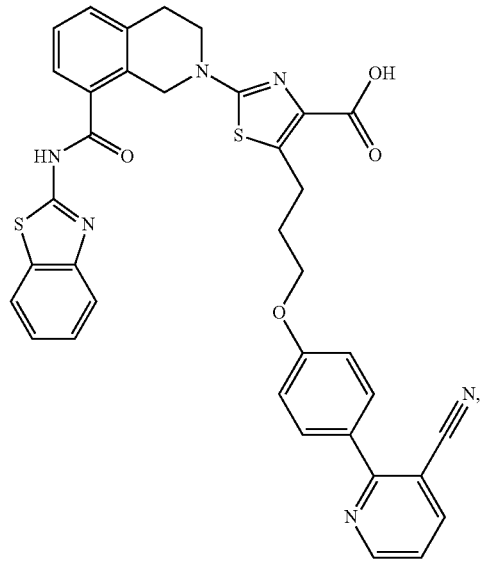

363
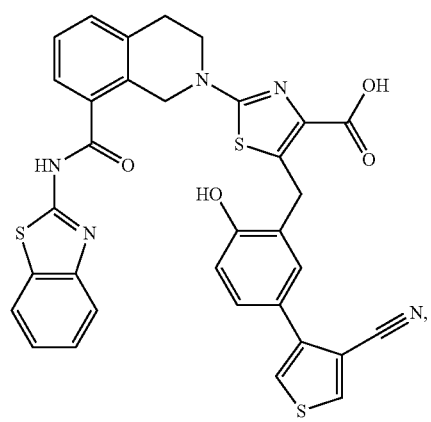
364
-continued
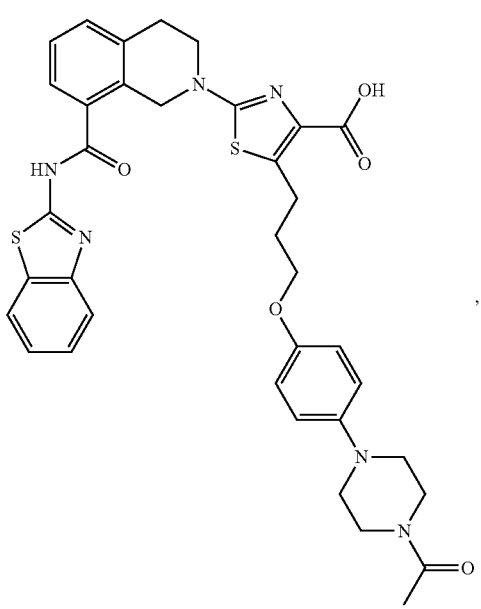
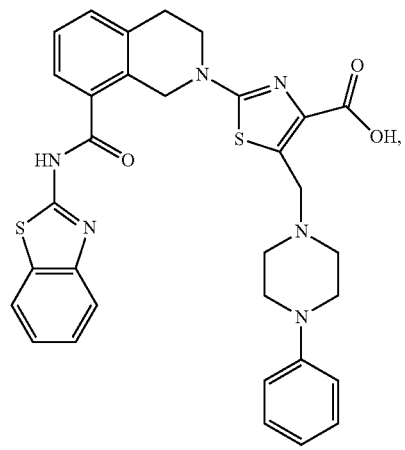
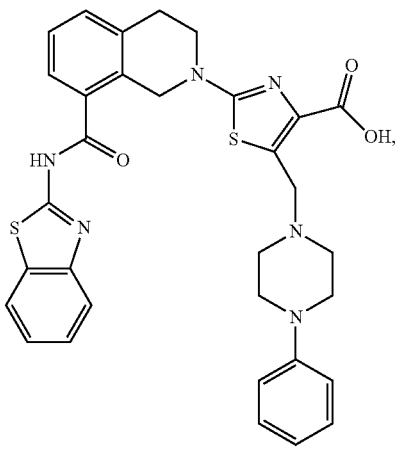
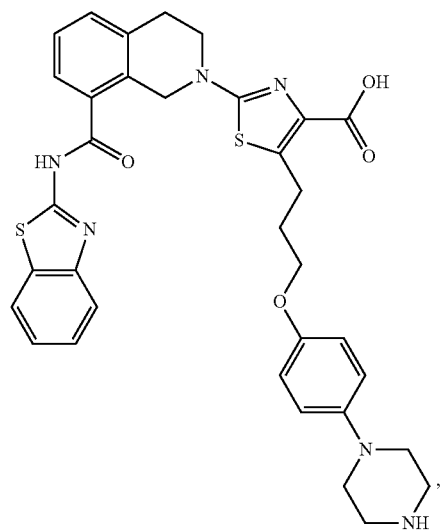
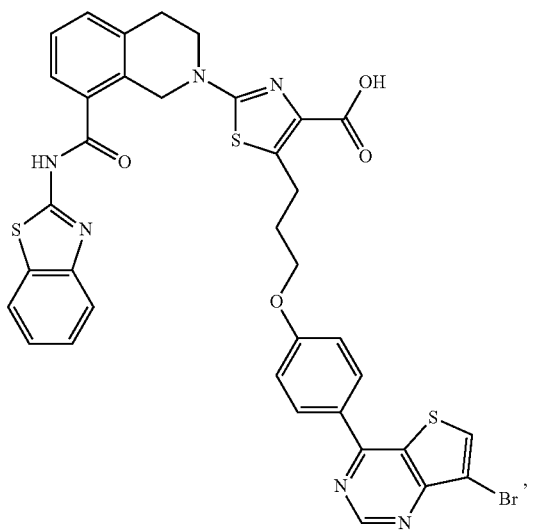

365
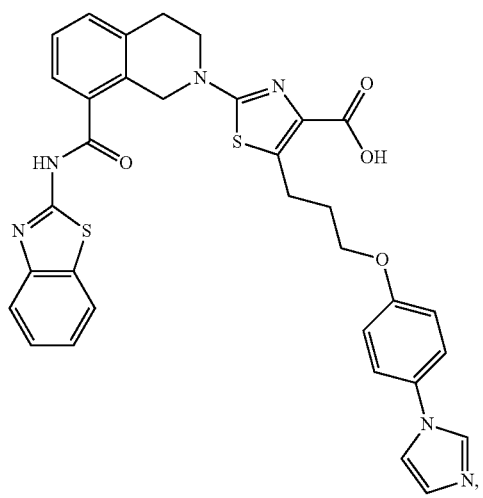
366
-continued
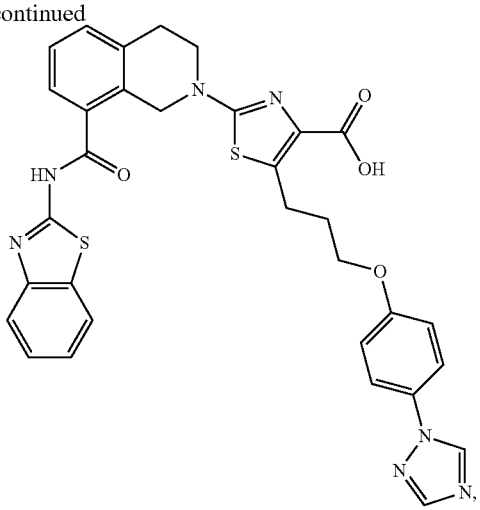
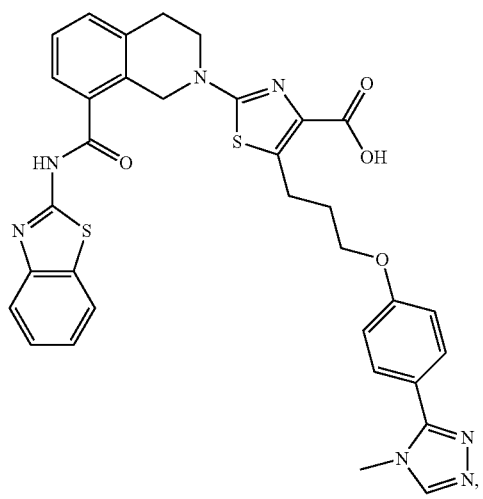
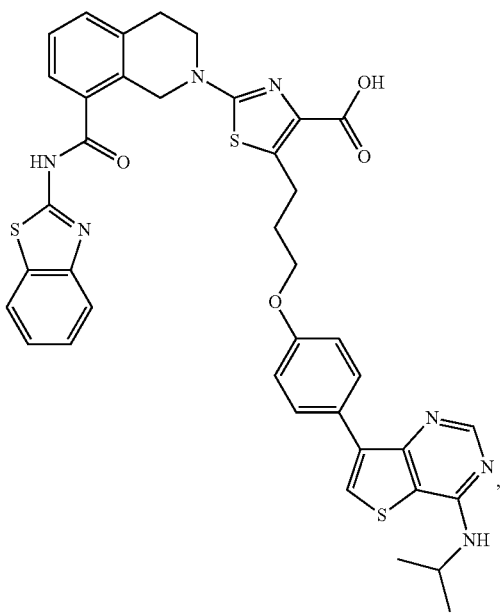
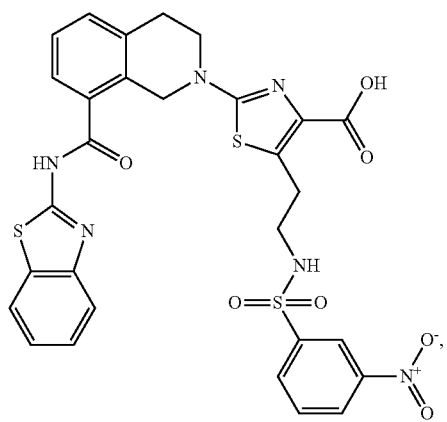

367
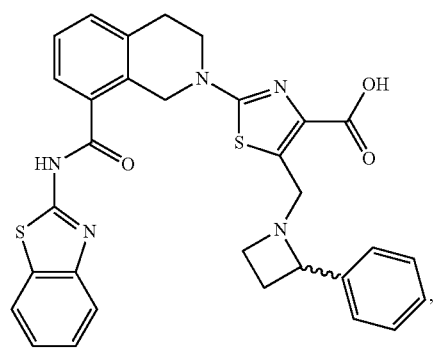
368
-continued
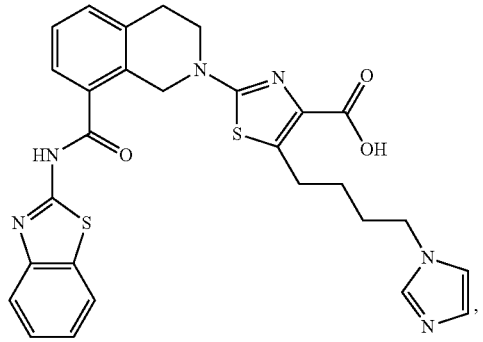
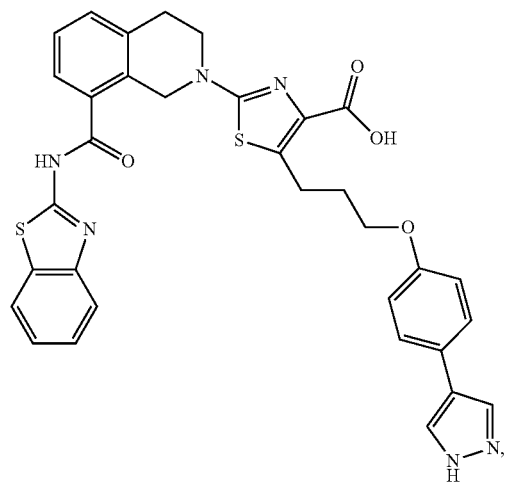
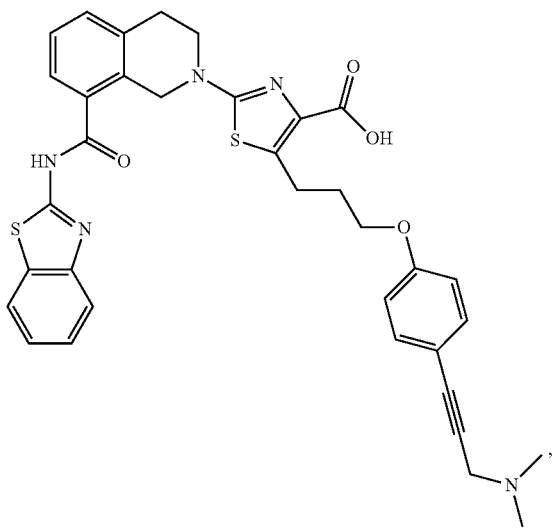
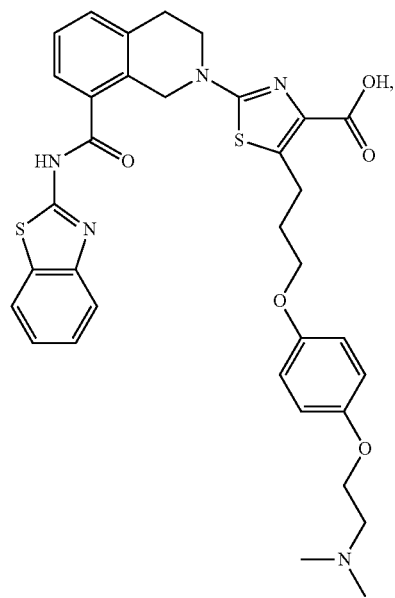
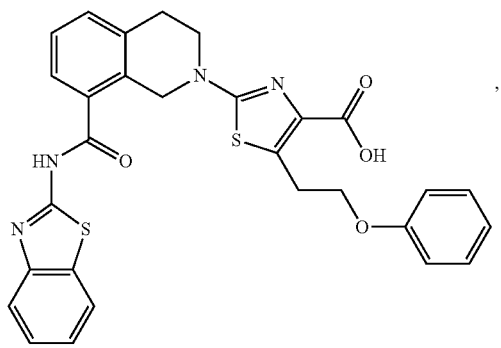

369
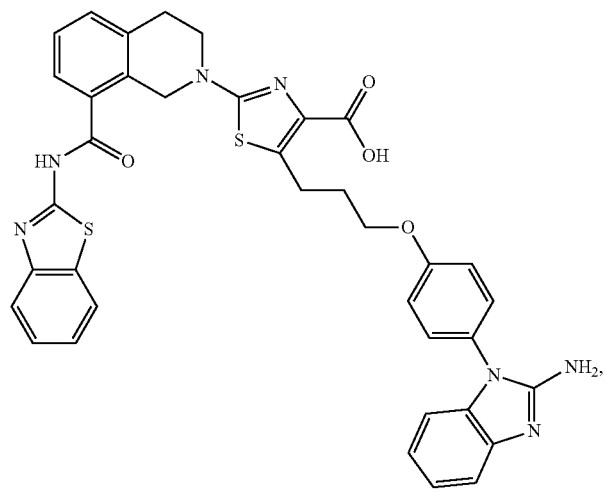
370
-continued
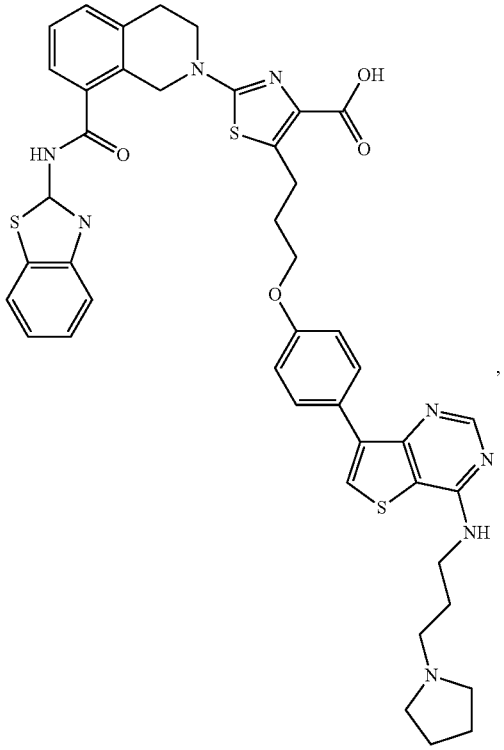
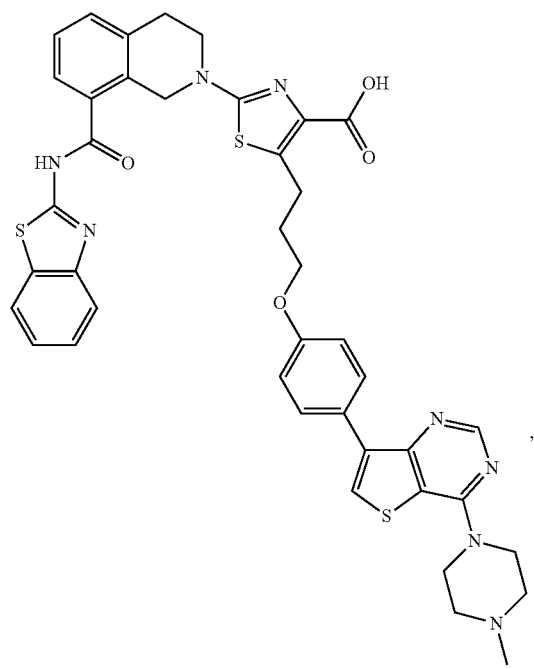
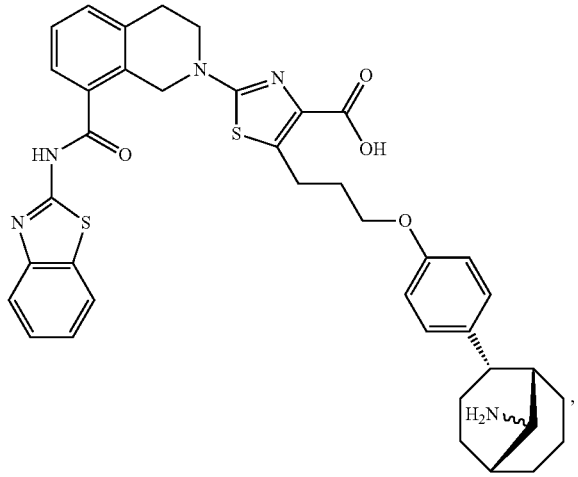

371
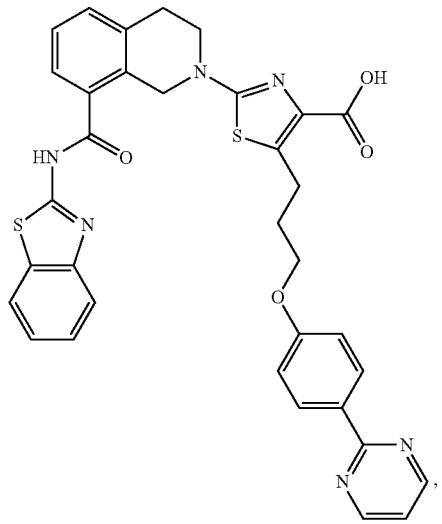
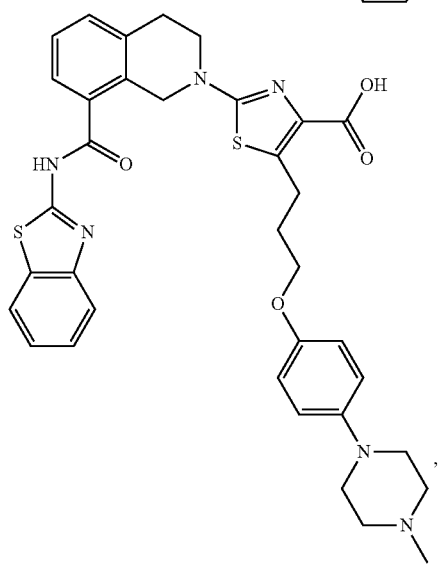
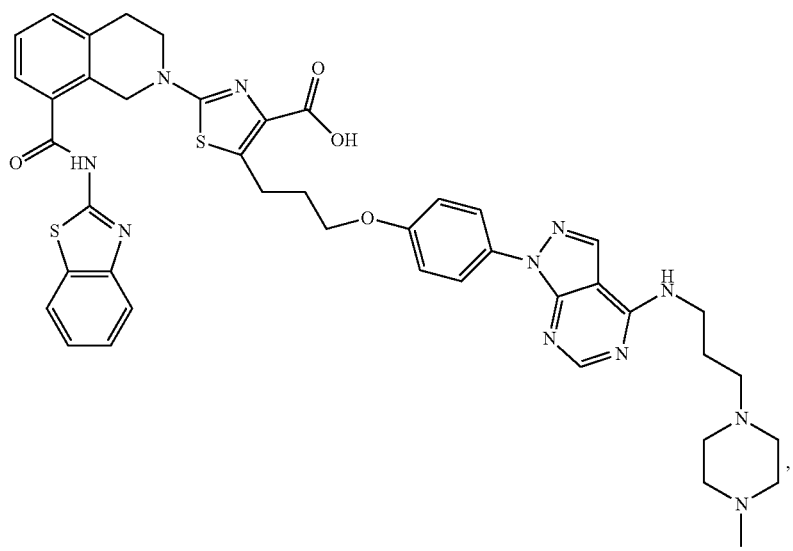
-continued
372
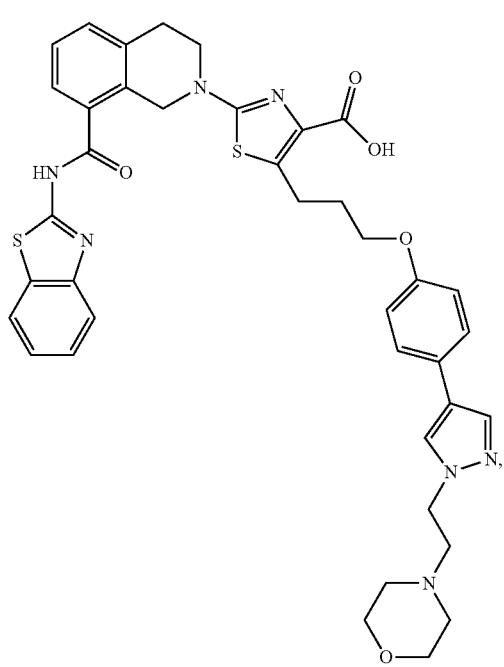

-continued
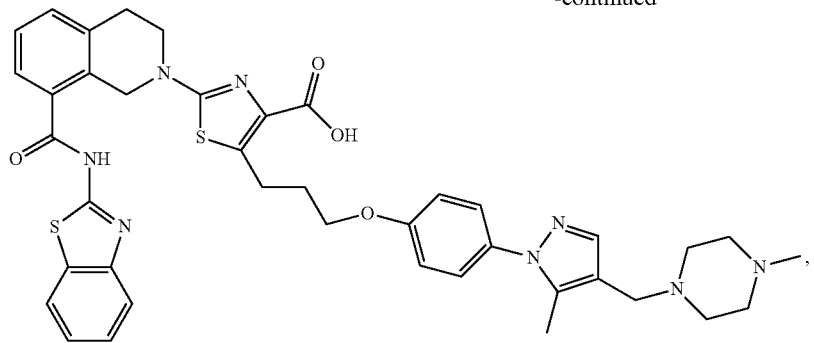
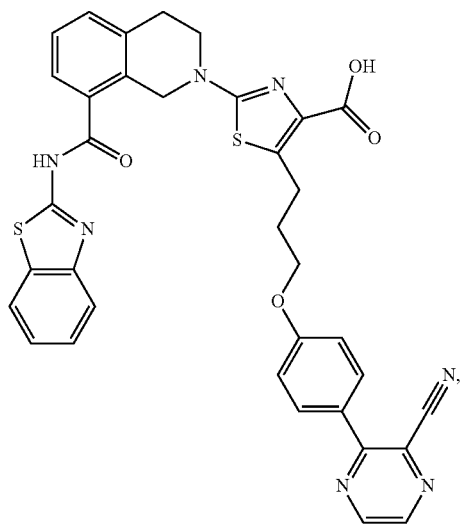
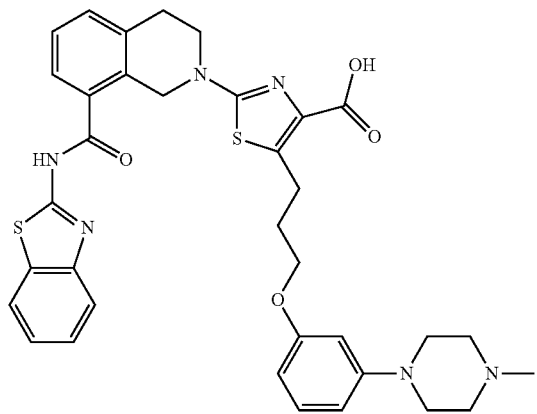
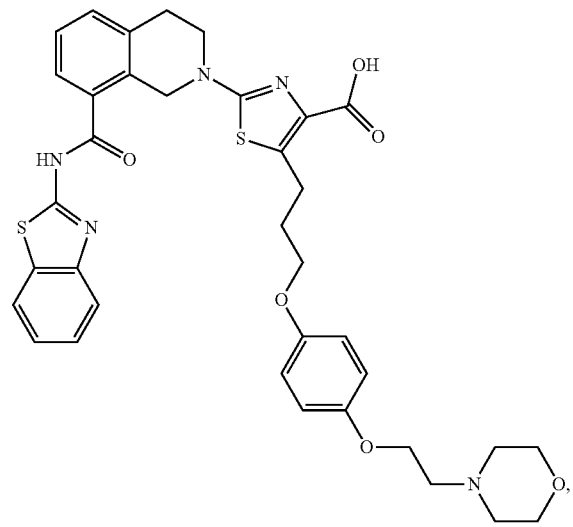

375
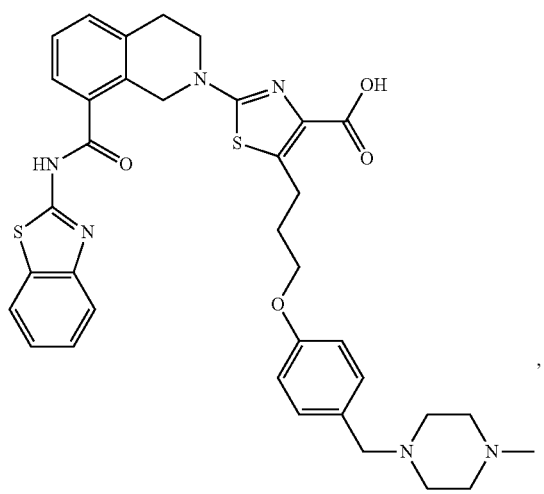
376
-continued
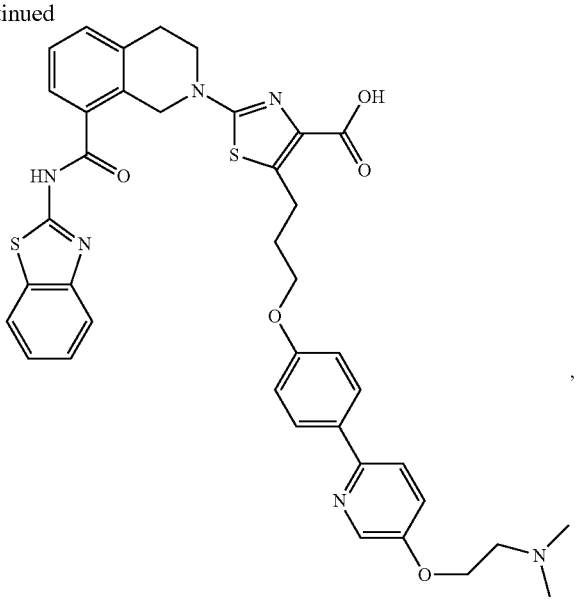
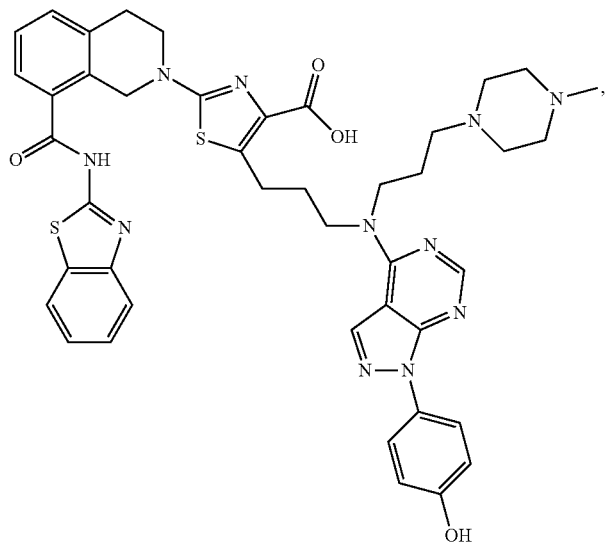
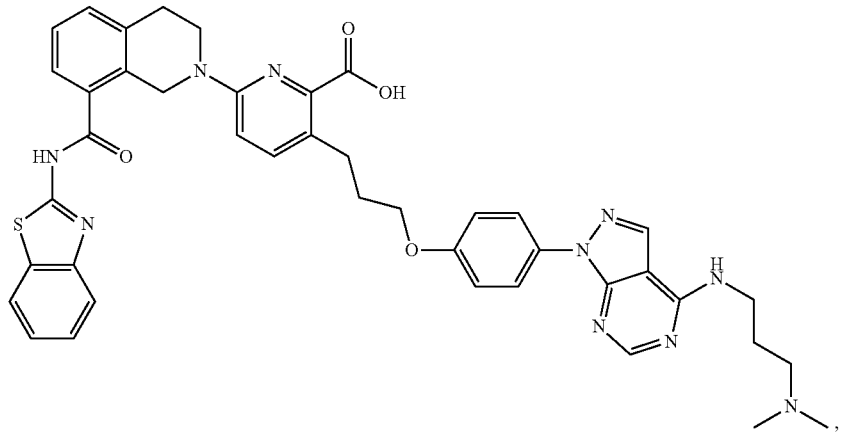

-continued
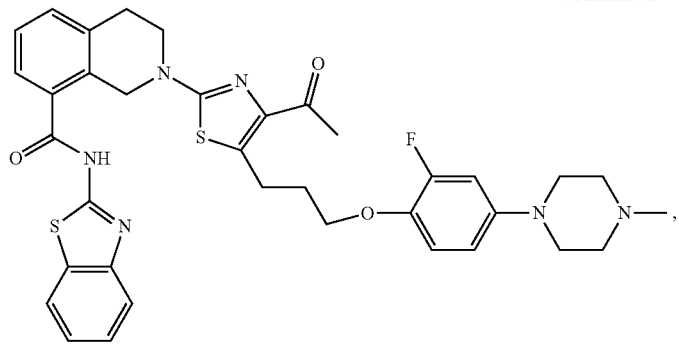
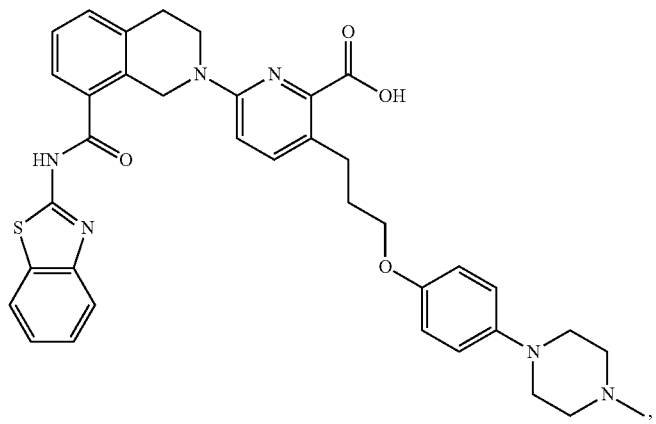
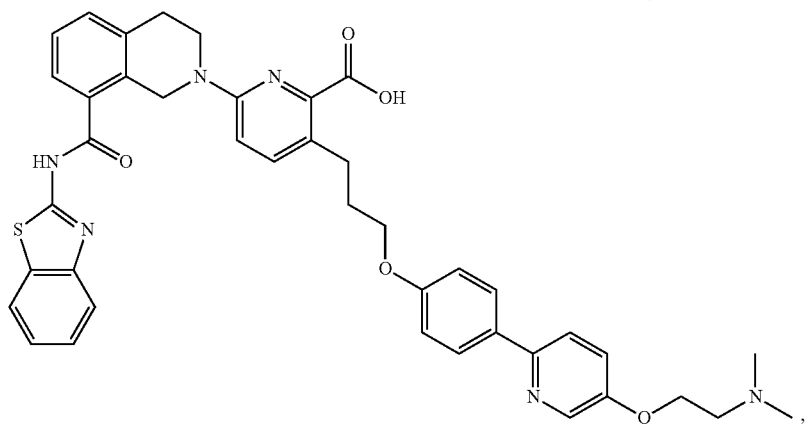
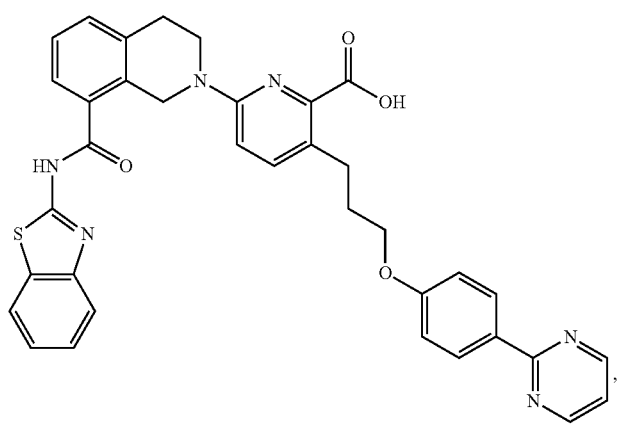

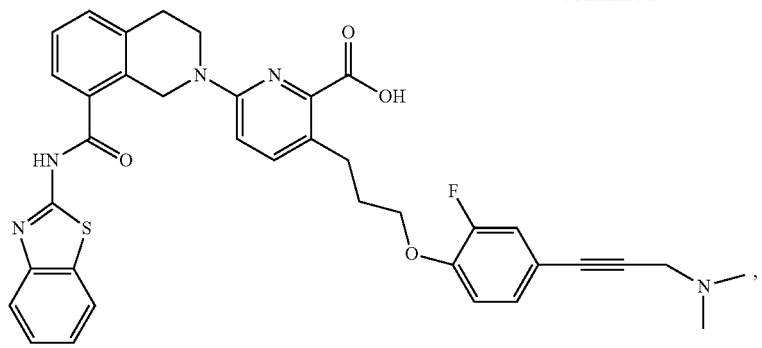
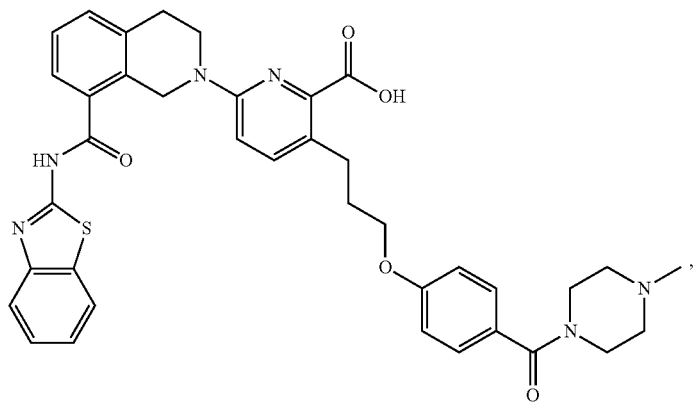
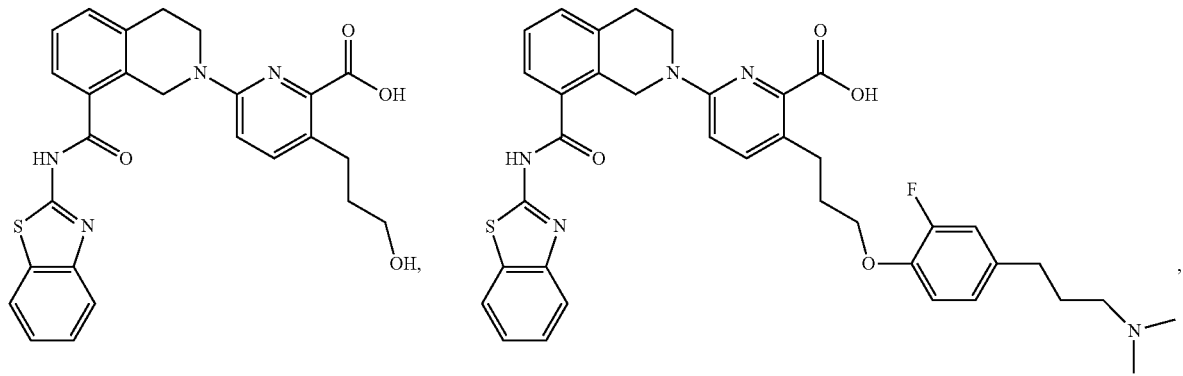
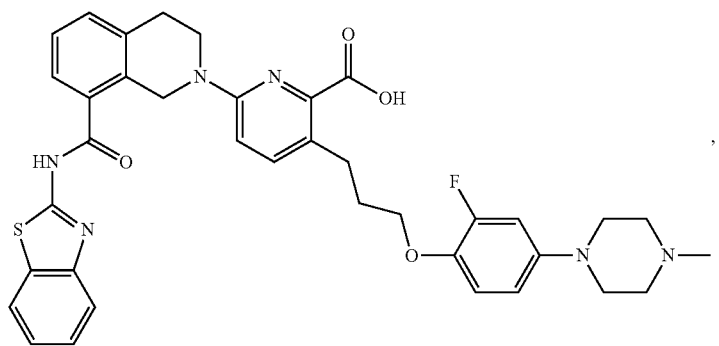
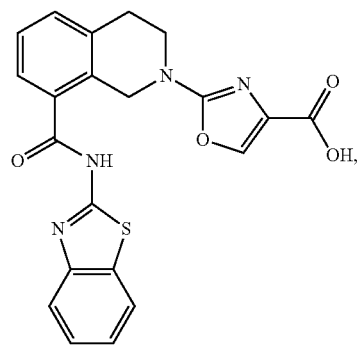

381
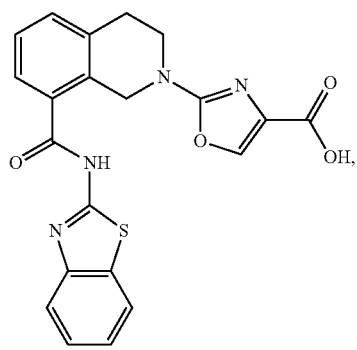 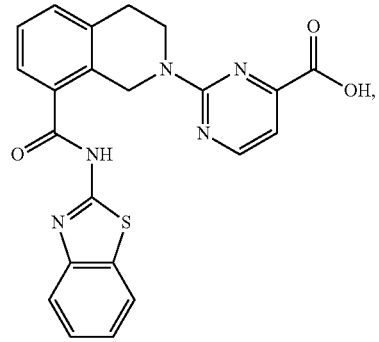 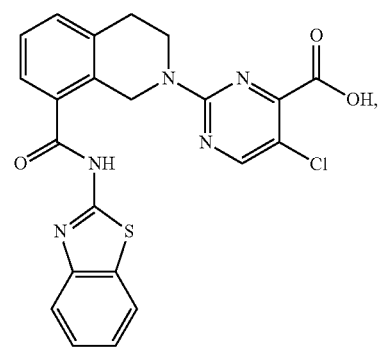
382
-continued
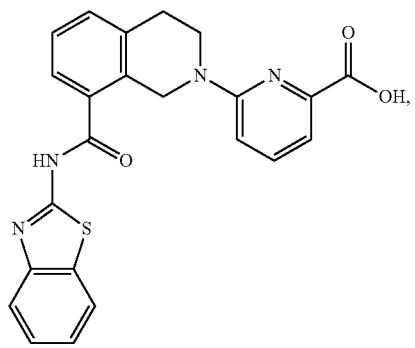
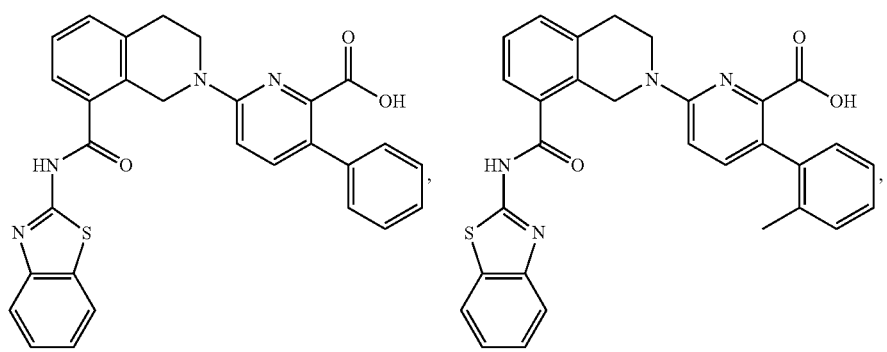
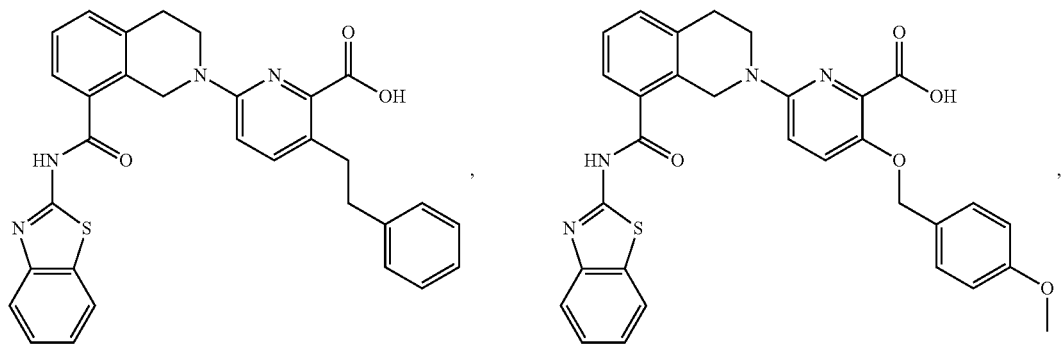

383
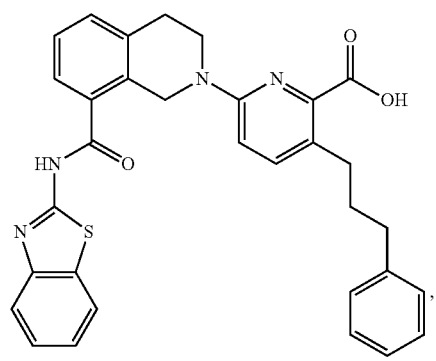
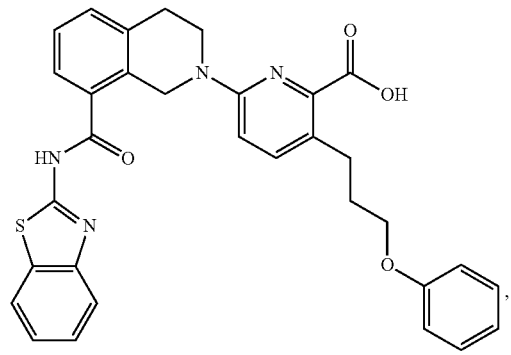
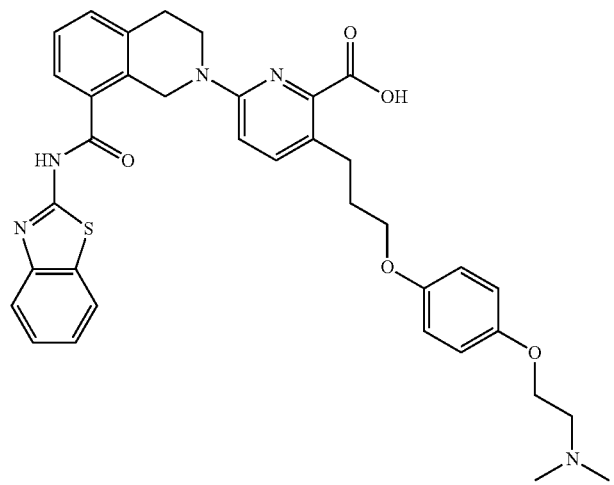
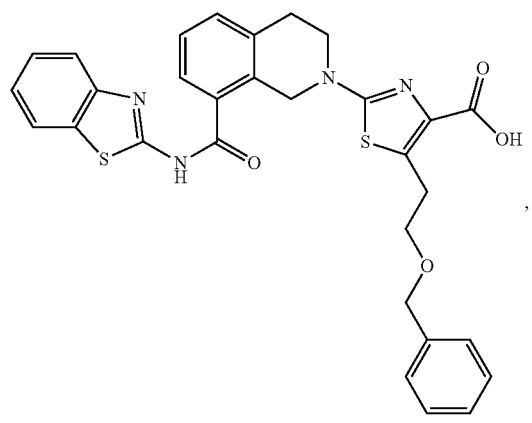
384
-continued
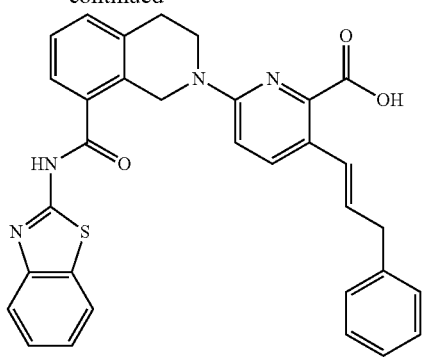
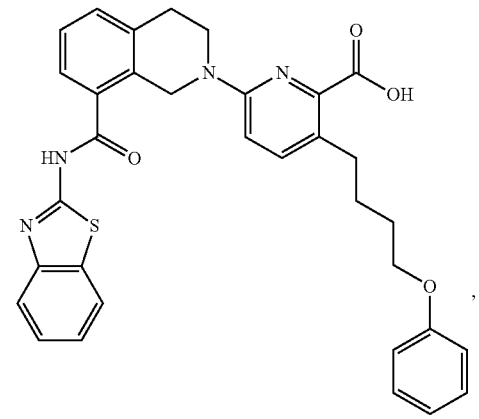
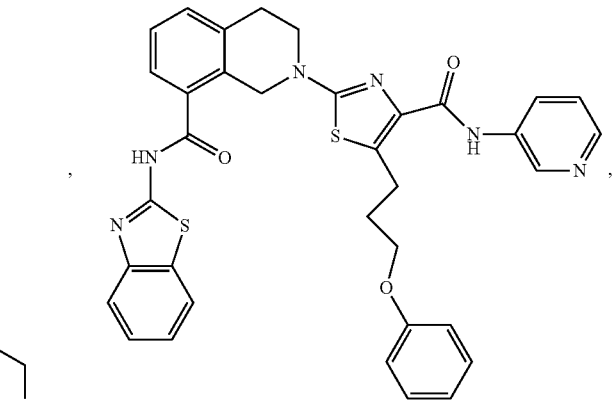
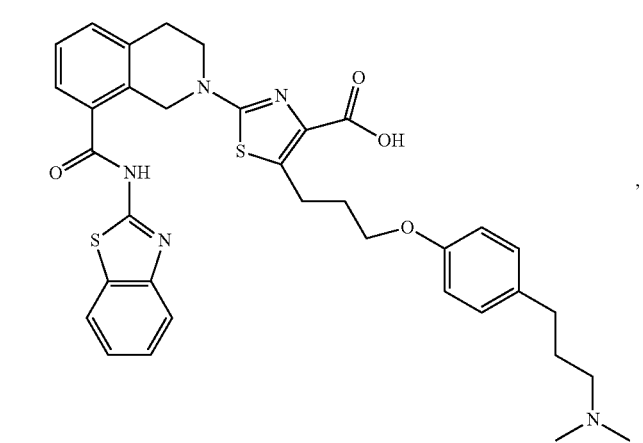

-continued
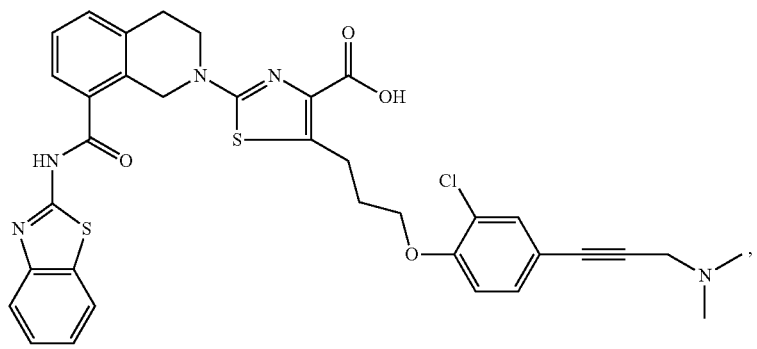
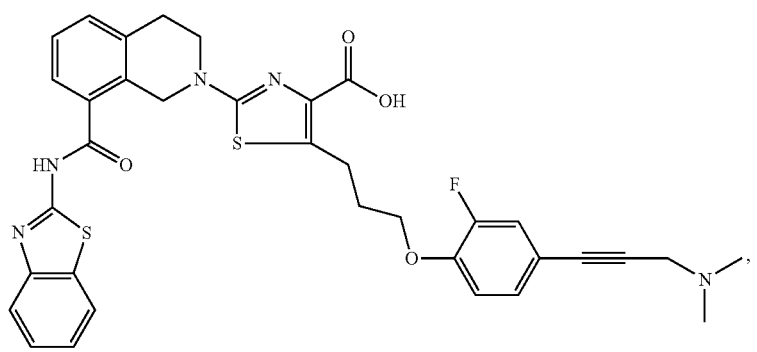
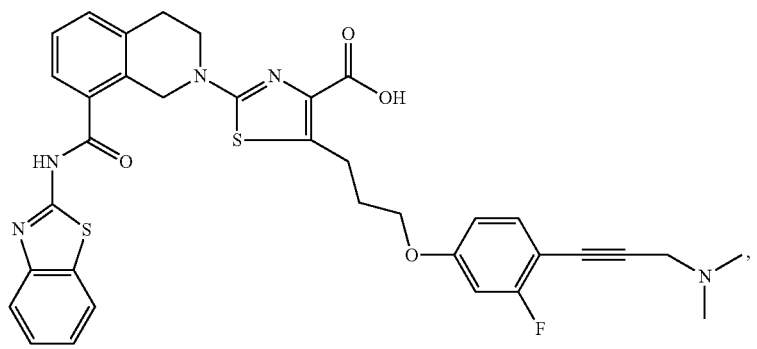
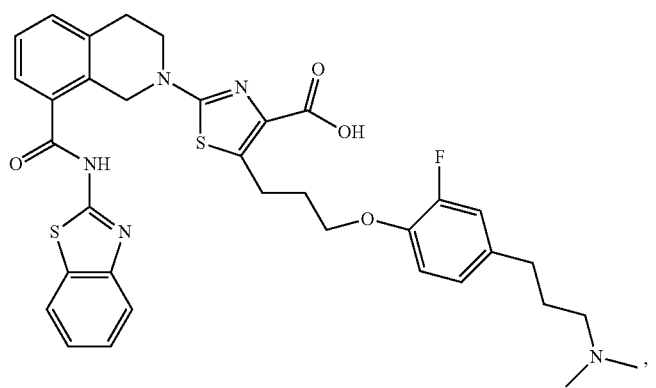

387
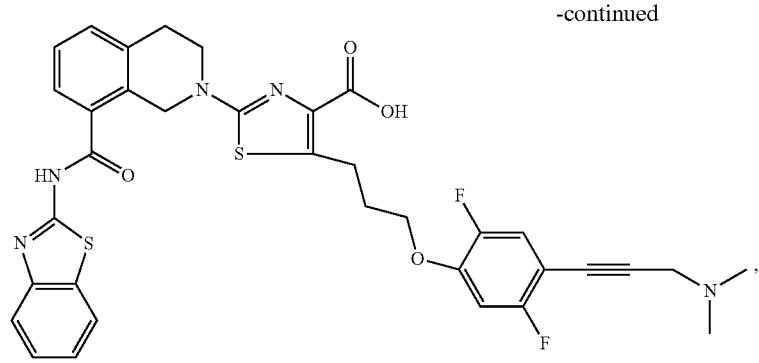
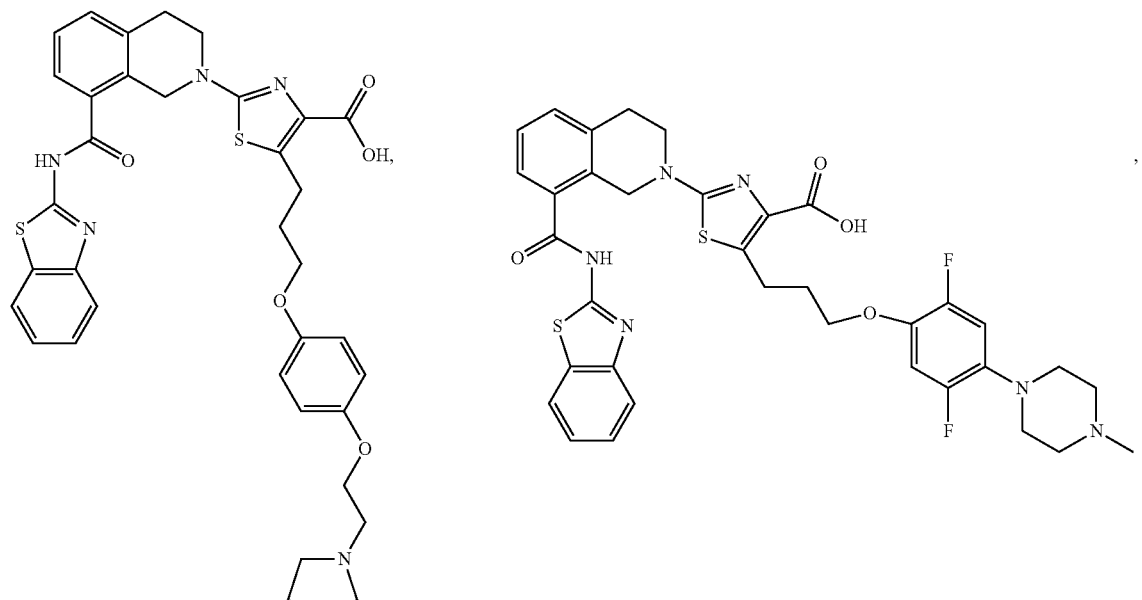
388
-continued
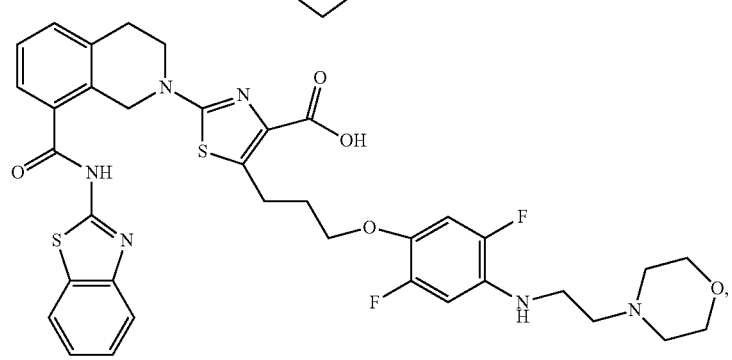
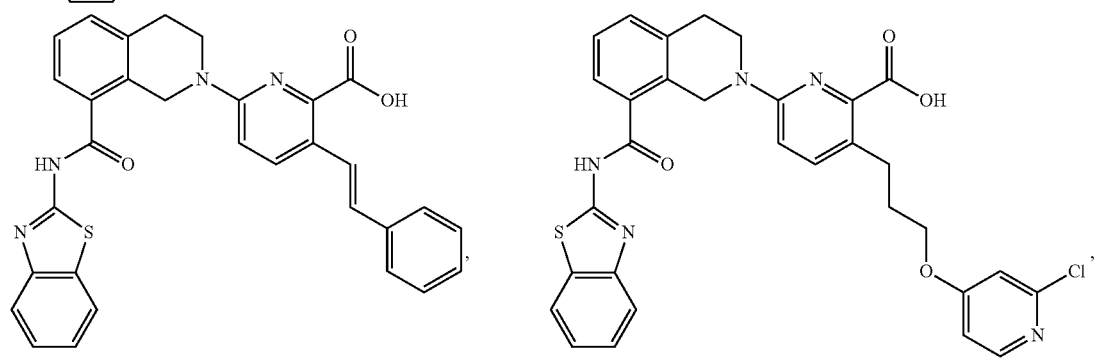

389
-continued
390
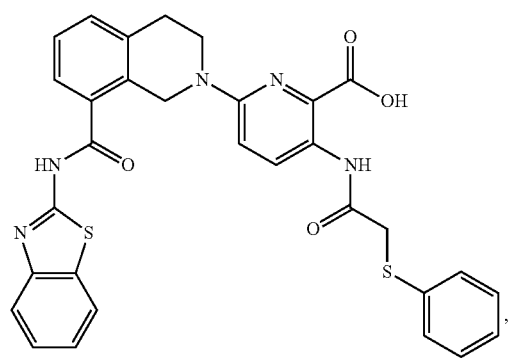
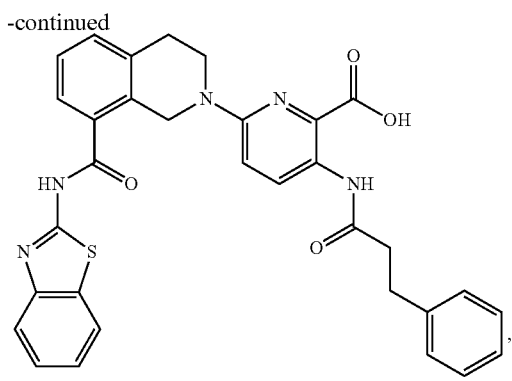
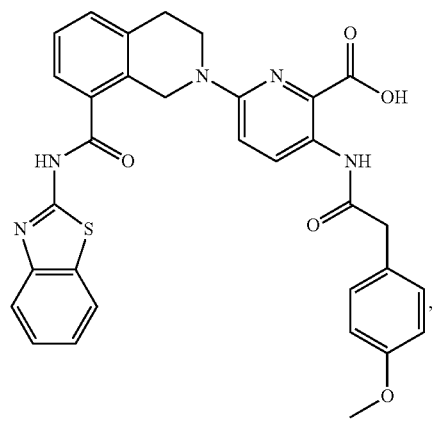
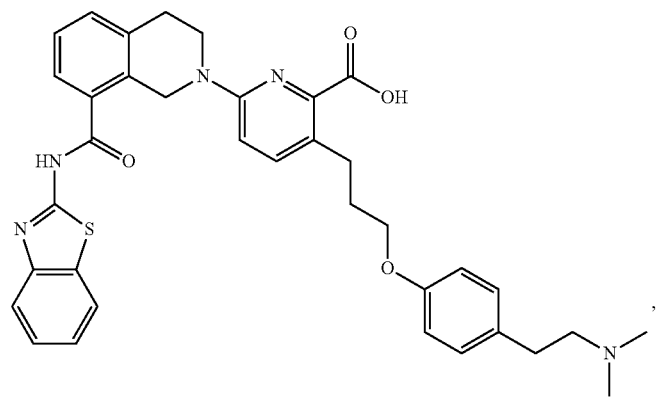
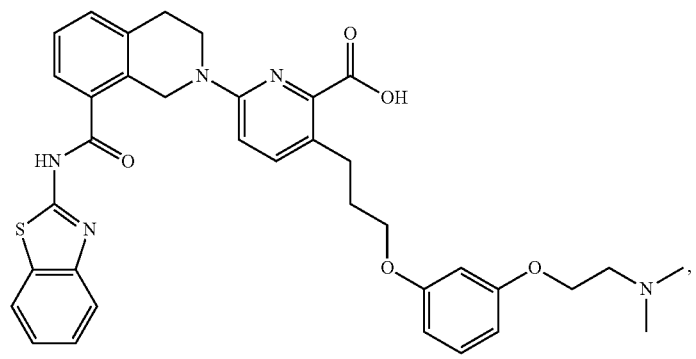
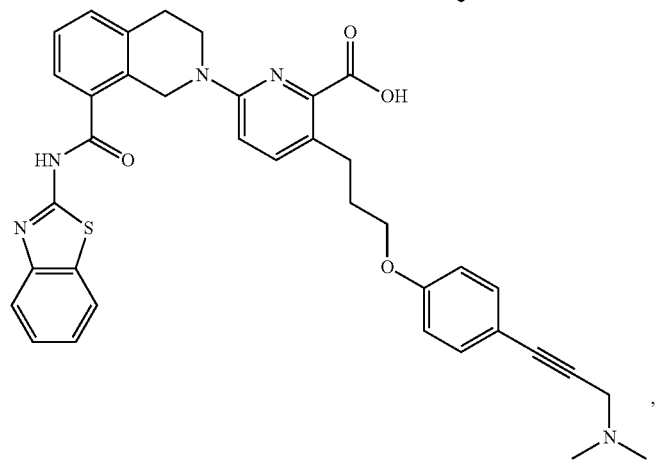

-continued
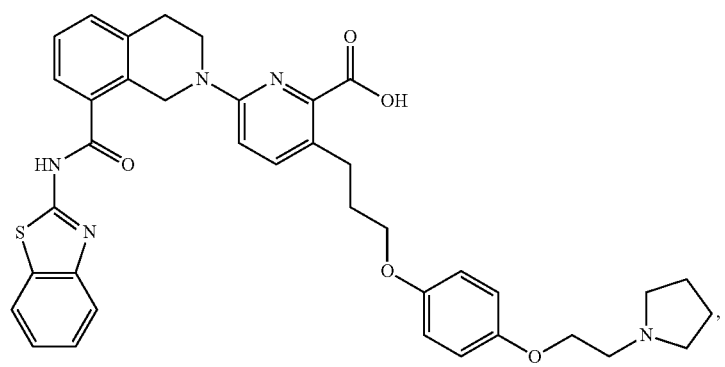
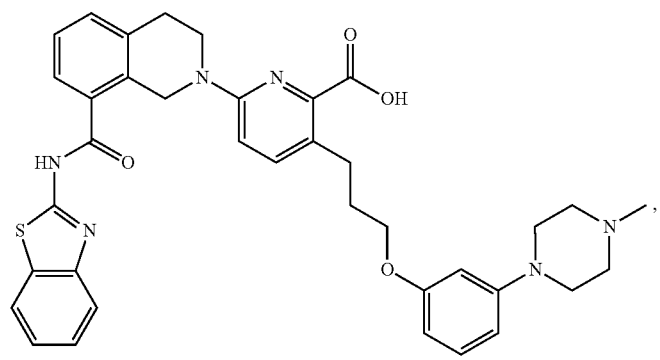
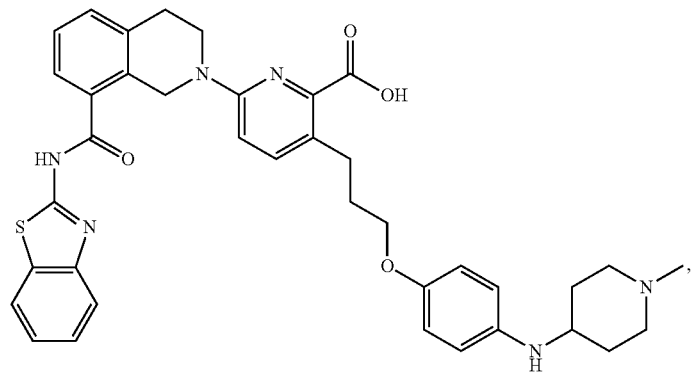
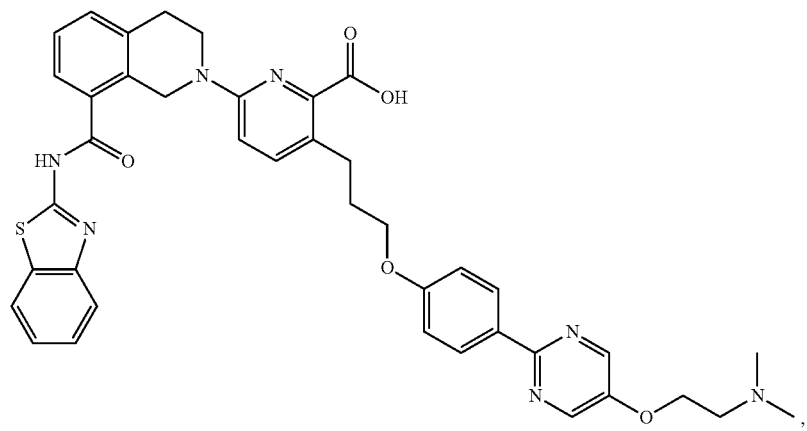

-continued
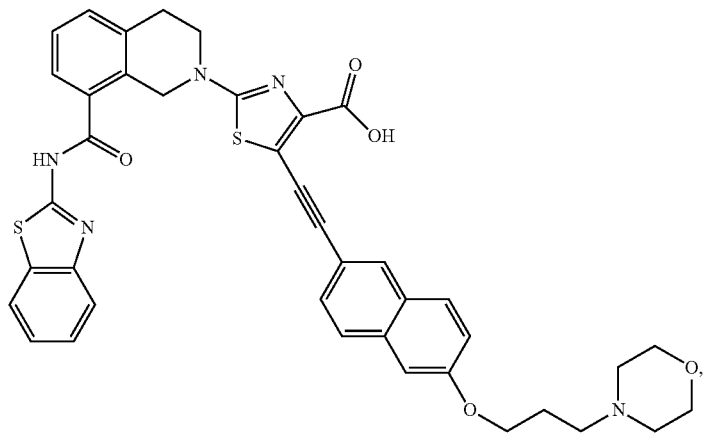
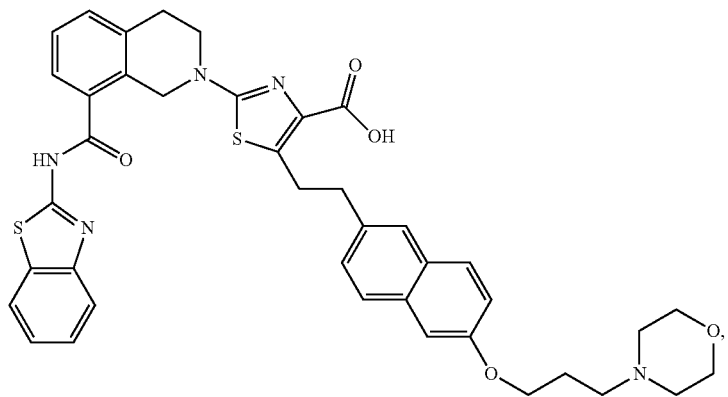
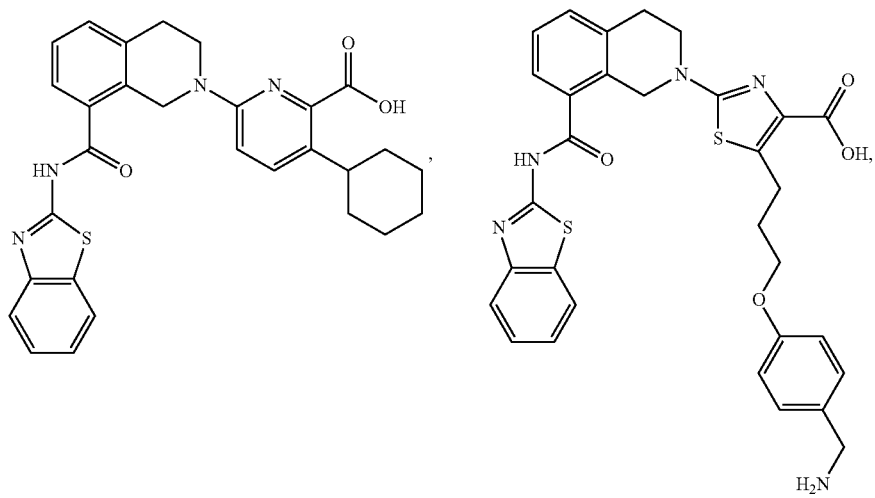

395
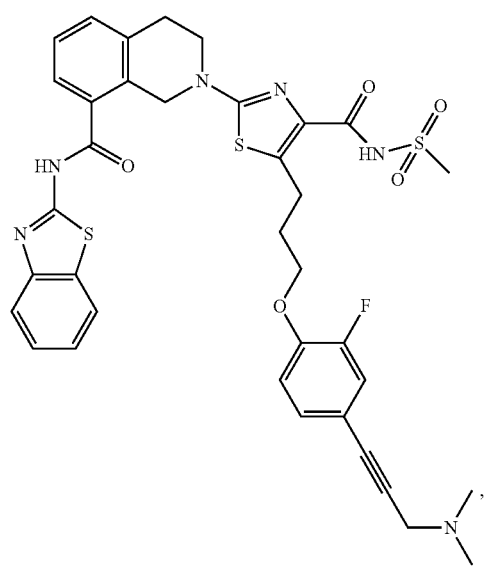
396
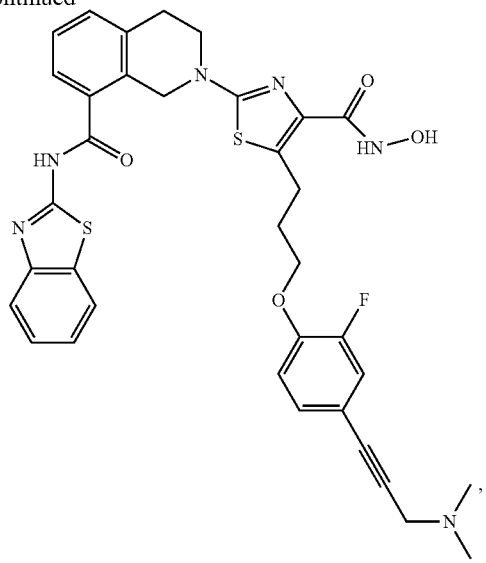
-continued
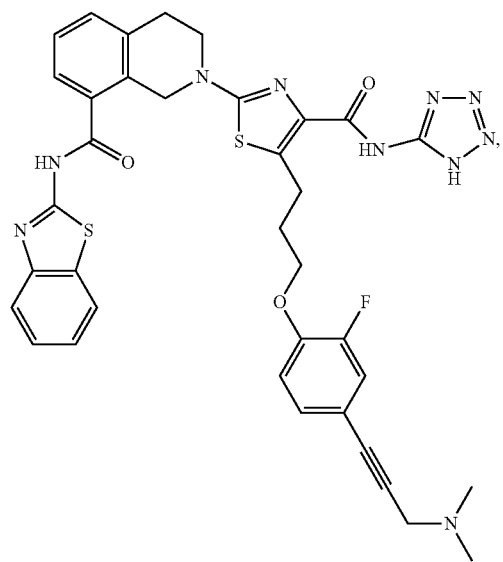
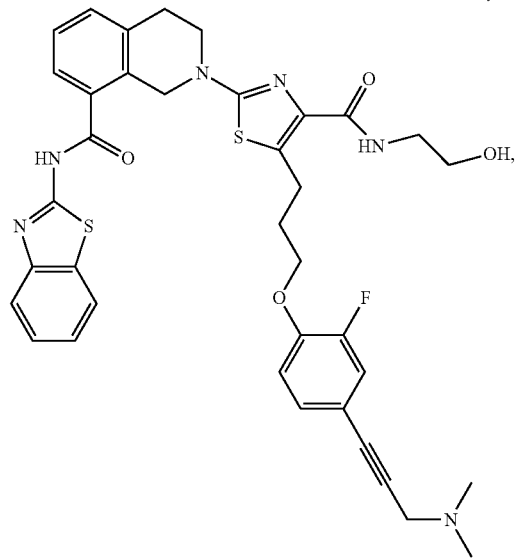
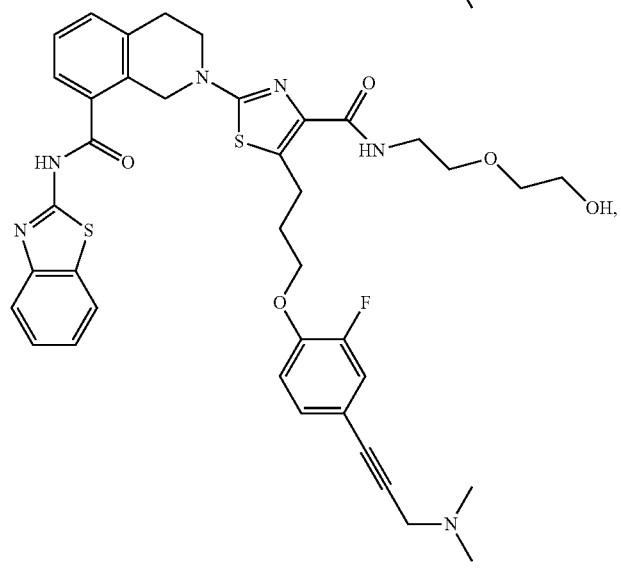
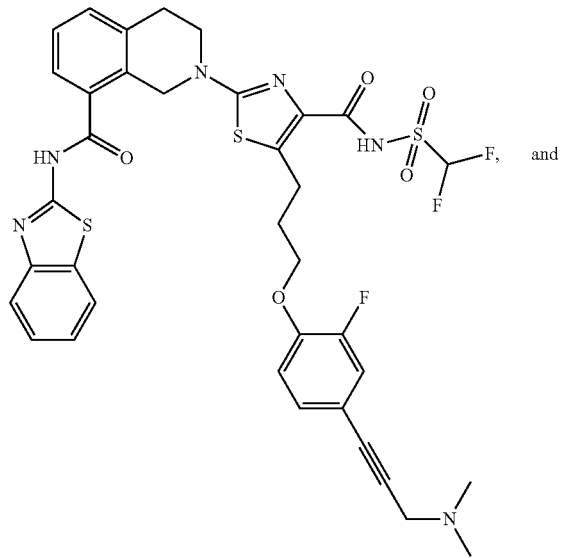
and -continued

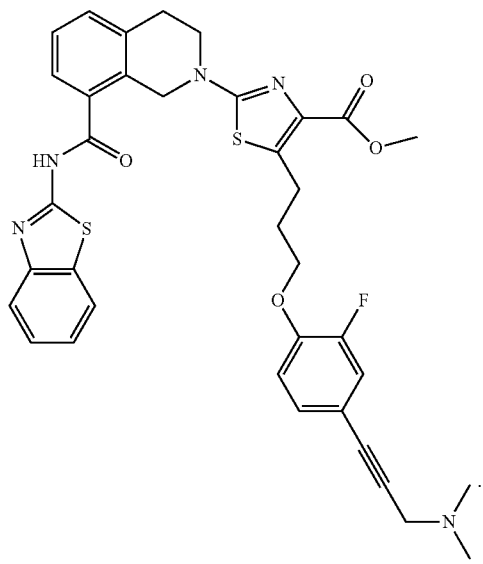

30. A pharmaceutical composition comprising a compound of claim 1, or pharmaceutically acceptable salt thereof, and at least one pharmaceutically acceptable diluent, carrier or excipient.

31. A method of treating non-small cell lung cancer, or small cell lung cancer in a patient, said method comprising administering to the patient a therapeutically effective amount of a compound of claim 1, or pharmaceutically acceptable salt thereof.

* * * * *

UNITED STATES PATENT AND TRADEMARK OFFICE
CERTIFICATE OF CORRECTION

PATENT NO.         : 8,232,273 B2
APPLICATION NO.    : 12/641141
DATED              : July 31, 2012
INVENTOR(S)        : Jonathan Bayldon Baell et al.

It is certified that error appears in the above-identified patent and that said Letters Patent is hereby corrected as shown below:

In the Claims

In column 318, lines 19–20, replace "–NR–$^p$R$^q$" with -- –NR$^p$R$^q$ --.

In column 321, line 12, replace "–NR$^h$C(O)NR$^i$R$^i$" with -- –NR$^h$C(O)NR$^h$R$^i$ --.

In column 331, lines 12–20, the structure IV-c should appear as follows:

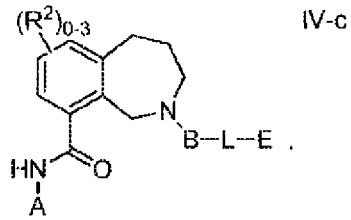

In column 337, lines 6–12, the structure on the left should appear as follows:

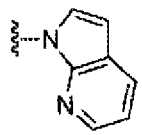

In column 337, lines 6–12, the structure on the right should appear as follows:

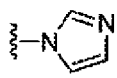

Signed and Sealed this
Sixth Day of May, 2014

Michelle K. Lee
*Deputy Director of the United States Patent and Trademark Office*

CERTIFICATE OF CORRECTION (continued)
U.S. Pat. No. 8,232,273 B2

In column 340, lines 12–20, add a -- , -- after the structure 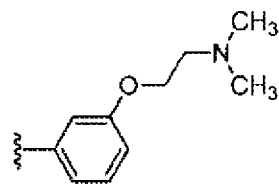 .

In column 364, the second structure from the top should appear as follows:

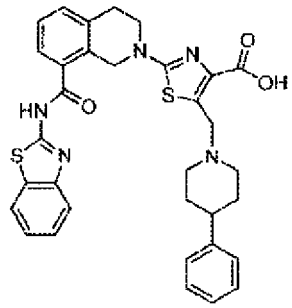

In column 377, the first structure should appear as follows:

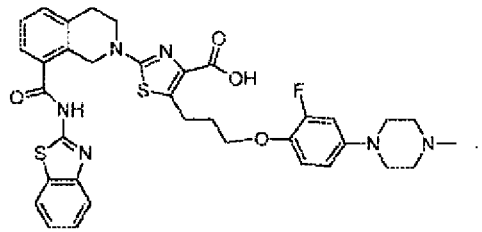 .

In column 381, the first structure at the top left of the column which has the following structure should be deleted:

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Assay protein
<220> FEATURE:
<221> NAME/KEY: MOD_RES
<222> LOCATION: 13
<223> OTHER INFORMATION: Lys is modified with 6-FAM
<220> FEATURE:
<221> NAME/KEY: MOD_RES
<222> LOCATION: 16
```

-continued

<223> OTHER INFORMATION: Arg is modified with amide

<400> SEQUENCE: 1

Gly Gln Val Gly Arg Gln Leu Ala Ile Ile Gly Asp Lys Ile Asn Arg
1               5                   10                  15